US010626445B2

(12) United States Patent
Meissner et al.

(10) Patent No.: US 10,626,445 B2
(45) Date of Patent: Apr. 21, 2020

(54) EARLY DEVELOPMENTAL GENOMIC ASSAY FOR CHARACTERIZING PLURIPOTENT STEM CELL UTILITY AND SAFETY

(71) Applicant: PRESIDENT AND FELLOWS OF HARVARD COLLEGE, Cambridge, MA (US)

(72) Inventors: Alexander Meissner, Cambridge, MA (US); Alexander Tsankov, Cambridge, MA (US); Veronika Akopian, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/983,209

(22) Filed: May 18, 2018

(65) Prior Publication Data

US 2018/0251818 A1    Sep. 6, 2018

Related U.S. Application Data

(63) Continuation of application No. 14/897,410, filed as application No. PCT/US2014/041513 on Jun. 9, 2014.

(60) Provisional application No. 61/833,092, filed on Jun. 10, 2013.

(51) Int. Cl.
*C12Q 1/6806* (2018.01)
*C12Q 1/6837* (2018.01)
*C12Q 1/6876* (2018.01)

(52) U.S. Cl.
CPC ......... *C12Q 1/6806* (2013.01); *C12Q 1/6837* (2013.01); *C12Q 1/6876* (2013.01); *C12N 2506/00* (2013.01); *C12N 2506/03* (2013.01); *C12Q 2600/158* (2013.01); *C12Q 2600/16* (2013.01)

(58) Field of Classification Search
CPC .. C12Q 1/6806; C12Q 1/6837; C12Q 1/6876; C12Q 2600/158; C12Q 2600/16; C12N 2506/00; C12N 2506/03; Y02A 50/57
USPC .............. 506/16, 17; 435/6.11, 12
See application file for complete search history.

(56) References Cited

U.S. PATENT DOCUMENTS

| | | | |
|---|---|---|---|
| 8,460,928 B2 | 6/2013 | Bakre | |
| 2003/0113910 A1 | 6/2003 | Levanduski | |
| 2004/0180347 A1 | 9/2004 | Stanton | |
| 2009/0123430 A1 | 5/2009 | De Sousa | |
| 2009/0191159 A1 | 7/2009 | Sakurada | |
| 2010/0003674 A1 | 1/2010 | Cope | |
| 2011/0287974 A1 | 11/2011 | Benevesnisty | |
| 2012/0329152 A1 | 12/2012 | Pera | |
| 2016/0115455 A1* | 4/2016 | Mikkelsen | C12N 5/0696 506/10 |

FOREIGN PATENT DOCUMENTS

| | | |
|---|---|---|
| WO | 2002/010347 A2 | 2/2002 |
| WO | 2003/093445 A2 | 11/2003 |
| WO | 2004/009758 A2 | 1/2004 |
| WO | 2004/097005 A2 | 11/2004 |
| WO | 2005/120547 A1 | 12/2005 |
| WO | 2009/131568 A1 | 10/2009 |
| WO | 2010/009015 A2 | 1/2010 |
| WO | 2010/111422 A2 | 9/2010 |
| WO | 2011/008541 A2 | 1/2011 |
| WO | 2011/046635 A1 | 4/2011 |
| WO | 2011/146607 A2 | 11/2011 |
| WO | 2012/037456 A1 | 3/2012 |

OTHER PUBLICATIONS

Kopper et al. Stem Cell Research, vol. 8, Issue 3, May 2012, pp. 335-345. (Year: 2012).*
Fogel et al. Human Molecular Genetics, 2012, vol. 21, No. 19, pp. 4171-4186. (Year: 2012).*
Gan et al. Stem Cells, vol. 25, Issue: 1, pp. 2-9, Journal; General Review, 2007, abstract summary (Year: 2007).*
Riemenschneider et al. Acta Neuropathol (2004) 107 : 277-282. (Year: 2004).*
Applied Biosystems Protocol, Introduction to TaqMan and SYBR Green Chemistries for Real-Time PCR, Applied Biosystems Protocol, 2010, 1-11.
Applied Biosystems Signature Array, TaqMan Human Stem Cells Pluripotency Array, Applied Biosystems, 2008, 1-2.
Applied Biosystems User Guide, TaqMan Array Micro Fluidic Cards, Applied Biosystems User Guide, 2010, 1-20.
Applied Biosystems, Applied Biosystems Pluripotency Array 4385344, 2009, 1-3.
Gifford et al., "Transcriptional and epigenetic dynamics during specification of human embryonic stem cells", Cell 153(5) 1149-1163 (2013).

(Continued)

*Primary Examiner* — Janet L Epps-Smith
(74) *Attorney, Agent, or Firm* — Nixon Peabody, LLP

(57) ABSTRACT

The present invention generally relates to a set of early developmental reference data or "lineage scorecard" for stem cells, and methods, systems and kits to generate a lineage scorecard for predicting the functionality and suitability of stem cell lines. In some aspects, methods for generating a scorecard comprises measuring the gene expression of a plurality of early developmental genes, such as pluripotent, early ectoderm, early mesoderm and early endoderm genes to predict the pluripotency and differentiation potential of the stem cell line and its functionality and/or suitability for a desired use. In some embodiments, a reference scorecard can be compared with the test stem cell line scorecard to accurately predict the utility and/or identify specific characteristics of the stem cell line, e.g., to determine its suitability for downstream applications, e.g., therapeutic use, drug screening, toxicity assays, differentiation into a desired cell lineage, etc.

7 Claims, 14 Drawing Sheets

Specification includes a Sequence Listing.

(56) References Cited

OTHER PUBLICATIONS

Livak et al., "Analysis of Relative Gene Expression Data Using Real-Time Quantitative PCR and the 2-ΔΔCT Method" Methods 25:402-408 (2001).
Mandal et al., "Characterization and in vitro differentiation potential of a new human embryonic stem cell line, ReliCellhES1", Differentiation 74(2-3) 81-90 (2006).
Rosenkranz et al., "Characterizing the mouse ES cell transcriptome with Illumina sequencing", Genomics 92(4) 187-194 (2008).
ThermoFisher Scientific, TaqMan Array Human NFAT & Cardiac Hypertrophy 96-Well Plate, 2010, 1 (2010) (cited only because cited in related U.S. application).
Urbach et al., "Studying early lethality of 45,XO (Turner's syndrome) embryos using human embryonic stem cells", PLoS One 4(1) e4175 (2009) (cited only because cited in related U.S. application).
Miura et al., "Variation in the safety of induced pluripotent stem cell lines", Nat Biotechnol 27(8) 742-745 (2009).
Muller et al., "Regulatory networks define phenotypic classes of human stem cell lines", Nature 455(7211) 401-405 (2008).
Nam et al., "Gene-set approach for expression pattern analysis", Brief Bioinfomi 9(3) 189-197 (2008).
Osafune et al., "Marked differences in differentiation propensity among human embryonic stem cell lines", Nat Biotechnol 26(3) 313-315 (2008).
Park et al., "ChIP-seq: advantages and challenges of a maturing technology", Nat Rev Genet 10(1) 669-680 (2009).
Park et al., "Disease-specific induced pluripotent stem cells", Cell 134(5) 877-886 (2008).
Park et al., "Reprogramming of human somatic cells to pluripotency with defined factors", Nature 451(7175) 141-146 (2008).
Polo et al., "Cell type of origin influences the molecular and functional properties of mouse induced pluripotent stem cells", Nat Biotechnol 28(8) 848-855 (2010).
Reik et al., "Stability and flexibility of epigenetic gene regulation in mammalian development", Nature 447(7143) 425-432 (2007).
Rossant et al., "Stem cells and early lineage development", Cell 132(4) 527-531 (2008).
Segev et al., "Differentiation of human embryonic stem cells into insulin-producing clusters", Stem Cells 22(3) 265-274 (2004).
Smith et al., "High-throughput bisulfite sequencing in mammalian genomes", Methods 48(3) 226-232 (2009).
Squazzo et al., "Suz12 binds to silenced regions of the genome in a cell-type-specific manner", Genome Res 16(7) 890-900 (2006).
Stadtfeld et al., "Aberrant silencing of imprinted genes on chromosome 12qF1 in mouse induced pluripotent stem cells", Nature 465(7295) 175-181 (2010).
Storey et al., "Statistical significance for genomewide studies", Proc Natl Acad Sci USA 100(16) 9440-9445 (2003).
Subramanian et al., "Gene set enrichment analysis: a knowledge-based approach for interpreting genome-wide expression profiles", Proc Natl Acad Sci USA 102(43) 15545-15550 (2005).
Takahashi Et al., "Induction of pluripotent stem cells from adult human fibroblasts by defined factors", Cell 131(5) 861-872 (2007).
Takahashi et al., "Induction of pluripotent stem cells from mouse embryonic and adult fibroblast cultures by defined factors", Cell 126(4) 663-676 (2006).
Thomson et al., "Embryonic stem cell lines derived from human blastocysts", Science 282(5391) 1145-1147 (1998).
Wichterle et al., "Directed differentiation of embryonic stem cells into motor neurons", Cell 110(3) 385-397 (2002).
Xu et al., "Endoderm and pancreatic islet lineage differentiation from human embryonic stem cells", Cloning Stem Cells 8(2) 96-107 (2006).
Yoon et al., "Enhanced differentiation of human embryonic stem cells into cardiomyocytes by combining hanging drop culture and 5-azacytidine treatment", Differentiation 74(4) 149-159 (2006).
Yu et al., "Induced pluripotent stem cell lines derived from human somatic cells", Science 318(5858) 1917-1920 (2007).
Zhao et al., "iPS cells produce viable mice through tetraploid complementation", Nature 461(7260) 86-90 (2009).
Adewumi et al., "Characterization of human embryonic stem cell lines by the International Stem Cell Initiative", Nat Biotechnol 25(7) 803-816 (2007).
Baumann et al., "Stem cells: holding on to the memories", Nat Rev Mol Cell Biol 11(9) 601 (2010).
Beqqali et al., "Genome-wide transcriptional profiling of human embryonic stem cells differentiating to cardiomyocytes", Stem Cells 24(8) 1956-1967 (2006).
Bird et al., "DNA methylation patterns and epigenetic memory", Genes Dev 16(1) 6-21 (2002).
Bock et al., "Computational epigenetics", Bioinformatics 24(1) 1-10 (2008).
Bock et al., "CpG island methylation in human lymphocytes is highly correlated with DNA sequence, repeats, and predicted DNA structure", PLoS Genet 2(3) e26 (2006).
Bock et al., "EpiGRAPH: user-friendly software for statistical analysis and prediction of (epi)genomic data", Genome Biol 10(2) R14 (2009).
Bock et al., "Quantitative comparison of genome-wide DNA methylation mapping technologies", Nat Biotechnol 28(1) 1106-1114 (2010).
Bock et al., "Reference Maps of human ES and iPS cell variation enable high-throughput characterization of pluripotent cell lines", Cell 144(3) 439-452 (2011).
Boland et al., "Adult mice generated from induced pluripotent stem cells", Nature 461(7260) 91-94 (2009).
Borowiak et al., "Small molecules efficiently direct endodermal differentiation of mouse and human embryonic stem cells", Cell Stem Cell 4(4) 348-358 (2009).
Boulting et al., "A functionally characterized test set of human induced pluripotent stem cells", Nat Biotechnol 29(3) 279-286 (2011).
Chen et al., "Optimal timing of inner cell mass isolation increases the efficiency of human embryonic stem cell derivation and allows generation of sibling cell lines", Cell Stem Cell 4(2) 103-106 (2009).
Chin et al., "Induced pluripotent stem cells and embryonic stem cells are distinguished by gene expression signatures", Cell Stem Cell 5(1) 111-123 (2009).
Colman et al., "Pluripotent stem cells and disease modeling", Cell Stem Cell 5(3) 244-247 (2009).
Cowan et al., "Derivation of embryonic stem-cell lines from human blastocysts", N Engl J Med 350(13) 1353-1356 (2004).
Daley, "Straight talk with . . . George Daley. Interview by Elie Dolgin", Nat Med 16(6) 624 (2010).
Di Giorgio et al., "Human embryonic stem cell-derived motor neurons are sensitive to the toxic effect of glial cells carrying an ALS-causing mutation", Cell Stem Cell 3(6) 637-648 (2008).
Dimos et al., "Induced pluripotent stem cells generated from patients with ALS can be differentiated into motor neurons", Science 321(5893) 1218-1221 (2008).
Doi et al., "Differential methylation of tissue- and cancer-specific CpG island shores distinguishes human induced pluripotent stem cells, embryonic stem cells and fibroblasts", Nat Genet 41(12) 1350-1353 (2009).
Ebert et al., "Induced pluripotent stem cells from a spinal muscular atrophy patient", Nature 457(7227) 277-280 (2009).
Eiges et al., "Developmental study of fragile X syndrome using human embryonic stem cells derived from preimplantation genetically diagnosed embryos", Cell Stem Cell 1(5) 568-577 (2007).
Encode Project Consortium, "Identification and analysis of functional elements in 1% of the human genome by the Encode pilot project", Nature 447(7146) 799-816 (2007).
Flintoft et al., "Evolution: Gene duplicate holds back its sister", Nat Rev Genet 11(9) 593 (2010).
Geiss et al., "Direct multiplexed measurement of gene expression with color-coded probe pairs", Nat Biotechnol 26(3) 317-325 (2008).
Gu et al., "Genome-scale DNA methylation mapping of clinical samples at single-nucleotide resolution", Nat Methods 7(2) 133-136 (2010).

(56) References Cited

OTHER PUBLICATIONS

Hanna et al., "Human embryonic stem cells with biological and epigenetic characteristics similar to those of mouse ESCs", Proc Natl Acad Sci USA 107(20) 9222-9227 (2010).

Hemberger et al., "Epigenetic dynamics of stem cells and cell lineage commitment: digging Waddington's canal", Nat Rev Mol Cell Biol 10(8) 526-537 (2009).

Hu et al., "Neural differentiation of human induced pluripotent stem cells follows developmental principles but with variable potency", Proc Natl Acad Sci USA 107(9) 4335-4340 (2010).

Huang et al., "David Bioinformatics Resources: expanded annotation database and novel algorithms to better extract biology from large gene lists", Nucleic Acids Res 35(Suppl 2) W169-W175 (2007).

Huber et al., "Variance stabilization applied to microarray data calibration and to the quantification of differential expression", Bioinformatics 18(Suppl 1) S96-S104 (2002).

Irizarry et al., "Multiple-laboratory comparison of microarray platforms", Nat Methods 2(5) 345-350 (2005).

Kauffmann et al., "arrayQualityMetrics—a bioconductor package for quality assessment of microarray data", Bioinformatics 25(3) 415-416 (2009).

Keshet et al., "Evidence for an instructive mechanism of de novo methylation in cancer cells", Nat Genet 38(2) 149-153 (2006).

Laird et al., "Cancer epigenetics", Hum Mol Genet 14(Sep No. 1) R65-R76 (2005).

Laird et al., "Principles and challenges of genomewide DNA methylation analysis", Nat Rev Genet 11(3) 191-203 (2010).

Laird et al., "The power and the promise of DNA methylation markers", Nat Rev Cancer 3(4) 253-266 (2003).

Lee et al., "Modelling pathogenesis and treatment of familial dysautonomia using patient-specific iPSCs", Nature 461 (7262) 402-406 (2009).

Lengner et al., "Derivation of pre-X inactivation human embryonic stem cells under physiological oxygen concentrations", Cell 141(5) 872-883 (2010).

Li et al., "Mapping short DNA sequencing reads and calling variants using mapping quality scores", Genome Res 18(11) 1851-1858 (2008).

Lieb et al., "Applying whole-genome studies of epigenetic regulation to study human disease", Cytogenet Genome Res 114(1) 1-15 (2006).

Lister et al., "Human DNA methylomes at base resolution show widespread epigenomic differences", Nature 462 (7271) 315-322 (2009).

Liu et al., "Activation of the imprinted Dlk1-Dio3 region correlates with pluripotency levels of mouse stem cells", J Biol Chem 285(25) 19483-19490 (2010).

Lu et al., "Systems-level dynamic analyses of fate change in murine embryonic stem cells", Nature 462(7271) 358-362 (2009).

Maherali Et al., "Guidelines and techniques for the generation of induced pluripotent stem cells", Cell Stem Cell 3(6) 595-605 (2008).

Meissner et al., "Genome-scale DNA methylation maps of pluripotent and differentiated cells", Nature 454(7205) 766-770 (2008).

Meneghel-Rozzo et al., "In vivo and in vitro development of mouse pancreatic beta-cells in organotypic slices", Cell Tissue Res 316(3) 295-303 (2004).

Mikkelsen et al., "Dissecting direct reprogramming through integrative genomic analysis", Nature 454(7200) 49-55 (2008).

Mikkelsen Et al., "Genome-wide maps of chromatin state in pluripotent and lineage-committed cells", Nature 448 (7153) 553-560 (2007).

Mitalipova et al., "Human embryonic stem cell lines derived from discarded embryos", Stem Cells 21(5) 521-526 (2003).

* cited by examiner

DIFFERENTIATION PROPENSITY:
HIGH ↑
MEDIUM ↗→↘
LOW ↓

| CELL LINE | NEURAL LINEAGE | | HEMATOPOIETIC LINEAGE | | ECTODERM GERM LAYER | | MESODERM GERM LAYER | | ENDODERM GERM LAYER | |
|---|---|---|---|---|---|---|---|---|---|---|
| HUES1 | ↓ | -1.84 | → | -0.30 | ↓ | -1.56 | → | 0.06 | ↘ | -0.59 |
| HUES3 | → | -0.29 | → | -0.01 | → | -0.23 | → | -0.07 | → | 0.08 |
| HUES6 | ↘ | -0.78 | → | -0.26 | ↘ | -0.51 | → | -0.05 | → | -0.47 |
| HUES8 | → | -0.15 | ↗ | 0.69 | → | -0.17 | ↗ | 0.68 | ↗ | 1.45 |
| HUES9 | ↘ | -0.89 | → | 0.31 | ↘ | -0.75 | ↗ | 0.51 | → | 0.37 |
| HUES28 | ↘ | -1.33 | → | -0.11 | ↘ | -0.91 | ↗ | 1.03 | → | -0.07 |
| HUES44 | ↗ | 0.70 | → | -0.27 | ↗ | 0.52 | → | -0.48 | → | -0.45 |
| HUES45 | → | -0.46 | → | -0.26 | → | -0.49 | → | -0.02 | ↗ | 0.65 |
| HUES48 | ↗ | 0.83 | → | 0.18 | ↗ | 0.70 | → | 0.24 | ↗ | 0.55 |
| HUES49 | → | 0.19 | → | 0.07 | → | 0.03 | ↘ | -0.66 | → | -0.26 |
| HUES53 | ↘ | -0.95 | ↗ | 0.65 | ↘ | -1.19 | → | -0.22 | → | -0.20 |
| HUES62 | → | 0.25 | → | -0.15 | → | 0.15 | ↘ | -0.60 | → | 0.24 |
| HUES63 | ↗ | 0.62 | → | 0.39 | ↗ | 0.72 | → | 0.34 | ↗ | 0.61 |
| HUES64 | ↗ | 1.45 | → | -0.07 | ↗ | 1.44 | ↘ | -0.56 | ↘ | -0.61 |
| HUES65 | → | 0.19 | → | 0.02 | → | 0.22 | → | 0.19 | → | -0.15 |
| HUES66 | ↗ | 0.59 | ↘ | -0.67 | → | 0.36 | ↘ | -1.22 | → | -0.37 |
| H1 | ↑ | 1.54 | → | -0.29 | ↗ | 1.21 | → | 0.07 | ↘ | -0.56 |
| H9 | ↗ | 1.08 | → | 0.01 | ↗ | 1.10 | ↗ | 0.55 | → | -0.16 |

*FIG. 1B*
*PRIOR ART*

DIFFERENTIATION PROPENSITY:
HIGH ↑
MEDIUM ↗ → ↘
LOW ↓

| CELL LINE | NEURAL LINEAGE | | HEMATOPOIETIC LINEAGE | | ECTODERM GERM LAYER | | MESODERM GERM LAYER | | ENDODERM GERM LAYER | |
|---|---|---|---|---|---|---|---|---|---|---|
| hiPS 11a | ↘ | -0.69 | → | 0.18 | → | -0.37 | → | -0.23 | ↗ | 0.83 |
| hiPS 11b | ↘ | -1.17 | → | -0.23 | ↘ | -0.96 | ↘ | -1.03 | → | 0.47 |
| hiPS 11c | → | -0.22 | → | 0.40 | → | -0.03 | → | -0.16 | → | 0.37 |
| hiPS 15b | → | -0.48 | ↘ | -0.78 | ↘ | -0.63 | ↘ | -1.11 | ↓ | -2.49 |
| hiPS 17a | → | 0.19 | → | 0.05 | → | 0.33 | → | 0.00 | ↗ | 1.16 |
| hiPS 17b | → | -0.07 | → | -0.48 | → | -0.02 | ↘ | -0.83 | → | 0.20 |
| hiPS 18a | → | 0.28 | ↘ | -0.52 | → | 0.31 | ↘ | -0.67 | → | 0.20 |
| hiPS 18b | ↗ | 0.80 | ↘ | -0.72 | ↗ | 0.84 | ↘ | -0.62 | → | 0.15 |
| hiPS 18c | ↗ | 0.93 | ↘ | -0.65 | ↗ | 1.05 | → | -0.41 | → | 0.10 |
| hiPS 20b | → | -0.37 | → | -0.47 | → | -0.30 | ↘ | -1.16 | ↗ | 0.56 |
| hiPS 27b | ↗ | 0.52 | → | -0.50 | ↗ | 0.68 | ↘ | -0.71 | → | -0.42 |
| hiPS 27e | ↓ | -1.61 | ↘ | -1.04 | ↓ | -2.12 | ↓ | -1.82 | ↓ | -3.27 |
| hiPS 29d | → | -0.25 | → | -0.04 | → | 0.00 | → | -0.11 | ↗ | 0.83 |
| hiPS 29e | ↘ | -0.99 | ↘ | -0.60 | ↘ | -1.15 | ↘ | -1.14 | ↘ | -1.08 |

*FIG. 1D*
*PRIOR ART* t VALUES RELATIVE TO REFERENCE SAMPLE POPULATION 0-1: COMPARABLE EXPRESSION TO THE REFERENCE LEVEL
>1: HIGHER EXPRESSION
<0: LOWER EXPRESSION

| | CONTROL | | PLURI | | ENDO | | MESENDO | | MESO | | ECTO | |
|---|---|---|---|---|---|---|---|---|---|---|---|---|
| | mu | sig | mu | sig | mu | sig | mu | sig | mu | sig | mu | sig |
| BJ FIBROBLAST | -0.16 | 4.49 | -7.53 | 4.88 | 1.04 | 3.10 | -2.13 | 4.46 | 2.74 | 4.81 | 0.96 | 3.25 |
| H9 ESC | -0.06 | 0.64 | -0.32 | 1.83 | 0.97 | 1.06 | 0.39 | 0.75 | -0.10 | 0.85 | 0.20 | 1.02 |
| hNSC | -0.70 | 2.43 | -9.46 | 8.03 | -0.53 | 4.81 | -2.42 | 1.73 | -0.29 | 2.46 | 1.26 | 2.75 | p VALUES RELATIVE TO REFERENCE SAMPLE POPULATION

| | CONTROL | | PLURI | | ENDO | | MESENDO | | MESO | | ECTO | |
|---|---|---|---|---|---|---|---|---|---|---|---|---|
| | MIN | MAX | MIN | MAX | MIN | MAX | MIN | MAX | MIN | MAX | MIN | MAX |
| BJ FIBROBLAST | 0.00 | 0.40 | 0.00 | 0.07 | 0.00 | 0.97 | 0.00 | 0.98 | 0.00 | 0.90 | 0.00 | 0.82 |
| H9 ESC | 0.36 | 0.90 | 0.00 | 0.90 | 0.01 | 0.71 | 0.18 | 0.80 | 0.06 | 1.00 | 0.03 | 0.97 |
| hNSC | 0.00 | 0.50 | 0.00 | 0.43 | 0.00 | 0.75 | 0.00 | 0.74 | 0.00 | 0.93 | 0.00 | 0.86 |

*FIG. 3*

EXPRESSION RELATIVE TO A REFERENCE STANDARD (E.G., REFERENCE LEVEL FOR THE CLASS OF EARLY DEVELOPMENTAL GENE)

| SAMPLES | EXPECTED CATEGORY | CONTROL | MESENDO | PLURI | ENDO | MESO | ECTO |
|---|---|---|---|---|---|---|---|
| H9 ESC-CM/Gtx | PLURI | -0.11 ↑ | 0.39 ↑ | -1.39 ↑ | -0.26 ↑ | 0.71 ↗ | 0.62 ↗ |
| H9 ESC-Day7EB | ENDO, ECTO, MESO | 0.04 ↑ | 0.96 ↗ | -2.89 ↓ | 1.77 ↑ | 4.22 ↑ | 0.87 ↑ |
| H9 ESC-Day14EB | ENDO, ECTO, MESO | -1.43 ↓ | -1.17 ↓ | -7.27 ↓ | 1.98 ↑ | 4.78 ↑ | 1.03 ↑ |
| BS3C iPSC | PLURI | -0.34 ↑ | -0.18 ↑ | -0.54 ↗ | 0.20 ↑ | 0.52 ↗ | 0.25 ↑ |
| BS3C-Day7EB | ENDO, ECTO, MESO | 0.13 ↑ | 0.96 ↗ | -2.23 ↓ | 1.62 ↑ | 3.55 ↑ | 1.98 ↑ |
| BS3C-Day14EB | ENDO, ECTO, MESO | -0.13 ↑ | -0.40 ↓ | -3.59 ↓ | 2.67 ↑ | 5.13 ↑ | 2.20 ↑ |
| H9 ESC Undiff | PLURI | 0.63 ↗ | -0.19 ↑ | -0.86 ↗ | 0.90 ↗ | 1.39 ↑ | 2.20 ↑ |
| H9 ESC-Day7EB | ENDO, ECTO, MESO | 0.24 ↑ | 0.56 ↗ | -3.48 ↓ | 1.75 ↑ | 3.16 ↑ | 2.79 ↑ |
| H9 ESC-Day14EB | ENDO, ECTO, MESO | 0.47 ↑ | -0.42 ↓ | -4.26 ↓ | 3.07 ↑ | 4.57 ↑ | 3.11 ↑ |
| BS3iii iPSC SP/GTX | PLURI | -0.09 ↑ | 0.75 ↗ | -0.75 ↗ | -1.03 ↓ | -0.99 ↗ | -1.58 ↓ |
| BS3iii SP/GTX-Day7EB | ENDO, ECTO, MESO | 0.19 ↑ | -0.39 ↓ | -1.73 ↓ | 0.14 ↑ | 1.37 ↑ | 1.70 ↑ |
| BS3iii SP/GTX-Day14EB | ENDO, ECTO, MESO | 0.26 ↑ | 0.22 ↑ | -3.26 ↓ | 2.03 ↑ | 4.34 ↑ | 2.68 ↑ |
| BS3-iii iPSC E8-VTN | PLURI | -0.68 ↗ | -1.43 ↓ | -0.03 ↑ | -1.40 ↓ | -1.43 ↓ | -0.61 ↗ |
| BS3-iii-E8-VTN-Day7EB | ENDO, ECTO, MESO | -0.32 ↑ | 1.03 ↑ | -1.86 ↓ | 1.16 ↑ | 2.67 ↑ | 2.24 ↑ |
| BS3-iii-E8-VTN-Day14EB | ENDO, ECTO, MESO | 0.11 ↑ | 0.11 ↑ | -3.31 ↓ | 2.79 ↑ | 4.22 ↑ | 2.47 ↑ |
| BFiPSC-4 P6 | PLURI | -0.21 ↑ | -1.00 ↓ | 0.04 ↑ | -0.91 ↓ | -0.92 ↗ | 0.88 ↑ |
| BFiPSC-4 P13 | PLURI | -0.26 ↑ | -1.29 ↓ | -0.25 ↑ | -0.65 ↓ | 0.13 ↑ | 0.83 ↗ |
| BFiPSC-4-Day7EB | ENDO, ECTO, MESO | 0.05 ↑ | 1.07 ↑ | -2.53 ↓ | 1.56 ↑ | 3.93 ↑ | 2.26 ↑ |
| BFiPSC-4-Day14EB | ENDO, ECTO, MESO | -0.09 ↑ | -0.28 ↓ | -5.63 ↓ | 2.46 ↑ | 5.24 ↑ | 2.14 ↑ |

↑ HIGHER
↗ COMPARABLE
↓ LOWER

*FIG. 4*

HIGHER ↑
COMPARABLE ↗ ↘
LOWER ↓

| | | DAY 0 | DAY 2 | DAY 4 | DAY 7 | DAY 9 | DAY 11 | DAY 14 |
|---|---|---|---|---|---|---|---|---|
| | | SUSPENSION EB | | | SEEDED AS MONOLAYER | | | |
| SAMPLES | EXPECTED CATEGORY | CONTROL | | MESENDO | PLURI | ENDO | MESO | ECTO |
| H9-Undiff | PLURI | ↑ 0.09 | | ↓ -0.68 | ↑ -0.04 | ↑ -0.27 | ↑ -0.45 | ↑ 0.19 |
| H9-ESC-P50 | ENDO, ECTO, MESO | ↓ -0.18 | | ↑ 0.21 | ↑ 0.31 | ↑ 0.43 | ↑ -0.12 | ↗ 0.67 |
| EB Day2 | ENDO, ECTO, MESO | ↓ -0.07 | | ↓ -0.26 | ↓ -1.20 | ↗ 0.72 | ↑ 0.38 | ↑ 1.48 |
| EB Day4 | ENDO, ECTO, MESO | ↓ -0.02 | | ↓ -0.35 | ↓ -2.54 | ↑ 1.21 | ↑ 1.67 | ↑ 3.19 |
| EB Day7 | ENDO, ECTO, MESO | ↗ -0.54 | | ↑ 0.04 | ↓ -4.25 | ↑ 1.33 | ↑ 2.42 | ↑ 3.02 |
| EB Day9 | ENDO, ECTO, MESO | ↓ -0.12 | | ↓ -0.59 | ↓ -5.32 | ↑ 2.78 | ↑ 4.55 | ↑ 3.07 |
| EB Day11 | ENDO, ECTO, MESO | ↑ 0.04 | | ↓ -0.23 | ↓ -4.39 | ↑ 2.72 | ↑ 4.30 | ↑ 3.23 |
| EB Day14 | ENDO, ECTO, MESO | ↑ 0.04 | | ↓ -0.23 | ↓ -4.39 | ↑ 2.72 | ↑ 4.30 | ↑ 3.23 |

FIG. 5

DAY 0      DAY 4      DAY 7

SEEDED AS MONOLAYER

SUSPENSION EB    SEEDED AS MONOLAYER

SUSPENSION EB

HIGHER ↑
COMPARABLE ↗
LOWER ↓

| SAMPLES | EXPECTED CATEGORY | CONTROL | MESENDO | PLURI | ENDO | MESO | ECTO |
|---|---|---|---|---|---|---|---|
| H9 ESC | PLURI | -0.06 ↑ | 0.39 ↑ | -0.32 ↑ | 0.97 ↗ | -0.10 ↑ | 0.20 ↑ 100% SSEA4+ |
| H9-D4 EBmonolayer | ENDO, ECTO, MESO | 0.65 ↗ | 0.34 ↑ | -2.70 ↓ | 1.89 ↑ | 2.05 ↑ | 3.54 ↑ 77% SSEA4+ |
| EB-D7 EBmonolayer | ENDO, ECTO, MESO | 1.42 ↑ | -0.51 ↗ | -3.74 ↓ | 2.44 ↑ | 3.24 ↑ | 3.95 ↑ 87% SSEA4+ |
| EB-D4 EBsuspension | ENDO, ECTO, MESO | 0.59 ↗ | 1.16 ↑ | -2.65 ↓ | 3.22 ↑ | 2.85 ↑ | 3.38 ↑ 40% SSEA4+ |
| EB-D7 EBsuspension | ENDO, ECTO, MESO | 0.70 ↑ | 0.76 ↑ | -3.28 ↓ | 3.29 ↑ | 3.73 ↑ | 3.61 ↑ 12% SSEA4+ |
| EB-D7 EBtraditional (4+3) | ENDO, ECTO, MESO | 0.26 ↑ | 0.25 ↑ | -4.32 ↓ | 2.32 ↑ | 3.36 ↑ | 2.41 ↑ 14% SSEA4+ |

FIG. 6

PLURIPOTENT CELLS

HIGHER ↑
COMPARABLE ↗
LOWER ↓

| SAMPLES | EXPECTED CATEGORY | CONTROL | MESENDO | PLURI | ENDO | MESO | ECTO | |
|---|---|---|---|---|---|---|---|---|
| BS4-iPS3 P8 | PLURI | -0.18 ↑ | 0.21 ↑ | 0.31 ↑ | 0.43 ↑ | -0.12 ↑ | 0.67 ↗ | |
| BS4-iPS5 P8 | PLURI | -0.12 ↑ | -0.59 ↗ | -5.32 ↓ | 2.78 ↑ | 4.55 ↑ | 3.07 ↑ | BAD CLONE OR BAD CULTURE? |
| BS4-iPS7 P8 | PLURI | 0.09 ↑ | -0.68 ↗ | -0.04 ↑ | -0.27 ↑ | -0.45 ↑ | 0.19 ↑ | |
| BS4-iPS8 P8 | PLURI | -0.38 ↗ | 1.08 ↑ | 0.52 ↑ | 0.27 ↑ | -0.22 ↑ | -0.10 ↑ | |
| BS4-iPS1 P8 | PLURI | -0.13 ↑ | 0.92 ↑ | 0.30 ↑ | 0.49 ↑ | -0.14 ↑ | 0.10 ↑ | |

LINEAGE-SKEWED CELLS

| SAMPLES | EXPECTED CATEGORY | CONTROL | MESENDO | PLURI | ENDO | MESO | ECTO | |
|---|---|---|---|---|---|---|---|---|
| H9 ESC | PLURI | -0.06 ↑ | 0.39 ↑ | -0.32 ↑ | 0.97 ↗ | -0.10 ↑ | 0.20 ↑ | |
| hNSC | ECTO | -0.70 ↗ | -2.42 ↓ | -9.46 ↓ | -0.53 ↘ | -0.29 ↑ | 1.26 ↑ | |
| hNSCDup | ECTO | -0.18 ↑ | -2.25 ↓ | -6.18 ↓ | -0.01 ↑ | -0.40 ↑ | 2.04 ↑ | |
| hNSC-D5 Diff | ECTO | -0.35 ↑ | -3.33 ↓ | -4.69 ↓ | 0.07 ↑ | -1.54 ↓ | 1.56 ↑ | SKEWED TO ECTODERM |

HIGHER ↑
COMPARABLE →
LOWER ↓

FIG. 7C

NON-PLURIPOTENT CELLS

| SAMPLES | EXPECTED CATEGORY | CONTROL | MESENDO | PLURI | ENDO | MESO | ECTO | |
|---|---|---|---|---|---|---|---|---|
| BJ FIBROBLAST | NON-PLURI | -0.16 ↑ | -2.13 ↓ | -7.53 ↓ | 1.04 ↑ | 2.74 ↑ | 0.96 ↗ | NOT PLURIPOTENT |
| HDFfetal | NON-PLURI | -2.79 ↓ | -2.74 ↓ | -12.73 ↓ | -1.91 ↓ | 0.37 ↑ | -0.30 ↓ | |
| MEF | NON-PLURI | -6.75 ↓ | -7.75 ↓ | -8.12 ↓ | -0.24 ↑ | 3.41 ↑ | 4.14 ↑ | ~10 PRIMERS CROSS REACT WITH MOUSE |
| MEF + H9ESC (500 TO ~3-5 MILLION CELLS - 10-15% MEF CONTAMINATION) | PLURI WITH NON-PLURI CONTAMINATION | -0.16 ↑ | 0.01 ↑ | -0.10 ↑ | 0.62 ↑ | 0.05 ↑ | 0.28 ↑ | MEF PRESENCE HAS MINIMAL IMPACT ON ESC SIGNATURE |

HIGHER ↑
COMPARABLE →
LOWER ↓

SEQUENCE LISTING

<160> NUMBER OF SEQ ID NOS: 96

<210> SEQ ID NO 1
<211> LENGTH: 3075
<212> TYPE: DNA
<213> ORGANISM: Homo sapiens

<400> SEQUENCE: 1

| | | | | | | |
|---|---|---|---|---|---|---|
| agatgcatga | agattcagct | gtgaagatac | tataaaaagg | gaagagaagg | accgagacag | 60 |
| aagcaacaac | ggaactgtca | gtgcggagta | gggctaaact | cagttccatt | gttaagcaag | 120 |
| gaaaaacaaa | caatacattg | aatttgacaa | cccactgaag | ttgcagataa | tgaggactta | 180 |
| ccattatata | ccattattca | tctggaccta | tatgttccat | acagttgaca | ccatcctatt | 240 |
| acaagaaaaa | cctaacagtt | atttatcaag | caaaaagata | gcgggtctga | caaaagatga | 300 |
| cggtaaaatg | ctacgtcgca | ccaagcgtgg | ctggatgtgg | aatcagttct | tcttattgga | 360 |
| agagtacaca | ggtactgaca | cacaatatgt | aggcaagctt | cacactgacc | aagataaagg | 420 |
| agatggaaat | ttaaaataca | tactaacagg | agatggggct | ggcagtctat | ttgttataga | 480 |
| tgaaaataca | ggagacattc | atgctgcaaa | gaaactagac | agagaagaaa | aatctctgta | 540 |
| cattcttcgt | gccaaggcta | tagacagaaa | aactgggcgg | caggtggaac | cggaatcgga | 600 |
| atttatcatt | aaaatacatg | atatcaatga | caatgagcca | aaatttacaa | aagacttata | 660 |
| cactgccagt | gttcctgaaa | tgtctggagt | cggtacatct | gttatacaag | taactgcaac | 720 |
| agatgcagat | gacgccaact | atggaaatag | tgccaaagtg | gtctatagca | tattgcaagg | 780 |
| acagccatat | ttttcagtgg | acccagaatc | aggcataata | aaaactgcat | accagacat | 840 |
| gagcagagaa | aatagagagc | agtaccaggt | tgttatacag | gccaaagaca | tgggtggcca | 900 |
| gatgggaggc | ctttctggaa | ccaccacagt | gaacatcacg | ctgacagatg | tcaacaacaa | 960 |
| ccctcctcga | tttccccaga | gtacgtatca | atttaattct | cctgagtctg | tacctcttgg | 1020 |
| aactcatctt | ggaaggataa | aagccaatga | ccctgacgtg | ggggaaaatg | cagaaatgga | 1080 |
| gtatagcatt | gctgaaggag | atggtgcaga | catgttcgat | gtcatcactg | acaaggatac | 1140 |
| acaggaaggg | attataactg | tcaaacagaa | tttagatttt | gaaaatcaaa | tgctctatac | 1200 |
| tttaagagtg | gatgcaagta | acactcaccc | tgatccacga | ttcttacacc | tgggacctt | 1260 |
| caaagataca | gctgtggtca | aaatatctgt | ggaagatata | gatgagcctc | ctgtgttcac | 1320 |
| taaagtctct | tacttgatag | aagtagatga | agatgtaaag | gagggcagta | tcattggaca | 1380 |
| ggttacagca | tacgatccag | atgccaggaa | caatttaata | aagtactctg | ttgatcggca | 1440 |
| tactgatatg | gaccgtattt | ttggtattca | ctcagaaaat | ggttctattt | tcacttttgaa | 1500 |
| agcccttgac | cgggaatcat | ctccttggca | taacatcact | gttacagcca | cagaaataaa | 1560 |
| taacccaaaa | caaagtagcc | acatccctgt | cttcatcaga | attctagata | taaatgacca | 1620 |
| tgctccggaa | tttgccatgt | attatgaaac | atttgtttgt | gaaaatgcaa | acctgggca | 1680 |
| gttgattcag | actgtcagtg | tcatggataa | ggatgaccct | ccccgaggtc | acaaattctt | 1740 |
| ttttgaacca | gtgccagaat | ttactctcaa | tccgaatttc | accattgtag | ataataaaga | 1800 |
| taatacagca | ggaatcatga | ctcggaaaga | tggctacagt | cgcaacaaaa | tgagcaccta | 1860 |
| cttattgccg | attttaatct | ttgacaacga | ttatccaatt | caaagcagca | ctggtacact | 1920 |
| cactatccgt | gtgtgtgcct | gcgataatca | aggaaacatg | caatcctgca | ccgcagaagc | 1980 |
| cctgatcctt | tcagccggcc | tgagcacggg | agctctcgtt | gcgattctac | tctgtgtcct | 2040 |
| catactgctt | attttagtcg | tgttgtttgc | tgcattgaag | aggcaaagaa | aaaaggaacc | 2100 |

```
tctgataatt tcaaaagacg atgtccggga caacattgtg acctacaacg atgaaggcgg    2160
cggggaagaa gatacccaag cttttgacat tggcacatta aggaatccag aggcaagaga    2220
agacagtaaa cttagacggg atgtaatgcc tgaaactatt tttcagataa ggaggactgt    2280
gcctctgtgg gaaatattg atgtacaaga ttttatccat cgaagattaa agaaaacga     2340 cgcagaccca agtgcacctc catatgattc gctggcaacg tatgcctatg aagggaatga    2400
ttccatagca gattcgctca gttctttgga atctctcaca gctgattgta accaagatta    2460
tgattacctc agtgactggg ggcctcgttt caaaaaactt gccgatatgt atggggtga     2520 tgatagtgac cgagactaag aggattgttt gacttaatca atattagtgg aagtactgtc    2580
tatgttatta gattgagtgg cctgcattct cttcctggga ggaaatcttt caaaaattga    2640
agttacaaac aatacgtaga tgttgtcaag tagggatttg cttaatcagt aagtctttgt    2700
gaatgaatac gaatgataca gattttaaa aaagtaataa ccagttcacc ctctttgcct     2760
aacaatctcg gaaggaaaat atatcacatc aataatcaat aaaataagt aaaaggcttt     2820 ttgtgccttt tcttaggtat aataatttat aaatgttttc ttaactgact ttcagtcacc    2880
tttacaatta aactaaatat tgtgcaaccg ctttgtaaat taatatgaag aagatatatc    2940
cctaatgaaa taggaatgac tattactgcc atatttattt agttgaagaa tgtctttgtg    3000
ttaattcatt catattttta taaatgtata tttatatttt tgtattttta tgaaataaac    3060
tagtatttat aaaac                                                     3075
```

<210> SEQ ID NO 2
<211> LENGTH: 5087
<212> TYPE: DNA
<213> ORGANISM: Homo sapiens

<400> SEQUENCE: 2

```
aacgggcgcc gcggcgggga gaagacgcag agcgctgctg ggctgccggg tctcccgctt      60
ccccctcctg ctccaagggc ctcctgcatg agggcgcggt agagacccgg acccgcgccg     120
tgctcctgcc gtttcgctgc gctccgcccg ggcccggctc agccaggccc cgcggtgagc     180
catgattcgc ctcgggctc cccagacgct ggtgctgctg acgctgctcg tcgccgctgt      240
ccttcggtgt cagggccagg atgtccagga ggctggcagc tgtgtgcagg atgggcagag     300
gtataatgat aaggatgtgt ggaagccgga gccctgccgg atctgtgtct gtgacactgg    360
gactgtcctc tgcgacgaca atctgtga agacgtgaaa gactgcctca gccctgagat     420
ccccttcgga gagtgctgcc ccatctgccc aactgacctc gccactgcca gtgggcaacc    480
aggaccaaag ggacagaaag gagaacctgg agacatcaag gatattgtag acccaaagg     540 acctcctggg cctcagggac ctgcagggga acaaggaccc agaggggatc gtggtgacaa    600
aggtgaaaaa ggtgcccctg gacctcgtgg cagagatgga gaacctggga ccctggaaa     660 tcctggcccc cctggtcctc ccggcccccc tggtcccct ggtcttggtg aaactttgc      720 tgcccagatg gctggaggat tgatgaaaa ggctggtggc gcccagttgg gagtaatgca     780
aggaccaatg ggccccatgg gacctcgagg acctccaggc cctgcaggtg ctcctgggcc    840
tcaaggattt caaggcaatc ctggtgaacc tggtgaacct ggtgtctctg gtcccatggg    900
tccccgtggt cctcctggtc cccctggaaa gcctggtgat gatggtgaag ctggaaaacc    960
tggaaaagct ggtgaaaggg gtccgcctgg tcctcagggt gctcgtggtt tcccaggaac   1020
cccaggcctt cctggtgtca aggtcacag aggttatcca ggcctggacg gtgctaaggg    1080
```

-continued

| | |
|---|---|
| agaggcgggt gctcctggtg tgaagggtga gagtggttcc ccgggtgaga acggatctcc | 1140 |
| gggcccaatg ggtcctcgtg gcctgcctgg tgaaagagga cggactggcc ctgctggcgc | 1200 |
| tgcgggtgcc cgaggcaacg atggtcagcc aggccccgca gggcctccgg gtcctgtcgg | 1260 |
| tcctgctggt ggtcctggct tccctggtgc tcctggagcc aagggtgaag ccggccccac | 1320 |
| tggtgcccgt ggtcctgaag gtgctcaagg tcctcgcggt gaacctggta ctcctgggtc | 1380 |
| ccctgggcct gctggtgcct ccggtaaccc tggaacagat ggaattcctg agccaaagg | 1440 |
| atctgctggt gctcctggca ttgctggtgc tcctggcttc cctgggccac ggggccctcc | 1500 |
| tggcccctcaa ggtgcaactg gtcctctggg cccgaaaggt cagacgggtg aacctggtat | 1560 |
| tgctggcttc aaaggtgaac aaggccccaa gggagaacct ggccctgctg gccccaggg | 1620 |
| agccctggga cccgctggtg aagaaggcaa gagaggtgcc cgtggagagc ctggtggcgt | 1680 |
| tgggcccatc ggtccccctg gagaaagagg tgctcccggc aaccgcggtt tcccaggtca | 1740 |
| agatggtctg gcaggtccca agggagcccc tggagagcga gggcccagtg gtcttgctgg | 1800 |
| ccccaaggga gccaacggtg accctggccg tcctggagaa cctggccttc ctggagcccg | 1860 |
| gggtctcact ggccgccctg gtgatgctgg tcctcaaggc aaagttggcc cttctggagc | 1920 |
| ccctggtgaa gatggtcgtc ctggacctcc aggtcctcag ggggctcgtg ggcagcctgg | 1980 |
| tgtcatgggt ttccctggcc ccaaaggtgc caacggtgag cctggcaaag ctggtgagaa | 2040 |
| gggactgcct ggtgctcctg gtctgagggg tcttcctggc aaagatggtg agacaggtgc | 2100 |
| tgcaggaccc cctggcccct ctggacctgc tggtgaacga ggcgagcagg gtgctcctgg | 2160 |
| gccatctggg ttccagggac ttcctggccc tcctggtccc caggtgaag gtggaaaacc | 2220 |
| aggtgaccag ggtgttcccg gtgaagctgg agccctggc ctcgtgggtc caggggtga | 2280 |
| acgaggtttc ccaggtgaac gtggctctcc cggtgcccag ggcctccagg gtccccgtgg | 2340 |
| cctccccggc actcctggca ctgatggtcc caaaggtgca tctggcccag caggccccc | 2400 |
| tggggctcag ggccctccag gtcttcaggg aatgcctggc gagaggggag cagctggtat | 2460 |
| cgctggccc aaaggcgaca ggggtgacgt tggtgagaaa ggccctgagg gagcccctgg | 2520 |
| aaaggatggt ggacgaggcc tgacaggtcc cattggcccc cctggcccag ctggtgctaa | 2580 |
| tggcgagaag ggagaagttg gacctcctgg tcctgcagga agtgctggtg ctcgtggcgc | 2640 |
| tccgggtgaa cgtggagaga ctgggccccc cggaccagcg ggatttgctg gcctcctgg | 2700 |
| tgctgatggc cagcctgggg ccaagggtga gcaaggagag gccggccaga aaggcgatgc | 2760 |
| tggtgccct ggtcctcagg gccctctgg agcacctggg cctcagggtc ctactggagt | 2820 |
| gactggtcct aaaggagccc gaggtgccca aggccccccg ggagccactg gattccctgg | 2880 |
| agctgctggc cgcgttggac ccccaggctc caatggcaac cctggacccc ctggtccccc | 2940 |
| tggtccttct ggaaaagatg gtcccaaagg tgctcgagga acagcggcc cccctggccg | 3000 |
| agctggtgaa cccggcctcc aaggtcctgc tggacccct ggcgagaagg gagagcctgg | 3060 |
| agatgacggt ccctctggtg ccgaaggtcc accaggtccc caggctctgg ctggtcagag | 3120 |
| aggcatcgtc ggtctgcctg ggcaacgtgg tgagagagga ttccctggct gcctggccc | 3180 |
| gtcgggtgag cccggcaagc aggtgctcc tggagcatct ggagacagag gtcctcctgg | 3240 |
| ccccgtgggt cctcctggcc tgacgggtcc tgcaggtgaa cctggacgag agggaagccc | 3300 |
| cggtgctgat ggcccccctg gcagagatgg cgctgctgga gtcaagggtg atcgtggtga | 3360 |
| gactggtgct gtgggagctc ctggagcccc tgggcccct ggctcccctg gccccgctgg | 3420 |
| tccaactggc aagcaaggag acagaggaga agctggtgca caaggcccca tgggaccctc | 3480 |

| | |
|---|---|
| aggaccagct ggagcccggg gaatccaggg tcctcaaggc cccagaggtg acaaaggaga | 3540 |
| ggctggagag cctggcgaga gaggcctgaa gggacaccgt ggcttcactg gtctgcaggg | 3600 |
| tctgcccggc cctcctggtc cttctggaga ccaaggtgct tctggtcctg ctggtccttc | 3660 |
| tggccctaga ggtcctcctg gccccgtcgg tccctctggc aaagatggtg ctaatggaat | 3720 |
| ccctggcccc attgggcctc ctggtccccg tggacgatca ggcgaaaccg gccctgctgg | 3780 |
| tcctcctgga aatcctggac cccctggtcc tccaggtccc cctggccctg gcatcgacat | 3840 |
| gtccgccttt gctggcttag gcccgagaga aagggcccc gacccctgc agtacatgcg | 3900 |
| ggccgaccag gcagccggtg gcctgagaca gcatgacgcc gaggtggatg ccacactcaa | 3960 |
| gtccctcaac aaccagattg agagcatccg cagccccgag ggctcccgca agaaccctgc | 4020 |
| tcgcacctgc agagacctga aactctgcca ccctgagtgg aagagtggag actactggat | 4080 |
| tgaccccaac caaggctgca ccttggacgc catgaaggtt ttctgcaaca tggagactgg | 4140 |
| cgagacttgc gtctacccca atccagcaaa cgttcccaag aagaactggt ggagcagcaa | 4200 |
| gagcaaggag aagaaacaca tctggtttgg agaaaccatc aatggtggct ccatttcag | 4260 |
| ctatggagat gacaatctgg ctcccaacac tgccaacgtc cagatgacct tcctacgcct | 4320 |
| gctgtccacg gaaggctccc agaacatcac ctaccactgc aagaacagca ttgcctatct | 4380 |
| ggacgaagca gctggcaacc tcaagaaggc cctgctcatc cagggctcca atgacgtgga | 4440 |
| gatccgggca gagggcaata gcaggttcac gtacactgcc ctgaaggatg gctgcacgaa | 4500 |
| acataccggt aagtgggca agactgttat cgagtaccgg tcacagaaga cctcacgcct | 4560 |
| ccccatcatt gacattgcac ccatggacat aggagggccc gagcaggaat cggtgtgga | 4620 |
| catagggccg gtctgcttct tgtaaaaacc tgaacccaga acaacacaa tccgttgcaa | 4680 |
| acccaaagga cccaagtact ttccaatctc agtcactcta ggactctgca ctgaatggct | 4740 |
| gacctgacct gatgtccatt catcccaccc tctcacagtt cggacttttc tcccctctct | 4800 |
| ttctaagaga cctgaactgg gcagactgca aaataaaatc tcggtgttct atttatttat | 4860 |
| tgtcttcctg taagacccttc gggtcaaggc agaggcagga aactaactgg tgtgagtcaa | 4920 |
| atgcccctg agtgactgcc cccagcccag gccagaagac ctcccttcag gtgccgggcg | 4980 |
| caggaactgt gtgtgtccta cacaatggtg ctattctgtg tcaaacacct ctgtattttt | 5040 |
| taaaacatca attgatatta aaaatgaaaa gattattgga aagtaca | 5087 |

```
<210> SEQ ID NO 3
<211> LENGTH: 2896
<212> TYPE: DNA
<213> ORGANISM: Homo sapiens

<400> SEQUENCE: 3
```

| | |
|---|---|
| taggcggatg ccgccatgca gcactacggg gtgaacggct actcactgca cgccatgaac | 60 |
| tcactcagcg ccatgtacaa cctgcaccag caggcagccc agcaggccca gcatgccccc | 120 |
| gactaccggc cttcagtgca tgcgcttaca ttggctgagc gcctggctgg ctgtacattt | 180 |
| caagacatca tcttggaggc ccgttatggt tcccagcacc gcaaacaacg tcgcagccgc | 240 |
| acagcgttca cggctcagca gctcgaggcc ctggaaaaga ccttccagaa gactcactac | 300 |
| ccagatgtgg tgatgcgtga gggctggcc atgtgcacca acctgcctga ggcccgggtg | 360 |
| caggtgtggt tcaagaaccg ccgggccaag ttccggaaga agcagcgtag cctgcagaag | 420 |
| gaacagctcc agaagcagaa ggaggctgag ggctcccatg gggaaggcaa ggccgaggcc | 480 |

```
cccactccag ataccoagct ggacactgag cagcccccac gtctgcctgg cagcgacccc      540
cctgctgagc ttcacctgag tctgtctgag cagtcagcca gtgagtcagc ccccgaggat      600
cagccggacc gtgaggagga ccccagggca ggggctgagg accccaaagc tgagaagagc      660
cctggggctg acagcaaggg gctgggctgc aagaggggca gccccaaggc agattcccca      720
ggcagcctga ccatcactcc tgtggcccca ggggtggcc tcctgggccc ctcccactcc       780
tattcctcgt ccccgctgag cctcttccgt ctgcaggagc aattccgcca gcacatggcg      840
gccaccaaca acctggtgca ctactcgtcc ttcgaagtag ggggtccggc ccctgctgct      900
gcagcggcgg ctgctgctgt gccctacctg ggcgtcaaca tggccccgct gggctcactg      960
cactgccagt cctactacca gtccctgtca gcagccgctg ctgcccacca gggtgtgtgg     1020
gggtctcctc tgctgcctgc acccccagca ggcctggctc ctgcatcagc taccctgaac     1080
agtaaaacca caagcatcga gaacctgcgg ctccgggcca agcagcacgc ggcctccctg     1140
ggactcgata cgctgcccaa ctgactgtct ggcttccaac ccagccaggg gtcttaggtg     1200
tcccctccta gccctgtggt tatccctagg tggctctcga ggagttaact ccatgagccc     1260
agggatccta gggcctgggg tcctgttccc tgctccgctt ccccataccc cagcccgagg     1320
tgaagcccac acctacacac cctctgcatg gccctgcctg gacccatgg aggccgaata      1380
gggaggaggt gagaggctgg ggtgccccaa gcttccctcg gagaagtgag aggctctccc     1440
tggctagatc ctcatctcaa tagcacctcc tcccttttct ccctatcctt ctgccccta     1500
gtaagtctac gtgtggaatg tgagatataa atataaatat ataaagctat attttcaggc    1560
tcctgcctgc cccaggcccc ctgccccact cccatctctt cttccctgcc accctccct    1620
gcagcctccg cggctcactc cagccatccc ttctgtttct ccttctctct ccttccttct    1680
tcccttgatc tccctcttcc tgtctctgtc ctggtccctg ccccgtctc ggcccagcct     1740
ctgtattctc caccttgat ctttctcctt gtctctcccg ctgcccctgg tttcttcctt     1800
tggtgttggc tgtgttggta tcatcagttc ttgagctata ttttgtttgg ggttgtggct    1860
ggttttggtt ttagtaattt tgcgacttcc cgttgctctc cttctattcc cttccttctg   1920
ccctgcctgc ctcctgcac ctgcggcctc tctaggaagc tgttcctttc tatgcccaat     1980
agaagcaaca aggccctagc tggagactct ggggatctgg agctgcaggc aggaggtggc    2040
actggctccc actcccaccc ctgcccaggc tggcatctag aaggcgtcat gaattacttt    2100
ctcttctctc ttctcaattt tgaggtcctc attcccaaga ttgaggaggc agtagttaat    2160
ctgggaaggc agtagaatgg ccagcattcc tgcctgtaag tcttcccaag acagaggccc    2220
ggtgacacag ttcagccagg actgaccaca gggctctaga gctctctttg gtgagacttc    2280
cctggatgga gagcagcagc aggggaagag gtgctctcag agacagcagg gctggtgctc    2340
ttctcccaca agctgagcct ccacgttcag cagatactgt ccaaggcagg ggtacggctg    2400
accaggaatg aaggttgaac tctgctcctg agcacggtgc gtgcaaagca tatagcagca    2460
cataggctca ggcttctgta ggcttcctgt cccagagcca attatggaag taagggcttc    2520
cctccagcta gtcactggaa tggaaaagtg tgttcctgtt catagccagg aaacccagct    2580
cagcaaactc cctttcaaag ctgtgtgacc ggctgggcat ggtggctcac acctgtaatc    2640
ccagcacttt gggaggccaa ggcaggcaat cacctgaggt caggagttca agaccagcct    2700
ggctaacatg tgaaactaat aataatacaa aaattagctg ggcgtggtgg cacatgcctg    2760
taatcccagc tacttgggag gctgagttgg gaggattgct gcaatctggg aggtggaagt    2820
tgcagtgagc cgagatcatg ccactgcact ccagcctggg cgacggagtg agactccatc    2880
```

```
tcaaaaaaaa aaaaaa                                                     2896
```

<210> SEQ ID NO 4
<211> LENGTH: 1378
<212> TYPE: DNA
<213> ORGANISM: Homo sapiens

<400> SEQUENCE: 4

```
atggggaacc gcagcaccgc ggacgcggac gggctgctgg ctgggcgcgg gccggccgcg     60
ggggcatctg cggggggcatc tgcggggctg gctgggcagg gcgcggcggc gctggtgggg   120
ggcgtgctgc tcatcggcgc ggtgctcgcg gggaactcgc tcgtgtgcgt gagcgtggcc   180
accgagcgcg ccctgcagac gcccaccaac tccttcatcg tgagcctggc ggccgccgac   240
ctcctcctcg ctctcctggt gctgccgctc ttcgtctact ccgaggtcca gggtggcgcg   300
tggctgctga gccccgcct gtgcgacgcc ctcatggcca tggacgtcat gctgtgcacc   360
gcctccatct tcaacctgtg cgccatcagc gtggacaggt tcgtggccgt ggccgtgccg   420
ctgcgctaca accggcaggg tgggagccgc cggcagctgc tgctcatcgg cgccacgtgg   480
ctgctgtccg cggcggtggc ggcgcccgta ctgtgcggcc tcaacgacgt gcgcggccgc   540
gaccccgccg tgtgccgcct ggaggaccgc gactacgtgg tctactcgtc cgtgtgctcc   600
ttcttcctac cctgcccgct catgctgctg ctctactggg ccacgttccg cggcctgcag   660
cgctgggagg tggcacgtcg cgccaagctg cacggccgcg cgccccgccg acccagcggc   720
cctggcccgc cttcccccac gccaccgcg ccccgcctcc ccaggaccc ctgcggcccc     780
gactgtgcgc ccccgcgcc cggccttccc cggggtccct gcggccccga ctgtgcgccc   840
gccgcgccca gcctccccca ggaccccctgc ggccccgact gtgcgccccc cgcgccggc   900
ctccccccgg accctgcgg ctccaactgt gctccccccg acgccgtcag agccgccgcg   960
ctcccacccc agactccacc gcagaccgc aggaggcgc gtgccaagat caccggccgg  1020
gagcgcaagg ccatgaggt cctgccggtg gtggtcgggg ccttcctgct gtgctggacg  1080
cccttcttcg tggtgcacat cacgcaggcg ctgtgtccctg cctgctccgt gcccccgcgg  1140
ctggtcagcg ccgtcacctg gctgggctac gtcaacagcg ccctcaaccc cgtcatctac  1200
actgtcttca acgccgagtt ccgcaacgtc ttccgcaagg ccctgcgtgc ctgctgctga  1260
gccgggcacc cccggacgcc ccccggcctg atggccaggc tcagggacc aaggagatgg  1320
ggagggcgct tttgtacgtt aattaaacaa attccttccc aaaaaaaaaa aaaaaaa     1378
```

<210> SEQ ID NO 5
<211> LENGTH: 2962
<212> TYPE: DNA
<213> ORGANISM: Homo sapiens

<400> SEQUENCE: 5

```
agctcacaga cccataatcc tgcatttctc taacaagttg tttatggagt tgcttctcca     60
tttgcctaca tcccaaaatt caccctccc gggtttcttc tgcccctcc tgagtcccgg   120
cctgaaggag ggggagggac gcgggtgcgg gcgcggggtgg gggagggcgg acccgacgca   180
cagggccagc gccgaggcgc cccctctccg ccagcggttg acgccccccgg attatttatc   240
cgcaaagtcc cgcgcgcgcc cattgggccg aggcccgagt gtcagcgcga gtcccggctc   300
gccattggct ccgcacacgt gcgggcctga ctcacgtgct tccggtttga aggcaaaaag   360
tgtgcctggg tgatttttttt tttaagcgag agagtttgtg caaagatccg agctgtcaga   420
```

```
gatttgaaaa aaaaaaaaaa aaaaaaaaaa aaaaaaacag cccggcgctg gcggagacgc    480
gctctccctg caaaaaaagc aaaggcgatt aaaggcgctg ccagcctcac gctctgggca    540
cagctgagcg tgacactcgg ggaagtcaaa cccctcacta ctgcctagga agatggctag    600
actttaaata ctattttttt ccctttaaga aaaaaattat tggagctttt tttcttgctt    660
tcttttttcct tttctttttc ttttttttcct tcatttttttt ggccgtggct tactccccat    720
ttaaatcaaa tcattgaatc tggttgcaga agaaaaaag aaatagccaa gtgtctccat    780
atctggatgt ctacaaatta gagagggaga gacagcgaga tctatctgct agataagaac    840
gagcgatcca ggccagacgc ctgagctttt ttcctgcacc cgccccgtgc cttcgctgag    900
gcttcgcctg cctccttcct ccgcgcaccc ccacgggccg ctggcaaagt ggggtgggga    960
gcgaggcggt ggggcgggg gccggcgcgg cggccggggc ggcggggcgg ccgagcatgg   1020
aagaacagca gccggaacct aaaagtcagc gcgactcggc cctcggcgcg gcggcggcgg   1080
cgactccggg cggcctcagc ctgagcctca gtccgggcgc cagcggcagc agcggcagcg   1140
gcagcgatgg agacagcgtg ccggtgtccc cgcagcctgc gccccctcg ccgcccgcgg   1200
cgccttgcct ccgcccctg cccaccacc cgcacctccc cccacacccc ccgccccgc   1260
cgcctcagca tctcgcggcg cctgctcacc agccgcagcc agcggcccag ctgcaccgca   1320
ccaccaactt tttcatcgac aacatcctga ggccggactt cggctgcaaa aaggagcagc   1380
cgccaccgca gcttctggtg gctgcggcgg ccagaggagg cgcaggagga ggaggccggg   1440
tcgagcgtga cagaggccag actgccgcag gtagagaccc tgtccacccg ttgggcaccc   1500
gggcgccagg cgctgcctcg ctcctgtgcg ccccggacgc gaactgtggc ccacccgacg   1560
gctcccagcc agccgccgcc ggcgcgggcg cgtctaaagc tgggaacccg gctgcggcgg   1620
cggcggcggc cgcggcggca gtggcggcgg cggcggcggc cgcagcagcc aagccctcgg   1680
acaccggtgg cggcggcagt ggaggcggcg cggggagccc cggagcgcag ggcaccaaat   1740
acccggagca cggcaacccg gctatcctac ttatgggctc agccaacggc gggcccgtgg   1800
tcaaaactga ctcgcagcag cctctcgtat ggcccgcctg ggtgtactgc acacgttatt   1860
cggatcgtcc atcctccggt ccgcgcacca ggaagctgaa gaagaagaag aacgagaagg   1920
aggacaagcg gccgcggacc gcgttcacgg ccgagcagct gcagagactc aaggcggagt   1980
tccaggcaaa ccgctacatc acggagcagc ggcggcagac cctggcccag gaactcagcc   2040
tcaacgagtc ccagatcaag atctggttcc agaacaagcg cgccaagatc aagaaagcca   2100
caggcatcaa gaacggcctg gcgctgcacc tcatggccca gggactgtac aaccactcca   2160
ccaccacggt ccaggacaaa gacgagagcg agtagccgcc acaggccggg ccgcgcccg   2220
cgccccctcc cggcaccgcc gccgtcgtct cccggcccct cgctggggga aaagcatct   2280
gctccaagga gggagggagc gcagggaaaa gagcgagaga gacagaaaga gagcctcaga   2340
atggacaatg acgttgaaac gcagcatttt tgaaaaggga gaaagactcg gacaggtgct   2400
atcgaaaaat aagatccatt ctctattccc agtataaggg acgaaactgc gaactcctta   2460
aagctctatc tagccaaacc gcttacgacc ttgtatatat ttaatttcag gtaaggaaaa   2520
cacatacgtg tagcgatctc tatttgctgg acatttttat taatctcctt tattattatt   2580
gttataatta ttataattat tataattatt ttatcccctc ccccaccgcc tcgctgcccc   2640
cgcccagttt cgttttcgtt gccttttca tttgaatgtc attgcttctc cggtgcctcc   2700
cgacccgcat cgccggccct ggtttctctg ggactttct ttgtgtgcga gagtgtgttt   2760
cctttcgtgt ctgcccacct cttctccccc acctcccggg tcccttctgt cggtctgtct   2820
```

```
gttctgcccc cctttcgttt tccggagact tgttgagaaa tacgacccca cagactgcga      2880
gactgaaccg ccgctacaag ccaaagattt tattatgttc agaaacctgt agtctgaaat      2940
aaagtgtaca ctgtgctcac ga                                               2962

<210> SEQ ID NO 6
<211> LENGTH: 2657
<212> TYPE: DNA
<213> ORGANISM: Homo sapiens

<400> SEQUENCE: 6 tggcttttc cacttggtgt ggtggtttgg ggattcattc attcctattt cagcattcca        60
ctgtatagtc cagaggtgag caaggcaagg ctggtgggtg gctctgttat ccatctcctg      120
tgtccaagcg actgctccag ttgtcaccat gtttccagtc accaggtgag agagactctg      180
gctgcagaga cagggctgag tgtccgtgtc gtccaggtgt ggttccaaaa ccagagagcg      240
aagatgaaga agctggccag gcgacagcag cagcagcagc aagatcagca gaacacccag      300
aggctgagct ctgctcagac aaacggtggt gggagtgctg ggatggaagg aatcatgaac      360
ccctacacgg ctctgcccac cccacagcag ctcctggcca tcgagcagag tgtctacagc      420
tcagatccct tccgacaggg tctcaccccca ccccagatgc ctggagacca catgcaccct      480
tatggtgccg agccctttt ccatgacctg gatagcgacg acacctccct cagtaacctg      540
ggtgactgtt tcctagcaac ctcagaagct gggcctctgc agtccagagt gggaaacccc      600
attgaccatc tgtactccat gcagaattct tacttcacat cttgagtctt ccctagagt       660 tctgtgacta ggctcccata tggaacaacc atattctttg aggggtcact ggctttagga      720
cagggaggcc agggaagagg tgggttgggg agggagtttt gttggggatg ctgttgtata      780
atgatatggt gtagctcagc atttccaaag actgaataca ttatggattg catagtttaa      840
tgtttctaat aagagtctta gcattagata tgaagacgtg tttatcatta aggacagaga      900
cttttaatat agacattctc atgcaaacta gatacttagg gactcctaac aacttcccac      960
catgtcgggg aagctcttgt caagaggtgc atatgtctat ccatctacac accaatagac     1020
agaaggacag atagatagat gtgtgtgtgt gagtgtgtaa cctttcgtat tttaccctca     1080
aagtttattc ctaattataa cagacaccaa ctgtacagca aaagtaactt tattttcagt     1140
gtgaactata tttaaggaaa tgcttgatgc acttaagtta taaaatgaga taatttactt     1200
ttataaactt tattttagc ttgacaagac ttgtcagcag ggcagagagg ctgctccac       1260 ctagccccat agctttgagt gctggggttc attctgtttt cagagtgtct ttcagatctg     1320
gaaagaaatt ctgtgtggct gatggtgttc tcttcttgcat tcttgctctc tttggggttg    1380
aatcactggg caggggtggg acagaataat ctctgatcat gttctgagaa aatgtaaagc     1440
ccagactcct gggctttctt ttaaattctg acaagtggtt gttgggcagt gctaggatga     1500
ttggttcagc tcttgagctt cagcatctgc aaatgtggat gaggctaata gtatgtacct     1560
acctcactgg gaaacaccaa ggcttaattc attcccagga cacatgagca gggctgagac     1620
taatatctga tatttgttta agatacaacc aggccactca cttggcaaag gagggtacat     1680
agggttgcag agcaggaggg ctcctgaact ccagagggca gttctgcctg ctgaagtccc     1740
tctgcaaagc ctgtgctgaa ggagacacca gctcagagca gttcagaggg atcccagagt     1800
cccagagtgg ggaggaggtg aaggctgagg ggatagagga gggcctggtg gtgttctaga    1860
gcagggttgg gcaaactcct gcttgcgggc ctgctttcta tggcttgcca gcaaagaatg     1920
```

-continued

```
gtttttactt tttttttgag gtcattaaaa aaaaggagaa gaagaatata taacaggctg    1980
tctgtggcct ggaaagcctg aaatatttgc tatctgtatt gtctggccct tacagaaaaa    2040
gtttggggcc ccttgtttta gagggtctgt ttctaaagaa cctcatggcg ctcatagagg    2100
cagaaggttc cagtggaaac ccttggctct tccttccaac tcactcctct gatcctcggc    2160
acagaagacc cagcagccat tgtacatggg gacagttcca caccctggtc tccagttgcg    2220
gtgctaggat ggtattgttc tgtgctagga agtctcctgg gaacccagaa tgagttggtg    2280
gggaagacag cgggtcactg tggacccatc caggagggggc caggataggc ttggcctcat   2340
ttctggggac atcattggag acttgaacac agagacacgt ccctatcact ctggcaaggc    2400
cagagggaac atgtcccctt atggtagagt ctatgttgtg tgattttttgt gctcttgttt   2460 ataatttatg caaccacca agaaacccaa accagtctga tgagtgaaaa ttatgcagat    2520
gctgtatggc cccacaggtt tctgtggtaa agaccagttg gagaatgtag agatactat    2580 gtgagtgaaa atgaatagag atccttattc cactccttaa tggcatacca agatgaaatt    2640
aaaatctctt acaaatg                                                   2657
```

<210> SEQ ID NO 7
<211> LENGTH: 9538
<212> TYPE: DNA
<213> ORGANISM: Homo sapiens

<400> SEQUENCE: 7

```
gggataatgc tcccggagaa ggattctgca gcagttctca aaggctagac ttgagtggta      60
ttgctgcata tgcgctgatt cttcagcttg tctctaaccg aggaagcatt gattgggagc     120
tactcattca gaaaattaaa agaaagaagc cagaaaatat tatcaaccct ttgagaacac     180
gacacaacga actttatatt ttaccacttc cttgaatagt tgcaggagaa ataacaaggc     240
attgaagaat ggcagatgaa cggaaagatg aagcaaaggc acctcactgg acctcagcac     300
cgctaacaga ggcatctgca cactcacatc caccctgagat taaggatcaa gcggagcag     360 gggaaggact tgtccgaagc gccaatggat tcccatacag ggaggatgaa gagggtgcct     420
ttggagagca tgggtcacag ggcacctatt caaataccaa agagaatggg atcaacggag     480
agctgacctc agctgacaga gaaacagcag aggaggtgtc tgcaaggata gttcaagtag     540
tcactgctga ggctgtagca gtcctgaaag gtgaacaaga gaaagaagct caacataaag     600
accagactgc agctctgcct ttagcagctg aagaaacagc taatctgcct ccttctccac     660
ccccatcacc tgcctcagaa cagactgtca cagtggagga agatttactt acagcctcga     720
agatggagtt ccacgatcaa caggaattga ctccctctac agctgagcct tcagaccaga     780
aggaaaagga gtcagagaag caaagtaagc ctggtgaaga ccttaaacat gctgccttag     840
tttctcagcc agagacaact aaaacttacc ctgataaaaa ggacatgcaa ggcacggaag     900
aagaaaaagc accctagct tgtttgggc acactcttgt tgccagcctg gaagacatga       960
aacagaagac agaaccaagc cttgtagtac ctggcattga cctccctaaa gagcctccaa    1020
ctccaaaaga acaaaaggac tggttcatcg aaatgccaac ggaagcaaaa aaggatgagt    1080 gggtttagt tgcccccata tctcctggcc ctctgactcc catgagggaa aaagatgtat    1140
ttgatgatat cccaaaatgg gaagggaaac agtttgattc tccatgcca agtcccttc     1200 aaggggaag cttcactctt cctttagatg tcatgaagaa tgaaatagtt acagaaacat    1260 cgcccttgc cctgccttt ttacagccag atgacaaaaa atctctgcaa caaaccagtg     1320
gcccagctac tgccaaagat agttttaaaa ttgaagagcc ccatgaggct aaacctgaca    1380
```

```
aaatggcaga agcaccaccc tcagaggcaa tgaccttacc caaagatgct cacattccag    1440
ttgtagaaga acatgttatg gggaaagttt tagaggaaga aaaggaggcc ataaatcaag    1500
agactgtgca gcaaagggat actttcaccc ccagtggaca ggaacctata cttactgaaa    1560
aggaaactga gctgaagctt gaagaaaaaa ccaccatttc tgacaaagaa gctgtgccaa    1620
aagagagtaa acccccaaaa cctgcagatg aagaaatagg cataattcag acctccacag    1680
agcacacttt ctcagaacag aaagaccaag agcctaccac agatatgttg aaacaggact    1740
cgttccctgt aagtttggag caagcagtta cagattcagc catgacctct aaaacactgg    1800
agaaagccat gaccgaacca tctgcattaa ttgaaaagag ctcaattcag gaacttttg     1860 aaatgagagt tgatgacaaa gataagattg aaggagttgg agctgcaaca tcagctgagc    1920
ttgatatgcc attttatgaa gataaatcag gaatgtccaa gtactttgaa acatctgcct    1980
tgaaagaaga agcaacaaaa agcattgagc caggcagtga ttactatgaa ctgagtgaca    2040
ctagagaaag tgtccatgag tctattgata ccatgtctcc catgcataaa aatggtgaca    2100
aggagtttca aacaggaaaa gaatcccagc ccagtcctcc agcacaagaa gcagggtaca    2160
gcactctcgc acagagttat ccatcagatt tacctgaaga acccagttct cctcaagaaa    2220
gaatgttcac tattgatcca aaagtgtatg gagagaaaag ggacctccac agtaagaata    2280
aggatgattt gacccttagc aggagtttag acttggtgg taggtctgca atagaacaaa     2340
gaagcatgtc aatcaatttg ccgatgtctt gcctagattc catagccctt ggatttaact    2400
ttggtcgggg acatgatctt tctcctctgg cttccgatat tctaaccaac actagtggaa    2460
gtatggatga aggggatgat taccttccag ccaccacacc tgcactggag aaagccccctt   2520 gcttccctgt agaaagcaaa gaggaagaac agatagagaa agtaaaagct actggagaag    2580
aaagtactca agcggagata tcatgtgagt ctccttttcct agccaaagat ttttacaaaa   2640
atggtactgt catggcacct gaccttcctg aaatgctaga tctggcaggc acaaggtcaa    2700
gattggcttc tgtgagtgca gatgctgagg ttgccaggag gaaatcagtc ccatcagaga    2760
ctgtggttga ggatagtcgt actggcttgc ccccggtaac tgatgaaaac catgtcattg    2820
taaaaacgga cagtcagctc gaagacctgg gctactgtgt gttcaataag tacacagtcc    2880
cattgccatc acctgttcaa gacagtgaga atttatcagg ggagagtggt accttttacg    2940
aaggcactga tgataaagtt cgaagagatt tggccacaga cctttcactg attgaagtga    3000
aactggcagc agccggaaga gtcaaagatg agttcagtgt tgacaaagaa gcatccgcgc    3060
atatctctgg tgacaaatca ggactgagta aggagtttga ccaagagaag aaagctaatg    3120
ataggttgga tactgtacta gaaaagagtg aagaacatgc tgattcaaaa gaacatgcca    3180
agaaaactga gaggctggt gatgaaatag aaacattcgg attaggagta acctatgagc     3240
aagctttggc caaagatttg tcaataccaa cagatgcatc ctctgagaaa gcagagaagg    3300
gtcttagttc agtgccagag atagctgagg tagaaccatc caaaaggtg gaacaaggtc     3360 tggattttgc tgtccagggt caactagatg ttaaaattag tgactttgga cagatggctt    3420
cagggctaaa catagatgat agaagggcaa cagagctaaa acttgaggct acacaggaca    3480
tgaccccctc atccaaagca ccgcaggagg cagatgcatt tatgggtgtt gagtctggcc    3540
acatgaaaga aggcactaaa gttagtgaga cagaagtcaa agagaaggtg gccaagcctg    3600
acttggtgca ccaggaggct gtagacaagg aggagtccta tgaatctagt ggtgagcatg    3660
aaagtctcac catggagtcc ttgaaagctg atgagggcaa gaaggaaaca tctccagaat    3720
```

```
catctctaat tcaagatgag attgccgtca aattgtcagt ggaaatacct tgcccacctg   3780
ctgtttcaga ggctgattta gccacagatg agagagctga tgtccagatg gaatttattc   3840
aggggccaaa agaagaaagc aaagagaccc cagatatatc catcacgcct tctgatgttg   3900
cagagccatt gcatgaaacg atcgtatctg aaccagcaga gattcagagt gaggaagaag   3960
agatagaagc ccagggagaa tatgataaac tgctcttccg ctcagacacc cttcagataa   4020
ctgacctggg tgtctcaggt gccagggagg aatttgtgga gacctgccca agtgaacaca   4080
aaggagtgat tgagtctgtt gtgaccatcg aggatgattt catcactgta gtgcaaacca   4140
caactgatga aggggagtca gggtcccaca gcgtgcgttt tgcagcccta gagcagcctg   4200
aggtggaaag gagaccatct cctcatgatg aagaagagtt tgaagtagaa gaggcagctg   4260
aagcccaggc agaacccaaa gatggttccc cagaggctcc agcttcccct gagagagaag   4320
aggttgcact ttctgaatat aagacagaaa cctatgacga ttacaaagat gagaccacca   4380
ttgacgactc catcatggac gctgacagcc tctgggtgga cactcaagat gatgatagga   4440
gcatcatgac agaacagtta gaaactattc ctaaagagga gaaagctgaa aaggaagctc   4500
ggagatcatc tcttgagaaa catagaaaag aaaagccttt taaaaccggg agaggcagaa   4560
tttccactcc tgaaagaaaa gtagctaaaa aggaacctag cacagtctcc agagatgaag   4620
tgagaaggaa aaaagcagtt tataagaagg ctgaacttgc taaaaaaaca gaagttcagg   4680
cccactctcc ctccaggaaa ttcattttaa aacctgctat caaatatact agaccaactc   4740
atctctcctg tgttaagcgg aaaaccacag cagcaggtgg ggaatcagct ctggctccca   4800
gtgtatttaa acaggcaaag gacaaagtct ctgacggagt aaccaagagc ccagaaaagc   4860
gctcttctct cccaagacct tcctccattc tccctcctcg gcgaggtgtg tcaggagaca   4920
gagatgagaa ttccttctct ctcaacagtt ctatctcttc ttcagcacgg cggaccacca   4980
ggtcagagcc aattcgcaga gcagggaaga gtggtacctc aacacccact acccctgggt   5040
ctactgccat cactcctggc accccaccaa gttattcttc acgcacacca ggcactcctg   5100 gaaccctag ctatcccagg acccctcaca caccaggaac ccccaagtct gccatcttgg   5160
tgccgagtga aagaaggtc gccatcatac gtactcctcc aaaatctcct gcgactccca   5220
agcagcttcg gcttattaac caaccactgc cagacctgaa gaatgtcaaa tccaaaatcg   5280
gatcaacaga caacatcaaa taccagccta aaggggggca ggttaggatt ttaaacaaga   5340
agatcgattt tagcaaagtt cagtccagat gtggttccaa ggataacatc aaacattcgg   5400 ctggggggcgg aaatgtacaa attgttacca agaaaataga cctaagccat gtgacatcca   5460
aatgtggctc tctgaagaac atccgccaca ggccaggtgg cggacgtgtg aaaattgaga   5520
gtgtaaaact agatttcaaa gaaaaggccc aagctaaagt tggttctctt gataatgctc   5580
atcatgtacc tggaggtggt aatgtcaaga ttgacagcca aaagttgaac ttcagagagc   5640
atgctaaagc ccgtgtggac catggggctg agatcattac acagtcccca ggcagatcca   5700
gcgtggcatc accccgacga ctcagcaatg tctcctcgtc tggaagcatc aacctgctcg   5760
aatctcctca gcttgccact ttggctgagg atgtcactgc tgcactcgct aagcagggct   5820
tgtgaatatt tctcatttag cattgaaata ataatattta ggcatgagct cttggcagga   5880
gtgggctctg agcagttgtt atattcattc tttataaacc ataaaataaa taatctcatc   5940
cccaaactgt agtaattgtt acaatttttct atttaaaaaa tgaatagtac atgcagaaat   6000
tgacctgatt tccatttgca acaggaagac actggcttta catgggttca attggacaat   6060
tatttttgct ctgctctgtt ttgcatggag tattattatt ttaaaaattg cattttttacc   6120
```

```
tttcatgtgc ctgaaggcta tccactacat tctgaaggcc ttgttaaaat ccaagctgct      6180
catttcacta ttctgtttct gagtgagaag ataaaaactg cccattgtaa cttatttcag      6240
gttaaattaa accaaggagt ctgattgcag gaagggaaga gcatgtaaga aataagtttt      6300
tttaaagtgt tattttgtat aaatgggaag aaagattcaa ttaagttatt aacatttggg      6360
acctggataa ttatatcaga gtatgtcagt ccaataaatt atttaactaa ttaaaaaata      6420
gttgcaaagc atttgagctg tggttgagga agtggtgtaa aagtgcatcc attaggaatg      6480
atgcactttc attaggatgg actcgtgtct gattagaatg tcagttgatc agctagattt      6540
gtgtccacac taccagtttc acaccccctt tccatctgtt tgatacagta ttatagatat      6600
aaatatatat atatttctct gtggccattt gtgatacttc ctcatatact tgaatattat      6660
acttctttat tcacagtatc tgtgtctcct gcacccttttg gtgttgcaat tttagatatg      6720
tgaaagtaga tgttagcagg gttctctccc tatttaaaaa aaatacatta aaaaagacaa      6780
aaaattttag catgaagttg ctttctgtaa caactcaaag ccgtaaccct gttttagtgc      6840
cagatacaag tctctcccgt gatgctagac aaaaaattat ttttctttgc tttcaccaac      6900
atggagtttg tggggtggg tccagttata catgaaaggg tttacagatt gttggtttaa      6960
gattatggat ttatctcatt tttaatcaca ggatagtttg gggtttattc ctattattat      7020
tcatgaaacc gacttaagat ttttctttta tttttctttt tttttccatt tgctaaagtt      7080
gaaagttgaa actaactata atagtttgaa acatgttttc tcattttttcc aaatagtatc      7140 tgttattaa attctctaat agaagatgtt tgtctttctt acccaaagta aagatcccct      7200
gatcagaaag aaaaaaatca aactttgggg aagctatagc tataaaacac ttgagacaca      7260
gatatctaaa tcagttttttt tccaagactc caacattgca ctctgtaaag taacacactg      7320
tgatctagta ttatttatca gtagataata ctgttctgac tgtatataca gtctagaact      7380
cacaaatcaa ttagttcctc tcacaaatca ttcatcttag acttacaaat aaggaatgaa      7440
atagtcaatg gcctgattaa ggcaaagagc taccaggcta gatggacact ttttaaaaat      7500
tttatctgtt cttttttcttg ctcagggctg gtaggttgga tctgaaccat taaaatcaaa      7560
tggtccacta ggcgtatgat ctctttgagc caaatcagtt cctgaatata aaggaggaaa      7620
tgatgaggat gtactgaggc aacggggaag tatagaaaca tccaagacaa aagccaaggg      7680
atgcaaaggc agagacacag gtgctttttg gtgacccagt ggatatggca accagtgtaa      7740
ctgccataca agaaacccta ggagcaaacc cacaccactc attctcagct aagagatttt      7800
acacaggcaa acgtgtctta aaccatctat aaatcagtta ttttatatga cagtcaaaac      7860
cttagaaacc ttaggatcat tatatctatt ttctgcctat taattgctgt gaggtttgat      7920
ttgaccaatc tgggcaattt attcatcagc ttcccttgaa gtgcaccaga aaatagaaga      7980
aaggtgtgtg gagacttagg gtattttatt acatgttttc atagtcttaa atagtgatta      8040
aatttctcta gaaagaagtt aacagctcat tagaaaagtt ttaacctgtg aaataagtat      8100
ttttctcaac attctttaaa gtttttatat aagttaacac taggtaaaca ttctgcatac      8160
tagaagtcag tttattacaa atacatgtca aaaataaaga ttatacaagg caccaaaacta      8220 ctagatttgg cattaaaaca aatgtttatt tctaatcaca acaaaattat aatgaataaa      8280
tgttcttgct ttgtatggaa atacaattct ttattaaagt taacagaaag gaactgatcg      8340
tttgtaccag taaaagagag aaacacacag gttaaatatc ttcttgtggg gttaaggggt      8400
agaacctatc ttgccttcac tctcaagata acgactcaaa ttaagctttt tgagcaccac      8460
```

| | |
|---|---|
| tcttgtgggg acacacatac gctgatctag gaatgaaatc ttcgtggtct caattctaga | 8520 |
| tctactatgc cagtttctct ctggctttag cctttgagaa cctgtataag aatacgtaag | 8580 |
| taatccagag ctgtgaagag tttaaaggcc aacttctcca gtgaactcaa cctctgggtc | 8640 |
| acttgcaacc agaaattgga tacctcataa tgatgcagga agacccgag ttcatgatga | 8700 |
| gtttcaaagg ccacgttcat ttaggaacca actctctctg gatttacctg ctgagttcca | 8760 |
| gcagcgtgat gggctgacat cccacctaca agtatgacac ctgtgtaaca ccagctaggt | 8820 |
| acggctggag aaggctgaag agagaatgcc attaaatgga agaatgtact gattgtagtg | 8880 |
| accttctcca cacacacaca cacacacaca cacacacaca cctacagtaa tacagcaagc | 8940 |
| gtggaataat cagccaatat ataacattcc atcagtattt tattaaggaa ataacctgaa | 9000 |
| tgtggttgat tttgacatag ctgcaattac agttttcttc tattttttcaa gccacaataa | 9060 |
| ggaaaataaa ctactcatgg tctaaatact agagataaag tagattcatg gcttggtaag | 9120 |
| gaaattttaa gcattccttc aaagattgac gtgctaaaat aagcattgat gttttgagtt | 9180 |
| tttttacacc taggattttt agcttgggtg tgtaggtgaa ggccaagact ctctgcagga | 9240 |
| aaaagcttat tttcaaactc agaaaataaa atgtcaatca taaaaatcta cttcaacttt | 9300 |
| agcaaaaaga aaaaaaaatc aacaaaaagt atactctgta tgctgggatt ccgaggttcc | 9360 |
| aacacactgt tacaaatctg tgggggtttt cttcttctg ataattctag agcctgttac | 9420 |
| catagaaagg catttcttca atggctggtt gtagttagtt catgttttc aatcaaattt | 9480 |
| gcaaatgtat ttgttgctgt atagtgattg ttttgcaaaa taaaattgct tgtcacct | 9538 |

<210> SEQ ID NO 8
<211> LENGTH: 6230
<212> TYPE: DNA
<213> ORGANISM: Homo sapiens

<400> SEQUENCE: 8

| | |
|---|---|
| ctagatcgaa agtcctttgg taatgatgtg tcatacattc tagtcatcaa agacaccatt | 60 |
| ttctgggcct gaagtgttct gctggttttt ggaggaatga gaatccaatc tctcataagc | 120 |
| cggattcaga aaataggtca tcgatgaaac atctgtatgg attatttcac tataatccta | 180 |
| tgatgcttgg acttgaatca cttccagatc ccacagacac ctgggaaatt atagagacca | 240 |
| ttggtaaagg cacctatggc aaagtctaca aggtaactaa caagagagat gggagcctgg | 300 |
| ctgcagtgaa aattctggat ccagtcagtg atatggatga agaaattgag gcagaataca | 360 |
| acattttgca gttccttcct aatcatccca atgttgtaaa gttttatggg atgttttaca | 420 |
| aagcggatca ctgtgtaggg ggacagctgt ggctggtcct ggagctgtgt aatgggggct | 480 |
| cagtcactga gcttgtcaaa ggtctactca gatgtggcca gcggttggat gaagcaatga | 540 |
| tctcatacat cttgtacggg gccctcttgg gccttcagca tttgcacaac aaccgaatca | 600 |
| tccaccgtga tgtgaagggg aataacattc ttctgacaac agaaggagga gttaagctcg | 660 |
| ttgactttgg tgtttcagct caactcacca gtacacgtct gcggagaaac acatctgttg | 720 |
| gcacccgtt ctggatggcc cctgaggtca ttgcctgtga gcagcagtat gactcttcct | 780 |
| atgacgctcg ctgtgacgtc tggtccttgg ggatcacagc tattgaactg ggggatggag | 840 |
| accctcccct cttttgacatg catcctgtga aaacactctt taagattcca agaaatcctc | 900 |
| cacctacttt acttcatcca gaaaaatggt gtgaagaatt caaccacttt atttcacagt | 960 |
| gtcttattaa ggattttgaa aggcgacctt ccgtcacaca tctccttgac cacccattta | 1020 |
| ttaaaggagt acatggaaaa gttctgtttc tgcaaaaaca gctggccaag gttctccaag | 1080 |

```
accagaagca tcaaaatcct gttgctaaaa ccaggcatga gaggatgcat accagaagac   1140
cttatcatgt ggaagatgct gaaaaatact gccttgagga tgatttggtc aacctagagg   1200
ttctggatga ggatacaatt atccatcagt tgcagaaacg ttatgcagac ttgctaattt   1260
acacatatgt tggagacatc ttaattgcct taaaccccett ccagaatcta agcatatact   1320
ctccacagtt ttccagactt tatcatgggg tgaaacgcgc ctccaatccc ccccacatat   1380
ttgcatcagc agatgctgct taccagtgca tggttactct cagcaaagac cagtgcattg   1440
tcatcagcgg agagagtggc tctgggaaga cagaaagcgc ccacctgatt gttcagcatt   1500
tgactttctt gggaaaggcc aataatcaga ccttgagaga gaaaattcta caagtcaact   1560
ccctggtgga agcctttggg aactcatgca ctgccatcaa tgacaactcg agccgttttg   1620
gaaaatatct ggaaatgatg tttacaccaa ctggagttgt gatgggggca agaatctctg   1680
aatatctcct ggaaaaatcc agagttataa acaggcagc gagagagaaa aattttcata    1740
tattttacta tatttatgct ggtcttcatc accaaaagaa gctttctgat ttcagacttc   1800
ctgaggaaaa acctcctagg tacatagctg atgaaactgg aagggtgatg cacgacataa   1860
cttccaagga gtcttacaga agacaattcg aagcaattca gcattgcttc aggattatag   1920
ggttcacgga caaagaggtg cactcagtgt acagaatttt ggctgggatt ttgaatattg   1980
ggaacattga gttcgcagct atttcctctc aacatcagac tgataaaagt gaggtgccca   2040
atgctgaagc tttgcaaaat gctgcctctg ttctgtgcat tagccctgaa gagctccagg   2100
aggccctcac ctcccactgt gtggtcaccc ggggcgagac catcatccgt gccaacactg   2160
tagacagggc tgcggacgtt cgagacgcca tgtccaaagc cctgtatggg aggctcttca   2220
gctggattgt gaatcgcatt aatacactcc tgcagccaga cgaaaacata tgtagtgcag   2280
gaggtggaat gaatgtgggg atcttggata tctttggatt cgagaatttt cagagaaatt   2340
catttgagca gctctgcata aacatcgcca atgagcaaat ccagtactat ttcaatcagc   2400 atgttttttgc tcttgagcag atggaatatc agaatgaagg cattgatgct gtacccgtgg   2460
aatatgagga caaccgcccg ctcttggaca tgttcctcca gaaacccctg ggactgcttg   2520 cactttttgga tgaggaaagt cggtttcccc aagcaactga ccagaccctg gttgataaat   2580
ttgaagataa tctacgatgc aaatacttct ggaggcccaa aggagtggaa ctgtgctttg   2640
gcattcagca ttatgctgga aaggtattat atgatgcttc tggggttctt gagaaaaata   2700
gagacactct ccctgccgat gtggttgtgg tcctgagaac gtcagaaaac aagcttcttc   2760
agcagctctt ctcaatccct ctgaccaaaa caggtaattt ggcccagaca agagctagga   2820
taacagtggc ctcaagttct ttgcctccac atttcagtgc tgggaaagcc aaggtggaca   2880
ctctggaggt gatacggcat ccggaagaaa ccaccaacat gaagaggcaa actgtggctt   2940
cttacttccg gtattctctg atggacctgc tctccaaaat ggtggttgga cagccccact   3000
ttgtgcgctg cattaaaccc aatgatgacc gagaggccct gcagttctct cgagagaggg   3060
tgctggccca gctccgctcc acagggattc tggagacagt cagcatccgc cgccagggct   3120
attcccaccg catcctttttt gaagaatttg tgaaaaggta ttattacttg gcattcacag   3180
cacatcaaac acctcttgct agcaaagaga gctgtgtggc tatcttggaa aagtccagat   3240
tagatcactg ggtactggga aaaacaaagg ttttttctcaa atattaccat gttgagcaat   3300
taaatttgct gcttcgagaa gtcataggca gagtggttgt gctgcaggca tataccaagg   3360
ggtggcttgg agccaggaga tacaaagggg tcagagagaa gagagagaag ggagccattg   3420
```

```
ccatccagtc agcctggaga ggatatgatg ctcggaggaa atttaagaaa ataagcaaca    3480
gaaggaatga gtctgctgct cataatcaag caggggacac ttcaaaccaa agcagtgggc    3540
cacattcccc cgtcgcagca ggtacgaggg gaagtgccga ggttcaagac tgcagcgagc    3600
ctggtgacca taaagttctc aggggctctg tacatcgtag gagccattca caagcagaat    3660
ccaacaatgg ccgtacacag acttcaagca actctcctgc tgtcacagag aaaaatgggc    3720
attcacaagc ccagagttct ccaaaagggt gcgatatctt cgcaggacat gcaaacaagc    3780
actcggtttc tgggactgat ttgctgtctt ctcggatatg ccatcctgct ccagatcagc    3840
aaggattgag tctctgggga gcccctcaaa agcctggttc agaaaatggt cttgcacaga    3900
agcatcgaac acctcgccga cgatgtcagc agcccaaaat gctgagtagc cctgaggaca    3960
ccatgtacta taaccagtta aatggaactc tagaatatca agggagcaag aggaagccaa    4020
gaaaacttgg ccaaatcaaa gtacttgatg gggaagatga atattacaaa tctctgtcac    4080
cagtggactg tatccctgag gagaacaact cagcccaccc ttcctttttt tcttcatcct    4140
caaaaggaga ctcttttgct caacattaaa ttgtgcttcc taaccctaaa tctgtccaga    4200
gtaggaacat tcatggtaat cgactgtctg tcattgcgta agaaagcact gatatggggt    4260
cagcttcttt ggacatatgg tccatgcctg aaccttactg aaccacttgc agattccaaa    4320
acatcttatc ctatcctcta ccactctccc acatgtgttg tgcagcctga gctgggcgct    4380
gccttccttt ctcatcccat ggggcccgtg ggacactga gaacaccttt acaatagttt    4440
aaacagtcat tcatgccccc agtgtctagg aagataacag ccagtctcac cccagtctaa    4500
tcatggaccc tgataatatt gcttgatttt tcctatcaag ttactttca atccattcag    4560
aatctgcccc agtggagacc caggagttcc tttcctgcac tcttctccat cctcccacct    4620
ttgctgggct tttctatcac tcccacctcc cccagagtca gggctccatt gctgagtgcc    4680
ccatcctgga ggattggccc caagatctcc tagaacagga taattgcctg tgtttaggca    4740
gataggccta aatctttcag attctttcta caaggcaaat aaccccctctc ttgttaatta    4800
tgatgctgag aaagcctctg tctctttatt tcaccttgcc aagacaccca cactactttg    4860
gtgatgaaaa gaaaggaatg agagggaaag tttggacctg tcactttggt gacagggaaa    4920
gtccaggtca ctttattctg taactctcca ttcactggtc aaataactcc atgaggctat    4980
cagtggctac agtggaagga cctgatcttg tccatctttg tgtgcacaga gcctagcaca    5040
gggcttggta gagggtatat ctagtgaatg gagaatacat ggagaaactt aactaagtta    5100
cacaagcata tctgacagga atgttacctt caattgtatg ttacatatga ttagtcactt    5160
ttcatacact ataacctctg attttcact caagtttggg ctgattatat tgtaatgatg    5220
ttagataata ctcaacatga ttcagtatga caaacttttt tgagcaccta ctttatataa    5280
aacatgacaa attgcagtgt gatgtaatca aaaacaaaga agccctataa gaccatttct    5340
ctagaacaga tgttcttaat attttttctta ctctaaaata tgtggtagat agtatgcaag    5400
aaaagccggg tgcggtggct caggcctgta atcccagcac tttgggaggc caagatgggc    5460
ggatcatgaa gtcaggagtt cgagaccagc ctgaccaaca tggtgaaacc ccgtctctac    5520
taaaaaaaat aatgataata caaaaattag cccagcatgg tggtgcatac ctgtaatccc    5580
agctactcag gaggctgacg caggagaatc acttgaaccc gggaagcaaa ggttgcagtc    5640
agctgagagc gcaccactgc actccagcct gggcgacagg gcaagactct gtctcaaaaa    5700
aaaaaaaaaa aaaaaaaaa agagatagta tgcaagaaga cacctaaatt ttgagagaaa    5760
taaccttgaa gaaaatcttg ttatcagagt tttgaaaggg agcacattaa taggcctttt    5820
```

| | |
|---|---:|
| atgaagataa ataatgaaat gaggtattta aagatctcag aaattgtaat tttacaagta | 5880 |
| aaataaatat agccaattt tcaatagctg aacttcaccc aaaaggtaat gtttataagt | 5940 |
| agagcagaaa aaatgcagat aaattttatt ttattgttta aaaaataatg tgtagaatat | 6000 |
| ataaattttt tatgttactg ttaatatacg agtgcttttg gaagtttcac tttttgtcact | 6060 |
| gattgtctac ttttggtttg ataatatgag ctgcttttca aattgttgaa tggaaatgtt | 6120 |
| cataactccc tgcttgtccg tgcacaatgt aattctaaac ctggcttgtt tctcatttaa | 6180 |
| atatatctat aaataaactt aaaagaaaa caaaaaaaa aaaaaaaaa | 6230 |

<210> SEQ ID NO 9
<211> LENGTH: 4104
<212> TYPE: DNA
<213> ORGANISM: Homo sapiens

<400> SEQUENCE: 9

| | |
|---|---:|
| ataactttgt agcgagtcga aaactgaggc tccggccgca gagaactcag cctcattcct | 60 |
| gctttaaaat ctctcggcca cctttgatga ggggactggg cagttctaga cagtcccgaa | 120 |
| gttctcaagg cacaggtctc ttcctggttt gactgtcctt accccgggga ggcagtgcag | 180 |
| ccagctgcaa gccccacagt gaagaacatc tgagctcaaa tccagataag tgacataagt | 240 |
| gacctgcttt gtaaagccat agagatggcc tgtccttgga aatttctgtt caagaccaaa | 300 |
| ttccaccagt atgcaatgaa tggggaaaaa gacatcaaca acaatgtgga gaaagccccc | 360 |
| tgtgccacct ccagtccagt gacacaggat gaccttcagt atcacaacct cagcaagcag | 420 |
| cagaatgagt ccccgcagcc cctcgtggag acgggaaaga agtctccaga atctctggtc | 480 |
| aagctggatg caaccccatt gtcctcccca cggcatgtga ggatcaaaaa ctggggcagc | 540 |
| gggatgactt tccaagacac acttcaccat aaggccaaag ggatttttaac ttgcaggtcc | 600 |
| aaatcttgcc tggggtccat tatgactccc aaaagtttga ccagaggacc cagggacaag | 660 |
| cctacccctc cagatgagct tctacctcaa gctatcgaat ttgtcaacca atattacggc | 720 |
| tccttcaaag aggcaaaaat agaggaacat ctggccaggg tggaagcggt aacaaaggag | 780 |
| atagaaacaa caggaaccta ccaactgacg ggagatgagc tcatcttcgc caccaagcag | 840 |
| gcctggcgca tgccccacg ctgcattggg aggatccagt ggtccaacct gcaggtcttc | 900 |
| gatgcccgca gctgttccac tgcccgggaa atgtttgaac acatctgcag acacgtgcgt | 960 |
| tactccacca caatggcaa catcaggtcg gccatcaccg tgttcccccca gcggagtgat | 1020 |
| ggcaagcacg acttccgggt gtggaatgct cagctgtgca tcgacctggg ctggaagccc | 1080 |
| aatggccgtg accctgagct cttcgaaatc ccacctgacc ttgtgcttga ggtggccatg | 1140 |
| gaacatccca aatacgagtg gtttcgggaa ctggagctaa agtggtacgc cctgcctgca | 1200 |
| gtggccaaca tgctgcttga ggtgggcggc ctggagttcc agggtgccc cttcaatggc | 1260 |
| tggtacatgg gcacagagat cggagtccgg gacttctgtg acgtccagcg ctacaacatc | 1320 |
| ctggaggaag tgggcaggag aatgggcctg gaaacgcaca agctggcctc gctctggaaa | 1380 |
| gaccaggctg tcgttgagat caacattgct gtgctccata gtttccagaa gcagaatgtg | 1440 |
| accatcatgg accaccactc ggctgcagaa tccttcatga gtacatgca gaatgaatac | 1500 |
| cggtcccgtg ggggctgccc ggcagactgg atttggctgg tccctcccat gtctgggagc | 1560 |
| atcaccccg tgtttcacca ggagatgctg aactacgtcc tgtccccttt ctactactat | 1620 |
| caggtagagg cctggaaaac ccatgtctgg caggacgaga agcggagacc caagagaaga | 1680 |

-continued

```
gagattccat tgaaagtctt ggtcaaagct gtgctctttg cctgtatgct gatgcgcaag    1740
acaatggcgt cccgagtcag agtcaccatc ctctttgcga cagagacagg aaaatcagag    1800
gcgctggcct gggacctggg ggccttattc agctgtgcct tcaaccccaa ggttgtctgc    1860
atggataagt acaggctgag ctgcctggag gaggaacggc tgctgttggt ggtgaccagt    1920
acgtttggca atggagactg ccctggcaat ggagagaaac tgaagaaatc gctcttcatg    1980
ctgaaagagc tcaacaacaa attcaggtac gctgtgtttg ccctcggctc cagcatgtac    2040
cctcggttct gcgcctttgc tcatgacatt gatcagaagc tgtcccacct ggggggcctct    2100 cagctcaccc cgatgggaga aggggatgag ctcagtgggc aggaggacgc cttccgcagc    2160
tgggccgtgc aaaccttcaa ggcagcctgt gagacgtttg atgtccgagg caaacagcac    2220
attcagatcc ccaagctcta cacctccaat gtgacctggg acccgcacca ctacaggctc    2280
gtgcaggact cacagccttt ggacctcagc aaagccctca gcagcatgca tgccaagaac    2340
gtgttcacca tgaggctcaa atctcggcag aatctacaaa gtccgacatc cagccgtgcc    2400
accatcctgg tggaactctc ctgtgaggat ggccaaggcc tgaactacct gccggggag    2460 caccttgggg tttgcccagg caaccagccg gccctggtcc aaggtatcct ggagcgagtg    2520
gtggatggcc ccacacccca ccagacagtg cgcctggagg ccctggatga gagtggcagc    2580
tactgggtca gtgacaagag gctgccccc tgctcactca gccaggccct cacctacttc    2640
ctggacatca ccacaccccc aacccagctg ctgctccaaa agctggccca ggtggccaca    2700
gaagagcctg agagacagag gctggaggcc ctgtgccagc cctcagagta cagcaagtgg    2760
aagttcacca acagccccac attcctggag gtgctagagg agttcccgtc cctgcgggtg    2820
tctgctggct tcctgctttc ccagctcccc attctgaagc ccaggttcta ctccatcagc    2880
tcctcccggg atcacacgcc cacagagatc cacctgactg tggccgtggt cacctaccac    2940
acccgagatg ccagggtcc cctgcaccac ggcgtctgca gcacatggct caacagcctg    3000 aagcccaag acccagtgcc ctgctttgtg cggaatgcca gcggcttcca cctccccgag    3060
gatccctccc atccttgcat cctcatcggg cctggcacag gcatcgcgcc cttccgcagt    3120
ttctggcagc aacggctcca tgactcccag cacaagggag tgcggggagg ccgcatgacc    3180
ttggtgtttg ggtgccgccg cccagatgag gaccacatct accaggagga gatgctggag    3240
atggcccaga aggggtgct gcatgcggtg cacacagcct attcccgcct gcctggcaag    3300
cccaaggtct atgttcagga catcctgcgg cagcagctgg ccagcgaggt gctccgtgtg    3360
ctccacaagg agccaggcca cctctatgtt gcgggatg tgcgcatggc ccgggacgtg    3420
gcccacaccc tgaagcagct ggtggctgcc aagctgaaat tgaatgagga gcaggtcgag    3480
gactatttct ttcagctcaa gagccagaag cgctatcacg aagatatctt tggtgctgta    3540
tttccttacg aggcgaagaa ggacagggtg gcggtgcagc cagcagcct ggagatgtca    3600 gcgctctgag ggcctacagg aggggttaaa gctgccggca cagaacttaa ggatggagcc    3660
agctctgcat tatctgaggt cacagggcct ggggagatgg aggaaagtga tatccccccag    3720 cctcaagtct tatttcctca acgttgctcc ccatcaagcc ctttacttga cctcctaaca    3780
agtagcaccc tggattgatc ggagcctcct ctctcaaact ggggcctccc tggtcccttg    3840
gagacaaaat cttaaatgcc aggcctggca agtgggtgaa agatggaact tgctgctgag    3900
tgcaccactt caagtgacca ccaggaggtg ctatcgcacc actgtgtatt taactgcctt    3960
gtgtacagtt atttatgcct ctgtatttaa aaaactaaca cccagtctgt tccccatggc    4020
cacttgggtc ttccctgtat gattccttga tggagatatt tacatgaatt gcattttact    4080
```

```
ttaatcacaa aaaaaaaaaa aaaa                                          4104

<210> SEQ ID NO 10
<211> LENGTH: 3734
<212> TYPE: DNA
<213> ORGANISM: Homo sapiens

<400> SEQUENCE: 10
cctctttctc cccctctct ccctcctctc ctctctctct cctctcttct ctgaacctct     60
cttctctttc tcttttctta catattctac tagttgtttt ccccttcttc ttctcctttc    120
tctccttttt ctccctcctc cttgtctctt ttactccatt cctgcagaag agagagggct    180
aaacttaaag aaaaaaaaa ggaggaggag gaggaggagg caccccttc gtattcttct     240 tatcgttatt ttatacatat atgattttt ttggagggag ggtgttggtt gccggctgaa    300
gagcacttat ttaaaatact aaaaaaagaa cattttggg cgatctccag ggtttttta    360 actagctctg tgtgttatag cagaagaagc agaagaagga gcaagaaaga ggaaaagaag    420
aggattattt attcgaccta ctttggatgt ctctctcgct tttccttttt cctttttttg    480
gcaattattt tcttctgatt tttatttttt ctatttcgct gtgatttcgt cgccggcgtg    540
aattatcccg tattttctc cccttccgt cacctcccga agaagaagg cagcgagagc     600 ccggcgccac cggcacaaca aaagagcaa agtgtgtgat cttcctcgcc ggctgcctcc    660
cgctctccag cgctgccttc ctgaatggct ggctgcgtcc ggccctggac ctggccccc    720 gacacccgcg cgccctgatc gccgcggca gcctcgccca cgccctgct cggctcaccg    780 cgctccccgc actcccgagc ccggcgaggg ctcccgccgg gacagcggcg cgccgcggg    840 cggccccggc ctccgctcgc gctccggctg cggcccgac tcctgctcgg actccggccc    900
gggtcccggc tcctccagcg cgctcgccg cagcagctcc ggcggcagct ccagcggcgc    960
ctgcagccgc gacctcctcc tcctccgccg ccgccgccgc ctcgccctc gccggcttcc   1020 tctatgtcgg ctcagcccgc gcgctgcgcg tagcccgagc ggccggcggg cgggcgcccg   1080
gcgcgggtga gcgactgtgt gtgcgagtgt gtgtgtgcgc ggggtgcgg gcgaggcgga   1140 gggcgagtgt gtgcgcgcgc cgtggcccat gcccgccgcc ccggcgctg cgccccgcgc   1200 cgctcccggc tgccgcctgt gccatttctg atttgcaac ttggggaaga agaaaaaagc   1260
gagagaaggg agcttgctcg ccggggggtg gggaggggg aaggagagcg cggcccccc    1320 aggaacggag cgcgggggga gcgggcgagg ggagcagggg tgttgggggg ggagcctgag   1380
agcctggggg ggctgcaaaa agagagaaag aaaacagcag gaaccacaac aaaacgccag   1440
cagggcgggc gggcgcgcag cagcagcggg gcggccgagg cagtagcggc ggcagcggcg   1500 gcggcggcg aggcagcggc cggtgtccgg ctcgggctcg gctcctgcga ccccggggcg   1560
cccggcgggc ccccgccc ctcccctcc ccccttcccc ttccccttcc cctcccagcg   1620
cgcccgcgcg ccccgcggcc ctcggcgagc agctcggctc ccccagcgc tccccgggcc   1680 caaagatatg gcaatggtag ttagcagctg gcagatccg caggacgacg tggccggggg   1740
caaccccggc ggccccaacc ccgcagcgca ggcggcccgc ggcggcggcg cggcgccgg   1800 cgagcagcag cagcaggcgg gctcgggcgc gccgcacacg ccgcagaccc cgggccagcc   1860
cggagcgccc gccacccccg gcacggcggg ggacaagggc cagggcccgc ccggttcggg   1920
ccagagccag cagcacatcg agtgcgtggt gtgcgggac aagtcgagcg gcaagcacta   1980
cggccaattc acctgcgagg gctgcaaaag tttcttcaag aggagcgtcc gcaggaactt   2040
```

| | | | | |
|---|---|---|---|---|
| aacttacaca | tgccgtgcca | acaggaactg | tcccatcgac | cagcaccacc | gcaaccagtg | 2100 |
| ccaatactgc | cgcctcaaga | agtgcctcaa | agtgggcatg | aggcgggaag | cggttcagcg | 2160 |
| aggaagaatg | cctccaaccc | agcccaatcc | aggccagtac | gcactcacca | acggggaccc | 2220 |
| cctcaacggc | cactgctacc | tgtccggcta | catctcgctg | ctgctgcgcg | ccgagcccta | 2280 |
| ccccacgtcg | cgctacggca | gccagtgcat | gcagcccaac | aacattatgg | gcatcgagaa | 2340 |
| catctgcgag | ctggccgcgc | gcctgctctt | cagcgccgtc | gagtgggccc | gcaacatccc | 2400 |
| cttcttcccg | gatctgcaga | tcaccgacca | ggtgtccctg | ctacgcctca | cctggagcga | 2460 |
| gctgttcgtg | ctcaacgcgg | cccagtgctc | tatgccgctg | cacgtggcgc | cgttgctggc | 2520 |
| cgccgccggc | ctgcatgcct | cgcccatgtc | tgccgaccgc | gtcgtggcct | tcatggacca | 2580 |
| catccgcatc | ttccaggagc | aggtggagaa | gctcaaggcg | ctacacgtcg | actcagccga | 2640 |
| gtacagctgc | ctcaaagcca | tcgtgctgtt | cacgtcagac | gcctgtggcc | tgtcggatgc | 2700 |
| ggcccacatc | gagagcctgc | aggagaagtc | gcagtgcgca | ctggaggagt | acgtgaggag | 2760 |
| ccagtacccc | aaccagccca | gccgttttgg | caaactgctg | ctgcgactgc | cctcgctgcg | 2820 |
| caccgtgtcc | tcctccgtca | tcgagcagct | cttcttcgtc | cgtttggtag | gtaaaacccc | 2880 |
| catcgaaact | ctcatccgcg | atatgttact | gtctgggagc | agcttcaact | ggccttacat | 2940 |
| gtccatccag | tgctcctaga | ccttgggcgc | ttcccacctg | cccgtcccc | ctagagactc | 3000 |
| agaggaccca | cctgggccaa | ggactccaaa | gccgcgggga | caccgggaag | tgcagcgggc | 3060 |
| caggcaggct | gggtgggagg | gaggagggcc | gagacaggag | cagcccaccc | agcagaaata | 3120 |
| caatccgagc | tacaaagcat | gggaaaaaga | gactctttta | ggatcagatc | tgtgagcacg | 3180 |
| ttggcgagga | aaacaaaac | aaacaaaaaa | aagaaccttg | tgtctgtctg | gtgaaaaaaa | 3240 |
| gaaaaacaaa | ttggaagaga | ggaccatgag | aatttaata | aaacagaagg | aaactaatgg | 3300 |
| accttccagg | atttattgtg | gacggatgtg | gatatattct | gtacaggaac | aacacatatg | 3360 |
| gaagtggact | gaagcctatg | tagaaacaca | cacacactga | acattgttat | tcattttgta | 3420 |
| aaatactagt | ctttattttc | atttttgta | aaatttaaac | atcgtatgcg | cataaagaaa | 3480 |
| aaggaaacaa | gaattagggg | aaaataacat | tttccaaata | attataaaaa | attgtcctgt | 3540 |
| gtctatgtat | ctatatctgt | tttgtatttt | tttctggttc | caaaccagat | ttcctgtgat | 3600 |
| tctatactaa | taattttga | tataacccctt | tgcttcttat | aatgagtgcg | atatatgttg | 3660 |
| tcgaggctgt | tcttcaagaa | ttaaaattga | agtgaaaatt | taaacaaaaa | taaagaatt | 3720 |
| tagcaaaaaa | aaaa | | | | | 3734 |

<210> SEQ ID NO 11
<211> LENGTH: 5110
<212> TYPE: DNA
<213> ORGANISM: Homo sapiens

<400> SEQUENCE: 11

| | | | | |
|---|---|---|---|---|
| gccgtactgc | cttttttccc | ctctttcatt | ctttctctcc | gtcttttct | ccccctctg | 60 |
| cgcacgaagg | atgtgcttct | aggtggtgat | ctgccctcct | ctctctcttt | tatcatttct | 120 |
| ccccgccgc | cggcgagttg | actctttccc | tatgtgtgtg | aggcggcggc | ggcagcagca | 180 |
| gcagcagcgg | ctccggcggc | ggcagcagcg | gcagcagcga | cttcagcggc | ggcggcggcg | 240 |
| ctagacgcag | cggctccggg | cccgacccgg | cggcttcggc | ggcggctccg | gcggcagcgg | 300 |
| cggcccgggc | ggcccgcagg | gaacggcgag | cggcctccac | ccagcgactg | cgggcggcgg | 360 |
| cggccggaga | gagcgaggcg | cgcgccggac | gcccggggca | ggcggcggcg | gcggcggccc | 420 |

```
agcgccagga cgacgccgcg cagcgcccga cgcggaccac tttcatgctg attccccgg      480
acccgggcag cgctccggcc actccgcggg ccgccggcct ccgccccggc ctgcctggct     540
ccctgggcgc gcccgcaccc ggcgcctccg atctcctagt cctcctgatt tcgatggctt     600
tcctgaatgg ctgactgtgg gctgccctgg acttggcccc cggacagtcg cctctcctcc     660
tcctctacct cctccttcac caccacctcc tcttcctcct cctcctcctc ctcctcctcc     720
gccaactcct cggctgcaca ccagctctaa gagcgagagt gaacgagaga gggagggaga     780
gagtgagagc gagcgagatc tttggagaga ttttttttt tgcctcctac ttctgtcttg      840
aagccagaca atcgacttca gctctccctc cctccctct ttctccacgt tctgctccca      900
ctcgctctcc tgtccccttc cctcccctc ccggcggaaa gccccccgaa accaacaaag      960
ctgagccgag agaaacaaac aaaacaaaca caccgggcca gacaagccat cgacaaaact    1020
ttgcaaaagc aaaacaaaa aaggaaaaac taaccaacct caaccaacca gccccgagc     1080
cacccgggc gccctcccgc gccctcttgc accctcgcac acacaaaagg cggcgcgccg    1140
gagcccgaga cccggggagc cgccgccgcc ccgccgccgc ccgcagccag gggagcagga    1200
agtccggacg cagcccccat agatatggca atggtagtca gcacgtggcg cgaccccag    1260
gacgaggtgc ccggctcaca gggcagccag gcctcgcagg cgccgcccgt gcccggcccg    1320
ccgcccggcg ccccgcacac gccacagacg cccggccaag ggggcccagc cagcacgcca    1380
gcccagacgg cggccggtgg ccagggcggc cctggcggcc cgggtagcga caagcagcag    1440
cagcagcaac acatcgagtg cgtggtgtgc ggagacaagt cgagcggcaa gcactacggc    1500
cagttcacgt gcgagggctg caagagcttc ttcaagcgca gcgtgcggag gaacctgagc    1560
tacacgtgcc gcgccaaccg gaactgtccc atcgaccagc accatcgcaa ccagtgccag    1620
tactgccgcc tcaaaaagtg cctcaaagtg ggcatgagac gggaagcggt gcagaggggc    1680
aggatgccgc cgacccagcc gacccacggg cagttcgcgc tgaccaacgg ggatcccctc    1740
aactgccact cgtacctgtc cggatatatt tccctgctgt gcgcgcgga gccctatccc    1800
acgtcgcgct tcggcagcca atgcatgcag cccaacaaca tcatgggtat cgagaacatt    1860
tgcgaactgg ccgcgaggat gctcttcagc gccgtcgagt gggcccggaa catccccttc    1920
ttccccgacc tgcagatcac ggaccaggtg gccctgcttc gcctcacctg gagcgagctg    1980
tttgtgttga atgcggcgca gtgctccatg ccccctccacg tcgccccgct cctggccgcc    2040
gccggcctgc atgcttcgcc catgtccgcc gaccgggtgg tcgcctttat ggaccacata    2100
cggatcttcc aagagcaagt ggagaagctc aaggcgctgc acgttgactc agccgagtac    2160
agctgcctca aggccatagt cctgttcacc tcagatgcct gtggtctctc tgatgtagcc    2220
catgtggaaa gcttgcagga aaagtctcag tgtgctttgg aagaatacgt taggagccag    2280
taccccaacc agccgacgag attcggaaag cttttgcttc gcctcccttc cctccgcacc    2340
gtctcctcct cagtcataga gcaattgttt ttcgtccgtt tggtaggtaa accccccatc    2400
gaaaccctca tccgggatat gttactgtcc ggcagcagtt ttaactggcc gtatatggca    2460
attcaataaa taaataaaat aagaagggg agtgaaacag agaaagaaaa ggcaaaagac    2520
tggtttgttt gcttaatttc cttctgttaa gaaaggatat aaaaggatgt tacaagtttg    2580
ctaaaagaag agaggggaag aatttaatgg actgtgaatt tcaaaaaaaa aaaaaagac    2640
tgtcaaatga acttttacag aatgcattaa aaaaaaaaaa aaactcctgt gtcggtcaga    2700
acaacttgct acttatcatt tttgtataaa aaggaaatta gtcttttttct tttttggta    2760
```

-continued

```
aatttttgaa aaatattgct aaaagtgcat ttaaggagat tgggagacaa ttagcagaat      2820
ggagaaagta agtctttttt ttttccaaat tattaattgt cctgtgtcta tgtacctcta      2880
gctgttcttt tttgtacttt tctggttcca aaccagttta ttctgtggtt ctataataag      2940
ttttgatata atcttggctt cttaaaaact gtgtatcatt aaaatatatg ttctgcaaga      3000
attaaaactg agtccatgaa aataccatag gaagacataa aactttaaaa ggcaactcaa      3060
agatgatgga aacgcactta caagtggtga ccaaaatttt taggtgaagt cgagcactct      3120
aattagagaa ctggaggaac cacatataac acttaacttc ccctaccctg cccctcccca      3180
aaagaaacca tgacaaacct agcttttaaa aaatatttta agaaagagaa tgaactgtgg      3240
aatttattgg cagccaagga atgtgtccaa gacacatgct gaggttttga ataaaaagtg      3300
aacttttgta atttgaattg ggtcccgctt agttcttgaa ttgttatgaa aatcctatat      3360
ctgtttgtat atttgcaaac cctttgtatt ataattgttg atattttccc ttttaaaaa      3420
ataccattga aatcagcatg acaaaaataa cactgttggc acttataggt aacgtgattg      3480
attcagtatc ttagagttta cagtttgtgt tttaaaaaaa ctgaaggttt ttttttttaag     3540
tgcaacattt ctgtatactg taaaagttat aataactgaa ctgtttggtc gagtctttgt      3600
gtgttatatt ccaaggaaaa ttgaaagtat tcagaaatta aaatattatt tgatatctga      3660
aacctggctg tccccactca ctgtctttac atctagaaga gcccctgtga gctctcgctt      3720
agctggccgg gcgggggggtg gtgggggggg gcatttgttt actcccctca gtcagtttgt     3780
tcaaaggtgg actactgtat ttgcctgttt aatttgggtg tgtgtgtgtt ggggggggag      3840
ctgaagttaa tggtttatct atggtttagg aagtgccata ctgatatagt aaaccacccc      3900
cattcaccta atcctccttt taattaaaaa tggatttttcc aggaaaaaaa aaaaggccct     3960
tatatttgtc acacttaagt gcctgcttag ggaaggtatt gtgaaaaagt attagaaatc      4020
ttgagatcag tatctatttt atgatcagaa aaaaatactc ttttgtacat ttctgacagt      4080
tactcagaag atcgttcaag caagctaatc acagcattgt aactagagga cagttgtttg      4140
cagtgagttt ttccttaagt aggtacgatt ttttaaaata ttctgtgatt ctactctagc      4200
gtggttgttg agagagtttc aaattcagtg atacaggttc taagactgaa aggtctactt      4260
ttaatgtata tatgataact tgcagttggt ttccctctcc cctcccccc tttaccttca       4320
gtctgtgaga gcatgaccac agggtcaagg gaatcttttc cattggagtt atgtacataa      4380
aaacacatcg acattttgac atttcagatt gtgtggctac aatctgtact gctcttggga     4440
tcctttgtcc ttagaagcca aattaaggaa gagaaagcag acagagaaa aagaaagaag       4500
gaaggaggga aactttacag ggtgtgctga tttggaagta gtaactattt cttttggagt     4560
cttttttca tttttcctct ttctctttc ctggttggaa ggaagctcgg tgctgggagc        4620
ttgcaattt gttcttattc aaggtttcca acccacccc ccaccgccag tacttcatca       4680
tgttgtggtt taattctaat tggtggggg ggggaggac tagtgaggga ggtgaaagaa        4740
cagggataat tttgtaaagt gtattaaacg ttaatattca gatccagtca atacatgcag      4800
accagtaaaa tctgatttgt gcagagttct ccatctgact ctcacttatt tctgtagata     4860
tatacatata taaatacaag tatgttctta cggcacagta ttgctgacct ttagttcgag     4920
gttttgtcgg ttgttgttga ttttcttcct cttgcaagtg ctatccatgt gagtgtgtga     4980
agtttctcta ataagtaaaa cacaggcct tttccttgtt tgttttgtgt tagtttattg      5040
taaacagcca tttgttgtaa attattattg gcattaaatt ataatttatg attttcaaag    5100
caaaagacaa                                                            5110
```

<210> SEQ ID NO 12
<211> LENGTH: 3477
<212> TYPE: DNA
<213> ORGANISM: Homo sapiens

<400> SEQUENCE: 12

```
gtagtgatgt catatccgtt gtccaggtct ccacacctct ctcagcagtt aatcccttta      60
tctattcctt gggtcaaaac ttttgaggtg ggctagctat atagcagcgg gggagagggt     120
aaactggggc gcgcggttg gaggcgcttc agcaccgcgg ccagcgccca ctgcagccca      180
acccactctc tagagctccc ggactcctag ctctgagaat gcctgcggaa tgatcgcccc     240
ccagggcggc tgccgccgct gccgctgctg ctgttattgc tactgctgct gccgccgcct     300
ctgcttccac tcggctctga ctggcaggca gaaagtgcaa ctgacgaggg aaaggtctct     360
gcagtgagtg gagagcctac ataaaagaga gtaaagaggg gcaaaaaccc agatcagaat     420
gcaggcgacg tccaaccttc tcaacctcct gctgctgtct ttgtttgccg gattagatcc     480
ttccaagact cagattagtc ctaaagaagg gtggcaggtg tacagctcag ctcaggatcc     540
tgatgggcgg tgcatttgca cagttgttgc tccagaacaa aacctgtgtt cccgggatgc     600
caaaagcagg caacttcgcc aactactgga aaaggttcag aacatgtccc agtctattga     660
agtcttaaac ttgagaactc agagagattt ccaatatgtt ttaaaaatgg aaacccaaat     720
gaaagggctg aaggcaaaat tcggcagat tgaagatgat cgaaagacac ttatgaccaa     780
gcattttcag gagttgaaag agaaaatgga cgagctcctg cctttgatcc ccgtgctgga     840
acagtacaaa acagatgcta agttaatcac ccagttcaag gaggaaataa ggaatctgtc     900
tgctgtcctc actggtattc aggaggaaat tggtgcctat gactacgagg aactacacca     960
agagtgctg agcttggaaa caagacttcg tgactgcatg aaaaagctaa catgtggcaa    1020
actgatgaaa atcacaggcc cagttacagt caagacatct ggaacccgat ttggtgcttg    1080
gatgacagac cctttagcat ctgagaaaaa caacagagtc tggtacatgg acagttatac    1140
taacaataaa attgttcgtg aatacaaatc aattgcagac tttgtcagtg ggctgaatc     1200
aaggacatac aaccttcctt tcaagtgggc aggaactaac catgttgtct acaatggctc    1260
actctatttt aacaagtatc agagtaatat catcatcaaa tacagctttg atatggggag    1320
agtgcttgcc caacgaagcc tggagtatgc tggttttcat aatgtttacc ctacacatg     1380
gggtggattc tctgacatcg acctaatggc tgatgaaatc gggctgtggg ctgtgtatgc    1440
aactaaccag aatgcaggca atattgtcat cagccaactt aaccaagata ccttggaggt    1500
gatgaagagc tggagcactg gctaccccaa gagaagtgca ggggaatctt tcatgatctg    1560
tgggacactg tatgtcacca actcccactt aactggagcc aaggtgtatt attcctattc    1620
caccaaaacc tccacatatg agtacacaga cattcccttc cataaccaat actttcacat    1680
atccatgctt gactacaatg caagagatcg agctctctat gcctggaaca atggccacca    1740
ggtgctgttc aatgtcaccc ttttccatat catcaagaca gaggatgaca cataggcaaa    1800
tgtgacatgt tttcattgat ttaaacagtg tgatttgtga taaactctat aagacccctt    1860
ccgttttttt cttcactatt attttcatc atttctccaa agcaaagcat ttttattgta    1920
aagttggtgt ttcaaaaaca tagctgagct tgtctaactt accatgttgg aaacacatct    1980
taacttctaa atttacaagg cctatcatgt ccttgtcatg aaaagcacta aaaaaaaaa     2040
gagtttaagt ggctaaagtc atagttttgc aagagattaa tgatctgcct tatattagag    2100
```

| | |
|---|---:|
| tcagagacta atggtggctt aaatgcacga atgtctttt ttttaaaact gtcattttt | 2160 |
| actgtctttt gctccatatc aggaaatatt ttggtaggaa ttaggagaac aaaaagcact | 2220 |
| tttatcccat ttatttcttt aaaaaatgta aggatttcat ttatattgaa aataatatt | 2280 |
| aatcattttg ctgttaacac aattctctga tgcggtgctg tacagtcatt tttaaatctc | 2340 |
| ttgctaacat tttattggca gtatgtattt ctaccattgt aaccaccatt gtgctattgt | 2400 |
| atctcttcac ttctgtgaaa gtaatatttt ttataaaata cactgaaatt taacctcagt | 2460 |
| aattgagtcc attttcaagt gtggtcaaga ataatcttct tggcttaccc ctttacataa | 2520 |
| gcattataaa ctaaaatgaa aaccaaacca gacacctgac atagagtctt tattttaccc | 2580 |
| caagtttttt gggccactga cattgaatgc aacaactgat ttcatacaac tgagttactc | 2640 |
| tgttcactcc actgaatgca acccatatag tttcttgcac aaggtgcatc tggattccaa | 2700 |
| atattggatt tgagttgact ctactcattt attatacact aaagaaattt tgttcttcat | 2760 |
| agttaaatgt actagcattt aatttatatt ttacatacaa cttgcaataa tgaaattcct | 2820 |
| tatgtcagga ccctgaaaat aagcacattt gaaaactctt agaaaaaaaa aattctgtaa | 2880 |
| tgtcctctag atttagatta tgagccctga ggagttattg gcaagatttg tgcaaaataa | 2940 |
| aatatgggga gacttgggag ttgtctttgt ggtttcaaaa gtgtaaataa ccaattcaga | 3000 |
| aaacaaaatg gaaaaacgac cccttgttac cttgattcac tgtatgtgga aaaataatgt | 3060 |
| aaccaaaagg gaagagcttt aataatactt atgttaataa ctctatgaaa catataagct | 3120 |
| aactatatat caaacatttc attgagtttg gatgtatttt ccacatatta aaaaaatagt | 3180 |
| tccctaaggc agctttatgg aaactaatat aggttggttt tacaatttaa aaagtatatt | 3240 |
| ctataataaa taataaaaca aattgtttta aatgtttagt ttcacacata catagtacca | 3300 |
| tgattttctt tgaaagataa ggatgtaatg atttagataa agcatcatgt aaagaaatcc | 3360 |
| taacatttaa gtgtaattca tttcaaatgt cacaagtaaa gcatcatcct caaatatctc | 3420 |
| actgtcaaaa ttgtagaatt aaataaccca atcttgaaac tgtcaaaaaa aaaaaaa | 3477 |

<210> SEQ ID NO 13
<211> LENGTH: 5849
<212> TYPE: DNA
<213> ORGANISM: Homo sapiens

<400> SEQUENCE: 13

| | |
|---|---:|
| gcgttccttg cggcccggcc gacctcgcgg gcttgggcct gggcgggcac cgacggagcg | 60 |
| gccctggctg cagcctcccg gcgccagcga agacaggctg agatgcggct gctcctgctc | 120 |
| gtgccgctgc tgctggctcc agcgcccggg tcctcggctc ccaaggtgag gcggcagagt | 180 |
| gacacctggg gaccctggag ccagtggagc ccctgcagcc ggacctgtgg aggggtgtc | 240 |
| agcttccggg agcgcccctg ctactcccag aggagagatg gaggctccag ctgcgtgggc | 300 |
| cccgccggac gccaccgctc ttgtcgcacg gagagctgcc ccgacggcgc ccggacttc | 360 |
| cgggccgagc agtgcgcgga gttcgacgga gcggagttcc aggggcggcg gtatcggtgg | 420 |
| ctgccctact acagcgcccc aaacaagtgt gaactgaact gcattcccaa gggggagaac | 480 |
| ttctactaca gcacaggga ggctgtggtt gatgggacgc cctgcgagcc tggcaagagg | 540 |
| gatgtctgtg tggatggcag ctgccggtt gtcggctgtg atcacgagct ggactcgtcc | 600 |
| aagcaggagg acaagtgtct gcggtgtggg ggtgacggca cgacctgcta ccccgtcgca | 660 |
| ggcaccttg acgctaatga cctcagccga gctgtgaaga atgttcgtgg ggaatactac | 720 |
| ctcaatgggc actggaccat cgaggcggcc cgggccctgc cagcagccag caccatcctg | 780 |

```
cattacgagc ggggtgctga gggggacctg gcccctgagc gactccatgc ccggggcccc   840
acctcggagc ccctggtcat cgagctcatc agccaggagc ccaaccccgg tgtgcactat   900
gagtaccacc tgcccctgcg ccgcccagc cccggcttca gctggagcca cggctcatgg    960
agtgactgca gcgcggagtg tggcggaggt caccagtccc gcctggtgtt ctgcaccatc  1020
gaccatgagg cctaccccga ccacatgtgc cagcgccagc cacggccagc tgaccggcgt  1080
tcctgcaatc ttcacccttg cccggagacc aagcgctgga aggcagggcc atgggcaccc  1140
tgctcagcct cctgtggagg aggctcccag tcccgctccg tgtactgcat ctcgtctgac  1200
ggggccggca tccaggaggc cgtggaggag gctgagtgtg ccgggctgcc tgggaagccc  1260
cctgccattc aggcctgtaa cctgcagcgc tgtgcagcct ggagcccgga gccctgggga  1320
gagtgttctg tcagttgtgg cgttggcgtc cggaagcgga gcgttacttg ccggggtgaa  1380
aggggttctt tgctccatac cgcagcgtgc tccttggaag accggccacc tctgactgag  1440
ccctgtgtgc atgaggactg ccccctcctc agtgaccagg cctggcatgt tggcacctgg  1500
ggtctatgct ccaagagctg cagctcgggc actcggaggc gacaggtcat ctgtgccatt  1560
gggccgccca gccactgcgg gagcctgcag cactccaagc ctgtggatgt ggagccttgt  1620
aacacgcagc cctgtcatct cccccaggag gtccccagca tgcaggatgt gcacacccct  1680
gccagcaacc cctggatgcc gttgggccct caggagtccc ctgcctcaga ctccagaggc  1740
cagtggtggg cagcccagga acaccctca gccagggtg accacagggg agaacgaggt   1800
gaccccaggg gcgaccaagg cacccacctg tcagccctgg gccccgctcc ctctctgcag  1860
cagcccccat accagcaacc cctgcggtcg ggctcagggc ccacgactg cagacacagt    1920
cctcacgggt gctgccccga tggccacacg gcatctctcg ggcctcagtg caaggctgc   1980
cctggggccc cctgtcagca gagcaggtac gggtgctgcc ctgacagggt atctgtcgct  2040
gagggggccc atcacgctgg ctgcacaaag tcgtatggtg gtgacagcac cggggggcatg 2100
cccaggtcaa gggcagtggc ttctacagtc cacaacaccc accagcccca ggcccagcag  2160
aatgagccca gtgagtgccg gggctcccag tttggctgtt gctatgacaa cgtggccact  2220
gcagccggtc ctcttgggga aggctgtgtg gccagccca gccatgccta ccccgtgcgg   2280
tgcctgctgc ccagtgccca tggctcttgc gcagactggg ctgcccgctg gtacttcgtt  2340
gcctctgtgg gccaatgtaa ccgcttctgg tatggcggct ccatggcaa tgccaataac   2400
tttgcctcgg agcaagagtg catgagcagc tgccagggat ctctccatgg gccccgtcgt  2460
ccccagcctg gggcttctgg aaggagcacc cacacgatg tggcggcag cagtcctgca   2520
ggcgagcagg aacccagcca gcacaggaca ggggccgcgg tgcagagaaa gccctggcct  2580
tctggtggtc tctggcggca agaccaacag cctgggccag ggggaggcccc ccacacccag 2640
gcctttggag aatggccatg ggggcaggag cttgggtcca gggcccctgg actgggtgga  2700
gatgccggat caccagcgcc acccttccac agctcctcct acaggattag cttggcaggt  2760
gtggagccct cgttggtgca ggcagccctg gggcagttgg tgcggctctc ctgctcagac  2820
gacactgccc cggaatccca ggctgcctgg cagaaagatg ccagcccat tcctctgac   2880
aggcacaggc tgcagttcga cggatccctg atcatccacc cctgcaggc agaggacgcg  2940
ggcacctaca gctgtggcag cacccggcca ggccgcgact cccagaagat ccaacttcgc  3000
atcataggggg gtgacatggc cgtgctgtct gaggctgagc tgagccgctt ccctcagccc  3060
agggacccag ctcaggactt tggccaagcg ggggctgctg ggcccctggg ggccatcccc  3120
```

```
tcttcacacc cacagcctgc aaacaggctg cgtttggacc agaaccagcc ccgggtggtg    3180
gatgccagtc caggccagcg gatccggatg acctgccgtg ccgaaggctt cccgccccca    3240
gccatcgagt ggcagagaga tgggcagcct gtctcttctc ccagacacca gctgcagcct    3300
gatggctccc tggtcattag ccgagtggct gtagaagatg cgggcttcta cacctgtgtc    3360
gctttcaatg ggcaggaccg agaccagcga tgggtccagc tcagagttct gggggagctg    3420
acaatctcag gactgccccc tactgtgaca gtgccagagg gtgatacggc caggctattg    3480
tgtgtggtag caggagaaag tgtgaacatc aggtggtcca ggaacgggct acctgtgcag    3540
gctgatggcc accgtgtcca ccagtcccca gatggcacgc tgctcattta caacttgcgg    3600
gccagggatg agggctccta cacgtgcagt gcctaccagg ggagccaggc agtcagccgc    3660
agcaccgagg tgaaggtggt ctcaccagca cccaccgccc agcccaggga ccctggcagg    3720
gactgcgtcg accagccaga gctggccaac tgtgatttga tcctgcaggc ccagctttgt    3780
ggcaatgagt attactccag cttctgctgt gccagctgtt cacgtttcca gcctcacgct    3840
cagcccatct ggcagtaggg atgaaggcta gttccagccc cagtccaaaa tagttcatag    3900
ggctagggag aaaggaagat ggactcttgg cttcctctct ctggctggca aagggagtta    3960
tcttctggaa tacattagct cttttcaaaaa cccacccagt gtttagcctc aacggcagcc    4020
agttaccagc ttctctctgt agccttcagc agtgtttgca tctctgacat aaccacaggc    4080
tgctgttttc aagaagagca atctgtttgg ataagaaaaa cctttacttt acagcttccc    4140
tttataattt gttacacagg aatagttaaa tgcatttgtt tgtttgtttt ttgagacaga    4200
gtttcactct tgttgcccag gctggagggc aatggcgcga tctcagctca ctgcaacctc    4260
cgtctcctgg gttcttgatt ctcctgtgtc agccttctga gtagctagga ttacagatgc    4320
ctatcaccat gcctgggtaa ttttttgtatt tttagttgag atggggtttc accatgttgg    4380
ccaggctggt ctcgaacttc tgacctcaga tgatctgccc gcctcagcct cccaaagtgc    4440
tgggattaca ggcatgagcc accacgccca gccatcaatg catttttttt attttttttt    4500
tgagacagag tttcgcactt cttgcccagg ctggagtaca atggtgcgat cttggctcac    4560
tgcaacctcc acctcctggg ttcaagcgct tctccagcct cagcctcctg agtagctggg    4620
attacaggta tgtgccacca tgcctggcta attttgtatt tttagtagag acggggtttc    4680
tccatgttgg tcagactggt cttgaactcc cgacctcagg taatccgccc gcctcggcct    4740
cccaaaatgc tgggattaga ggtgtgagcc actgtgccca gcccatcaat gtgttttaaa    4800
gctagctgtc agggttccac ttaatttaaa gctgggcagg gagatgtgta atgatttcaa    4860
agttaacacc tgtttgtttt ctaaagggca tgccaagtcc tgctgtatca gggaagtatt    4920
ctgtgctaaa atcagcgatg gttcattgct ctagtctctc tcaccttct aggcagtgca    4980
tcagtcagct ctaaatctgg tgcagagggt taacagcata acccttgttg gcaaaatgga    5040
atagatgtta agacctcaaa tagggatttg ggatgaaaca gctgcagtta gcactgttat    5100
ctgagcatga aagaactgga aacgctcctt acgtcgagat gttggacctt gaagccctcc    5160
tgaggccaac atgcaaatct ggctgtgacg gttcatctga cacctgtgta aagctgacca    5220
gcctgctctg tacagtgaca atgaggagcc cctctcttcc ttaagtagga atctgtgaag    5280
caaaatgttt gctgccaaag acaaatcaga ctgtcagtca ttaaaaacag cattagcagg    5340
atgaggatag caatgggaa gggttgtggg caatgcagta acagggaaat ggcttcagaa    5400
atggtttgag ttggaagaca acattcttca tctctcagga cttctaattc cttgatgcta    5460
aaagaagagg catggattct atgagcttcc aagtcccttt ccactttaac cttctacaaa    5520
```

```
tctttcagag gactgcctag tagcaaaggt tattcctgga cacaggaaag acgggcatta    5580
cagggaccaa agctctgaaa ggtgactttt attaccaaca cactggctgg aaaagggaca    5640
aaccacatca cgggtgagtg atacttctca gtcttctcta ctcattcaac aaaggaaatg    5700
tgggctgggg cagaggtctt ttttcattta atactgaaaa atattgaag  agcatccatg    5760 ttcacttatg gctggttttg ctatagaaat tggaaaataa aggccacttt tttgaaatcc    5820
ccagtttaat taaaaaaaaa aaaaaaaa                                       5849

<210> SEQ ID NO 14
<211> LENGTH: 2032
<212> TYPE: DNA
<213> ORGANISM: Homo sapiens

<400> SEQUENCE: 14
actcggtgtc accacaggag gagactcagg caggccgcgc tccagcctca ccaggctccc     60
cggctcgccg tggctctctg agccccctt  tcagggaccc cagtcgctgg aacatttgcc    120
cagactcgta ccaaactttt ccgccctggg ctcgggatcc tggactccgg ggcctccccg    180
tcctcccctt tcccgggttc cagctccggc ctctggacta ggaaccgaca gcccccctcc    240
ccgcgtccct ccctctctct ccagccgttt tggggagggg ctctccacgc tccggatagt    300
tcccgagggt catccgcgcc gcactcgcct ttccgtttcg ccttcacctg gatataattt    360
ccgagcgaag ctgcccccag gatgaccacg ctggccggcg ctgtgcccag gatgatgcgg    420
ccgggcccgg ggcagaacta cccgcgtagc gggttcccgc tggaagtgtc cactcccctc    480
ggccagggcc gcgtcaacca gctcggcggt gttttatca  acggcaggcc gctgcccaac    540
cacatccgcc acaagatcgt ggagatggcc caccacggca tccggccctg cgtcatctcg    600
cgccagctgc gcgtgtccca cggctgcgtc tccaagatcc tgtgcaggta ccaggagact    660
ggctccatac gtcctggtgc catcggcggc agcaagccca agcaggtgac aacgcctgac    720
gtggagaaga aaattgagga atacaaaaga gagaacccgg gcatgttcag ctgggaaatc    780
cgagacaaat tactcaagga cgcggtctgt gatcgaaaca ccgtgccgtc agtgagttcc    840
atcagccgca tcctgagaag taaattcggg aaaggtgaag aggaggaggc cgacttggag    900
aggaaggagg cagaggaaag cgagaagaag gccaaacaca gcatcgacgg catcctgagc    960
gagcgagcct cagcaccccca atcagatgaa ggctctgata ttgactctga accagattta   1020
ccactaaaga ggaaacagcg cagaagccga accaccttca cagcagaaca gctggaggaa   1080
ctggagcgtg cttttgagag aactcattac cctgacattt atactaggga ggaactggcc   1140
cagagggcga agctcaccga ggcccgagta caggtctggt ttagcaaccg ccgtgcaaga   1200
tggaggaagc aagctgggc  caatcaactg atggctttca accatctcat tcccgggggg   1260
ttccctccca ctgccatgcc gaccttgcca acgtaccagc tgtcggagac ctcttaccag   1320
cccacatcta ttcacaagc  tgtgtcagat cccagcagca ccgttcacag acctcaaccg   1380
cttcctccaa gcactgtaca ccaaagcacg attccttcca acccagacag cagctctgcc   1440
tactgcctcc ccagcaccag gcatggattt tccagctata cagacagctt tgtgcctccg   1500
tcggggccct ccaaccccat gaaccccacc attggcaatg gcctctcacc tcaggtaatg   1560
ggactcctga ccaaccacgg tggggtacct catcagcccc agactgatta cgcgctctcc   1620
cctctcaccg ggggtctgga acctaccacc acggtgtcgg ccagctgcag tcagagacta   1680
gaccatatga agagcttgga cagtctgcca acatctcagt cctactgtcc acccacctat   1740
```

```
agcaccacag gctacagtat ggaccctgtc acaggctacc aatatgggca gtatggacaa    1800
agtaagcctt ggactttta gggggcaatt tctcctggaa gggagataaa ctcaactctt    1860
ccttaagaaa ggtgaattag aggcaagatt aagccacaca tgccggtatc aattttttt    1920 tttttttgca aagccagctg actgttccag caggggcttc cttgtgtaat tattttctta    1980
actgatgtca acaacatctt gcggttatta attgttgaga cgtgaaacct ga           2032

<210> SEQ ID NO 15
<211> LENGTH: 6969
<212> TYPE: DNA
<213> ORGANISM: Homo sapiens

<400> SEQUENCE: 15
aatattttgt gtgagagcga gcggtgcatt tgcatgttgc ggagtgatta gtgggtttga      60
aaagggaacc gtggctcggc ctcatttccc gctctggttc aggcgcagga ggaagtgttt     120
tgctggagga tgatgacaga ggtcaggctt cgctaatggg ccagtgagga gcggtggagg     180
cgaggccggg cgccggcaca cacacattaa cacacttgag ccatcaccaa tcagcatagg     240
aatctgagaa ttgctctcac acaccaaccc agcaacatcc gtggagaaaa ctctcaccag     300
caactccttt aaaacaccgt catttcaaac cattgtggtc ttcaagcaac aacagcagca     360 caaaaaccc caaccaaaca aaactcttga cagaagctgt gacaaccaga aaggatgcct     420
cataaagggg gaagacttta actaggggcg cgcagatgtg tgaggccttt tattgtgaga     480
gtggacagac atccgagatt tcagagcccc atattcgagc cccgtggaat cccgcggccc     540
ccagccagag ccagcatgca gaacagtcac agcggagtga atcagctcgg tggtgtcttt     600
gtcaacgggc ggccactgcc ggactccacc cggcagaaga ttgtagagct agctcacagc     660
ggggcccggc cgtgcgacat ttcccgaatt ctgcaggtgt ccaacggatg tgtgagtaaa     720
attctgggca ggtattacga gactggctcc atcagaccca gggcaatcgg tggtagtaaa     780
ccgagagtag cgactccaga agttgtaagc aaaatagccc agtataagcg ggagtgcccg     840
tccatctttg cttgggaaat ccgagacaga ttactgtccg agggggtctg taccaacgat     900
aacataccaa gcgtgtcatc aataaacaga gttcttcgca acctggctag cgaaaagcaa     960
cagatgggcg cagacggcat gtatgataaa ctaaggatgt tgaacgggca gaccggaagc    1020
tggggcaccc gccctggttg gtatccgggg acttcggtgc cagggcaacc tacgcaagat    1080
ggctgccagc aacaggaagg aggggggagag aataccaact ccatcagttc caacggagaa    1140
gattcagatg aggctcaaat gcgacttcag ctgaagcgga agctgcaaag aaatagaaca    1200
tcctttaccc aagagcaaat tgaggccctg gagaaagagt ttgagagaac ccattatcca    1260
gatgtgtttg cccgagaaag actagcagcc aaaatagatc tacctgaagc aagaatacag    1320
gtatggtttt ctaatcgaag ggccaaatgg agaagagaag aaaaactgag gaatcagaga    1380
agacaggcca gcaacacacc tagtcatatt cctatcagca gtagtttcag caccagtgtc    1440
taccaaccaa ttccacaacc caccacaccg gtttcctcct tcacatctgg ctccatgttg    1500
ggccgaacag acacagccct cacaaacacc tacagcgctc tgccgcctat gcccagcttc    1560
accatggcaa ataacctgcc tatgcaaccc ccagtcccca gccagacctc ctcatactcc    1620
tgcatgctgc ccaccagccc ttcggtgaat gggcggagtt atgataccta cacccccca    1680 catatgcaga cacacatgaa cagtcagcca atgggcacct cgggcaccac ttcaacagga    1740
ctcatttccc ctggtgtgtc agttccagtt caagttcccg gaagtgaacc tgatatgtct    1800
caatactggc caagattaca gtaaaaaaa aaaaaaaaaa aaaaggaaa ggaaatattg    1860
```

```
tgttaattca gtcagtgact atggggacac aacagttgag ctttcaggaa agaaagaaaa    1920
atggctgtta gagccgcttc agttctacaa ttgtgtcctg tattgtacca ctggggaagg    1980
aatggacttg aaacaaggac ctttgtatac agaaggcacg atatcagttg aacaaatct     2040 tcattttggt atccaaactt ttattcattt tggtgtatta tttgtaaatg ggcatttgta    2100
tgttataatg aaaaaaagaa caatgtagac tggatggatg tttgatctgt gttggtcatg    2160
aagttgtttt ttttttttt aaaaagaaaa ccatgatcaa caagctttgc cacgaattta     2220
agagttttat caagatatat cgaatacttc tacccatctg ttcatagttt atggactgat    2280
gttccaagtt tgtatcattc ctttgcatat aattaaacct ggaacaacat gcactagatt    2340
tatgtcagaa atatctgttg gttttccaaa ggttgttaac agatgaagtt tatgtgcaaa    2400
aaagggtaag atataaattc aaggaagaaa aaaagttgat agctaaaagg tagagtgtgt    2460
cttcgatata atccaatttg ttttatgtca aaatgtaagt atttgtcttc cctagaaatc    2520
ctcagaatga tttctataat aaagttaatt tcatttatat ttgacaagaa tatagatgtt    2580
ttatacacat tttcatgcaa tcatacgttt cttttttggc cagcaaaagt taattgttct    2640
tagatatagt tgtattactg ttcacggtcc aatcattttg tgcatctaga gttcattcct    2700
aatcaattaa aagtgcttgc aagagtttta aacttaagtg ttttgaagtt gttcacaact    2760
acatatcaaa attaaccatt gttgattgta aaaaaccatg ccaaagcctt tgtatttcct    2820
ttattataca gttttctttt taaccttata gtgtggtgtt acaaatttta tttccatgtt    2880
agatcaacat tctaaaccaa tggttacttt cacacacact ctgttttaca tcctgatgat    2940
ccttaaaaaa taatccttat agataccata aatcaaaaac gtgttagaaa aaaattccac    3000
ttacagcagg gtgtagatct gtgcccattt atacccacaa catatataca aaatggtaac    3060
atttcccagt tagccattta attctaaagc tcaaagtcta gaataatttt aaaaatgcaa    3120
caagcgatta gctaggaatt gtttttttgaa ttaggactgg cattttcaat ctgggcagat    3180
ttccattgtc agcctatttc aacaatgatt tcactgaagt atattcaaaa gtagatttct    3240
taaaggagac tttctgaaag ctgttgcctt tttcaaatag gccctctccc ttttctgtct    3300 ccctccccctt tgcacaagag gcatcatttc ccattgaacc actacagctg ttcccatttg    3360
aatcttgctt tctgtgcggt tgtggatggt tggagggtgg aggggggatg ttgcatgtca    3420
aggaataatg agcacagaca catcaacaga caacaacaaa gcagactgtg actggccggt    3480
gggaattaaa ggccttcagt cattggcagc ttaagccaaa cattcccaaa tctatgaagc    3540
agggcccatt gttggtcagt tgttatttgc aatgaagcac agttctgatc atgtttaaag    3600
tggaggcacg cagggcagga gtgcttgagc ccaagcaaag gatggaaaaa aataagcctt    3660
tgttgggtaa aaaaggactg tctgagactt tcatttgttc tgtgcaacat ataagtcaat    3720
acagataagt cttcctctgc aaacttcact aaaaagcctg ggggttctgg cagtctagat    3780
taaaatgctt gcacatgcag aaacctctgg ggacaaagac acacttccac tgaattatac    3840
tctgctttaa aaaaatcccc aaaagcaaat gatcagaaat gtagaaatta atggaaggat    3900
ttaaacatga ccttctcgtt caatatctac tgtttttag ttaaggaatt acttgtgaac     3960
agataattga gattcattgc tccggcatga aatatactaa taattttatt ccaccagagt    4020
tgctgcacat ttggagacac cttcctaagt tgcagttttt gtatgtgtgc atgtagtttt    4080
gttcagtgtc agcctgcact gcacagcagc acatttctgc aggggagtga gcacacatac    4140
gcactgttgg tacaattgcc ggtgcagaca tttctacctc ctgacatttt gcagcctaca    4200
```

```
ttccctgagg gctgtgtgct gagggaactg tcagagaagg gctatgtggg agtgcatgcc    4260
acagctgctg gctggcttac ttcttccttc tcgctggctg taatttccac cacggtcagg    4320
cagccagttc cggcccacgg ttctgttgtg tagacagcag agactttgga gacccggatg    4380
tcgcacgcca ggtgcaagag gtgggaatgg agaaaaagga gtgacgtggg agcggagggt    4440
ctgtatgtgt gcacttgggc acgtatatgt gtgctctgaa ggtcaggatt gccagggcaa    4500
agtagcacag tctggtatag tctgaagaag cggctgctca gctgcagaag ccctctggtc    4560
cggcaggatg ggaacggctg ccttgccttc tgcccacacc ctagggacat gagctgtcct    4620
tccaaacaga gctccaggca ctctcttggg gacagcatgg caggctctgt gtggtagcag    4680
tgcctgggag ttggcctttt actcattgtt gaaataattt ttgtttatta tttatttaac    4740
gatacatata tttatatatt tatcaatggg gtatctgcag ggatgttttg acaccatctt    4800
ccaggatgga gattatttgt gaagacttca gtagaatccc aggactaaac gtctaaattt    4860
tttctccaaa cttgactgac ttgggaaaac caggtgaata gaataagagc tgaatgtttt    4920
aagtaataaa cgttcaaact gctctaagta aaaaaatgca ttttactgca atgaatttct    4980
agaatatttt tcccccaaag ctatgcctcc taacccttaa atggtgaaca actggtttct    5040
tgctacagct cactgccatt tcttcttact atcatcacta ggtttcctaa gattcactca    5100
tacagtatta tttgaagatt cagctttgtt ctgtgaatgt catcttagga ttgtgtctat    5160
attcttttgc ttatttcttt ttactctggg cctctcatac tagtaagatt ttaaaaagcc    5220
ttttcttctc tgtatgtttg gctcaccaag gcgaaatata tattcttctc ttttcattt    5280 ctcaagaata aacctcatct gctttttgt tttctgtgt tttggcttgg tactgaatga    5340
ctcaactgct cggttttaaa gttcaaagtg taagtactta gggttagtac tgcttatttc    5400
aataatgttg acgtgactaa tctttggaaa gcagtaacat gctgtcttag aaatgacatt    5460
aataatgggc ttaaacaaat gaatagggg gtcccccac tctccttttg tatgcctatg    5520
tgtgtctgat ttgttaaaag atggacaggg aattgattgc agagtgtcgc ttccttctaa    5580
agtagtttta ttttgtctac tgttagtatt taaagatcct ggaggtggac ataaggaata    5640
aatggaagag aaaagtagat attgtatggt ggctactaaa aggaaattca aaagtctta    5700 gaacccgagc acctgagcaa actgcagtag tcaaaatatt tatctcatgt taaagaaagg    5760
caaatctagt gtaagaaatg agtaccatat agggttttga agttcatata ctagaaacac    5820
ttaaaagata tcatttcaga tattacgttt ggcattgttc ttaagtattt atatctttga    5880
gtcaagctga taattaaaaa aaatctgtta atggagtgta tatttcataa tgtatcaaaa    5940
tggtgtctat acctaaggta gcattattga agagagatat gtttatgtag taagttatta    6000
acataatgag taacaaataa tgtttccaga agaaaggaaa acacattttc agagtgcgtt    6060
tttatcagag gaagacaaaa atacacaccc ctctccagta gcttattttt acaaagccgg    6120
cccagtgaat tagaaaaaca aagcacttgg atatgatttt tggaaagccc aggtacactt    6180
attattcaaa atgcactttt actgagtttg aaaagtttct tttatattta aaataagggt    6240
tcaaatatgc atattcaatt tttatagtag ttatctattt gcaaagcata tattaactag    6300
taattggctg ttaattttat agacatggta gccagggaag tatatcaatg acctattaag    6360
tattttgaca agcaatttac atatctgatg acctcgtatc tcttttcag caagtcaaat    6420 gctatgtaat tgttccattg tgtgttgtat aaaatgaatc aacacggtaa gaaaaaggtt    6480
agagttatta aaataataaa ctgactaaaa tactcatttg aatttattca gaatgttcat    6540
aatgctttca aaggacatag cagagctttt gtggagtatc cgcacaacat tatttattat    6600
```

```
ctatggacta aatcaattt  ttgaagttgc tttaaaattt aaaagcacct ttgcttaata    6660
taaagcccct taattttaac tgacagatca attctgaaac tttatttga aaagaaaatg    6720
gggaagaatc tgtgtcttta gaattaaaag aaatgaaaaa aataaacccg acattctaaa   6780
aaaatagaat aagaaacctg attttagta ctaatgaaat agcgggtgac aaaatagttg    6840
tcttttgat  tttgatcaca aaaaataaac tggtagtgac aggatatgat ggagagattt   6900
gacatcctgg caaatcactg tcattgattc aattattcta attctgaata aaagctgtat   6960
acagtaaaa                                                           6969
```

<210> SEQ ID NO 16
<211> LENGTH: 3817
<212> TYPE: DNA
<213> ORGANISM: Homo sapiens

<400> SEQUENCE: 16

```
gcggggctag agctgtcgga gaagcgggac cgcgaggccg cgcgcggcg ctctgcgcgg      60
tcagagggag cgcctggcag cagcaggagc agcagcagca gcccgcggcg ggccgccgc    120
cagccgccgc gaccgccgcg gctgcagcct ccgaagggag gccgggtgag ccggcgtacg   180
cactttcccg cggactttcg gagtgttgt ggatatacat gccaagccgc cacgatgatg    240
tccatgaaca gcaagcagcc tcactttgcc atgcatccca ccctccctga gcacaagtac   300
ccgtcgctgc actccagctc cgaggccatc cggcgggcct gctgcccac gccgccgctg    360
cagagcaacc tcttcgccag cctggacgag acgctgctgg cgcgggccga ggcgctggcg   420
gccgtggaca tcgccgtgtc ccagggcaag agccatcctt tcaagccgga cgccacgtac   480
cacacgatga acagcgtgcc gtgcacgtcc acttccacgg tgcctctggc gcaccaccac   540
caccaccacc accaccacca ggcgctcgaa cccggcgatc tgctggacca catctcctcg   600
ccgtcgctcg cgctcatggc cggcgcgggc ggcgcgggcg cggcggccgg cggcggcggc   660
gcccacgacg gcccgggggg cggtggcggc ccggcggcg gcggcggccc gggcggcggc   720
cccgggggag gcggcggtgg cggcccgggg gcggcggcg gcggcccggg cggcgggctc   780
ctgggcggct ccgcgcaccc tcacccgcat atgcacagcc tgggccacct gtcgcacccc   840
gcggcggcgg ccgccatgaa catgccgtcc gggctgccgc accccgggct ggtggcggcg   900
gcggcgcacc acgcgcgggc agcggcagcg cggcggcgg cggccgggca ggtggcagcg   960
gcatcggcgg cggcggccgt ggtgggcgca gcgggcctgg cgtccatctg cgactcggac  1020
acggaccccg cgcgagctcga ggcgttcgcg gagcgcttca gcagcggcg catcaagctg  1080
ggcgtgacgc aggccgacgt gggctcggcg ctggccaacc tcaagatccc gggcgtgggc  1140
tcactcagcc agagcaccat ctgcaggttc gagtcgctca cgctctcgca caacaacatg  1200
atcgcgctca gcccatcct gcaggcgtgg ctcgaggagg ccgagggcgc ccagcgcgag  1260
aaaatgaaca gcctgagct cttcaacggc ggcgagaaga gcgcaagcg gacttccatc   1320
gccgcgcccg agaagcgctc cctcgaggcc tacttcgccg tgcagccccg gccctcgtcc   1380
gagaagatcg ccgccatcgc cgagaaactg gacctcaaaa agaacgtggt gcgggtgtgg  1440
ttttgcaacc agagacagaa gcagaagcgg atgaaattct ctgccactta ctgagggggc  1500
tgggaggtgt cgggcgggac agaatgggga gctgaggagg cattttggg gggcttcct   1560
ctgcttgcct cccctcggat ttggagtgtc cgttatcctg cctgcatttg gggagtccct   1620
tctcgctctc tttcctccac ccattctctg attttcctgc ctttgctgtc ccctagcctt   1680
```

```
gaggactggg gtgctgggtg tggggattgg agtataggt aggggagaag ggggggagca   1740
ttcgggggag tggggagtgg ggggaaggaa agcggagacc cgagcagggg ttttaaggag   1800
caggatggtt ctggggtttg ggtgggggga gacgcgggaa gggtaggaaa atggactgtt   1860
tctgaccaga gacacttacc taaatatcct ggggaccaag gaactatgta caaaaacaaa   1920
cctaccaacc accaaaaact agacaaataa agacaaacta aaacaaaaca gaacaaaagc   1980
aaaggaaaat gctttagaaa ttttaactcc ggggagccat aatctgcaac ttcattttcc   2040
cccatagaag agaaaaaaga gcaccaccat tattaccacc tccccaaccc tacacgcacg   2100
aactgagtcg aaaaacgaaa accaaacgag cgagaagttg aagttctggg tatcaaagct   2160
agttgttctg tctgcgtgtt taatttttcc ctctctcacc tccaccccat ccatatcctc   2220
tttatttcct ccgttccaat gagaggccta tggctgctct ccaatcccgg gaagtgagtg   2280
ggagcacagc tgaaaagaga gggtcagggg gaggctggct gcttgcttag gtggaatcca   2340
agttttcccg tggccctgcc tatactctgg tggcctggtc ctgttggggt ggggtctttt   2400
ggagagaagg gcatagtctt tgagctacta aaaagcagaa ttccggagct tcgagatatc   2460
ttattctagg aaaatgaaac aatttttaaca acagttttttt ttcctcttat gtcgaagatc   2520
tagttttaga caatttcaaa ataagctttt cccactcata gaactttaac ttgcccttc   2580
agttttatct tttttttaga gagaggttta aactactgat ttttcctgtt gattcaaata   2640
gactaatggg gtgaaagtta ttaggagaga tactctctcc tgttttctcc actgaacgag   2700
actcatcttg ctcttctagg tcccgtttct tcctctcttg gaggacatga aattatagaa   2760
atgttgagaa gttcctgctt tcttttgcgg taggacttgg ctgtgagaaa atcacctaaa   2820
tcccagaaaa gaggaagaca gatttaaagt gcccccaccc ccatttgttt caagaggtc   2880
tgcatgttgg gcgaaaacag aacaactgtg tttccttta cttgttctta ttattcaaga   2940
gtcatttatt acaggggata aatgttgggt agcaagaact ttaatttgca ctaccagtct   3000
cccaaataga aaatcatgta tagtatttca tagtaataat caggtacctt acaagctgct   3060
ggtggatttt aaaaaattaa gatagttgaa ggtggttagg taaaatgcct gctttgtgta   3120
caagatactc tttggatctc tcgtagagat ggtttgttac catcctttaa tcataactaa   3180
aacattgaaa acagaacaaa tgagaaaaga aaaaaaacct gccgattaac aagactgaaa   3240
tcatgcatga tctgaaaggt gtggaaagaa acacaattag gtctcactct ggttaggcat   3300
tatttatta attatgttgt atatcattgt ttgcagggca aacattctat gcatttgaaa   3360
ctgagcacta aactgggcta gctttctggt agaccgtttt gtggctagtg cgatttcaca   3420
gtctactgcc tgtttccact gaaaacattt ttgtcatatt cttgtattca agaaaaaagg   3480
aaaaagatt attgtaaata tttttattaa tgcacacatt cacacagtgg taacagactg   3540
ccagtgttca tcctgaaatg tctcacggat tgatctacct gtccatgtat gtctgctgag   3600
ctttctcctt ggttatgttt tttctctttt acctttctcc tcccttactt ctatcagaac   3660
caattctatg cgccaaaata caacagggg atgtgtccca gtacacttac aaataaaaca   3720
taactgaaag aagagcagtt ttatgatttg ggtgcgtttt tgtgtttata ctgggccagg   3780
tcctggtaga acctttcaac aaacaaccaa acaaaaa                           3817
```

<210> SEQ ID NO 17
<211> LENGTH: 8787
<212> TYPE: DNA
<213> ORGANISM: Homo sapiens

<400> SEQUENCE: 17

```
ggccgcagct ccccggcgga ggcaagaggt ggttgggggg gaccatggct gacgttttcc      60
cgggcaacga ctccacggcg tctcaggacg tggccaaccg cttcgcccgc aaaggggcgc     120
tgaggcagaa gaacgtgcac gaggtgaagg accacaaatt catcgcgcgc ttcttcaagc     180
agcccacctt ctgcagccac tgcaccgact tcatctgggg gtttgggaaa caaggcttcc     240
agtgccaagt ttgctgtttt gtggtccaca agaggtgcca tgaatttgtt acttttctt      300
gtccgggtgc ggataaggga cccgacactg atgaccccag gagcaagcac aagttcaaaa     360
tccacactta cggaagcccc accttctgcg atcactgtgg gtcactgctc tatggactta     420
tccatcaagg gatgaaatgt gacacctgcg atatgaacgt tcacaagcaa tgcgtcatca     480
atgtccccag cctctgcgga atggatcaca ctgagaagag ggggcggatt tacctaaagg     540
ctgaggttgc tgatgaaaag ctccatgtca cagtacgaga tgcaaaaaat ctaatccta      600
tggatccaaa cgggctttca gatccttatg tgaagctgaa acttattcct gatcccaaga     660
atgaaagcaa gcaaaaaacc aaaccatcc gctccacact aaatccgcag tggaatgagt       720
cctttacatt caaattgaaa ccttcagaca agaccgacg actgtctgta gaaatctggg      780
actgggatcg aacaacaagg aatgacttca tgggatccct ttcctttgga gtttcggagc     840
tgatgaagat gccggccagt ggatggtaca agttgcttaa ccaagaagaa ggtgagtact     900
acaacgtacc cattccggaa ggggacgagg aaggaaacat ggaactcagg cagaaattcg     960
agaaagccaa acttggccct gctggcaaca aagtcatcag tccctctgaa gacaggaaac    1020
aaccttccaa caaccttgac cgagtgaaac tcacggactt caatttcctc atggtgttgg    1080
gaaaggggag ttttggaaag gtgatgcttg ccgacaggaa gggcacagaa gaactgtatg    1140
caatcaaaat cctgaagaag gatgtggtga ttcaggatga tgacgtggag tgcaccatgg    1200
tagaaaagcg agtcttggcc ctgcttgaca aaccccgtt cttgacgcag ctgcactcct     1260
gcttccagac agtggatcgg ctgtacttcg tcatggaata tgtcaacggt ggggacctca    1320
tgtaccacat tcagcaagta ggaaaattta aggaaccaca agcagtattc tatgcggcag    1380
agatttccat cggattgttc tttcttcata aagaggaat catttatagg gatctgaagt      1440
tagataacgt catgttggat tcagaaggac atatcaaaat tgctgacttt gggatgtgca    1500
aggaacacat gatggatgga gtcacgacca ggaccttctg tgggactcca gattatatcg    1560
ccccagagat aatcgcttat cagccgtatg gaaaatctgt ggactggtgg gcctatggcg    1620
tcctgttgta tgaaatgctt gccgggcagc ctccatttga tggtgaagat gaagacgagc    1680
tatttcagtc tatcatggag cacaacgttt cctatccaaa atccttgtcc aaggaggctg    1740
tttctatctg caaaggactg atgaccaaac acccagccaa gcggctgggc tgtgggcctg    1800
agggggagag ggacgtgaga gagcatgcct tcttccggag gatcgactgg gaaaaactgg    1860
agaacaggga gatccagcca ccattcaagc ccaaagtgtg tggcaaagga gcagagaact    1920
ttgacaagtt cttcacacga ggacagcccg tcttaacacc acctgatcag ctggttattg    1980
ctaacataga ccagtctgat tttgaagggt tctcgtatgt caacccccag tttgtgcacc    2040
ccatcttaca gagtgcagta tgaaactcac cagcgagaac aaaacacctcc ccagccccca    2100
gccctccccg cagtgggaag tgaatcctta accctaaaat tttaaggcca cggccttgtg    2160
tctgattcca tatggaggcc tgaaaattgt agggttatta gtccaaatgt gatcaactgt    2220
tcagggtctc tcttacaa ccaagaacat tatcttagtg aagatggta cgtcatgctc       2280
agtgtccagt ttaattctgt agaagttacg tctggctcta ggttaaccct tcctagaaag    2340
```

```
caagcagact gttgccccat tttgggtaca atttgatata ctttccatac cctccatctg    2400 tggattttc  agcattggaa tcccccaacc agagatgtta aagtgagcct gtcccaggaa    2460
acatctccac ccaagacgtc tttggaatcc aagaacagga agccaagaga gtgagcaggg    2520
agggattggg ggtgggggag gcctcaaaat accgactgcg tccattctct gcctccatgg    2580
aaacagcccc tagaatctga aaggccggga taaacctaat cactgttccc aaacattgac    2640
aaatcctaac ccaaccatgg tccagcagtt accagtttaa acaaaaaaac ctcagatgag    2700
tgttgggtga atctgtcatc tggtaccctc cttggttgat aactgtcttg atacttttca    2760
ttctttgtaa gaggccaaat cgtctaagga cgttgctgaa caagcgtgtg aaatcatttc    2820
agatcaagga taagccagtg tgtacatatg ttcattttaa tctctgggag attattttc    2880 catccagggt gccatcagta atcatgccac tactcaccag tgttgttcgc aacacccac     2940 ccccacacac accaacattt tgctgcctac cttgttatcc ttctcaagaa gctgaagtgt    3000
acgccctctc cccttttgtg cttatttatt taataggctg cagtgtcgct tatgaaagta    3060
cgatgtacag taacttaatg gaagtgctga ctctagcatc agcctctacc gattgatttt    3120
cctcccttct ctagccctgg atgtccactt agggataaaa agaatatggt tttggttccc    3180
atttctagtt cacgttgaat gacaggcctg gagctgtaga atcaggaaac ccggatgcct    3240
aacagctcaa agatgttttg ttaatagaag gattttaata cgttttgcaa atgcatcatg    3300
caatgaattt tgcatgttta taaaaacct taataacaag tgaatctata ttattgatat     3360
aatcgtatca agtataaaga gagtattata ataatttat  aagacacaat tgtgctctat    3420
ttgtgcaggt tcttgtttct aatcctcttt tctaattaag ttttagctga atcccttgct    3480
tctgtgcttt ccctccctgc acatgggcac tgtatcagat agattacttt ttaaatgtag    3540
ataaaatttc aaaaatgaat ggctagttta cgtgatagat taggctctta ctacatatgt    3600
gtgtgtatat atatgtattt gattctacct gcaaacaaat ttttattggt gaggactatt    3660
tttgagctga cactccctct tagtttcttc atgtcacctt tcgtcctggt tcctccgcca    3720
ctcttcctct tggggacaac aggaagtgtc tgattccagt ctgcctagta cgttggtaca    3780
cacgtggcat tgccgcagca cctgggctga cctttgtgtg tgcgtgtgtg tgtgtttcct    3840
tcttcccttc agcctgtgac tgttgctgac tccaggggtg ggagggatgg ggagactccc    3900
ctcttgctgt gtgtactgga cacgcaggaa gcatgctgtc ttgctgcctc tgcaacgacc    3960
tgtcgtttgc tccagcatgc acaaacttcg tgagaccaac acagccgtgc cctgcaggca    4020
ccagcacgtg cttttcagag gctgcggact ttcttccagc cattgtggca ttggcctttc    4080
cagtcttggg aggagcgcgc tgctttggtg agacaccccc atgcaaggtc ctcagagtag    4140
ccgggttcta ccacaaacag aaacagaatg aaagtagctg tcagtccttg tagagagccg    4200
ctctgtttcc tcccagaagc atctcccagc taagctcgca ttatttttct cctctggctg    4260
tttgcctgaa gttcacagaa cacacaacca tgaaaggctt tttgaggtga gaggcccagg    4320
tggtcctggc aaccctgagt agaaggagag acggggtagg gaacgggccc ggccagaaaa    4380
gaaccatttc ttctgccatc ttttatgcac catagacatc gagactccag ggggtcctgg    4440
ctcccctgtc cctgcagccc tgcaggtcag tgcatgatct gggttcgtgt cctgaccagg    4500
tgctcctcct ttgatccgag gggaaaggga ctggtttata gaaagagcct aggagacaaa    4560
agggccagtc cccctgccca gaatggagca gcagcaggac agaccccac  gaggcccccc    4620 agagaggagg aagatcccac ggaggaacac atgaggttag ggacccttgt tcagcacccc    4680
aaacagcctg cctgtttaaa gcaggcagca ggcttaggcc ttccctgcaa ccccaacacc    4740
```

```
cacaagtttg tttctctagg aaacacattc actgtctcag ctggctgtta ctctctcaga   4800
ccatatggca aagtttttcca agaaaatgcc ccgacagggg tgcccagcac actgcctgag   4860
ggacaacaga catcagaaca aaccccccaga gagaaacagt caaaatcagg gcccggtgca   4920
gtgttgtcat gtggaacctg ctttatccat tgctgagtgt tgaatgtggg taatggttag   4980
ggctttccag atctcagcag ccaaagacag ttattgttgg aagactgtca tgtagataac   5040
catgagcaat ggctcgcctc agaatcagtt cataaaattc tatggtactg gcccttcgt    5100 gggtattgtg tgaaatgaga tggtggcgag gggtgcgctg tggaactgcc gcagccacgc   5160
aggaggtccc tgggggatgc tttgggaagt ccttgcccct gagcactgcc tgattgccag   5220
ggcctgtgga ggtctaggcc gcctggcaga atctagcacc gtccgaatcc ccgcaggacc   5280
catggagcta tgaccacacc aggccattca aatggctctg cattatcttc ccttggaagg   5340
tggccactcc tcggtggcag ggcctttccc tgaggctgca ggccgtgggc tggcagcccg   5400
tctcttggca tttcaattga aggtcaccag gtgctgggtt tgaaaggaag tcactggagt   5460
gctgccaggg gccgccctcc aaggttaatg agaggcccac atccaggcaa gaactaattc   5520
aaaaggcaga tcagaaacca caggagtcaa aattattgct ccggcagtgc ttcccttcct   5580
ttcatccact ggcctcgtgt ggtccatgca gggccactgt ctgccctttc tgatgccacg   5640
tattaggctt tcttactcag aatttttgata gaaaaccatg gggccaagag ctctggaagc   5700
ctggccggaa agaccaaggt tcatgcagcc caacaaatga ttgttgagca cctctcggag   5760
ccaaagtcct taggcgagtg tggtgacttc ctggaaggag gatgcagact tccagagagc   5820 cccccccaacg gacgtgctga aagggagag ggaggcgggg gctgtagtca ggaaggagcc   5880
agagaagaac agggtttggg tgcatccaga aatatgcctg cagtaggagg gagaggaagg   5940
ggtgccaccg tcaacggctt cccatcggag gtggttggtg cagatggaag tttctgtctg   6000
ctggccctca agagagtgtt ttgccaggga cacagtctgt tcctcctcag aaaacacccc   6060
ccaaatgcta acaacatccc caccagctgc tagaagcccc tttcccctcc ccaccttgaa   6120
gtagctcata gttctctggg cagagccaga ccatccagtg taccccagag gccagtaggt   6180
tcctgcccat tttcctctct ggcttcctgc caagaattat ggcagctgag gatgaatgga   6240
gaagtaaaaa caactaacac cgcacaacta acaactaaca ccgcagttcc cacctgggtt   6300
ccacttagca ggagacattt cggagggttt ttttttgtttt tgttcctgtt ttttttttttt  6360 ttgctggaat ttgttttctc agtactgaaa agagaaaaag tgacaatctt gtattttaa    6420 aagcctcgga aaggtgatac catctgacag tcatttttctc acgttggtct tctaaagtca   6480
cctatttctt gtgtgtgcac atcacaccat ttcctgtttc tttataaccc gacaagggta   6540
ggagtgcctg tttcccctgc tgggcacacc agacaatcgt aatcacaaaa cagacactga   6600
gccaggggcc caaagggtgt gatcatgaga gttaccggga cagcagtagg catgacagtc   6660
accaggaagg acaagggtgc tctgttgtta gtggccacac accaatttga caaggagtgt   6720
tgcgaaattt ttatttattt atttattttat tttgagatgg agtttcactc ttgttgccca    6780
ggctggagtg cggtggtaca atctcggctc actgcaacct ccacctccca ggttcaagcg   6840
attctcctgc ctcagcctcc caagtacctg ggactacagg tgcgtgccac cacacccagc   6900
taaattttgt gttttttagta gagatggggt ttcaccatgt tggccaggat ggtcttgaac   6960
ccctgacctc atgatctgcc tgcctcggcc tcccaaagtg ctgggattac aggcatgagc   7020
caccacgccc agccaaaata tttttttttaaa gtcatttttcc ttaagctgct tgggctacat   7080
```

```
gtgaaataca ctggacggtc aacattcctg tctcctccca tttgggctga tgcagcagat      7140
ccagggaatg ttacctgttt ctgctgctag aagatccagg aaattgggaa ggttacctga      7200
cgcacacatg gatgaaggcc atcatctaga aatggggtca accacaattg tgttaattcc      7260
gtagtgtcag ggattcttcg ggaaggtcaa cagtatgaag gattctgacc cctgtgcctc      7320
ccatttatgt gatcaggtga cagttaataa ccgtggaggt cacactcagc catccaacag      7380
ccttacagtg accctacaca aaagccccca aattccaaag acttttcctt aacctaaagg      7440
aagaaattat ttgttaattc cagtagagca actgaatata ctgggctatt tgtacttttt      7500
tatagagaac tttaataata attctttaaa aatgagtttt tagaacaaag caactgacga      7560
tttcctaaga ttccaatgcc ctggagcttg taggaggact tagcctgggt cagctggagc      7620
acccccgacc tgatctccca ctgccagatt ttcccatgct cctagggtat ggagtccacg      7680
tgggaatgac tgcaagttca ggtggaactt ggccgactga tgctctgcga gtttttaata      7740
gacactgggg acaactgctt aaggtttaga aacttccaaa ccacaggaaa gacattttta      7800
gtgtccccca tccagaggca gccctggaat aggattccca ggggtttctg gaccccttt       7860 ccttgctccg tgaggctctg tggccatctt ttggcaggag gaggatgctt ccttggctct      7920
gtgcccagac ccgcctggtc cccaggtctc tcaccttggg tgaagattca gagatgccct      7980
gtaaggattt tgcccactgg gcaactcaga aatacttcga tctcccaaga tataagaggc      8040
agcagcaaac gtgcctattg acgtctgttt catagttacc acttacgcga gtagacagaa      8100
ctcggctttt cagaaaatag gtgtcaagtc cactttataa gaacctttt ttctaaaata      8160 agataaaagg tggctttgca ttttctgatt aaacgactgt gtctttgtca cctctgctta      8220
actttaggag tatccattcc tgtgattgta gacttttgtt gatattcttc ctggaagaat      8280
atcattcttt tcttgaaggg ttggtttact agaatattca aaatcaatca tgaaggcagt      8340
tactattttg agtctaaagg ttttctaaaa attaacctca catcccttct gttagggtct      8400
ttcagaatat cttttataaa cagaagcatt tgaagtcatt gcttttgcta catgatttgt      8460
gtgtgtgaag gacataccac gtttaaatca ttaattgaaa aacatcatat aagccccaac      8520
tttgtttgga ggaagagacg gaggttgagg ttttccttc tgtataagca cctactgaca      8580
aaatgtagag gccattcaac cgtcaaacac catttggtta tatcgcagag gagacggatg      8640
tgtaaattac tgcattgctt tttttttcag tttgtataac ctctaatctc cgtttgcatg      8700
atacgctttg ttagaaacat taattgtagt ttggaagcaa gtgtgtatga ataaagataa      8760
tgatcattcc aaaaaaaaaa aaaaaaa                                         8787

<210> SEQ ID NO 18
<211> LENGTH: 3485
<212> TYPE: DNA
<213> ORGANISM: Homo sapiens

<400> SEQUENCE: 18
agtcgcccag gggagcccgg agaagcaggc tcaggaggga gggagccaga ggaaaagaag       60
aggaggagaa ggaggaggac ccggggaggg aggcgcggcg cgggaggagg aggggcgcag      120
ccgcggagcc agtggccccg cttggacgcg ctgctctcca gataccccg gagctccagc       180 cgcgcggatc gcgcgctccc gccgctctgc ccctaaactt ctgccgtagc tcccttcaa       240 gccagcgaat ttattcctta aaaccagaaa ctgaacctcg gcacgggaaa ggagtccgcg      300
gaggagcaaa accacagcag agcaagaaga gcttcagaga gcagccttcc cggagcacca      360
actccgtgtc gggagtgcag aaaccaacaa gtgagagggc gccgcgttcc cggggcgcag      420
```

```
ctgcgggcgg cgggagcagg cgcaggagga ggaagcgagc gcccccgagc cccgagcccg   480
agtccccgag cctgagccgc aatcgctgcg gtactctgct ccggattcgt gtgcgcgggc   540
tgcgccgagc gctgggcagg aggcttcgtt ttgccctggt tgcaagcagc ggctgggagc   600
agccggtccc tggggaatat gcggcgcgcg tggatcctgc tcaccttggg cttggtggcc   660
tgcgtgtcgg cggagtcgag agcagagctg acatctgata agacatgta ccttgacaac    720 agctccattg aagaagcttc aggagtgtat cctattgatg acgatgacta cgcttctgcg   780
tctggctcgg gagctgatga ggatgtagag agtccagagc tgacaacatc tcgaccactt   840
ccaaagatac tgttgactag tgctgctcca aaagtggaaa ccacgacgct gaatatacag   900
aacaagatac ctgctcagac aaagtcacct gaagaaactg ataagagaa agttcacctc    960 tctgactcag aaaggaaaat ggacccagcc gaagaggata caaatgtgta tactgagaaa  1020
cactcagaca gtctgtttaa acggacagaa gtcctagcag ctgtcattgc tggtggagtt  1080
attggctttc tctttgcaat ttttcttatc ctgctgttgg tgtatcgcat gagaaagaag  1140
gatgaaggaa gctatgacct tggagaacgc aaaccatcca gtgctgctta tcagaaggca  1200
cctactaagg agttttatgc gtaaaactcc aacttagtgt ctctatttat gagatcactg  1260
aacttttcaa ataaagcttt tgcatagaa taatgaagat cttttgttttt tgttttcatt   1320 aaagagccat tctggcactt taatgataaa atcccattgt atttaaaaca tttcatgtat  1380
ttctttagaa caacataaaa ttaaaattta acatctgcag tgttctgtga atagcagtgg  1440
caaaatatta tgttatgaaa accctcgatg ttcatggaat tggtttaaac ttttatgcgc  1500
aaatacaaaa tgattgtctt tttcctatga ctcaaagatg aaagctgttt catttgtgtc  1560
agcatgtctc agattgacct taccaagttg gtcttacttt gttaatttat ctgttgtccc  1620
cttcctctcc tctgccctcc cttcttgtgc ccttaaaacc aaaccctatg ccttttgtag  1680
ctgtcatggt gcaatttgtc tttggaaaat tcagataatg gtaatttagt gtatatgtga  1740
ttttcaaata tgtaaacttt aacttccact ttgtataaat ttttaagtgt cagactatcc  1800
attttacact tgcttttattt ttcattacct gtagctttgg gcagatttgc aacagcaaat  1860
taatgtgtaa aattggatta ttactacaaa accgttttagt catatctatc taatcagatc  1920
ttcttttggg aggatttgat gtaagttact gacaagcctc agcaaaccca aagatgttaa  1980
cagtatttta agaagttgct gcagattcct ttggccactg tatttgttaa tttcttgcaa  2040
tttgaaggta cgagtagagg tttaaagaaa aatcagtttt tgttcttaaa aatgcattta  2100
agttgtaaac gtcttttttaa gcctttgaag tgcctctgat tctatgtaac ttgttgcaga  2160
ctggtgttaa tgagtatatg taacagttta aaaaaaaagt tggtatttta taagcacaga  2220
caattctaat ggtaactttt gtagtcttat gaatagacat aaattgtaat ttgggaacat  2280
aaaaactact gaataaatca tgtggcctaa tattgaaaat gtcactgtta taaattttgt  2340
acatttttga tcaaatgtac atctccccctt tgctaacggc cgtctgctct caaggatgac  2400
gtgggtttga tttctaagtg tttcacagtg tctgtaaatc aagaccaaag agcctgtcga  2460
tgagactgtt tattaccaga ttcacttctg aattggccag aggaaatctg aatgtattat  2520
cctgtgtgtg tctaggtaga gatattggaa ggctgccagg ggatttcgaa gtttgcaacc  2580
tttataggat aactgatggc aatattaaga cagacgcctg cttttgcaaa taacttacaa  2640
gactgtaaat tccaaagatc tgaatggggc tttcctgatg ttggtatcta aggcttaggc  2700
ctatagattg atttaccttt ggaattgtgc tccaaatgtc tactgaagct taaccgaaga  2760
```

| | |
|---|---:|
| actaataaat ggactacagt agctcacgtt acagggaagg agggtaggca gggaggctct | 2820 |
| gtgtgttaaa atgagggtct cactgcttta ggattgaagt ggctggaaag agtgatgcct | 2880 |
| ggggaaggag atggagttat gagggtactg tggctggtac tttctgtact aaacatttcc | 2940 |
| tttttctatt ttaccactaa ttttgtttta aactgtgagc cgtccaagtc agaagaagac | 3000 |
| agcaaaaaaa gcaacttttc caacatacaa tttactttta ataaagtatg aatatttcat | 3060 |
| tttgagaaca ttccctggaa ttgccacata attcattaaa acatttttt taagcaacac | 3120 |
| ttggaacagt gtttacttta aatccttaat ggccttaatt aattctcaga ttcctgcccc | 3180 |
| atcacttaca gaaccaattc actttagagt gactaaaagg aaacgatagc ctagctttct | 3240 |
| aaagccacgc tgtgtccctc aattacagag ggtaggaatg ggtatacctc taactgtgca | 3300 |
| aagcagagtg aaattcaatt catagaataa caactgctgg gaatatccgt gccaggaaaa | 3360 |
| gaaaaatttc tggcaaatat tttgtcactg ctgtaaagca aaatatttgt gaaagtgcca | 3420 |
| aaataaagtc tgtcatgcca aaagtaaatc attgtataga ctgacatcca gttttcttca | 3480 |
| actgt | 3485 |

<210> SEQ ID NO 19
<211> LENGTH: 4108
<212> TYPE: DNA
<213> ORGANISM: Homo sapiens

<400> SEQUENCE: 19

| | |
|---|---:|
| ccggccgtct atgctccagg ccctctcctc gcggtgccgg tgaacccgcc agccgccccg | 60 |
| atgtacagca tgatgatgga gaccgacctg cactcgcccg gcggcgccca ggcccccacg | 120 |
| aacctctcgg gccccgccgg ggcgggcggc ggcggggggcg gaggcggggg cggcggcggc | 180 |
| ggcgggggcg ccaaggccaa ccaggaccgg gtcaaacggc ccatgaacgc cttcatggtg | 240 |
| tggtcccgcg ggcagcggcg caagatggcc caggagaacc ccaagatgca caactcggag | 300 |
| atcagcaagc gcctggggc cgagtggaag gtcatgtccg aggccgagaa gcggccgttc | 360 |
| atcgacgagg ccaagcggct gcgcgcgctg cacatgaagg agcacccgga ttacaagtac | 420 |
| cggccgcgcc gcaagaccaa gacgctgctc aagaaggaca gtactcgct ggccggcggg | 480 |
| ctcctggcgg ccggcgcggg tggcggcggc gcggctgtgg ccatgggcgt gggcgtgggc | 540 |
| gtgggcgcgg cggccgtggg ccagcgcctg gagagcccag gcggcgcggc gggcggcggc | 600 |
| tacgcgcacg tcaacggctg gccaacggc gcctacccccg gctcggtggc ggcggcggcg | 660 |
| gcggccgcgg ccatgatgca ggaggcgcag ctggcctacg gcagcaccc gggcgcgggc | 720 |
| ggcgcgcacc cgcacgcgca ccccgcgcac ccgcacccgc accacccgca cgcgcacccg | 780 |
| cacaacccgc agcccatgca ccgctacgac atgggcgcgc tgcagtacag ccccatctcc | 840 |
| aactcgcagg gctacatgag cgcgtcgccc tcgggctacg gcggcctccc ctacggcgcc | 900 |
| gcggccgccg ccgccgccgc tgcggcggc gcgcaccaga actcggccgt ggcggcggcg | 960 |
| gcggcggcg cggccgcgtc gtcgggcgcc ctggcgcgc tgggctctct ggtgaagtcg | 1020 |
| gagcccagcg gcagcccgcc cgccccagcg cactcgcggg cgccgtgccc cggggacctg | 1080 |
| cgcgagatga tcagcatgta cttgcccggc gcgaggggg cgacccggc ggcggcagca | 1140 |
| cggccgcgg cgcagagccg gctgcactcg ctgccgcagc actaccaggg cgcgggcgcg | 1200 |
| ggcgtgaacg gcacggtgcc cctgacgcac atctagcgcc ttcgggacgc cggggactct | 1260 |
| gcggcggcga cccacgagct cgcggcccgc gcccggctcc cgcccgccc cggcgcggcg | 1320 |
| tggcttttgt acagacgttc ccacattctt gtcaaaagga aaatactgga gacgaacgcc | 1380 |

```
gggtgacgcg tgtcccccac tcaccttccc cggagaccct ggcgaccgcc gggcgctgac    1440
accagacttg ggttttagac tgaacttcgg tgttttcttg agactttttg tacagtattt    1500
atcacctacg gaggaagcgg aaagcgtttt ctttgctcga ggggacaaaa aagtcaaaac    1560
gaggcgagag gcgaagccca cttttgtata ccggccggcg cgctcacttt cctccgcgtt    1620
gcttccggac ggcgccgacc gccggagccc aagtgacgcg gagctcgtcg catttgttat    1680
aaatgtagta aggcaggtcc aagcacttac aagttttttg tagttgttac cgctcttttg    1740
ggttggtttg ttaatttata caaagagatt accaccacca cccctcctt cagacggcgg    1800 agttatattc tgggttttgt aaaactttat gtatctgagc atttccattt ttttttttgg    1860
gttttgtatt atttcttgta aatgcattgt gaaaatttt attttcggcg ttgcaatgcg    1920
gggaggagaa gtcagattat gtacatagtt ttctaaaaag cctttcttct aaaaacgaaa    1980
aaagaccccc cacccaaaat gtttcgagtc aacaaattta agagacagag cccatttttct   2040 ccataaattt gtaacatgct atttttatgt gcatgtttta tgagttcaaa atgcaatgag    2100
gaaatctgac agggaaatta tctgtatgaa ctaaagtaa gggaaccccg gggaatggga    2160
ggacaggatt tttcaaggaa cctttttcaa tgaaagagaa ggaagttaaa acctataggt    2220
tattttgtag agctgagtgt taatacgggc cgagaaataa aagtatcttc tgctccggct    2280
gtttcactgc ggacggctgg ggctgctgcg cgttaccttg ctgcaagcgg ggcgccttcc    2340
acctggctgg gggtctgcgc cacagtttgg tccagaggag ggaggaggaa gggaagaccc    2400
cagtggtggg accctggacc aggccatgga tgaaggacaa agaccagggc aggtcacggg    2460
tttcccaatt ccccagcaat taagatttcg agcagaattt atctaaatgt gtttcaagga    2520
aacacaatcg ctgaaccaaa acgtactgca gccgagcccc ctccgtccat cctctgcccc    2580 tcccctggc ttctttctct tgggaaaacg ggcaaaataa ttgtgctgga ttctcacaca    2640
cacagaaata tcgaccatca ccctcccccg cgtgaactgg gatgcaagtt gctaaccgat    2700
gtgaacgcaa aatgccttgt tcattattcc tgacgagatc ttgaggttgt ttgatgcttt    2760
aaatttttta attatattat tttctaggtg tttattggta cattgcagtt ttttttttga    2820
aatttaaaaa tttctgtaaa actttgtctt caagtaatct gacagcatta aatattgcat    2880
ttaaaaatta tactgtagca aatacattta aaaattaatc acaacgttaa gatgaaatta    2940 tattttgga aaaaaaaaac acttgaagcc cagatggaaa tacgtttatt tcagcagcct    3000
taggtttccc ctcgctttct caacacccctt ccttgtcctg gagtatggac tgtccgtcca    3060
aaagtgagcc tatgctataa gtttaatgag aaccgaattc agcctgcatt cgagaatagc    3120
tttaagtata atgctgatct gacaattgac gtgtaatttg ggaagtcatt ttgataattt    3180
tgcttaaacc actcattcgt taaagtgatt acaaaaaagt tcaagaatga tgtccactgc    3240
tttctaacaa gataataaac ccccccctc ttttctttt ctttattttt atttctttta    3300
gctatttgat cctttctgaa gcagttgttt ctggaagagt ctgtgcgccc atggatggct    3360
gagcaccact acgacttagt ccgggataag ggcctcccca gtcctctccg ggagatgatt    3420
tgggaaattt tataatgctt gttctgttaa ctcaccggga ccttgagggt ccaatgggac    3480
cttgagggtt ttctctgaaa tatacaaact taaaggactc tctctgaggt tctttgactg    3540
acgtccactc tcagtctggc ccctgtgctc ccctgtgtgt accctggagt ttctgtgtcc    3600
aattgttggc atctaggtct tggctcaaga ttaggatgtg ggcccacttt tagaggcaca    3660
gactatgaaa agctgagtta gtgcgcccgg gacgccaggc aagcagcttt tacagtttgg    3720
```

| | |
|---|---|
| catcttattg caggtgcttc gtgcacagtc agctgaaata gccaatgcca ggtgctccaa | 3780 |
| ccaccttatt tccttgtttt gttgattaga acaacacaga aaaaagcaaa tataaatttt | 3840 |
| taatgactcc atttaaaaat atcacagggt gggggcaagg aaattagctg agattcatct | 3900 |
| caggattgag attctatccc cccttccccg cccccagcag tgtcgctcca attcaaatta | 3960 |
| gtggagaaaa gattacagta ggccctgagc cgactgtgaa ttcggtgctt ggccaaggta | 4020 |
| acactcatcg tattcacgga gtgaaatact atatgatgat agttattata ttatatgacg | 4080 |
| acttcattca cttcccaaat cacagggt | 4108 |

<210> SEQ ID NO 20
<211> LENGTH: 5621
<212> TYPE: DNA
<213> ORGANISM: Homo sapiens

<400> SEQUENCE: 20

| | |
|---|---|
| aagaaaatcc tgcttgacaa aaaccgtcac ttaggaaaag atgtcctttc gggcagccag | 60 |
| gctcagcatg aggaacagaa ggaatgacac tctggacagc acccggaccc tgtactccag | 120 |
| cgcgtctcgg agcacagact tgtcttacag tgaaagcgac ttggtgaatt ttattcaagc | 180 |
| aaattttaag aaacgagaat gtgtcttctt taccaaagat tccaaggcca cggagaatgt | 240 |
| gtgcaagtgt ggctatgccc agagccagca catggaaggc acccagatca accaaagtga | 300 |
| gaaatggaac tacaagaaac acaccaagga atttcctacc gacgcctttg gggatattca | 360 |
| gtttgagaca ctggggaaga aagggaagta tacgtctg tcctgcgaca cggacgcgga | 420 |
| aatcctttac gagctgctga cccagcactg gcacctgaaa acacccaacc tggtcatttc | 480 |
| tgtgaccggg ggcgccaaga acttcgccct gaagccgcgc atgcgcaaga tcttcagccg | 540 |
| gctcatctac atcgcgcagt ccaaaggtgc ttggattctc acgggaggca cccattatgg | 600 |
| cctgatgaag tacatcgggg aggtggtgag agataacacc atcagcagga gttcagagga | 660 |
| gaatattgtg gccattggca tagcagcttg gggcatggtc tccaaccggg acaccctcat | 720 |
| caggaattgc gatgctgagg gctattttt agcccagtac cttatggatg acttcacaag | 780 |
| agatccactg tatatcctgg acaacaacca cacacatttg ctgctcgtgg acaatggctg | 840 |
| tcatggacat cccactgtcg aagcaaagct ccggaatcag ctagagaagt atatctctga | 900 |
| gcgcactatt caagattcca actatggtgg caagatcccc attgtgtgtt ttgcccaagg | 960 |
| aggtggaaaa gagactttga agccatcaa tacctccatc aaaaataaaa ttccttgtgt | 1020 |
| ggtggtggaa ggctcgggcc agatcgctga tgtgatcgct agcctggtgg aggtggagga | 1080 |
| tgccctgaca tcttctgccg tcaaggagaa gctggtgcgc ttttaccccc gcacggtgtc | 1140 |
| ccggctgcct gaggaggaga ctgagagttg gatcaaatgg ctcaaagaaa ttctcgaatg | 1200 |
| ttctcaccta ttaacagtta ttaaaatgga agaagctggg gatgaaattg tgagcaatgc | 1260 |
| catctcctac gctctatca aagccttcag caccagtgag caagacaagg ataactggaa | 1320 |
| tgggcagctg aagcttctgc tggagtgaa ccagctggac ttagccaatg atgagatttt | 1380 |
| caccaatgac cgccgatggg agtctgctga ccttcaagaa gtcatgttta cggctctcat | 1440 |
| aaaggacaga cccaagtttg tccgcctctt tctggagaat ggcttgaacc tacgaagtt | 1500 |
| tctcacccat gatgtcctca ctgaactctt ctccaaccac ttcagcacgc ttgtgtaccg | 1560 |
| gaatctgcag atcgccaaga attcctataa tgatgccctc tcacgtttg tctggaaact | 1620 |
| ggttgcgaac ttccgaagag gcttccggaa ggaagacaga aatggcccgg acgagatgga | 1680 |
| catagaactc cacgacgtgt ctcctattac tcggcacccc ctgcaagctc tcttcatctg | 1740 |

```
ggccattctt cagaataaga aggaactctc caaagtcatt tgggagcaga ccaggggctg    1800
cactctggca gccctgggag ccagcaagct tctgaagact ctggccaaag tgaagaacga    1860
catcaatgct gctggggagt ccgaggagct ggctaatgag tacgagaccc gggctgttga    1920
gctgttcact gagtgttaca gcagcgatga agacttggca gaacagctgc tggtctattc    1980
ctgtgaagct tggggtggaa gcaactgtct ggagctggcg gtggaggcca cagaccagca    2040
tttcatcgcc cagcctgggg tccagaattt tcttctaag caatggtatg gagagatttc     2100
ccgagacacc aagaactgga agattatcct gtgtctgttt attataccct tggtgggctg    2160
tggctttgta tcatttagga agaaacctgt cgacaagcac aagaagctgc tttggtacta    2220
tgtggcgttc ttcacctccc ccttcgtggt cttctcctgg aatgtggtct tctacatcgc    2280
cttcctcctg ctgtttgcct acgtgctgct catggatttc cattcggtgc acaccccccc    2340
cgagctggtc ctgtactcgc tggtctttgt cctcttctgt gatgaagtga cagtggta     2400 cgtaaatggg gtgaattatt ttactgacct gtggaatgtg atggacacgc tggggctttt    2460
ttacttcata gcaggaattg tatttcggct ccactcttct aataaaagct ctttgtattc    2520
tggacgagtc attttctgtc tggactacat tattttcact ctaagattga tccacatttt    2580
tactgtaagc agaaacttag gacccaagat tataatgctg cagaggatgc tgatcgatgt    2640
gttcttcttc ctgttcctct tgcggtgtg gatggtggcc tttggcgtgg ccaggcaagg    2700
gatccttagg cagaatgagc agcgctggag gtggatattc cgttcggtca tctacgagcc    2760
ctacctggcc atgttcggcc aggtgcccag tgacgtggat ggtaccacgt atgactttgc    2820
ccactgcacc ttcactggga atgagtccaa gccactgtgt gtggagctgg atgagcacaa    2880
cctgccccgg ttccccgagt ggatcaccat cccctggtg tgcatctaca tgttatccac     2940
caacatcctg ctggtcaacc tgctggtcgc catgtttggc tacacggtgg gcaccgtcca    3000
ggagaacaat gaccaggtct ggaagttcca gaggtacttc ctggtgcagg agtactgcag    3060
ccgcctcaat atccccttcc ccttcatcgt cttcgcttac ttctacatgg tggtgaagaa    3120
gtgcttcaag tgttgctgca aggagaaaaa catggagtct tctgtctgct gtttcaaaaa    3180
tgaagacaat gagactctgg catgggaggg tgtcatgaag gaaaactacc ttgtcaagat    3240
caacacaaaa gccaacgaca cctcagagga aatgaggcat cgatttagac aactggatac    3300
aaagcttaat gatctcaagg gtcttctgaa agagattgct aataaaatca ataaaactg     3360 tatgaactct aatggagaaa aatctaatta tagcaagatc atattaagga atgctgatga    3420
acaatttgtc tatcgactac taaatgagag attttcagac ccctgggtac atggtggatg    3480 atttttaaatc accctagtgt gctgagacct tgagaataaa gtgtgtgatt ggtttcatac    3540
ttgaagacga atataaagga agaatatttc ctttatgtgt ttctccagaa tggtgcctgt    3600
ttctctctgt gtctcaatgc ctgggactgg aggttgatag tttaagtgtg ttcttaccgc    3660 ctccttttc cttaatctt attttttgatg aacacatata taggagaaca tctatcctat    3720
gaataagaac ctggtcatgc tttactcctg tattgttatt ttgttcattt ccaattgatt    3780 ctctacttt cccttttttg tattatgtga ctaattagtt ggcatattgt taaaagtctc     3840
tcaaattagg ccagattcta aaacatgctg cagcaagaga accccgctct cttcaggaaa    3900
agtgttttca tttctcagga tgcttcttac ctgtcagagg aggtgacaag gcagtctctt    3960
gctctcttgg actcaccagg ctcctattga aggaaccacc cccattccta aatatgtgaa    4020
aagtcgccca aaatgcaacc ttgaaaggca ctactgactt tgttcttatt ggatactcct    4080
```

```
cttattattt ttccattaaa aataatagct ggctattata gaaaatttag accatacaga    4140
gatgtagaaa gaacataaat tgtccccatt accttaaggt aatcactgct aacaatttct    4200
ggatggtttt tcaagtctat ttttttttcta tgtatgtctc aattctcttt caaaatttta   4260
cagaatgtta tcatactaca tatatacttt ttatgtaagc ttttcactt agtatttat     4320 caaatatgtt tttattatat tcatagcctt cttaaacatt atatcaataa ttgcataata   4380
ggcaacctct agcgattacc ataattttgc tcattgaagg ctatctccag ttgatcattg   4440
ggatgagcat ctttgtgcat gaatcctatt gctgtatttg ggaaaatttt ccaaggttag   4500
attccaataa atatctattt attattaaat attaaaatat ctatttatta ttaaaaccat   4560
ttataaggct ttttcataaa tgtatagcaa ataggaatta ttaacttgag cataagatat   4620
gagatacatg aacctgaact attaaaataa aatattatat ttaacccta gtttaagaag    4680 aagtcaatat gcttatttaa atattatgga tggtgggcag atcacttgag gtcaggagtt   4740
cgagaccagc ctggccaaca tggcaaaacc acatctctac taaaaataaa aaaattagct   4800
gggtgtggtg gtgcactcct gtaatcccag ctactcagaa ggctgaggta caagaattgc   4860
tggaacctgg gaggcggagg ttgcagtgaa ccaagattgc accactgcac tccagccggg   4920
gtgacagagt gagactccga ctgaaaataa ataaataaat aaataaataa ataaataaat   4980
attatggatg gtgaagggaa tggtatagaa ttggagagat tatcttactg aacacctgta   5040
gtcccagctt tctctggaag tggtcgtatt tgagcaggat gtgcacaagg caattgaaat   5100
gcccataatt agtttctcag ctttgaatac actataaact cactggctga aggaggaaat   5160
tttagaagga agctactaaa agatctaatt tgaaaaacta caaagcatt aactaaaaaa    5220 gtttattttc cttttgtctg ggcagtagtg aaaataacta ctcacaacat tcactatgtt   5280
tgcaaggaat taacacaaat aaaagatgcc ttttactta aacaccaaga cagaaaactt    5340
gcccaatact gagaagcaac ttgcattaga gagggaactg ttaaatgttt tcaacccagt   5400
tcatctggtg gatgtttttg caggttactc tgagaatttt gcttatgaaa aatcattatt   5460
tttagtgtag ttcacaataa tgtattgaac atacttctaa tcaaaggtgc tatgtccttg   5520
tgtatggtac taaatgtgtc ctgtgtactt ttgcacaact gagaatcctg cagcttggtt   5580
taatgagtgt gttcatgaaa taaataatgg aggaattgtc a                      5621
```

<210> SEQ ID NO 21
<211> LENGTH: 2284
<212> TYPE: DNA
<213> ORGANISM: Homo sapiens

<400> SEQUENCE: 21

```
gcggtgccgc cgccgtggc cgcctcagcc caccagccgg gaccgcgagc catgctgtcc      60
gccgcccgcc cccagggttg ttaaagccag actgcgaact ctcgccactg ccgccaccgc    120
cgcgtcccgt cccaccgtcg cgggcaacaa ccaaagtcgc cgcaactgca gcacagagcg    180
ggcaaagcca ggcaggccat ggggctctgg cgctgttgc ctggctgggt ttctgctacg    240
ctgctgctgg cgctggccgc tctgcccgca gccctggctg ccaacagcag tggccgatgg    300
tggggtattg tgaacgtagc ctcctccacg aacctgctta cagactccaa gagtctgcaa    360
ctggtactcg agcccagtct gcagctgttg agccgcaaac agcggcgtct gatacgccaa    420
aatccgggga tcctgcacag cgtgagtggg gggctgcaga gtgccgtgcg cgagtgcaag    480
tggcagttcc ggaatcgccg ctggaactgt cccactgctc cagggcccca cctcttcggc    540
aagatcgtca accgaggctg tcgagaaacg gcgtttatct tcgctatcac ctccgccggg    600
```

```
gtcacccatt cggtggcgcg ctcctgctca gaaggttcca tcgaatcctg cacgtgtgac      660
taccggcggc gcggcccggg gggccccgac tggcactggg ggggctgcag cgacaacatt      720
gacttcggcc gcctcttcgg ccgggagttc gtggactccg gggagaaggg gcgggacctg      780
cgcttcctca tgaaccttca caacaacgag gcaggccgta cgaccgtatt ctccgagatg      840
cgccaggagt gcaagtgcca cgggatgtcc ggctcatgca cggtgcgcac gtgctggatg      900
cggctgccca cgctgcgcgc cgtgggcgat gtgctgcgcg accgcttcga cggcgcctcg      960
cgcgtcctgt acggcaaccg cggcagcaac cgcgcttcgc gggcggagct gctgcgcctg     1020
gagccggaag acccggccca caaaccgccc tccccccacg acctcgtcta cttcgagaaa     1080
tcgcccaact tctgcacgta cagcggacgc ctgggcacag caggcacggc agggcgcgcc     1140
tgtaacagct cgtcgcccgc gctggacggc tgcgagctgc tctgctgcgg caggggccac     1200
cgcacgcgca cgcagcgcgt caccgagcgc tgcaactgca ccttccactg gtgctgccac     1260
gtcagctgcc gcaactgcac gcacacgcgc gtactgcacg agtgtctgtg aggcgctgcg     1320
cggactcgcc cccaggaacg ctctcctcga gccctccccc aaacagactc gctagcactc     1380
aagacccggt tattcgccca cccgagtacc tccagtcaca ctccccgcgg ttcatacgca     1440
tcccatctct cccacttcct cctacctggg gactcctcaa accacttgcc tggggcggca     1500
tgaaccctct gccatcctg atggacctgc cccggaccta cctccctccc tctccgcggg     1560 agacccttg ttgcactgcc ccctgcttgg ccaggaggtg agagaaggat gggtcccctc     1620
cgccatgggg tcggctcctg atggtgtcat tctgcctgct ccatcgcgcc agcgaccttct    1680 ctgcctctct tcttcccctt tgtcctgcgt tttctccggg tcctcctaag tcccttccta    1740
ttctcctgcc atgggtgcag accctgaacc cacacctggg catcagggcc tttctcctcc    1800
ccacctgtag ctgaagcagg aggttacagg gcaaaagggc agctgtgatg atgtggaaat    1860
gaggttgggg gaaccagcag aaatgccccc attctcccag tctctgtcgt ggagccattg    1920
aacagctgtg agccatgcct ccctgggcca cctcctaccc cttcctgtcc tgcctcctca    1980
tcagtgtgta aataatttgc actgaaacgt ggatacagag ccacgagttt ggatgttgta    2040
aataaaacta tttattgtgc tgggtcccag cctggtttgc aaagaccacc tccaacccaa    2100
cccaatccct ctccactctt ctctcctttc tccctgcagc cttttctggt ccctcttctc    2160
tcctcagttt ctcaaagatg cgtttgcctc ctggaatcag tatttccttc cactgtagct    2220
attagcggct cctcgccccc accagtgtag catcttcctc tgcagaataa aatctctatt    2280
ttta                                                                 2284

<210> SEQ ID NO 22
<211> LENGTH: 2417
<212> TYPE: DNA
<213> ORGANISM: Homo sapiens

<400> SEQUENCE: 22
gcagcagaga ggagttgagg gcgatgagag cgggtactgc gaactgccgg gcgatgctgt       60
cgctgccgcc gtgatacgga gagcaacagt tccccagcaa cacccctccc cgacacaggc      120
acacaccccc cgacaggcac gcacacccac cccacagtgc ccggctcggc tgcgcctcct      180
ctattggccc aggaagccca cccagccccg ccacgcagag cccagaagga agaaagcct      240 catgcctgag ccgaggggag caccatggat ctgacaaaaa tggcatgat ccagctgcag       300 aaccctagcc accccacggg gctactgtgc aaggccaacc agatgcggct ggccgggact      360
```

```
ttgtgcgatg tggtcatcat ggtggacagc caggagttcc acgcccaccg gacggtgctg        420
gcctgcacca gcaagatgtt tgagatcctc ttccaccgca atagtcaaca ctatactttg        480
gacttcctct cgccaaagac cttccagcag attctggagt atgcatatac agccacgctg        540
caagccaagg cggaggacct ggatgacctg ctgtatgcgg ccgagatcct ggagatcgag        600
tacctggagg aacagtgcct gaagatgctg agaccatcc aggcctcaga cgacaatgac         660
acggaggcca ccatggccga tggcggggcc gaggaagaag aggaccgcaa ggctcggtac        720
ctcaagaaca tcttcatctc gaagcattcc agcgaggaga gtgggtatgc cagtgtggct        780
ggacagagcc tccctgggcc catggtggac cagagccctt cagtctccac ttcatttggt        840
ctttcagcca tgagtcccac caaggctgca gtggacagtt tgatgaccat aggacagtct       900
ctcctgcagg gaactcttca gccacctgca gggcccgagg agccaactct ggctgggggt        960
gggcggcacc ctggggtggc tgaggtgaag acggagatga tgcaggtgga tgaggtgccc       1020
agccaggaca gccctgggc agccgagtcc agcatctcag agggatggg ggacaaggtt        1080 gaggaaagag gcaaagaggg gcctgggacc ccgactcgaa gcagcgtcat caccagtgct      1140
agggagctac actatgggcg agaggagagt gccgagcagg tgccaccccc agctgaggct      1200
ggccaggccc ccactggccg acctgagcac ccagcacccc cgcctgagaa gcatctgggc      1260
atctactccg tgttgcccaa ccacaaggct gacgctgtat tgagcatgcc gtcttccgtg       1320
acctctggcc tccacgtgca gctgccctg gctgtctcca tggacttcag cacctatggg        1380
gggctgctgc cccagggctt catccagagg gagctgttca gcaagctggg ggagctggct      1440
gtgggcatga agtcagagag ccggaccatc ggagagcagt gcagcgtgtg tggggtcgag      1500
cttcctgata cgaggctgt ggagcagcac aggaagctgc acagtgggat gaagacgtac       1560
gggtgcgagc tctgcgggaa gcggttcctg gatagtttgc ggctgagaat gcacttactg      1620
gctcattcag cgggtgccaa agcctttgtc tgtgatcagt gcggtgcaca gttttcgaag      1680
gaggatgccc tggagacaca caggcagacc catactggca ctgacatggc cgtcttctgt      1740
ctgctgtgtg gaagcgcttt ccaggcgcag agcgcactgc agcagcacat ggaggtccac      1800
gcgggcgtgc gcagctacat ctgcagtgag tgcaaccgca ccttcccag ccacacggct       1860 ctcaaacgcc acctgcgctc acatacaggc gaccaccct acgagtgtga gttctgtggc       1920
agctgcttcc gggatgagag cacactcaag agccacaaac gcatccacac gggtgagaaa     1980
ccctacgagt gcaatggctg tgcaagaag ttcagcctca agcatcagct ggagacgcac       2040
tatagggtgc acacaggtga gaagcccttt gagtgtaagc tctgccacca gcgctccgg       2100 gactactcgg ccatgatcaa gcacctgaga acgcacaacg gcgcctcgcc ctaccagtgc      2160
accatctgca gagtactg ccccagcctc tcctccatgc agaagcacat gaagggccac        2220
aagcccgagg agatcccgcc cgactggagg atagagaaga cgtacctcta cctgtgctat      2280
gtgtgaaggg aggcccgcgg cggtggagcc gagcggggag ccaggaaaga agagttggag      2340
tgagatgaag gaaggactat gacaaataaa aaggaaaag aaaaaaaaaa acagaaggaa      2400
aaggaaaaaa aaaaaaa                                                      2417
```

<210> SEQ ID NO 23
<211> LENGTH: 2057
<212> TYPE: DNA
<213> ORGANISM: Homo sapiens

<400> SEQUENCE: 23

```
atattgtgct tccaccactg ccaataacaa ataactagc aaccatgaag tgggtggaat         60
```

```
caattttttt aattttccta ctaaatttta ctgaatccag aacactgcat agaaatgaat        120
atggaatagc ttccatattg gattcttacc aatgtactgc agagataagt ttagctgacc        180
tggctaccat attttttgcc cagtttgttc aagaagccac ttacaaggaa gtaagcaaaa        240
tggtgaaaga tgcattgact gcaattgaga acccactgg agatgaacag tcttcagggt         300
gtttagaaaa ccagctacct gcctttctgg aagaactttg ccatgagaaa gaaattttgg        360
agaagtacgg acattcagac tgctgcagcc aaagtgaaga gggaagacat aactgttttc       420
ttgcacacaa aaagcccact ccagcatcga tcccactttt ccaagttcca gaacctgtca        480
caagctgtga agcatatgaa gaagacaggg agacattcat gaacaaattc atttatgaga       540
tagcaagaag gcatcccttc ctgtatgcac ctacaattct tctttgggct gctcgctatg        600
acaaaataat tccatcttgc tgcaaagctg aaaatgcagt tgaatgcttc caaacaaagg       660
cagcaacagt tacaaaagaa ttaagagaaa gcagcttgtt aaatcaacat gcatgtgcag       720
taatgaaaaa ttttgggacc cgaactttcc aagccataac tgttactaaa ctgagtcaga       780
agtttaccaa agttaatttt actgaaatcc agaaactagt cctggatgtg gcccatgtac       840
atgagcactg ttgcagagga gatgtgctgg attgtctgca ggatggggaa aaaatcatgt       900
cctacatatg ttctcaacaa gacactctgt caaacaaaat aacagaatgc tgcaaactga       960
ccacgctgga acgtggtcaa tgtataattc atgcagaaaa tgatgaaaaa cctgaaggtc       1020
tatctccaaa tctaaacagg tttttaggag atagagattt taaccaattt tcttcagggg       1080
aaaaaaatat cttcttggca agttttgttc atgaatattc aagaagacat cctcagcttg       1140
ctgtctcagt aattctaaga gttgctaaag gataccagga gttattggag aagtgtttcc       1200
agactgaaaa ccctcttgaa tgccaagata aggagaaga agaattacag aaatacatcc        1260
aggagagcca agcattggca aagcgaagct gcggcctctt ccagaaacta ggagaatatt       1320
acttacaaaa tgcgtttctc gttgcttaca caagagaagc cccccagctg acctcgtcgg       1380
agctgatggc catcaccaga aaaatggcag ccacagcagc cacttgttgc caactcagtg       1440 aggacaaaact attggcctgt ggcgaggag cggctgacat tattatcgga cacttatgta       1500
tcagacatga aatgactcca gtaaaccctg gtgttggcca gtgctgcact tcttcatatg       1560
ccaacaggag gccatgcttc agcagcttgg tggtggatga acatatgtc cctcctgcat        1620 tctctgatga caagttcatt ttccataagg atctgtgcca agctcagggt gtagcgctgc       1680
aaacgatgaa gcaagagttt ctcattaacc ttgtgaagca aaagccacaa ataacagagg       1740
aacaacttga ggctgtcatt gcagatttct caggcctgtt ggagaaatgc tgccaaggcc       1800
aggaacagga agtctgcttt gctgaagagg acaaaaact gatttcaaaa actcgtgctg       1860
ctttgggagt ttaaaattact tcaggggaag agaagacaaa acgagtcttt cattcggtgt       1920
gaacttttct ctttaatttt aactgattta acacttttg tgaattaatg aaatgataaa        1980
gacttttatg tgagatttcc ttatcacaga aataaaatat ctccaaatgt ttccttttca       2040
aaaaaaaaaa aaaaaaa                                                      2057

<210> SEQ ID NO 24
<211> LENGTH: 3001
<212> TYPE: DNA
<213> ORGANISM: Homo sapiens

<400> SEQUENCE: 24
ggggccgcca ccggcccatg agccccggcc tcaaagtttg cggcgggcgg gcgggcgcgg         60
```

-continued

| | |
|---|---|
| agcctccaag atgccgttcc acccggtgac ggcggcgttg atgtaccggg gcatctacac | 120 |
| cgtgcccaac ctgctgtcgg agcagcgccc ggtggacatc ccggaggacg agctggagga | 180 |
| gatccgagag gccttcaagg tgtttgaccg tgacggcaat ggcttcatct ccaagcagga | 240 |
| gctgggcaca gccatgcgct cactgggtta catgcccaac gaggtggagc tggaggtcat | 300 |
| catccagcgg ctggacatgg atggtgatgg tcaagtggac tttgaggagt tgtgacccct | 360 |
| tctgggaccc aaactctcca cctcagggat cccagagaag ttccatggca ccgactttga | 420 |
| tactgtcttc tggaagtgcg acatgcagaa gctgacggtg gatgagctga agcggctgct | 480 |
| ctacgacacc ttctgcgagc acctgtccat gaaggacata gagaacatca tcatgacgga | 540 |
| ggaggagagc cacctgggca cagccgagga gtgtcccgtg gatgtggaga cctgctccaa | 600 |
| ccagcagatc cgccagactt gcgtgcgcaa gagtctcatc tgcgccttcg ccatcgcctt | 660 |
| catcatcagt gtcatgctca ttgcggccaa ccaggtgctg cgcagtggca tgaagtagac | 720 |
| gccacctgga tgccccatcc accgcatgcg gtgcccgtgg cccgcccac accaccgccg | 780 |
| cctgcagacc tctcccttgg ccggctccct gggccgccat ctgcgtgtac ttcagggcct | 840 |
| gggtatccag cgagccctcc ccacccaccc acggtcctca cctggagctg tggcctggct | 900 |
| gtggagggcc ggtggtggc tctgaggatg gtccccagcc ccaccctgtc cccaccctgg | 960 |
| cctgtaagga gcactcactc ttcctaccat ccagggctc ctgggaaatt aaggagggat | 1020 |
| ttgcacagga accccagga cccagtcgct gctgtggtcc cttgggcagg agcgggcacc | 1080 |
| ctgtgccttg agacagcagc ctatctgggg ccacacagcc aacccagccc tggtccctga | 1140 |
| ggtctgccca gggcacaggg cacaggcagg gacagaaagc cttctcctgg gggagggtgg | 1200 |
| gaagccaggg tgtcctgggc cttgctgcct ggcatagcct gaggaggccc ctggtcttct | 1260 |
| ccttgggccc cttcctctga ccctcgttgg accccaaccc agaccccctt ttctccatgt | 1320 |
| acctgctggg ccagcccatt tcacaggtga ggaacccgag gctcagggcc ccgagacttg | 1380 |
| gcctcagttc ttccttccac agggattttc aggaaaggca gaagctcgtg gaggatgggc | 1440 |
| atctgaggtg gccctgcagc ccccaccctt ctggccctcc caccagaggc ccagctacca | 1500 |
| aggccacatt gtccaccacc ccagcctaga gcctagaact gtagtccagc tgaggaagga | 1560 |
| ggcagagctg gggcctgaag gctctgagca gcctccagcc aggggctcc tccagggctg | 1620 |
| aactttggga gggcccctgt actacctcct gggccaagaa actggcacag ccccacactg | 1680 |
| tcagtgccaa gaggctgcgc caggccactc tctcagccca gggcctgccc tcctgtcctc | 1740 |
| ccacttctct acgccctcaa ggttggagac cccgctccca tgccccagct gtgccatccc | 1800 |
| aaatacttgg gcagcagctc agcatgggca gacatggggg ctgtggattc ttccagggcg | 1860 |
| gggatggcag atggagccct ggggctcctt gggcctagag ccacttctta ccaggcaacg | 1920 |
| ggcacagcca cctggcaca ccctctgcct ggccgtgctg aacctctgct ggtcccaagg | 1980 |
| gagaagggag tgagcgtggg tcacctgggg aaaatctcat ctgattccct ccttgcccga | 2040 |
| cctctgctag gggctggaga acagagctca gagcacccag tgtagggaaa cacagccaga | 2100 |
| ccactgtggt gacagacttt ctttataaac atttggaagt tttctccccc atcttcttaa | 2160 |
| gaagcagggg ggcaggtgga ggagagtgag gggagagctg cccggtgcag acccaggacg | 2220 |
| agggctgcac ttggtgtggc cgtgtcctga gcctcagtga ggctgggcag atggtctcgg | 2280 |
| agcctccatg gggcgtagca ggaaccgggc ttggcttcct attgtgactg atgagaaaag | 2340 |
| tgaccacgtg ggggtcagtc gggggcaagg ggctcagccc cactggactc tgggctgcag | 2400 |
| aggccacccc ccaggtgggg gtgcccgcag ggatggaggc agctcctgaa ctggtggcca | 2460 |

```
gcccacgggg tactggaaga cagtggttct gatgggttca gccctagaga gagagagaga    2520
agcggggaga ataagagtgc actacagccc aggcttatgc cacccccagc ccacctgcct    2580
caccaccctg gctgtgggga gggtcagctg cctgcatgac ttttctggaa ggcagagcct    2640
cgaaaatagg cagaccgttt gagccagcga cctcacctct aggaactgag cccaaggaaa    2700
tagcggggtt gcaggcagac attgagctgc gagacaatgg gaataacctt cgtgtccacc    2760
tgtgggggac tgattcaata catatgcacg tccacagcag agaatgccat gcggcctgtg    2820
taagaattaa ggcagattta tatgcactga tgaggaaaga catactgtgt gatagggaga    2880
aaaagcagct tataaaataa tgtatatagc atgatactat ttttgtttaa aaatatataa    2940
aatatataaa tgcataaaaa aatcctggaa gacacagcaa aaaaaaaaa aaaaaaaaa     3000 a                                                                   3001

<210> SEQ ID NO 25
<211> LENGTH: 2855
<212> TYPE: DNA
<213> ORGANISM: Homo sapiens

<400> SEQUENCE: 25
cctggcaatc ccatgtggac ttctggtaga atgagcaatg caaagaactg gcttggactt      60
ggcatgtcct tgtacttctg ggggctgatg gaccttacga ccaccgttct ctcggacacc     120
ccaacaccac aaggtgaatt agaagcactc ctgtcagaca agccacagtc acatcagcgg     180
accaagagga gctgggtttg gaaccagttt ttcgttctgg aagagtacac tgggaccgac     240
cctttgtatg tcggcaagct tcattcagat atggacaggg gagacggatc catcaaatac     300
atcctctcgg gagaaggtgc tggcatcgtg tttaccatcg acgacaccac tggagacatc     360
cacgccattc agaggctcga ccgagaggaa agagcccagt atactctaag ggctcaagcc     420
ctagacaggc ggacgggcag gccaatggag cccgagtcag agttcatcat caaaattcaa     480
gacatcaatg acaatgagcc caagttcctg gacggacctt atgtggccac tgtgccagaa     540
atgtcccctg tgggtacctc cgtcatccaa gtgacagcca cagatgcaga tgacccgacc     600
tacggcaaca gtgccagggt ggtgtacagc attcttcagg gccagccata ttttctgtg     660 gactctaaaa caggtgtaat taggacagcg ctcatgaaca tggacagaga agccaaagaa     720
tactacgaag tgattatcca agccaaggac atgggagggc agcttggagg attagctggg     780
accacaacag tcaacatcac cctctcagat gtcaatgata cccaccccg ctttccccag     840 aaacattacc agatgagtgt gttggaatca gctccaatta gctccactgt cgggagagtg     900
tttgccaagg acttggatga aggcatcaat gcagagatga aatatactat tgtggatgga     960
gatggtcagc atgcctttga cattagcaca gatcccaatt ccaagttgg tatcataact    1020 gtgaagaagc ccctgagttt tgaaagcaag aaaagctaca ccttaaaggt ggagggagcc    1080
aatcctcacc tagagatgcg ttttctgaac ttgggcccat tcaggacac aacaacagtg    1140 cacatcagtg tggaagacgt ggacgagccc cctgtgtttg aacctggctt ttactttgtg    1200
gaggtgcctg aggatgtggc gattggaaca accatacaga tcatttctgc caaggaccca    1260
gatgtgacca caactcaat cagatactcc attgataaga gcagtgaccc tggaagattt    1320
ttctatgttg acattacaac aggtgcccta atgacagcaa gaccctaga ccgggaagaa    1380 ttttcttggc ataatatcac tgtccttgct atggaaatga acaatccctc ccaggttgga    1440
agtgttcctg tcacaatcaa agtcttagat gtgaatgaca atgctccaga gttccccaga    1500
```

| | |
|---|---|
| ttctatgaag cttttgtctg tgagaacgcc aaggcaggac agctgatcca gacagtgagt | 1560 |
| gcggtggacc aagatgaccc acgcaatggt cagcatttct actacagctt ggctcctgag | 1620 |
| gctgctaaca accccaactt taccataagg gacaaccaag ataacacagc acggattcta | 1680 |
| accaggaggt ctggtttccg gcagcaggag cagagtgtct ttcacctgcc tatcctgata | 1740 |
| gcagatagcg ggcagcccgt gctgagcagc acaggcacac tgaccatcca agtgtgcagc | 1800 |
| tgtgatgacg acggccacgt catgtcctgc agcccagagg cctacatgct cccagtcagt | 1860 |
| ttgagccggg gcgccctcat tgccatcctc gcctgcatct ttgtcctctt agtgctggtg | 1920 |
| ttgctcattt tgtccatgag gcggcaccgg aaacaaccat acatcatcga cgacgaggaa | 1980 |
| aacatccacg agaacatcgt ccgctacgac gacgagggcg gcggcgagga ggacaccgag | 2040 |
| gccttcgaca tcgcggccat gtggaacccc cgggaggcgc aggcggggc cgcccccaag | 2100 |
| acgcggcagg acatgctgcc cgagatcgag agcctctccc gctacgtgcc tcagacgtgc | 2160 |
| gcagtgaaca gcactgtcca cagctacgtg ctggccaagc tctacgaggc cgacatggac | 2220 |
| ctgtgggcac cgcccttcga ctccctccag acgtatatgt tcgagggga cggctctgtg | 2280 |
| gcggggtcgc tgagctccct gcagtcggcc acgtcggact cggaacagag cttcgacttc | 2340 |
| ctgacggact gggggcccg cttccggaag ctggccgagc tctacggggc gtcggaggga | 2400 |
| cccgcgccgc tgtggtgacg gaagccagga ggcaggcgcg cgtccaaatc cagacgttct | 2460 |
| ccgcgggtgc ttcgcggaca aggtgcagcc aaccacacga gcaatactgt gctggagagt | 2520 |
| gagaatgggg gtgagcaggc gaacagagct ctctctggat cagctttact gggtagatt | 2580 |
| aagttaaata agcaaaagga aacccagaag gaagagggca gaatctttaa ttacctttt | 2640 |
| ttcttttctt tttgattttt ctgacactgt gtgcgaaggc ttggagtcca aggtgttctg | 2700 |
| acaagggtgg cttttctctg ccattcgcta aggccttttgt cacttttcca ccacagaaag | 2760 |
| gctctggcct tggatacaga gatgccaatt gaaagcagaa agttctactc tcgtatctgt | 2820 |
| tttttatctt atcttattct ccatttaaga gtttt | 2855 |

<210> SEQ ID NO 26
<211> LENGTH: 3452
<212> TYPE: DNA
<213> ORGANISM: Homo sapiens

<400> SEQUENCE: 26

| | |
|---|---|
| gtctcagttc ccgagcctgg gagcaaccgc agcttctagt atccagactc cagcgccgcc | 60 |
| ccgggcgcgg accccaaccc cgacccgag cttctccagc ggcggcgcag cgagcagggc | 120 |
| tccccgcctt aacttcctcc gcggggccca gccaccttcg ggagtccggg ttgcccacct | 180 |
| gcaaactctc cgccttctgc acctgccacc cctgagccag cgcggcgcc cgagcgagtc | 240 |
| atggccaacg cggggctgca gctgttgggc ttcattctcg ccttcctggg atggatcggc | 300 |
| gccatcgtca gcactgccct gccccagtgg aggatttact cctatgccgg cgacaacatc | 360 |
| gtgaccgccc aggccatgta cgaggggctg tggatgtcct gcgtgtcgca gagcaccggg | 420 |
| cagatccagt gcaaagtctt tgactccttg ctgaatctga gcagcacatt gcaagcaacc | 480 |
| cgtgccttga tggtgttgg catcctcctg ggagtgatag caatctttgt ggccaccgtt | 540 |
| ggcatgaagt gtatgaagtg cttggaagac gatgaggtgc agaagatgag gatggctgtc | 600 |
| attgggggtg cgatatttct tcttgcaggt ctggctattt tagttgccac agcatggtat | 660 |
| ggcaatagaa tcgttcaaga attctatgac cctatgaccc cagtcaatgc caggtacgaa | 720 |
| tttggtcagg ctctcttcac tggctggct gctgcttctc tctgccttct gggaggtgcc | 780 |

```
ctactttgct gttcctgtcc ccgaaaaaca acctcttacc caacaccaag gccctatcca    840
aaacctgcac cttccagcgg gaaagactac gtgtgacaca gaggcaaaag gagaaaatca    900
tgttgaaaca aaccgaaaat ggacattgag atactatcat taacattagg accttagaat    960
tttgggtatt gtaatctgaa gtatggtatt acaaaacaaa caaacaaaca aaaaacccat   1020
gtgttaaaat actcagtgct aaacatggct taatcttatt ttatcttctt tcctcaatat   1080
aggagggaag attttccat ttgtattact gcttcccatt gagtaatcat actcaactgg    1140 gggaagggt gctccttaaa tatatataga tatgtatata tacatgtttt tctattaaaa    1200
atagacagta aaatactatt ctcattatgt tgatactagc atacttaaaa tatctctaaa   1260
ataggtaaat gtatttaatt ccatattgat gaagatgttt attggtatat tttcttttc    1320 gtctatatat acatatgtaa cagtcaaata tcatttactc ttcttcatta gctttgggtg   1380
cctttgccac aagacctagc ctaatttacc aaggatgaat tctttcaatt cttcatgcgt   1440 gccctttca tatacttatt ttattttta ccataatctt atagcacttg catcgttatt    1500
aagcccttat ttgttttgtg tttcattggt ctctatctcc tgaatctaac acatttcata   1560
gcctacattt tagtttctaa agccaagaag aatttattac aaatcagaac tttggaggca   1620
aatctttctg catgaccaaa gtgataaatt cctgttgacc ttcccacaca atccctgtac   1680
tctgacccat agcactcttg tttgctttga aaatatttgt ccaattgagt agctgcatgc   1740
tgttccccca ggtgttgtaa cacaacttta ttgattgaat ttttaagcta cttattcata   1800
gttttatatc ccctaaaact accttttgt tccccattcc ttaattgtat tgttttccca    1860
agtgtaatta tcatgcgttt tatatcttcc taataaggtg tggtctgttt gtctgaacaa   1920
agtgctagac tttctggagt gataatctgg tgacaaatat tctctctgta gctgtaagca   1980
agtcacttaa tctttctacc tctttttct atctgccaaa ttgagataat gatacttaac    2040
cagttagaag aggtagtgtg aatattaatt agtttatatt actctcattc tttgaacatg   2100
aactatgcct atgtagtgtc tttatttgct cagctggctg agacactgaa gaagtcactg   2160
aacaaaacct acacacgtac cttcatgtga ttcactgcct tcctctctct accagtctat   2220
ttccactgaa caaaacctac acacatacct tcatgtggtt cagtgccttc ctctctctac   2280 cagtctatttt ccactgaaca aaacctacgc acataccttc atgtggctca gtgccttcct   2340
ctctctacca gtctatttcc attctttcag ctgtgtctga catgtttgtg ctctgttcca   2400
ttttaacaac tgctcttact tttccagtct gtacagaatg ctatttcact tgagcaagat   2460
gatgtaatgg aaagggtgtt ggcattggtg tctggagacc tggatttgag tcttggtgct   2520
atcaatcacc gtctgtgttt gagcaaggca tttggctgct gtaagcttat tgcttcatct   2580
gtaagcggtg gtttgtaatt cctgatcttc ccacctcaca gtgatgttgt ggggatccag   2640
tgagatagaa tacatgtaag tgtggttttg taatttaaaa agtgctatac taagggaaag   2700
aattgaggaa ttaactgcat acgttttggt gttgcttttc aaatgtttga aaacaaaaaa   2760
aatgttaaga aatgggtttc ttgccttaac cagtctctca agtgatgaga cagtgaagta   2820
aaattgagtg cactaaacaa ataagattct gaggaagtct tatcttctgc agtgagtatg   2880
gcccgatgct ttctgtggct aaacagatgt aatgggaaga aataaaagcc tacgtgttgg   2940
taaatccaac agcaagggag attttgaat cataataact cataaggtgc tatctgttca    3000
gtgatgccct cagagctctt gctgttagct ggcagctgac gctgctagga tagttagttt   3060
ggaaatggta cttcataata aactcacaca ggaaagtcag ccactgtgtc ttatgaggaa   3120
```

| | |
|---|---|
| ttggacctaa taaattttag tgtgccttcc aaacctgaga atatatgctt ttggaagtta | 3180 |
| aaatttaaat ggcttttgcc acatacatag atcttcatga tgtgtgagtg taattccatg | 3240 |
| tggatatcag ttaccaaaca ttacaaaaaa attttatggc ccaaaatgac caacgaaatt | 3300 |
| gttacaatag aatttatcca attttgatct ttttatattc ttctaccaca cctggaaaca | 3360 |
| gaccaataga cattttgggg ttttataata ggaatttgta taaagcatta ctcttttttca | 3420 |
| ataaattgtt ttttaattta aaaaaaggat ta | 3452 |

<210> SEQ ID NO 27
<211> LENGTH: 4676
<212> TYPE: DNA
<213> ORGANISM: Homo sapiens

<400> SEQUENCE: 27

| | |
|---|---|
| catctggaag gggagcggta aacgtcagg gcccggctga ggggcgtgat tggagggcgc | 60 |
| cttcggcagc cgcccgcggc agaagccgcg gctccagctc gcctggcgga attgcacgcg | 120 |
| gcggcggag ctggaatagc agaaggaacc acctcgtgga gtcgggccgg agccctgcag | 180 |
| tggctcagac ggttgcaggg accgccaggt tgtcacatct tcccaagcca ggccagccag | 240 |
| gagcgctgca tgcaaattct gccgtgggct aaggcacgct aaccagagcc ggcggcatgg | 300 |
| acttcgtcat gaagcaggcc cttggagggg ccacaaagga catggggaag atgctggggg | 360 |
| gagaggagga gaaggacccc gacgcgcaga aaaaggagga ggagcggcag gaggcgctgc | 420 |
| ggcagcagga ggaggagcgt aaggccaagc acgcgcgcat ggaggcggag cgggagaagg | 480 |
| tccggcagca gatccgagat aagtatgggc tgaagaagaa ggaggagaag gaagcagagg | 540 |
| agaaagcagc cctggagcag ccctgcgagg ggagcctgac ccggcccaag aaggccatcc | 600 |
| ctgcgggctg cggggacgag gaggaggagg aagaggagag catcctggac acggtgctca | 660 |
| aatacctgcc cgggccgctg caggacatgt tcaagaagta accaggcctc ctgccccagc | 720 |
| ctactccacc tgttactact tcttttttggt tctttctttt cttttttatta ggttaagtct | 780 |
| caattctgaa ggggaaaacc tcagttggcc tctgcccctc ttccctggcc aggggcttct | 840 |
| cccccctcagc tctccctcac acctccctttc atcccagggt atccacctgc accccactcc | 900 |
| caagtagctt gaaaaaggga ggacagtctt tcccagcag gggtcagggg ggcccctcag | 960 |
| gaagcctaag gtcgtgctag tgtggtgacc cccatacatt cctccctgct ccccactgcc | 1020 |
| aggaggacca ctgtccccag ccagccaaag taatgacaca ttccagccct gcccagcatg | 1080 |
| ctgacctttg gcctctaacc ctcagtgggc cccaggtca gggcaggggc actgagtggc | 1140 |
| ctggctctga ggaagggagt caggggaagc ctgtcccggg aaggcccagg ctgagaggcc | 1200 |
| ctggctctgg ccaggctggg atctgggtgg gaggctgggg ctcttcttct tccatctcct | 1260 |
| tggtgacacc cagcccaggg gcaccccctt ccccagcccc cacctggaga gacatggccc | 1320 |
| ctgccaagct ggtcccttca aatggatcct ttgtggactt tagctcattt gtggaggaac | 1380 |
| cccaggtagg gacgccccctt gttcctcacc cccacccac ttaggtcctg gccccccact | 1440 |
| gccaggctgg gccagcttg ctcagtcaag gggctgccag gccccagaa aacacttgga | 1500 |
| gccatcgggt agcgatggtc tatgccatgg ggaacacctc cattggtgtg gccaagctgc | 1560 |
| ccccattcct atccaccct ctccccaccc cgtcctgtcc atgcgcttcc agggccccac | 1620 |
| ggtccccagg aggacgcttc ctggccaaag cccaagcct ttggtgagaa gccaattccc | 1680 |
| acttgacaga aggcgtccat ccattcatct cattggccaa ggacaaactc tcctctggga | 1740 |
| cgtctgggac tggcatttgt cccccactca aattatcaaa gctttctgct cagtcagttg | 1800 |

```
tgtggggatg gtgagggaag aggggtcaca tgagggagga aactgtatcc atgcatgcat    1860
gataatgcgt ggcagagact gcaacaggga ttgtgtgttc agagatcata tgcatatgtg    1920
tagggctgga gcgtgtgtgt gtcttgagat tgtgtgtgtt gcagtcatca tatctatgtg    1980
ttacagattg tgtatgttag ccttgtgtat gtgtgcttga ttgaggtggt gtatttgggt    2040
tgaaattgtg tcatatgtgt gtgctatcca tctcgtgttt agaggctgta tatgttagct    2100
tgtgtaagaa tgtgttttca aaacagtgtg tgtattggga gtgatgggta tgtgttaggt    2160
atgtgatggg ttgtagaagc gtgtgtttga gagaattcag agacatttga aggctgctgt    2220
gtgcatgttt gggggtctga aaagacagtt gtgtgcatgg atgtgtgcgt ggggagaaag    2280
aacgtgggta agatgtccct tcccagccct gagaccactg gtcacagttg gccacctcca    2340
acgggagacc ttgtccttgg cctagagtcc tccaccctt gggggctcc tgcctgaggt      2400 cctcagaatc ccactgcaat ggacccaggc agcgcccag gaagccatgc tgggcccccg     2460
ccagggccta tcccaaaagc aggggccagg gaggggcga cttgcctgcc cctgaagccc     2520
ttgttcccat tggccccagt ttgcattctg caggttttcc attttagtgg gttctgcttt    2580
tatttcagag acagacatgt gtcttctctg tccgttttcca ataggtaaag ccatatcagt   2640
tagactgcaa tactttaaac acgagacaaa acaatccata tgtttaggga accagaaaag    2700
tcccctggtc tgtcccttct ttggggagca gggcctcgac agctccagct cccttgacct    2760
accttcctcc ccgcaccccg cccccacctt gtgccctgt gtccagcccc caggggggcc    2820
tgtgtctgtg tctgtgcctg tgtctgtgat ggggagccgc ctcgcacccc tgttgtctgc    2880
ttgtctcttt gtgtctgtta tcctgggcag gatggtcatt ctcaaaaacc ctggggtcct    2940
gggccagaga caggcagggc ccagtccagg ggccccaggc ctccccagtc ccagtgtgcg    3000
agccccactt ggacacaagt gttcagagag gtccccctct gccacttgac agggaccttc    3060
aaacctcgac agtgatgcaa ggacacagag agtaccagat aggtagcaga gaccaaggcg    3120
cagggtgctt cagatgagca agagaaccca gtcgaaccag ataccccagg tgggccggag    3180
ggaccccaga ccttcagagg gctgccctgg tgttctccac agtgcagtcc ctctgtattc    3240
ccagagtggg atcggggctt tcagccccac cctgatgcct gccctccagg atggctggtt    3300
tagtctgggt ccatgtccca gacccctcta ttctgctcca ggacagcagg acttcaggtc    3360
ttcctggggg tggatatagg agaaaatttc tgcctggcac acacctggct ccaaccactg    3420
ccaagtgatc actcttaggc ccaggggaac acaatgacta tcattactga tgcagacctg    3480
gctgtggaga gcagctaatg tgtgcccag agagcctgtc tgtgtggagc acgtagtgca     3540
cagaatacgt gagagttgct ctggcagggg cagaatcctc acaggatcgc ctgggaggtg    3600
aggtgtgtgt gacccactgg atgggaggc aatgagtgtg cacatacaaa tggggcagtg     3660
tgcatgcaac acacttaggg gaggagtggc cccagaattc agcacgcaca caacacacaa    3720
gggagagaac cccagatgaa aaatagga aggagcaatc atttgtagat gggtgaaaaa      3780
agaatgaggt tcaagggagc gtgcaccagg tgaggtgagc gtgtgtgctc tcaggggagg    3840
gcccaggatc ccatgcctgg gaggagctgc cagagagaag caaaaaggcg gctgtggatc    3900
gccctgggct gggcaccagt gacaggtcag gatctccaaa catggacgtc ctcccctcca    3960
aatccagaag ctcccagaag gtgtccttaa ctgcaaagct gtgcagggta ctcctccaga    4020
tggaatcagg aagtcgagac accatcccag gtgtgtgtaa gagagagaga gagaacaggg    4080
aggatacaga agtattgcag cccagatccc ctatcagggg gacagctggt gggcaaagca    4140
```

-continued

| | |
|---|---|
| gccaccccac agccttgtgg ctagagtaca gtggggtaga ccctccagcc ccaatagccc | 4200 |
| tagtacccag ctggcagggt tgcccacccc tgctgtccac ctgctccatc ctctagggtt | 4260 |
| ccacaggccc ctgaccgcac agggaggctg gggccagcct ggtctcccag gcctgaggac | 4320 |
| atgcctccca ccaaatgtcc cctgctccag tcccactcct gtcacccac gctctgcact | 4380 |
| ggggagaaaa cgggaggtgc tcgtgctggc cctgggtggg agcggggagt cctggtgaga | 4440 |
| ccccggtgag atggaccatc ctgccccgt ggggatccc ctttcccaca tccgtgctgt | 4500 |
| gtcattgttg ctctgcttcc tttcaatgtg tcagtgcctg gggggagggg aggagcaccc | 4560 |
| cctcagcccc cctgaacctg accaaaagcc atggctgttg ctcccccctt tgtatgatgc | 4620 |
| aaatgctgaa atgtacaaaa tcaaccatga caacaaagaa aaagaccttg tacagc | 4676 |

<210> SEQ ID NO 28
<211> LENGTH: 4661
<212> TYPE: DNA
<213> ORGANISM: Homo sapiens

<400> SEQUENCE: 28

| | |
|---|---|
| ggacttgaac acacgggacc ggacaggacc gaccgagggg cggcggcgaa aggcagagcg | 60 |
| ccgcgatctc tgtcgggaag cgcaacctcc ccgggcccg cggggccgcg caggggggcgt | 120 |
| cctcaacccc gcgcccgctc cctctttcca tccctgccg cccgcaggcc accccggggc | 180 |
| ccggccatcc gcgcgcgcat ccccgggttc gggcccgtcc ctggccctcg agggagccgc | 240 |
| cgccttcatc gccacatctg cagcggccgc accagaggcc gcccgggcgg daccccagcg | 300 |
| tgagcatcgg gcgcccccct aggagtgcac caccccccgga gcccccctca cacggaccg | 360 |
| cgcccgccgg gcacacaaga atggtcactc agatactggg ggccatggag tctcaggtgg | 420 |
| ggggggggccc ggccggcccg gccctgccca acgggccact ccttggtaca aatggagcca | 480 |
| ctgacgacag caagaccaac ctcatcgtca actacctgcc ccagaacatg acccaggatg | 540 |
| agttcaagag tctcttcggc agcattggcg acatcgagtc ctgcaagttg gttcgggaca | 600 |
| agatcacagg gcagagcctt ggctacgggt ttgtgaacta ttctgacccc aatgatgcag | 660 |
| acaaagccat caacaccctc aacggcctca aattacagac gaagaccatc aaggtgtcct | 720 |
| atgccagacc cagttcagca tccatccggg atgctaacct gtacgtcagc gggctcccca | 780 |
| agaccatgag ccagaaagag atggagcagc tcttctccca gtacggccgc atcatcacgt | 840 |
| cccgcatcct ggtggaccag gtcacaggtg tctctcgggg tgtgggattc atccgctttg | 900 |
| acaagaggat tgaggccgaa gaggctatca aaggactgaa tggcagaag ccgctgggcg | 960 |
| cagctgagcc catcacagtc aagttcgcga acaacccaag tcagaagacg gggcaggcgc | 1020 |
| tgctcaccca cctctaccag tcatccgccc ggcgctacgc aggcccccta caccatcaga | 1080 |
| cccagcgttt ccggctggac aatttgctca acatggccta cggcgtcaag aggttctcgc | 1140 |
| cgatcgccat cgatggtatg agcggcctgg cgggcgtggg cctgtcgggg ggcgcggcgg | 1200 |
| gcgccggctg gtgcatcttc gtgtacaacc tgtcaccgga ggcagacgag agcgtgctgt | 1260 |
| ggcagctgtt cgggccttttt ggggcagtca ccaacgtcaa ggtcatccgt gatttcacca | 1320 |
| ccaacaagtg caagggtttc ggcttcgtga ccatgaccaa ctatgacgag gcggccatgg | 1380 |
| ccatcgccag cctgaacggc tatcgcctgg gcgagcgcgt gctgcaggtc tccttcaaga | 1440 |
| ccagcaaaca gcacaaggcg tgagcccacc ccgcctgccc tcccaccccc tcccgggca | 1500 |
| gcagagagag agagagagaa agagagagag agagagaaa ggggcccaag agagacagca | 1560 |
| caggcagccc cacggacgac gcgagggccc cacgtccctg cggaagccac agggtgagca | 1620 |

```
ctctggggtg ggagggtctg cagggaattg ggggggtgcc cggggatccc ccgccccatc    1680
ctcctgcccc caccccaggc tgggctgttc actctctcgt cttggtttgg ttcatggtga    1740 aggttttgt  ttcttttttc ggctaaaaag aatgcagaga tgtgccccca cccccaccct    1800
cgaccacccc cgatgggatg gcttgggggg ctccagggg  tgccctccca gacccccttg    1860
cccaggcctc cccagcacct aggtggggcc tgggtagga  ggaacaggtt taaaaatccc    1920
caaaaaagcg aaccgtgagg aggggtgtgg gcaccccgg  cccagtgccc ctggtggaa     1980 tgcgggggag caggcagtgg ggctggaagc agaaacaaaa tgaaaaaaaa agggggtgg     2040 gaggggaaga aaaactctat ttttgtaaaa agggaaaaag acctcgtgga gaattttac     2100 tggggattct tgaacttgaa aaaaaaaac  acaaaaaaag acaaaaaaaa aaaagaaaa     2160 tattttggca ggtatgtttt accaactggg gcggggtgg  ggggggccca gggagcaggg    2220
cttaggggct agcagcccac ggggccacac agagaaacaa ccacgcagac agtcacacca    2280
cggggacaca cggacagacg cagcggaca  cagcgcatg  cccagacac  gttaagggac    2340 tggttggcca aactcagaca cgtggacagg gatagacaga aagagacaga agctggggct    2400
acgtccatgt ggacacagac cacagatgtg gcacacgaa  tccatccacc tgtccacgtg    2460
cacacgtgaa tgtagcgata gatatttgga catcaaattt ggacaccagg tcacggagaa    2520
acacaaacac cacccaggaa cacgcagaca tatgcccata gcatcccaca ggcccaggca    2580
ggaggtccca ccccagaccc tgccccagac gctccctcac cctctcggcc cctcgccct    2640 ggcccccagg ttctctgcag agatctctcc tggaccccca gcggtctcct tggcgccac     2700 gaacacaggc gtgcacacgc agcgcacatg cattgagaca cacgatacct cgttccacct    2760
tggcgtcacg gtgggctgga ggcagccccc cccccacaa  cacttgaggc caaaggacac    2820
ccctgtcccc ggggctcagc ctcccctgg  gccgaggcct tgcccacac  agctgaggga    2880 gaggcccagc cctgagcctc ccccaccagg actgggcctc cccggcagca agaccccggc    2940 actcccgcc  aggcccaggg tggggtggat gggcccaaag gcccagcccc acactccttt    3000
cccgtccact tgtcacctac ctatcccctt tcggtttgtt gggttttttcg tctttccaga    3060 ttgcagtgga cacagccccc gatctcgagc cccggccccc ggcttctgtc tggacattgc    3120
atcgccctag ttttctttct ttaaaaaaaa aaaattccaa cagaagccac aggccggagc    3180
ccctgggagc cctcgcaccg ctccccaccc cactcagcgg ccccatcgga actgagaatt    3240
gcaaaacccc cgactttagc tatagttaag ttgccttccc ccggtgtccc cacgtttggt    3300
gtctggctat ggcgccccca tctgactgtc cagctctctc tcccccaccc ctcccggtgt    3360
tgttattaaa cgtctgtgga gcttctgctg caaggaacaa aaaagaaaaa aatcaaaaaa    3420
gcgacaaaaa aacacaaaca gaagaggaaa aaaagcaac  aaaaaaagaa aacacacaga    3480
agagatttaa aaaaaaaaa  ggaaaaaaa  aaaagacata aactggcacc agttaacttt    3540
cttgtacttt tttgctgaat ttagcttctt gtagttttaa cttattgcta tgttaactat    3600
ttattctcct cgttgccctg taaggacatc cgtgtatatt tctgttactt catccggttt    3660
gcaagttaaa ggaacgacaa tgttctcttt gtttctttaa gttttgccga gacatggtta    3720
tgcctaattt atttataaaa ggggaagtgg aatcattaaa gtaataataa ttattaataa    3780
cagtaatggt agccgagtgg cacgcggggg cgtgtgctct gcgggacagt ccccacggcc    3840
agcgacgtcc aggtcaccaa tgggattctt tttgctcttg tcttgagaat ttttcagtc     3900 ctatttagct ggtgaaatcc ctagcttgtt cttgatacac gaacctattt attctcgtgg    3960
```

| | |
|---|---|
| ttttaagtcc tccctgccct ctctcctctc ccctgcagca gggcagggac ccctctcccc | 4020 |
| tgctgtctct tggggctctc tcccctccgc cctctgcatt cgggaacacg cacgtccgcg | 4080 |
| tgggaagctt gcagcagggc gtccgagcaa taagggctgg gtttgtcccc caccctgggg | 4140 |
| ggggccaggc tccagagagg gggcacctcc ccacacaccc ccccccacc gaggcctagg | 4200 |
| cccctgccac ccccaagact gggaggggac ttcttttct aaaacacaaa actcagccca | 4260 |
| gccaggcccc ctccctggag gccagcccct cccgcaggg ggccaggccg gggctcccag | 4320 |
| gcgaggggga cttgggcctt ccacgtccct gggggcagg ggccaggcca gggggaggg | 4380 |
| ggctcagccc ctccacccct cccttcatcc tgttatttat tcggaaggtt tcaaatcacg | 4440 |
| acagagtcca tgttggaggt gataaaaaac tgtaaaaaaa aaaaaaaaaa aaaagacaaa | 4500 |
| acaaaagaca aaaaaaaaa aaaaacccaa caagaacact tcgcgttgcg tttagactat | 4560 |
| ttattaccgg gatcacaggc ctggccgcgg taacagactt ttacatggaa ttgtttaatt | 4620 |
| atttgtactt ttcatgccag aaaataaaag ttcagaatct t | 4661 |

<210> SEQ ID NO 29
<211> LENGTH: 3396
<212> TYPE: DNA
<213> ORGANISM: Homo sapiens

<400> SEQUENCE: 29

| | |
|---|---|
| gggcttcctc ttcgcccggg tggcgttggg cccgcgcggg cgctcgggtg actgcagctg | 60 |
| ctcagctccc ctcccccgcc ccgcgccgcg cggccgcccg tcgcttcgca cagggctgga | 120 |
| tggttgtatt gggcagggtg gctccaggat gttaggaact gtgaagatgg aagggcatga | 180 |
| aaccagcgac tggaacagct actacgcaga cacgcaggag gcctactcct ccgtcccggt | 240 |
| cagcaacatg aactcaggcc tgggctccat gaactccatg aacacctaca tgaccatgaa | 300 |
| caccatgact acgagcggca acatgacccc ggcgtccttc aacatgtcct atgccaaccc | 360 |
| gggcctaggg gccggcctga gtccggcgcg agtagccggc atgccggggg gctcggcggg | 420 |
| cgccatgaac agcatgactg cggccggcgt gacggccatg ggtacggcgc tgagcccgag | 480 |
| cggcatgggc gccatgggtg cgcagcaggc ggcctccatg aatggcctgg cccctacgc | 540 |
| ggccgccatg aacccgtgca tgagccccat ggcgtacgcg ccgtccaacc tgggccgcag | 600 |
| ccgcgcgggc ggcggcggcg acgccaagac gttcaagcgc agctacccgc acgccaagcc | 660 |
| gccctactcg tacatctcgc tcatcaccat ggccatccag caggcgccca gcaagatgct | 720 |
| cacgctgagc gagatctacc agtggatcat ggacctcttc ccctattacc ggcagaacca | 780 |
| gcagcgctgg cagaactcca tccgccactc gctgtccttc aatgactgct tcgtcaaggt | 840 |
| ggcacgctcc ccggacaagc cgggcaaggg ctcctactgg acgctgcacc cggactccgg | 900 |
| caacatgttc gagaacggct gctacttgcg ccgccagaag cgcttcaagt gcgagaagca | 960 |
| gccgggggcc ggcggcgggg gcgggagcgg aagcggggc agcggcgcca agggcggccc | 1020 |
| tgagagccgc aaggaccccc tggcgcctc taaccccagc gccgactcgc ccctccatcg | 1080 |
| gggtgtgcac gggaagaccg gccagctaga gggcgcgccg gcccccgggc ccgccgccag | 1140 |
| ccccccagact ctggaccaca gtggggcgac ggcgacaggg ggcgcctcgg agttgaagac | 1200 |
| tccagcctcc tcaactgcgc ccccataag ctccgggccc ggggcgctgg cctctgtgcc | 1260 |
| cgcctctcac ccggcacacg gcttggcacc ccacgagtcc cagctgcacc tgaaagggga | 1320 |
| cccccactac tccttcaacc accgttctc catcaacaac ctcatgtcct cctcggagca | 1380 |
| gcagcataag ctggacttca aggcatacga acaggcactg caatactcgc cttacggctc | 1440 |

-continued

| | |
|---|---|
| tacgttgccc gccagcctgc ctctaggcag cgcctcggtg accaccagga gccccatcga | 1500 |
| gccctcagcc ctggagccgg cgtactacca aggtgtgtat tccagacccg tcctaaacac | 1560 |
| ttcctagctc ccgggactgg ggggtttgtc tggcatagcc atgctggtag caagagagaa | 1620 |
| aaaatcaaca gcaaacaaaa ccacacaaac caaaccgtca acagcataat aaaatcccaa | 1680 |
| caactatttt tatttcattt ttcatgcaca acctttcccc cagtgcaaaa gactgttact | 1740 |
| ttattattgt attcaaaatt cattgtgtat attactacaa agacaacccc aaaccaattt | 1800 |
| ttttcctgcg aagtttaatg atccacaagt gtatatatga aattctcctc cttccttgcc | 1860 |
| cccctctctt tcttccctct ttcccctcca gacattctag tttgtggagg gttatttaaa | 1920 |
| aaaacaaaaa aggaagatgg tcaagtttgt aaaatatttg tttgtgctttt tcccccctcc | 1980 |
| ttacctgacc ccctacgagt ttacaggtct gtggcaatac tcttaaccat aagaattgaa | 2040 |
| atggtgaaga aacaagtata cactagaggc tcttaaaagt attgaaagac aatactgctg | 2100 |
| ttatatagca agacataaac agattataaa catcagagcc atttgcttct cagtttacat | 2160 |
| ttctgataca tgcagatagc agatgtcttt aaatgaaata catgtatatt gtgtatggac | 2220 |
| ttaattatgc acatgctcag atgtgtagac atcctccgta tatttacata acatatagag | 2280 |
| gtaatagata ggtgatatac atgatacatt ctcaagagtt gcttgaccga aagttacaag | 2340 |
| gaccccaacc cctttgtcct ctctacccac agatggccct gggaatcaat tcctcaggaa | 2400 |
| ttgccctcaa gaactctgct tcttgctttg cagagtgcca tggtcatgtc attctgaggt | 2460 |
| cacataacac ataaaattag tttctatgag tgtataccat ttaaagaatt ttttttttcag | 2520 |
| taaaagggaa tattacaatg ttggaggaga gataagttat agggagctgg atttcaaaac | 2580 |
| gtggtccaag attcaaaaat cctattgata gtggccattt taatcattgc catcgtgtgc | 2640 |
| ttgtttcatc cagtgttatg cactttccac agttggacat ggtgttagta tagccagacg | 2700 |
| ggtttcatta ttatttctct ttgctttctc aatgttaatt tattgcatgg tttattcttt | 2760 |
| ttctttacag ctgaaattgc tttaaatgat ggttaaaatt acaaattaaa ttgttaattt | 2820 |
| ttatcaatgt gattgtaatt aaaaatattt tgatttaaat aacaaaaata ataccagatt | 2880 |
| ttaagccgtg gaaaatgttc ttgatcattt gcagttaagg actttaaata aatcaaatgt | 2940 |
| taacaaaaga gcatttctgt tattttttttt cacttaacta aatccgaagt gaatatttct | 3000 |
| gaatacgata ttttttcaaat tctagaactg aatataaatg acaaaaatga aaataaaatt | 3060 |
| gttttgtctg ttgttataat gaatgtgtag ctagtaaaaa ggagtgaaag aaattcaagt | 3120 |
| aaagtgtata agttgattta atattccaag agttgagatt tttaagattc tttattccca | 3180 |
| gtgatgttta cttcattttt ttttttttttt ttgacaccgg cttaagcctt ctgtgtttcc | 3240 |
| tttgagcctt tcactacaa aatcaaatat taatttaact acctttcctc cttccccaat | 3300 |
| gtatcacttt tctttatctg agaattcttc caatgaaaat aaaatatcag ctgtggctga | 3360 |
| tagaattaag ttgtgtccaa aaaaaaaaaa aaaaaa | 3396 |

<210> SEQ ID NO 30
<211> LENGTH: 2415
<212> TYPE: DNA
<213> ORGANISM: Homo sapiens

<400> SEQUENCE: 30

| | |
|---|---|
| cggccgctgc tagaggggct gcttgcgcca ggcgccggcc gccccactgc gggtccctgg | 60 |
| cggccggtgt ctgaggagtc ggagagccga ggcggccaga ccgtgcgccc cgcgcttctc | 120 |

```
ccgaggccgt tccgggtctg aactgtaaca gggaggggcc tcgcaggagc agcagcgggc    180
gagttaaagt atgctgggag cggtgaagat ggaaggcac  gagccgtccg actggagcag    240
ctactatgca gagcccgagg gctactcctc cgtgagcaac atgaacgccg gcctggggat    300
gaacggcatg aacacgtaca tgagcatgtc ggcggccgcc atgggcagcg gctcgggcaa    360
catgagcgcg ggctccatga acatgtcgtc gtacgtgggc gctggcatga gcccgtccct    420
ggcggggatg tccccccggcg cgggcgccat ggcgggcatg ggcggctcgg ccggggcggc    480
cggcgtggcg ggcatggggc gcacttgag  tcccagcctg agcccgctcg ggggcaggc     540
ggccggggcc atgggcggcc tggccccta  cgccaacatg aactccatga gccccatgta    600
cgggcaggcg ggcctgagcc gcgcccgcga ccccaagacc tacaggcgca gctacacgca    660
cgcaaagccg ccctactcgt acatctcgct catcaccatg gccatccagc agagccccaa    720
caagatgctg acgctgagcg agatctacca gtggatcatg gacctcttcc ccttctaccg    780
gcagaaccag cagcgctggc agaactccat ccgccactcg ctctccttca acgactgttt    840
cctgaaggtg ccccgctcgc ccgacaagcc cggcaagggc tccttctgga ccctgcaccc    900
tgactcgggc aacatgttcg agaacggctg ctacctgcgc cgccagaagc gcttcaagtg    960
cgagaagcag ctggcgctga aggaggccgc aggcgccgcc ggcagcggca agaaggcggc   1020
cgccggagcc caggcctcac aggctcaact cggggaggcc gccgggccgg cctccgagac   1080
tccggcgggc accgagtcgc tcactcgag  cgcctccccg tgccaggagc acaagcgagg   1140
gggcctggga gagctgaagg ggacgccggc tgcggcgctg agccccccag agccggcgcc   1200
ctctcccggg cagcagcagc aggccgcggc ccacctgctg ggcccgcccc accaccgggg   1260
cctgccgcct gaggcccacc tgaagccgga acaccactac gccttcaacc acccgttctc   1320
catcaacaac ctcatgtcct cggagcagca gcaccaccac agccaccacc accaccaacc   1380
ccacaaaatg gacctcaagg cctacgaaca ggtgatgcac taccccggct acggttcccc   1440
catgcctggc agcttggcca tgggcccggt cacgaacaaa acgggcctgg acgcctcgcc   1500
cctggccgca gataccctcc tactaccaggg ggtgtactcc cggcccatta tgaactcctc   1560
ttaagaagac gacggcttca ggcccggcta actctggcac cccggatcga ggacaagtga   1620
gagagcaagt gggggtcgag actttgggga acggtgttg  cagagacgca agggagaaga   1680
aatccataac ccccacccc  caacacccccc aagacagcag tcttcttcac ccgctgcagc   1740
cgttccgtcc caaacagagg gccacacaga taccccacgt tctatataag gaggaaaacg   1800
ggaaagaata taaagttaaa aaaaagcctc cggtttccac tactgtgtag actcctgctt   1860
cttcaagcac ctgcagattc tgattttttt gttgttgttg ttctcctcca ttgctgttgt   1920
tgcagggaag tcttacttaa aaaaaaaaaa aaatttgtg  agtgactcgg tgtaaaacca   1980
tgtagtttta acagaaccag agggttgtac tattgtttaa aaacaggaaa aaaataatg    2040
taagggtctg ttgtaaatga ccaagaaaaa gaaaaaaaaa gcattcccaa tcttgacacg   2100
gtgaaatcca ggtctcgggt ccgattaatt tatggtttct gcgtgcttta tttatggctt   2160
ataaatgtgt attctggctg caagggccag agttccacaa atctatatta aagtgttata   2220
cccggttta  tcccttgaat cttttcttcc agatttttct tttctttact ggcttacaa    2280
aatatacagg cttggaaatt atttcaagaa ggagggaggg ataccctgtc tggttgcagg   2340
ttgtatttta ttttggccca gggagtgttg ctgttttccc aacatttat  taataaaatt   2400
ttcagacata aaaaa                                                    2415
```

<210> SEQ ID NO 31
<211> LENGTH: 6373
<212> TYPE: DNA
<213> ORGANISM: Homo sapiens

<400> SEQUENCE: 31

| | | | | | |
|---|---|---|---|---|---|
| cttgaacctt | tgtcacccct | cacgttgcac | accaaagaca | taccctagtg | attaaatgct | 60 |
| gattttgtgt | acgattgtcc | acggacgcca | aaacaatcac | agagctgctt | gatttgtttt | 120 |
| aattaccagc | acaaaatgcc | atcagtctgg | gacgtgatcg | ggcagaggtg | tactcacagt | 180 |
| agtgtaaata | ctgctgtaaa | tagttgtctg | atggtggctt | tgacagtgag | ctagcttctg | 240 |
| agttttccct | tcttttata | ctgttttctg | tgctggcttt | tttgaatctt | cctaattttt | 300 |
| catctcttta | acaaactcct | atgaagttga | aaccgggaag | tttgctctaa | catttccaga | 360 |
| gaaggtatta | agtcatgatg | caggaatctg | cgacagagac | aataagcaac | agttcaatga | 420 |
| atcaaaatgg | aatgagcact | ctaagcagcc | aattagatgc | tggcagcaga | gatggaagat | 480 |
| caagtggtga | caccagctct | gaagtaagca | cagtagaact | gctgcatctg | caacaacagc | 540 |
| aggctctcca | ggcagcaaga | caacttcttt | tacagcagca | aacaagtgga | ttgaaatctc | 600 |
| ctaagacag | tgataaacag | agaccactgc | aggtgcctgt | gtcagtggcc | atgatgactc | 660 |
| cccaggtgat | cacccctcag | caaatgcagc | agatccttca | gcaacaagtc | ctgtctcctc | 720 |
| agcagctaca | agcccttctc | caacaacagc | aggctgtcat | gctgcagcag | caacaactac | 780 |
| aagagttta | caagaaacag | caagagcagt | tacatcttca | gcttttgcag | cagcagcagc | 840 |
| aacagcagca | gcagcaacaa | cagcagcaac | aacagcagca | gcaacaacaa | caacaacagc | 900 |
| agcaacaaca | gcagcagcag | cagcaacagc | agcagcagca | gcaacagcat | cctggaaagc | 960 |
| aagcgaaaga | gcagcagcag | cagcagcagc | agcaacagca | attggcagcc | cagcagcttg | 1020 |
| tcttccagca | gcagcttctc | cagatgcaac | aactccagca | gcagcagcat | ctgctcagcc | 1080 |
| ttcagcgtca | gggactcatc | tccattccac | ctggccaggc | agcacttcct | gtccaatcgc | 1140 |
| tgcctcaagc | tggcttaagt | cctgctgaga | ttcagcagtt | atggaaagaa | gtgactggag | 1200 |
| ttcacagtat | ggaagacaat | ggcattaaac | atggagggct | agacctcact | actaacaatt | 1260 |
| cctcctcgac | tacctcctcc | aacacttcca | agcatcacc | accaataact | catcattcca | 1320 |
| tagtgaatgg | acagtcttca | gttctaagtg | caagacgaga | cagctcgtca | catgaggaga | 1380 |
| ctggggcctc | tcacactctc | tatggccatg | gagtttgcaa | atggcaggc | tgtgaaagca | 1440 |
| tttgtgaaga | ttttggacag | tttttaaagc | accttaacaa | tgaacacgca | ttggatgacc | 1500 |
| gaagcactgc | tcagtgtcga | gtgcaaatgc | aggtggtgca | acagttagaa | atacagcttt | 1560 |
| ctaaagaacg | cgaacgtctt | caagcaatga | tgacccactt | gcacatgcga | ccctcagagc | 1620 |
| ccaaccatc | tcccaaacct | ctaaatctgg | tgtctagtgt | caccatgtcg | aagaatatgt | 1680 |
| tggagacatc | cccacagagc | ttacctcaaa | cccctaccac | accaacggcc | ccagtcaccc | 1740 |
| cgattaccca | gggaccctca | gtaatcaccc | cagccagtgt | gcccaatgtg | ggagccatac | 1800 |
| gaaggcgaca | ttcagacaaa | tacaacattc | ccatgtcatc | agaaattgcc | ccaaactatg | 1860 |
| aattttataa | aaatgcagat | gtcagacctc | catttactta | tgcaactctc | ataaggcagg | 1920 |
| ctatcatgga | gtcatctgac | aggcagttaa | cacttaatga | aatttacagc | tggtttacac | 1980 |
| ggacatttgc | ttacttcagg | cgtaatgcag | caacttggaa | gaatgcagta | cgtcataatc | 2040 |
| ttagcctgca | caagtgtttt | gttcgagtag | aaaatgttaa | aggagcagta | tggactgtgg | 2100 |
| atgaagtaga | ataccagaag | cgaaggtcac | aaaagataac | aggaagtcca | accttagtaa | 2160 |

```
aaaatatacc taccagttta ggctatggag cagctcttaa tgccagtttg caggctgcct    2220
tggcagagag cagtttacct ttgctaagta atcctggact gataaataat gcatccagtg    2280
gcctactgca ggccgtccac gaagacctca atggttctct ggatcacatt gacagcaatg    2340
gaaacagtag tccgggctgc tcacctcagc cgcacataca ttcaatccac gtcaaggaag    2400
agccagtgat tgcagaggat gaagactgcc caatgtcctt agtgacaaca gctaatcaca    2460
gtccagaatt agaagacgac agagagattg aagaagagcc tttatctgaa gatctggaat    2520
gagaactgac ttgtgaaacc tcagcgtgaa gggacatatc actgaccttc ataaccactc    2580
cacaaccatg aatatttgac aaattttttac tgtgactatt tattaagcat ggataaagga    2640
gacagcccta aggaactta ctaagccagc cctttgggat tcagtaccaa caggcaaatt    2700
gcttgttttc ttcttcttct tcttcttttt tttttttttt ttagaaaaaa agacaaaaac    2760
tgattttctt gaaaaaaaaa aatgaactgt tctttctata atggctttgc ccatttaaaa    2820
aatgtggctc ttaagggttc atgaaatgac tgaatatgag gatacatgtc ctgtagaaag    2880
caaatgcgcc tcatatactg ccaaaaatag tgttagtttc attaatgtga attttccagc    2940
attcagtagt tgtaatgtta gaaacaattg ctggtcaagt tcaacttgtt gctattgttt    3000
ttaatttgca caggagtagt atcagaaatt agtgtcactg cttgtatcta gctgaatttt    3060
aaacaacaga acattagttt tttatgttgg tgccaccaac tgtaaatgac ataagttagt    3120
tattacaaaa cacagtaatt agactgttgc aaccatctaa aaccttaggc ttccagtctg    3180
tgctgttagt gttaagatgt aaagtgcaat cctaagctaa cattatctgt gcaagcacca    3240
tagaaacatt tgcatatctg catagatctt acaactgtac tctttacctc cttgtgataa    3300
agctttgtct acctgcaaac acagtcaaag gctacagctg caaaccaaag ccaactctaa    3360
ccatggccaa gagctcaagg acagaagcag ccacatgctt tggtcagcct tctgtaactt    3420
caattagtac aaaggaacct tttccatgaa ctacctgctg ttttctgatg acctctggga    3480
tcttttcatt tagccctaaa caaagaaaca aatatgacaa aaaccacaac taaaaaatgt    3540
taattcagtc acagagtaat cttctgaggc caaaagtcca tctaaatgca atgaagattt    3600
gctttcatta aagacagagg tgaggacaaa atccgcagtg gaagttatga tatgctagaa    3660
agcaacaaat gtggatcact gaccaaaacg attatgtact tgatgcaaat gcagattgca    3720
tattgttata tatatagtac tttgtgtttt tgttttccct cattcagtca gttattttca    3780
gtggtgaata catgttgtta gaagatgtct tgtatggtct taatctttgt tgtgtactat    3840 tttttttatag tcttaagtta taatgaaaaa acaaaaagta ggaaccaaac ataaaaggtc    3900
tagtaaagcc aaaaattaat ttcatattga ttttaaagtg atctagctga gtttttacac    3960
tgaaagcaaa gattatagca attgtagtcc atggtattta ttttcagtca aaccaaagtt    4020
acatataatt ctgcctctgc ttatacggga tattaacact aacaatacac tcccttcaaa    4080
gacttgcaca ggccaaattg ttggaatgct ggttttcttg acaattccaa accccaaaac    4140
tatgataatg agttatgatg tagttgaaaa tagcatagtc agatgtttgc ttaaaaccta    4200
gaaacttaac atgttgcttt tcatgtgctg tgccaagtct tgataatact ttttccccca    4260
accaagggac ctcataacct gattatggtt attgctttac aaacagttttt gacagaaggt    4320 ggctgctaga gcttaacata cgttcccgtt ccatgtgatg gaaccggttc ttgcaaacta    4380
agctcatcat tgattctttg ctgaagtcag caaatagagt tagagagata cccagtcatc    4440
tatcacacca aataaaagga cataacggct ttcaaagggg ttttcccact tacccaaaag    4500
gctttctgaa agcttctacc tctgcaaaaa aaaaaaaga aaaaaaaaaa aagaaaaaca    4560
```

```
ttagaacaat tatggcagat tgcatgaaac gtgagaacgt cacagtaact gctacttttc    4620
attatgtttg tctttgggtc atgatcaacg aaccggaagt ttacaatatg gtattaaaag    4680
aaagatgggt atggtgaaag atggttttca gtcatctagg atcctactgt aaggattatc    4740
tgaaaggaaa aatgggtctt tcaggtgcat gttcaaaagg ctttgaggga ctggaagtaa    4800
ctgcgagagt tgtaccatca gaagggtggc ctaagactac aatgctaaag tatgcatacc    4860
tcagttagaa aacttttgaa aggaagtctc agccacagaa tgcatatacc tgtagagttt    4920
tgcatgggtt ttatatgaat acaattttaa aaaatagctg cttgcacatt ataccagaaa    4980
aacctccaaa actgcaattg ctttgaaaat agatttta gg ttttttggag tttcctgaaa    5040
tgcttggtct gtattttgat aattgtgcat attatgtaaa aatgttggtg gacccataaa    5100
tgaccagact ttttctaaga aaaatgttgc tttaatgcat ttcatgaatt tttactctta    5160
tatcattgct tgctagtaat agcaaatctg cttttctgca tctgctttgc gtagctattg    5220
taaggctttg aactaatgta tgtatttatt gcttgaactt ctgtgcatac cttataaagc    5280
ataatgtctg acaatttaaa tggctcatgt attcttgctt ctatcataag ctgattatgg    5340
ggactatgat cttttgtata cagcaaattt taaactgtag cacaaacatc tgtttatgta    5400
ttggtggaat atcctgtttt tatttatctt ttttgaggta aactaatttt tgatactttt    5460
cattactgtg tactatgttc atactttgaa ttctctgacg ttagaagtca tggttgagaa    5520
ttgtaacagc tgttattcgt tctgtattca tggctttcac tgctgaataa aataaaggac    5580
caaacctagg atttgaaaga aaactgtcta cctctaacac cagggagtta tcagatttta    5640
ttttacatag ttttagtcta caaagacaca attgcttaaa cctagtgggc ttaaggctta    5700
tattctatgt ggttggattc gtggcacagt tgtactattt gaaaatcaat taaaatttta    5760
tgtgaatgtt acaagtattt ggtagaatta ccactaactg ggttttcttt agataactca    5820
gatatggaga aaatgtcatc agcattctgt gtctacagct gcttaacttc ataagaatgc    5880
atttctttgt gattagggaa tcgaagaata gtcagctagg aatagagcta cagaagtaca    5940
cttacataaa ccatcctgga ctttaatgtc cctgggcaga ttcagtcgca aaatccaata    6000 tgatatttg taaagttttc aagttggaca tttacatttt tgagaatttt gagacttcat    6060
cttacacatg ccagtattaa cacacatttg dacaatagct ttattaagtc tataaagcta    6120
ttgaaaggaa catggcttac ccttgttatt tcactagttc aggttgcaac gaaaggtttt    6180
tttgtccatg aacacttggc atatcttact tagcaaaaaa gaaggatgta cattttacta    6240
tagaattaat gtatgaacag tgtgtcactg ctgttggatg taaaaatgta tatgaaacca    6300
tttcattcac ttgattacat ttctgaagta taaataaaaa aatctaattc tttttgaccc    6360
atttataaaa aaa                                                      6373

<210> SEQ ID NO 32
<211> LENGTH: 3419
<212> TYPE: DNA
<213> ORGANISM: Homo sapiens

<400> SEQUENCE: 32
ttggaggcgg ccggcgcagg ggccgcgaga ggcttcgtcg ccgctgcagc tccggggggct     60 cccaggggag cgtgcgcgga acctccaggc ccagcaggac cccggctgcg gcgaggagga    120
aggagccagc ctagcagctt ctgcgcctgt ggccgcgggt gtcctggagg cctctcggtg    180
tgacgagtgg gggacccgaa ggctcgtgcg ccacctccag gcctggacgc tgccctccgt    240
```

```
cttctgcccc caataggtgc gccggacctt caggccctgg ggtgaattca gctgctccta    300
catcagcttc cggaaccacc aaaaattcaa attgggattt tccggagtaa acaagagcct    360
agagcccttt gctcaatgct ggatttaata cgtatatatt tttaagcgag ttggtttttt    420
cccctttgat ttttgatctt cgcgacagtt cctcccacgc atattatcgt tgttgccgtc    480
gttttctctc cccgcgtggc tccttgacct gcgagggaga gagaggacac cgaagccggg    540
agctcgcagg gaccatgtat cagagcttgg ccatggccgc caaccacggg ccgccccccg    600
gtgcctacga ggcgggcggc cccggcgcct tcatgcacgg cgcgggcgcc gcgtcctcgc    660
cagtctacgt gcccacaccg cgggtgccct cctccgtgct gggcctgtcc tacctccagg    720
gcggaggcgc gggctctgcg tccggaggcg cctcgggcgg cagctccggt ggggccgcgt    780
ctggtgcggg gccgggacc cagcagggca gcccgggatg gagccaggcg ggagccgacg    840
gagccgctta caccccgccg ccggtgtcgc cgcgcttctc cttcccgggg accaccgggt    900
ccctggcggc cgccgccgcc gctgccgcgg cccgggaagc tgcggcctac agcagtggcg    960
gcggagcggc gggtgcgggc ctggcgggcc gcgagcagta cggcgcgcc ggcttcgcgg   1020
gctcctactc cagcccctac ccggcttaca tggccgacgt gggcgcgtcc tgggccgcag   1080
ccgccgccgc ctccgccggc cccttcgaca gcccggtcct gcacagcctg ccggccggg   1140
ccaacccggc cgcccgacac cccaatctcg atatgtttga cgacttctca gaaggcagag   1200
agtgtgtcaa ctgtggggct atgtccaccc gctctggag gcgagatggg acgggtcact   1260
atctgtgcaa cgcctgcggc ctctaccaca agatgaacgg catcaaccgg ccgctcatca   1320
agcctcagcg ccggctgtcc gcctcccgcc gagtgggcct ctcctgtgcc aactgccaga   1380
ccaccaccac cacgctgtgg cgccgcaatg cggagggcga gcctgtgtgc aatgcctgcg   1440
gcctctacat gaagctccac ggggtcccca ggcctcttgc aatgcggaaa gaggggatcc   1500
aaaccagaaa acggaagccc aagaacctga ataaatctaa gacaccagca gctccttcag   1560
gcagtgagag ccttcctccc gccagcggtg cttccagcaa ctccagcaac gccaccacca   1620
gcagcagcga ggagatgcgt cccatcaaga cggagcctgg cctgtcatct cactacgggc   1680
acagcagctc cgtgtcccag acgttctcag tcagtgcgat gtctggccat gggccctcca   1740
tccaccctgt cctctcggcc ctgaagctct ccccacaagg ctatgcgtct cccgtcagcc   1800
agtctccaca gaccagctcc aagcaggact cttggaacag cctggtcttg gccgacagtc   1860
acggggacat aatcactgcg taatcttccc tcttccctcc tcaaattcct gcacggacct   1920
gggacttgga ggatagcaaa gaaggaggcc ctgggctccc aggggccggc ctcctctgcc   1980
tggtaatgac tccagaacaa caactgggaa gaaacttgaa gtcgacaatc tggttagggg   2040
aagcgggtgt tggattttct cagatgcctt tacacgctga tgggactgga gggagcccac   2100
ccttcagcac gagcacactg catctctcct gtgagttgga gacttctttc ccaagatgtc   2160
cttgtccccct gcgttcccca ctgtggccta gaccgtgggt tttgcattgt gtttctagca   2220
ccgaggatct gagaacaagc ggagggccgg gccctgggac cctgctcca gcccgaatga   2280
cggcatctgt ttgccatgta cctggatgcg acgggcccct ggggacaggc ccttgcccca   2340
tccatccgct tgaggcatgg caccgccctg catccctaat accaaatctg actccaaaat   2400
tgtggggtgt gacatacaag tgactgaaca cttcctgggg agctacaggg gcacttaacc   2460
caccacagca cagcctcatc aaaatgcagc tggcaacttc tccccaggt gccttccccc   2520
tgctgccggc ctttgctcct tcacttccaa catctctcaa aataaaaatc cctcttcccg   2580
ctctgagcga ttcagctctg cccgcagctt gtacatgtct ctcccctggc aaaacaagag   2640
```

| | | | | |
|---|---|---|---|---|
| ctgggtagtt | tagccaaacg | gcacccctc | gagttcactg | cagacccttc gttcaccgtg | 2700 |
| tcacacatag | agggttctg | agtaagaaca | aaacgttctg | ctgctcaagc cagtctggca | 2760 |
| agcactcagc | ccagcctcga | ggtccttctg | gggagagtgt | aagtggacag agtcctggtc | 2820 |
| agggggcagg | agtgtcccaa | gggctggccc | acctgctgtc | tgtctgctcc tcctagccct | 2880 |
| tggtcagatg | gcagccagag | tccctcagga | cctgcagcct | cgccccggca gaagtctttt | 2940 |
| gtccaggagg | caaaaagcca | gagattctgc | aacacgaatt | cgaagcaaac aaacacaaca | 3000 |
| caacagaatt | cctggaaaga | gacgactgc | taagacacgg | caggggggcc tggagggagc | 3060 |
| ctccgactct | gagctgctcc | gggatctgcc | gcgttctcct | ctgcacattg ctgtttctgc | 3120 |
| ccctgatgct | ggagctcaag | gagactcctt | cctctttctc | agcagagctg tagctgactg | 3180 |
| tggcattact | acgcctcccc | acacgcccag | acccctcact | ccaaaatcct actggctgta | 3240 |
| gcagagaata | cctttgaacc | aagattctgt | tttaatcatc | atttacattg ttttcttcca | 3300 |
| aaggccccct | cgtataccct | ccctaaccca | caaacctgtt | aacattgtct taaggtgaaa | 3360 |
| tggctggaaa | atcagtattt | aactaataaa | tttatctgta | ttcctcttaa aaaaaaaaa | 3419 |

<210> SEQ ID NO 33
<211> LENGTH: 3785
<212> TYPE: DNA
<213> ORGANISM: Homo sapiens

<400> SEQUENCE: 33

| | | | | |
|---|---|---|---|---|
| agttccgacc | cacagcctgg | caccttcgg | cgagcgctgt | tgtttaggg ctcggtgagt | 60 |
| ccaatcagga | gcccaggctg | cagttttccg | gcagagcagt | aagaggcgcc tcctctctcc | 120 |
| tttttattca | ccagcagcgc | ggcgcagacc | ccggactcgc | gctcgcccgc tggcgccctc | 180 |
| ggcttctctc | cgcgcctggg | agcaccctcc | gccgcggccg | ttctccatgc gcagcgcccg | 240 |
| cccgaggagc | tagacgtcag | cttggagcgg | cgccggaccg | tggatggcct tgactgacgg | 300 |
| cggctggtgc | ttgccgaagc | gcttcggggc | gcgggtgcg | gacgccagcg actccagagc | 360 |
| cttttccagcg | cgggagccct | ccacgccgcc | ttccccatc | tcttcctcgt cctcctcctg | 420 |
| ctcccggggc | ggagagcggg | gccccggcgg | cgccagcaac | tgcggacgc ctcagctcga | 480 |
| cacggaggcg | gcggccggac | ccccggcccg | ctcgctgctg | ctcagttcct acgcttcgca | 540 |
| tcccttcggg | gctccccacg | gaccttcggc | gcctggggtc | gcgggccccg ggggcaacct | 600 |
| gtcgagctgg | gaggacttgc | tgctgttcac | tgacctcgac | caagccgcga ccgccagcaa | 660 |
| gctgctgtgg | tccagccgcg | gcgccaagct | gagccccttc | gcaccccgagc agccggagga | 720 |
| gatgtaccag | accctcgccg | ctctctccag | ccagggtccg | gccgcctacg acggcgcgcc | 780 |
| cggcggcttc | gtgcactctg | cggccgcggc | ggcagcagcc | gcggcggcgg ccagctcccc | 840 |
| ggtctacgtg | cccaccaccc | gcgtgggttc | catgctgccc | ggcctaccgt accacctgca | 900 |
| gggtcgggc | agtgggccag | ccaaccacgc | gggcggcgcg | ggcgcgcacc ccggctggcc | 960 |
| tcaggcctcg | gccgacagcc | ctccatacgg | cagcggaggc | ggcgcggctg gcggcgggc | 1020 |
| cgcggggcct | ggcggcgctg | gctcagccgc | ggcgcacgtc | tcggcgcgct tccctactc | 1080 |
| tcccagcccg | cccatggcca | acggcgccgc | gcggagccg | ggaggctacg cggcggcggg | 1140 |
| cagtgggggc | gcgggaggcg | tgagcggcgg | cggcagtagc | ctggcggcca tgggcggccg | 1200 |
| cgagccccag | tacagctcgc | tgtcggccgc | gcggccgctg | aacgggacgt accaccacca | 1260 |
| ccaccaccac | caccaccacc | atccgagccc | ctactcgccc | tacgtggggg cgccactgac | 1320 |

```
gcctgcctgg cccgccggac ccttcgagac cccggtgctg cacagcctgc agagccgcgc   1380 cggagcccg ctcccggtgc cccggggtcc cagtgcagac ctgctggagg acctgtccga    1440
gagccgcgag tgcgtgaact gcggctccat ccagacgccg ctgtggcggc gggacggcac   1500
cggccactac ctgtgcaacg cctgcgggct ctacagcaag atgaacgcc tcagccggcc    1560 cctcatcaag ccgcagaagc gcgtgccttc atcacggcgg cttggattgt cctgtgccaa   1620
ctgtcacacc acaactacca ccttatggcg cagaaacgcc gagggtgaac ccgtgtgcaa   1680
tgcttgtgga ctctacatga aactccatgg ggtgcccaga ccacttgcta tgaaaaaga   1740 gggaattcaa accaggaaac gaaaacctaa gaacataaat aaatcaaaga cttgctctgg   1800
taatagcaat aattccattc ccatgactcc aacttccacc tcttctaact cagatgattg    1860
cagcaaaaat acttcccca caacacaacc tacagcctca ggggcgggtg ccccggtgat    1920
gactggtgcg ggagagagca ccaatcccga gaacagcgag ctcaagtatt cgggtcaaga   1980
tgggctctac ataggcgtca gtctcgcctc gccggccgaa gtcacgtcct ccgtgcgacc    2040
ggattcctgg tgcgccctgg ccctggcctg agcccacgcc gccaggaggc agggagggct   2100
ccgccgcggg cctcactcca ctcgtgtctg cttttgtgca gcggtccaga cagtggcgac    2160
tgcgctgaca gaacgtgatt ctcgtgcctt tattttgaaa gagatgtttt tcccaagagg   2220
cttgctgaaa gagtgagaga agatggaagg gaagggccag tgcaactggg cgcttgggcc   2280
actccagcca gcccgcctcc ggggcggacc ctgctccact tccagaagcc aggactagga   2340
cctgggcctt gcctgctatg gaatattgag agagatttt taaaaagat tttgcatttt     2400 gtccaaaatc atgtgcttct tctgatcaat tttggttgtt ccagaatttc ttcataccttt  2460 ttccacatcc agatttcatg tgcgttcatg gagaagatca cttgaggcca tttggtacac   2520
atctctggag gctgagtcgg ttcatgaggt ctcttatcaa aaatattact cagtttgcaa    2580
gactgcattg taactttaac atacactgtg actgacgttt ctcaaagttc atattgtgtg   2640
gctgatctga agtcagtcgg aatttgtaaa cagggtagca aacaagatat ttttcttcca   2700
tgtatacaat aatttttta aaaagtgcaa tttgcgttgc agcaatcagt gttaaatcat    2760
ttgcataaga tttaacagca ttttttataa tgaatgtaaa catttaact taatggtact    2820 taaaataatt taaagaaaa atgttaactt agacattctt atgcttcttt tacaactaca    2880 tcccattta tatttccaat tgttaaagaa aaatatttca agaacaaatc ttctctcagg    2940
aaaattgcct ttctctattt gttaagaatt tttatacaag aacaccaata tacccccttt   3000
attttactgt ggaatatgtg ctggaaaaat tgcaacaaca ctttactacc taacggatag   3060
catttgtaaa tactctaggt atctgtaaac actctgatga agtctgtata gtgtgactaa   3120
cccacaggca ggttggttta cattaatttt tttttttgaa tgggatgtcc tatggaaacc   3180
tatttcacca gagtttaaa aataaaaagg gtattgtttt gtcttctgta cagtgagttc    3240 cttcccttt caaagctttc tttttatgct gtatgtgact atagatattc atataaaaca    3300
agtgcacgtg aagtttgcaa aatgctttaa ggccttcctt tcaaagcata gtccttttgg   3360
agccgttttg tacctttat accttggctt atttgaagtt gacacatggg gttagttact   3420
actctccatg tgcattgggg acagttttta taagtgggaa ggactcagta ttattatatt  3480
tgagatgata agcattttgt ttgggaacaa tgcttaaaaa tattccagaa agttcagatt   3540
ttttttcttt gtgaatgaaa tatattctgg cccacgaaca gggcgatttc ctttcagttt   3600
tttccttttg caacgtgcct tgaagtctca agctcacct gaggttgcag acgttacccc    3660
caacagaaga taggtagaaa tgattccagt ggcctctttg tattttcttc attgttgagt   3720
```

<210> SEQ ID NO 34
<211> LENGTH: 1772
<212> TYPE: DNA
<213> ORGANISM: Homo sapiens

<400> SEQUENCE: 34

```
ggataaatgt agcgccgcgg cgcgggccag cagctctgcg aggggccgga gcgcggcgga      60
gccatgcagt acccgcaccc cgggccggcg gcgggcgccg tggggggtgcc gctgtacgcg    120
cccacgccgc tgctgcaacc cgcacacccg acgccctttt acatcgagga catcctgggc    180
cgcgggcccg ccgcgcccac gcccgccccc acgctgccgt cccccaactc ctccttcacc    240
agcctcgtgt cccccctaccg gaccccggtg tacgagccca cgccgatcca tccagccttc    300
tcgcaccact ccgccgccgc gctggccgct gcctacggac ccggcggctt cgggggccct    360
ctgtaccct tcccgcggac ggtgaacgac tacacgcacg ccctgctccg ccacgacccc    420
ctgggcaaac ctctactctg gagccccttc ttgcagaggc ctctgcataa aggaaaggc     480
ggccaggtga gattctccaa cgaccagacc atcgagctgg agaagaaatt cgagacgcag    540
aaatatctct ctccgcccga gaggaagcgt ctggccaaga tgctgcagct cagcgagaga    600
caggtcaaaa cctggtttca gaatcgacgc gctaaatgga ggagactaaa acaggagaac    660
cctcaaagca ataaaaaaga gaactggaaa gtttggaca gttcctgtga tcagaggcaa    720
gatttgccca gtgaacagaa taaaggtgct tctttggata gctctcaatg ttcgccctcc    780
cctgcctccc aggaagacct tgaatcagag atttcagagg attctgatca ggaagtggac    840
attgagggcg ataaaagcta ttttaatgct ggatgatgac cactggcatt ggcatgttca    900
gaaaactgga tttaggaata atgttttgct acagaaaatc ttcatagaag aactggaagg    960
ctatataaga aagggaatca attctctggt attctggaaa cctaaaaata tttggtgcac   1020
tgctcaatta acaaacctac atggagacct taattttgac ttaacaaata gtttatgtac   1080
tgctcttagg ttgttttgat aaagtgacat tatagtgatt aaattcttcc cccttaaaa   1140
aaacagttag tggttttcac tatttataaa aaattaattt tgaacttttt gttaaatttt   1200
taagttatag ctttaaaggt tttaatagga ccttcttgaa cgacttttct gtaatctgtt   1260
tatctcccac ttaatggaaa ggcaaggggg taccccaaat ccagaggtgc ctacatttca   1320
ggcagccttg gagtatttta aaggaaaac attctttact tttatatgac attcttatac   1380
tgctgtctca aatccaaaaa catttcagag ctcttgtctc agagatgtgt gttctttttg   1440
tcagagatat ggttgatgag aatcttaaat gcttgtttg cactatcact tagtacctgt   1500
ttgaccaagg tgttaagggg atagtacctc ccaattcaag cagagaaact gacctgacta   1560
aagttaatcg cagatgaact agaagtcaca ggttaattaa atgtaagtag attgtagata   1620
ctgttttata tcaaacaatg tttataatgt gtatatagaa ttgttcactg taaaaaaaat   1680
ggccaaaatg tgttttttttt ttaataagta acttgactat aaaataaagc cgtccgtggg   1740
acgactgacc tcgttgcaaa aaaaaaaaaa aa                                 1772
```

<210> SEQ ID NO 35
<211> LENGTH: 2473
<212> TYPE: DNA
<213> ORGANISM: Homo sapiens

<400> SEQUENCE: 35

```
acagatggtg tgggagcgcg ttccccggta ggaggggggcg cgagcgagca agcaggcagg      60
cagctgccag gagctcttcc ctgctcgctc acgcctgctc tcagaagctc cgatccagac     120
acacgcgagg cgctgtcctt tcagcaccac aagctcgggc tgaggaggga ggactcctgg     180
ccgtcctcct cctcttcaaa ttggcttgaa tctgctctga ccccccacga gtgcagcaca     240
gtctgggaag aaaggcgtaa ggatggtgaa gctgaacagt aaccccagcg agaagggaac     300
caagccgcct tcagttgagg atggcttcca gaccgtccct ctcatcactc ccttggaggt     360
taatcactta cagctgcctg ctccagaaaa ggtgattgtg aagacaagaa cggaatatca     420
gccggaacag aagaacaaag ggaagttccg ggtgccgaaa atcgctgaat ttacggtcac     480
catccttgtc agcctggccc tagctttcct tgcgtgcatc gtgttcctgg tggtttacaa     540
agccttcacc tatgatcaca gctgcccaga gggattcgtc tataagcaca aacgctgtat     600
cccagcctcc ctggatgctt actactcctc ccaggacccc aattccagaa gccgcttcta     660
cacagtcatc agccactaca gcgtggccaa gcagagcact gcccgggcca tcgggccgtg     720
gctgtcagca gccgctgtca tccatgagcc caagccgccc aagacccagg gccactagag     780
gcctgcccca gccagaatgg ggggcggggt ggagaggagg accccccttg gctaagccaa     840
gctccagtta caagacaaca ctgtactcct gggatatggg ggcgggggcg gggcagggca     900
gggtggggggg aagaacgcac caaaaacgtg gtgtgtgctg gagttgtctg aaccgatatt     960
tcttttttgtt ccttggtatt gttgattcgt cgccgagtca ggctcatgta caaaggcatg    1020
tttcgtgttg attgttccca tgtaagatat ttttaaagcc actgcttatt ctttgttagg    1080
aaaatgtaac agcagaaaag gaaagaaaca agaacatga acaaaaagca ttaaactggc    1140
tccatcagaa gacgttgaag ggcagtgaag agcacagact ctgtgggctt cttagataag    1200
aaaacgtagc ttcagtgggg gctccagggt tgcagagtat gagtgacaca gaccgggact    1260
attccattag cctgtggtct gcagggtagg cccgcaggaa atgaggaatg gccgagctgg    1320
agagaagagc tgattttggc attactaagc ccagaacgca cataacccat agtgaaatgt    1380
gctggcctct ggtgcatttt gcaagatgag cacaaacttt ctgggcctcc atcctaggac    1440
ctgggcagac ccacatggcc tgggctctga atgcccaccc tgcgacggtg ggttctgcat    1500
cagcaaacgc tgaggagtgg gcagatttc tttgtcttt gcttgcattt tctagatcca    1560
cacctggata ctgcccatgt tgacgagaca gcagcagggg gagagggagg gaaggaaggt    1620
gcggctgcaa gaaggaaggc acgggacagg catgtgacac taggccacaa gcgataagca    1680
caggcacctg acttttaagt ttttgtttgt tgttgtttc ccaaagtgct gataacaata    1740
acaacaacaa taggattcca accaggagcc tcaagtgaca gccaggaaga gacctgaagg    1800
ttggggccac cacaatgcca aatcgtttct aaaggaagct gaaaaatggg actgtctttt    1860
gcccacttcg ttgtgttaaa aggggacatt tgtccaaact ccccaaccga gttctagaag    1920
ctcctgacaa ggaggcagca tccagccttg accaggcctc ccagttccct ggaaccgtat    1980
caggcattcg cctgcctctc acaaatgttt cagggaggcc agttctgcag ggtgtcagct    2040
ccaggaccca cagggccaga accagctggg agaattggtt atttgagatg tggtactgct    2100
tcctcacaag tctcccacag gccatgtaaa gggtattttt ttgtggcttg ctgtgttgct    2160
gagatcatcg tatgcaacag ctgggtaata agactagcat agctcaaact atcctgccaa    2220
acgctctcat ctgattttc ctcccttctc ccccaacctc caatcaccct gagtcacctg    2280
taaattcatt tgtcattcaa agcggaataa caagttgtcc ctagcaaaac cgctgagcgc    2340
```

-continued

| | |
|---|---|
| tttataattt tgtggtgtat ttttgtcagt aggtagcaga ggcggaagta ttttttggtg | 2400 |
| taattcttga aattttctga caggaaacaa ataaagatag atgtgtctga gaaaaaaaaa | 2460 |
| aaaaaaaaaa aaa | 2473 |

<210> SEQ ID NO 36
<211> LENGTH: 2842
<212> TYPE: DNA
<213> ORGANISM: Homo sapiens

<400> SEQUENCE: 36

| | |
|---|---|
| aatttgcata tcttatatgg cctaatggtg gcgatcatgg caagttagaa gttttctgac | 60 |
| tcctttcgga ggagcctccg ggaccccggg gagtaacagg tgtctggagg ctgaagggtg | 120 |
| gagggggttcc tggatttggg gtttgcttgt gaaactcccc tccaccctcc tctctcgcac | 180 |
| ccacccaccc cctcaccccc ttcttttttcc gtccttggaa aatggtgtcc aagctcacgt | 240 |
| cgctccagca agaactcctg agcgccctgc tgagctccgg ggtcaccaag gaggtgctgg | 300 |
| ttcaggcctt ggaggagttg ctgccatccc cgaacttcgg ggtgaagctg gagacgctgc | 360 |
| ccctgtcccc tggcagcggg gccgagcccg acaccaagcc ggtcttccat actctcacca | 420 |
| acggccacgc caagggccgc ttgtccggcg acgagggctc cgaggacggc gacgactatg | 480 |
| acacacctcc catcctcaag gagctgcagg cgctcaacac cgaggaggcg gcggagcagc | 540 |
| gggcggaggt ggaccggatg ctcagtgagg acccttggag ggctgctaaa atgatcaagg | 600 |
| gttacatgca gcaacacaac atcccccaga ggaggtggt cgatgtcacc ggcctgaacc | 660 |
| agtcgcacct ctcccagcat ctcaacaagg gcacccctat gaagacccag aagcgtgccg | 720 |
| ctctgtacac ctggtacgtc agaaagcaac gagagatcct ccgacaattc aaccagacag | 780 |
| tccagagttc tggaaatatg acagacaaaa gcagtcagga tcagctgctg tttctctttc | 840 |
| cagagttcag tcaacagagc catgggcctg gcagtccga tgatgcctgc tctgagccca | 900 |
| ccaacaagaa gatgcgccgc aaccggttca atgggggcc cgcgtcccag caaatcttgt | 960 |
| accaggccta cgatcggcaa aagaacccca gcaaggaaga gagagaggcc ttagtggagg | 1020 |
| aatgcaacag ggcagaatgt ttgcagcgag gggtgtcccc ctccaaagcc cacggcctgg | 1080 |
| gctccaactt ggtcactgag gtccgtgtct acaactggtt tgcaaaccgc aggaaggagg | 1140 |
| aggcattccg gcaaaagctg gccatggacg cctatagctc caaccagact cacagcctga | 1200 |
| accctctgct ctcccacggc tccccccacc accagcccag ctcctctcct ccaaacaagc | 1260 |
| tgtcaggagt gcgctacagc cagcagggaa acaatgagat cacttcctcc tcaacaatca | 1320 |
| gtcaccatgg caacagcgcc atggtgacca gccagtcggt tttacagcaa gtctccccag | 1380 |
| ccagcctgga cccaggccac aatctcctct cacctgatgg taaaatgatc tcagtctcag | 1440 |
| gaggaggttt gccccagtc agcaccttga cgaatatcca cagcctctcc caccataatc | 1500 |
| cccagcaatc tcaaaacctc atcatgacac ccctctctgg agtcatggca attgcacaaa | 1560 |
| gcctcaacac ctcccaagca cagagtgtcc ctgtcatcaa cagtgtggcc ggcagcctgg | 1620 |
| cagccctgca gccgtccag ttctcccagc agctgcacag ccctcaccag cagcccctca | 1680 |
| tgcagcagag cccaggcagc cacatggccc agcagccctt catggcagct gtgactcagc | 1740 |
| tgcagaactc acacatgtac gcacacaagc aggaaccccc ccagtattcc cacacctccc | 1800 |
| ggtttccatc tgcaatggtg gtcacagata ccagcagcat cagtacactc accaacatgt | 1860 |
| cttcaagtaa acagtgtcct ctacaagcct ggtgatgccc acacaccact tacttcgtgc | 1920 |

| | |
|---|---:|
| gcaacaacaa ggaccctgtt ttccacacca tcaccctctg ggcagctgtc atggaaaagc | 1980 |
| ccagtgacct gaccggcacc tgcgagaggt ccctgcttac ctgacggacg tcctgctggc | 2040 |
| acctcagaca atccactctc aggaggcgca gcccgaagcc cagtttccct tctatgcagt | 2100 |
| attgccacaa tgcctctccc acgatgtcaa ggactcctgt ctgtcctgga ggtgggagac | 2160 |
| aaggaaccac cgaagaggaa gcaagaaagc cgtactgtct atgttgtgat ccttcatcga | 2220 |
| acaaactgat gcgaaaactt gaatctgtta ctgaaatgag gagagaagga catgtgctat | 2280 |
| tgaactgagc caaacacact gtaaatatcc acagactccc tcccctgccc ccatcccaca | 2340 |
| tgatcttgag atttctttta aagaagtaaa tttgtccaat ggctgtaaac tataaactac | 2400 |
| tgtaattaag tgcaatttcc cctctgtgtc ctctcccctc tgccctgtat ataatactaa | 2460 |
| agtgtctatt agttttcttt gtaaaggtca gagtcaaaat ttcaaaagtg atctgtcccc | 2520 |
| tctcccctca tggagaaaca tcctaagtgg gaagtgaagc cccttgtcct ctcccgcggg | 2580 |
| cctggacact tatggggaca gcataccttg gactgactac cagctaactc cagtctcctg | 2640 |
| acattaagac acacctctgg atccctggag gggctgaatg tagtgtgtca gagtaacatg | 2700 |
| ccagcttcct gtgggccagg agctcagccg tgcactccct aagaaacccc agggcaggga | 2760 |
| aactggctgt tgatagcag aagaaaaagt tgcagtctca gaaagccttc cattaaaaca | 2820 |
| atttatttta tcactaaaaa aa | 2842 |

<210> SEQ ID NO 37
<211> LENGTH: 4707
<212> TYPE: DNA
<213> ORGANISM: Homo sapiens

<400> SEQUENCE: 37

| | |
|---|---:|
| ggtttgaaag gaaggcagag agggcactgg gaggaggcag tgggagggcg gagggcgggg | 60 |
| gccttcgggg tgggcgccca gggtagggca ggtggccgcg gcgtggaggc agggagaatg | 120 |
| cgactctcca aaaccctcgt cgacatggac atggccgact acagtgctgc actggaccca | 180 |
| gcctacacca ccctggaatt tgagaatgtg caggtgttga cgatgggcaa tgacacgtcc | 240 |
| ccatcagaag gcaccaacct caacgcgccc aacagcctgg tgtcagcgc cctgtgtgcc | 300 |
| atctgcgggg accgggccac gggcaaacac tacggtgcct cgagctgtga cggctgcaag | 360 |
| ggcttcttcc ggaggagcgt gcggaagaac cacatgtact cctgcagatt tagccggcag | 420 |
| tgcgtggtgg acaaagacaa gaggaaccag tgccgctact gcaggctcaa gaaatgcttc | 480 |
| cgggctggca tgaagaagga agccgtccag aatgagcggg accggatcag cactcgaagg | 540 |
| tcaagctatg aggacagcag cctgccctcc atcaatgcgc tcctgcaggc ggaggtcctg | 600 |
| tcccgacaga tcacctcccc cgtctccggg atcaacggcg acattcgggc gaagaagatt | 660 |
| gccagcatcg cagatgtgtg tgagtccatg aaggagcagc tgctggttct cgttgagtgg | 720 |
| gccaagtaca tccagctttt ctgcgagctc ccctggacg accaggtggc cctgctcaga | 780 |
| gcccatgctg gcgagcacct gctgctcgga gccaccaaga gatccatggt gttcaaggac | 840 |
| gtgctgctcc taggcaatga ctacattgtc cctcggcact gccggagct ggcggagatg | 900 |
| agccgggtgt ccatacgcat ccttgacgag ctggtgctgc ccttccagga gctgcagatc | 960 |
| gatgacaatg agtatgccta cctcaaagcc atcatcttct ttgacccaga tgccaagggg | 1020 |
| ctgagcgatc cagggaagat caagcggctg cgttcccagg tgcaggtgag cttggaggac | 1080 |
| tacatcaacg accgccagta tgactcgcgt ggccgctttg agagctgct gctgctgctg | 1140 |
| cccaccttgc agagcatcac ctggcagatg atcgagcaga tccagttcat caagctcttc | 1200 |

```
ggcatggcca agattgacaa cctgttgcag gagatgctgc tgggagggtc ccccagcgat    1260
gcaccccatg cccaccaccc cctgcaccct cacctgatgc aggaacatat gggaaccaac    1320
gtcatcgttg ccaacacaat gcccactcac ctcagcaacg gacagatgtc caccccctgag   1380 accccacagc cctcaccgcc aggtggctca gggtctgagc cctataagct cctgccggga    1440
gccgtcgcca caatcgtcaa gcccctctct gccatccccc agccgaccat caccaagcag    1500
gaagttatct agcaagccgc tggggcttgg ggctccact ggctccccc agcccctaa       1560 gagagcacct ggtgatcacg tggtcacggc aaaggaagac gtgatgccag gaccagtccc    1620
agagcaggaa tggaaggat gaagggcccg agaacatggc ctaagggcca catcccactg     1680
ccacccttga cgccctgctc tggataacaa gactttgact tggggagacc tctactgcct    1740
tggacaactt ttctcatgtt gaagccactg ccttcacctt caccttcatc catgtccaac    1800
ccccgacttc atcccaaagg acagccgcct ggagatgact tgaggcctta cttaaaccca    1860
gctcccttct tccctagcct ggtgcttctc ctctcctagc ccctgtcatg gtgtccagac    1920
agagccctgt gaggctgggt ccaattgtgg cacttgggc accttgctcc tccttctgct    1980
gctgccccca cctctgctgc ctccctctgc tgtcaccttg ctcagccatc ccgtcttctc    2040
caacaccacc tctccagagg ccaaggaggc cttggaaacg attcccccag tcattctggg    2100
aacatgttgt aagcactgac tgggaccagg caccaggcag ggtctagaag ctgtggtga    2160 gggaagacgc ctttctcctc caacccaacc tcatcctcct tcttcaggga cttgggtggg    2220
tacttgggtg aggatccctg aaggccttca acccgagaaa acaaacccag gttggcgact    2280
gcaacaggaa cttggagtgg agaggaaaag catcagaaag aggcagacca tccaccaggc    2340
ctttgagaaa gggtagaatt ctggctggta gagcaggtga gatgggacat tccaaagaac    2400
agcctgagcc aaggcctagt ggtagtaaga atctagcaag aattgaggaa gaatggtgtg    2460
ggagagggat gatgaagaga gagagggcct gctggagagc atagggtctg gaacaccagg    2520
ctgaggtcct gatcagcttc aaggagtatg cagggagctg ggcttccaga aaatgaacac    2580
agcagttctg cagaggacgg gaggctggaa gctgggaggt caggtgggt ggatgatata    2640 atgcgggtga gagtaatgag gcttggggct ggagaggaca agatgggtaa accctcacat    2700
cagagtgaca tccaggagga ataagctccc agggcctgtc tcaagctctt ccttactccc    2760
aggcactgtc ttaaggcatc tgacatgcat catctcattt aatcctccct tcctccctat    2820
taacctagag attgttttg tttttattc tcctcctccc tccccgccct caccgcccc      2880 actccctcct aacctagaga ttgttacaga agctgaaatt gcgttctaag aggtgaagtg    2940 atttttttc tgaaactcac acaactagga agtggctgag tcaggacttg aacccaggtc    3000
tccctggatc agaacaggag ctcttaacta cagtggctga atagcttctc caaaggctcc    3060
ctgtgttctc accgtgatca agttgagggg cttccggctc ccttctacag cctcagaaac    3120
cagactcgtt cttctgggaa ccctgcccac tccaggacc aagattggcc tgaggctgca    3180
ctaaaattca cttagggtcg agcatcctgt ttgctgataa atattaagga gaattcatga    3240
ctcttgacag cttttctctc ttcactcccc aagtcaaggg gagggtggc aggggtctgt    3300 ttcctggaag tcaggctcat ctggcctgtt ggcatggggg tgggacagtg tgcacagtgt    3360
gggggcaggg gagggctaag caggcctggg tttgagggct gctccggaga ccgtcactcc    3420
aggtgcattc tggaagcatt agaccccagg atggagcgac cagcatgtca tccatgtgga    3480
atcttggtgg ctttgaggac attctggaaa atgccactga ccagtgtgaa caaagggat    3540
```

-continued

| | |
|---|---|
| gtgttatggg gctggaggtg tgattaggta ggagggaaac tgttggaccg actcctgccc | 3600 |
| cctgctcaac actgacccct ctgagtggtt ggaggcagtg ccccagtgcc cagaaatccc | 3660 |
| accattagtg attgttttt atgagaaaga ggcgtggaga agtattgggg caatgtgtca | 3720 |
| gggaggaatc accacatccc tacggcagtc ccagccaagc ccccaatccc agcggagact | 3780 |
| gtgccctgct cagagctccc aagccttccc ccaccacctc actcaagtgc ccctgaaatc | 3840 |
| cctgccagac ggctcagcct ggtctgcggt aaggcaggga ggctggaacc atttctgggc | 3900 |
| attgtggtca ttcccactgt gttcctccac ctcctccctc cagcgttgct cagacctctg | 3960 |
| tcttgggaga aaggttgaga taagaatgtc ccatggagtg ccgtgggcaa cagtggccct | 4020 |
| tcatgggaac aatctgttgg agcaggtggt cagttctctg ctgggaatct accccttct | 4080 |
| ggaggagaaa cccattccac cttaataact ttattgtaat gtgagaaaca caaaacaaag | 4140 |
| tttactttt tgactctaag ctgacatgat attagaaaat ctctcgctct cttttttttt | 4200 |
| tttttttt tttttggcta cttgagttgt ggtcctaaaa cataaaatct gatggacaaa | 4260 |
| cagagggttg ctgggggggac aagcgtgggc acaatttccc caccaagaca ccctgatctt | 4320 |
| caggcgggtc tcaggagctt ctaaaaatcc gcatggctct cctgagagtg gacagaggag | 4380 |
| aggagagggt cagaaatgaa cgctcttcta tttcttgtca ttaccaagcc aattactttt | 4440 |
| gccaaatttt tctgtgatct gccctgatta agatgaattg tgaaatttac atcaagcaat | 4500 |
| tatcaaagcg ggctgggtcc catcagaacg acccacatct ttctgtgggt gtgaatgtca | 4560 |
| ttaggtcttg cgctgacccc tgagccccca tcactgccgc ctgatggggc aaagaaacaa | 4620 |
| aaaacatttc ttactcttct gtgttttaac aaaagtttat aaaacaaaat aaatggcgca | 4680 |
| tatgttttct aaaaaaaaaa aaaaaaa | 4707 |

<210> SEQ ID NO 38
<211> LENGTH: 3583
<212> TYPE: DNA
<213> ORGANISM: Homo sapiens

<400> SEQUENCE: 38

| | |
|---|---|
| gcggccgccc tgcgcgcgaa gctcgtggcc cgagagggggt gcggtcgggc cgacggaggc | 60 |
| ggggcccctgg ctgcctctct ccctgctcat aggctggccg ctcaggcctg gccggcctcg | 120 |
| gggcctcggg attcgcggcg cgctgccaa tcaggcgatc gggcccccgcc ccccggagt | 180 |
| tgggtgaaat agaggcgggc gtcaagtgtc agtagtcgcg gggcaggtac gtgcgctcgc | 240 |
| ggttctctcg cggaggtcgg cggtggcggg agcgggctcc ggagagcctg agagcacggt | 300 |
| ggggcggggc gggagaaagt ggccgcccgg aggacgttgg cgtttacgtg tggaagagcg | 360 |
| gaagagttt gcttttcgtg cgcgccttcg aaaactgcct gccgctgtct gaggagtcca | 420 |
| cccgaaacct ccctcctcc gccggcagcc ccgcgctgag ctcgccgacc caagccagcg | 480 |
| tgggcgaggt gggaagtgcg cccgacccgc gcctggagct gcgcccccga gtgcccatgg | 540 |
| ctacaagggt gctgagcatg agcgcccgcc tgggacccgt gccccagccg ccggcgccgc | 600 |
| aggacgagcc ggtgttcgcg cagctcaagc cggtgctggg cgccgcgaat ccggcccgcg | 660 |
| acgcggcgct cttccccggc gaggagctga agcacgcgca ccaccgcccg caggcgcagc | 720 |
| ccgcgcccgc gcaggccccg cagccggccc agccgcccgc caccggcccg cggctgcctc | 780 |
| cagaggacct ggtccagaca agatgtgaaa tggagaagta tctgacacct cagcttcctc | 840 |
| cagttcctat aattccagag cataaaaagt atagacgaga cagtgcctca gtcgtagacc | 900 |
| agttcttcac tgacactgaa gggttacctt acagtatcaa catgaacgtc ttcctccctg | 960 |

```
acatcactca cctgagaact ggcctctaca atcccagag accgtgcgta acacacatca    1020
agacagaacc tgttgccatt ttcagccacc agagtgaaac gactgcccct cctccggccc    1080
cgacccaggc cctccctgag ttcaccagta tattcagctc acaccagacc gcagctccag    1140
aggtgaacaa tattttcatc aaacaagaac ttcctacacc agatcttcat ctttctgtcc    1200
ctacccagca gggccacctg taccagctac tgaatacacc ggatctagat atgcccagtt    1260
ctacaaatca gacagcagca atggacactc ttaatgtttc tatgtcagct gccatggcag    1320
gccttaacac acacacctct gctgttccgc agactgcagt gaaacaattc cagggcatgc    1380
ccccttgcac atacacaatg ccaagtcagt ttcttccaca acaggccact tactttcccc    1440
cgtcaccacc aagctcagag cctggaagtc cagatagaca agcagagatg ctccagaatt    1500
taaccccacc tccatcctat gctgctacaa ttgcttctaa actggcaatt cacaatccaa    1560
atttacccac caccctgcca gttaactcac aaaacatcca acctgtcaga tacaatagaa    1620
ggagtaaccc cgatttggag aaacgacgca tccactactg cgattaccct ggttgcacaa    1680
aagtttatac caagtcttct catttaaaag ctcacctgag gactcacact ggtgaaaagc    1740
catacaagtg tacctgggaa ggctgcgact ggaggttcgc gcgatcggat gagctgaccc    1800
gccactaccg gaagcacaca ggcgccaagc ccttccagtg cggggtgtgc aaccgcagct    1860
tctcgcgctc tgaccacctg gccctgcata tgaagaggca ccagaactga gcactgcccg    1920
tgtgacccgt tccaggtccc ctgggctccc tcaaatgaca gacctaacta ttcctgtgta    1980
aaaacaacaa aaacaaacaa aagcaagaaa accacaacta aaactggaaa tgtatatttt    2040
gtatatttga gaaaacaggg aatacattgt attaatacca aagtgtttgg tcattttaag    2100
aatctggaat gcttgctgta atgtatatgg ctttactcaa gcagatctca tctcatgaca    2160
ggcagccacg tctcaacatg ggtaaggggt ggggtggag gggagtgtgt gcagcgtttt    2220
tacctaggca ccatcattta atgtgacagt gttcagtaaa caaatcagtt ggcaggcacc    2280
agaagaagaa tggattgtat gtcaagattt tacttggcat tgagtagttt ttttcaatag    2340
taggtaattc cttagagata cagtataccl ggcaattcac aaatagccat tgaacaaatg    2400
tgtgggtttt taaaaattat atacatatat gagttgccta tatttgctat tcaaaatttt    2460
gtaaatatgc aaatcagctt tataggttta ttacaagttt tttaggattc ttttggggaa    2520
gagtcataat tcttttgaaa ataaccatga atacacttac agttaggatt tgtggtaagg    2580
tacctctcaa cattaccaaa atcatttctt tagagggaag gaataatcat tcaaatgaac    2640
tttaaaaaag caaatttcat gcactgatta aaataggatt atttttaaata caaaggcat    2700 tttatatgaa ttataaactg aagagcttaa agatagttac aaaatacaaa agttcaacct    2760
cttacaataa gctaaacgca atgtcatttt taaaagaag gacttagggt gtcgttttca    2820
catatgacaa tgttgcattt atgatgcagt ttcaagtacc aaaacgttga attgatgatg    2880
cagttttcat atatcgagat gttcgctcgt gcagtactgt tggttaaatg acaatttatg    2940 tggatttttgc atgtaataca cagtgagaca cagtaatttt atctaaatta cagtgcagtt    3000
tagttaatct attaatactg actcagtgtc tgcctttaaa tataaatgat atgttgaaaa    3060
cttaaggaag caaatgctac atatatgcaa tataaaatag taatgtgatg ctgatgctgt    3120
taaccaaagg gcagaataaa taagcaaaat gccaaagggg gtcttaattg aaatgaaaat    3180
ttaattttgt ttttaaaata ttgttttatct ttatttattt tgtggtaata tagtaagttt    3240
ttttagaaga caattttcat aacttgataa attatagttt tgtttgttag aaaagttgct    3300
```

```
cttaaaagat gtaaatagat gacaaacgat gtaaataatt ttgtaagagg cttcaaaatg    3360
tttatacgtg gaaacacacc tacatgaaaa gcagaaatcg gttgctgttt tgcttctttt    3420
tccctcttat ttttgtattg tggtcatttc ctatgcaaat aatggagcaa acagctgtat    3480
agttgtagaa tttttttgaga gaatgagatg tttatatatt aacgacaatt ttttttttgg    3540
aaaataaaaa gtgcctaaaa gatgtaaaaa aaaaaaaaaa aaa                       3583
```

<210> SEQ ID NO 39
<211> LENGTH: 2187
<212> TYPE: DNA
<213> ORGANISM: Homo sapiens

<400> SEQUENCE: 39

```
gtcctttcta gacagccccc tcctccaggc tcagggacct gtctggctgt gagctcccag      60
gaggtcccag gggtgtgacc tccctccctc cctccctccc tcttcccttc acccccaggcc    120 agcccagggc cagctataaa gctggcccag cctggctctc agcacaccca gctgcctgag    180
accctccttc aacctcccta gaggacagcc ccactctgcc tcctgctccc caggggcagc    240
accatgtggc cctgtggct ctgctgggca ctctgggtgc tgcccctggc tggccccggg      300
gcggccctga ccgaggagca gctcctgggc agcctgctgc ggcagctgca gctcagcgag    360
gtgcccgtac tggacagggc cgacatggag aagctggtca tccccgccca cgtgagggcc    420
cagtatgtag tcctgctgcg cgcgcagcca cggggaccgct cccgcggaaa gaggttcagc    480
cagagcttcc gagaggtggc cggcaggttc ctggcgtcgg aggccagcac acacctgctg    540
gtgttcggca tggagcagcg gctgccgccc aacagcgagc tggtgcaggc cgtgctgcgg    600
ctcttccagg agccggtccc caaggccgcg ctgcacaggc acgggcggct gtccccgcgc    660
agcgcccagg cccgggtgac cgtcgagtgg ctgcgcgtcc gcgacgacgg ctccaaccgc    720 acctcccctca tcgactccag gctggtgtcc gtccacgaga gcggctggaa ggccttcgac    780
gtgaccgagg ccgtgaactt ctggcagcag ctgagccggc cccggcagcc gctgctgcta    840
caggtgtcgg tgcagaggga gcatctgggc ccgctggcgt ccggcgccca aagctggtc      900 cgcttttgcct cgcagggggc gccagccggg cttggggagc cccagctgga gctgcacacc    960
ctggacctca gggactatgg agctcagggc gactgtgacc ctgaagcacc aatgaccgag    1020 ggcaccgct gctgccgcca ggagatgtac attgacctgc aggggatgaa gtgggccaag   1080
aactgggtgc tggagccccc gggcttcctg gcttacagt gtgtgggcac ctgccagcag    1140 ccccgagg ccctggcctt caattggcca tttctgggc cgcgacagtg tatcgcctcg    1200
gagactgcct cgctgcccat gatcgtcagc atcaaggagg gaggcaggac caggcccag    1260 gtggtcagcc tgcccaacat gagggtgcag aagtgcagct gtgcctcgga tgggcgctc    1320 gtgccaagga ggctccagcc ataggcgcct ggtgtatcca ttgagccctc taactgaacg    1380
tgtgcataga ggtggtctta atgtaggtct aactttata cttagcaagt tactccatcc    1440
caatttagtg ctcctgtgtg accttcgccc tgtgtccttc catttcctgt ctttcccgtc    1500
catcacccat cctaagcact tacgtgagta aataatgcag ctcagatgct gagctctagt    1560
aggaaatgct ggcatgctga ttacaagata cagctgagca atgcacacat tttcagctgg    1620
gagtttctgt tctctggcaa attcttcact gagtctggaa caataatacc ctatgattag    1680
aactggggaa acagaactga attgctgtgt tatatgagga attaaaacct tcaaatctct    1740
atttccccca aatactgacc cattctggac ttttgtaaac ataccctaggc ccctgttccc   1800 ctgagagggt gctaagagga aggatgaagg gcttcaggct gggggcagtg gacagggaat    1860
```

```
tgggatacct ggattctggt tctgacaggg ccacaagcta ggatctctaa caaacgcaga    1920
aggctttggc tcgtcatttc ctcttaaaaa ggaggagctg ggcttcagct ctaagaactt    1980
cattgccctg gggatcagac agcccctacc tacccctgcc cactcctctg gagactgagc    2040
cttgcccgtg catatttagg tcatttccca cactgtctta gagaacttgt caccagaaac    2100
cacatgtatt tgcatgtttt ttgttaattt agctaaagca attgaatgta gatactcaga    2160
agaaataaaa aatgatgttt cactctg                                        2187
```

<210> SEQ ID NO 40
<211> LENGTH: 3033
<212> TYPE: DNA
<213> ORGANISM: Homo sapiens

<400> SEQUENCE: 40

```
ttaaattcta attagagatg caggaatcaa tgatagggag gttggacagc tcagttcccc      60
agtgccagcc caatagacgg atgagttatt gtcatgtaaa aagcgccagc aataagacca     120
accgctttgc tattgtccaa gtggaaagag ccaagtttat tatgaggact atatgctcta     180
gagacctcag acaaggcatc tcataggagg cttttttcata aaactaggct ctgctggtag    240
taaggaggcc agtttggagg caggcgttga gctgtgcaca tctccccact ccagccacct    300
tctccatatc catcttttat ttcattttc cacttggctg agccatccag aaccttttca     360
atgtataaaa tggaatattc ttacctcaat tcctctgcct acgagtcctg tatggctggg    420
atggacacct cgagcctggc ttcagcctat gctgacttca gttcctgcag ccaggccagt    480
ggcttccagt ataacccgat aaggaccact tttggggcca cgtccggctg cccttccctc    540
acgccgggat cctgcagcct gggcaccctc agggaccacc agagcagtcc gtacgccgca    600
gttccttaca aactcttcac ggaccacggc ggcctcaacg agaagcgcaa gcagcggcgc    660
atccgcacca ctttcaccag tgcccagctc aaagagctgg aaagggtctt cgcggagact    720 cactacccg acatctacac tcgggaggag ctggccctga agatcgacct cacagaggcg     780
cgagtccagg tgtggttcca gaaccgccgc gccaagtttc gcaagcagga gcgcgcagcg    840
gcagccgcag cggccgcggc caagaacggc tcctcgggca aaaagtctga ctcttccagg    900
gacgacgaga gcaaagaggc caagagcact gaccccggaca gcactggggg cccaggtccc    960
aatcccaacc ccaccccag ctgcggggcg aatggaggcg gcggcggcgg gcccagcccg    1020
gctggagctc cggggggcggc ggggcccggg ggcccgggag gcgaacccgg caagggcggc    1080
gcagcagcag cggcggcggc cgcggcagcg gcggcggcgg cagcggcagc ggcggcagct    1140
ggaggcctgg ctgcggctgg gggccctgga caaggctggg ctcccggccc cggccccatc    1200
acctccatcc cggattcgct tggggtccc ttcgccagcg tcctatcttc gctccaaaga    1260
cccaacggtg ccaaagccgc cttagtgaag agcagtatgt tctgatctgg aatcctgcgg    1320
cggcggcggc ggcggcgaca gcgggcgagc cagggcccgg gcgggcgagt gggcgagcgg    1380
gtaggcccaa ggctattgtc gtcgctgctg ccatggcttt ttcattgagg gcctaaagta    1440
atcgcgctaa gaataaaggg aaaacggcgt cgccctcatt tcaacccac tcctaccccc    1500 ttcctcaacc cccaaacaaa acaaacaaac ttccctggct tcgcacctgc ctggggcctc    1560 gcagcgggc cagggctccg cctgctgatc ggggggttgtg agcagcgcgg cctggacgcg    1620
gggcactctc aggggggctgt gtctgcgtgt cagtttgtgt ctgtctcggg gaatgtgtgt    1680
ctgtggccca agcaggtgac aggaagagat ggggggcctc aaccaactta gtgacttgtt    1740
```

```
tagaaaaaaa agacaaaaaa gtaaaaataa aaacaaaaaa gttggaaggc agaaaccatt    1800
aaaaaacaaa aagccaacaa cccagaaagg tttaaaaaac ataaggaaaa aaaagacaaa    1860
ttaaaggagg ggctagggga gaagctgcag ctggagctga aggctcgatc ttgtgaaccc    1920
ctaaatccgc tccctcctaa cagcacggat tctcttgggg ctcttcttca gggaagagta    1980
gggacgccgt tccagccccc cttcctatcg tgtccttggg ttcgggtcac tgcggcgacg    2040
acttgctcag actgtcccgg cggccggagt gactttctcg caccccttg cctgtcccac     2100 ctcgctgaac accatcccgc cattagcgca tcggaacccc acacagttgc aactcccaac    2160
cccgaatctt tgcagccgtt cggccctgaa agatgcccta tccatgagat gccttttcat    2220
ctgcaaactc tgcaaaatgt gtctcatgtt tcgcaactct ttttttcccc ctcgctcccg    2280
cctaccccgt cggcatttc ttcttccacc agctttact gaacttttg gcactgcttt        2340 ggattggggt caattgcagt ccacgtaact ggctgcagag aaatctaccg agcaaggaaa    2400
aggcacacac acacgtttgc aggggtgtct cggtttgcat ttctgttgga atgatccgaa    2460
ctggactcac atcctgtatg gtggatggac tgtatattga gggttccatt cttcgcgcag    2520
tttagacatc tctgttttga ttctttgttg ttgttttat tttaaaaggc acaaactcta      2580
gatattagtt gaatgttgag gctttaactt tttcggtgtc tttctacaac tgtgttctgt    2640
gactcaattg tatcgtgtta atatcagtgc agactgtctc ctctacgtga ccgtataatg    2700
tttttctctt cttgtagtct ctatggcgtg tctttatggt gtaataaggt tctcacgggt    2760
tcaatctttt gtgtttagag aggccacggt tcagacaatg gtatatattt ttgttatcag    2820
gtgcatgtct gtctgatttc ttttttttc ctgttggact atgtttgtga acataattgt      2880
cataagttat gtttcagatt tttgaattta tttatatgtg ttataatgaa tgcttctatt    2940
taaaagggaa atatttctac atgtgcatat agttttccaa gagtgtacca ttaacttgat    3000
tgttgataat aaaaacaaaa agcaagtcta aaa                                 3033

<210> SEQ ID NO 41
<211> LENGTH: 1503
<212> TYPE: DNA
<213> ORGANISM: Homo sapiens

<400> SEQUENCE: 41
atggccacgg cggcttctaa cccctacctg ccggggaaca gcctgctcgc ggccggctct      60
attgtgcact cggacgcggc aggggctggc ggcggcgggg gtggcggcgg cggcggcggc    120 ggggcggcg caggggcgg gggcggcggc atgcagccgg gcagcgccgc cgtgacctcg       180
ggcgcctacc gggggaccc gtcctctgtc aagatggtcc agagcgactt catgcagggg    240
gccatggccg ccagcaacgg cggccatatg ctgagccacg cgcaccagtg ggtcacagcc    300
ctgccccacg ccgccgccgc cgccgccgct gccgccgccg ccgccgtgga ggcgagctcg    360
ccgtggtcgg gcagcgccgt gggcatggct ggcagccccc agcagccacc gcagccgccg    420
ccgccaccgc cgcagggccc cgacgtgaag ggcggcgccg ggcgcgacga cctgcacgcg    480
ggcacagcgc tgcaccaccg cgggccgccg cacctcggac cccgccgcc gccccacac     540 cagggccacc ctggggctg gggggcggcc ccgctgccg cagccgcagc cgcgccgcc       600 gccgccgccg cgcacctccc gtccatggcc ggggccagc agccgccgcc gcagagtctg    660
ctctactcgc agcccggagg cttcacggtg aacggcatgc tgagcgcgcc accggggccc    720
ggcggcggcg gcgcggcgc gggcggtgga gcccagagct ggtgcaccc ggggctggtg     780 cgcggggaca cgccagagct ggccgagcac caccaccacc accaccacca cgcgcatcct    840
```

```
cacccgccgc acccgcacca cgcgcaggga ccccgcacc acggcggcgg cggcggcggc    900
gcggggcctg gactcaacag ccacgacccg cactcggacg aggacacgcc gacgtcggac    960
gacctggagc agttcgccaa gcagttcaag cagcggcgca tcaagctggg cttcacgcag   1020
gccgacgtgg ggttggcgct gggcacactc tacggcaacg tgttctcgca gaccaccatc   1080
tgccgcttcg aggccctgca gctgagcttc aagaacatgt gcaagctcaa gccgctgctg   1140
aacaagtggc tggaggaggc ggactcaagc ccggcagcc cacaagcat cgacaagatc     1200 gcggcgcagg gccgcaagcg caagaagcgg acctctatcg aggtgagcgt caagggcgcg   1260
ctggagagcc acttcctcaa gtgccccaag ccctccgcgc aggagatcac caacctggcc   1320
gacagcctgc agctcgagaa ggaggtggtg cgggtctggt tctgcaatcg cgccaaaag    1380 gagaagcgca tgacgccgcc cgggatccaa cagcagacgc ccgacgacgt ctactcgcag   1440
gtgggcaccg tgagcgccga cacgccgccg cctcaccacg ggctgcagac gagcgttcag   1500
tga                                                                 1503

<210> SEQ ID NO 42
<211> LENGTH: 4753
<212> TYPE: DNA
<213> ORGANISM: Homo sapiens

<400> SEQUENCE: 42
agtttgacgt cgtcagccgg cttggtcttc tacccagtga ctcaaagcac taaaagtcag     60
cataatcgga actgaagtca gtagcatcgc ccatttgcca ttcactgcag tagcaaaagt    120
agtactctgt ggtgggttaa tcggtttgag gcagctcctt aaatgaacat tgtgtttca    180 tttttctgtt attttcccga acatgaaaag acgataaaac tgaaatggaa aagatctatt    240
ccagagggga gcttcaccac ttcattgacg gctttaatga agagaaaagc aactggatgc    300
gctatgtgaa tccagcacac tctccccggg agcaaaacct ggctgcgtgt cagaacggga    360
tgaacatcta cttctacacc attaagccca tccctgccaa ccaggaactt cttgtgtggt    420
attgtcggga ctttgcagaa aggcttcact cccttatcc cggagagctg acaatgatga    480
atctcacaca aacacagagc agtctaaagc aaccgagcac tgagaaaaat gaactctgcc    540
caaagaatgt cccaaagaga gagtacagcg tgaaagaaat cctaaaattg gactccaacc    600
cctccaaagg aaaggacctc taccgttcta acatttcacc cctcacatca gaaaggacc    660 tcgatgactt tagaagacgt gggagccccg aaatgcccct ctaccctcgg gtcgtttacc    720
ccatccgggc ccctctgcca gaagactttt tgaaagcttc cctggcctac gggatcgaga    780
gacccacgta catcactcgc tcccccattc atcctccac cactccaagc cctctgcaa     840 gaagcagccc cgaccaaagc ctcaagagct ccagccctca cagcagccct gggaatacgg    900
tgtcccctgt gggccccggc tctcaagagc accgggactc ctacgcttac ttgaacgcgt    960 cctacgcac ggaaggtttg gctcctacc ctggctacgc accctgccc cacctccgc       1020 cagcttcat cccctcgtac aacgctcact acccaagtt cctcttgccc cctacggca      1080 tgaattgtaa tggcctgagc gctgtgagca gcatgaatgg catcaacaac tttggcctct    1140 tccgaggct gtgccctgtc tacagcaatc tcctcggtgg gggcagcctg ccccacccca    1200
tgctcaaccc cacttctctc ccgagctcgc tgccctcaga tggagcccgg aggttgctcc    1260
agccggagca tccagggag gtgcttgtcc cggcgcccca cagtgccttc tccttttaccg    1320 gggccgccgc cagcatgaag gacaaggcct gtagccccac aagcgggtct cccacggcgg    1380
```

```
gaacagccgc cacggcagaa catgtggtgc agcccaaagc tacctcagca gcgatggcag    1440
cccccagcag cgacgaagcc atgaatctca ttaaaaacaa agaaacatg accggctaca     1500 agacccttcc ctacccgctg aagaagcaga acggcaagat caagtacgaa tgcaacgttt    1560
gcgccaagac tttcggccag ctctccaatc tgaaggtcca cctgagagtg cacagtggag    1620
aacggccttt caaatgtcag acttgcaaca agggctttac tcagctcgcc cacctgcaga    1680
aacactacct ggtacacacg ggagaaaagc cacatgaatg ccaggtctgc cacaagagat    1740
ttagcagcac cagcaatctc aagacccacc tgcgactcca ttctggagag aaaccatacc    1800
aatgcaaggt gtgccctgcc aagttcaccc agtttgtgca cctgaaactg cacaagcgtc    1860
tgcacacccg ggagcggccc cacaagtgct cccagtgcca caagaactac atccatctct    1920
gtagcctcaa ggttcacctg aaagggaact gcgctgcggc cccggcgcct gggctgccct    1980
tggaagatct gacccgaatc aatgaagaaa tcgagaagtt tgacatcagt gacaatgctg    2040
accggctcga ggacgtggag gatgacatca gtgtgatctc tgtagtggag aaggaaattc    2100
tggccgtggt cagaaaagag aaagaagaaa ctggcctgaa agtgtctttg caaagaaaca    2160
tggggaatgg actcctctcc tcagggtgca gcctttatga gtcatcagat ctacccctca    2220
tgaagttgcc tcccagcaac ccactacctc tggtacctgt aaaggtcaaa caagaaacag    2280
ttgaaccaat ggatccttaa gattttcaga aaacacttat tttgtttctt aagttatgac    2340
ttggtgagtc agggtgcctg taggaagtgg cttgtacata atcccagctc tgcaaagctc    2400
tctcgacagc aaatggtttc ccctcacctc tggaattaaa aaggaactc caaagttact     2460 gaaatctcag ggcatgaaca aggcaaaggc catatatata tatatatata tatctgtata    2520
catattatat atacttattt acacctgtgt ctatatattt gcccctgtgt attttgaata    2580
tttgtgtgga catgtttgca tagccttccc attactaaga ctattaccta gtcataatta    2640
ttttttcaat gataatcctt cataatttat tatacaattt atcattcaga aagcaataat    2700
taaaaaagtt tacaatgact ggaaagattc cttgtaattt gagtataaat gtattttttgt   2760 cttgtggcca ttctttgtag ataatttctg cacatctgta taagtaccta agatttagtt    2820
aaacaaatat atgacttcag tcaacctctc tctctaataa tggtttgaaa atgaggtttg    2880
ggtaattgcc aatgttggac agttgatgtg ttcattcctg ggatcctatc atttgaacag    2940
cattgtacat aacttgggggg tatgtgtgca ggattaccca agaataactt aagtagaaga   3000
aacaagaaag ggaatcttgt atattttttgt tgatagttca tgttttttccc ccagccacaa  3060 ttttaccgga agggtgacag gaaggcttta ccaacctgtc tctccctcca aaagagcaga    3120
atcctcccac cgccctgccc tccccaccga gtcctgtggc cattcagagc ggccacatga    3180
cttttgcatc cattgtatta tcagaaaatg tgaagaagaa aaaatgcca tgttttaaaa     3240 ccactgcgaa aatttcccca agcataggt ggctttgtgt gtgtgcgatt tggggggcttg    3300 agtctgggtg tgttttttgtt gttggttttt gttgcttttt ttttttttttt tttttttaatg 3360 tcaaaattgc acaaacatgg tgctctacca ggaaggattc gaggtagata ggctcaggcc    3420
acactttaaa aacaaacaca caaacaacaa aaaacgggta ttctagtcat cttggggtaa    3480
aagcgggtaa tgaacattcc tatccccaac acatcaattg tattttttct gtaaaactca    3540
gattttcctc agtatttgtg ttttacatt ttatggttaa tttaatggaa gatgaaaggg     3600
cattgcaaag ttgttcaaca acagttacct cattgagtgt gtccagtagt gcaggaaatg    3660
atgtcttatc taatgatttg cttctctaga ggagaaaccg agtaaatgtg ctccagcaag    3720
atagactttg tgttattcta tcttttattc tgctaagccc aaagattaca tgttggtgtt    3780
```

-continued

```
caaagtgtag caaaaaatga tgtatattta taaatctatt tataccacta tatcatatgt    3840
atatatattt ataaccactt aaattgtgag ccaagccatg taaaagatct acttttcta    3900 agggcaaaaa aaaaaaaaaa aaaaaagaa cactcctttc tgagactttg cttaatactt    3960
ggtgacctca caatcacgtc ggtatgattg ggcacccttg cctactgtaa gagaccctaa    4020
aaccttggtg cagtggtggg gaccacaaaa caaccaggga ggaagagata catcattttt    4080
tagtattaag gaccatctaa gacagctcta ttttttttt gccactttat gattatgtgg    4140
tcacacccaa gtcacagaaa taaaaaactg actttaccgc tgcaatttt ctgttttcct    4200 ccttactaaa tactgataca ttactccaat ctatttata attatatttg acattttgtt    4260
cacatcaact aatgttcacc tgtagaagag aacaaatttc gaataatcca gggaaaccca    4320
agagccttac tggtcttctg taacttccaa gactgacagc ttttatgta tcagtgtttg    4380 ataaacacag tccttaactg aaggtaaacc aaagcatcac gttgacatta gaccaaatac    4440
ttttgattcc caactactcg tttgttcttt ttctcctttt gtgctttccc atagtgagaa    4500
tttttataaa gacttcttgc ttctctcacc atccatcctt ctcttttctg cctcttacat    4560
gtgaatgttg agcccacaat caacagtggt tttatttttt cctctactca aagttaaaac    4620
tgaccaaagt tactggcttt ttactttgct agaacaacaa actatcttat gtttacatac    4680
tggtttacaa tgttatttat gtgcaaattg tcaaaatgta aattaaatat aaatgttcat    4740
gctttaccaa aat                                                      4753
```

<210> SEQ ID NO 43
<211> LENGTH: 2205
<212> TYPE: DNA
<213> ORGANISM: Homo sapiens

<400> SEQUENCE: 43

```
acctacaccg ggcggtcata catcgattgg cttcctagat aatagatcgt gccacccggt      60
agggacctct ggggacgcgc cgggagctgg aagagtcgca cgcagcagcc caaccctgag     120
ttaatcaaac tagcaacagg atctcaagca gcagcgacgg cggtggcaag agtagcggtg     180
acggcggcgg cggcggcggc ggcagcatta tgcgtgatta ctgacaggca ccagctgctg     240
ccgccacagc cgtctcaaac gcactatgtg gactctccga tctagaggca gattcctgac     300
taatcccaga gggctggccc agcctgtgct ccccgggctg ctaggaagcg atgaccactc     360
ttgttagccc aagttgaaga aagccggggct gtgcctggga gccgagagag cggtaatat     420 ttagaagctg cacaggagag gaacatgaac tgacgagtaa acatgtatgg aaattattct     480
cacttcatga gtttcccgc aggctatgga ggctcccctg ccacactgg ctctacatcc     540 atgagcccat cagcagcctt gtccacaggg aagccaatgg acagccaccc cagctacaca     600 gatacccag tgagtgcccc acggactctg agtgcagtgg ggacccccct caatgccctg     660
ggctctccat atcgagtcat cacctctgcc atgggcccac cctcaggagc acttgcagcg     720
cctccaggaa tcaacttggt tgccccaccc agctctcagc taaatgtggt caacagtgtc     780
agcagttcag aggacatcaa gcccttacca gggcttcccg ggattggaaa catgaactac     840
ccatccacca gccccggatc tctggttaaa cacatctgtg ccatctgtgg agacagatcc     900
tcaggaaagc actacggggt atacagttgt gaaggctgca aagggttctt caagaggacg     960
ataaggaagg acctcatcta cacgtgtcgg gataataaag actgcctcat tgacaagcgt    1020
cagcgcaacc gctgccagta ctgtcgctat cagaagtgcc ttgtcatggg catgaagagg    1080
```

| | |
|---|---|
| gaagctgtgc aagaagaaag acagaggagc cgagagcgag ctgagagtga ggcagaatgt | 1140 |
| gctaccagtg gtcatgaaga catgcctgtg gagaggattc tagaagctga acttgctgtt | 1200 |
| gaaccaaaga cagaatccta tggtgacatg aatatggaga actcgacaaa tgaccctgtt | 1260 |
| accaacatat gtcatgctgc tgacaagcag ctttttcaccc tcgttgaatg ggccaagcgt | 1320 |
| attccccact tctctgacct caccttggag gaccaggtca ttttgcttcg ggcagggtgg | 1380 |
| aatgaattgc tgattgcctc tttctcccac cgctcagttt ccgtgcagga tggcatcctt | 1440 |
| ctggccacgg gtttacatgt ccaccggagc agtgcccaca gtgctggggt cggctccatc | 1500 |
| tttgacagag tcctaactga gctggtttcc aaaatgaaag acatgcagat ggacaagtcg | 1560 |
| gaactgggat gcctgcgagc cattgtactc tttaacccag atgccaaggg cctgtccaac | 1620 |
| ccctctgagg tggagactct gcgagagaag gtttatgcca cccttgaggc ctacaccaag | 1680 |
| cagaagtatc cggaacagcc aggcaggttt gccaagctgc tgctgcgcct cccagctctg | 1740 |
| cgttccattg gcttgaaatg cctggagcac ctcttcttct tcaagctcat cggggacacc | 1800 |
| cccattgaca ccttcctcat ggagatgttg gagacccccgc tgcagatcac ctgagcccca | 1860 |
| ccagccacag cctcccccacc caggatgacc cctgggcagg tgtgtgtgga cccccacccct | 1920 |
| gcactttcct ccacctccca ccctgacccc cttcctgtcc ccaaaatgtg atgcttataa | 1980 |
| taaagaaaac ctttctacac atgagacttt tataggtgga cttttgtata gatgttaaag | 2040 |
| gtaatacgct ttgctgtcta cagggctggg agactttctg gaagttcttg ggaaaactaa | 2100 |
| tcaagcctct gtacatacaa ttggtttaaa ttatttttc acttgccctg gaaagcaaac | 2160 |
| aaatgagtaa taaataata tgtgtgaaat tggcaaaaaa aaaaa | 2205 |

<210> SEQ ID NO 44
<211> LENGTH: 2350
<212> TYPE: DNA
<213> ORGANISM: Homo sapiens

<400> SEQUENCE: 44

| | |
|---|---|
| gcagtgtcac taggccggct gggggccctg ggtacgctgt agaccagacc gcgacaggcc | 60 |
| agaacacggg cggcggcttc gggccgggag acccgcgcag ccctcgggc atctcagtgc | 120 |
| ctcactcccc accccctccc ccgggtcggg ggaggcggcg cgtccggcgg agggttgagg | 180 |
| ggagcggggc aggcctggag cgccatgagc agcccggatg cgggatacgc cagtgacgac | 240 |
| cagagccaga cccagagcgc gctgccgcg gtgatggccg ggctgggccc ctgcccctgg | 300 |
| gccgagtcgc tgagcccat cggggacatg aaggtgaagg gcgaggcgcc ggcgaacagc | 360 |
| ggagcaccgg ccggggccgc gggccgagcc aagggcgagt cccgtatccg gcggccgatg | 420 |
| aacgctttca tggtgtgggc taaggacgag cgcaagcggc tggcgcagca gaatccagac | 480 |
| ctgcacaacg ccgagttgag caagatgctg ggcaagtcgt ggaaggcgct gacgctggcg | 540 |
| gagaagcggc ccttcgtgga ggaggcagag cggctgcgcg tgcagcacat gcaggaccac | 600 |
| cccaactaca gtaccggcc gcggcggcgc aagcaggtga agcggctgaa gcgggtggag | 660 |
| ggcggcttcc tgcacggcct ggctgagccg caggcggccg cgctgggccc cgagggcggc | 720 |
| cgcgtggcca tggacggcct gggcctccag ttccccgagc agggcttccc cgccggcccg | 780 |
| ccgctgctgc ctccgcacat gggcggccac taccgcgact gccagagtct gggcgcgcct | 840 |
| ccgctcgacg gctaccgtt gcccacgccc gacgtcccc gctggacgg cgtggacccc | 900 |
| gaccggcctt tcttcgcccgc cccgatgccc ggggactgcc cggcggccgg cacctacagc | 960 |
| tacgcgcagg tctcggacta cgctggcccc ccggagcctc ccgccggtcc catgcacccc | 1020 |

```
cgactcggcc cagagcccgc gggtccctcg attccgggcc tcctggcgcc acccagcgcc    1080
cttcacgtgt actacggcgc gatgggctcg cccggggcgg gcggcgggcg cggcttccag    1140
atgcagccgc aacaccagca ccagcaccag caccagcacc accccccggg ccccggacag    1200
ccgtcgcccc ctccggaggc actgccctgc cgggacggca cggaccccag tcagcccgcc    1260
gagctcctcg gggaggtgga ccgcacggaa tttgaacagt atctgcactt cgtgtgcaag    1320
cctgagatgg gcctccccta ccaggggcat gactccggtg tgaatctccc cgacagccac    1380
ggggccattt cctcggtggt gtccgacgcc agctccgcgg tatattactg caactatcct    1440
gacgtgtgac aggtccctga tccgccccag cctgcaggcc agaagcagtg ttacacactt    1500
cctggaggag ctaaggaaat cctcagactc ctgggttttt gttgttgctg ttgttgtttt    1560
ttaaaaggtg tgttggcata taatttatgg taatttattt tgtctgccac ttgaacagtt    1620
tgggggggtg aggtttcatt taaaatttgt tcagagattt gtttcccata gttggattgt    1680
caaaacccta tttccaagtt caagttaact agctttgaat gtgtcccaaa acagcttcct    1740
ccatttcctg aaagtttatt gatcaaagaa atgttgtcct gggtgtgttt tttcaatctt    1800
ctaaaaaata aaatctggaa tcctgctttt ttgctctact agtacctctg tcacactagt    1860
cttatcaaaa accagttctt aagatcaatg ttaagtttat tagttaatgt aaatttctca    1920
tcctcgaaaa gggtgaacat aaatgccttt aaggagtata tctaaaaata aacattagga    1980
tatctaagtt tgatgtaatt gtttcaggaa ggaaaaaaga aaagcattct ggaatgagcc    2040
tacttcaagt aatcttagtt tctaaaacta acagttaata tttttcaattc cagtatatca    2100 ctttaagtag aaggggatgt ccaagtaatt ttggttttct aactgttgaa tcataagctt    2160
gacctgcccc cagaggcttt ttggatgttt ttatctgtgt tttgccatct ctttacactc    2220
ctcgacattc agtttacctt aatcttcaca tttttacacc ttgggaagtg gcaagcatcg    2280
ctgggtttaa gataaaggag tcacaaaaac taatcaaaat aaaatttgca ttatgacaac    2340
ttttaataca                                                          2350
```

<210> SEQ ID NO 45
<211> LENGTH: 3617
<212> TYPE: DNA
<213> ORGANISM: Homo sapiens

<400> SEQUENCE: 45

```
aagtttccaa gtggtcaact tgaccgatgc tttggcaatt gaaaaagggc agaaaggcgc     60
gggctagtgg gtggatgggg acaaagatct aagtcacctt cttccagcgt gtgagcctgg    120
gaggagggtg ggggtcctga ggagcaagag gtacgaggaa ggaaaaggag agggcttctg    180
ggttagtttc cacctcctgc tttcaactcc acggcgcttt ccttccggaa aggacgctgg    240
attcagggcg cgccagtacg cgcagtagcg gcccgcgagt cggcaggtgg gtagccccgg    300
cgcgggagga aggggaagtt accttcccct cggaagaggg cgctggctcc cccatcctgc    360
ctttataata aggccaccgg aggagaggaa gcagccagct gccgtctgcg ctttgcaaag    420
catgcagtta ggggagcagc tcttggtgag ctcagtgaac ctgcctggcg cgcacttcta    480
cccgctggag agtgcgcgag gcggcagcgg cgggagcgct ggccacctcc ccagcgcggc    540
cccctctcct cagaagttgg acttagacaa agcgtccaag aagtttccg gcagtctctc    600 ctgcgaggcg gtgagcgggg agccgcagc cgccagcgca ggggccccg cggccatgct    660 tagtgacacc gacgccgggg acgcatttgc cagcgctgcg gcagtggcca agccggggcc    720
```

```
cccggacggc cgcaagggct ccccctgcgg ggaggaggag ctgccctccg ccgctgcagc    780
cgccgccgcc gccgccgccg cggctgcggc cactgcgcgc tactccatgg acagcctgag    840
ctccgagcgg tactacctcc agtccccctcgg tcctcagggg tcggagctgg ctgcgccctg    900
```

```
cccggacggc cgcaagggct ccccctgcgg ggaggaggag ctgccctccg ccgctgcagc    780
cgccgccgcc gccgccgccg cggctgcggc cactgcgcgc tactccatgg acagcctgag    840
ctccgagcgg tactacctcc agtccccccgg tcctcagggg tcggagctgg ctgcgccctg    900
ctcactcttc ccgtaccagg cggcggctgg ggcgccccac ggacctgtgt acccggctcc    960
taacggggcg cgctacccct acggctccat gctgccccccc ggcggcttcc ccgcggctgt   1020
gtgcccaccc gggagggcgc agttcggccc aggagccggt gcgggcagtg gcgcgggcgg   1080
tagcagcggc gggggcggcg gcccgggcac ctatcagtac agccaggggg ctccgctcta   1140
cgggccgtac cctggagccg cagcggcggg atcttgcgga ggactggggg gcctgggggt   1200
tccaggttct ggcttccgtg cccacgtcta cctgtgcaac cggcctctgt ggctcaaatt   1260
ccaccgccac caaactgaga tgatcattac gaaacagggc aggcgcatgt ttcctttctt   1320
gagcttcaac ataaacggac tcaatcccac tgcccactac aatgtgttcg tagaggtggt   1380
gctggcggac cccaaccact ggcgcttcca gggggcaaa tgggtgacct gtggcaaagc   1440
cgacaataac atgcagggca acaaaatgta tgttcaccca gagtctccta atactggttc   1500
ccactggatg agacaggaga tttcattcgg gaaattaaaa ctcaccaata acaaaggcgc   1560
aaataacaac aacaccccaga tgatagtctt acaatcctta cacaaatacc aaccccgact   1620
gcatattgtt gaagttacag aggatggcgt ggaggacttg aatgagccct caaagaccca   1680
gacttttacc ttctcagaaa cgcaattcat tgcagtgact gcctaccaaa acaccgatat   1740
tactcaacta aagattgatc ataacccctt tgcaaaaggc ttcagagaca actatgattc   1800
atcccatcag attgtccctg gaggtcggta cggcgttcaa tccttcttcc cggagccctt   1860
tgtcaacact ttacctcaag cccgctatta taatggcgag agaaccgtgc cacagaccaa   1920
cggcctcctt tcaccccaac agagcgaaga ggtggccaac cctccccagc ggtggccttgt   1980
cacgcctgtc cagcaacctg ggaccaacaa actagacatc agttcctatg aatctgaata   2040
tacttctagc acattgctcc catatggcat taaatccttg ccccttcaga catcccatgc   2100
cctggggtat tacccagacc caacctttcc tgcaatggca gggtggggag gtcgaggttc   2160
ttaccagagc aagatggcag ctggactacc atggacctcc agaacaagcc ccactgtgtt   2220
ctctgaagat cagctctcca aggagaaagt gaaagaggaa attggctctt cttggataga   2280
gacacccccct tccatcaaat ctctagattc caatgattca ggagtataca ccagtgcttg   2340
taagcgaagg cggctgtctc ctagcaactc cagtaatgaa aattcaccct ccataaagtg   2400
tgaggacatt aatgctgaag agtatagtaa agacacctca aaaggcatgg gagggtatta   2460
tgcttttttac acaactccct aaagagttat tttaacctca aaaattagct aacttttgc   2520
agatggactt ggtggtgttt tttgttgtct tctttgccta ggttgccaaa agatgtttg   2580
ccttccacct tgatgcatcc tgttttgtgc aattctctaa agaaggtgc caaagctttt   2640
tgattgctgc aggtaactga aacaaaccta gcatttttaa aaaataagat taatggaaga   2700
ctttaaggta ttttaaaatt cgaagggtat ccaaggttct gtatttattt attggggaga   2760
cactaaccct tcaaagaagc aggctgtgaa cattgggtgc ccagtgctat cagatgagtt   2820
aaaaccttg attctcattt ctatttgtaa attcttaagc aaatagaagc cgagtgttaa   2880
ggtgttttgc ttctgaaaga gggctgtgcc ttccgtttca gaggagaca ttttgctgtt   2940
acattctgcc aggggcaaaa gatactaggc ccaggagtca gaaaagctt ttgtgaaagt   3000
gatagtttca cctgactttg attccttaac ccccggcttt tggaacaagc catgtttgcc   3060
ctagtccagg attgcctcac ttgagacttg ctaggcctct gctgtgtgct ggggtggcca   3120
```

```
gtgggactca ggagagagca agctaaggag tcaccaaaaa aaaaaaaaaa aaaaagggag      3180
aatttaaaag tgtacagttg tgtgtttaga tacactatag aataatgtgg tatatattgt      3240
acaaatagtc tacataggtg tctgggataa tgtaaaactg gtgctttggc tttgtaaaga      3300
atttgcaaat cacttaacag ctgcaggggc aaggggagag tttcatcatc ccatgatat       3360 ttgggaatat tctgtttact tcttagatag ttaagaatgt attcagctac tatgtactaa      3420
cttgaaccgt gtttaaggaa aactcctatt tcatcctctt cttgcgccat cccctctccc      3480
taacttggta atgtgaagaa actaaaacct gataccacag ctcctatagg catttttagag     3540 atcttggatt tttatgtaca gtcttagtca tttttaataa atgtggttca gtaagggaac      3600
ggaaaaaaaa aaaaaaa                                                     3617

<210> SEQ ID NO 46
<211> LENGTH: 1220
<212> TYPE: DNA
<213> ORGANISM: Homo sapiens

<400> SEQUENCE: 46
gggagcgggc gagtaggagg gggcgccggg ctatatatat agcggctcgg cctcgggcgg        60
gcctggcgct cagggaggcg cgcactgctc ctcagagtcc cagctccagc cgcgcgcttt       120
ccgcccggct cgccgctcca tgcagccggg gtagagcccg cgcccggggg ccccgtcgc        180 ttgcctcccg cacctcctcg gttgcgcact cctgcccgag gtcggccgtg cgctcccgcg       240
ggacgccaca ggcgcagctc tgcccccag cttcccgggc gcactgaccg cctgaccgac        300
gcacggccct cgggccggga tgtcggggcc cgggacggcc gcggtagcgc tgctcccggc       360
ggtcctgctg gccttgctgg cgccctgggc gggccgaggg ggcgccgccg cacccactgc       420
acccaacggc acgctggagg ccgagctgga gcgccgctgg gagagcctgg tggcgctctc       480
gttggcgcgc ctgccggtgg cagcgcagcc caaggaggcg gccgtccaga gcggcgccgg       540
cgactacctg ctgggcatca gcggctgcg gcggctctac tgcaacgtgg gcatcggctt       600
ccacctccag gcgctccccg acggccgcat cggcggcgcg cacgcggaca cccgcgacag       660
cctgctggag ctctcgcccg tggagcgggg cgtggtgagc atcttcggcg tggccagccg       720
gttcttcgtg gccatgagca gcaagggcaa gctctatggc tcgcccttct tcaccgatga       780
gtgcacgttc aaggagattc tccttcccaa caactacaac gcctacgagt cctacaagta       840
ccccggcatg ttcatcgccc tgagcaagaa tgggaagacc aagaagggga accgagtgtc       900
gcccaccatg aaggtcaccc acttcctccc caggctgtga ccctcagag gacccttgcc       960 tcagcctcgg gaagccctg ggagggcagt gccgagggtc accttggtgc actttcttcg      1020
gatgaagagt ttaatgcaag agtaggtgta agatatttaa attaattatt taaatgtgta      1080
tatattgcca ccaaattatt tatagttctg cgggtgtgtt ttttaattttt ctgggggaa      1140 aaaaagacaa aacaaaaaac caactctgac ttttctggtg caacagtgga gaatcttacc      1200
attggatttc tttaacttgt                                                 1220

<210> SEQ ID NO 47
<211> LENGTH: 1224
<212> TYPE: DNA
<213> ORGANISM: Homo sapiens

<400> SEQUENCE: 47
ggagctctcc ccggtctgac agccactcca gaggccatgc ttcgtttctt gccagatttg        60
```

```
gctttcagct tcctgttaat tctggctttg ggccaggcag tccaatttca agaatatgtc      120
tttctccaat ttctgggctt agataaggcg ccttcacccc agaagttcca acctgtgcct      180
tatatcttga agaaaatttt ccaggatcgc gaggcagcag cgaccactgg ggtctcccga      240
gacttatgct acgtaaagga gctgggcgtc cgcgggaatg tacttcgctt tctcccagac      300
caaggtttct ttctttaccc aaagaaaatt tcccaagctt cctcctgcct gcagaagctc      360
ctctacttta acctgtctgc catcaaagaa agggaacagt tgacattggc ccagctgggc      420
ctggacttgg ggcccaattc ttactataac ctgggaccag agctggaact ggctctgttc      480
ctggttcagg agcctcatgt gtggggccag accaccccta agccaggtaa aatgtttgtg      540
ttgcggtcag tcccatggcc acaaggtgct gttcacttca acctgctgga tgtagctaag      600
gattggaatg acaaccccg gaaaaatttc gggttattcc tggagatact ggtcaaagaa      660
gatagagact caggggtgaa ttttcagcct gaagacacct gtgccagact aagatgctcc      720
cttcatgctt ccctgctggt ggtgactctc aaccctgatc agtgccaccc ttctcggaaa      780
aggagagcag ccatccctgt ccccaagctt tcttgtaaga acctctgcca ccgtcaccag      840
ctattcatta acttccggga cctgggttgg cacaagtgga tcattgcccc caaggggttc      900
atggcaaatt actgccatgg agagtgtccc ttctcactga ccatctctct caacagctcc      960
aattatgctt tcatgcaagc cctgatgcat gccgttgacc cagagatccc ccaggctgtg      1020
tgtatcccca ccaagctgtc tcccatttcc atgctctacc aggacaataa tgacaatgtc      1080
attctacgac attatgaaga catggtagtc gatgaatgtg ggtgtgggta ggatgtcaga      1140
aatgggaata gaaggagtgt tcttagggta aatctcttaa taaactacc tatctggttt      1200 atgaccactt agatcgaaat gtca                                              1224

<210> SEQ ID NO 48
<211> LENGTH: 1644
<212> TYPE: DNA
<213> ORGANISM: Homo sapiens

<400> SEQUENCE: 48
acatccagct gcctgagacc ctcctgcagc cttctcaagg gacagcccca ctctgcctct       60
tgctcctcca gggcagcacc atgcagcccc tgtggctctg ctgggcactc tgggtgttgc      120
ccctggccag ccccgggggcc gcccctgaccg gggagcagct cctgggcagc tgctgcggc      180 agctgcagct caaagaggtg cccaccctgg acagggccga catggaggag ctggtcatcc      240
ccacccacgt gagggcccag tacgtggccc tgctgcagcg cagccacggg gaccgctccc      300
gcggaaagag gttcagccag agcttccgag aggtggccgg caggttcctg gcgttggagg      360
ccagcacaca cctgctggtg ttcggcatgg agcagcggct gccgcccaac agcgagctgg      420
tgcaggccgt gctgcggctc ttccaggagc cggtccccaa ggccgcgctg cacaggcacg      480
ggcggctgtc cccgcgcagc gcccgggccc gggtgaccgt cgagtggctg cgcgtccgcg      540
acgacggctc caaccgcacc tccctcatcg actccaggct ggtgtccgtc cacgagagcg      600
gctggaaggc cttcgacgtg accgaggccg tgaacttctg gcagcagctg agccggcccc      660
ggcagccgct gctgctacag gtgtcggtgc agagggagca tctgggcccg ctggcgtccg      720
gcgcccacaa gctggtccgc tttgcctcgc agggggcgcc agccgggctt ggggagcccc      780
agctggagct gcacaccctg gaccttgggg actatggagc tcaggcgac tgtgaccctg      840 aagcaccaat gaccgagggc acccgctgct gccgccagga gatgtacatt gacctgcagg      900
ggatgaagtg ggccgagaac tgggtgctgg agccccgggg cttcctggct tatgagtgtg      960
```

| | |
|---|---|
| tgggcacctg ccggcagccc ccggaggccc tggccttcaa gtggccgttt ctggggcctc | 1020 |
| gacagtgcat cgcctcggag actgactcgc tgcccatgat cgtcagcatc aaggagggag | 1080 |
| gcaggaccag gccccaggtg gtcagcctgc ccaacatgag ggtgcagaag tgcagctgtg | 1140 |
| cctcggatgg tgcgctcgtg ccaaggaggc tccagccata ggcgcctagt gtagccatcg | 1200 |
| agggacttga cttgtgtgtg tttctgaagt gttcgagggt accaggagag ctggcgatga | 1260 |
| ctgaactgct gatggacaaa tgctctgtgc tctctagtga gccctgaatt tgcttcctct | 1320 |
| gacaagttac ctcacctaat ttttgcttct caggaatgag aatctttggc cactggagag | 1380 |
| cccttgctca gttttctcta ttcttattat tcactgcact atattctaag cacttacatg | 1440 |
| tggagatact gtaacctgag ggcagaaagc ccaatgtgtc attgtttact tgtcctgtca | 1500 |
| ctggatctgg gctaaagtcc tccaccacca ctctggacct aagacctggg gttaagtgtg | 1560 |
| ggttgtgcat ccccaatcca gataataaag actttgtaaa acatgaataa aacacatttt | 1620 |
| attctaaaaa aaaaaaaaaa aaaa | 1644 |

<210> SEQ ID NO 49
<211> LENGTH: 2086
<212> TYPE: DNA
<213> ORGANISM: Homo sapiens

<400> SEQUENCE: 49

| | |
|---|---|
| ataagggctg gaggtgctgc tttcaggcct ggccagccca ccatgcacgc ccactgcctg | 60 |
| cccttccttc tgcacgcctg gtgggcccta ctccaggcgg gtgctgcgac ggtggccact | 120 |
| gcgctcctgc gtacgcgggg gcagccctcg tcgccatccc ctctggcgta catgctgagc | 180 |
| ctctaccgcg acccgctgcc gagggcagac atcatccgca gcctacaggc agaagatgtg | 240 |
| gcagtggatg ggcagaactg gacgtttgct tttgacttct ccttcctgag ccaacaagag | 300 |
| gatctggcat gggctgagct ccggctgcag ctgtccagcc ctgtggacct ccccactgag | 360 |
| ggctcacttg ccattgagat tttccaccag ccaaagcccg acacagagca ggcttcagac | 420 |
| agctgcttag agcggtttca gatggaccta ttcactgtca ctttgtccca ggtcaccttt | 480 |
| tccttgggca gcatggtttt ggaggtgacc aggcctctct ccaagtggct gaagcaccct | 540 |
| ggggccctgg agaagcagat gtccagggta gctggagagt gctggccgcg gccccccaca | 600 |
| ccgcctgcca ccaatgtgct ccttatgctc tactccaacc tctcgcagga gcagaggcag | 660 |
| ctgggtgggt ccaccttgct gtgggaagcc gagagctcct ggcgggccca ggagggacag | 720 |
| ctgtcctggg agtggggcaa gaggcaccgt cgacatcact tgccagacag aagtcaactg | 780 |
| tgtcggaagg tcaagttcca ggtggacttc aacctgatcg gatgggctc ctggatcatc | 840 |
| taccccaagc agtacaacgc ctatcgctgt gagggcgagt gtcctaatcc tgttggggag | 900 |
| gagtttcatc cgaccaacca tgcatacatc cagagtctgc tgaaacgtta ccagccccac | 960 |
| cgagtccctt ccacttgttg tgccccagtg aagaccaagc cgctgagcat gctgtatgtg | 1020 |
| gataatggca gagtgctcct agatcaccat aaagacatga tcgtggaaga atgtgggtgc | 1080 |
| ctctgatgac atcctggagg gagactggat tgcctgcac tctggaaggc tgggaaactc | 1140 |
| ctggaagaca tgataaccat ctaatccagt aaggagaaac agagaggggc aaagttgctc | 1200 |
| tgcccaccag aactgaagag gaggggctgc ccactctgta aatgaagggc tcagtggagt | 1260 |
| ctggccaagc acagaggctg ctgtcaggaa gaggaggaa gaagcctgtg caggggctg | 1320 |
| gctggatgtt ctctttactg aaaagacagt ggcaaggaaa agcacaagtg catgagttct | 1380 |

```
ttactggatt ttttaaaaac ctgtgaaccc cccgaaactg tatgtgaaag ttgagacata   1440
tgtgcatgta ttttggaggt gggatgaagt cacctatagc tttcatgtat tctccaaagt   1500
agtctgtgtg tgacctgtcc ccctccccaa agattaagga tcactgtata gattaaaaag   1560
agtccgtcaa tctcattgcc tcaggctggg ttggggagc cccacagctt tctggctggc     1620
cagtggcaat ctactggcct tgtccagagg ctcactggag tggttctctg ctaatgagct   1680
gtacaacaat aaagccattg tctagttctc ctgggccagc tggtgcctgt gaaggcagag   1740
gcaggaactc atccaagagg accggccatg ttgggttaca gaagacatcc ctgcgtcagt   1800
ctgcttcggc agacacagcc tgagtttgtt aaagttggtg acaatccacc tcagtctctc   1860
aatgtgtgct attaatgagg cctctgagct tcctatccag cagtggtgaa ggccttgccc   1920
tgggtggcaa gatacttgct ctatggtcac agctcagcca ctggaagctg tgcgacctca   1980
ggtgagcaat tcactgtcca gtctccactt gtaaaaggaa cgctggtgaa tcctaatgca   2040
ttcatattaa atgtctgttg tcaggctcag aagagccatg agcttt                  2086

<210> SEQ ID NO 50
<211> LENGTH: 708
<212> TYPE: DNA
<213> ORGANISM: Homo sapiens

<400> SEQUENCE: 50
ccccgcaggc tgagggcagg tgggaagcaa accggacgc atcgcagcag cagcagcagc      60
agcagaagca gcagcagcag cctccgcagt ccctccagag acatggatcc ccagacagca   120
ccttcccggg cgctcctgct cctgctcttc ttgcatctgg ctttcctggg aggtcgttcc   180
cacccgctgg gcagccccgg ttcagcctcg gacttggaaa cgtccgggtt acaggagcag   240
cgcaaccatt tgcagggcaa actgtcggag ctgcaggtgg agcagacatc cctggagccc   300
ctccaggaga gcccccgtcc cacaggtgtc tggaagtccc gggaggtagc caccgagggc   360
atccgtgggc accgcaaaat ggtcctctac accctgcggg caccacgaag ccccaagatg   420
gtgcaagggt ctggctgctt tgggaggaag atggaccgga tcagctcctc cagtggcctg   480
ggctgcaaag tgctgaggcg gcattaagag gaagtcctgg ctgcagacac ctgcttctga   540
ttccacaagg ggcttttttcc tcaaccctgt ggccgccttt gaagtgactc atttttttaa   600
tgtatttatg tatttatttg attgttttat ataagatggt ttcttacctt tgagcacaaa   660
atttccacgg tgaaataaag tcaacattat aagctttaaa aaaaaaaa                 708

<210> SEQ ID NO 51
<211> LENGTH: 5094
<212> TYPE: DNA
<213> ORGANISM: Homo sapiens

<400> SEQUENCE: 51
gaaactggat acatggttta cagcaggtca ctaatgttgg aaaaagtaca gagtccaggg     60
aaagacttgc ttgtaacttt atgaattctg gattttttt ttttcctttgc tttttcttaa    120 cttttcactaa gggttactgt agtctgatgt gtccttccca aggccacgaa atttgacaag   180
ctgcactttt cttttgctca atgatttctg ctttaagcca aagaactgcc tataatttca   240
ctaagaatgt cttctaattc agatactggg gatttacaag agtctttaaa gcacggactt   300
acacctattg gtgctgggct tccggaccga cacggatccc ccatcccgc cgcggtcgc    360 cttgtcatgc tgcccaaagt gggagacgga gccctgggac tggctcgatc gcatgggaa    420 cagggccaga tgccggaaaa catgcaagtg tctcaattta aaatggtgaa ttactcctat   480
```

-continued

```
gatgaagatc tggaagagct ttgtcccgtg tgtggagata aagtgtctgg gtaccattat    540
gggctcctca cctgtgaaag ctgcaaggga ttttttaagc gaacagtcca aaataataaa    600
aggtacacat gtatagaaaa ccagaactgc caaattgaca aaacacagag aaagcgttgt    660
ccttactgtc gttttcaaaa atgtctaagt gttggaatga agctagaagc tgtaagggcc    720
gaccgaatgc gtggaggaag gaataagttt gggccaatgt acaagagaga cagggccctg    780
aagcaacaga aaaaagccct catccgagcc aatggactta agctagaagc catgtctcag    840
gtgatccaag ctatgccctc tgacctgacc atttcctctg caattcaaaa catccactct    900
gcctccaaag gctacctct gaaccatgct gccttgcctc ctacagacta tgacagaagt      960
cccttttgtaa catcccccat tagcatgaca atgccccctc acggcagcct gcaaggttac   1020
caaacatatg gccactttcc tagccgggcc atcaagtctg agtacccaga ccctatacc    1080
agctcacccg agtccataat gggctattca tatatggata gttaccagac gagctctcca   1140
gcaagcatcc cacatctgat actggaactt ttgaagtgtg agccagatga gcctcaagtc   1200
caggctaaaa tcatggccta tttgcagcaa gagcaggcta accgaagcaa gcacgaaaag   1260
ctgagcacct ttgggcttat gtgcaaaatg gcagatcaaa ctctcttctc cattgtcgag   1320
tgggccagga gtagtatctt cttcagagaa cttaaggttg atgaccaaat gaagctgctt   1380
cagaactgct ggagtgagct cttaatcctc gaccacattt accgacaagt ggtacatgga   1440
aaggaaggat ccatcttcct ggttactggg caacaagtgg actattccat aatagcatca   1500
caagccggag ccaccctcaa caacctcatg agtcatgcac aggagttagt ggcaaaactt   1560
cgttctctcc agtttgatca acgagagttc gtatgtctga aattcttggt gctctttagt   1620
ttagatgtca aaaaccttga aaacttccag ctggtagaag gtgtccagga acaagtcaat   1680
gccgccctgc tggactacac aatgtgtaac tacccgcagc agacagagaa atttggacag   1740
ctacttcttc gactacccga aatccgggcc atcagtatgc aggctgaaga ataacctctac   1800
tacaagcacc tgaacgggga tgtgccctat aataaccttc tcattgaaat gttgcatgcc   1860
aaaagagcat aagttacaac ccctaggagc tctgctttca aaacaaaaag agattgggg   1920
agtgggagg gggaagaaga acaggaagaa aaaaagtact ctgaactgct ccaagtaacg   1980
ctaattaaaa acttgcttta aagatattga atttaaaaag gcataataat caaatactta   2040
atagcaaata aatgatgtat cagggtattt gtattgcaaa ctgtgaatca aaggcttcac   2100
agccccagag gattccatat aaaagacatt gtaatggagt ggattgaact cacagatgga   2160
taccaacacg gtcagaagaa aaacggacag aacggttctt gtatatttaa actgatctcc   2220
actatgaaga aatttaggaa ctaatcttat taattaggct tatacagcgg gggatttgag   2280
cttacaggat tcctccatgg taaagctgaa ctgaaacaat tctcaagaat gcatcagctg   2340
tacctacaat agcccctccc tcttcctttg aaggcccag cacctctgcc ctgtggtcac     2400
cgaatctgta ctaaggacct gtgttcagcc acacccagtg gtagctccac caaatcatga   2460
acagcctaat tttgagtgtc tgtgtcttag acctgcaaac agctaatagg aaattctatt   2520
aatatgttag cttgccatt taaatatgtt ctgagggttg ttttgtctcg tgttcatgat    2580
gttaagaaaa tgcaggcagt atccctcatc ttatgtaagt gttaattaat attaagggaa   2640
atgactacaa actttcaaag caaatgctcc atagctaaag caacttagac cttatttctg   2700
ctactgttgc tgaaatgtgg ctttggcatt gttggatttc ataaaaaatt ctgcgcagga   2760
agtcttgtta gtatacatca gtcttttca tcatccaagt ttgtagttca tttaaaaata   2820
```

```
caacattaaa cacattttgc taggatgtca aatagtcaca gttctaagta gttggaaaca    2880
aaattgacgc atgttaatct atgcaaagag aaaggaaagg atgaggtgat gtattgactc    2940
aaggttcatt cttgctgcaa ttgaacatcc tcaagagttg ggatggaaat ggtgattttt    3000
acatgtgtcc tggaaagata ttaaagtaat tcaaatcttc cccaaagggg aaaggaagag    3060
agtgatactg acctttttaa gtcatagacc aaagtctgct gtagaacaaa tatgggagga    3120
caaagaatcg caaattcttc aaatgactat tatcagtatt attaacatgc gatgccacag    3180
gtatgaaagt cttgccttat ttcacaattt taaaaggtag ctgtgcagat gtggatcaac    3240
atttgtttaa aataaagtat taatacttta aagtcaaata agatatagtg tttacattct    3300
ttaggtcctg aggggcaggg ggatctgtga tataacaaaa tagcaaaagc ggtaatttcc    3360
ttaatgttat ttttctgatt ggtaattatt tttaacagta cttaattatt ctatgtcgtg    3420
agacactaaa atcaaaaacg ggaatctcat ttagacttta atttttttga gattatcggc    3480
ggcacaatca ctttgtagaa actgtaaaaa ataaaagtat ctcctagtcc cttaatttt     3540
tcataaatat ttctggcttt tgagtagtgt atttatattg tatatcatac tttcaactgt    3600
agacaattat gatgctaatt tattgtttct tggtttcacc tttgtataag atatagccaa    3660
gactgaagaa accaaatata tgtgtttact gtagcatgtc ttcaaattag tggaacttag    3720
ttcagggaca tagaagagtc ttaatgaatt aaaatcattc acttgattaa atgtctgtaa    3780
atcttcatca ttcctactgt agtttatta  atatctattg taaattatgt gacttgtagc    3840
ttcctctggt tttcaagtaa actcaacaag gtggagtctt acctggtttt cctttccaag    3900
cattgtaaat tgtataccaa agatattagt tattacttct gtgtgtacaa agaggattat    3960
tttattatgt ttattaatca cctctaatac tcatccacat gaagggtaca cattaggtaa    4020
gctgggcgtt gactcatgcg cagtctcagt cacccgtgtt atcttcgtgg ctcaaaggac    4080
aatgcaaaat cgccgatcag agctcatacc caaagcatta cagagaacag cagcatcatt    4140
gccctcccca gctgaaaaac aagttggcta aagatacat  ggagaggaat ggtgtggtca    4200
acagttaatg aaacggttct atcatgcatg tgtaatgtgg atggagacaa ttataagatt    4260
tgactataac tatttggagg gtctttaaca ttgccaaaaa aacaaatatg ttgatttta    4320
ttttatttta ttttttattt taagaggcgg gatcttgatc tcacatgttg cccaggctgg    4380
ccttgaactc ctgggctcaa gcattcctcc tgcctcagcc tccccatag  ctgggactag    4440
gggtgcatgc cagcatacct ggctacgttg actcttaaaa tctatgttct cttattttaa    4500
agatacagtg ctccccactg aaaattaaac ctaaaaaatg tcacatattg gtatgttgtt    4560
aacctggtag attaaatcat gagaatgatt agaaagacgg gcaacacagc gggttacatc    4620
cacactgctg atcacaccaa cgacaggagc tgataagcaa gaaagcgtca cagccagcgt    4680
ctgttcaccc aaggttgaca agtgaagttt ctctaatgtt gattgttagc cgatttgtaa    4740
cctggcattt acttagcaac tgccttatca attacaggat ttgccggtaa aagcagactc    4800
aaatataaag gttttggct  taacttggtt tattatagtt gctctatgtt tgtaaacaga    4860
caatctctaa tgtctgatta tttgtatcac agatctgcag ctgccttgga cttgaatcca    4920
tgcaatgttt agagtgtgaa gtcagttact tgttgatgtt tcttactgt  atcaatgaaa    4980
tacatattgt catgtcagtt cttgccagga acttctcaac aaaatggaat ttttttttc    5040
agtatttcaa taaatattga tatgcccagc ctgataattt ttaaaaaaaa aaaa          5094
```

<210> SEQ ID NO 52
<211> LENGTH: 1862

<212> TYPE: DNA
<213> ORGANISM: Homo sapiens

<400> SEQUENCE: 52

```
ctggttcgca aagaagctga cttcagaggg ggaaactttc ttcttttagg aggcggttag      60
ccctgttcca cgaacccagg agaactgctg gccagattaa ttagacattg ctatgggaga     120
cgtgtaaaca cactacttat cattgatgca tatataaaac cattttattt tcgctattat     180
ttcagaggaa gcgcctctga tttgtttctt ttttcccttt ttgctctttc tggctgtgtg     240
gtttggagaa agcacagttg gagtagccgg ttgctaaata agtcccgagc gcgagcggag     300
acgatgcagc ggagactggt tcagcagtgg agcgtcgcgg tgttcctgct gagctacgcg     360
gtgccctcct gcgggcgctc ggtggagggt ctcagccgcc gcctcaaaag agctgtgtct     420
gaacatcagc tcctccatga caaggggaag tccatccaag atttacggcg acgattcttc     480
cttcaccatc tgatcgcaga aatccacaca gctgaaatca gagctacctc ggaggtgtcc     540
cctaactcca agccctctcc caacacaaag aaccacccccg tccgatttgg gtctgatgat     600
gagggcagat acctaactca ggaaactaac aaggtggaga cgtacaaaga gcagccgctc     660
aagacacctg ggaagaaaaa gaaaggcaag cccgggaaac gcaaggagca ggaaaagaaa     720
aaacggcgaa ctcgctctgc ctggttagac tctggagtga ctgggagtgg gctagaaggg     780
gaccacctgt ctgacacctc cacaacgtcg ctggagctcg attcacggta acaggcttct     840
ctggcccgta gcctcagcgg ggtgctctca gctgggtttt ggagcctccc ttctgccttg     900
gcttggacaa acctagaatt ttctccctttt atgtatctct atcgattgtg tagcaattga     960
cagagaataa ctcagaatat tgtctgcctt aaagcagtac ccccctacca cacacacccc    1020
tgtcctccag caccatagag aggcgctaga gccccattcct ctttctccac cgtcacccaa    1080
catcaatcct ttaccactct accaaataat ttcatattca agcttcagaa gctagtgacc    1140
atcttcataa tttgctggag aagtgtgttt cttcccctta ctctcacacc tgggcaaact    1200
ttcttcagtg ttttttcattt cttacgttct ttcacttcaa gggagaatat agaagcattt    1260
gatattatct acaaacactg cagaacagca tcatgtcata aacgattctg agccattcac    1320
acttttatt taattaaatg tatttaatta aatctcaaat ttattttaat gtaaagaact    1380
taaattatgt tttaaacaca tgccttaaat ttgtttaatt aaatttaact ctggtttcta    1440
ccagctcata caaaataaat ggtttctgaa atgtttaag tattaactta caaggatata    1500
ggttttctc atgtatcttt ttgttcattg gcaagatgaa ataattttc tagggtaatg    1560
ccgtaggaaa aataaaactt cacatttatg tggcttgttt atccttagct cacagattga    1620
ggtaataatg acactcctag actttgggat caaataactt agggccaagt cttgggtctg    1680
aatttattta agttcacaac ctagggcaag ttactctgcc tttctaagac tcacttacat    1740
cttctgtgaa atataattgt accaacctca tagagtttgg tgtcaactaa atgagattat    1800
atgtggacta aatatctgtc atatagtaaa cactcaataa attgcaacat attaaaaaaa    1860
aa                                                                   1862
```

<210> SEQ ID NO 53
<211> LENGTH: 2500
<212> TYPE: DNA
<213> ORGANISM: Homo sapiens

<400> SEQUENCE: 53

```
ggaggacact tctcagaagg ggttgttttg cttttgctta tttccgtcca tttccctctc      60
```

```
tgcgcgcgga ccttccttt ccagatggtg agagccgcgg ggacacccga cgccggggca    120
ggctgatcca cgatcctggg tgtgcgtaac gccgcctggg gctccgtggg cgagggacgt    180
gtggggacag gtgcaccgga aactgccaga ctggagagtt gaggcatcgg aggcgcgaga    240
acagcactac tactgcggcg agacgagcgc ggcgcatccc aaagcccggc caaatgcgct    300
cgtccctggg aggggaggga ggcgcgcctg gagcgggac agtcttggtc cgcgccctcc    360
tcccgggtct gtgccgggac ccgggacccg ggagccgtcg caggtctcgg tccaaggggc    420
cccttttctc ggaagggcgg cggccaagag cagggaaggt ggatctcagg tagcgagtct    480
gggcttcggg gacggcgggg aggggagccg gacgggagga tgagctcccc tggcaccgag    540
agcgcgggaa agagcctgca gtaccgagtg gaccacctgc tgagcgccgt ggagaatgag    600
ctgcaggcgg gcagcgagaa gggcgacccc acagagcgcg aactgcgcgt gggcctggag    660
gagagcgagc tgtggctgcg cttcaaggag ctcaccaatg agatgatcgt gaccaagaac    720
ggcaggagga tgtttccggt gctgaaggtg aacgtgtctg gcctggaccc caacgccatg    780
tactccttcc tgctggactt cgtggcggcg acaaccacc gctggaagta cgtgaacggg    840
gaatgggtgc cggggggcaa gccggagccg caggcgccca gctgcgtcta catccacccc    900
gactcgccca cttcgggggc ccactggatg aaggctcccg tctccttcag caaagtcaag    960
ctcaccaaca agctcaacgg agggggccag atcatgctga actccttgca taagtatgag   1020
cctcgaatcc acatagtgag agttggggggt ccacagcgca tgatcaccag ccactgcttc   1080
cctgagaccc agttcatagc ggtgactgct tatcagaacg aggagatcac agctcttaaa   1140
attaagtaca atccatttgc aaaagctttc cttgatgcaa aggaaagaag tgatcacaaa   1200
gagatgatgg aggaacccgg agacagccag caacctgggt actcccaatg ggggtggctt   1260
cttcctggaa ccagcaccct gtgtccacct gcaaatcctc atcctcagtt tggaggtgcc   1320
ctctcctcc cctccacgca cagctgtgac aggtacccaa ccctgaggag ccaccggtcc   1380
tcaccctacc ccagccccta tgctcatcgg aacaattctc caacctattc tgacaactca   1440
cctgcatgtt tatccatgct gcaatccat gacaattggt ccagccttgg aatgcctgcc   1500
catcccagca tgctccccgt gagccacaat gccagcccac ctaccagctc cagtcagtac   1560
cccagcctgt ggtctgtgag caacggcgcc gtcacccgg gctcccaggc agcagccgtg   1620
tccaacgggt ggggggccca gttcttccgg ggctcccccg cgcactacac accctcacc   1680
catccggtct cggcgccctc ttcctcggga tccccactgt acgaaggggc ggccgcggcc   1740
acagacatcg tggacagcca gtacgacgcc gcagcccaag gccgcctcat agcctcatgg   1800
acacctgtgt cgccaccttc catgtgaagc agcaaggccc aggtcccgaa agatgcagtg   1860
actttttgtc gtggcagcca gtggtgactg gattgaccta ctaggtaccc agtggcagtc   1920
tcaggttaag aaggaaatgc agcctcagta acttccttt caaagcagtg gaggagcaca   1980
cggcaccttt ccccagagcc ccagcatccc ttgctcacac ctgcagtagc ggtgctgtcc   2040
caggtggctt acagatgaac ccaactgtgg agatgatgca gttggcccaa cctcactgac   2100
ggtgaaaaaa tgtttgccag ggtccagaaa cttttttgg tttatttctc atacagtgta   2160
ttggcaactt tggcacacca gaatttgtaa actccaccag tcctacttta gtgagataaa   2220
aagcacactc ttaatcttct tccttgttgc tttcaagtag ttagagttga gctgttaagg   2280
acagaataaa atcatagttg aggacagcag gttttagttg aattgaaaat ttgactgctc   2340
tgccccctag aatgtgtgta ttttaagcat atgtagctaa tctcttgtgt tgttaaacta   2400
taactgtttc atattttct tttgacaaag tagccaaaga caatcagcag aaagcatttt   2460
```

```
ctgcaaaata aacgcaatat gcaaaaaaaa aaaaaaaaa                           2500
```

<210> SEQ ID NO 54
<211> LENGTH: 7326
<212> TYPE: DNA
<213> ORGANISM: Homo sapiens

<400> SEQUENCE: 54

```
aggacacagc gtccggagcc agaggcgctc ttaacggcgt ttatgtcctt tgctgtctga     60
ggggcctcag ctctgaccaa tctggtcttc gtgtggtcat tagcatgggc ttcgtgagac    120
agatacagct tttgctctgg aagaactgga ccctgcggaa aaggcaaaag attcgctttg    180
tggtggaact cgtgtggcct ttatctttat ttctggtctt gatctggtta aggaatgcca    240
acccgctcta cagccatcat gaatgccatt tccccaacaa ggcgatgccc tcagcaggaa    300
tgctgccgtg gctccagggg atcttctgca atgtgaacaa tccctgtttt caaagcccca    360
ccccaggaga atcccctgga attgtgtcaa actataacaa ctccatcttg gcaagggtat    420
atcgagattt tcaagaactc ctcatgaatg caccagagag ccagcacctt ggccgtattt    480
ggacagagct acacatcttg tcccaattca tggacaccct ccggactcac ccggagagaa    540
ttgcaggaag aggaatacga ataagggata tcttgaaaga tgaagaaaca ctgacactat    600
ttctcattaa aaacatcggc ctgtctgact cagtggtcta ccttctgatc aactctcaag    660
tccgtccaga gcagttcgct catggagtcc cggacctggc gctgaaggac atcgcctgca    720
gcgaggccct cctggagcgc ttcatcatct tcagccagag acgcggggca aagacggtgc    780
gctatgccct gtgctccctc tcccagggca ccctacagtg gatagaagac actctgtatg    840
ccaacgtgga cttcttcaag ctcttccgtg tgcttcccac actcctagac agccgttctc    900
aaggtatcaa tctgagatct tggggaggaa tattatctga tatgtcacca agaattcaag    960
agtttatcca tcggccgagt atgcaggact tgctgtgggt gaccaggccc ctcatgcaga   1020
atggtggtcc agagaccttt acaaagctga tgggcatcct gtctgacctc ctgtgtggct   1080
accccgaggg aggtggctct cgggtgctct ccttcaactg gtatgaagac aataactata   1140
aggcctttct ggggattgac tccacaagga aggatcctat ctattcttat gacagaagaa   1200
caacatcctt ttgtaatgca ttgatccaga gcctggagtc aaatccttta accaaaatcg   1260
cttggagggc ggcaaagcct ttgctgatgg gaaaaatcct gtacactcct gattcacctg   1320
cagcacgaag gatactgaag aatgccaact caactttga agaactggaa cacgttagga   1380
agttggtcaa agcctgggaa gaagtagggc cccagatctg gtacttcttt gacaacagca   1440
cacagatgaa catgatcaga gataccctgg ggaacccaac agtaaaagac ttttttgaata   1500
ggcagcttgg tgaagaaggt attactgctg aagccatcct aaacttcctc tacaagggcc   1560
ctcgggaaag ccaggctgac gacatggcca acttcgactg gagggacata tttaacatca   1620
ctgatcgcac cctccgcctg gtcaatcaat acctggagtg cttggtcctg gataagtttg   1680
aaagctacaa tgatgaaact cagctcaccc aacgtgccct ctctctactg gaggaaaaca   1740
tgttctgggc cggagtggta ttccctgaca tgtatcccctg gaccagctct ctaccacccc   1800
acgtgaagta taagatccga atggacatag acgtggtgga gaaaaccaat aagattaaag   1860
acaggtattg ggattctggt cccagagctg atcccgtgga gatttccgg tacatctggg   1920
gcggtttgc ctatctgcag gacatggttg aacaggggat cacaaggagc caggtgcagg   1980
cggaggctcc agttggaatc tacctccagc agatgcccta cccctgcttc gtggacgatt   2040
```

```
ctttcatgat catcctgaac cgctgtttcc ctatcttcat ggtgctggca tggatctact    2100
ctgtctccat gactgtgaag agcatcgtct tggagaagga gttgcgactg aaggagacct    2160
tgaaaaatca gggtgtctcc aatgcagtga tttggtgtac ctggttcctg gacagcttct    2220
ccatcatgtc gatgagcatc ttcctcctga cgatattcat catgcatgga agaatcctac    2280
attacagcga cccattcatc ctcttcctgt tcttgttggc tttctccact gccaccatca    2340
tgctgtgctt tctgctcagc accttcttct ccaaggccag tctggcagca gcctgtagtg    2400
gtgtcatcta tttcacccte tacctgccac acatcctgtg cttcgcctgg caggaccgca    2460
tgaccgctga gctgaagaag gctgtgagct actgtctccc ggtggcattt ggatttggca    2520
ctgagtacct ggttcgcttt gaagagcaag gcctggggct gcagtggagc aacatcggga    2580
acagtcccac ggaaggggac gaattcagct tcctgctgtc catgcagatg atgctccttg    2640
atgctgctgt ctatggctta ctcgcttggt accttgatca ggtgtttcca ggagactatg    2700
gaaccccact tccttggtac tttcttctac aagagtcgta ttggcttggc ggtgaagggt    2760
gttcaaccag agaagaaaga gccctggaaa agaccgagcc cctaacagag gaaacggagg    2820
atccagagca cccagaagga atacacgact ccttctttga acgtgagcat ccagggtggg    2880
ttcctggggt atgcgtgaag aatctggtaa agattttga gccctgtggc cggccagctg    2940
tggaccgtct gaacatcacc ttctacgaga accagatcac cgcattcctg gccacaatg    3000
gagctgggaa aaccaccacc ttgtccatcc tgacgggtct gttgccacca acctctggga    3060
ctgtgctcgt tggggaagg acattgaaa ccagcctgga tgcagtccgg cagagccttg    3120
gcatgtgtcc acagcacaac atcctgttcc accacctcac ggtggctgag cacatgctgt    3180
tctatgccca gctgaaagga agtcccagg aggaggccca gctggagatg aagccatgt    3240
tggaggacac aggcctccac cacaagcgga atgaagaggc tcaggaccta tcaggtggca    3300
tgcagagaaa gctgtcggtt gccattgcct ttgtgggaga tgccaaggtg gtgattctgg    3360
acgaacccac ctctggggtg gaccctact cgagacgctc aatctgggat ctgctcctga    3420
agtatcgctc aggcagaacc atcatcatgt ccactcacca catggacgag gccgacctcc    3480
ttggggaccg cattgccatc attgcccagg gaaggctcta ctgctcaggc accccactct    3540
tcctgaagaa ctgctttggc acaggcttgt acttaacctt ggtgcgcaag atgaaaaaca    3600
tccagagcca aaggaaaggc agtgagggga cctgcagctg ctcgtctaag ggtttctcca    3660
ccacgtgtcc agcccacgtc gatgacctaa ctccagaaca agtcctggat ggggatgtaa    3720
atgagctgat ggatgtagtt ctccaccatg ttccagaggc aaagctggtg gagtgcattg    3780
gtcaagaact tatcttcctt cttccaaata gaacttcaa gcacagagca tatgccagcc    3840
ttttcagaga gctggaggag acgctggctg accttggtct cagcagtttt ggaatttctg    3900
acactcccct ggaagagatt tttctgaagg tcacggagga ttctgattca ggacctctgt    3960
ttgcgggtgg cgctcagcag aaaagagaaa acgtcaaccc cgacacccc tgcttgggtc    4020
ccagagagaa ggctggacag acaccccagg actccaatgt ctgctcccca ggggcgccgg    4080
ctgctcaccc agagggccag cctccccag agccagagtg cccaggcccg cagctcaaca    4140
cggggacaca gctggtcctc cagcatgtgc aggcgctgct ggtcaagaga ttccaacaca    4200
ccatccgcag ccacaaggac ttcctggcgc agatcgtgct cccggctacc tttgtgtttt    4260
tggctctgat gctttctatt gttatccctc cttttggcga ataccccgct ttgacccttc    4320
accccctggat atatgggcag cagtacacct tcttcagcat ggatgaacca ggcagtgagc    4380
agttcacggt acttgcagac gtcctcctga ataagccagg cttttggcaac cgctgcctga    4440
```

-continued

```
aggaagggtg gcttccggag taccoctgtg gcaactcaac accctggaag actccttctg   4500
tgtccccaaa catcacccag ctgttccaga agcagaaatg dacacaggtc aacccttcac   4560
catcctgcag gtgcagcacc agggagaagc tcaccatgct gccagagtgc cccgagggtg   4620
ccgggggcct cccgcccccc cagagaacac agcgcagcac ggaaattcta caagacctga   4680
cggacaggaa catctccgac ttcttggtaa aaacgtatcc tgctcttata agaagcagct   4740
taaagagcaa attctgggtc aatgaacaga ggtatggagg aatttccatt ggaggaaagc   4800
tcccagtcgt ccccatcacg ggggaagcac ttgttgggtt tttaagcgac cttggccgga   4860
tcatgaatgt gagcggggc cctatcacta gagaggcctc taaagaaata cctgatttcc    4920
ttaaacatct agaaactgaa gacaacatta aggtgtggtt taataacaaa ggctggcatg   4980
ccctggtcag ctttctcaat gtggcccaca acgccatctt acgggccagc ctgcctaagg   5040
acaggagccc cgaggagtat ggaatcaccg tcattagcca acccctgaac ctgaccaagg   5100
agcagctctc agagattaca gtgctgacca cttcagtgga tgctgtggtt gccatctgcg   5160
tgattttctc catgtccttc gtcccagcca gctttgtcct ttatttgatc caggagcggg   5220
tgaacaaatc caagcacctc cagtttatca gtggagtgag ccccaccacc tactgggtga   5280
ccaacttcct ctgggacatc atgaattatt ccgtgagtgc tgggctggtg gtgggcatct   5340
tcatcgggtt tcagaagaaa gcctacactt ctccagaaaa ccttcctgcc cttgtggcac   5400
tgctcctgct gtatggatgg gcggtcattc ccatgatgta cccagcatcc ttcctgtttg   5460
atgtccccag cacagcctat gtggctttat cttgtgctaa tctgttcatc ggcatcaaca   5520
gcagtgctat taccttcatc ttggaattat ttgagaataa ccggacgctg ctcaggttca   5580
acgccgtgct gaggaagctg ctcattgtct tcccccactt ctgcctgggc cggggcctca   5640
ttgaccttgc actgagccag gctgtgacag atgtctatgc ccggtttggt gaggagcact   5700
ctgcaaatcc gttccactgg gacctgattg gaagaacct gtttgccatg gtggtggaag    5760
gggtggtgta cttcctcctg accctgctgg tccagcgcca cttcttcctc tcccaatgga   5820
ttgccgagcc cactaaggag cccattgttg atgaagatga tgatgtggct gaagaaagac   5880
aaagaattat tactggtgga aataaaactg acatcttaag gctacatgaa ctaaccaaga   5940
tttatccagg cacctccagc ccagcagtgg acaggctgtg tgtcggagtt cgccctggag   6000
agtgctttgg cctcctggga gtgaatggtg ccggcaaaac aaccacattc aagatgctca   6060
ctggggacac cacagtgacc tcaggggatg ccaccgtagc aggcaagagt attttaacca   6120
atatttctga agtccatcaa aatatgggct actgtcctca gtttgatgca attgatgagc   6180
tgctcacagg acgagaacat ctttacctt atgcccggct tcgaggtgta ccagcagaag    6240
aaatcgaaaa ggttgcaaac tggagtatta agagcctggg cctgactgtc tacgccgact   6300
gcctggctgg cacgtacagt gggggcaaca agcggaaact ctccacagcc atcgcactca   6360
ttggctgccc accgctggtg ctgctggatg agccccaccac agggatggac ccccaggcac   6420
gccgcatgct gtggaacgtc atcgtgagca tcatcagaga agggagggct gtggtcctca   6480
catcccacag catggaagaa tgtgaggcac tgtgtacccg gctggccatc atggtaaagg   6540
gcgcctttcg atgtatgggc accattcagc atctcaagtc caaatttgga gatggctata   6600
tcgtcacaat gaagatcaaa tccccgaagg acgacctgct tcctgacctg aaccctgtgg   6660
agcagttctt ccagggggaac ttcccaggca gtgtgcagag ggagaggcac tacaacatgc   6720
tccagttcca ggtctcctcc tcctcccctgg cgaggatctt ccagctcctc ctctcccaca   6780
```

| | |
|---|---:|
| aggacagcct gctcatcgag gagtactcag tcacacagac cacactggac caggtgtttg | 6840 |
| taaattttgc taaacagcag actgaaagtc atgacctccc tctgcaccct cgagctgctg | 6900 |
| gagccagtcg acaagcccag gactgatctt tcacaccgct cgttcctgca gccagaaagg | 6960 |
| aactctgggc agctggaggc gcaggagcct gtgcccatat ggtcatccaa atggactggc | 7020 |
| cagcgtaaat gaccccactg cagcagaaaa caaacacacg aggagcatgc agcgaattca | 7080 |
| gaaagaggtc tttcagaagg aaaccgaaac tgacttgctc acctggaaca cctgatggtg | 7140 |
| aaaccaaaca aatacaaaat ccttctccag accccagaac tagaaacccc gggccatccc | 7200 |
| actagcagct ttggcctcca tattgctctc atttcaagca gatctgcttt tctgcatgtt | 7260 |
| tgtctgtgtg tctgcgttgt gtgtgatttt catggaaaaa taaaatgcaa atgcactcat | 7320 |
| cacaaa | 7326 |

<210> SEQ ID NO 55
<211> LENGTH: 2707
<212> TYPE: DNA
<213> ORGANISM: Homo sapiens

<400> SEQUENCE: 55

| | |
|---|---:|
| catctttgag caagatgggt ctctaccgca tccgcgtgtc cactggggcc tcgctctatg | 60 |
| ccggttccaa caaccaggtg cagctgtggc tggtcggcca gcacggggag gcggcgctcg | 120 |
| ggaagcgact gtggcccgca cggggcaagg agacagaact caaggtggaa gtaccggagt | 180 |
| atctggggcc gctgctgttt gtgaaactgc gcaaacggca cctccttaag gacgacgcct | 240 |
| ggttctgcaa ctgatctct gtgcaggcc ccggagccgg gacgaggtc aggttccctt | 300 |
| gttaccgctg ggtggagggc aacggcgtcc tgagcctgcc tgaaggcacc ggccgcactg | 360 |
| tgggcgagga ccctcaggc ctgttccaga acaccgggga agaagagctg aagagagaa | 420 |
| ggaagttgta ccggtgggga aactggaagg acgggttaat tctgaatatg gctggggcca | 480 |
| aactatatga cctcccctgtg gatgagcgat ttctggaaga caagagagtt gactttgagg | 540 |
| tttcgctggc caaggggctg gccgacctcg ctatcaaaga ctctctaaat gttctgactt | 600 |
| gctggaagga tctagatgac ttcaaccgga ttttctggtg tggtcagagc aagctggctg | 660 |
| agcgcgtgcg ggactcctgg aaggaagatg ccttatttgg gtaccagttt cttaatggcg | 720 |
| ccaaccccgt ggtgctgagg cgctctgctc accttcctgc tcgcctagtg ttccctccag | 780 |
| gcatggagga actgcaggcc cagctggaga aggagctgga gggaggcaca ctgttcgaag | 840 |
| ctgacttctc cctgctggat gggatcaagg ccaacgtcat tctctgtagc cagcagcacc | 900 |
| tggctgcccc tctagtcatg ctgaaattgc agcctgatgg gaaactcttg cccatggtca | 960 |
| tccagctcca gctgccccgc acaggatccc caccacctcc ccttttcttg cctacggatc | 1020 |
| ccccaatggc ctggcttctg gccaaatgct gggtgcgcag ctctgacttc cagctccatg | 1080 |
| agctgcagtc tcatcttctg aggggacact gatggctga ggtcattgtt gtggccacca | 1140 |
| tgaggtgcct gccgtcgata catcctatct tcaagcttat aattccccac ctgcgataca | 1200 |
| ccctggaaat taacgtccgg gccaggactg ggctggtctc tgacatggga atttttcgacc | 1260 |
| agataatgag cactggtggg ggaggccacg tgcagctgct caagcaagct ggagccttcc | 1320 |
| taacctacag ctccttctgt cccctgatg acttggccga ccgggggctc ctgggagtga | 1380 |
| agtcttcctt ctatgcccaa gatgcgctgc ggctctggga aatcatctat cggtatgtgg | 1440 |
| aaggaatcgt gagtctccac tataagacag acgtggctgt gaaagacgac ccagagctgc | 1500 |
| agacctggtg tcgagagatc actgaaatcg ggctgcaagg ggcccaggac cgagggtttc | 1560 |

```
ctgtctcttt acaggctcgg gaccaggttt gccactttgt caccatgtgt atcttcacct    1620
gcaccggcca acacgcctct gtgcacctgg gccagctgga ctggtactct tgggtgccta    1680
atgcaccctg cacgatgcgg ctgccccgc caaccaccaa ggatgcaacg ctggagacag     1740
tgatggcgac actgcccaac ttccaccagg cttctctcca gatgtccatc acttggcagc    1800
tgggcagacg ccagcccgtt atggtggctg tgggccagca tgaggaggag tattttcgg    1860 gccctgagcc taaggctgtg ctgaagaagt tcagggagga gctggctgcc ctggataagg    1920
aaattgagat ccggaatgca aagctggaca tgccctacga gtacctgcgg cccagcgtgg    1980
tggaaaacag tgtggccatc taagcgtcgc caccctttgg ttatttcagc ccccatcacc    2040
caagccacaa gctgacccct tcgtggttat agccctgccc tcccaagtcc accctcttc    2100 ccatgtccca ccctccctag aggggcacct tttcatggtc tctgcaccca gtgaacacat    2160
tttactctag aggcatcacc tgggacctta ctcctctttc cttccttcct cctttcctat    2220
cttccttcct ctctctcttc ctcttttcttc attcagatct atatggcaaa tagccacaat    2280
tatataaatc atttcaagac tagaataggg ggatataata catattactc cacaccttt    2340 atgaatcaaa tatgattttt ttgttgttgt taagacagag tctcactttg cacccaggc    2400 tggagtgcag tggtgccatc accacggctc actgcagcct cagcgtcctg ggctcaaatg    2460
atcctcccac ctcagcctcc tgagtagctg ggactacagg ctcatgccat catgcccagc    2520 taatatttt ttattttcgt ggagacgggg cctcactatg ttgcctaggc tggaaatagg    2580
attttgaacc caaattgagt ttaacaataa taaaaagttg ttttacgcta agatggaaa    2640 agaactagga ctgaactatt ttaaataaaa tattggcaaa agaaaaaaaa aaaaaaaaaa    2700
aaaaaaa                                                              2707
```

<210> SEQ ID NO 56
<211> LENGTH: 1584
<212> TYPE: DNA
<213> ORGANISM: Homo sapiens

<400> SEQUENCE: 56

```
ggggagagga agagtggtag ggggagggag agagagagga agagtttcca aacttgtctc     60
cagtgacagg agacatttac gttccacaag ataaaactgc cacttagagc ccagggaagc    120
taaaccttcc tggcttggcc taggagctcg agcggagtca tgggctctct ggtcctgaca    180
ctgtgcgctc ttttctgcct ggcagcttac ttggtttctg gcagccccat catgaaccta    240
gagcagtctc ctctggaaga agatatgtcc ctctttggtg atgttttctc agagcaagac    300
ggtgtcgact ttaacacact gctccagagc atgaaggatg agtttcttaa gacactaaac    360
ctctctgaca tccccacgca ggattcagcc aaggtggacc accagagta catgttggaa    420 ctctacaaca aatttgcaac agatcggacc tccatgccct ctgccaacat cattaggagt    480
ttcaagaatg aagatctgtt tcccagccg gtcagttta tgggctccg aaaataccc      540 ctcctcttca atgtgtccat tcctcaccat gaagaggtca tcatggctga acttaggcta    600
tacacactgg tgcaaaggga tcgtatgata tacgatggag tagaccggaa aattaccatt    660
tttgaagtgc tggagagcaa aggggataat gagggagaaa gaaacatgct ggtcttggtg    720 tctgggaga tatatggaac caacagtgag tgggagactt tgatgtcac agatgccatc    780 agacgttggc aaaagtcagg ctcatccacc accagctgg aggtccacat tgagagcaaa    840
cacgatgaag ctgaggatgc cagcagtgga cggctagaaa tagataccag tgcccagaat    900
```

-continued

```
aagcataacc ctttgctcat cgtgttttct gatgaccaaa gcagtgacaa ggagaggaag      960
gaggaactga atgaaatgat ttcccatgag caacttccag agctggacaa cttgggcctg     1020
gatagctttt ccagtggacc tggggaagag gctttgttgc agatgagatc aaacatcatc     1080
tatgactcca ctgcccgaat cagaaggaac gccaaaggaa actactgtaa gaggaccccg     1140
ctctacatcg acttcaagga gattgggtgg gactcctgga tcatcgctcc gcctggatac     1200
gaagcctatg aatgccgtgg tgtttgtaac taccccctgg cagagcatct cacacccaca     1260
aagcatgcaa ttatccaggc cttggtccac ctcaagaatt cccagaaagc ttccaaagcc     1320
tgctgtgtgc ccacaaagct agagcccatc tccatcctct atttagacaa aggcgtcgtc     1380
acctacaagt ttaaatacga aggcatggcc gtctccgaat gtggctgtag atagaagaag     1440
agtcctatgg cttatttaat aactgtaaat gtgtatattt ggtgttccta tttaatgaga     1500
ttatttaata agggtgtaca gtaataagagg cttgctgcct tcaggaaatg gacaggtcag     1560
tttgttgtag gaaatgcata tttt                                            1584

<210> SEQ ID NO 57
<211> LENGTH: 4134
<212> TYPE: DNA
<213> ORGANISM: Homo sapiens

<400> SEQUENCE: 57
aggcctccct cgccagcggg gtgtggctcc cctccaaaga cggtcggctg acaggctcca       60
cagagctcca ctcacgctca gccctggacg acaggcagt ccaacggaac agaaacatcc      120
ctcagcccac aggcacgatc tgttcctcct gggaagatgc agaggctcat gatgctcctc      180
gccacatcgg gcgcctgcct gggcctgctg gcagtggcag cagtggcagc agcaggtgct      240
aaccctgccc aacgggacac ccacagcctg ctgcccaccc accggcgcca aaagagagat      300
tggatttgga accagatgca cattgatgaa gagaaaaaca cctcacttcc ccatcatgta      360
ggcaagatca agtcaagcgt gagtcgcaag aatgccaagt acctgctcaa aggagaatat      420
gtgggcaagg tcttccgggt cgatgcagag acaggagacg tgttcgccat tgagaggctg      480
gaccgggaga atatctcaga gtaccactc actgctgtca ttgtggacaa ggacactggc      540
gaaaacctgg agactccttc cagcttcacc atcaaagttc atgacgtgaa cgacaactgg      600
cctgtgttca cgcatcggtt gttcaatgcg tccgtgcctg agtcgtcggc tgtggggacc      660
tcagtcatct ctgtgacagc agtggatgca gacgacccca ctgtgggaga ccacgcctct      720
gtcatgtacc aaatcctgaa ggggaaagag tattttgcca tcgataattc tggacgtatt      780
atcacaataa cgaaaagctt ggaccgagag aagcaggcca ggtatgagat cgtggtggaa      840
gcgcgagatg cccagggcct ccggggggac tcgggcacgg ccaccgtgct ggtcactctg      900
caagacatca atgacaactt cccttcttc acccagacca agtacacatt tgtcgtgcct      960
gaagacaccc gtgtgggcac ctctgtgggc tctctgtttg ttgaggaccc agatgagccc     1020
cagaaccgga tgaccaagta cagcatcttg cggggcgact accaggacgc tttcaccatt     1080
gagacaaacc ccgcccacaa cgagggcatc atcaagccca tgaagcctct ggattatgaa     1140
tacatccagc aatacagctt catcgtcgag gccacagacc ccaccatcga cctccgatac     1200
atgagccctc ccgcgggaaa cagagcccag gtcattatca acatcacaga tgtggacgag     1260
cccccccatt tccagcagcc tttctaccac ttccagctga aggaaaaacca gaagaagcct     1320
ctgattggca cagtgctggc catggaccct gatgcggcta gcatagcat tggatactcc     1380
atccgcagga ccagtgacaa gggccagttc ttccgagtca caaaaaaggg ggacatttac     1440
```

```
aatgagaaag aactggacag agaagtctac ccctggtata acctgactgt ggaggccaaa   1500
gaactggatt ccactggaac ccccacagga aaagaatcca ttgtgcaagt ccacattgaa   1560
gttttggatg agaatgacaa tgccccggag tttgccaagc cctaccagcc caaagtgtgt   1620
gagaacgctg tccatggcca gctggtcctg cagatctccg caatagacaa ggacataaca   1680
ccacgaaacg tgaagttcaa attcatcttg aatactgaga caactttac cctcacggat    1740 aatcacgata cacgccaa catcacagtc aagtatgggc agtttgaccg ggagcatacc     1800
aaggtccact tcctacccgt ggtcatctca gacaatggga tgccaagtcg cacgggcacc   1860
agcacgctga ccgtggccgt gtgcaagtgc aacgagcagg gcgagttcac cttctgcgag   1920
gatatggccg cccaggtggg cgtgagcatc caggcagtgg tagccatctt actctgcatc   1980
ctcaccatca cagtgatcac cctgctcatc ttcctgcggc ggcggctccg gaagcaggcc   2040
cgcgcgcacg gcaagagcgt gccggagatc cacgagcagc tggtcaccta cgacgaggag   2100
ggcggcggcg agatggacac caccagctac gatgtgtcgg tgctcaactc ggtgcgccgc   2160
ggcggggcca agcccccgcg gcccgcgctg gacgcccggc cttccctcta tgcgcaggtg   2220
cagaagccac cgaggcacgc gcctggggca acggagggc ccggggagat ggcagccatg     2280
atcgaggtga agaaggacga ggcggaccac gacggcgacg gcccccccta cgacacgctg   2340
cacatctacg gctacgaggg ctccgagtcc atagccgagt ccctcagctc cctgggcacc   2400
gactcatccg actctgacgt ggattacgac ttccttaacg actggggacc caggtttaag   2460
atgctggctg agctgtacgg ctcggacccc cgggaggagc tgctgtatta ggcggccgag   2520
gtcactctgg gcctggggac ccaaaccccc tgcagcccag gccagtcaga cgccaggcac   2580
cacagcctcc aaaatggca gtgactccc agcccagcac ccttcctcg tgggtcccag       2640 agacctcatc agccttggga tagcaaactc caggttcctg aaatatccag gaatatatgt   2700
cagtgatgac tattctcaaa tgctggcaaa tccaggctgg tgttctgtct gggctcagac   2760
atccacataa ccctgtcacc cacagaccgc cgtctaactc aaagacttcc tctggctccc   2820
caaggctgca aagcaaaaca gactgtgttt aactgctgca gggtcttttt ctagggtccc   2880
tgaacgccct ggtaaggctg gtgaggtcct ggtgcctatc tgcctggagg caaaggcctg   2940
gacagcttga cttgtggggc aggattctct gcagcccatt cccaagggag actgaccatc   3000
atgccctctc tcgggagccc tagccctgct ccaactccat actccactcc aagtgcccca   3060
ccactcccca acccctctcc aggcctgtca agagggagga aggggcccca tggcagctcc   3120
tgaccttggg tcctgaagtg acctcactgg cctgccatgc cagtaactgt gctgtactga   3180
gcactgaacc acattcaggg aaatggctta ttaaactttg aagcaactgt gaattcattc   3240
tggaggggca gtggagatca ggagtgacag atcacagggt gagggccacc tccacaccca   3300 cccctctgg agaaggcctg aagagctga ccttgctt tgagactcct cagcacccct        3360
ccagttttgc ctgagaaggg gcagatgttc ccggagcaga agacgtctcc ccttctctgc   3420
ctcacctggt cgccaatcca tgctctcttt ctttttctctg tctactcctt atcccttggt  3480
ttagaggaac ccaagatgtg gccttttagca aaactggaca atgtccaaac ccactcatga  3540
ctgcatgacg gagccgagcc atgtgtcttt acacctcgct gttgtcacat ctcagggaac   3600
tgaccctcag gcacaccttg cagaaggcaa ggccctgccc tgcccaacct ctgtggtcac   3660
ccatgcatct tccactggaa cgtttcactg caaacacacc ttggagaagt ggcatcagtc   3720
aacagagagg ggcagggaag gagacaccaa gctcacccctt cgtcatggac cgaggttccc  3780
```

| | |
|---|---|
| actctgggca aagcccctca cactgcaagg gattgtagat aacactgact tgtttgtttt | 3840 |
| aaccaataac tagcttctta taatgatttt tttactaatg atacttacaa gtttctagct | 3900 |
| ctcacagaca tatagaataa gggttttttgc ataataagca ggttgttatt taggttaaca | 3960 |
| atattaattc aggttttta gttggaaaaa caattcctgt aaccttctat tttctataat | 4020 |
| tgtagtaatt gctctacaga taatgtctat atattggcca aactggtgca tgacaagtac | 4080 |
| tgtatttttt tatacctaaa taaagaaaaa tctttagcct gggcaacaaa aaaa | 4134 |

<210> SEQ ID NO 58
<211> LENGTH: 2370
<212> TYPE: DNA
<213> ORGANISM: Homo sapiens

<400> SEQUENCE: 58

| | |
|---|---|
| ctccaaccat tggtgtctgt gtcattacta atagagtctt gtaaacactc gttaatcacg | 60 |
| gaaggccgcc ggcctggggc tccgcacgcc agcctgtggc gggtcttccc cgcctctgca | 120 |
| gcctagtggg aaggaggtgg gaggaaagaa ggaagaaagg gagggaggga ggaggcaggc | 180 |
| cagagggagg gaccgcctcg gaggcagaag agccgcgagg agccagcgga gcaccgcggg | 240 |
| ctggggcgca gccacccgcc gctcctcgag tcccctcgcc cctttccctt cgtgccccc | 300 |
| ggcagcctcc agcgtcggtc cccaggcagc atggtgaggt ctgctcccgg accctcgcca | 360 |
| ccatgtacgt gagctacctc ctggacaagg acgtgagcat gtaccctagc tccgtgcgcc | 420 |
| actctggcgg cctcaacctg gcgccgcaga acttcgtcag ccccccgcag tacccggact | 480 |
| acggcggtta ccacgtggcg gccgcagctg cagcggcagc gaacttggac agcgcgcagt | 540 |
| ccccgggggcc atcctggccg gcagcgtatg gcgccccact ccgggaggac tggaatggct | 600 |
| acgcgcccgg aggcgccgcg gccgccgcca acgccgtggc tcacgcctc aacggtggct | 660 |
| ccccggccgc agccatgggc tacagcagcc ccgcagacta ccatccgcac caccacccgc | 720 |
| atcaccaccc gcaccacccg gccgccgcgc cttcctgcgc ttctgggctg ctgcaaacgc | 780 |
| tcaaccccgg ccctcctggg cccgccgcca ccgctgccgc cgagcagctg tctcccggcg | 840 |
| gccagcggcg gaacctgtgc gagtggatgc ggaagccggc gcagcagtcc ctcggcagcc | 900 |
| aagtgaaaac caggacgaaa gacaaatatc gagtggtgta cacggaccac cagcggctgg | 960 |
| agctggagaa ggagtttcac tacagtcgct acatcaccat ccggaggaaa gccgagctag | 1020 |
| ccgccacgct ggggctctct gagaggcagg ttaaaatctg gttcagaac cgcagagcaa | 1080 |
| aggagaggaa aatcaacaag aagaagttgc agcagcaaca gcagcagcag ccaccacagc | 1140 |
| cgcctccgcc gccaccacag cctccccagc tcagccagg tcctctgaga agtgtcccag | 1200 |
| agcccttgag tccggtgtct ccctgcaag cctcagtgtc tggctctgtc cctgggttc | 1260 |
| tggggccaac tggggggtg ctaaacccca ccgtcaccca gtgacccacc gggttctgca | 1320 |
| gcggcagagc aattccaggc tgagccatga ggagcgtgga ctctgctaga ctcctcagga | 1380 |
| gagaccctc cctcccacc cacagccata gacctacaga cctggctctc agaggaaaaa | 1440 |
| tgggagccag gagtaagaca agtgggattt ggggcctcaa gaaatatact ctcccagatt | 1500 |
| tttactttt cccatctggc ttttctgcc actgaggaga cagaaagcct ccgctgggct | 1560 |
| tcattccgga ctggcagaag cattgcctgg actgaccaca ccaaccaggc cttcatcctc | 1620 |
| ctccccagct cttctcttcc tagatctgca ggctgcacct ctggctagag ccgaggggag | 1680 |
| agagggactc aagggaaagg caagcttgag gccaagatgg ctgctgcctg tcatggccc | 1740 |
| tcggaggtcc agctgggcct cctgcctccg ggcaggcaag gtttacactg cggaagccaa | 1800 |

```
aggcagctaa gatagaaagc tggactgacc aaagactgca gaacccccag gtggcctgcg   1860
tctttttct  cttcccttcc cagaccagga aaggcttggc tggtgtatgc acagggtgtg   1920
gtatgagggg gtggttattg gactccaggc ctgaccaggg ggcccgaaca gggacttgtt   1980
tagagagcct gtcaccagag cttctctggg ctgaatgtat gtcagtgcta taaatgccag   2040
agccaacctg gacttcctgt cattttcaca atcttggggc tgatgaagaa gggggtgggg   2100
ggagtttgtg ttgttgttgc tgctgtttgg gttgttggtc tgtgtaacat ccaagccaga   2160
gtttttaaag ccttctggat ccatgggggg agaagtgata tggtgaaggg aagtggggag   2220
tatttgaaca cagttgaatt ttttctaaaa agaaaaagag ataaatgagc tttccagatt   2280
tcagattctg tatttatctt cagattttgt ctgcaactat tttttatttt ttaaagaaat   2340
gaaatatctt caaaaaaaaa aaaaaaaaaa                                    2370
```

<210> SEQ ID NO 59
<211> LENGTH: 1708
<212> TYPE: DNA
<213> ORGANISM: Homo sapiens

<400> SEQUENCE: 59

```
aaatacttcc ccttcttccc caaagcagga ggttttattt aaaataaagc tgtttatttg     60
gcatttctgg gagacccttt tctgaggaac cacagcaatg aatggctttg catccttgct    120
tcgaagaaac caatttatcc tcctggtact atttcttttg caaattcaga gtctgggtct    180
ggatattgat agccgtccta ccgctgaagt ctgtgccaca cacacaattt caccaggacc    240
caaaggagat gatggtgaaa aaggagatcc aggagaagag ggaaagcatg gcaaagtggg    300
acgcatgggg ccgaaaggaa ttaaaggaga actgggtgat atgggagatc agggcaatat    360
tggcaagact gggcccattg ggaagaaggg tgacaaaggg gaaaaaggtt tgcttggaat    420
acctggagaa aaaggcaaag caggtactgt ctgtgattgt ggaagatacc ggaaatttgt    480
tggacaactg gatattagta ttgctcggct caagacatct atgaagtttg tcaagaatgt    540
gatagcaggg attagggaaa ctgaagagaa attctactac atcgtgcagg aagagaagaa    600
ctacagggaa tccctaaccc actgcaggat tcggggtgga atgctagcca tgcccaagga    660
tgaagctgcc aacacactca tcgctgacta tgttgccaag agtggcttct ttcgggtgtt    720
cattggcgtg aatgaccttg aaagggaggg acagtacatg ttcacagaca acactccact    780
gcagaactat agcaactgga atgaggggga acccagcgac ccctatggtc atgaggactg    840
tgtggagatg ctgagctctg gcagatggaa tgacacagag tgccatctta ccatgtactt    900
tgtctgtgag ttcatcaaga agaaaaagta acttccctca tcctacgtat ttgctatttt    960
cctgtgaccg tcattacagt tattgttatc catccttttt ttcctgattg tactacattt   1020
gatctgagtc aacatagcta gaaaatgcta aactgaggta tggagcctcc atcatcatgc   1080
tcttttgtga tgattttcat attttcacac atggtatatt attgacccaa taactcgcca   1140
ggttacatgg gtcttgagag agaattttaa ttactaattg tgcacgagat agttggttgt   1200
ctatatgtca aatgagttgt tctcttggta tttgctctac catctctccc tagagcactc   1260
tgtgtctatc ccagtggata atttcccagt ttactggtga tgattaggaa ggttgttgat   1320
ggttaggcta acctgccctg gcccaaagcc agacatgtac aagggctttc tgtgagcaat   1380
gataagatct ttgaatccaa gatgcccaga tcttttacca gtcacaccct atggccatgg   1440
ctatacttgg aagttctcct tgttggcaca gacatagaaa tgctttaacc ccaaaccttt   1500
```

```
atatgggga cttctagctt tgtgtcttgt ttcagaccat gtggaatgat aaatactctt      1560
tttgtgcttc tgatctatcg atttcactaa catataccaa gtaggtgctt tgaacccctt      1620
tctgtaggct cacaccttaa tctcaggccc ctatatagtc acactttgat ttaagaaaaa      1680
tggagctctt gaaatcaaaa gaaaaaaa                                         1708

<210> SEQ ID NO 60
<211> LENGTH: 2089
<212> TYPE: DNA
<213> ORGANISM: Homo sapiens

<400> SEQUENCE: 60
agtttggacg gctgcttccc accagcaaag accacgactg gagagccgag ccggaggcag        60
ctgggaaaca tgaagagcgt cttgctgctg accacgctcc tcgtgcctgc acacctggtg       120
gccgcctgga gcaataatta tgcggtggac tgccctcaac actgtgacag cagtgagtgc       180
aaaagcagcc cgcgctgcaa gaggacagtg ctcgacgact gtggctgctg ccgagtgtgc       240
gctgcagggc ggggagaaac ttgctaccgc acagtctcag gcatggatgg catgaagtgt       300
ggcccggggc tgaggtgtca gccttctaat ggggaggatc cttttggtga agagtttggt       360
atctgcaaag actgtcccta cggcaccttc gggatggatt gcagagagac ctgcaactgc       420
cagtcaggca tctgtgacag ggggacggga aaatgcctga attcccctt cttccaatat       480 tcagtaacca agtcttccaa cagatttgtt tctctcacgg agcatgacat ggcatctgga       540
gatggcaata ttgtgagaga agaagttgtg aaagagaatg ctgccgggtc tcccgtaatg       600
aggaaatggt taaatccacg ctgatcccgg ctgtgatttc tgagagaagg ctctattttc       660
gtgattgttc aacacacagc caacatttta ggaactttct agattatagc ataaggacat       720 gtaattttg aagaccaaat gtgatgcatg gtggatccag aaaacaaaaa gtaggatact        780
tacaatccat aacatccata tgactgaaca cttgtatgtg tttgttaaat attcgaatgc       840
atgtagattt gttaaatgtg tgtgtatagt aacactgaag aactaaaaat gcaatttagg       900
taatcttacg tggagacagg tcaaccaaag agggagctag gcaaagctga agaccgcagt       960
gagtcaaatt agttctttga cttttgatgta cattaatgtt gggatatgga atgaagactt      1020
aagagcagga gaagatgggg aggggtggg agtgggaaat aaaatattta gcccttcctt      1080
ggtaggtagc ttctctagaa tttaattgtg cttttttttt tttttttggc tttgggaaaa      1140
gtcaaaataa aacaaccaga aaaccctga aggaagtaag atgtttgaag cttatggaaa      1200
tttgagtaac aaacagcttt gaactgagag caatttcaaa aggctgctga tgtagttccc      1260
gggttacctg tatctgaagg acggttctgg ggcataggaa acacatacac ttccataaat      1320
agctttaacg tatgccacct cagagataaa tctaagaagt attttaccca ctggtggttt      1380
gtgtgtgtat gaaggtaaat atttatatat ttttataaat aaatgtgtta gtgcaagtca      1440
tcttccctac ccatatttat catcctcttg aggaaagaaa tctagtatta tttgttgaaa      1500
atggttagaa taaaactatg actctataag gttttcaaac atctgaggca tgataaattt      1560
attatccata attatagtaa taataacctt aataagcata agaaaaacag agtcactctg      1620
gatttcaaaa atgtcaaaaa atgagcaaca gagggtcctt atttaaacat aagtgctgtg      1680
acttaggtga attttcaatt taaggtagaa aataagtttt taggaggttt gtaaaagaag      1740 aatcaattt cagcagaaaa catgtcaact ttaaaatata gtttattttc atatttttt       1800 cttttaaact tggttgataa gtggaattag gagtatattt gaaagaatct tagcacaaac      1860
aggactgttg tactagatgt tcttaggaaa tatctcagaa gtattttatt tgaagtgaag      1920
```

| | |
|---|---:|
| aacttattta agaattattt cagtatttac ctgtatttta ttcttgaagt tggccaacag | 1980 |
| agttgtgaat gtgtgtggga aggcctttga atgtaaagct gcataagctg ttaggttttg | 2040 |
| ttttaaaagg acatgtttat tattgttcaa taaaaaagaa caagataca | 2089 |

<210> SEQ ID NO 61
<211> LENGTH: 1059
<212> TYPE: DNA
<213> ORGANISM: Homo sapiens

<400> SEQUENCE: 61

| | |
|---|---:|
| agcaagatgg atctactgtg gatcctgccc tccctgtggc ttctcctgct tgggggggcct | 60 |
| gcctgcctga agacccagga acaccccagc tgcccaggac ccagggaact ggaagccagc | 120 |
| aaagttgtcc tcctgcccag ttgtcccgga gctccaggaa gtcctgggga aagggagcc | 180 |
| ccaggtcctc aagggccacc tggaccacca ggcaagatgg gccccaaggg tgagccagga | 240 |
| gatccagtga acctgctccg gtgccaggaa ggccccagaa actgccggga gctgttgagc | 300 |
| cagggcgcca ccttgagcgg ctggtaccat ctgtgcctac ctgagggcag ggccctccca | 360 |
| gtcttttgtg acatggacac cgagggggc ggctggctgg tgtttcagag cgccaggat | 420 |
| ggttctgtgg atttcttccg ctcttggtcc tcctacagag caggttttgg gaaccaagag | 480 |
| tctgaattct ggctgggaaa tgagaatttg caccagctta ctctccaggg taactgggag | 540 |
| ctgcgggtag agctggaaga cttaatggt aaccgtactt tcgcccacta tgcgaccttc | 600 |
| cgcctcctcg gtgaggtaga ccactaccag ctggcactgg gcaagttctc agagggcact | 660 |
| gcagggatt ccctgagcct ccacagtggg aggccctta ccacctatga cgctgaccac | 720 |
| gattcaagca acagcaactg tgcagtgatt gtccacggtg cctggtggta tgcatcctgt | 780 |
| taccgatcaa atctcaatgg tcgctatgca gtgtctgagg ctgccgccca caaatatggc | 840 |
| attgactggg cctcaggccg tggtgtgggc caccccctacc gcagggttcg gatgatgctt | 900 |
| cgatagggca ctctggcagc cagtgccctt atctctcctg tacagcttcc ggatcgtcag | 960 |
| ccaccttgcc tttgccaacc acctctgctt gcctgtccac atttaaaaat aaaatcattt | 1020 |
| tagccctttc aaaaaaaaaa aaaaaaaaa aaaaaaaa | 1059 |

<210> SEQ ID NO 62
<211> LENGTH: 2579
<212> TYPE: DNA
<213> ORGANISM: Homo sapiens

<400> SEQUENCE: 62

| | |
|---|---:|
| gcagagcagc ggcggcagcg gcggcggcgg cagcagccac ccgatgtctt cggcgcccga | 60 |
| gaagcagcag ccaccgcacg gcggcggcgg cggcggcggc gggggaggcg gcgcggccat | 120 |
| ggaccccgcg tcgtccggcc cgtccaaggc caagaagacc aacgccggca tccggcgccc | 180 |
| ggagaagccg cccctattcct acatcgcgct catcgtcatg gccatccaga gttcacccac | 240 |
| caagcgcctg acgctgagcg agatctacca gttcctgcag agccgcttcc ccttcttccg | 300 |
| gggctcctac cagggctgga gaactccgt gcgccacaac ctctcgctca acgagtgctt | 360 |
| catcaagcta cccaagggcc ttgggcggcc ggcaagggc cactactgga ccatcgaccc | 420 |
| ggccagcgag ttcatgttcg aggagggctc cttttcggcgg cggccgcgcg gcttccgaag | 480 |
| gaaatgccag gcgctcaagc ccatgtacag catgatgaac gggctcggct tcaaccacct | 540 |
| cccggacacc tacggcttcc agggctcggc cggcggcctc tcgtgcccgc ccaacagcct | 600 |

| | |
|---|---:|
| ggcgctggag ggcggcctgg gcatgatgaa cggccacttg ccgggcaacg tggacggcat | 660 |
| ggccctgccc agccactcgg tgccccacct gccttccaac ggcggccact cgtacatggg | 720 |
| cggctgcggc ggcgcggcgg ccggcgagta cccgcaccac gacagctcgg tgcccgcctc | 780 |
| cccgctgctg cccaccggcg ccggtggggt catggagccg cacgccgtct actcgggctc | 840 |
| ggcggcggcc tggccgccct cggcgtccgc ggcgctcaac agcggcgcct cttatatcaa | 900 |
| gcagcagccc ctgtcccct gtaacccgc ggccaacccc ctgtccggca gcctctccac | 960 |
| gcactccctg gagcagccgt atctgcacca gaacagccac aacgcccag ccgagctgca | 1020 |
| aggcatcccg cggtatcact cgcagtcgcc cagcatgtgt gaccgaaagg agtttgtctt | 1080 |
| ctcttcaac gccatggcgt cctcttccat gcactcggcc ggcggggct cctactacca | 1140 |
| ccagcaggtc acctaccaag acatcaagcc ttgcgtgatg tgaggctgcc gccgcaggcc | 1200 |
| ctcctggtgc aggcaggcgg gtcacaggga ccctggaccg gcacaagaaa ctgctttctt | 1260 |
| ctcgaggtat aaccgtcggc agaagaaaag ggttccacct ctccccaacc ggagttttg | 1320 |
| gcaaggagtc cccaatgcaa agacacacg ctgcggttgg cacctcttc ctcactcctt | 1380 |
| caaaattgtt aagaaatgtt agtggtgggt ctgatctgac tgcagccatc ggtaaataaa | 1440 |
| agttttgat cctgttgaac ccgcctgaga cggtgctgtg caggggaaag cccccgcacc | 1500 |
| cacacaggaa ttctgctgag gtccccctc cttccggcca atggcagaag tgggggaaaa | 1560 |
| tttttagaag aaaagcaaac atgtgagacc aatcattatc aaatacttt atttttggt | 1620 |
| tgagtattta tcttttatt ttttattttt ttttgaaag aatgtcttgg aatgcgcaag | 1680 |
| tctcccttta gagccgtctt ttgcaggag cgggaagtga caagagctca gatctccctc | 1740 |
| ccgatctccc tccccacctc cgaagtctcc tccgtggacc acaggtggat ctttgtgcga | 1800 |
| acaacttgca tttcggaagc cactgtccgt ctttaaacag aaagtcaaag gagccacgaa | 1860 |
| gcaagcggcc gtccgggcgt ccgcctccgt ccccttccat gttcctcctc ttccttcgct | 1920 |
| tcagcctctt ctgttatgtt ttgtcttgaa ttttatttag acttttttcag tgggtatttt | 1980 |
| tctgtctccc aacctctact gtaaactttc tggtccgaga acgagccgaa cacagcgcga | 2040 |
| cgcagggact aggacggccc ggtgaccgcg cggattcagg attgcgggga cgcagaaagg | 2100 |
| ttaaggcact tttaaaaact atagcaaggc tcctgtttat ttattctact ttctttccct | 2160 |
| aataatcaaa acaccgcgta ggctcctccg tttatcagta ttaatggtgt aactttgttg | 2220 |
| gcaatatttg ccgtgtagaa ttttttttag atatccattg taaatttgaa acaaagaccg | 2280 |
| atctgtgtaa aaacaaattt ccatatgttt tatataaata tatatataat atgaaggact | 2340 |
| accctccttt ttttttttg tatttggct gctagagtgc agcatttgtg acacgtattt | 2400 |
| gaaatttgaa atttccttct gcactgtata aaaggaccat ttgaggatgt tttgcctttt | 2460 |
| gtgtattttt tcctaaaaaa agaacaaaaa taaaaatgta taacatttgt acatggcctt | 2520 |
| taaaattgta tcaactagaa ataaaattgc atgagtattt taaaaaaaaa aaaaaaaa | 2579 |

<210> SEQ ID NO 63
<211> LENGTH: 1749
<212> TYPE: DNA
<213> ORGANISM: Homo sapiens
<400> SEQUENCE: 63

| | |
|---|---:|
| gcggtcttat ataagccaga tccgcagggg agtccgcaga agggttaaac aggtctttgg | 60 |
| gcttcggcga cctcgcccgc ggcagaaacc ggtaagaaga cagtgggctg cgcgtctcat | 120 |
| tttcagcctt gcccggactc tcccaaagcc ggcgcccagt agtggctcca gagcccacag | 180 |

```
gtggccccg gcagtctctg gggcgcatgg agcggcgtta ataggcgtgg cggcgcaggc    240
cagtagccgc tccaacatga acctcgtggg cagctacgca caccatcacc accatcacca    300
cccgcaccct gcgcacccca tgctccacga accttcctc ttcggtccgg cctcgcgctg    360
tcatcaggaa aggccctact tccagagctg gctgctgagc ccggctgacg ctgccccgga    420
cttccctgcg ggcgggccgc cgcccgcggc cgctgcagcc gccaccgcct atggtcctga    480
cgccaggcct gggcagagcc ccgggcggct ggaggcgctt ggcggccgtc ttggccggcg    540
gaaaggctca ggacccaaga aggagcggag acgcactgag agcattaaca gcgcattcgc    600
ggagttgcgc gagtgcatcc ccaacgtgcc ggccgacacc aagctctcca agatcaagac    660
tctgcgccta gccaccagct acatcgccta cctgatggac gtgctggcca aggatgcaca    720
gtctggcgat cccgaggcct tcaaggctga actcaagaag gcggatggcg gccgtgagag    780
caagcggaaa agggagctgc agcagcacga aggttttcct cctgccctgg gcccagtcga    840
gaagaggatt aaaggacgca ccggctggcc gcagcaagtc tgggcgctgg agttaaacca    900
gtgagccgag gcccgcgccg aggacctggc caggccagcc actcctgaag ccccgggagg    960
agaggaaggc agcggcgaac gccaggctct gggctccggc gactggtgct acgcatcccg   1020
cggagcttct gctgagcgcc ggcaggtcgt cggctgcaac cacacacttg gatcgcacgt   1080
gcaatgtcct tgattttttt ttaatacatt aagagaaaga gaatatata tatatccacc   1140 cccagcccaa ccgagggcgg cccttggcgg caacatgcaa gaaggaggga ctgtcgaacc   1200
caagggctca aagacgcact cttccaccct tttggagcga atttagaacc tcagccctat   1260
ctccatttcc ctatctggct ctttctctct tgtccctcca tatgatccgc cccgacgccg   1320
tcttctctaa ttaaaatgca ataaggaatc aattcttttc tgcctgagaa agagaaccag   1380
acgcaggaag atgaaaggct gcccttttgt cttcgaatcg tggtggtttt attttatttt   1440 tcttttttgtc gctgcacttc ctgtttagtt ccaagggaaa cactttctct ctttctctgt   1500
ctctctcttt tcttccttct tttccttcct ttttgtttct atctaaataa aagctttccc   1560
tgtgttggaa agtttttatg tatttaaact acctaccatg cctgttgtgc tcaggtgttt   1620
gttcatcctg ccatccccaa cccttttcta cctcaagtct gtgtgaccac tcacagcccc   1680
cctcccttcg ccaaagcagt gtctatgctc ttgattaata aaacatttttc tgaaatcaaa   1740 aaaaaaaaa                                                            1749

<210> SEQ ID NO 64
<211> LENGTH: 2368
<212> TYPE: DNA
<213> ORGANISM: Homo sapiens

<400> SEQUENCE: 64
ctgtacatgg agatcttgct gggaaaatcc gcttgctccc ctcacgtcgt ccagcccagg     60
agaaccaccg ccgtcacccc ggagcttcct cggccaccgc gcagagccct ccgagagccc    120
gagccgcggt cttcgagctc caaggctcat tcagggcccc agatccttgc cccgaaagga    180
gaggatctga gaaatggat gcactgagac ctctctgaaa accctccgag agagcgcgag    240
aggagcgagg acacgttact cgcagctaaa atcacattta aggaccaaaa caacaacaac    300
caaaaatttc attaaaacaa taagcgccca agaacccaga tcgggctggt ggggggaggg    360
gaagaggcgg gaaggggagg gtcgcacgga ggtagctttg cagtgagcag tcgacccgc    420 cgccccccgg cacagctgga ccggctcctc cagccgcggc tcagactcgc ccctggattc    480
```

-continued

| | |
|---|---|
| cgggttagct tcggtgccag gaccgcggcc cgggcttgga ttcccgagac tccgcgtacc | 540 |
| agcctcgcgg gagccccggc acctttgtat gagcacgaga ggattctgcc tccgcgcagc | 600 |
| agcccgggaa gcaggagccg aagcgcgggc cgtggagcaa ggcgggaacc ggaggcggcg | 660 |
| gcggcggcgg ccaggggcgc acggtgccag gaccagctcg ccgcgcccca tggggagccg | 720 |
| gcggccgcag cgctgctgag gcgggcccgg ctggccaggc gggggggacgg ggcccgggct | 780 |
| gcagcagccc cctctgcggc tgccgggcgg gcccgggcgc ccgggggctg ggggggtgggg | 840 |
| ggtgggggag gacgccgagc gctgaggcag gggcccgggc cgagggcgcg gcggggctgc | 900 |
| gcgcacgctg gggcgcgtgg aggggcgcgg agggcgaaat gagtctggta ggtggttttc | 960 |
| cccaccaccc ggtggtgcac cacgagggct acccgtttgc cgccgccgcc gccgcagctg | 1020 |
| ccgccgccgc cgccagccgc tgcagccatg aggagaaccc ctacttccat ggctggctca | 1080 |
| tcggccaccc cgagatgtcg cccccgact acagcatggc cctgtcctac agccccgagt | 1140 |
| atgccagcgg cgccgccggc ctggaccact cccattacgg gggggtgccg ccgggcgccg | 1200 |
| ggccccgggg cctgggggg ccgcgcccgg tgaagcgccg aggcaccgcc aaccgcaagg | 1260 |
| agcggcgcag gactcagagc atcaacagcg ccttcgccga actgcgcgag tgcatcccca | 1320 |
| acgtacccgc cgacaccaaa ctctccaaaa tcaagaccct cgcctggcc accagctaca | 1380 |
| tcgcctacct catggacctg ctggccaagg acgaccagaa tggcgaggcg gaggccttca | 1440 |
| aggcagagat caagaagacc gacgtgaaag aggagaagag gaagaaggag ctgaacgaaa | 1500 |
| tcttgaaaag cacagtgagc agcaacgaca agaaaaccaa aggccggacg ggctggccgc | 1560 |
| agcacgtctg ggccctggag ctcaagcagt gaggaggagg agaaggagga ggaggagagc | 1620 |
| gcgagtgagc aggggccaag gcgccagatg cagacccagg actccggaaa agccgtccgc | 1680 |
| gctccgctct gaggactcct tgcatttgga atcatccggt ttatttatgt gcaatttcct | 1740 |
| tccccctctct ttgacccct ttgaggcatc tgctccccgt ctcccccctcc aaaaaaaaag | 1800 |
| tggatatttg aagaaaagca ttccatattt taatacgaag aggacactcc cgtgtggtaa | 1860 |
| gggatcccgt cgtctcatag attctgtgtg cgtgaatgtt ccctcttggc tgtgtagaca | 1920 |
| ccagcgttgc cccccgccaa cctactcaac cccttccaga taaagacagt gggcactagt | 1980 |
| gcgtttgtga agtgtatctt taatacttgg cctttggata taaatattcc tgggtattat | 2040 |
| aaagttttat ttcaaagcag aaaacagggc cgctaacatt tccgttgggg tcggtatcta | 2100 |
| gtgctatcca ttcatctgtg gtcgttccct ctttgaagat gtttccaaca gccacttgtt | 2160 |
| ttgtgcactt ccgtcctcta aaactaaatg gaatttaatt aatattgaag gtgtaaacgt | 2220 |
| tgtaagtatt caataaaccca ctgtgttttt tttttacaaa aaccttaatc ttttaatggc | 2280 |
| tgatacctca aaagagtttt gaaaacaaag ctgttatact tgttttcgta atatttaaaa | 2340 |
| tattcagaag taaactaaat tatcatga | 2368 |

<210> SEQ ID NO 65
<211> LENGTH: 2319
<212> TYPE: DNA
<213> ORGANISM: Homo sapiens

<400> SEQUENCE: 65

| | |
|---|---|
| ttccccactc ccccgccctc cccagggccc tgggaagggg ctcagcgtgg gaaaggatgg | 60 |
| ttgagtttta accagaggca aagcgtgagc gggatcagtg tgtgcggaac gcaagcagcc | 120 |
| gagagcggag aggcgccgct gtagttaact cctccctgcc cgccgcgccg accctccccca | 180 |
| ggaaccccca gggagccagc atgaagcgag ctcaccccga gtacagctcc tcggacagcg | 240 |

```
agctggacga gaccatcgag gtggagaagg agagtgcgga cgagaatgga aacttgagtt    300
cggctctagg ttccatgtcc ccaactacat cttcccagat tttggccaga aaaagacgga    360
gaggaataat tgagaagcgc cgacgagacc ggatcaataa cagtttgtct gagctgagaa    420
ggctggtacc cagtgctttt gagaagcagg gatctgctaa gctagaaaaa gccgagatcc    480
tgcagatgac cgtggatcac ctgaaaatgc tgcatacggc aggagggaaa ggttactttg    540
acgcgcacgc ccttgctatg gactatcgga gtttgggatt cgggaatgc ctggcagaag     600 ttgcgcgtta tctgagcatc attgaaggac tagatgcctc tgacccgctt cgagttcgac    660
tggtttcgca tctcaacaac tacgcttccc agcgggaagc cgcgagcggc gcccacgcgg    720
gcctcggaca cattccctgg gggaccgtct tcggacatca cccgcacatc gcgcacccgc    780
tgttgctgcc ccagaacggc cacgggaacg cgggcaccac ggcctcaccc acggaaccgc    840
accaccaggg caggctgggc tcggcacatc cggaggcgcc tgctttgcga gcgcccccta    900
gcggcagcct cggaccggtg ctccctgtgg tcacctccgc ctccaaactg tcgccgcctc    960
tgctctcctc agtggcctcc ctgtcggcct tcccttctc tttcggctcc ttccacttac    1020
tgtctcccaa tgcactgagc ccttcagcac ccacgcaggc tgcaaacctt ggcaagccct    1080
atagaccttg ggggacggag atcggagctt tttaaagaac tgatgtagaa tgagggaggg    1140
gaaagtttaa aatcccagct gggctggact gttgccaaca tcaccttaaa gtcgtcagta    1200
aaagtaaaaa ggaaaaaggt acactttcag ataatttttt ttttaaagac taaaggtttg    1260
ttggtttact tttatctttt ttaatgtttt tttcatcatg tcatgtatta gcagttttta    1320
aaaactagtt gttaaatttt gttcaagaca ttaaattgaa atagtgagta taagccaaca    1380
ctttgtgata ggtttgtact gtgcctaatt tactttgtaa accagaatga ttccgttttt    1440
gcctcaaaat ttggggaatc ttaacattta gtattttgg tctgtttttc tccttgtata     1500
gttatggtct gttttagaa ttaatttttcc aaaccactat gcttaatgtt aacatgattc    1560
tgtttgttaa tattttgaca gattaaggtg ttgtataaat aatattctt tgggggagg      1620 ggaactatat tgaattttat atttctgagc aaagcgttga caaatcagat gatcagcttt    1680
atccaagaaa gaagactagt aaattgtctg cctcctatag cagaaaggtg aatgtacaaa    1740
ctgttggtgg ccctgaatcc atctgaccag ctgctggtat ctgccaggac tggcagttct    1800
gatttagtta ggagagagcc gctgataggt taggtctcat ttggagtgtt ggtggaaagg    1860
aaactgaagg taattgaata gaatacgcct gcatttacca gccccagcaa cacaagaat     1920 ttttaatcac acggatctca aattcacaaa tgttaacatg gataagtgat catggtgtgc    1980
gagtggtcaa ttgagtagta cagtggaaac tgttaaatgc ataacctaat ttcctggga    2040 ctgccatatt ttcttttaac tggaaatttt tatgtgagtt ttccttttgg tgcatggaac    2100
tgtggttgcc aaggtattta aaagggcttt cctgcctcct tctctttgat ttatttaatt    2160
tgatttgggc tataaaatat cattttcag gttattctt ttagcaggtg tagttaaacg      2220
acctccactg aactgggttt gacctctgtt gtactgatgt gttgtgacta aataaaaaag    2280
aaagaacaaa gtaaaaaaaa aaaaaaaaa aaaaaaaaa                            2319
```

<210> SEQ ID NO 66  
<211> LENGTH: 1198  
<212> TYPE: DNA  
<213> ORGANISM: Homo sapiens

<400> SEQUENCE: 66

```
gagacagaag gccgcctacc ggggaggccg gaggccggct agtcgcggac tcgggcgaac      60
ccaccctcgc gatctgtcaa gtctgtcccc aggggaggtc ccccttttcgg gaggaagttt    120 ttaaggggat ttctcaaaat caccccccgcg cttccttcac tccttcctta gagccggagg   180
tcggtgaggg cccgcggaat catctatctc gccccgtcg cagcgcgcag ggaccatgtc      240
ggcggagacc gcgagcggcc ccacagagga ccaggtggaa atcctggagt acaacttcaa    300
caaggtcgac aagcacccgg attccaccac gctgtgcctc atcgcggccg aggcaggcct    360
ttccgaggag gagacccaga aatggtttaa gcagcgcctg gcaaagtggc ggcgctcaga    420
aggcctgccc tcagagtgca gatccgtcac agactaagga gatggcaggc attgacagct    480
tcactccatg aaggccatct ctgtttctct cctccgctta accaagctgt tgtggttttt    540
cagcatagtg ttgtatgttc cattgctagc tgtcctgctg tttaacacag tgttgtattt    600
tttttctaaa tgtacataat tagaaaagaa ataacaata ggaagctatg tgtatcttct     660
gtgtaaagca gtggcttcac tggaaaaatg gtgtggctag catttccctt tgagtcatga    720
tgacagatgg tgtgaaaacc atctaagttt gcttttgacc atcacctccc agtagcaatt    780
tgctttcata atccatttag caatccaggc ctctgttgaa aagataatat gagggagaag    840
ggaacacatt tccttctgaa cttacttccc taagtcactt tccttatgta tcatctaata    900
caatgatggt tgagtgaaaa tacagaaggg gtgtttgagt attcagattt cataaaacac    960
ttccttggaa tatagctgca ttaacttgga aagaagcctg ttgggccaga agacagaaac   1020
tccaactggc aaaaaagcaa gcatctaaga aaaaaaacca ccaaagttct tgaatttact   1080
atatttaaat gcattggtta agtttatttt gctaaataaa gtgaactgct ttttgtctct   1140
aaaatgatat tctaaataaa accttaactt tttgttgaag atgcactgaa aaaaaaaa    1198
```

<210> SEQ ID NO 67
<211> LENGTH: 8988
<212> TYPE: DNA
<213> ORGANISM: Homo sapiens

<400> SEQUENCE: 67

```
actggggtgg cgcgctacct ctgcggagaa ggatctgaca gtgttccgga gccggggcga     60
gcagccaaaa ggcccgcgga gtcgcgctgg gccgccccgg cgcagctgaa ccgggggccg   120
cgcctgccag gccgacgggt ctggcccagc ctggcgccaa ggggttcgtg cgctgtggag   180
acgcggaggg tcgaggcggc gcggcctgag tgaaacccaa tggaaaaagc atgacattta   240
gaagtagaag acttagcttc aaatcccctac tccttcactt actaattttg tgatttggaa    300
atatccgcgc aagatgttga cgttgcagac ttggctagtg caagccttgt ttattttcct    360
caccactgaa tctacaggtg aacttctaga tccatgtggt tatatcagtc ctgaatctcc    420
agttgtacaa cttcattcta atttcactgc agtttgtgtg ctaaaggaaa aatgtatgga    480
ttattttcat gtaaatgcta attacattgt ctggaaaaca aaccatttta ctattcctaa    540
ggagcaatat actatcataa acagaacagc atccagtgtc acctttacag atatagcttc    600
attaaatatt cagctcactt gcaacattct tacattcgga cagcttgaac agaatgttta    660
tggaatcaca ataatttcag gcttgcctcc agaaaaacct aaaaatttga gttgcattgt    720
gaacgagggg aagaaaatga ggtgtgagtg ggatggtgga agggaaacac acttggagac    780
aaacttcact ttaaaatctg aatgggcaac acacaagttt gctgattgca aagcaaaacg    840
tgacaccccc acctcatgca ctgttgatta ttctactgtg tattttgtca acattgaagt    900
ctgggtagaa gcagagaatg cccttgggaa ggttacatca gatcatatca attttgatcc    960
```

```
tgtatataaa gtgaagccca atccgccaca taatttatca gtgatcaact cagaggaact    1020
gtctagtatc ttaaaattga catggaccaa cccaagtatt aagagtgtta taatactaaa    1080
atataacatt caatatagga ccaaagatgc ctcaacttgg agccagattc ctcctgaaga    1140
cacagcatcc acccgatctt cattcactgt ccaagacctt aaacctttta cagaatatgt    1200
gtttaggatt cgctgtatga aggaagatgg taagggatac tggagtgact ggagtgaaga    1260
agcaagtggg atcacctatg aagataacat tgcctccttt tgaagccaat ggaaaaatct    1320
tggattatga agtgactctc acaagatgga aatcacattt acaaaattac acagttaatg    1380
ccacaaaact gacagtaaat ctcacaaatg atcgctatct agcaacccta acagtaagaa    1440
atcttgttgg caaatcagat gcagctgttt taactatccc tgcctgtgac tttcaagcta    1500
ctcaccctgt aatggatctt aaagcattcc ccaaagataa catgctttgg gtggaatgga    1560
ctactccaag ggaatctgta aagaaatata tacttgagtg gtgtgtgtta tcagataaag    1620
caccctgtat cacagactgg caacaagaag atggtaccgt gcatcgcacc tatttaagag    1680
ggaacttagc agagagcaaa tgctatttga taacagttac tccagtatat gctgatggac    1740
caggaagccc tgaatccata aaggcatacc ttaaacaagc tccaccttcc aaaggaccta    1800
ctgttcggac aaaaaaagta gggaaaaacg aagctgtctt agagtgggac caacttcctg    1860
ttgatgttca gaatggattt atcagaaatt atactatatt ttatagaacc atcattggaa    1920
atgaaactgc tgtgaatgtg gattcttccc acacagaata tacattgtcc tctttgacta    1980
gtgcacacatt gtacatggta cgaatggcag catacacaga tgaaggtggg aaggatggtc    2040
cagaattcac ttttactacc ccaaagtttg ctcaaggaga aattgaagcc atagtcgtgc    2100
ctgtttgctt agcattccta ttgacaactc ttctgggagt gctgttctgc tttaataagc    2160
gagacctaat taaaaaacac atctggccta atgttccaga tccttcaaag agtcatattg    2220
cccagtggtc acctcacact cctccaaggc acaattttaa ttcaaaagat caaatgtatt    2280
cagatggcaa tttcactgat gtaagtgttg tggaaataga agcaaatgac aaaaagcctt    2340
ttccagaaga tctgaaatca ttggacctgt tcaaaaagga aaaaattaat actgaaggac    2400
acagcagtgg tattgggggg tcttcatgca tgtcatcttc taggccaagc atttctagca    2460
gtgatgaaaa tgaatcttca caaaacactt cgagcactgt ccagtattct accgtggtac    2520
acagtggcta cagacaccaa gttccgtcag tccaagtctt ctcaagatcc gagtctaccc    2580
agcccttgtt agattcagag gagcggccag aagatctaca attagtagat catgtagatg    2640
gcggtgatgg tatttttgccc aggcaacagt acttcaaaca gaactgcagt cagcatgaat    2700
ccagtccaga tatttcacat tttgaaaggt caaagcaagt ttcatcagtc aatgaggaag    2760
attttgttag acttaaacag cagatttcag atcatatttc acaatcctgt ggatctgggc    2820
aaatgaaaat gtttcaggaa gtttctgcag cagatgcttt tggtccaggt actgagggac    2880
aagtagaaag atttgaaaca gttggcatgg aggctgcgac tgatgaaggc atgcctaaaa    2940
gttacttacc acagactgta cggcaaggcg gctacatgcc tcagtgaagg actagtagtt    3000
cctgctacaa cttcagcagt acctataaag taaagctaaa atgattttat ctgtgaattc    3060
agatttaaa aagtcttcac tctctgaaga tgatcatttg cccttaagga caaaaatgaa    3120
ctgaagtttc acatgagcta tttccattcc agaatatctg ggattctact taagcacta    3180
cataaactga cttatcctc agactagctg aatgattttg tgctgtttca ggatgtttgc    3240
actgaagaaa aacagaaagc ttatctgaaa tttataaaac ttttttgtttt gctacataga    3300
```

```
aaacagaagg tatttgaata ataagcagtg atatgcttag tgagcacagc tatactgatt    3360
ttgattagaa tagtcatcag agtggcttag ggacagttaa tataaaagag gagcaaggtg    3420
tagaccatca tctacttctg ctaaaataac ttaaaaagag gtccataggc cataactaca    3480
tgagcccagc ttttgtaatc tgacaaaaaa atgaggagca gcttcgtgta tatcagtgta    3540
cacggtattc cttaggtccc ttccattggt agtgatgctg cgagttatta ctggagaaaa    3600
ggaattctag agctttaact tggcagatta aaagtactca tttttattc atcaataatt     3660 agtaatctca ctagttttca aaaatttgca tattattgac aacctctttg aagatgcatt    3720
tcacaaactc aacagagtgc catgataaga gctagggatc ccccaaacta tctcaagcat    3780
ctaaaaaatt gccattttta aaggcttaaa ttgtagtagt aaaggggaaa acaggaagta    3840
gtagtaaagg ggaaaaaaaa ccaataaagc atctaaaaaa ttggcatgtt aaaaggctta    3900
aattgctaat gtgtgtatat atatatatat atatacacac acatatcatt gacttttctt    3960
aagacttcag agtactgggt agatgaacac tttatacagt atatatcttc agcttaaatt    4020
tgttttgagt atttttttta tttttaaata agtaggcaaa gatttaaatt ttttatttt    4080 tagtaaatgt ttgaggcaca ctaagacaac ttgggcaata tttgccaaaa caaaacagaa    4140
ccccaaaaaa tgtacatctt gttcttagca aatatcatta ttgtagagac acttaataaa    4200
gagatggtat tttaatgtct gcagttctga ggtagggtgg aacttagttc tacattgtga    4260
tttaggaatt tttaaaacct tttttcttca agggagaagt gacccaggcc tcgagtttag    4320
tgctaaagcc gctagtgtac ttatgctgtc ccctaaccac cacgtgcgat atggaagcag    4380
atgctaaata tagggttttt cttagaaagt aagaggaaat tagcaagcgt tattagtgat    4440
tgactactgc tatcaagtga attcaaagga acaggttttt tatgccatat ttaagttaca    4500
gaaaccaggc atgcttagaa tagtttctag aggttattgg agaatagaaa gctaagaaaa    4560
cttggtatac atttacaatg gaaatataat tacacttttt actctcagaa tattgttcac    4620
attagacttc ctgtttatct tttatattct tgcatttata taatgcctca tcctttcaaa    4680
gttctttcac atattatatg atcttcttta tgaaaaaaat agatgtttca ttctgatata    4740 ttcagttttcc cactttaggc aaaagtagat taatagaatg acgaattcaa agtgatgag    4800 gaaaatcagg cacagagaag taaggtagg gatagaccca aatttacaca acaagataat    4860
gacatctcca gcttttaagt tgatcatcaa aggctgggct ggatttgtct tgctgtatgt    4920
gtcaggaaat ttatacctat tacatttcc atttctcaa aattaagtc acatgactaa     4980 tatttagctg caacttttcct cataacaaat agtgtcatga agaatgttgt agtgtgaagt    5040
ttgtacattt cagggtcaga tatacaatat gaactcttaa tctacaggaa tgagaatgga    5100
ggatcattga aggccatgat ataaacaaat ttgcatgttg aagcctgtat aaaacatggt    5160
acagtgagtg aatataccc catccccaag aacactttat acatattaaa tggatatatg    5220
attactgtgc aaaaattcat tctggaaatg aacatatatt tgagcactaa tatgtaatgt    5280
acacctgccc taaggagaaa ataaattata aaactttta cattcaaaat tactttccca    5340
agcatgtctt agaataatct atgtgttgat gcatgtaaat tgtactttag gtaggcaaag    5400
aaatctggtt atttatgtaa aaactagtct aataaagtta gttagtggct ttatcacttt    5460
aaatctttag tgtccaaaag tggtgtttaa agtaatagca catcagaaaa ccttgtctgg    5520
acaaaactag ttcactcact gcttctgcac ctgcagttgc tccctttagg gttataaaat    5580
aatgacccaa atgttacatg tgttgatatt ataacttgtc agttactgat gtctgtggta    5640 tcctacccctc atctctgaaa gggataatac tgaataatta ttagaaaact ataaaacttc    5700
```

```
acactttgta ccattaaaac ctaaaatttt aatcttgtcc ttttttacta tggatcagtc   5760
ggcactcggg aacagcagca aggaaaaaaa gcaaatttca ttcacatgtt ctgtgttcat   5820
acctcttctc tacctaattg ttcatttaaa tttcagcctt attccttgat aagggatttt   5880
accacatgaa gtcatccagt gaccctagct cttattgtga agttagtgga gtatacttag   5940
aaatgttaca actttaaaat gttacaaaac attcattaaa gctcatattt aaagtagagc   6000
atctagtttg agaaatagaa atcaattatt aaagatgtct tttttctacc catttaacta   6060
gttaaaacca tgacatgtaa atgtagaagt agaataatca tagaattccc taaaatattt   6120
ctgtttacta acatatattg accaagtaca tcaagcagga gagatcttcc ttcattctgt   6180
tatagtccac atcattctaa ttttgctcag ttgttattaa gagcatattc ctaaaccata   6240 cactttgtt tcaataaagt tttattttgt tgagatgaat aaaataacaa agttataagc   6300
tgcataagac aaaagttcaa ttgttcaaaa aaaatttact gggatagctt tctattacag   6360
gtattgttag attatattgt gctgataaga ttactttcta aaaaatttgt acttttctgt   6420
aaattaaaag aatatggagt cataaaatgg caagtgtttt aggattagcc taaaattgga   6480
cattgtcatt gatttcaaag aaggtatgaa ctagcagtct tacagcctaa ttcttctttg   6540
gactggtcct tggcagcagt tccttttcag actcgataaa cagaattcag atgatgtaag   6600
tcaaaacaaa actttacaaa gccaagcgta ttatcttttg cattaaccta tttttttcca   6660
tcatacatgc tactagtatg tgcattagca tgatattctc atatacattg cattaaaaat   6720
taaaaggtgg cagctcaggg tgagctcttc tgttgctcat ttgttcctaa attttttaagg   6780 gcttttctc agtcaatagt ttgtacaaac tggttagttt aacttcatta cccatttcat   6840
taaagttgat gggtcgtgtg atgagatgca tttaaggccg atagtgatag atgttttttt   6900
tatttcttga acacaggctt tgtctgaatg atgttctttt atctcttgaa cacaagcttt   6960
gaatgataac tacaggtttt aagtgctgtt acattaatac cataatgtga tgtgttagaa   7020
acaaagggat atttcaaagg tagatatttg aaaattctct agtctcaata tgtatgtgta   7080
ttgaatatac tctaaaaata aatgtgcaat ttgctagtag gacaatgcag tgactgacta   7140
gcattaggta tgtttctttt atatcctagc tatgtcccac tttcttctaa gtgcaatcct   7200
ttcatgttca cttgctgttt taccccatct actctaactt catttggaag gcttgtctag   7260
agtatagcat gtattttac ctttgcagtg aattgcatgt gctaattgta accacagcta   7320
tttttatgtt gacataactc caaatgttat attaaatgtt ctattatata ttagctctaa   7380
tcccttaagt aaatttaag aaataaatac ttgttcaaat ttttttttctg tatgtggtta   7440 ctatcatctg actatgcata tttgtaacag catttatcat tagtggtgtt agctaaataa   7500
gcatcttagt gtaaatgaga tgcttcgtgt gggttttgtg acatttaaa tgacataatg   7560 gaatgtgatt taaagaaaa ccagtacact atcttggtct taataacata gaatggagat   7620
ggcaaattta tccactagtt ttccagattt actatttaat agctgaggtc tgaaatcgta   7680
gcatcctccc tcctagtgga cattaaaaaa aaaaaaaaa aaaaaaacct acttggttgt   7740
caagagccca gtatggagg tgctgcgcca tcttgtggcc tgtctgtgcc caccctgcac   7800
tctgctggag tctccatcct tgttgcagtg agacttgaag ttcaagattg atacatggca   7860
tcctcctgct acttcttgag gttactaagt agtatatgaa actaatcagt cagcaagtcc   7920
acctggaagg aaaagaaaat ctcaactatt aatgtgcctt cacattgtga ttttgtctaa   7980
aaaaatgtag tgagtcaaaa aacccacaag ccagccaaca gtaactcctt cacatatata   8040
```

| | |
|---|---|
| ccagagttta tagaaataac atgtcagctt tgggctatgt gctcctttgt ttaaaatctt | 8100 |
| ctatttggtt atggcttgta taggctcaag cctgatttct ttaaggtgtg gtggctcatc | 8160 |
| ttatcctaat gtgtatgata gatacagtcc atcctgcttt ggaaaagatt atgtaactcc | 8220 |
| ttgagagcat actctttctc tagcccaaag gcagtgagag agttttcttg ttcaggattg | 8280 |
| cttaactttc catttaagct ttttcttttt aaattaatac aaacttctac actttcaaaa | 8340 |
| tacgaaatat attacaactg cgtataggct cttccatact taagtccagt gcttgggcaa | 8400 |
| gttaatggag tgaaagacta caagcaaaga ggaactgagg tagaaaaaga agaatgtgtg | 8460 |
| aaagcagcag gaagctcagc caactcgaaa gcagggtgaa cagcttgagt cctgttgctg | 8520 |
| ctgatcgggg ttggctcttg gacaacttag taagatcatg gaaaggctgc ttgggttctc | 8580 |
| catagaaaag ttctgtctcc atcaagggag gaaaatgtac cttttcaactc aaaattcaat | 8640 |
| atttgttttt aaatatagct attttcccca accgctaaag attttcaaca gatacgaagc | 8700 |
| cagagcttag ttttagaaac ctgtggacat tcaaacctga ttctttattc cctgtgacta | 8760 |
| tggttatgtc attttacatg tcaaaaaagt gtatctagaa ttgtcatttc ttattttga | 8820 |
| gcttttttta gtgagaatta tccctcact taaatggctt tttatttaaa catctgtgca | 8880 |
| ttctgtatga aattgtagtc tttctgggat aacatggtga gctatatggt ggtaatccac | 8940 |
| acacacaaaa ataaaagcca aaaaaaaacc aaaaaaaaaa aaaaaaa | 8988 |

<210> SEQ ID NO 68
<211> LENGTH: 1669
<212> TYPE: DNA
<213> ORGANISM: Homo sapiens

<400> SEQUENCE: 68

| | |
|---|---|
| gctcctgtca tcgaggcccc tggcccaatg gcaggctgag tcccctcct ctggcctggt | 60 |
| cccgcctctc ctgccccttg tgctcagcgc tacctgctgc ccggacacat ccagagctgg | 120 |
| ccgacgggtg cgcgggcggg cggcggcacc atgcagggaa gctgccaggg gccgtgggca | 180 |
| gcgccgcttt ctgccgccca cctggcgctg tgagactggc gctgccacca tgttccccag | 240 |
| ccctgctctc acgcccacgc ccttctcagt caaagacatc ctaaacctgg aacagcagca | 300 |
| gcgcagcctg gctgccgccg gagagctctc tgcccgcctg gaggcgaccc tggcgccctc | 360 |
| ctcctgcatg ctgccgcct tcaagccaga ggcctacgct gggcccgagg cggctgcgcc | 420 |
| gggcctccca gagctgcgcg cagagctggg ccgcgcgcct tcaccggcca agtgtgcgtc | 480 |
| tgcctttccc gccgccccg ccttctatcc acgtgcctac agcgacccg acccagccaa | 540 |
| ggaccctaga gccgaaaaga aagagctgtg cgcgctgcag aaggcggtgg agctggagaa | 600 |
| gacagaggcg gacaacgcgg agcggccccg ggcgcgacgg cggaggaagc cgcgcgtgct | 660 |
| cttctcgcag gcgcaggtct atgagctgga gcggcgcttc aagcagcagc ggtacctgtc | 720 |
| ggcccccgaa cgcgaccagc tggccagcgt gctgaaactc acgtccacgc aggtcaagat | 780 |
| ctggttccag aaccggcgct acaagtgcaa gcggcagcgg caggaccaga ctctggagct | 840 |
| ggtggggctg cccccgccgc cgccgccgcc tgcccgcagg atcgcggtgc cagtgctggt | 900 |
| gcgcgatggc aagccatgcc tagggactc ggcgccctac gcgcctgcct acggcgtggg | 960 |
| cctcaatccc tacggttata cgcctaccc cgcctatccg ggttacggcg gcgcggcctg | 1020 |
| cagccctggc tacagctgca ctgccgctta cccgccggg ccttcccag cgcagccggc | 1080 |
| cactgccgcc gccaacaaca acttcgtgaa cttcggcgtc gggacttga atgcggttca | 1140 |
| gagccccggg attccgcaga gcaactcggg agtgtccacg ctgcatggta tccgagcctg | 1200 |

| | | |
|---|---|---|
| gtagggaagg dacccgcgtg gcgcgaccct gaccgatccc acctcaacag ctccctgact | 1260 |
| ctcgggggga gaaggggctc ccaacatgac cctgagtccc ctggattttg cattcactcc | 1320 |
| tgcggagacc taggaacttt ttctgtccca cgcgcgtttg ttcttgcgca cgggagagtt | 1380 |
| tgtggcggcg attatgcagc gtgcaatgag tgatcctgca gcctggtgtc ttagctgtcc | 1440 |
| ccccaggagt gccctccgag agtccatggg caccccggt tggaactggg actgagctcg | 1500 |
| ggcacgcagg gcctgagatc tggccgccca ttccgcgagc cagggccggg cgcccgggcc | 1560 |
| tttgctatct cgccgtcgcc cgcccacgca cccacccgta tttatgtttt tacctattgc | 1620 |
| tgtaagaaat gacgatcccc ttcccattaa agagagtgcg ttgaccccg | 1669 |

<210> SEQ ID NO 69
<211> LENGTH: 1301
<212> TYPE: DNA
<213> ORGANISM: Homo sapiens

<400> SEQUENCE: 69

| | | |
|---|---|---|
| agatatatca tacgaaaatg aaaattataa ttcttcttgg attcctggga gccacattgt | 60 |
| cagcccact tatcccacag cgtctcatgt ctgccagcaa tagcaatgag ttacttctta | 120 |
| atcttaataa tggtcaactt tgccactac aacttcaggg cccacttaat tcatggattc | 180 |
| cacctttctc tggaatttta caacagcagc agcaggctca aattccagga ctctcccagt | 240 |
| tctctttatc agctctagac cagtttgctg gactgctccc aaatcagata cccttaacag | 300 |
| gagaggccag ttttgcccaa ggagcccagg caggccaagt tgatcccta cagcttcaaa | 360 |
| caccgcctca gacacaacca ggccccagtc acgtgatgcc ctatgtattc tccttcaaaa | 420 |
| tgcctcaaga gcaaggacag atgtttcaat actatccagt ttacatggtc ctaccctggg | 480 |
| aacaacctca gcaaacagtt ccaaggtcac ctcaacaaac aagacagcaa cagtatgagg | 540 |
| agcagatacc attctatgct caatttggat acattccaca actagcagaa cctgctatat | 600 |
| caggaggaca gcagcaacta gcttttgatc cccaactagg cacagctcct gaaattgctg | 660 |
| tgatgtcaac aggagaagag ataccatatt tacaaaaaga agcgatcaac tttagacatg | 720 |
| acagtgcagg agttttcatg ccctcaactt caccaaaacc cagcacaacc aatgttttca | 780 |
| cttctgctgt agaccaaaact attacccag agctcccaga agagaaggac aagactgaca | 840 |
| gcctaaggga accataagaa gttgccctga tcattcagac attttgggaa aaagatgtgg | 900 |
| ccatgccttg gatataattt taggctatta gcttcctcaa tactagtatc agttctttgg | 960 |
| aatacatgaa atatcttgac tcttctccta aatttgtttt tacttataca tgttattaaa | 1020 |
| ctctttaaat atgtcataga aaataataca atcatgtaat gagtcttgtc ttacaaaatt | 1080 |
| atatgtctct tcaaatatcc tatcattgta taatatggaa tataataaca cagaataaag | 1140 |
| ctagtatcat taaatcaatt ggataattgc attagtaaat gatgcctctg caaaatggta | 1200 |
| gtacccatga agatatgtat attgtcattg gatgtatgat gagtgttgtg attggaactg | 1260 |
| atgaagtaaa ataagtatct agatttgaaa aaaaaaaaa a | 1301 |

<210> SEQ ID NO 70
<211> LENGTH: 6574
<212> TYPE: DNA
<213> ORGANISM: Homo sapiens

<400> SEQUENCE: 70

| | | |
|---|---|---|
| aagagcaaaa agcgaaggcg caatctggac actgggagat tcggagcgca gggagtttga | 60 |

| | |
|---|---|
| gagaaacttt tattttgaag agaccaaggt tgagggggggg cttatttcct gacagctatt | 120 |
| tacttagagc aaatgattag ttttagaagg atggactata acattgaatc aattacaaaa | 180 |
| cgcggttttt gagcccatta ctgttggagc tacagggaga gaaacagagg aggagactgc | 240 |
| aagagatcat tggaggccgt gggcacgctc tttactccat gtgtgggaca ttcattgcgg | 300 |
| aataacatcg gaggagaagt ttcccagagc tatgggggact tcccatccgg cgttcctggt | 360 |
| cttaggctgt cttctcacag ggctgagcct aatcctctgc cagctttcat taccctctat | 420 |
| ccttccaaat gaaatgaaa aggttgtgca gctgaattca tccttttctc tgagatgctt | 480 |
| tggggagagt gaagtgagct ggcagtaccc catgtctgaa gaagagagct ccgatgtgga | 540 |
| aatcagaaat gaagaaaaca acagcggcct ttttgtgacg gtcttggaag tgagcagtgc | 600 |
| ctcggcggcc cacacagggt tgtacacttg ctattacaac cacactcaga cagaagagaa | 660 |
| tgagcttgaa ggcaggcaca tttacatcta tgtgccagac ccagatgtag cctttgtacc | 720 |
| tctaggaatg acggattatt tagtcatcgt ggaggatgat gattctgcca ttataccttg | 780 |
| tcgcacaact gatcccgaga ctcctgtaac cttacacaac agtgaggggg tggtacctgc | 840 |
| ctcctacgac agcagacagg gctttaatgg gaccttcact gtagggcct atatctgtga | 900 |
| ggccaccgtc aaaggaaaga agttccgaca catcccattt aatgtttatg ctttaaaagc | 960 |
| aacatcagag ctggatctag aaatggaagc tcttaaaacc gtgtataagt caggggaaac | 1020 |
| gattgtggtc acctgtgctg ttttttaacaa tgaggtggtt gaccttcaat ggacttaccc | 1080 |
| tggagaagtg aaaggcaaag gcatcacaat gctggaagaa atcaaagtcc catccatcaa | 1140 |
| attggtgtac actttgacgg tccccgaggc cacggtgaaa gacagtggag attacgaatg | 1200 |
| tgctgcccgc caggctacca gggaggtcaa agaaatgaag aaagtcacta tttctgtcca | 1260 |
| tgagaaaggt ttcattgaaa tcaaacccac cttcagccag ttggaagctg tcaacctgca | 1320 |
| tgaagtcaaa cattttgttg tagaggtgcg ggcctaccca cctcccagga tatcctggct | 1380 |
| gaaaaacaat ctgactctga ttgaaaatct cactgagatc accactgatg tggaaaagat | 1440 |
| tcaggaaata aggtatcgaa gcaaattaaa gctgatccgt gctaaggaag aagacagtgg | 1500 |
| ccattatact attgtagctc aaaatgaaga tgctgtgaag agctatactt ttgaactgtt | 1560 |
| aactcaagtt ccttcatcca ttctggactt ggtcgatgat caccatggct caactggggg | 1620 |
| acagacggtg aggtgcacag ctgaaggcac gccgcttcct gatattgagt ggatgatatg | 1680 |
| caaagatatt aagaaatgta ataatgaaac ttcctggact attttggcca acaatgtctc | 1740 |
| aaacatcatc acggagatcc actcccgaga caggagtacc gtggagggcc gtgtgacttt | 1800 |
| cgccaaagtg gaggagacca tcgccgtgcg atgcctggct aagaatctcc ttggagctga | 1860 |
| gaaccgagag ctgaagctgg tggctcccac cctgcgttct gaactcacgg tggctgctgc | 1920 |
| agtcctggtg ctgttggtga ttgtgatcat ctcacttatt gtcctggttg tcatttggaa | 1980 |
| acagaaaccg aggtatgaaa ttcgctggag ggtcattgaa tcaatcagcc cagatggaca | 2040 |
| tgaatatatt tatgtggacc cgatgcagct gccttatgac tcaagatggg agtttccaag | 2100 |
| agatggacta gtgcttggtc gggtcttggg gtctggagcg tttgggaagg tggttgaagg | 2160 |
| aacagcctat ggattaagcc ggtcccaacc tgtcatgaaa gttgcagtga agatgctaaa | 2220 |
| acccacggcc agatccagtg aaaaacaagc tctcatgtct gaactgaaga taatgactca | 2280 |
| cctgggggcca catttgaaca ttgtaaactt gctgggagcc tgcaccaagt cagggccccat | 2340 |
| ttacatcatc acagagtatt gcttctatgg agatttggtc aactattttgc ataagaatag | 2400 |
| ggatagcttc ctgagccacc acccagagaa gccaaagaaa gagctggata tctttggatt | 2460 |

```
gaaccctgct gatgaaagca cacggagcta tgttatttta tcttttgaaa acaatggtga    2520
ctacatggac atgaagcagg ctgatactac acagtatgtc cccatgctag aaaggaaaga    2580
ggtttctaaa tattccgaca tccagagatc actctatgat cgtccagcct catataagaa    2640
gaaatctatg ttagactcag aagtcaaaaa cctcctttca gatgataact cagaaggcct    2700
tactttattg gatttgttga gcttcaccta tcaagttgcc cgaggaatgg agttttttggc   2760 ttcaaaaaat tgtgtccacc gtgatctggc tgctcgcaac gtcctcctgg cacaaggaaa    2820
aattgtgaag atctgtgact ttggcctggc cagagacatc atgcatgatt cgaactatgt    2880
gtcgaaaggc agtacctttc tgcccgtgaa gtggatggct cctgagagca tctttgacaa    2940
cctctacacc acactgagtg atgtctggtc ttatggcatt ctgctctggg agatcttttc    3000
ccttggtggc accccttacc ccggcatgat ggtggattct actttctaca ataagatcaa    3060
gagtgggtac cggatggcca agcctgacca cgctaccagt gaagtctacg agatcatggt    3120
gaaatgctgg aacagtgagc ggagaagag accctccttt taccacctga gtgagattgt     3180
ggagaatctg ctgcctggac aatataaaaa gagttatgaa aaaattcacc tggacttcct    3240
gaagagtgac catcctgctg tggcacgcat gcgtgtggac tcagacaatg catacattgg    3300
tgtcacctac aaaaacgagg aagacaagct gaaggactgg gagggtggtc tggatgagca    3360
gagactgagc gctgacagtg gctacatcat tcctctgcct gacattgacc ctgtccctga    3420
ggaggaggac ctgggcaaga ggaacagaca cagctcgcag acctctgaag agagtgccat    3480
tgagacgggt tccagcagtt ccaccttcat caagagagag gacgagacca ttgaagacat    3540
cgacatgatg gatgacatcg gcatagactc ttcagacctg gtggaagaca gcttcctgta    3600
actggcggat tcgaggggtt ccttccactt ctggggccac ctctggatcc cgttcagaaa    3660
accactttat tgcaatgcag aggttgagag gaggacttgg ttgatgttta aagagaagtt    3720
cccagccaag ggcctcgggg agcgttctaa atatgaatga atgggatatt ttgaaatgaa    3780
ctttgtcagt gttgcctctt gcaatgcctc agtagcatct cagtggtgtg tgaagtttgg    3840
agatagatgg ataagggaat aataggccac agaaggtgaa ctttgtgctt caaggacatt    3900
ggtgagagtc caacagacac aatttatact gcgacagaac ttcagcattg taattatgta    3960
aataactcta accaaggctg tgtttagatt gtattaacta tcttctttgg acttctgaag    4020
agaccactca atccatccat gtacttccct cttgaaacct gatgtcagct gctgttgaac    4080
tttttaaaga agtgcatgaa aaaccatttt tgaaccttaa aaggtactgg tactatagca    4140
ttttgctatc ttttttagtg ttaaagagat aaagaataat aattaaccaa ccttgtttaa    4200
tagatttggg tcatttagaa gcctgacaac tcattttcat attgtaatct atgtttataa    4260
tactactact gttatcagta atgctaaatg tgtaataatg taacatgatt tccctccaga    4320
gaaagcacaa tttaaaacaa tccttactaa gtaggtgatg agtttgacag ttttttgacat   4380 ttatattaaa taacatgttt ctctataaag tatggtaata gctttagtga attaaattta    4440
gttgagcata gagaacaaag taaaagtagt gttgtccagg aagtcagaat ttttaactgt    4500
actgaatagg ttccccaatc catcgtatta aaaaacaatt aactgccctc tgaaataatg    4560
ggattagaaa caaacaaaac tcttaagtcc taaaagttct caatgtagag gcataaacct    4620
gtgctgaaca taacttctca tgtatattac ccaatggaaa atataatgat cagcaaaaag    4680
actggatttg cagaagtttt ttttttttttt ttcttcatgc ctgatgaaag ctttggcgac    4740
cccaatatat gtatttttttg aatctatgaa cctgaaaagg gtcagaagga tgcccagaca    4800
```

| | |
|---|---|
| tcagcctcct tctttcaccc cttaccccaa agagaaagag tttgaaactc gagaccataa | 4860 |
| agatattctt tagtggaggc tggatgtgca ttagcctgga tcctcagttc tcaaatgtgt | 4920 |
| gtggcagcca ggatgactag atcctgggtt tccatccttg agattctgaa gtatgaagtc | 4980 |
| tgagggaaac cagagtctgt attttttctaa actccctggc tgttctgatc ggccagtttt | 5040 |
| cggaaacact gacttaggtt tcaggaagtt gccatgggaa acaaataatt tgaactttgg | 5100 |
| aacagggttg gcattcaacc acgcaggaag cctactattt aaatccttgg cttcaggtta | 5160 |
| gtgacattta atgccatcta gctagcaatt gcgaccttaa tttaactttc cagtcttagc | 5220 |
| tgaggctgag aaagctaaag tttggttttg acaggttttc caaaagtaaa gatgctactt | 5280 |
| cccactgtat gggggagatt gaactttccc cgtctcccgt cttctgcctc ccactccata | 5340 |
| ccccgccaag gaaaggcatg tacaaaaatt atgcaattca gtgttccaag tctctgtgta | 5400 |
| accagctcag tgttttggtg gaaaaaacat tttaagtttt actgataatt tgaggttaga | 5460 |
| tgggaggatg aattgtcaca tctatccaca ctgtcaaaca ggttggtgtg ggttcattgg | 5520 |
| cattctttgc aatactgctt aattgctgat accatatgaa tgaaacatgg gctgtgatta | 5580 |
| ctgcaatcac tgtgctatcg gcagatgatg ctttggaaga tgcagaagca ataataaagt | 5640 |
| acttgactac ctactggtgt aatctcaatg caagccccaa ctttcttatc caacttttc | 5700 |
| atagtaagtg cgaagactga gccagattgg ccaattaaaa acgaaaacct gactaggttc | 5760 |
| tgtagagcca attagacttg aaatacgttt gtgtttctag aatcacagct caagcattct | 5820 |
| gtttatcgct cactctcct tgtacagcct tattttgttg gtgctttgca ttttgatatt | 5880 |
| gctgtgagcc ttgcatgaca tcatgaggcc ggatgaaact tctcagtcca gcagtttcca | 5940 |
| gtcctaacaa atgctcccac ctgaatttgt atatgactgc atttgtgtgt gtgtgtgtgt | 6000 |
| tttcagcaaa ttccagattt gtttccttt ggcctcctgc aaagtctcca gaagaaaatt | 6060 |
| tgccaatctt tcctactttc tatttttatg atgacaatca aagccggcct gagaaacact | 6120 |
| atttgtgact ttttaaacga ttagtgatgt ccttaaaatg tggtctgcca atctgtacaa | 6180 |
| aatggtccta tttttgtgaa gagggacata agataaaatg atgttataca tcaatatgta | 6240 |
| tatatgtatt tctatataga cttggagaat actgccaaaa catttatgac aagctgtatc | 6300 |
| actgccttcg tttatatttt tttaactgtg ataatcccca caggcacatt aactgttgca | 6360 |
| cttttgaatg tccaaaattt atattttaga aataataaaa agaaagatac ttacatgttc | 6420 |
| ccaaaacaat ggtgtggtga atgtgtgaga aaaactaact tgatagggtc taccaataca | 6480 |
| aaatgtatta cgaatgcccc tgttcatgtt tttgttttaa aacgtgtaaa tgaagatctt | 6540 |
| tatatttcaa taaatgatat ataatttaaa gtta | 6574 |

<210> SEQ ID NO 71
<211> LENGTH: 2317
<212> TYPE: DNA
<213> ORGANISM: Homo sapiens

<400> SEQUENCE: 71

| | |
|---|---|
| cggacgcgtg ggtgagcagg acggtgcac cggacggcgg gatcgagcaa atgggtctgg | 60 |
| ccatggagca cggagggtcc tacgctcggg cgggggcag ctctcgggc tgctggtatt | 120 |
| acctgcgcta cttcttcctc ttcgtctccc tcatccaatt cctcatcatc ctggggctcg | 180 |
| tgctcttcat ggtctatggc aacgtgcacg tgagcacaga gtccaacctg caggccaccg | 240 |
| agcgccgagc cgagggccta tacagtcagc tcctagggct cacggcctcc cagtccaact | 300 |
| tgaccaagga gctcaacttc accacccgcg ccaaggatgc catcatgcag atgtggctga | 360 |

```
atgctcgccg cgacctggac cgcatcaatg ccagcttccg ccagtgccag ggtgaccggg    420
tcatctacac gaacaatcag aggtacatgg ctgccatcat cttgagtgag aagcaatgca    480
gagatcaatt caaggacatg aacaagagct gcgatgcctt gctcttcatg ctgaatcaga    540
aggtgaagac gctggaggtg gagatagcca aggagaagac catttgcact aaggataagg    600
aaagcgtgct gctgaacaaa cgcgtggcgg aggaacagct ggttgaatgc gtgaaaaccc    660
gggagctgca gcaccaagag cgccagctgg ccaaggagca actgcaaaag gtgcaagccc    720
tctgcctgcc cctggacaag gacaagtttg agatggacct tcgtaacctg tggagggact    780
ccattatccc acgcagcctg acaacctggg gttacaacct ctaccatccc ctgggctcgg    840
aattggcctc catccgcaga gcctgcgacc acatgcccag cctcatgagc tccaaggtgg    900
aggagctggc ccggagcctc cgggcggata tcgaacgcgt ggcccgcgag aactcagacc    960
tccaacgcca gaagctggaa gcccagcagg gcctgcgggc cagtcaggag gcgaaacaga   1020
aggtggagaa ggaggctcag gcccgggagg ccaagctcca agctgaatgc tcccggcaga   1080
cccagctagc gctggaggag aaggcggtgc tgcggaagga acgagacaac ctggccaagg   1140
agctggaaga gaagaagagg gaggcggagc agctcaggat ggagctggcc atcagaaact   1200
cagccctgga cacctgcatc aagaccaagt cgcagccgat gatgccagtg tcaaggccca   1260
tgggccctgt ccccaacccc cagcccatcg acccagctag cctggaggag ttcaaggaga   1320
agatcctgga gtcccagagg ccccctgcag gcatccctgt agccccatcc agtggctgag   1380
gaggctccag gcctgaggac caagggatgg cccgactcgg cggtttgcgg aggatgcagg   1440
gatatgctca cagcgcccga cacaaccccc tcccgccgcc cccaaccacc cagggccacc   1500
atcagacaac tccctgcatg caaacccctc gtaccctctc acaccgcac ccgcgcctca   1560 cgatccctca cccagagcac acggccgcgg agatgacgtc acgcaagcaa cggcgctgac   1620
gtcacatatc accgtggtga tggcgtcacg tggccatgta gacgtcacga agagatatag   1680
cgatggcgtc gtgcagatgc agcacgtcgc acacagacat ggggaacttg gcatgacgtc   1740
acaccgagat gcagcaacga cgtcacgggc catgtcgacg tcacacatat taatgtcaca   1800
cagacgcggc gatggcatca cacagacggt gatgatgtca cacacagaca cagtgacaac   1860
acacaccatg acaacgacac ctatagatat ggcaccaaca tcacatgcac gcatgccctt   1920
tcacacacac tttctaccca attctcacct agtgtcacgt tccccgacc ctggcacacg    1980 ggccaaggta cccacaggat cccatcccct cccgcacagc cctgggcccc agcacctccc   2040
ctcctccagc ttcctggcct cccagccact tcctcacccc cagtgcctgg acccggaggt   2100
gagaacagga agccattcac ctccgctcct tgagcgtgag tgtttccagg accccctcgg   2160
ggccctgagc cggggtgag ggtcacctgt tgtcggagg ggagccactc cttctccccc    2220
aactcccagc cctgcctgtg gcccgttgaa atgttggtgg cacttaataa atattagtaa   2280
atccttaaaa aaaaaaaaaa aaaaaaaaaa aaaaaaa                            2317
```

<210> SEQ ID NO 72
<211> LENGTH: 3371
<212> TYPE: DNA
<213> ORGANISM: Homo sapiens

<400> SEQUENCE: 72

```
attgggagtc agctcctaag taagctccag aattcctgct ggtacttttc cttccaggaa     60
gcaacttcct tgatattttt tttttacagg catatgaata aaaactatat tttgcagcat    120
```

```
tgtacactttt ttttccttttt ctagaaattc taaacctctg acattggtgg agacattgag    180
tacatttttt cccatatccc tacttttcag aaggatttc tctgctcgtt cacttaacat      240
tgctgatgcg tcagtctttt cttcctcatc tctttcaggg gctggagagg cagagggaga    300
cagaggagct ggtactgcag agcggtcgtc tgattggctg gacggtcgta gctgggctat    360
aaaagagacc cctacaggct tagcaggaag acgctcagag gattctgaca atatctttac   420
cggagaagag gcaaagtacg ctcaaagccg aagccacagc tcctcctgcc gcatttcttt    480
cctgcttgcg aattccaagc tgttaaataa gatgtgcaaa gggcttgcag gtctgccggc    540
ttcttgcttg aggagtgcaa aagatatgaa acatcggcta ggtttcctgc tgcaaaaatc    600
tgattcctgt gaacacaatt cttcccacaa caagaaggac aaagtggtta tttgccagag    660
agtgagccaa gaggaagtca agaaatgggc tgaatcactg gaaaacctga ttagtcatga    720
atgtgggctg gcagctttca aagctttctt gaagtctgaa tatagtgagg agaatattga    780
cttctggatc agctgtgaag agtacaagaa aatcaaatca ccatctaaac taagtcccaa    840
ggccaaaaag atctataatg aattcatctc agtccaggca accaagagg tgaacctgga     900
ttcttgcacc agggaagaga caagccggaa catgctagag cctacaataa cctgctttga    960
tgaggcccag aagaagattt tcaacctgat ggagaaggat tcctaccgcc gcttcctcaa   1020
gtctcgattc tatcttgatt tggtcaaccc gtccagctgt ggggcagaaa agcagaaagg   1080
agccaagagt tcagcagact gtgcttccct ggtccctcag tgtgcctaat tctcacctga   1140
aggcagaggg atgaaatgcc aagactctat gctctggaaa acctgaggcc aaatattgat   1200
ctgtattaag ctccagtgct ttatccacat tgtagcctaa tattcatgct gcctgccatg   1260
tgtgagtcac ttctacgcat aaactagata tagcttttgg tgtttgagtg ttcatcaggg   1320
tgggacccca ttccagtcca atttcctaa gtttctttga gggttccatg ggagcaaata    1380
tctaaataat ggcctggtag gtctggattt tcaaagattg ttggcagttt cctcctccca   1440
acagttttac ctcgggatgg ttggttagtg catgtcacat gacatccaca tgcacatgta   1500
ttctgttggc cagcacgttc tccagactct agatgtttag atgaggttga gctatgatat   1560
gtgcttgtgt gtatgtctat gtgtatatat tatatataca ttagacacac atatacatta   1620
tttctgtata tagatgtctg tgtatacata tgtatgtgtg agtgtatgta tacacacaca   1680
cacacacaca cacacacact tttgcaagag tgatgggaaa gaccctaggt gctcataact   1740
agagtatgtg tatgtactta catgggtgtt ttgatctctg ttctttcata ctacatttga   1800
acagggcaaa atgaactaac tgccatgtag gctaagaaag aaatgctaac ctgtggaaag   1860
ttggttttgt aaaattccat ggatcttgct ggagaagcat ccaaggaact tcatgcttga   1920
tttgaccact gacagcctcc accttgagca ctattctaag gagcaaatac cttagctccc   1980
ttgagctggt tttctctgat ggcacttttg agctcctaag ctgccagcct tcccttcttt   2040
tcctgggtgc tcagggcatg cttattagca gctgggttgg tatggagttg cagacagga    2100
tgttcaactt aatgaagaaa tacagctaag gccttgccag caacacctgc cgtaagttac   2160
tggctgagtg agggcataga agttaaaggt tactgttttt atcctctatc cttttttcct   2220
ttcctgatca aggtgctctt ctcatttttt cctgagaacc ttagccatca gatgaggctc   2280
cttagtttat tgtggttggt tgttttttct ttataatggc tctgggctat atgcctatat   2340
ttataaacca gcagcagggg aaagattata tttataaga gggaacaaat tttcacaatt    2400
tgaaaagccc acataagttt tctcttttaa ggtagaatct tgttaatttc attccaaaca   2460
tcggggctaa cagagactgg aggcatttct ttttaggctc tgagactaaa tgagaggaaa   2520
```

```
agaaaagaaa aaaaaaatga ttgtctaacc aattgtgaga attactgttt gaaacttttc    2580
aaggcacatt gaaatacttg aaaacttctc atttatgtta tttatgatgt tattttgtac    2640
gtgttattat tattatattg ttttataaat ggaggtacag gatatcacct gaattattaa    2700
tgaatgccca ggaagtaatt ttcttctcat tcttctaaaa ctactgcctt tcaaagtgca    2760
cacacacgcg tccacataca ctgcattcgt tgctccagta taaattacat gcatgagcac    2820
ctttctggct tttaagccaa tataatgggc tgcaaaatga agacaccaga gtgtatgcat    2880
acaaatctca ctgtattaaa gatgcaggtt ttctaattgt acccttcttg tctctctggc    2940
aatcttgccc ttaatatccc tggagttcct catcagtgtc attttctgtt atacacagtt    3000
ccacaatttt gtctctagtt gacttcaaat gtgtaacttt attggtcttg ccctattata    3060
attgtcatga ctttcagatt gtatctgaac tcacagactg ctgtcttact aataggtctg    3120
gaaggtcacg ctgaatgaga agtaaattat tttatgtaat acattttga gtgtgttttt    3180 cagttgtatt tccctgttat ttcatcacta tttccaatgg tgagcttgcc tgctcatgct    3240
ccctggacag aatactcctt cctttttgcat gcctgtttct atcatgtgct tgataggcct    3300
caaagctaat gcttccagtg aaacacacgc atcttaataa taagggtaaa taaacgctcc    3360
atatgaaact a                                                          3371

<210> SEQ ID NO 73
<211> LENGTH: 2112
<212> TYPE: DNA
<213> ORGANISM: Homo sapiens

<400> SEQUENCE: 73
aaaacgggct cagttcgtaa aggagccggg tgacttcaga ggcgccggcc cgtccgtctg     60
ccgcacctga gcacggcccc tgcccgagcc tggcccgccg cgatgctgta gggaccgccg    120
tgtcctcccg ccggaccgtt atccgcgccg ggcgcccgcc agaccccgctg gcaagatgcc    180 gcgctccttc ctggtcaaga agcatttcaa cgcctccaaa aagccaaaact acagcgaact    240 ggacacacat acagtgatta tttccccgta tctctatgag agttactcca tgcctgtcat    300
accacaacca gagatcctca gctcaggagc atacagcccc atcactgtgt ggactaccgc    360
tgctccattc cacgcccagc tacccaatgg cctctctcct cttttccggat actcctcatc    420 tttggggcga gtgagtcccc ctcctccatc tgacacctcc tccaaggacc acagtggctc    480 agaaaagcccc attagtgatg aagaggaaag actacagtcc aagctttcag accccccatgc    540 cattgaagct gaaaagtttc agtgcaattt atgcaataag acctattcaa cttttttctgg    600 gctggccaaa cataagcagc tgcactgcga tgcccagtct agaaaatctt tcagctgtaa    660
atactgtgac aaggaatatg tgagcctggg cgccctgaag atgcatattc ggacccacac    720 attccttgt gtttgcaaga tctgcggcaa ggcgttttcc agaccctggt tgcttcaagg    780
acacattaga actcacacgg gggagaagcc ttttttcttgc cctcactgca acagagcatt    840
tgcagacagg tcaaatctga gggctcatct gcagacccat tctgatgtaa agaaatacca    900
gtgcaaaaac tgctccaaaa cctttctccag aatgtctctc ctgcacaaac atgaggaatc    960
tggctgctgt gtagcacact gagtgacgca atcaatgttt actcgaacag aatgcatttc   1020
ttcactccga agccaaatga caaataaagt ccaaaggcat tttctcctgt gctgaccaac   1080
caaataatat gtatagacac acacacatat gcacacacac acacacacac ccacagagag   1140
agagctgcaa gagcatggaa ttcatgtgtt taaagataat cctttccatg tgaagtttaa   1200
```

```
aattactata tatttgctga tggctagatt gagagaataa aagacagtaa ccttctctct    1260
caaagataaa atgaaaagca cattgcatct tttcttccta aaaaaatgca aagatttaca    1320
ttgctgccaa atcatttcaa ctgaaaagaa cagtattgct ttgtaataga gtctgtaata    1380
ggatttccca taggaagaga tctgccagac gcgaactcag gtgccttaaa aagtattcca    1440
agtttactcc attacatgtc ggttgtctgg ttgccattgt tgaactaaag ccttttttttg   1500 attacctgta gtgctttaaa gtatatttttt aaaagggagg aaaaaaataa caagaacaaa   1560
acacaggaga atgtattaaa agtattttg ttttgttttg ttttttgccaa ttaacagtat    1620 gtgccttggg ggaggaggga aagattagct ttgaacattc ctggcgcatg ctccattgtc    1680
ttactatttt aaaacatttt aataattttt gaaaattaat taaagatggg aataagtgca    1740
aaagaggatt cttacaaatt cattaatgta cttaaactat ttcaaatgca taccacaaat    1800
gcaataatac aatacccctt ccaagtgcct ttttaaattg tatagttgat gagtcaatgt    1860
aaatttgtgt ttattttttat atgattgaat gagttctgta tgaaactgag atgttgtcta   1920
tagctatgtc tataaacaac ctgaagactt gtgaaatcaa tgtttctttt ttaaaaaaca    1980
attttcaagt tttttttaca ataaacagtt ttgatttaaa atctcgtttg tatactatttt   2040 tcagagactt tacttgcttc atgattagta ccaaaccact gtacaaagaa ttgtttgtta    2100
acaagaaaaa aa                                                       2112

<210> SEQ ID NO 74
<211> LENGTH: 665
<212> TYPE: DNA
<213> ORGANISM: Homo sapiens

<400> SEQUENCE: 74
gggagacggt tgagagcaca caagccgctt taggagcgag gttcggagcc atcgctgctg      60
cctgctgatc cgcgcctaga gtttgaccag ccactctcca gctcggcttt cgcggcgccg     120
agatgctgtc ctgccgcctc cagtgcgcgc tggctgcgct gtccatcgtc ctggccctgg     180
gctgtgtcac cggcgctccc tcggacccca gactccgtca gtttctgcag aagtccctgg     240
ctgctgccgc ggggaagcag gaactggcca agtacttctt ggcagagctg ctgtctgaac     300
ccaaccagac ggagaatgat gccctggaac ctgaagatct gtcccaggct gctgagcagg     360
atgaaatgag gcttgagctg cagagatctg ctaactcaaa cccggctatg gcaccccgag     420
aacgcaaagc tggctgcaag aatttcttct ggaagacttt cacatcctgt tagctttctt     480
aactagtatt gtccatatca gacctctgat ccctcgcccc cacaccccat ctctcttccc     540
taatcctcca gtcttcagc gagacccttg cattagaaac tgaaaactgt aaatacaaaa      600
taaaattatg gtgaaattat gaaaatgtg aaaaaaaaaa aaaaaaaaa aaaaaaaaaa       660 aaaaa                                                                665

<210> SEQ ID NO 75
<211> LENGTH: 4814
<212> TYPE: DNA
<213> ORGANISM: Homo sapiens

<400> SEQUENCE: 75
gaattctaga ggcggcggag ggtggcgagg agctctcgct ttctctcgct ccctcccctct     60 ccgactccgt ctctctctct ctctctctct ctccctccc tctctttccc tctgttccat     120
tttttccccc tctaaatcct ccctgccctg cgcgcctgga cacagattta ggaagcgaat     180
tcgctcacgt tttaggacaa ggaagagaga gaggcacggg agaagagccc agcaagattt     240
```

```
ggattgaaac cgagacaccc tccggaggct cggagcagag gaaggaggag gagggcggcg    300
aacggaagcc agtttgcaat tcaagttttg atagcgctgg tagaaggggg tttaaatcag    360
attttttttt ttttaaagga gagagacttt ttccgctctc tcgctccctg ttaaagccgg    420
gtctagcaca gctgcagacg ccaccagcga gaaagaggga gaggaagaca gatagggggc    480
gggggaagaa gaaaaagaaa ggtaaaaagt cttctaggag aacctttcac atttgcaaca    540
aaagacctag gggctggaga gagattcctg ggacgcaggg ctggagtgtc tatttcgagc    600
tcagcggcag ggctcgggcg cgagtcgaga ccctgctcgc tcctctcgct tctgaaaccg    660
acgttcagga gcggcttttt aaaaacgcaa ggcacaagga cggtcacccg cgcgactatg    720
tttgctgatt tttcgccttg ccctctttaa aagcggcctc ccattctcca aaagacactt    780
cccctcctcc ctttgaagtg cattagttgt gatttctgcc tccttttctt ttttcttttct    840 tttttgtttt gcttttccc ccctttgaa ttatgtgctg ctgttaaaca acaacaaaaa    900
aacaacaaaa cacagcagct gcggacttgt cccggctgg agcccagcgc ccgcctgga    960 gtggatgagc ctctccatga gagatccggt cattcctggg acaagcatgg cctaccatcc    1020
gttcctacct caccgggcgc cggacttcgc catgagcgcg gtgctgggtc accagccgcc    1080
gttcttcccc gcgctgacgc tgcctcccaa cggcgcggcg gcgctctcgc tgccgggcgc    1140
cctggccaag ccgatcatgg atcaattggt ggggggcggcc gagaccggca tcccgttctc    1200
ctccctgggg ccccaggcgc atctgaggcc tttgaagacc atggagcccg aagaagaggt    1260
ggaggacgac cccaaggtgc acctggaggc taaagaactt tgggatcagt ttcacaagcg    1320
gggcaccgag atggtcatta ccaagtcggg aaggcgaatg tttcctccat ttaaagtgag    1380
atgttctggg ctggataaaa aagccaaata cattttattg atggacatta tagctgctga    1440
tgactgtcgt tataaatttc acaattctcg gtggatggtg gctggtaagg ccgaccccga    1500
aatgccaaag aggatgtaca ttcacccgga cagccccgct actggggaac agtggatgtc    1560
caaagtcgtc actttccaca aactgaaact caccaacaac atttcagaca aacatggatt    1620
tactttggcc ttcccaagtg atcacgctac gtggcagggg aattatagtt ttggtactca    1680
gactatattg aactccatgc acaaatacca gccccggttc cacattgtaa gagccaatga    1740
catcttgaaa ctcccttata gtacatttcg gacatacttg ttccccgaaa ctgaattcat    1800
cgctgtgact gcataccaga atgataagat aacccagtta aaaatagaca acaaccctt    1860 tgcaaaaggt ttccgggaca ctggaaatgg ccgaagagaa aaaagaaaac agctcaccct    1920
gcagtccatg agggtgtttg atgaaagaca caaaaaggaa aatgggacct ctgatgagtc    1980
ctccagtgaa caagcagctt tcaactgctt cgcccaggct tcttctccag ccgcctccac    2040
tgtagggaca tcgaacctca agatttatg tcccagcgag ggtgagagcg acgccgaggc    2100
cgagagcaaa gaggagcatg gccccgaggc ctgcgacgcg gccaagatct ccaccaccac    2160
gtcggaggag ccctgccgtg acaagggcag ccccgcggtc aaggctcacc ttttcgctgc    2220
tgagcggccc cgggacagcg gcggctgga caaagcgtcg cccgactcac gccatagccc    2280
cgccaccatc tcgtccagca ctcgcggcct gggcgcggag gagcgcagga gcccggttcg    2340
cgagggcaca gcgccggcca aggtggaaga ggcgcgcgcg ctcccgggca aggaggcctt    2400
cgcgccgctc acggtgcaga cggacgcggc cgccgcgcac ctggcccagg gccccctgcc    2460
tggcctcggc ttcgccccgg gcctggcggg ccaacagttc ttcaacggc acccgctctt    2520 cctgcacccc agccagtttg ccatgggggg cgccttctcc agcatggcgg ccgctggcat    2580
```

```
gggtcccctc ctggccacgg tttctggggc ctccaccggt gtctcgggcc tggattccac    2640
ggccatggcc tctgccgctg cggcgcaggg actgtccggg gcgtccgcgg ccaccctgcc    2700
cttccacctc cagcagcacg tcctggcctc tcagggcctg gccatgtccc ctttcggaag    2760
cctgttccct taccCctaca cgtacatggc cgcagcggcg gccgcctcct ctgcggcagc    2820
ctccagctcg gtgcaccgcc acccCttcct caatctgaac accatgcgcc cgcggctgcg    2880
ctacagcccc tactccatcc cggtgccggt cccggacggc agcagtctgc tcaccaccgc    2940
cctgccctcc atggcggcgg ccgcggggcc cctggacggc aaagtcgccg ccctggccgc    3000
cagcccggcc tcggtggcag tggactcggg ctctgaactc aacagccgct cctccacgct    3060
ctcctccagc tccatgtcct tgtcgcccaa actctgcgcg gagaaagagg cggccaccag    3120
cgaactgcag agcatccagc ggttggttag cggcttggaa gccaagccgg acaggtcccg    3180
cagcgcgtcc ccgtagaccc gtcccagaca cgtcttttca ttccagtcca gttcaggctg    3240
ccgtgcactt tgtcggatat aaaataaacc acgggcccgc catggcgtta gcccttcctt    3300
ttgcagttgc gtctgggaag gggccccgga ctccctcgag agaatgtgct agagacagcc    3360
cctgtcttct tggcgtggtt tatatgtccg ggatctggat cagattctgg gggctcagaa    3420
acgtcggttg cattgagcta ctgggggtag gagttccaac atttatgtcc agagcaactt    3480
ccagcaaggc tggtctgggt ctctgcccac caggcgggga ggtgttcaaa gacatctccc    3540
tcagtgcgga tttatatata tattttttcct tcactgtgtc aagtggaaac aaaaacaaaa    3600
tctttcaaaa aaaaaatcgg gacaagtgaa cacattaaca tgattctgtt tgtgcagatt    3660
aaaaacttta tagggacttg cattatcggt tctcaataaa ttactgagca gctttgtttg    3720
gggagggaag tccctaccat ccttgtttag tctatattaa gaaaatctgt gtctttttaa    3780
tattcttgtg atgttttcag agccgctgta ggtctcttct tgcatgtcca cagtaatgta    3840
tttgtggttt ttattttgaa cgcttgcttt tagagagaaa acaatatagc cccctaccct    3900
tttcccaatc ctttgccctc aaatcagtga cccaagggag gggggggattt aaagggaagg    3960 agtgggcaaa acacataaaa tgaatttatt atatctaagc tctgtagcag gattcatgtc    4020
gttctttgac agttctttct cttttcctgta tatgcaataa caaggttta aaaaaataat    4080 aaagaagtga gactattaga caaagtattt atgtaattat ttgataactc ttgtaaatag    4140
gtggaatatg aatgcttgga aaattaaact ttaatttatt gacattgtac atagctctgt    4200
gtaaatagaa ttgcaactgt caggttttgt gttcttgttt tcctttagtt gggtttattt    4260
ccaggtcaca gaattgctgt taacactaga aaacacactt cctgcaccaa caccaatacc    4320 cttttcaaaag agttgtctgc aacatttttg ttttcttttt taatgtccaa aagtggggga    4380
aagtgctatt tcctattttc accaaaattg gggaaggagt gccactttcc agctccactt    4440
caaattcctt aaaatataac tgagattgct gtggggaggg aggagggcag aggctgcggt    4500 ttgactttt aattttttctt ttgttatttg tatttgctag tctctgattt cctcaaaacg    4560
aagtggaatt tactactgtt gtcagtatcg gtgttttgaa ttggtgcctg cctatagaga    4620
tatattcaca gttcaaaagt caggtgctga gagatggttt aaagacaaat tcatgaaggt    4680 atatttgtg ttatagttgt tgatgagttc tttggttttc tgtatttttc cccctctctt    4740
taaaacatca ctgaaatttc aataaatttt tattgaaatg tctaaaaaaa aaaaaaaaaa    4800
aaaaaaaaaa aaaa                                                      4814

<210> SEQ ID NO 76
<211> LENGTH: 1712
```

<212> TYPE: DNA
<213> ORGANISM: Homo sapiens

<400> SEQUENCE: 76

```
aagggcggga cattcccct gcctcttcgc accacagcca gagcctgcca ttaggaccaa      60
tgaaagcaaa gtacctcatc ccctcagtga ctaagaatcg cagtatttaa gaggtagcag    120
gaatgggctg agagtggtgt ttgctttctc caccagaagg gcacactttc atctaatttg    180
gggtatcact gagctgaaga caaagagaag ggggagaaaa cctagcagac caccatgtgc    240
tatgggaagt gtgcacgatg catcggacat tctctggtgg ggctcgccct cctgtgcatc    300
gcggctaata ttttgcttta cttcccaat gggaaacaa agtatgcctc cgaaaaccac     360
ctcagccgct tcgtgtggtt cttttctggc atcgtaggag gtggcctgct gatgctcctg    420
ccagcatttg tcttcattgg gctggaacag gatgactgct gtggctgctg tggccatgaa    480
aactgtggca acgatgtgc gatgctttct tctgtattgg ctgctctcat tggaattgca    540
ggatctggct actgtgtcat gtggcagcc cttggcttag cagaaggacc actatgtctt    600
gattccctcg gccagtggaa ctacaccttt gccagcactg agggccagta ccttctggat    660
acctccacat ggtccgagtg cactgaaccc aagcacattg tggaatggaa tgtatctctg    720
ttttctatcc tcttggctct tggtggaatt gaattcatct tgtgtcttat tcaagtaata    780
aatggagtgc ttgaaggcat atgtggcttt tgctgctctc accaacagca atatgactgc    840
taaaagaacc aacccaggac agagccacaa tcttcctcta tttcattgta atttatatat    900
ttcacttgta ttcatttgta aaactttgta ttagtgtaac atactcccca cagtctactt    960
ttacaaacgc ctgtaaagac tggcatcttc acaggatgtc agtgtttaaa tttagtaaac   1020
ttctttttg tttgtttatt tgttttgtt tttttttaag gaatgaggaa acaaaccacc    1080
ctctggggt aatttacaga ctgagtgaca gtactcagta tatctgagat aaactctata   1140
atgttttgga taaaataac attccaatca ctattgtata tatgtgcatg tatttttaa    1200
attaaagatg tctagttgct ttttataaga ccaagaagga gaaaatccga caacctggaa   1260
agattttgt tttcactgct tgtatgatgt ttcccattca tacacctata aatctctaac   1320
aagaggccct ttgaactgcc ttgtgttctg tgagaaacaa atatttactt agagtggaag   1380
gactgattga gaatgttcca atccaaatga atgcatcaca acttacaatg ctgctcattg   1440
ttgtgagtac tatgagattc aaattttct aacatatgga aagccttttg tcctccaaag   1500
atgagtacta gggatcatgt gtttaaaaaa agaaaggcta cgatgactgg gcaagaagaa   1560
agatgggaaa ctgaataaag cagttgatca gcatcattgg aacatgggga cgagtgacgg   1620
caggaggacc acgaggaaat accctcaaaa ctaacttgtt tacaacaaaa taaagtattc   1680
actaccatgt taaaaaaaaa aaaaaaaaa aa                                  1712
```

<210> SEQ ID NO 77
<211> LENGTH: 5748
<212> TYPE: DNA
<213> ORGANISM: Homo sapiens

<400> SEQUENCE: 77

```
gagaagaaag ccagtgcgtc tctgggcgca ggggccagtg gggctcggag gcacaggcac     60
cccgcgacac tccaggttcc ccgacccacg tccctggcag ccccgattat ttacagcctc    120
agcagagcac ggggcggggg cagaggggcc cgcccgggag ggctgctact tcttaaaacc    180
tctgcgggct gcttagtcac agccccctt gcttgggtgt gtccttcgct cgctccctcc    240
```

```
ctccgtctta ggtcactgtt ttcaacctcg aataaaaact gcagccaact tccgaggcag      300
cctcattgcc cagcggaccc cagcctctgc caggttcggt ccgccatcct cgtcccgtcc      360
tccgccggcc cctgccccgc gcccagggat cctccagctc ctttcgcccg cgccctccgt      420
tcgctccgga caccatggac aagtttggt ggcacgcagc ctgggactc tgcctcgtgc        480 cgctgagcct ggcgcagatc gatttgaata taacctgccg ctttgcaggt gtattccacg      540
tggagaaaaa tggtcgctac agcatctctc ggacggaggc cgctgacctc tgcaaggctt      600
tcaatagcac cttgcccaca atggcccaga tggagaaagc tctgagcatc ggatttgaga      660
cctgcaggta tgggttcata gaagggcacg tggtgattcc ccggatccac cccaactcca      720
tctgtgcagc aaacaacaca ggggtgtaca tcctcacatc aacacctcc cagtatgaca       780 catattgctt caatgcttca gctccacctg aagaagattg tacatcagtc acagacctgc      840
ccaatgcctt tgatggacca attaccataa ctattgttaa ccgtgatggc acccgctatg     900
tccagaaagg agaatacaga acgaatcctg aagacatcta ccccagcaac cctactgatg      960
atgacgtgag cagcggctcc tccagtgaaa ggagcagcac ttcaggaggt tacatctttt      1020 acacctttc tactgtacac cccatcccag acgaagacag tccctggatc accgacagca      1080
cagacagaat ccctgctacc actttgatga gcactagtgc tacagcaact gagacagcaa      1140
ccaagaggca agaaacctgg gattggtttt catggttgtt tctaccatca gagtcaaaga      1200
atcatcttca cacaacaaca caaatggctg gtacgtcttc aaataccatc tcagcaggct      1260
gggagccaaa tgaagaaaat gaagatgaaa gagacagaca cctcagtttt tctggatcag      1320
gcattgatga tgatgaagat tttatctcca gcaccatttc aaccacacca cgggcttttg      1380
accacacaaa acagaaccag gactggaccc agtggaaccc aagccattca aatccggaag      1440
tgctacttca gacaaccaca aggatgactg atgtagacag aaatggcacc actgcttatg      1500
aaggaaactg gaacccagaa gcacaccctc ccctcattca ccatgagcat catgaggaag      1560
aagagacccc acattctaca agcacaatcc aggcaactcc tagtagtaca acggaagaaa      1620
cagctaccca gaaggaacag tggtttggca acagatggca tgagggatat cgccaaacac      1680
ccaaagaaga ctcccattcg acaacaggga cagctgcagc ctcagctcat accagccatc      1740
caatgcaagg aaggacaaca ccaagcccag aggacagttc ctggactgat ttcttcaacc      1800
caatctcaca ccccatggga cgaggtcatc aagcaggaag aaggatggat atggactcca      1860
gtcatagtat aacgcttcag cctactgcaa atccaaacac aggtttggtg aagatttgg      1920 acaggacagg acctctttca atgacaacgc agcagagtaa ttctcagagc ttctctacat      1980
cacatgaagg cttggaagaa gataaagacc atccaacaac ttctactctg acatcaagca      2040
ataggaatga tgtcacaggt ggaagaagag acccaaatca ttctgaaggc tcaactactt      2100
tactggaagg ttatacctct cattacccac acacgaagga aagcaggacc ttcatcccag      2160
tgacctcagc taagactggg tccttttgag ttactgcagt tactgttgga gattccaact      2220
ctaatgtcaa tcgttcctta tcaggagacc aagacacatt ccaccccagt gggggtccc       2280 ataccactca tggatctgaa tcagatggac actcacatgg gagtcaagaa ggtggagcaa      2340
acacaacctc tggtccctata aggacacccc aaattccaga atggctgatc atcttggcat     2400
ccctcttggc cttggctttg attcttgcag tttgcattgc agtcaacagt cgaagaaggt      2460
gtgggcagaa gaaaaagcta gtgatcaaca gtggcaatgg agctgtggag acagaaagc     2520 caagtggact caacgagag gccagcaagt ctcaggaaat ggtgcatttg gtgaacaagg      2580
agtcgtcaga aactccagac cagtttatga cagctgatga gacaaggaac ctgcagaatg      2640
```

```
tggacatgaa gattggggtg taacacctac accattatct tggaaagaaa caaccgttgg    2700
aaacataacc attacaggga gctgggacac ttaacagatg caatgtgcta ctgattgttt    2760
cattgcgaat cttttttagc ataaaatttt ctactcttttt tgttttttgt gttttgttct    2820
ttaaagtcag gtccaatttg taaaaacagc attgctttct gaaattaggg cccaattaat    2880
aatcagcaag aatttgatcg ttccagttcc cacttggagg cctttcatcc ctcgggtgtg    2940
ctatggatgg cttctaacaa aaactacaca tatgtattcc tgatcgccaa cctttccccc    3000
accagctaag gacatttccc agggttaata gggcctggtc cctgggagga aatttgaatg    3060
ggtccatttt gccctccat agcctaatcc ctgggcattg cttccactg aggttggggg     3120 ttggggtgta ctagttacac atcttcaaca gacccctct agaaattttt cagatgcttc     3180
tgggagacac ccaaagggtg aagctattta tctgtagtaa actatttatc tgtgtttttg    3240
aaatattaaa ccctggatca gtcctttgat cagtataatt ttttaaagtt actttgtcag    3300
aggcacaaaa gggtttaaac tgattcataa taaatatctg tacttcttcg atcttcacct    3360
tttgtgctgt gattcttcag tttctaaacc agcactgtct gggtccctac aatgtatcag    3420
gaagagctga gaatggtaag gagactcttc taagtcttca tctcagagac cctgagttcc    3480
cactcagacc cactcagcca aatctcatgg aagaccaagg agggcagcac tgttttttgtt   3540 ttttgttttt tgttttttt ttttgacact gtccaaaggt tttccatcct gtcctggaat     3600
cagagttgga agctgaggag cttcagcctc ttttatggtt taatggccac ctgttctctc    3660
ctgtgaaagg ctttgcaaag tcacattaag tttgcatgac ctgttatccc tggggcccta   3720
tttcatagag gctggcccta ttagtgattt ccaaaaacaa tatggaagtg ccttttgatg    3780
tcttacaata agagaagaag ccaatggaaa tgaaagagat tggcaaaggg gaaggatgat    3840
gccatgtaga tcctgtttga catttttatg gctgtatttg taaacttaaa cacaccagtg    3900
tctgttcttg atgcagttgc tatttaggat gagttaagtg cctggggagt ccctcaaaag    3960
gttaaaggga ttcccatcat tggaatctta tcaccagata ggcaagttta tgaccaaaca    4020
agagagtact ggcttatcc tctaacctca tattttctcc cacttggcaa gtcctttgtg     4080
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
ctcctccctg tctaccctct cccctccctc tctccctcca cttcacccca caatcttgaa    4440
aaacttcctt tctcttctgt gaacatcatt ggccagatcc attttcagtg gtctggatttt   4500 ctttttatttt tcttttcaac ttgaaagaaa ctggacatta ggccactatg tgttgttact    4560
gccactagtt ttcaagtgcc tcttgttttc ccagagatttt cctgggtctg ccagaggccc   4620
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaaagaggc tgagacagga    4800
ggttattttc aatttttattt tggaattaaa tacttttttc cctttattac tgttgtagtc    4860
cctcacttgg atatacctct gttttcacga tagaaataag ggaggtctag agcttctatt    4920
ccttggccat tgtcaacgga gagctggcca agtcttcaca aacccttgca acattgcctg    4980
```

| | |
|---|---|
| aagtttatgg aataagatgt attctcactc ccttgatctc aagggcgtaa ctctggaagc | 5040 |
| acagcttgac tacacgtcat ttttaccaat gattttcagg tgacctgggc taagtcattt | 5100 |
| aaactgggtc tttataaaag taaaaggcca acatttaatt attttgcaaa gcaacctaag | 5160 |
| agctaaagat gtaattttc ttgcaattgt aaatcttttg tgtctcctga agacttccct | 5220 |
| taaaattagc tctgagtgaa aaatcaaaag agacaaaaga catcttcgaa tccatatttc | 5280 |
| aagcctggta gaattggctt ttctagcaga acctttccaa aagttttata ttgagattca | 5340 |
| taacaacacc aagaattgat tttgtagcca acattcattc aatactgtta tatcagagga | 5400 |
| gtaggagaga ggaaacattt gacttatctg gaaaagcaaa atgtacttaa gaataagaat | 5460 |
| aacatggtcc attcaccttt atgttataga tatgtctttg tgtaaatcat ttgttttgag | 5520 |
| ttttcaaaga atagcccatt gttcattctt gtgctgtaca atgaccactg ttattgttac | 5580 |
| tttgactttt cagagcacac ccttcctctg gttttttgtat atttattgat ggatcaataa | 5640 |
| taatgaggaa agcatgatat gtatattgct gagttgaaag cacttattgg aaaatattaa | 5700 |
| aaggctaaca ttaaaagact aaaggaaaca gaaaaaaaaa aaaaaaaa | 5748 |

<210> SEQ ID NO 78
<211> LENGTH: 4293
<212> TYPE: DNA
<213> ORGANISM: Homo sapiens

<400> SEQUENCE: 78

| | |
|---|---|
| acccactccc gctgccccgt ccggcccgcg ccgcttcctc gcagcagctg ctcccggctc | 60 |
| cgcggccgca gcccgcgtgg acgctccgag cgccccccga cggacgggac cggctccctg | 120 |
| gcggtcgggc gagcgggcgg caacgctgcc cggccggcag cgctgggggtt aagtggccca | 180 |
| agtaaaccta gctcggcgat cggcgccgga gattcgcgag cccagcgccc tgcacggccg | 240 |
| ccagccggcc tcccgccagc cagccccgac ccgcggctcc gccgcccagc cgcgccccag | 300 |
| ccagccctgc ggcaggaaag catgaaggga gacaccaggc atctcaatgg agaggaggac | 360 |
| gccggcggga gggaagactc gatcctcgtc aacggggcct gcagcgacca gtcctccgac | 420 |
| tcgcccccaa tcctggaggc tatccgcacc ccggagatca gaggccgaag atcaagctcg | 480 |
| cgactctcca gagggaggt gtccagtctg ctaagctaca cacaggactt gacaggcgat | 540 |
| ggcgacgggg aagatgggga tggctctgac acccccagtca tgccaaagct cttccgggaa | 600 |
| accaggactc gttcagaaag cccagctgtc cgaactcgaa ataacaacag tgtctccagc | 660 |
| cgggagaggc acaggccttc cccacgttcc acccgaggcc ggcagggccg caaccatgtg | 720 |
| gacgagtccc ccgtggagtt cccggctacc aggtccctga cggcgggc aacagcatcg | 780 |
| gcaggaacgc catggccgtc ccctcccagc tcttaccta ccatcgacct cacagacgac | 840 |
| acagaggaca cacatgggac gccccagagc agcagtaccc cctacgcccg cctagcccag | 900 |
| gacagccagc agggggggcat ggagtccccg caggtggagg cagacagtgg agatggagac | 960 |
| agttcagagt atcaggatgg gaaggagttt ggaataggg acctcgtgtg gggaaagatc | 1020 |
| aagggcttct cctggtggcc cgccatggtg gtgtcttgga aggccacctc caagcgacag | 1080 |
| gctatgtctg gcatgcggtg ggtccagtgg ttggcgatg gcaagttctc cgaggtctct | 1140 |
| gcagacaaac tggtggcact ggggctgttc agccagcact ttaatttggc caccttcaat | 1200 |
| aagctcgtct cctatcgaaa agccatgtac catgctctgg agaaagctag ggtgcgagct | 1260 |
| ggcaagacct tccccagcag ccctggagac tcattggagg accagctgaa gcccatgttg | 1320 |
| gagtgggccc acggggggctt caagcccact gggatcgagg gcctcaaacc caacaacacg | 1380 |

```
caaccagaga acaagactcg aagacgcaca gctgacgact cagccacctc tgactactgc    1440
cccgcaccca agcgcctcaa gacaaattgc tataacaacg gcaaagaccg aggggatgaa    1500
gatcagagcc gagaacaaat ggcttcagat gttgccaaca acaagagcag cctggaagat    1560
ggctgtttgt cttgtggcag gaaaaacccc gtgtccttcc accctctctt tgagggggg    1620 ctctgtcaga catgccggga tcgcttcctt gagctgtttt acatgtatga tgacgatggc    1680
tatcagtctt actgcactgt gtgctgcgag ggccgagagc tgctgctttg cagcaacacg    1740
agctgctgcc ggtgtttctg tgtggagtgc ctggaggtgc tggtgggcac aggcacagcg    1800
gccgaggcca agcttcagga gccctggagc tgttacatgt gtctcccgca gcgctgtcat    1860
ggcgtcctgc ggcgccggaa ggactggaac gtgcgcctgc aggccttctt caccagtgac    1920
acggggcttg aatatgaagc ccccaagctg taccctgcca ttcccgcagc ccgaaggcgg    1980
cccattcgag tcctgtcatt gtttgatggc atcgcgacag gctacctagt cctcaaagag    2040
ttgggcataa aggtaggaaa gtacgtcgct tctgaagtgt gtgaggagtc cattgctgtt    2100
ggaaccgtga agcacgaggg gaatatcaaa tacgtgaacg acgtgaggaa catcacaaag    2160
aaaaatattg aagaatgggg cccatttgac ttggtgattg gcggaagccc atgcaacgat    2220
ctctcaaatg tgaatccagc caggaaaggc ctgtatgagg gtacaggccg gctcttcttc    2280
gaattttacc acctgctgaa ttactcacgc cccaaggagg gtgatgaccg gccgttcttc    2340
tggatgtttg agaatgttgt agccatgaag gttggcgaca gagggacat ctcacggttc    2400 ctggagtgta atccagtgat gattgatgcc atcaaagttt ctgctgctca cagggcccga    2460
tacttctggg gcaacctacc cgggatgaac aggcccgtga tagcatcaaa gaatgataaa    2520
ctcgagctgc aggactgctt ggaatacaat aggatagcca agttaaagaa agtacagaca    2580
ataaccacca agtcgaactc gatcaaacag gggaaaaacc aacttttccc tgttgtcatg    2640
aatggcaaag aagatgtttt gtggtgcact gagctcgaaa ggatcttgg ctttcctgtg    2700 cactacacag acgtgtccaa catgggccgt ggtgcccgcc agaagctgct gggaaggtcc    2760
tggagcgtgc ctgtcatccg acacctcttc gcccctctga aggactactt tgcatgtgaa    2820
tagttccagc caggccccaa gcccactggg gtgtgtggca gagccaggac ccaggaggtg    2880
tgattcctga aggcatcccc aggccctgct cttcctcagc tgtgtgggtc ataccgtgta    2940
cctcagttcc ctcttgctca gtgggggcag agccacctga ctcttgcagg ggtagcctga    3000
ggtgccgcct ccttgtgcac aaatcagacc tggctgcttg gagcagccta acacggtgct    3060
cattttttct tctcctaaaa cttaaaact tgaagtaggg agcaacgtgg cttttttttt    3120
ttcccttcct gggtctacca ctcagagaaa caatggctaa gataccaaaa ccacagtgcc    3180
gacagctctc caatactcag gttaatgctg aaaaatcatc caagacagtt attgcaagag    3240
tttaattttt gaaaactggc tactgctctg tgtttacaga cgtgtgcagt tgtaggcatg    3300
tagctacagg acatttttaa gggcccagga tcgttttttc ccaggcaag cagaagagaa    3360 aatgttgtat atgtctttta cccggcacat tccccttgcc taaatacaag ggctggagtc    3420
tgcacgggac ctattagagt atttccaca atgatgatga tttcagcagg gatgacgtca    3480
tcatcacatt cagggctatt ttttcccca caaacccaag ggcaggggcc actcttagct    3540
aaatccctcc ccgtgactgc aatagaaccc tctggggagc tcaggaaggg gtgtgctgag    3600
ttctataata taagctgcca tatattttgt agacaagtat ggctcctcca tatctccctc    3660
ttccctagga gaggagtgtg aagcaaggag cttagataag acacccctc aaacccattc    3720
```

```
cctctccagg agacctaccc tccacaggca caggtcccca gatgagaagt ctgctaccct    3780
catttctcat cttttttacta aactcagagg cagtgacagc agtcagggac agacatacat    3840
ttctcatacc ttccccacat ctgagagatg acagggaaaa ctgcaaagct cggtgctccc    3900
tttggagatt ttttaatcct tttttattcc ataagaagtc gttttttaggg agaacgggaa    3960 ttcagacaag ctgcatttca gaaatgctgt cataatggtt tttaacacct tttactcttc    4020
ttactggtgc tattttgtag aataaggaac aacgttgaca agttttgtgg ggcttttttat    4080 acacttttta aaatctcaaa cttctatttt tatgtttaac gttttcatta aaatttttt    4140 tgtaactgga gccacgacgt aacaaatatg gggaaaaaac tgtgccttgt ttcaacagtt    4200
tttgctaatt tttaggctga aagatgacgg atgcctagag tttaccttat gtttaattaa    4260
aatcagtatt tgtctaaaaa aaaaaaaaaa aaa                                  4293
```

<210> SEQ ID NO 79
<211> LENGTH: 8761
<212> TYPE: DNA
<213> ORGANISM: Homo sapiens

<400> SEQUENCE: 79

```
gccgaggagg aagaggttga tggcggcggc ggagctccga gagacctcgg ctgggcaggg      60
gccggccgtg gcgggccggg gactgcgcct ctagagccgc gagttctcgg gaattcgccg     120
cagcggacgc gctcggcgaa tttgtgctct tgtgccctcc tccgggcttg ggcccaggcc     180
cggcccctcg cacttgccct taccttttct atcgagtccg catccctctc cagccactgc     240
gacccggcga agagaaaaag gaacttcccc caccccctcg ggtgccgtcg gagccccca      300 gcccaccct gggtgcggcg cggggacccc gggccgaaga agagatttcc tgaggattct     360
ggttttcctc gcttgtatct ccgaaagaat taaaaatggc cgagaatgtg gtggaaccgg     420
ggccgccttc agccaagcgg cctaaactct catctccggc cctctcggcg tccgccagcg     480
atggcacaga tttttgctct ctatttgact tggagcacga cttaccagat gaattaatca     540
actctacaga attgggacta accaatggtg gtgatattaa tcagcttcag acaagtcttg     600
gcatggtaca agatgcagct tctaaacata aacagctgtc agaattgctg cgatctggta     660
gttcccctaa cctcaatatg ggagttggtg gcccaggtca agtcatggcc agccaggccc     720
aacagagcag tcctggatta ggtttgataa atagcatggt caaaagccca atgcacagg     780 caggcttgac ttctcccaac atggggatgg gcactagtgg accaaatcag ggtcctacgc     840
agtcaacagg tatgatgaac agtccagtaa atcagcctgc catgggaatg aacacaggga     900
tgaatgcggg catgaatcct ggaatgttgg ctgcaggcaa tggacaaggg ataatgccta     960
atcaagtcat gaacggttca attggagcag gccgagggcg acagaatatg cagtacccaa    1020
acccaggcat gggaagtgct ggcaacttac tgactgagcc tcttcagcag ggctctcccc    1080
agatgggagg acaaacagga ttgagaggcc cccagcctct taagatggga atgatgaaca    1140
accccaatcc ttatggttca ccatatactc agaatcctgg acagcagatt ggagccagtg    1200
gccttggtct ccagattcag acaaaaactg tactatcaaa taacttatct ccatttgcta    1260
tggacaaaaa ggcagttcct ggtggaggaa tgcccaacat gggtcaacag ccagcccgc    1320 aggtccagca gccaggcctg gtgactccag ttgcccaagg gatgggttct ggagcacata    1380
cagctgatcc agagaagcgc aagctcatcc agcagcagct tgttctcctt ttgcatgctc    1440
acaagtgcca gcgccgggaa caggccaatg gggaagtgag gcagtgcaac cttccccact    1500
gtcgcacaat gaagaatgtc ctaaaccaca tgacacactg ccagtcaggc aagtcttgcc    1560
```

```
aagtggcaca ctgtgcatct tctcgacaaa tcatttcaca ctggaagaat tgtacaagac   1620
atgattgtcc tgtgtgtctc cccctcaaaa atgctggtga taagagaaat caacagccaa   1680
ttttgactgg agcacccgtt ggacttggaa atcctagctc tctaggggtg ggtcaacagt   1740
ctgcccccaa cctaagcact gttagtcaga ttgatcccag ctccatagaa agagcctatg   1800
cagctcttgg actaccctat caagtaaatc agatgccgac acaacccag gtgcaagcaa    1860 agaaccagca gaatcagcag cctgggcagt ctccccaagg catgcggccc atgagcaaca   1920
tgagtgctag tcctatggga gtaaatggag gtgtaggagt tcaaacgccg agtcttcttt   1980
ctgactcaat gttgcattca gccataaatt ctcaaaaccc aatgatgagt gaaaatgcca   2040
gtgtgccctc cctgggtcct atgccaacag cagctcaacc atccactact ggaattcgga   2100
aacagtggca cgaagatatt actcaggatc ttcgaaatca tcttgttcac aaactcgtcc   2160
aagccatatt tcctacgccg gatcctgctg ctttaaaaga cagacggatg gaaaacctag   2220
ttgcatatgc tcggaaagtt gaaggggaca tgtatgaatc tgcaaacaat cgagcggaat   2280
actaccacct tctagctgag aaaatctata agatccagaa agaactagaa gaaaaacgaa   2340
ggaccagact acagaagcag aacatgctac caaatgctgc aggcatggtt ccagtttcca   2400
tgaatccagg gcctaacatg ggacagccgc aaccaggaat gacttctaat ggccctctac   2460
ctgacccaag tatgatccgt ggcagtgtgc caaaccagat gatgcctcga ataactccac   2520
aatctggttt gaatcaattt ggccagatga gcatggccca gccccctatt gtaccccggc   2580
aaacccctcc tcttcagcac catggacagt tggctcaacc tggagctctc aacccgccta   2640
tgggctatgg gcctcgtatg caacagcctt ccaaccaggg ccagttcctt cctcagactc   2700
agttcccatc acagggaatg aatgtaacaa atatcccttt ggctccgtcc agcggtcaag   2760
ctccagtgtc tcaagcacaa atgtctagtt cttcctgccc ggtgaactct cctataatgc   2820
ctccagggtc tcaggggagc cacattcact gtccccagct tcctcaacca gctcttcatc   2880
agaattcacc ctcgcctgta cctagtcgta cccccacccc tcaccatact cccccaagca   2940
taggggctca gcagccacca gcaacaacaa ttccagcccc tgttcctaca cctcctgcca   3000
tgccacctgg gccacagtcc caggctctac atccccctcc aaggcagaca cctacaccac   3060
caacaacaca acttcctcaa caagtgcagc cttcacttcc tgctgcacct tctgctgacc   3120
agccccagca gcagcctcgc tcacagcaga gcacagcagc gtctgttcct accccaacag   3180
caccgctgct tcctccgcag cctgcaactc cactttccca gccagctgta agcattgaag   3240
gacaggtatc aaatcctcca tctactagta gcacagaagt gaattctcag gccattgctg   3300
agaagcagcc ttcccaggaa gtgaagatgg aggccaaaat ggaagtggat caaccagaac   3360
cagcagatac tcagccggag gatatttcag agtctaaagt ggaagactgt aaaatggaat   3420
ctaccgaaac agaagagaga agcactgagt taaaaactga aataaaagag gaggaagacc   3480
agccaagtac ttcagctacc cagtcatctc cggctccagg acagtcaaag aaaaagattt   3540
tcaaaccaga agaactacga caggcactga tgccaacttt ggaggcactt taccgtcagg   3600
atccagaatc ccttcccttt cgtcaacctg tggaccctca gcttttagga atccctgatt   3660
actttgatat tgtgaagagc cccatggatc tttctaccat taagaggaag ttagacactg   3720
gacagtatca ggagccctgg cagtatgtcg atgatatttg gcttatgttc aataatgcct   3780
ggttatataa ccgaaaaaca tcacgggtat acaaatactg ctccaagctc tctgaggtct   3840
ttgaacaaga aattgaccca gtgatgcaaa gccttggata ctgttgtggc agaaagttgg   3900
```

```
agttctctcc acagacactg tgttgctacg gcaaacagtt gtgcacaata cctcgtgatg   3960
ccacttatta cagttaccag aacaggtatc atttctgtga gaagtgtttc aatgagatcc   4020
aaggggagag cgtttctttg ggggatgacc cttcccagcc tcaaactaca ataaataaag   4080
aacaattttc caagagaaaa aatgacacac tggatcctga actgtttgtt gaatgtacag   4140
agtgcggaag aaagatgcat cagatctgtg tccttcacca tgagatcatc tggcctgctg   4200
gattcgtctg tgatggctgt ttaaagaaaa gtgcacgaac taggaaagaa ataagttttc   4260
tgctaaaag gttgccatct accagacttg gcacctttct agagaatcgt gtgaatgact   4320
ttctgaggcg acagaatcac cctgagtcag gagaggtcac tgttagagta gttcatgctt   4380
ctgacaaaac cgtggaagta aaaccaggca tgaaagcaag gtttgtggac agtggagaga   4440
tggcagaatc ctttccatac cgaaccaaag ccctctttgc cttgaagaa attgatggtg   4500
ttgacctgtg cttctttggc atgcatgttc aagagtatgg ctctgactgc cctccaccca   4560
accagaggag agtatacata tcttacctcg atagtgttca tttcttccgt cctaaatgct   4620
tgaggactgc agtctatcat gaaatcctaa ttggatattt agaatatgtc aagaaattag   4680
gttacacaac agggcatatt tgggcatgtc caccaagtga gggagatgat tatatcttcc   4740
attgccatcc tcctgaccag aagatcccca agcccaagcg actgcaggaa tggtacaaaa   4800
aaatgcttga caaggctgta tcagagcgta ttgtccatga ctacaaggat attttttaaac   4860
aagctactga agatagatta acaagtgcaa aggaattgcc ttatttcgag ggtgatttct   4920
ggcccaatgt tctggaagaa agcattaagg aactggaaca ggaggaagaa gagagaaaac   4980
gagaggaaaa caccagcaat gaaagcacag atgtgaccaa gggagacagc aaaaatgcta   5040
aaagaagaa taataagaaa accagcaaaa ataagagcag cctgagtagg ggcaacaaga   5100
agaaacccgg gatgcccaat gtatctaacg acctctcaca gaaactatat gccaccatgg   5160
agaagcataa agaggtcttc tttgtgatcc gcctcattgc tggccctgct gccaactccc   5220
tgcctcccat tgttgatcct gatcctctca tccctgcga tctgatggat ggtcgggatg   5280
cgtttctcac gctggcaagg gacaagcacc tggagttctc ttcactccga agagcccagt   5340
ggtccaccat gtgcatgctg gtggagctgc acacgcagag ccaggaccgc tttgtctaca   5400
cctgcaatga atgcaagcac catgtggaga cacgctggca ctgtactgtc tgtgaggatt   5460
atgacttgtg tatcacctgc tataacacta aaaaccatga ccacaaaatg gagaaactag   5520
gccttggctt agatgatgag agcaacaacc agcaggctgc agccacccag agcccaggcg   5580
attctcgccg cctgagtatc cagcgctgca tccagtctct ggtccatgct tgccagtgtc   5640
ggaatgccaa ttgctcactg ccatcctgcc agaagatgaa gcgggttgtg cagcatacca   5700
agggttgcaa acggaaaacc aatggcgggt gccccatctg caagcagctc attgccctct   5760
gctgctacca tgccaagcac tgccaggaga acaaatgccc ggtgccgttc tgcctaaaca   5820
tcaagcagaa gctccggcag caacagctgc agcaccgact acagcaggcc caaatgcttc   5880
gcaggaggat ggccagcatg cagcggactg gtgtggttgg gcagcaacag ggcctccctt   5940
cccccactcc tgccactcca acgacaccaa ctggccaaca gccaaccacc ccgcagacgc   6000
cccagcccac ttctcagcct cagcctaccc ctcccaatag catgccaccc tacttgccca   6060
ggactcaagc tgctggccct gtgtcccagg gtaaggcagc aggccaggtg acccctccaa   6120
cccctcctca gactgctcag ccaccccttc cagggcccc acctgcagca gtggaaatgg   6180
caatgcagat tcagagagca gcggagacgc agcgccagat ggcccacgtg caaattttc   6240
aaaggccaat ccaacaccag atgccccga tgactcccat ggcccccatg ggtatgaacc   6300
```

```
cacctcccat gaccagaggt cccagtgggc atttggagcc agggatggga ccgacaggga      6360
tgcagcaaca gccaccctgg agccaaggag gattgcctca gccccagcaa ctacagtctg      6420
ggatgccaag gccagccatg atgtcagtgg cccagcatgg tcaacctttg aacatggctc      6480
cacaaccagg attgggccag gtaggtatca gcccactcaa accaggcact gtgtctcaac      6540
aagccttaca aaaccttttg cggactctca ggtctcccag ctctcccctg cagcagcaac      6600
aggtgcttag tatccttcac gccaaccccc agctgttggc tgcattcatc aagcagcggg      6660
ctgccaagta tgccaactct aatccacaac ccatccctgg gcagcctggc atgccccagg      6720
ggcagccagg gctacagcca cctaccatgc caggtcagca gggggtccac tccaatccag      6780
ccatgcagaa catgaatcca atgcaggcgg gcgttcagag ggctggcctg ccccagcagc      6840
aaccacagca gcaactccag ccacccatgg gagggatgag cccccaggct cagcagatga      6900
acatgaacca caacaccatg ccttcacaat tccgagacat cttgagacga cagcaaatga      6960
tgcaacagca gcagcaacag ggagcagggc caggaatagg ccctggaatg gccaaccata      7020
accagttcca gcaaccccaa ggagttggct acccaccaca gcagcagcag cggatgcagc      7080
atcacatgca acagatgcaa caaggaaata tgggacagat aggccagctt ccccaggcct      7140
tgggagcaga ggcaggtgcc agtctacagg cctatcagca gcgactcctt cagcaacaga      7200
tggggtcccc tgttcagccc aaccccatga gcccccagca gcatatgctc ccaaatcagg      7260
cccagtcccc acacctacaa ggccagcaga tccctaattc tctctccaat caagtgcgct      7320
ctccccagcc tgtcccttct ccacggccac agtcccagcc cccccactcc agtccttccc      7380
caaggatgca gcctcagcct tctccacacc acgtttcccc acagacaagt tccccacatc      7440
ctggactggt agctgcccag gccaacccca tggaacaagg gcattttgcc agcccggacc      7500
agaattcaat gctttctcag cttgctagca atccaggcat ggcaaacctc catggtgcaa      7560
gcgccacgga cctgggactc agcaccgata actcagactt gaattcaaac ctctcacaga      7620
gtacactaga catacactag agacaccttg tagtattttg ggagcaaaaa aattatttc      7680 tcttaacaag acttttttgta ctgaaaacaa tttttttgaa tctttcgtag cctaaaagac      7740 aatttttcctt ggaacacata agaactgtgc agtagccgtt tgtggtttaa agcaaacatg      7800
caagatgaac ctgagggatg atagaataca aagaatatat ttttgttatg gctggttacc      7860
accagccttt cttccccttt gtgtgtgtgg ttcaagtgtg cactgggagg aggctgaggc      7920
ctgtgaagcc aaacaatatg ctcctgcctt gcacctccaa taggttttat tatttttttt      7980 aaaattaatga acatatgtaa tattaatagt tattatttac tggtgcagat ggttgacatt      8040
tttccctatt ttcctcactt tatggaagag ttaaaacatt tctaaaccag aggacaaaag      8100
gggttaatgt tactttaaaa ttacattcta tatatatata aatatatata aatatatatt      8160
aaaataccag ttttttttct ctgggtgcaa agatgttcat tcttttaaaa aatgtttaaa      8220
aaaaaaaaaa aactgccttt cttcccctca agtcaacttt tgtgctccag aaaattttct      8280
attctgtaag tctgagcgta aaacttcaag tattaaaata atttgtacat gtagagagaa      8340
aaatgacttt ttcaaaaata tacaggggca gctgccaaat tgatgtatta tatattgtgg      8400
tttctgtttc ttgaaagaat ttttttcgtt attttttacat ctaacaaagt aaaaaaatta      8460 aaagagggt aagaaacgat tccggtggga tgatttttaac atgcaaaatg tccctggggg      8520
tttcttcttt gcttgctttc ttcctcctta ccctaccccc cactcacaca cacacacaca      8580
cacacacaca cacacacaca cacacactt ctataaaact tgaaaatagc aaaaaccctc      8640
```

```
aactgttgta aatcatgcaa ttaaagttga ttacttataa atatgaactt tggatcactg    8700
tatagactgt taaatttgat ttcttattac ctattgttaa ataaactgtg tgagacagac    8760
a                                                                   8761

<210> SEQ ID NO 80
<211> LENGTH: 2379
<212> TYPE: DNA
<213> ORGANISM: Homo sapiens

<400> SEQUENCE: 80 gaccccgag ctgtgctgct cgcggccgcc accgccgggc ccggccgtc cctggctccc      60 ctcctgcctc gagaagggca gggcttctca gaggcttggc gggaaaaaga acggagggag   120
ggatcgcgct gagtataaaa gccggttttc ggggctttat ctaactcgct gtagtaattc   180
cagcgagagg cagagggagc gagcgggcgg ccggctaggt tggaagagcc gggcgagcag   240
agctgcgctg cgggcgtcct gggaagggag atccggagcg aatagggggc ttcgcctctg   300
gcccagccct cccgctgatc ccccagccag cggtccgcaa cccttgccgc atccacgaaa   360 cttttgcccat agcagcgggc gggcactttg cactggaact acaacaccc gagcaaggac    420 gcgactctcc cgacgcgggg aggctattct gcccatttgg ggacacttcc ccgccgctgc   480
caggacccgc ttctctgaaa ggctctcctt gcagctgctt agacgctgga ttttttttcgg   540 gtagtggaaa accagcagcc tcccgcgacg atgcccctca cgttagctt caccaacagg    600 aactatgacc tcgactacga ctcggtgcag ccgtatttct actgcgacga ggaggagaac   660
ttctaccagc agcagcagca gagcgagctg cagcccccgg cgcccagcga ggatatctgg   720
aagaaattcg agctgctgcc caccccgccc ctgtccccta gccgccgctc cgggctctgc   780
tcgccctcct acgttgcggt cacacccttc tcccttcggg gagacaacga cggcggtggc   840
gggagcttct ccacggccga ccagctggag atggtgaccg agctgctggg aggagacatg   900
gtgaaccaga gtttcatctg cgacccggac gacgagacct tcatcaaaaa catcatcatc   960
caggactgta tgtggagcgg cttctcggcc gccgccaagc tcgtctcaga aagctggcc   1020 tcctaccagc tgcgcgcaa agacagcggc agcccgaacc ccgccgcgg ccacagcgtc    1080 tgctccacct ccagcttgta cctgcaggat ctgagcgccg ccgcctcaga gtgcatcgac   1140
ccctcggtgg tcttccccta ccctctcaac gacagcagct cgcccaagtc ctgcgcctcg   1200
caagactcca gcgccttctc tccgtcctcg gattctctgc tctcctcgac ggagtcctcc   1260
ccgcagggca gccccgagcc cctggtgctc catgaggaga caccgccac caccagcagc   1320 gactctgagg aggaacaaga agatgaggaa gaaatcgatg ttgtttctgt ggaaaagagg   1380
caggctcctg gcaaaaggtc agagtctgga tcaccttctg ctggaggcca cagcaaacct   1440
cctcacagcc cactggtcct caagaggtgc cacgtctcca cacatcagca caactacgca   1500
gcgcctccct ccactcggaa ggactatcct gctgccaaga gggtcaagtt ggacagtgtc   1560
agagtcctga cagatcag caacaaccga aaatgcacca gccccaggtc ctcggacacc   1620
gaggagaatg tcaagaggcg aacacacaac gtcttggagc gccagaggag gaacgagcta   1680
aaacggagct ttttgccct gcgtgaccag atcccggagt tggaaaacaa tgaaaaggcc   1740
cccaaggtag ttatccttaa aaaagccaca gcatacatcc tgtccgtcca agcagaggag   1800
caaaagctca tttctgaaga ggacttgttg cggaaacgac gagaacagtt gaaacacaaa   1860
cttgaacagc tacggaactc ttgtgcgtaa ggaaaagtaa ggaaaacgat tccttctaac   1920
agaaatgtcc tgagcaatca cctatgaact tgtttcaaat gcatgatcaa atgcaacctc   1980
```

```
acaaccttgg ctgagtcttg agactgaaag atttagccat aatgtaaact gcctcaaatt    2040
ggactttggg cataaaagaa cttttttatg cttaccatct ttttttttc tttaacagat    2100 ttgtatttaa gaattgtttt taaaaaattt taagatttac acaatgtttc tctgtaaata    2160
ttgccattaa atgtaaataa ctttaataaa acgtttatag cagttacaca gaatttcaat    2220
cctagtatat agtacctagt attataggta ctataaaccc taatttttt tatttaagta    2280 cattttgctt tttaaagttg attttttct attgttttta gaaaaaataa aataactggc    2340
aaatatatca ttgagccaaa tcttaaaaaa aaaaaaaa                            2379
```

<210> SEQ ID NO 81
<211> LENGTH: 8758
<212> TYPE: DNA
<213> ORGANISM: Drosophila melanogaster

<400> SEQUENCE: 81

```
agttctgctg cgatcgcgcc actgcgcact acgtaacgct tcgggaatcg cacatccaga      60
tccagattca gatccacatc cagatatctg tgacattttg tcgagtgagt tgcgttctca    120
aagatacaag atacatccgt gcgcgtatgt gtgtgtttgc atgaatttcg gctctttaa    180 taccttttt ttttcgcgtg cactaagtgt tcctatgtgt gtgtgtgtgg agttgctttt    240
cagttggggc cgcaactgca acaataaaat gcaattaagc cgctcaaatc aacaataaat    300
tgaattaaag cgcgtgaaca gcgcttaaca acttcaacag cggcgattcg agcgaaatgt    360
gggtgagagt ttaaggctcc atcggttttg actttctgat tgtacaaata tgtatatata    420
tatactatag catacatacc ttcgactaat taatgcaaaa cgctggccgg cagcttttgc    480
ataatattct ctgaataact ttaatgcaat taatcccgct gtgatctttc gtgttttcac    540
tatttcgcgc ggtttattca atttgaattt caatttattt tcggttttc tgtttcattt    600 tgtttataca tatatatatt tgttcggtct agtctgctca tcgggcgatt taattaacat    660
tttccgtgct gctgtgctgt tgttgttgct gtttcgtttt cagtcaaatg cggcactaaa    720
atgttaattc agccaaagca aacaacgatt atcgagtgaa ataggaatcg aacgccacaa    780
atcgcgaact cggggtgaag atcgagtgcc tcgatgacta tgttttggca acaaaatgta    840
gaccaccagt cggatgagca ggacaaacag gcgaagggtg cggcgcccac aaagagattg    900
aacatcagct tcaatgtgaa gatcgcggtg aatgtgaata ccaagatgac caccacccac    960
atcaatcagc aggcacctgg cacctcctcc tcctcgtcga actcccagaa tgcctcaccc   1020
agcaagattg tggtccgcca gcagagcagc tccttcgatc tacgtcagca attggctcgc   1080
ttaggccgcc aattggccag tggccaggat ggccatggcg gcatatccac catactgatc   1140
atcaatcttc tcctgctcat tctactctcg atctgctgcg atgtctgccg atcgcacaac   1200
tatacggtgc accagagtcc cgaacccgtc tccaaagacc aaatgcgcct gctgcgtccc   1260
aagctggaca gcgatgtggt cgagaaggtg gccatctggc acaagcacgc cgccgcagct   1320
ccgccaagca ttgtcgaggg catcgccatc agcagcaggc cacagtcaac gatggcccat   1380
catccagatg atcgagatcg ggatcgtgat ccttcggagg aacagcatgg cgtcgacgag   1440
cgaatggtcc tggaacgcgt gaccagggat tgtgtgcagc gctgcattgt tgaggaggat   1500
ctgtttctgg acgaatttgg aatacagtgc gaaaaggcgg acaatggcga gaagtgctac   1560
aaaacacgat gcaccaaggg ctgtgcccag tggtatcgcg ccctcaagga gctggagtcc   1620
tgccaggagg cctgcctgtc cctccagttc tacccgtacg acatgccctg catcggtgcc   1680
```

-continued

```
tgcgagatgg cccagcggga ctactggcac ctccagcgac tggccatcag ccacctggtg   1740
gagcggacgc agccgcagct ggagcgagct cctcgggcgg acggacagtc cacgccactg   1800
accatccgct gggcgatgca cttttccgga aactacctgg ccagcagacc cttcaacatt   1860
cagtaccagt tgtggatca ccacggcgag gagctggatc tcgagcagga agaccaggat    1920
gcatccggag agacgggttc cagtgcctgg tttaacttag ccgattacga ctgtgacgag   1980
tattatgtgt gcgagatact ggaggccctg ataccctaca cacaatacag gttccgattt   2040
gagttgcctt tcggcgagaa tagagacgaa gtcctctact ctccggccac gcccgcctac   2100
caaacgccac ccgagggcgc gcccatctcg gctccggtca tcgagcatct gatgggtctc   2160
gacgacagcc acctggctgt ccactggcat cccggtcgct tcaccaatgg acccatcgag   2220
ggttaccgcc tgcgtttgag ttcctcgag ggaaacgcta caagtgaaca gctggttccg    2280
gccggacgag gtagctacat cttttcccag ctacaagccg gcaccaacta tccctggcg    2340
ctgagcatga tcaacaaaca gggtgagggt ccggtggcca agggatttgt gcagactcac   2400
tccgctcgaa atgaaaagcc tgccaaggat ctgacagaaa gtgtcctgct cgtcggacga   2460
agggctgtga tgtggcaatc gctggaaccg gctggtgaga actccatgat ctatcaatct   2520
caggaggaat tggctgatat cgcctggtca aagcgggagc aacaactgtg gctgctcaac   2580
gtccatggag agttgcgcag cttaaaattt gaatccggcc agatggtgag tccagcgcag   2640
cagctcaagc tggatctggg aaacatatcc agtggaagat gggttcctcg cagattgagc   2700
ttcgactggc tgcatcatcg actgtacttc gctatggagt cgccagagcg aaaccaatcc   2760
agctttcaga ttatcagcac agatttgctg ggtgaatcaa cgcagaaagt gggcgagtcc   2820
tttgatctgc ccgttgagca gttggaagtg gatgccctga atggctggat tttctggagg   2880
aacgaggagt cgctgtggcg tcaggatctg catggtcgaa tgatccatcg cctgttgagg   2940
atcaggcagc ccggttggtt cctggtgcag ccacaacact tcatcatcca tctaatgctt   3000
ccacaggagg gtaaattcct agagataagc tacgatggtg ggttcaagca tccactgccg   3060
ctaccaccgc cttcgaatgg agctggaaat ggacctgcat ccagccattg caaagctttt   3120
gccctgttgg gtcgctccct gctcctgccc gattctggtc agctgatcct ggttgagcag   3180
cagggtcagg cagccagtcc cagtgcctca tggcctctaa agaacttgcc cgactgttgg   3240
gccgtgatac tcctggtgcc ggaaagccaa ccactgacca gcgctggagg aaaaccgcac   3300
agcttgaagg ccttgctggg agcccaggcg gcaaagatct cgtggaagga gccggaacgc   3360
aatccctacc aatcggcgga tgcagcacgc agctggagct acgaactgga agtgcttgat   3420
gtggccagcc aaagtgcctt tagcattcgc aatattcgtg gacccatctt tggactgcag   3480
cgcctgcagc cggataatct ctatcaactg cgagttaggg caataaacgt ggatggagag   3540
ccgggcgagt ggactgaacc gttggctgcc cgcacctggc cactgggtcc acatcgcttg   3600
agatgggcca ccggcagggg aagcgtcatt cataccaacg agctgggcga gggcttggaa   3660
gtgcagcagg aacagttgga gcgactaccc ggacccatga ccatggtgaa tgaaagcgtg   3720
ggctactacg tcactggcga cggtctactg cactgcatca atctggtgca cagccagtgg   3780
ggatgcccaa tctcggagcc actgcagcac gtgggctcgg tgacttacga ctggcggggc   3840
ggaagagttt attggacgga tctggccagg aattgcgtgg tgcgcatgga tccatggtcg   3900
ggcagtcggg aactgttgcc cgtcttcgag gccaacttcc tggcattgga tccgcgtcaa   3960
ggccacctgt actatgccac cagctctcag ctgtcgcgac atggtccac gcccgatgaa   4020
gcggtcactt attatcgtgt taatgggctg gagggaagca tcgcctcctt tgtgctggac   4080
```

```
acccagcagg atcagctctt ctggcttgtt aaaggctctg gtgcactgcg tttgtatcgt    4140
gcgcccctga cagctggcgg ggattcactg cagatgatcc agcagattaa aggcgtcttt    4200
caggctgtcc cggacagttt gcagcttctg cggcccttgg gcgcacttct ttggctggag    4260
cggagtggca ggagagctcg cttggtccgc ctggctgctc ctctggatgt catggagcta    4320
ccgacaccgg accaggcctc tcctgcctcc gcattgcaat tattggaccc acaaccattg    4380
cctccgcggg atgagggggt tattccaatg accgtgctcc cggatagcgt gcgtctggac    4440
gatggccact gggacgactt ccatgtgcgc tggcagccat ccacttccgg tggcaatcac    4500
agcgtctcct atcgtctgct cctcgagttt ggccaaagac tacaaacctt ggatttgagc    4560
acaccatttg cccggctgac ccaattgccg caggctcaat tgcagctaaa gatcagcatc    4620
acaccgcgaa ccgcgtggcg aagtggagac accactcggg tgcagctcac caccccgccg    4680
gtggctccta gtcagcctcg tcgtctgcgc gtgttcgtgg agcgcttggc cactgccctg    4740
caggaggcta atgtgagtgc tgtgctccgc tgggatgcgc cggaacaggg tcaggaggcg    4800
ccgatgcagg cgctggagta tcacatcagc tgttgggtgg gctcagagct gcacgaggag    4860
ttgcgcctca atcagagtgc cctggaggcc cgcgtagagc acctgcaacc ggatcagacg    4920
taccacttcc aggtggaggc acgtgtggct gccacgggag cggcagcggg cgcagctagt    4980
catgccctcc atgtggcacc ggaggtgcag gcggtgccac gcgtactcta cgccaatgca    5040
gagtttattg gcgaactgga cctggacaca cggaatcgca ggcgactggt gcacacggcc    5100
agtccggttg agcatctggt ggggatcgag ggagagcagc gattgctgtg ggtcaacgag    5160
cacgtggagc tgctcaccca tgtcccggga tcagctccag caaagctggc cagaatgagg    5220
gccgaggtct tggcactggc cgtggactgg atacagcgta tcgtctactg gcgggaactg    5280
gatgctactg caccgcaggc ggcgataatc tatcgcctgg atctgtgcaa ctttgaaggg    5340
aagatcctgc agggcgagcg ggtgtggagc actcccaggg gacggttgct gaaggatctg    5400
gtggccctgc cacaggcgca atctctgatc tggttggagt acgagcaggg atctccgaga    5460
aatggttcgc tccggggcag aaatctaacc gatggctcgg agctggagtg ggcaacggtt    5520
cagccgctaa tccgtctgca tgctggaagc ttagagcccg gatcggagac cttgaacctg    5580
gtggacaacc agggcaagct gtgtgtctac gatgtggccc gtcagctgtg cacggccagc    5640
gctttgcggg cacagctgaa cttgctgggc gaggactcca ttgctggtca gttggcccag    5700
gattcgggat accttttacgc cgtgaaaaac tggagcattc gtgcttatgg tcgccggcgc    5760
cagcagctgg agtatacggt ggaactggag ccggaagagg tgcgtctgct ccaggcacac    5820
aactatcagg cctatccgcc caagaactgt ctgctccttc cttcatccgg cggatccctt    5880
ttgaaagcta ccgattgtga ggagcagaga tgcctattac acttacccat gatcacagcc    5940
tccgaagatt gtccactgcc tattcctggc gttagatacc aactgaatct tacgttggcc    6000
aaggagccgg gatccgagga gcacgatcat gggatggagc cctgggaca gtggctgctc    6060 ggtgctgggg aatcgttgaa tcttacagac ctgctgccct tcacccgtta tcgcgtgtct    6120
ggaattttga gcagctttta ccaaaagaag ttggcattac ccaccttggt gttggcacca    6180
ctggagctcc ttaccgcctc tgccacgccc tcgcctccaa ggaacttcag tgttcgtgtg    6240
cttagtccca gggaactgga ggtcagctgg ttgccgccgg agcagctgcg tagcgaaagt    6300
gtctactaca cgctccactg gcaacaggaa ctggatggtg aaaatgtcca ggatcggcgg    6360
gaatgggagg cacatgagcg gcgactggag acggcgggca ctcatcgatt gactggaatc    6420
```

```
aagccgggat ctgggtatag cctgtgggtt caggcccatg ccacgcccac caagagcaac   6480
agcagcgagc ggctgcatgt gcgtagtttc gccgaattac ccgagttgca gctcctggaa   6540
ctgggaccct attctctgag tctcacctgg gcgggaacac cggatccact gggatcgctg   6600
cagctcgaat gccgatcgtc ggctgagcaa ctgcgtcgca atgtggccgg aaatcacact   6660
aagatggtgg tggagccatt gcagccacgc acccgctacc agtgtcgcct gctcctgggc   6720
tatgcggcga cgccgggagc tccactgtac catggcactg cagaggtgta cgaaactctg   6780
ggagatgcgc ccagtcagcc gggcaagcca caattggagc acatcgctga ggaggttttc   6840
cgtgtcacct ggacggcggc ccgcggtaat ggagcaccca ttgctctcta caatctggag   6900
gcactccagg cgaggagcga cattcgccgg aggcgcagaa gaaggcgccg caatagcggt   6960
ggatcactag agcagttgcc gtgggctgag gaaccggtgg tcgtggagga tcagtggctg   7020
gacttctgca acaccaccga gctgagctgc attgtgaaga gtctgcattc gagcaggttg   7080
ctcctcttcc gtgtgcgtgc gcggagcttg gagcacggat ggggacctta cagcgaggag   7140
agcgaacggg tggcggagcc cttcgtttcg ccggagaaga gaggatcact ggtcctggcc   7200
atcattgcgc cggctgccat cgtttccagc tgcgttctgg cattggtgct cgttcgaaaa   7260
gttcaaaagc gacgactgcg tgccaagaaa ctgcttcagc agagccgtcc cagcatctgg   7320
agcaacctgt ccaccttgca gacgcaacag cagctgatgg ccgtcaggaa tcgcgccttc   7380
tccaccacgc tgagtgatgc ggacatcgct ctgctgcccc aaattaattg gagtcaactg   7440
aagttgctcc gatttcttgg cagcggtgct tttggtgagg tatacgaggg tcagttgaag   7500
acggaggact ccgaggagcc gcaacgagtg gccatcaaga gcctgcgcaa gggagccagt   7560
gaatttgccg agctgcttca ggaggctcag ctgatgagca acttcaagca cgagaacatt   7620
gtgtgcctgg tgggaatctg cttcgacacc gagtccatat ctctgattat ggagcacatg   7680
gaagcgggcg acttgctaag ctacctacgt gccgccaggg ctaccagcac caggagcca    7740
caacccactg ctggactctc gctctccgag ctcctggcca tgtgcattga tgtgccaac    7800
ggctgcagtt atctggagga catgcacttt gtgcatcgcg acctggcctg ccggaactgt   7860
ttggtcacgg aatcgacggg cagcacggat cgtcggcgca ccgtgaagat tggtgacttc   7920
ggattggcga gggacatcta caagagcgac tactaccgaa aggagggcga gggcctgcta   7980
ccggtgcgct ggatgtcgcc ggagagtctc gtcgacgggt tgttcaccac acagtcggat   8040
gtgtgggcct ttggagtgct ctgctgggag atcctcacac tgggccagca gccgtatgcg   8100
gcgaggaaca acttcgaggt gctggcccat gtcaaggagg cggacggct ccagcagccg    8160
cccatgtgta cggagaagct ttactccctg ctcctgcttt gctggcgaac ggatccgtgg   8220
gagcgaccca gtttccggcg ctgctacaac acactccatg ccatcagcac cgatttgcgg   8280
cgcacccaaa tggcctcggc aactgcggat acggttgtca gctgctccag gccggagttc   8340
aaggtgcgat tcgatggcca gccgctggag gagcatagag agcacaatga gcggccggag   8400
gatgagaacc tgacgctgcg ggaagtgccg ctcaaggata agcaactgta tgcaaacgag   8460
ggagtctcgc gactttagaa aggtgactcc catgtccttc acaaaggtcg tctcaaaacg   8520
attagctttc catttaatct aagttctaag tttaatatgt acgagaatat aaaatggtcg   8580
atgaggatgg caagtttgta ttctatttca gattaagata cttttttttt tcttctcaga   8640
tacaggaatt atgggcaagc gcattgccta taagttttat ttgcaccgct atttatttat   8700
tttctttaat atttcaatta atggatagac ttaaatatat tataaaattt ttggtact     8758
```

<210> SEQ ID NO 82
<211> LENGTH: 2505
<212> TYPE: DNA
<213> ORGANISM: Homo sapiens

<400> SEQUENCE: 82

```
agtggggaga gatgagtgta gataaaagga gtgcagaagg cacgaggaag ccacagtgct      60
ccggatcctc caatcttcgc tcctccaatc tccgctcctc cacccagttc aggaacccgc     120
gaccgctcgc agcgctctct tgaccactat gagcctcctg tccagccgcg cggcccgtgt     180
ccccggtcct tcgagctcct tgtgcgcgct gttggtgctg ctgctgctgc tgacgcagcc     240
agggcccatc gccagcgctg gtcctgccgc tgctgtgttg agagagctgc gttgcgtttg     300
tttacagacc acgcaaggag ttcatcccaa aatgatcagt aatctgcaag tgttcgccat     360
aggcccacag tgctccaagg tggaagtggt agcctccctg aagaacggga aggaaatttg     420
tcttgatcca gaagccccctt ttctaaagaa agtcatccag aaaattttgg acggtggaaa     480
caaggaaaac tgattaagag aaatgagcac gcatggaaaa gtttcccagt cttcagcaga     540
gaagttttct ggaggtctct gaacccaggg aagacaagaa ggaaagattt tgttgttgtt     600
tgtttatttg ttttccagt agttagcttt cttcctggat tcctcacttt gaagagtgtg     660
aggaaaacct atgtttgccg cttaagcttt cagctcagct aatgaagtgt ttagcatagt     720
acctctgcta tttgctgtta ttttatctgc tatgctattg aagttttggc aattgactat     780
agtgtgagcc aggaatcact ggctgttaat cttttcaaagt gtcttgaatt gtaggtgact     840
attatatttc caagaaatat tccttaagat attaactgag aaggctgtgg atttaatgtg     900
gaaatgatgt tcataagaa ttctgttgat ggaaatacac tgttatcttc acttttataa     960
gaaataggaa atattttaat gtttcttggg gaatatgtta gagaatttcc ttactcttga    1020
ttgtgggata ctatttaatt atttcacttt agaaagctga gtgtttcaca ccttatctat    1080
gtagaatata tttccttatt cagaatttct aaaagtttaa gttctatgag ggctaatatc    1140
ttatcttcct ataattttag acattcttta tcttttagt atggcaaact gccatcattt    1200
acttttaaac tttgattta tatgctattt attaagtatt ttattaggag taccataatt    1260
ctggtagcta aatatatatt ttagatagat gaagaagcta gaaaacaggc aaattcctga    1320
ctgctagttt atatagaaat gtattctttt agttttaaa gtaaaggcaa acttaacaat    1380
gacttgtact ctgaaagttt tggaaacgta ttcaaacaat ttgaatataa atttatcatt    1440
tagttataaa aatatatagc gacatcctcg aggccctagc atttctcctt ggataggga    1500
ccagagagag cttggaatgt taaaaacaaa acaaaacaaa aaaaaacaag gagaagttgt    1560
ccaagggatg tcaattttt atccctctgt atgggttaga ttttccaaaa tcataattttg    1620
aagaaggcca gcatttatgg tagaatatat aattatatat aaggtggcca cgctgggca    1680
agttccctcc ccactcacag ctttggcccc tttcacagag tagaacctgg gttagaggat    1740
tgcagaagac gagcggcagc ggggagggca ggaagatgc ctgtcgggtt tttagcacag    1800
ttcatttcac tgggattttg aagcatttct gtctgaatgt aaagcctgtt ctagtcctgg    1860
tgggacacac tggggttggg ggtgggggaa gatgcggtaa tgaaaccggt tagtcagtgt    1920
tgtcttaata tccttgataa tgctgtaaag tttatttta caaatatttc tgtttaagct    1980
atttcaccctt tgtttggaaa tccttccctt ttaaagagaa aatgtgacac ttgtgaaaag    2040
gcttgtagga aagctcctcc ctttttttct ttaaaccttt aaatgacaaa cctaggtaat    2100
taatggttgt gaatttctat ttttgctttg tttttaatga acatttgtct ttcagaatag    2160
```

```
gattctgtga taatatttaa atggcaaaaa caaaacataa ttttgtgcaa ttaacaaagc      2220
tactgcaaga aaaataaaac atttcttggt aaaaacgtat gtatttatat attatatatt      2280
tatatataat atatattata tatttagcat tgctgagctt tttagatgcc tattgtgtat      2340
cttttaaagg ttttgaccat tttgttatga gtaattacat atatattaca ttcactatat      2400
taaaattgta cttttttact atgtgtctca ttggttcata gtctttattt tgtcctttga      2460
ataaacatta aaagatttct aaacttcaaa aaaaaaaaa aaaaa                        2505
```

<210> SEQ ID NO 83
<211> LENGTH: 1182
<212> TYPE: DNA
<213> ORGANISM: Homo sapiens

<400> SEQUENCE: 83

```
ccacatttgt gcatcacttc tttagagaaa gttaagtctg tgttctgctt aggagagata       60 acacttttttg tccctgtagg tggccccct ggtgtagcca ttagttgcta attacttgca      120
aacaaataaa caattaactc cttaagctgc tggctgggca agtgttcatt gacatgctaa      180
aactttctaa gacaggattt taattagtga cgttctaaat ccagcccct tgtcagcgga       240 gctataaggt gaactgcagg aagatcccag ccctatacac gtggggcaga gccagcagag      300
gccagagctg ttgctctgtg cagaccacga gaggatgtct cccagccttc aggaaggcgc      360
tcagctcggg gaaaacaaac cctcaacttg ctccttttca attgagagaa tcttaggact      420
ggaccagaag aaagactgtg ttccattaat gaaaccccac aggccctggg cagacacctg      480
cagctcatca gggaaagatg gtaacttatg tctacatgtc ccaaatcctc ccagtgggat      540
ttcattccct agcgtggtgg atcacccaat gccagaagaa agagcttcga aatatgaaaa      600
ttacttttca gcctcagaaa gactgtcttt gaaaagagag ttgagttggt atagaggccg      660
aagaccaaga actgctttta ctcaaaacca gattgaagtg ttagaaaatg tctttagagt      720
aaactgctat cctggtatcg atattagaga agacttagct caaaaattga atctagagga      780
agacagaatc cagatttggt ttcaaaatcg gcgtgcaaaa ctgaaaaggt cccatagaga      840
atcacagttt ctaatggcga aaaaaaattt caacacaaat ctgctggaat agatagaaaa      900
ctaaacaagt gaaattatct tctaattgca gagcatgaag aatcagtgga aatattaagt      960
gttaaaatgt gatgttttct ttcctgcatt taatctgaat attgtcattt tttctgaaaa     1020
tatattgtaa atactattat agcatggtac atatttgggc acttttagtt atagtaaaga     1080
ccttttatat atattttaat aaacattttc agaaagatt gctattttt aagtaagcca      1140 aattaatcta ataaattagt ttgttaaaat caaaaaaaa aa                          1182
```

<210> SEQ ID NO 84
<211> LENGTH: 1944
<212> TYPE: DNA
<213> ORGANISM: Homo sapiens

<400> SEQUENCE: 84

```
aatttctcac tgcccctgtg ataaactgtg gtcactggct gtggcagcaa ctattataag       60
atgctctgaa aactcttcag acactgaggg gcaccagagg agcagactac aagaatggca      120
cacgctatgg aaaactcctg gacaatcagt aaagagtacc atattgatga agaagtgggc      180
tttgctctgc caaatccaca ggaaaatcta cctgattttt ataatgactg gatgttcatt      240
gctaaacatc tgcctgatct catagagtct ggccagcttc gagaaagagt tgagaagtta      300
aacatgctca gcattgatca tctcacagac cacaagtcac agcgccttgc acgtctagtt      360
```

```
ctgggatgca tcaccatggc atatgtgtgg ggcaaaggtc atggagatgt ccgtaaggtc      420
ttgccaagaa atattgctgt tccttactgc caactctcca agaaactgga actgcctcct      480
attttggttt atgcagactg tgtcttggca aactggaaga aaaggatcc taataagccc       540 ctgacttatg agaacatgga cgttttgttc tcatttcgtg atggagactg cagtaaagga      600
ttcttcctgg tctctctatt ggtggaaata gcagctgctt ctgcaatcaa agtaattcct      660
actgtattca aggcaatgca aatgcaagaa cgggacactt tgctaaaggc gctgttggaa      720
atagcttctt gcttggagaa agcccttcaa gtgtttcacc aaatccacga tcatgtgaac      780
ccaaaagcat ttttcagtgt tcttcgcata tatttgtctg gctggaaagg caacccccag      840
ctatcagacg gtctggtgta tgaagggttc tgggaagacc caaaggagtt tgcagggggc      900
agtgcaggcc aaagcagcgt ctttcagtgc tttgacgtcc tgctgggcat ccagcagact      960
gctggtggag acatgctgc tcagttcctc caggacatga aagatatat gccaccagct      1020 cacaggaact tcctgtgctc attagagtca aatccctcag tccgtgagtt tgtcctttca     1080
aaaggtgatg ctggcctgcg ggaagcttat gacgcctgtg tgaaagctct ggtctccctg     1140
aggagctacc atctgcaaat cgtgactaag tacatcctga ttcctgcaag ccagcagcca     1200
aaggagaata agacctctga agacccttca aaactggaag ccaaaggaac tggaggcact     1260
gatttaatga atttcctgaa gactgtaaga agtacaactg agaaatccct tttgaaggaa     1320
ggttaatgta acccaacaag agcacatttt atcatagcag agacatctgt atgcattcct     1380
gtcattaccc attgtaacag agccacaaac taatactatg caatgttta ccaataatgc      1440 aatacaaaag acctcaaaat acctgtgcat ttcttgtagg aaaacaacaa aaggtaatta     1500
tgtgtaatta tactagaagt tttgtaatct gtatcttatc attggaataa aatgacattc     1560
aataaataaa aatgcataag atatattctg tcggctgggc gcggtggctc acgcctgtaa     1620
tcccagcact ttgggaggcc gaggcgggcg gatcacaagg tcaggagatc gagaccatct     1680
tggctaacac ggtgaaaccc cgtctctact aaaaatacaa aaaattagcc gggcgcggtg     1740
gcgggcacct gtagtcccag ctactcggga ggctgaggca ggagaatggc gtgaacctgg     1800
gaggcggagc ttgcagtgag ccaagattgt gccactgcaa tccggcctgg gctaaagagc     1860
gggactccgt ctcaaaaaaa aaaaaaaaaa gatatattct gtcataataa ataaaaatgc     1920
ataagatata aaaaaaaaaa aaaa                                            1944

<210> SEQ ID NO 85
<211> LENGTH: 2119
<212> TYPE: DNA
<213> ORGANISM: Homo sapiens

<400> SEQUENCE: 85
aagtcagggt gggacgtggg cgcggggaga caggtggtgg ctacgacggc gaagggagct       60
gagactgtcc aggcagccag gttaggccag gaggaccatg tgaatgggc cagagggctc       120 ccgggctggg cagggaccat gggctgtggc tgcagctcac acccggaaga tgactggatg      180
gaaaacatcg atgtgtgtga gaactgccat tatcccatag tcccactgga tggcaagggc      240
acgctgctca tccgaaatgg ctctgagtg cgggaccca tggttaccta cgaaggctcc       300
aatccgccgg cttccccact gcaagacaac ctggttatcg ctctgcacag ctatgagccc      360
tctcacgacg gagatctggg cttttgagaag ggaacagc tccgcatcct ggagcagagc      420
ggcgagtggt ggaaggcgca gtccctgacc acgggccagg aaggcttcat cccccttcaat     480
```

| | |
|---|---|
| tttgtggcca aagcgaacag cctggagccc gaaccctggt tcttcaagaa cctgagccgc | 540 |
| aaggacgcgg agcggcagct cctggcgccc gggaacactc acggctcctt cctcatccgg | 600 |
| gagagcgaga gcaccgcggg atcgttttca ctgtcggtcc gggacttcga ccagaaccag | 660 |
| ggagaggtgg tgaaacatta caagatccgt aatctggaca acgtggcttc tacatctcc | 720 |
| cctcgaatca cttttcccgg cctgcatgaa ctggtccgcc attacaccaa tgcttcagat | 780 |
| gggctgtgca cacggttgag ccgcccctgc cagacccaga agcccagaa gccgtggtgg | 840 |
| gaggacgagt gggaggttcc cagggagacg ctgaagctgg tggagcggct ggggctgga | 900 |
| cagttcgggg aggtgtggat ggggtactac aacgggcaca cgaaggtggc ggtgaagagc | 960 |
| ctgaagcagg gcagcatgtc cccggacgcc ttcctggccg aggccaacct catgaagcag | 1020 |
| ctgcaacacc agcggctggt tcggctctac gctgtggtca cccaggagcc catctacatc | 1080 |
| atcactgaat acatggagaa tgggagtcta gtggattttc tcaagacccc ttcaggcatc | 1140 |
| aagttgacca tcaacaaact cctggacatg gcagcccaaa ttgcagaagg catggcattc | 1200 |
| attgaagagc ggaattatat tcatcgtgac cttcgggctg ccaacattct ggtgtctgac | 1260 |
| accctgagct gcaagattgc agactttggc ctagcacgcc tcattgagga caacgagtac | 1320 |
| acagccagga aggggccaa gtttcccatt aagtggacag cgccagaagc cattaactac | 1380 |
| gggacattca ccatcaagtc agatgtgtgg tcttttggga tcctgctgac ggaaattgtc | 1440 |
| acccacggcc gcatccctta cccagggatg accaacccgg aggtgattca gaacctggag | 1500 |
| cgaggctacc gcatggtgcg ccctgacaac tgtccagagg agctgtacca actcatgagg | 1560 |
| ctgtgctgga aggagcgccc agaggaccgg cccacctttg actacctgcg cagtgtgctg | 1620 |
| gaggacttct tcacggccac agagggccag taccagcctc agccttgaga ggccttgaga | 1680 |
| ggccctgggg ttctccccct ttctctccag cctgacttgg ggagatggag ttcttgtgcc | 1740 |
| atagtcacat ggcctatgca catatggact ctgcacatga atcccaccca catgtgacac | 1800 |
| atatgcacct tgtgtctgta cacgtgtcct gtagttgcgt ggactctgca catgtcttgt | 1860 |
| acatgtgtag cctgtgcatg tatgtcttgg acactgtaca aggtacccct ttctggctct | 1920 |
| cccatttcct gagaccacag agagagggga gaagcctggg attgacagaa gcttctgccc | 1980 |
| acctactttt cttcctcag atcatccaga agttcctcaa gggccaggac tttatctaat | 2040 |
| acctctgtgt gctcctcctt ggtgcctggc ctggcacaca tcaggagttc aataaatgtc | 2100 |
| tgttgatgac tgttgtaca | 2119 |

<210> SEQ ID NO 86
<211> LENGTH: 2098
<212> TYPE: DNA
<213> ORGANISM: Homo sapiens

<400> SEQUENCE: 86

| | |
|---|---|
| attataaatc tagagactcc aggattttaa cgttctgctg gactgagctg gttgcctcat | 60 |
| gttattatgc aggcaactca ctttatccca atttcttgat acttttcctt ctggaggtcc | 120 |
| tatttctcta acatcttcca gaaagtcttt aaagctgcct taaccttttt tccagtccac | 180 |
| ctcttaaatt ttttcctcct cttcctctat actaacatga gtgtggatcc agcttgtccc | 240 |
| caaagcttgc cttgctttga agcatccgac tgtaaagaat cttcacctat gcctgtgatt | 300 |
| tgtgggcctg aagaaaacta tccatccttg caaatgtctt ctgctgagat gcctcacacg | 360 |
| gagactgtct ctcctcttcc ttcctccatg gatctgctta ttcaggacag ccctgattct | 420 |
| tccaccagtc ccaaaggcaa acaacccact tctgcagaga agagtgtcgc aaaaaaggaa | 480 |

```
gacaaggtcc cggtcaagaa acagaagacc agaactgtgt tctcttccac ccagctgtgt    540
gtactcaatg atagatttca gagacagaaa tacctcagcc tccagcagat gcaagaactc    600
tccaacatcc tgaacctcag ctacaaacag gtgaagacct ggttccagaa ccagagaatg    660
aaatctaaga ggtggcagaa aaacaactgg ccgaagaata gcaatggtgt gacgcagaag    720
gcctcagcac ctacctaccc cagcctttac tcttcctacc accagggatg cctggtgaac    780
ccgactggga accttccaat gtggagcaac cagacctgga caattcaac ctggagcaac    840 cagacccaga catccagtc tggagcaac cactcctgga acactcagac tggtgcacc    900 caatcctgga caatcaggc ctggaacagt cccttctata actgtggaga ggaatctctg    960
cagtcctgca tgcagttcca gccaaattct cctgccagtg acttggaggc tgccttggaa   1020
gctgctgggg aaggccttaa tgtaatacag cagaccacta ggtattttag tactccacaa   1080
accatggatt tattcctaaa ctactccatg aacatgcaac ctgaagacgt gtgaagatga   1140
gtgaaactga tattactcaa tttcagtctg gacactggct gaatccttcc tctccctcc   1200 tcccatccct cataggattt ttcttgtttg aaaccacgt gttctggttt ccatgatgcc   1260
catccagtca atctcatgga gggtggagta tggttggagc taatcagcg aggtttcttt   1320 tttttttttt ttcctattgg atcttcctgg agaaaatact tttttttttt tttttttga    1380 aacggagtct tgctctgtcg cccaggctgg agtgcagtgg cgcggtcttg gctcactgca   1440
agctccgtct cccgggttca cgccattctc ctgcctcagc ctcccgagca gctgggacta   1500
caggcgcccg ccacctcgcc cggctaatat tttgtatttt tagtagagac ggggtttcac   1560
tgtgttagcc aggatggtct cgatctcctg accttgtgat ccacccgcct cggcctccct   1620
aacagctggg atttacaggc gtgagccacc gcgcccctgcc tagaaaagac attttaataa   1680
ccttggctgc cgtctctggc tatagataag tagatctaat actagtttgg atatctttag   1740
ggtttagaat ctaacctcaa gaataagaaa tacaagtaca aattggtgat gaagatgtat   1800
tcgtattgtt tgggattggg aggctttgct tatttttaa aaactattga ggtaaagggt   1860
taagctgtaa catacttaat tgatttctta ccgttttgg ctctgttttg ctatatcccc   1920
taatttgttg gttgtgctaa tctttgtaga aagaggctc gtatttgctg catcgtaatg   1980
acatgagtac tgctttagtt ggtttaagtt caaatgaatg aaacaactat ttttccttta   2040
gttgatttta ccctgatttc accgagtgtt tcaatgagta aatatacagc ttaaacat    2098
```

<210> SEQ ID NO 87
<211> LENGTH: 2075
<212> TYPE: DNA
<213> ORGANISM: Homo sapiens

<400> SEQUENCE: 87

```
ggaaaaaagg aaagtgcact tggaagagat ccaagtgggc aacttgaaga acaagtgcca     60
aatagcactt ctgtcatgct ggatgtcagg gctctttgtc cactttgtat agccgctggc    120
ttatagaagg tgctcgataa atctcttgaa tttaaaaatc aattaggatg cctctatagt    180 gaaaagata cagtaaagat gagggataat caatttaaaa aatgagtaag tacacacaaa    240
gcactttatc cattcttatg acacctgtta ctttttttgct gtgtttgtgt gtatgcatgc    300
catgttatag tttgtgggac cctcaaagca agctggggag agtatatact gaatttagct    360
tctgagacat gatgctcttc ctttttaatt aacccagaac ttagcagctt atctatttct    420
ctaatctcaa aacatcctta aactgggggt gatacttgag tgagagaatt ttgcaggtat    480
```

```
taaatgaact atcttctttt ttttttttct ttgagacaga gtcttgctct gtcacccagg    540
ctggagtgca gtggcgtgat ctcagctcac tgcaacctcc gcctcccggg ttcaagtgat    600
tctcctgcct cagcctcctg agtagctggg attacaggtg cgtgccaccg tgcccagcta    660
attttttgtgt ttttagtaga cacggggttt caccatgttg gccatgctgg tcttgaactc    720
ctgacctcgt gatctgccca cctcggcctc ccaaagtgct ggaattatag gcgtgagcca    780
ccgcgcccag caaagaactt ctaaccttca taacctgaca ggtgttctcg aggccagggt    840
ctctctttct gtcctttcac gatgctctgc atcccttgga tgtgccagtt tctgggggaa    900
gagtagtcct ttgttacatg catgagtcag tgaacaggga atgggtgaat gacatttgtg    960
ggtaggttat ttctagaagt taggtgggca gcttggaagg cagaggcact tctacagact   1020
attccttggg gccacacgta ggttcttgaa tcccgaatgg aaaggggaga ttgataactg   1080
gtgtgtttat gttcttacaa gtcttctgcc ttttaaaatc cagtcccagg acatcaaagc   1140
tctgcagaaa gaactcgagc aatttgccaa gctcctgaag cagaagagga tcaccctggg   1200
atatacacag gccgatgtgg ggctcaccct gggggttcta tttgggaagg tattcagcca   1260
aacgaccatc tgccgctttg aggctctgca gcttagcttc aagaacatgt gtaagctgcg   1320
gccccttgctg cagaagtggg tggaggaagc tgacaacaat gaaaatcttc aggagatatg   1380
caaagcagaa accctcgtgc aggcccgaaa gagaaagcga accagtatcg agaaccgagt   1440
gagaggcaac ctggagaatt tgttcctgca gtgcccgaaa cccacactgc agcagatcag   1500
ccacatcgcc cagcagcttg ggctcgagaa ggatgtggtc cgagtgtggt tctgtaaccg   1560
gcgccagaag ggcaagcgat caagcagcga ctatgcacaa cgagaggatt ttgaggctgc   1620
tgggtctcct ttctcagggg accagtgtc cttttcctctg gccccagggc cccattttgg   1680
taccccagcc tatgggagcc ctcacttcac tgcactgtac tcctcggtcc ctttccctga   1740
ggggaagcc tttcccctg tctccgtcac cactctgggc tctcccatgc attcaaactg   1800
aggtgcctgc ccttctagga atgggggaca ggggagggg aggagctagg aaagaaaac   1860
ctggagtttg tgccagggtt tttgggatta agttcttcat tcactaagga aggaattggg   1920
aacacaaagg gtgggggcag gggagtttgg ggcaactggt tggagggaag gtgaagttca   1980
atgatgctct tgattttaat cccacatcat gtatcacttt tttcttaaat aaagaagcct   2040
gggacacagt agatagacac acttaaaaaa aaaaa                              2075

<210> SEQ ID NO 88
<211> LENGTH: 2520
<212> TYPE: DNA
<213> ORGANISM: Homo sapiens

<400> SEQUENCE: 88
ggatggttgt ctattaactt gttcaaaaaa gtatcaggag ttgtcaaggc agagaagaga     60
gtgtttgcaa aagggggaaa gtagtttgct gcctctttaa gactaggact gagagaaaga    120
agaggagaga gaaagaaagg gagagaagtt tgagccccag gcttaagcct ttccaaaaaa    180
taataataac aatcatcggc ggcggcagga tcggccagag gaggagggaa gcgcttttt     240
tgatcctgat tccagtttgc ctctctcttt ttttccccca aattattctt cgcctgattt    300
tcctcgcgga gccctgcgct cccgacaccc ccgcccgcct cccctcctcc tctcccccg     360
cccgcgggcc cccaaagtc ccggccgggc cgagggtcgg cggccgcgg cgggccgggc    420
ccgcgcacag cgcccgcatg tacaacatga tggagacgga gctgaagccg ccgggccccg    480
agcaaacttc ggggggcggc ggcggcaact ccaccgcggc ggcggccggc ggcaaccaga    540
```

```
aaaacagccc ggaccgcgtc aagcggccca tgaatgcctt catggtgtgg tcccgcgggc    600
agcggcgcaa gatggcccag gagaacccca agatgcacaa ctcggagatc agcaagcgcc    660
tgggcgccga gtggaaactt ttgtcggaga cggagaagcg gccgttcatc gacgaggcta    720
agcggctgcg agcgctgcac atgaaggagc acccggatta taaataccgg ccccggcgga    780
aaaccaagac gctcatgaag aaggataagt acacgctgcc cggcgggctg ctggcccccg    840
gcggcaatag catggcgagc ggggtcgggg tgggcgccgg cctgggcgcg ggcgtgaacc    900
agcgcatgga cagttacgcg cacatgaacg gctggagcaa cggcagctac agcatgatgc    960
aggaccagct gggctacccg cagcacccgg gcctcaatgc gcacggcgca gcgcagatgc   1020
agcccatgca ccgctacgac gtgagcgccc tgcagtacaa ctccatgacc agctcgcaga   1080
cctacatgaa cggctcgccc acctacagca tgtcctactc gcagcagggc acccctggca   1140
tggctcttgg ctccatgggt tcggtggtca agtccgaggc cagctccagc ccccctgtgg   1200
ttacctcttc ctcccactcc agggcgccct gccaggccgg ggacctccgg gacatgatca   1260
gcatgtatct ccccggcgcc gaggtgccgg aacccgccgc cccagcagac cttcacatgt   1320
cccagcacta ccagagcggc ccggtgcccg gcacggccat taacggcaca ctgcccctct   1380
cacacatgtg agggccggac agcgaactgg aggggggaga aattttcaaa gaaaaacgag   1440
ggaaatggga ggggtgcaaa agaggagagt aagaaacagc atggagaaaa cccggtacgc   1500 tcaaaagaa aaggaaaaa aaaaaatccc atcacccaca gcaaatgaca gctgcaaaag   1560
agaacaccaa tcccatccac actcacgcaa aaaccgcgat gccgacaaga aaacttttat   1620
gagagagatc ctggacttct ttttgggga ctatttttgt acagagaaaa cctggggagg   1680
gtggggaggg cggggaatg gaccttgtat agatctggag gaaagaaagc tacgaaaaac   1740 ttttaaaag ttctagtggt acggtaggag ctttgcagga gtttgcaaa gtctttacc   1800 aataatattt agagctagtc tccaagcgac gaaaaaaatg ttttaatatt tgcaagcaac   1860
ttttgtacag tatttatcga gataaacatg gcaatcaaaa tgtccattgt ttataagctg   1920
agaatttgcc aatatttttc aaggagaggc ttcttgctga attttgattc tgcagctgaa   1980
atttaggaca gttgcaaacg tgaaagaag aaaattattc aaatttggac attttaattg   2040
tttaaaaatt gtacaaaagg aaaaaattag aataagtact ggcgaaccat ctctgtggtc   2100
ttgtttaaaa agggcaaaag ttttagactg tactaaattt tataacttac tgttaaaagc   2160
aaaaatggcc atgcaggttg acaccgttgg taatttataa agcttttgt tcgatcccaa   2220 cttccattt tgttcagata aaaaaaacca tgaaattact gtgtttgaaa tattttctta   2280
tggtttgtaa tatttctgta aatttattgt gatatttaa ggttttcccc cctttatttt   2340
ccgtagttgt attttaaaag attcggctct gtattatttg aatcagtctg ccagaatcc   2400 atgtatatat ttgaactaat atcatcctta taacaggtac attttcaact taagttttta   2460
ctccattatg cacagtttga gataaataaa ttttgaaat atggacactg aaaaaaaaaa   2520
```

<210> SEQ ID NO 89
<211> LENGTH: 3111
<212> TYPE: DNA
<213> ORGANISM: Homo sapiens

<400> SEQUENCE: 89

```
aaatattctt gcttgagtaa accacagtaa gaataaggaa gtagtgactg agtgccttgc     60
cagtacagca gatgctagaa cataatgtag cattactttc cccagggttt attgttatgt    120
```

```
aagttcttgt tcagcttcct ttgttttctt tcacttctga gaatttaact ttcgtttctc    180
actcagctcc tgtggggaaa ctcatttgtg gagaccagcc ctctggcttg gtgagtgaat    240
ctggtttaca ccggctcctg ccctgccttc actcttctcc cctgattcaa gactcctctg    300
ctttggactg aagcactgca ggagtttgtg accaagaact tcaagagtca agacagaagg    360
aagccaaggg agcagtgcaa tggatttctc agtaaaggta gacatagaga aggaggtgac    420
ctgccccatc tgcctggagc tcctgacaga acctctgagc ctagattgtg ccacagctt     480 ctgccaagcc tgcatcactg caaagatcaa ggagtcagtg atcatctcaa gaggggaaag    540
cagctgtcct gtgtgtcaga ccagattcca gcctgggaac ctccgaccta atcggcatct    600
ggccaacata gttgagagag tcaaagaggt caagatgagc ccacaggagg ggcagaagag    660
agatgtctgt gagcaccatg gaaaaaaact ccagatcttc tgtaaggagg atggaaaagt    720
catttgctgg gtttgtgaac tgtctcagga acaccaaggt caccaaacat tccgcataaa    780
cgaggtggtc aaggaatgtc aggaaaagct gcagtagcc ctgcagaggc tgataaagga     840
ggatcaagag gctgagaagc tggaagatga catcagacaa gagagaaccg cctggaagaa    900
ttatatccag atcgagagac agaagattct gaaagggttc aatgaaatga gagtcatctt    960
ggacaatgag gagcagagag agctgcaaaa gctggaggaa ggtgaggtga atgtgctgga   1020
taacctggca gcagctacag accagctggt ccagcagagg caggatgcca gcacgctcat   1080
ctcagatctc cagcggaggt tgaggggatc gtcagtagag atgctgcagg atgtgattga   1140
cgtcatgaaa aggagtgaaa gctggacatt gaagaagcca aaatctgttt ccaagaaact   1200 aaaagagtgta ttccgagtac cagatctgag tgggatgctg caagttctta aagagctgac  1260
agatgtccag tactactggg tggacgtgat gctgaatcca ggcagtgcca cttcgaatgt   1320
tgctatttct gtggatcaga gacaagtgaa aactgtacgc acctgcacat ttaagaattc   1380
aaatccatgt gatttttctg cttttggtgt cttcggctgc caatatttct cttcggggaa   1440
atattactgg gaagtagatg tgtctggaaa gattgcctgg atcctgggcg tacacagtaa   1500
aataagtagt ctgaataaaa ggaagagctc tgggtttgct tttgatccaa gtgtaaatta   1560
ttcaaaagtt tactccagat atagacctca atatggctac tgggttatag gattacagaa   1620
tacatgtgaa tataatgctt ttgaggactc ctcctcttct gatcccaagg ttttgactct   1680
ctttatggct gtgcctccct gtcgtattgg ggttttccta gactatgagg caggcattgt   1740 ctcattttc aatgtcacaa accacggagc actcatctac aagttctctg gatgtcgctt    1800
ttctcgacct gcttatccgt atttcaatcc ttggaactgc ctagtcccca tgactgtgtg   1860
cccaccgagc tcctgagtgt tctcattcct ttacccactt ctgcatagta gcccttgtgc   1920
tgagactcag attctgcacc tgagttcatc tctactgaga ccatctcttc ctttcttcc    1980 ccttctttta cttagaatgt ctttgtattc atttgctagg gcttccatag caaagcatca   2040
tagattgctg atttaaactg taattgtatt gccgtactgt gggctggaaa tcccaaatct   2100
agattccagc agagttggtt cttttctgagg tctgcaagga agggctctgt tccatgcctc   2160
tctccttggc ttgtagaagg catcttgtcc ctatgactct tcacattgtc tttatgtaca   2220
tctctgtgcc caagttttcc ctttttatta agacaccagt catactggct cagggcccac   2280
cgctaatgcc ttaatgaaat cattttaaca ttatattctc tacaaagacc ttatttccaa    2340
ataagataat atttggaggt attgggaata aaaactccaa catataaatt tgaggaaggc   2400
acgatttcac tcataacaat cttaccctt cttgcaagag atgcttgtac attatttcc     2460 taataccttg gtttcactag tagtaaacat tattatttt tttatatttg caaaggaaac    2520
```

| | |
|---|---|
| atatctaatc cttcctatag aaagaacagt attgctgtaa ttccttttct tttcttcctc | 2580 |
| atttcctctg ccccttaaaa gattgaagaa agagaaactt gtcaactcat atccacgtta | 2640 |
| tctagcaaag tacataagaa tctatcacta agtaatgtat ccttcagaat gtgttggttt | 2700 |
| accagtgaca ccccatattc atcacaaaat taaagcaaga agtccatagt aatttatttg | 2760 |
| ctaatagtgg atttttaatg ctcagagttt ctgaggtcaa attttatctt ttcacttaca | 2820 |
| agctctatga tcttaaataa tttacttaat gtattttggt gtattttcct caaattaata | 2880 |
| ttggtgttca agactatatc taattcctct gatcactttg agaaacaaac ttttattaaa | 2940 |
| tgtaaggcac ttttctatga atttttaaata taaaaataaa tattgttctg attattactg | 3000 |
| aaaagatgtc agccatttca atgtcttggg aaacaatttt ttgttttttgt tctgttttct | 3060 |
| ttttgcttca ataaaacaat agctggctct aaaaaaaaaa aaaaaaaaaa a | 3111 |

```
<210> SEQ ID NO 90
<211> LENGTH: 1852
<212> TYPE: DNA
<213> ORGANISM: Homo sapiens

<400> SEQUENCE: 90
```

| | |
|---|---|
| accgccgaga ccgcgtccgc cccgcgagca cagagcctcg cctttgccga tccgccgccc | 60 |
| gtccacaccc gccgccagct caccatggat gatgatatcg ccgcgctcgt cgtcgacaac | 120 |
| ggctccggca tgtgcaaggc cggcttcgcg ggcgacgatg ccccccgggc cgtcttcccc | 180 |
| tccatcgtgg ggcgcccag gcaccagggc gtgatggtgg gcatgggtca gaaggattcc | 240 |
| tatgtgggcg acgaggccca gagcaagaga ggcatcctca ccctgaagta ccccatcgag | 300 |
| cacggcatcg tcaccaactg ggacgacatg gagaaaatct ggcaccacac cttctacaat | 360 |
| gagctgcgtg tggctcccga ggagcacccc gtgctgctga ccgaggcccc cctgaacccc | 420 |
| aaggccaacc gcgagaagat gacccagatc atgtttgaga ccttcaacac cccagccatg | 480 |
| tacgttgcta tccaggctgt gctatccctg tacgcctctg gccgtaccac tggcatcgtg | 540 |
| atggactccg gtgacggggt cacccacact gtgcccatct acgaggggta tgccctcccc | 600 |
| catgccatcc tgcgtctgga cctggctggc cgggacctga ctgactacct catgaagatc | 660 |
| ctcaccgagc gcggctacag cttcaccacc acggccgagc gggaaatcgt gcgtgacatt | 720 |
| aaggagaagc tgtgctacgt cgccctggac ttcgagcaag agatggccac ggctgcttcc | 780 |
| agctcctccc tggagaagag ctacgagctg cctgacggcc aggtcatcac cattggcaat | 840 |
| gagcggttcc gctgccctga ggcactcttc agccttcct tcctgggcat ggagtcctgt | 900 |
| ggcatccacg aaactacctt caactccatc atgaagtgtg acgtggacat ccgcaaagac | 960 |
| ctgtacgcca acacagtgct gtctggcggc accaccatgt accctggcat tgccgacagg | 1020 |
| atgcagaagg agatcactgc cctggcaccc agcacaatga agatcaagat cattgctcct | 1080 |
| cctgagcgca agtactccgt gtggatcggc ggctccatcc tggcctcgct gtccaccttc | 1140 |
| cagcagatgt ggatcagcaa gcaggagtat gacgagtccg gcccctccat cgtccaccgc | 1200 |
| aaatgcttct aggcggacta tgacttagtt gcgttacacc ctttcttgac aaaacctaac | 1260 |
| ttgcgcagaa aacaagatga gattggcatg gctttatttg ttttttttgt tttgttttgg | 1320 |
| tttttttttt tttttttggct tgactcagga tttaaaaact ggaacggtga aggtgacagc | 1380 |
| agtcggttgg agcgagcatc ccccaaagtt cacaatgtgg ccgaggactt tgattgcaca | 1440 |
| ttgttgtttt tttaatagtc attccaaata tgagatgcgt tgttacagga agtcccttgc | 1500 |

| | |
|---|---|
| catcctaaaa gccaccccac ttctctctaa ggagaatggc ccagtcctct cccaagtcca | 1560 |
| cacaggggag gtgatagcat tgctttcgtg taaattatgt aatgcaaaat ttttttaatc | 1620 |
| ttcgccttaa tactttttta ttttgtttta ttttgaatga tgagccttcg tgccccccct | 1680 |
| tccccctttt ttgtcccca acttgagatg tatgaaggct tttggtctcc ctggagtgg | 1740 |
| gtggaggcag ccagggctta cctgtacact gacttgagac cagttgaata aaagtgcaca | 1800 |
| ccttaaaaat gaaaaaaaaa aaaaaaaaa aaaaaaaaaa aa | 1852 |

```
<210> SEQ ID NO 91
<211> LENGTH: 2985
<212> TYPE: DNA
<213> ORGANISM: Homo sapiens

<400> SEQUENCE: 91
```

| | |
|---|---|
| cccatgctgc cctgcgccaa cccctcccct cacctttcct ccccccgccct ctactcgccg | 60 |
| cccggccggt cccccaccc gtcccttccc ttatcagcac ccgcggcccc ggcagcgccg | 120 |
| acgcaggcgc actgcaccgc gccgccgcca ttttgtgtct gagcctgtgg agcgattaaa | 180 |
| ccgtgcgcgg agctgcttct ttggcggcag cggcggcggc ggtggccggt gcggacgcgc | 240 |
| ggagctcgcc ggagacgccg ggtggccgga gccgtggagc ggcggcggag cgggcgccgc | 300 |
| gggggggtgtg gcgcggagaa tgattacgga cctgaagcca aagaacaaga tgcgctagtg | 360 |
| gacagattgc tgaccagggg cttgagagct gggttctatt ttccctcctc aaactgactt | 420 |
| tgcagccacg gagaggtact cgtcctcaca agtgcccaga ctgcgacatg gcctttgtga | 480 |
| ccagtggaga attggttcgg catcgtcgtt acaaacacac ccacgagaag ccattcaagt | 540 |
| gttccatgtg cgattacgcc agtgtagaag tcagcaaatt aaaacgtcac attcgctctc | 600 |
| atactggaga gcgtccgttt cagtgcagtt tgtgcagtta tgccagcagg gacacataca | 660 |
| agctgaaaag gcacatgaga acccattcag gggaaaagcc ttatgaatgt tatatttgtc | 720 |
| atgctcggtt tacccaaagt ggtaccatga agatgcacat tttacagaag cacacagaaa | 780 |
| atgtggccaa atttcactgt ccccactgtg acacagtcat agcccgaaaa agtgatttgg | 840 |
| gtgtccactt gcgaaagcag cattcctata ttgagcaagg caagaaatgc cgttactgtg | 900 |
| atgctgtgtt tcatgagcgc tatgccctca tccagcatca gaagtcacac aagaatgaga | 960 |
| agcgctttaa gtgtgaccag tgtgattacg cttgtagaca ggagaggcac atgatcatgc | 1020 |
| acaagcgcac ccacaccggg gagaagcctt acgcctgcag ccactgcgat aagaccttcc | 1080 |
| gccagaagca gcttctcgac atgcacttca gcgctatca cgaccccaac ttcgtccctg | 1140 |
| cggcttttgt ctgttctaag tgtgggaaaa catttacacg tcggaatacc atggcaagac | 1200 |
| atgctgataa ttgtgctggc ccagatggcg tagaggggga aaatggagga gaaacgaaga | 1260 |
| agagtaaacg tggaagaaaa agaaagatgc gctctaagaa agaagattcc tctgacagtg | 1320 |
| aaaatgctga accagatctg gacgacaatg aggatgagga ggagcctgcc gtagaaattg | 1380 |
| aacctgagcc agagcctcag cctgtgaccc cagccccacc acccgccaag aagcggagag | 1440 |
| gacgaccccc tggcagaacc aaccagccca acagaaccca gccaacagct atcattcagg | 1500 |
| ttgaagacca gaatacaggt gcaattgaga acattatagt tgaagtaaaa aaagagccag | 1560 |
| atgctgagcc cgcagaggga gaggaagagg aggcccagcc agctgccaca gatgccccca | 1620 |
| acggagacct cacgcccgag atgatcctca gcatgatgga ccggtgatgg cggagccttg | 1680 |
| tgcgtcgcca ggacttctct gggctgtgtt taaacggccc gcatcttaat ttttctcct | 1740 |
| tctttctttt tttggctttg ggaaaagcat cattttacca aacataccga gaacgaaaac | 1800 |

```
ttcaaggatg atgttagaaa aaaatgtgat ttaactagaa cttgctgtct gatgttagca    1860
aatcatggaa tgttctgagt ccctgagggt ttactgtgaa gtgctgagga cagtgttgac    1920
aactaactcg ttttcctaga tggaaacgga gacattgacc cctccctcca tgtggtaaac    1980
cactccagaa tggccaccag gcttcccaga gttctatggt cttcttccca agagagtttt    2040
taattgtaaa tgcatacttg ggaaggactt agagttttaa actgtttttt gcttttgctt    2100
ttccctgact ccctttgctt ggagtcagct gcacaccagt agtatggcat gctacgatca    2160
ggttctgtcc tgaaagcttt gcctctttct tggcaaagtt tctggtatgg tcaagcttgt    2220
aaataacttt ttttacattt taatcttttc cattaattaa gaggttgaaa agaagtgcag    2280
tgtaagaaaa cccagcattt taattacttg caaattaagt taccacagac tctgtagtgt    2340
gtaaatgttg acaaggaatt ggatcacaat catgtagcag aatggcaccc agaccactgc    2400
ccaccagtga cggacatgca cgtggcagat catgatttcc agcccacgga gccagcattt    2460
gaaccttgta taattaactt tcagttatga tttcccatcg acattttctt tgccctgttt    2520
gtagctgatt gttgtgtttt ataaatcttc tgttaaggca gaagggtgat tatgagtggt    2580
tcacagcagc ccttataagc tgggccagaa aatttcacta ggtcagtaat ttaaaccttg    2640
gatcttcaaa aaataaaata atgtgaagca aaaccaacta aaaagtgatt cttgcacatg    2700
aactgtcaca tgtttaaaaa tgtgtttttt agagagcctc agtcttactg atttcaaaca    2760
cttttttctt ctgtgtattg cttttaagag agccatcagt tagctatcag actctaggtt    2820
gatgcatttt gtacttagct gtactgtgtg atatttttca ttattttagg acgccaacat    2880
gagacctgta ataaaatatg taatgggtt gaaagctggg gaggaggatc tactgctgta    2940
cagctaataa atcataacgg attaacaagt gctccaaaga aaaaa                   2985

<210> SEQ ID NO 92
<211> LENGTH: 3946
<212> TYPE: DNA
<213> ORGANISM: Homo sapiens

<400> SEQUENCE: 92
cccatgctgc cctgcgccaa cccctcccct cacctttcct ccccgccct ctactcgccg      60 cccggccggt ccccccaccc gtcccttccc ttatcagcac ccgcggcccc ggcagcgccg    120
acgcaggcgc actgcaccgc gccgccgcca ttttgtgtct gagcctgtgg agcgattaaa    180
ccgtgcgcgg agctgcttct ttggcggcag cggcggcggc ggtggccggt gcggacgcgc    240
ggagctcgcc ggagacgccg ggtggccgga gccgtggagc ggcggcggag cgggcgccgc    300 gggggggtgtg gcgcggagaa tgattacgga cctgaagcca agaacaaga tgcgctagtg    360 gacagattgc tgaccagggg cttgagagct gggttctatt ttccctcctc aaactgactt    420
tgcagccacg gagaggcagg ggaaatggaa ggtgatgcag tcgaagccat tgtggaggag    480
tccgaaactt ttattaaagg aaaggagaga aagacttacc agagacgccg ggaagggggc    540
caggaagaag atgcctgcca cttaccccag aaccagacgg atgggggtga ggtggtccag    600
gatgtcaaca gcagtgtaca gatggtgatg atggaacagc tggaccccac ccttcttcag    660
atgaagactg aagtaatgga gggcacagtg gctccagaag cagaggctgc tgtggacgat    720
acccagatta taactttaca ggttgtaaat atggaggaac agcccataaa cataggagaa    780
cttcagcttt gtcaagtacc tgttcctgtg actgtacctg ttgctaccac ttcagtagaa    840
gaacttcagg gggcttatga aaatgaagtg tctaaagagg gccttgcgga aagtgaaccc    900
```

```
atgatatgcc acaccctacc tttgcctgaa gggtttcagg tggttaaagt gggggccaat    960
ggagaggtgg agacactaga acaaggggaa cttccacccc aggaagatcc tagttggcaa   1020
aaagacccag actatcagcc accagccaaa aaacaaaga aaccaaaaa gagcaaactg    1080
cgttatacag aggagggcaa agatgtagat gtgtctgtct acgattttga ggaagaacag   1140
caggagggtc tgctatcaga ggttaatgca gagaaagtgg ttggtaatat gaagcctcca   1200
aagccaacaa aaattaaaaa gaaggtgta aagaagacat tccagtgtga gctttgcagt   1260
tacacgtgtc cacggcgttc aaatttggat cgtcacatga aaagccacac tgatgagaga   1320
ccacacaagt gccatctctg tggcagggca ttcagaacag tcaccctcct gaggaatcac   1380
cttaacacac acacaggtac tcgtcctcac aagtgcccag actgcgacat ggcctttgtg   1440
accagtggag aattggttcg gcatcgtcgt tacaaacaca cccacgagaa gccattcaag   1500
tgttccatgt gcgattacgc cagtgtagaa gtcagcaaat taaaacgtca cattcgctct   1560
catactggag agcgtccgtt tcagtgcagt ttgtgcagtt atgccagcag ggacacatac   1620
aagctgaaaa ggcacatgag aacccattca ggggaaaagc cttatgaatg ttatatttgt   1680
catgctcggt ttacccaaag tggtaccatg aagatgcaca ttttacagaa gcacacagaa   1740
aatgtggcca aatttcactg tccccactgt gacacagtca tagcccgaaa aagtgatttg   1800
ggtgtccact tgcgaaagca gcattcctat attgagcaag gcaagaaatg ccgttactgt   1860
gatgctgtgt tcatgagcg ctatgccctc atccagcatc agaagtcaca caagaatgag   1920
aagcgcttta gtgtgaccag tgtgattac gcttgtagac aggagaggca catgatcatg   1980
cacaagcgca cccacaccgg ggagaagcct tacgcctgca gccactgcga taagaccttc   2040
cgccagaagc agcttctcga catgcacttc aagcgctatc acgacccca cttcgtccct   2100
gcggcttttg tctgttctaa gtgtgggaaa acatttacac gtcggaatac catggcaaga   2160
catgctgata attgtgctgg cccagatggc gtagagggg aaaatggagg agaaacgaag   2220
aagagtaaac gtgaagaaa aagaaagatg cgctctaaga agaagattc ctctgacagt   2280
gaaaatgctg aaccagatct ggacgacaat gaggatgagg aggagcctgc cgtagaaatt   2340
gaacctgagc cagagcctca gcctgtgacc ccagccccac cacccgccaa gaagcggaga   2400
ggacgacccc ctggcagaac caaccagccc aaacagaacc agccaacagc tatcattcag   2460
gttgaagacc agaatacagg tgcaattgag aacattatag ttgaagtaaa aaaagagcca   2520
gatgctgagc ccgcagaggg agaggaagag gaggcccagc cagctgccac agatgccccc   2580
aacgagacc tcacgcccga tgatcctc agcatgatgg accggtgatg gcggagcctt    2640
gtgcgtcgcc aggacttctc tgggctgtgt ttaaacggcc cgcatcttaa ttttctccc    2700
ttctttcttt ttttggcttt gggaaaagca tcattttacc aaacataccg agaacgaaaa   2760
cttcaaggat gatgttagaa aaaaatgtga tttaactaga acttgctgtc tgatgttagc   2820
aaatcatgga atgttctgag tccctgaggg tttactgtga agtgctgagg acagtgttga   2880
caactaactc gttttcctag atggaaacgg agacattgac ccctcccccc atgtgggtaaa   2940
ccactccaga atggccacca ggcttcccag agttctatgg tcttcttccc aagagagttt   3000
ttaattgtaa atgcatactt gggaaggact tagagttta aactgttttt tgcttttgct   3060
tttccctgac tcccttgct tggagtcagc tgcacaccag tagtatggca tgctacgatc   3120
aggttctgtc ctgaaagctt tgcctctttc ttggcaaagt ttctggtatg gtcaagcttg   3180
taaataactt ttttacatt ttaatctttt ccattaatta agaggttgaa agaagtgca    3240
gtgtaagaaa acccagcatt ttaattactt gcaaattaag ttaccacaga ctctgtagtg   3300
```

```
tgtaaatgtt gacaaggaat tggatcacaa tcatgtagca gaatggcacc cagaccactg    3360
cccaccagtg acggacatgc acgtggcaga tcatgatttc agcccacgg agccagcatt     3420 tgaaccttgt ataattaact ttcagttatg atttcccatc gacattttct ttgccctgtt    3480
tgtagctgat tgttgtgttt tataaatctt ctgttaaggc agaagggtga ttatgagtgg    3540
ttcacagcag cccttataag ctgggccaga aaatttcact aggtcagtaa tttaaacctt    3600
ggatcttcaa aaaataaaat aatgtgaagc aaaaccaact aaaaagtgat tcttgcacat    3660
gaactgtcac atgtttaaaa atgtgttttt tagagagcct cagtcttact gatttcaaac    3720
acttttttct tctgtgtatt gcttttaaga gagccatcag ttagctatca gactctaggt    3780
tgatgcattt tgtacttagc tgtactgtgt gatattttc attattttag gacgccaaca    3840
tgagacctgt aataaaatat gtaatggggt tgaaagctgg ggaggaggat ctactgctgt    3900
acagctaata aatcataacg gattaacaag tgctccaaag aaaaaa                   3946

<210> SEQ ID NO 93
<211> LENGTH: 5612
<212> TYPE: DNA
<213> ORGANISM: Homo sapiens

<400> SEQUENCE: 93 gggcggggc gggggctgcc gcagagccgg gctgcggcgt gggaggagga agaggaggaa       60
gatgcgctcg gcctctgcct tccgctccgg agcgtcgcgc ttcccaccag gatgacagtg     120
atgggattcc gtggtcagaa gaacgggtgg tacgtaaagt cctttatttg tctctgaagg     180
agttcaagaa ttcccagaag aggcagcatg cggaaggcat tgctgggagc ctgaaaactg     240
tgaatgggct ccttggtaat gaccagtcta agggattagg accagcatca gaacagtcag     300
agaatgaaaa ggacgatgca tcccaagtgt cctccactag caacgatgtt agttcttcag     360
attttgaaga agggccgtcg aggaaaaggc ccaggctgca agcacaaagg aagtttgctc     420
agtctcagcc gaatagtccc agcacaactc cagtaaagat agtggagcca ttgctacccc     480
ctccagctac tcagatatca gacctctcta aaaggaagcc taagacagaa gattttctta    540
cctttctctg ccttcgaggt tctcctgcgc tgcccaacag catggtgtat tttggaagct    600
ctcaggatga ggaggaagtc gaggaggaag atgatgagac agaagacgtc aaaacagcca    660
ccaacaatgc ttcatcttca tgccagtcga ccccccaggaa aggaaaaacc cacaaacatg   720
ttcacaacgg gcatgttttc aatggttcca gcaggtcaac acgggagaag gaacctgttc    780
aaaaacacaa aagcaaagag gccactcccg caaggagaa gcacagcgat caccgggctg    840
acagccgccg ggagcaggct tcagctaacc ccccgcagc ggcccctcc acgggttcct      900 cggccaaggg gcttgctgcc acccatcacc acccccctct gcatcggtcg gctcaggact    960
tacggaaaca ggtttctaag gtaaacggag tcactcgaat gtcatctctg ggtgcaggtg   1020
taaccagtgc caaaagatg cgcgaggtca gaccttcacc atccaaaact gtgaagtaca    1080
ctgccacggt gacgaagggg gctgtcacat acaccaaagc caagagagaa ctggtcaagg   1140
acaccaaacc caatcaccac aagcccagtt ccgctgtcaa ccacacaatc tcagggaaaa    1200
ctgaaagtag caatgcaaaa acccgcaaac aggtgctatc cctcgggggg gcgtccaagt    1260
ccactgggcc cgccgtcaat ggcctcaagg tcagtggcag gttgaaccca aagtcatgca    1320
ctaaggaggt ggggggggcgg cagctgcggg agggcctgca gctgcgggag gggctgcgga    1380
actccaagag gagactggaa gaggcacacc aggcggagaa gccgcagtcg ccccccaaga    1440
```

-continued

```
agatgaaagg ggcggctggc cccgccgaag gccctggcaa gaaggccccg gccgagagag    1500
gtctgctgaa cggacacgtg aagaaggaag tgccggagcg cagtctggag aggaatcggc    1560
cgaagcgggc cacggccggg aagagcacgc caggcagaca agcacatggc aaggcggaca    1620
gcgcctcctg tgaaaatcgt tctacctcgc aaccggagtc cgtgcacaag ccgcaggact    1680
cgggcaaggc cgagaagggc ggcggcaagg ccgggtgggc ggccatggac gagatccccg    1740
tcctcaggcc ctccgccaag gagttccacg atccgctcat ctacatcgag tcggtccgcg    1800
ctcaggtgga gaagttcggg atgtgcaggg tgatccccc tccggactgg cggcccgagt     1860
gcaagctcaa cgatgagatg cggtttgtca cgcagattca gcacatccac aagctgggcc    1920
ggcgctgggg ccccaacgtg cagcggctgg cctgcatcaa gaagcacctc aaatctcagg    1980
gcatcaccat ggacgagctc ccgctcatag ggggctgtga gctcgacctg gcctgctttt    2040
tccggctgat taatgagatg gcggcatgc agcaagtgac tgacctcaaa aaatggaaca    2100
aactagcaga catgctgcgc atccccagaa ctgcccagga ccggctggcc aagctgcagg    2160
aggcctactg ccagtaccta ctctcctacg actccctgtc cccagaggag caccggcggc    2220
tggagaagga ggtgctgatg gagaaggaga tcctggagaa gcgcaagggg ccgctggaag    2280
gccacacaga gaacgaccac cacaagttcc accctctgcc ccgcttcgag cccaagaatg    2340
ggctcatcca cggcgtggcc cccaggaacg gcttccgcag caagctcaag gaggtgggcc    2400
aggcccagtt gaagactggc cggcggcgac tcttcgctca ggaaaagaa gtggtcaagg    2460 aagaggagga ggacaaaggc gtcctcaatg acttccacaa gtgcatctat aagggaaggt    2520
ctgtttctct aacaactttt tatcgaacag cgaggaatat catgagcatg tgtttcagca    2580
aggagcctgc cccagccgaa atcgagcaag agtactggag gctagtggaa gagaaggact    2640
gccacgtggc agtgcactgc ggcaaggtgg acaccaacac tcacggcagt ggattcccag    2700
taggaaaatc agaacccttt tcgaggcatg gatggaacct caccgtcctc cccaataaca    2760
cagggtccat cctgcgtcac ctcggtgctg tgcctggagt gactattccc tggctaaata    2820
ttggcatggt cttttctacc tcatgctggt ctcgagacca aaatcacctt ccatacattg    2880
actacttaca cactggtgct gactgcattt ggtattgcat tcctgctgag gaggagaaca    2940
agctggaaga tgtggtccac accctgctgc aagccaatgg caccccaggg ctgcagatgc    3000
tggaaagcaa cgtcatgatc tccccggagg tgctgtgcaa agaggggatc aaggtgcaca    3060
ggaccgtgca gcagagtggc cagtttgtcg tctgcttccc gggatccttt gtgtccaaag    3120
tgtgctgtgg gtacagcgtg tctgaaaccg tgcactttgc taccacccag tggacaagta    3180
tgggctttga gaccgccaag gaaatgaagc gtcgccatat agctaagcca ttctccatgg    3240
agaagttact ctaccagatt gcacaagcag aagcaaaaaa agaaaacggt cccactctca    3300
gtaccatctc agccctcctg gatgagctca gggatacaga gctgcggcag cgcaggcagc    3360
tgttcgaggc tggcctccac tcctccgcac gctatggcag ccacgatggc agcagcacgg    3420
tggcggacgg gaagaaaaag cctcgaaagt ggctgcagtt ggagacgtca gagaggaggt    3480
gtcagatctg ccagcacctg tgctacctgt ccatggtggt acaagagaac gaaaacgtcg    3540
tgttctgtct ggagtgtgct ctgcgccacg tggagaaaca gaagtcctgc cgagggctga    3600
agttgatgta ccgctacgat gaggaacaga ttatcagtct ggtcaatcag atctgcggca    3660
aagtgtctgg taaaaacggc agcattgaga actgtctcag taaacccaca ccaaaaagag    3720
gtccccgcaa gagagcgaca gtggacgtgc cccctcccg tctgtcagcc tccagttcat    3780
ccaaaagtgc ttcgagctca tcatgaagat gccaacgccc gtggtcgatt tatatatatt    3840
```

```
tttttgtaat tattatattc tagtttggag tacttgctgt aggattcaag ctgtctttgc    3900
actagctcta aagaagattt tcttctggtt ttagagaact aatttttgttt tagcattaaa    3960 ctgttgaact ttttttttgta cttagaaaac ctagatactg cagtcagatt ttggaaactg    4020
ccgtatagtc actgttttaa aaaccccgga ggggctgtat taatttgtat tgccccatgg    4080
ctgacaaaag cctttttttt tggttttgat tttttttttt ttgtaactgt tgggggaaa     4140 aaggcttttt aacccatttt tgaagagggt gaagtttgga gaacaaattt aaaaaccatc    4200
agtcatgtga gcagattttt tagaagggat aggagacaca cgcgcacaca cacacacaca    4260
cgaaacttga aatggctttg ctttggctgt cgtcttctgc cgtgtgccag atgagcttgt    4320
gatctgggaa gccggggcac ccccgttttg tttctctggg cggttgtggc agctgaaggc    4380
ggacgttgtt tcctaaccat aggtggaacg aggagacggg agcgagtggg ctctccacca    4440
gcacatcact atgcatctgt tccaggaaag aagaaaagcg agcgaggaag acggaaaaga    4500
ctgcctgcct tggaggggtc acatgaggga gacctgtgcc tgatttcatt aggaaatcca    4560
ttctgttatt ttttggtgct gttggctact ttatcaaaaa accccttcaat agcatcctta    4620 agatttaaaa aaaaaaaaaa aaaaaaggaa aaaaaagtga tggaagccgt aagtgcttct    4680
ttgtcatcga cgtgcaatct ttctaacatt ccatctccat ctcaccgctt cttgtttgac    4740
accttcacaa gtcagcatta atctttcttt taaaacttgt ttcatttatg atcatgtaga    4800
gagccactag gaggcctgca gttattttttg aatgtgaaaa tgcatttgcg ttcatcttgt    4860 ctatttttttc tcttcatgtt gtaacaaaaa ggaaaaaaga aaaaaaaatc ccatcccttt    4920
tgtacatatg cctgtaaatt gttttaaata cttgagcctt tttctcggtg gggggtgggg    4980
aggggggtga gaagacaaga tgaagaaaag ccttacattt cagtttcttc atcggttgga    5040
ttggatgctt acagggtttt tcttgtaaca tttataagtg ctgcttacat cactgaacaa    5100
caacaaaaaa ataataatgg agtagctgtt gcccttctcc ggttgtgtgt acagtatgtg    5160
tggaataaaa aagggaaact gttttcacaa gctgttcttt gtttcataat tggattcatc    5220
aatcccgtag ctacccatat tgcactgagc ttgccagtgg tgactgccag gaacgtccta    5280
tgatccactt tgttggttgt tgttgcagaa gactgaactg ttttggaata tttaacaatt    5340
acagaaacag tcaagtgttt tccaatgtgg ttgtccggtt tctatggcct tgctgtgtac    5400
tttccctctt tttgacagta aacttctgcc tatggcttac agtttgacat ttaatttatt    5460
agcgctgctc tgcacccctc ccttgggagg gagacttcat gtggtttatt gcgagttttt    5520
tgtttacttt tcaggtttgt actacaaggt ttaataataa aaacaaagtt ttttggacat    5580
ttgtctgtct tgtggaaaaa aaaaaaaaa aa                                   5612
```

<210> SEQ ID NO 94
<211> LENGTH: 6112
<212> TYPE: DNA
<213> ORGANISM: Homo sapiens

<400> SEQUENCE: 94

```
tggatagcct ctctctcatt ggttaggggg cttggaaaaa agagactcgg cgagccctcg      60
ctgtggtgct gccgccgccg ccgccgccgc cgctggagtt gactcttctg ctcgcactgc     120
tgctgcagca caaacgtgac ttccaacatt ttttatttat cttccccttt tcttttccaa     180
gatgtaacta cggatcagac actaaggacc ttcacgtttc gctgatgtag ttttggagg     240 aaaaaggggg gggagtgaag ggcgtcggtt tttttttgtg tgtgtgtgta tgtgtttcgg     300
```

```
gggaaatttt ccattatgag tgttttacta aagtgaattt ttttttgttt gcttcgttcg    360
tctttggctc ttttttttc cttcccaatt tcggatttat ttcaaggcga atctggcttt     420
gggggaagag gaagaaaagt cggattacaa gatcaaccac caccaacaac aataaaaacc    480
accaggatat tttttgcaa atttctgacg gctttaaatt catgaagcaa ttgtcccctt     540
ttgcaatcag catttggatc tcagaatgag caaggaaaga cccaagagga atatcattca    600
gaagaaatac gatgacagtg atgggattcc gtggtcagaa gaacgggtgg tacgtaaagt    660
cctttatttg tctctgaagg agttcaagaa ttcccagaag aggcagcatg cggaaggcat    720
tgctgggagc ctgaaaactg tgaatgggct ccttggtaat gaccagtcta agggattagg    780
accagcatca gaacagtcag agaatgaaaa ggacgatgca tcccaagtgt cctccactag    840
caacgatgtt agttcttcag attttgaaga agggccgtcg aggaaaaggc ccaggctgca    900
agcacaaagg aagtttgctc agtctcagcc gaatagtccc agcacaactc cagtaaagat    960
agtggagcca ttgctacccc ctccagctac tcagatatca gacctctcta aaaggaagcc   1020
taagacagaa gattttctta cctttctctg ccttcgaggt tctcctgcgc tgcccaacag   1080
catggtgtat tttggaagct ctcaggatga ggaggaagtc gaggaggaag atgatgagac   1140
agaagacgtc aaaacagcca ccaacaatgc ttcatcttca tgccagtcga cccccaggaa   1200
aggaaaaacc cacaaacatg ttcacaacgg gcatgttttc aatggttcca gcaggtcaac   1260
acgggagaag gaacctgttc aaaaacacaa agcaaagag gccactcccg caaggagaa    1320 gcacagcgat caccgggctg acagccgccg ggagcaggct tcagctaacc accccgcagc   1380
ggccccctcc acgggttcct cggccaaggg gcttgctgcc acccatcacc accccctct    1440 gcatcggtcg gctcaggact tacggaaaca ggtttctaag gtaaacggag tcactcgaat   1500
gtcatctctg ggtgcaggtg taaccagtgc caaaaagatg cgcgaggtca gaccttcacc   1560
atccaaaact gtgaagtaca ctgccacggt gacgaagggg gctgtcacat acaccaaagc   1620
caagagagaa ctggtcaagg acaccaaacc caatcaccac aagcccagtt ccgctgtcaa   1680
ccacacaatc tcagggaaaa ctgaaagtag caatgcaaaa acccgcaaac aggtgctatc   1740
cctcgggggg gcgtccaagt ccactgggcc cgccgtcaat ggcctcaagg tcagtggcag   1800
gttgaaccca aagtcatgca ctaaggaggt ggggggggcgg cagctgcggg agggcctgca   1860
gctgcgggag gggctgcgga actccaagag gagactggaa gaggcacacc aggcggagaa   1920
gccgcagtcg cccccaaga agatgaaagg ggcggctggc cccgccgaag gccctggcaa    1980
gaaggccccg gccgagagag gtctgctgaa cggacacgtg aagaaggaag tgccggagcg   2040
cagtctggag aggaatcggc cgaagcgggc cacggccggg aagagcacgc caggcagaca   2100
agcacatggc aaggcggaca cgcctcctg tgaaaatcgt tctacctcgc aaccggagtc    2160
cgtgcacaag ccgcaggact cgggcaaggc cgagaagggc ggcggcaagg ccgggtgggc   2220
ggccatggac gagatccccg tcctcaggcc ctccgccaag gagttccacg atccgctcat   2280
ctacatcgag tcggtccgcg ctcaggtgga gaagttcggg atgtgcaggg tgatccccc    2340 tccggactgg cggcccgagt gcaagctcaa cgatgagatg cggtttgtca cgcagattca   2400
gcacatccac aagctgggcc ggcgctgggc ccccaacgtg cagcggctgg cctgcatcaa   2460
gaagcacctc aaatctcagg gcatcaccat ggacgagctc ccgctcatag ggggctgtga   2520
gctcgacctg gcctgctttt tccggctgat taatgagatg ggcggcatgc agcaagtgac   2580
tgacctcaaa aaatgaaca aactagcaga catgctgcgc atcccagaa ctgcccagga    2640 ccggctggcc aagctgcagg aggcctactg ccagtaccta ctctcctacg actccctgtc   2700
```

```
cccagaggag caccggcggc tggagaagga ggtgctgatg gagaaggaga tcctggagaa   2760
gcgcaagggg ccgctggaag gccacacaga gaacgaccac cacaagttcc accctctgcc   2820
ccgcttcgag cccaagaatg ggctcatcca cggcgtggcc cccaggaacg gcttccgcag   2880
caagctcaag gaggtgggcc aggcccagtt gaagactggc cggcggcgac tcttcgctca   2940
ggaaaaagaa gtggtcaagg aagaggagga ggacaaaggc gtcctcaatg acttccacaa   3000
gtgcatctat aagggaaggt ctgtttctct aacaactttt tatcgaacag cgaggaatat   3060
catgagcatg tgtttcagca aggagcctgc cccagccgaa atcgagcaag agtactggag   3120
gctagtggaa gagaaggact gccacgtggc agtgcactgc ggcaaggtgg acaccaacac   3180
tcacggcagt ggattcccag taggaaaatc agaacccttt tcgaggcatg gatggaacct   3240
caccgtcctc cccaataaca cagggtccat cctgcgtcac ctcggtgctg tgcctggagt   3300
gactattccc tggctaaata ttggcatggt cttttctacc tcatgctggt ctcgagacca   3360
aaatcacctt ccatacattg actacttaca cactggtgct gactgcattt ggtattgcat   3420
tcctgctgag gaggagaaca agctggaaga tgtggtccac accctgctgc aagccaatgg   3480 cacccccaggg ctgcagatgc tggaaagcaa cgtcatgatc tccccggagg tgctgtgcaa   3540 agagggatc aaggtgcaca ggaccgtgca gcagagtggc cagtttgtcg tctgcttccc   3600
gggatccttt gtgtccaaag tgtgctgtgg gtacagcgtg tctgaaaccg tgcactttgc   3660
taccacccag tggacaagta tgggctttga accgccaag gaaatgaagc gtcgccatat   3720
agctaagcca ttctccatgg agaagttact ctaccagatt gcacaagcag aagcaaaaaa   3780
agaaaacggt cccactctca gtaccatctc agccctcctg gatgagctca gggatacaga   3840
gctgcggcag cgcaggcagc tgttcgaggc tggcctccac tcctccgcac gctatggcag   3900
ccacgatggc agcagcacgg tggcggacgg gaagaaaaag cctcgaaagt ggctgcagtt   3960
ggagacgtca gagaggaggt gtcagatctg ccagcacctg tgctacctgt ccatggtggt   4020
acaagagaac gaaaacgtcg tgttctgtct ggagtgtgct ctgcgccacg tggagaaaca   4080
gaagtcctgc cgagggctga agttgatgta ccgctacgat gaggaacaga ttatcagtct   4140
ggtcaatcag atctgcggca aagtgtctgg taaaaacggc agcattgaga actgtctcag   4200
taaacccaca ccaaaagag gtccccgcaa gagagcgaca gtggacgtgc cccctcccg    4260 tctgtcagcc tccagttcat ccaaaagtgc ttcgagctca tcatgaagat gccaacgccc   4320
gtggtcgatt tatatatatt tttttgtaat tattatattc tagtttggag tacttgctgt   4380
aggattcaag ctgtctttgc actagctcta aagaagattt tcttctggtt ttagagaact   4440
aattttgttt tagcattaaa ctgttgaact ttttttgta cttagaaaac ctagatactg    4500
cagtcagatt ttgaaaactg ccgtatagtc actgttttaa aaaccccgga ggggctgtat   4560
taatttgtat tgccccatgg ctgacaaaag cctttttttt tggttttgat tttttttttt   4620
ttgtaactgt tgggggaaa aaggcttttt aacccatttt tgaagagggt gaagtttgga   4680
gaacaaattt aaaaaccatc agtcatgtga gcagattttt tagaagggat aggagacaca   4740
cgcgcacaca cacacacaca cgaaacttga aatggctttg ctttggctgt cgtcttctgc   4800
cgtgtgccag atgagcttgt gatctgggaa gccggggcac ccccgttttg tttctctggg   4860
cggttgtggc agctgaaggc ggacgttgtt tcctaaccat aggtggaacg aggagacggg   4920
agcgagtggg ctctccacca gcacatcact atgcatctgt tccaggaaag aagaaaagcg   4980
agcgaggaag acgaaaaaga ctgcctgcct tggaggggtc acatgaggga gacctgtgcc   5040
```

| | |
|---|---|
| tgatttcatt aggaaatcca ttctgttatt ttttggtgct gttggctact ttatcaaaaa | 5100 |
| acccttcaat agcatcctta agatttaaaa aaaaaaaaaa aaaaaaggaa aaaaaagtga | 5160 |
| tggaagccgt aagtgcttct ttgtcatcga cgtgcaatct ttctaacatt ccatctccat | 5220 |
| ctcaccgctt cttgtttgac accttcacaa gtcagcatta atctttcttt taaaacttgt | 5280 |
| ttcatttatg atcatgtaga gagccactag gaggcctgca gttattttg aatgtgaaaa | 5340 |
| tgcatttgcg ttcatcttgt ctattttttc tcttcatgtt gtaacaaaaa ggaaaaaaga | 5400 |
| aaaaaaaatc ccatcccttt tgtacatatg cctgtaaatt gttttaaata cttgagcctt | 5460 |
| tttctcggtg gggggtgggg aggggggtga aagacaaga tgaagaaaag ccttacattt | 5520 |
| cagtttcttc atcggttgga ttggatgctt acagggtttt tcttgtaaca tttataagtg | 5580 |
| ctgcttacat cactgaacaa caacaaaaaa ataataatgg agtagctgtt gcccttctcc | 5640 |
| ggttgtgtgt acagtatgtg tggaataaaa aagggaaact gttttcacaa gctgttcttt | 5700 |
| gtttcataat tggattcatc aatcccgtag ctacccatat tgcactgagc ttgccagtgg | 5760 |
| tgactgccag gaacgtccta tgatccactt tgttggttgt tgttgcagaa gactgaactg | 5820 |
| ttttggaata tttaacaatt acagaaacag tcaagtgttt tccaatgtgg ttgtccggtt | 5880 |
| tctatggcct tgctgtgtac tttccctctt tttgacagta aacttctgcc tatggcttac | 5940 |
| agtttgacat ttaatttatt agcgctgctc tgcaccccte ccttgggagg gagacttcat | 6000 |
| gtggtttatt gcgagttttt tgtttacttt tcaggtttgt actacaaggt ttaataataa | 6060 |
| aaacaaagtt ttttggacat ttgtctgtct tgtggaaaaa aaaaaaaaaa aa | 6112 |

<210> SEQ ID NO 95
<211> LENGTH: 2880
<212> TYPE: DNA
<213> ORGANISM: Homo sapiens

<400> SEQUENCE: 95

| | |
|---|---|
| cactgcatgt gtattcgtga gttcgcggtt gaacaactgt tcctttactc tgctccctgt | 60 |
| ctttgtgctg actgggttac tttttttaaac actaggaatg gtaatttcta ctcttctgga | 120 |
| cttcaaacta agaagttaaa gagacttctc tgtaaataaa caaatctctt ctgctgtcct | 180 |
| tttgcatttg gagacagctt tatttcacca tatccaagga gtataactag tgctgtcatt | 240 |
| atgaatgtga caagtttatt tcctttaca agtccagctg tgaagagact tcttgggtgg | 300 |
| aaacagggcg atgaagaaga aaaatgggca gagaaagctg ttgatgcttt ggtgaaaaaa | 360 |
| ctgaagaaaa agaaggtgc catggaggaa ctggaaaagg ccttgagctg cccagggcaa | 420 |
| ccgagtaact gtgtcaccat tccccgctct ctggatggca ggctgcaagt ctcccaccgg | 480 |
| aagggactgc tcatgtcat ttactgccgt gtgtggcgct ggcccgatct tcagagccac | 540 |
| catgaactaa aaccactgga atgctgtgag tttccttttg gttccaagca aaggaggtc | 600 |
| tgcatcaatc cctaccacta taagagagta gaaagccctg tacttcctcc tgtgctggtt | 660 |
| ccaagacaca gcgaatataa tcctcagcac agcctcttag ctcagttccg taacttagga | 720 |
| caaaatgagc ctcacatgcc actcaacgcc acttttccag attctttcca gcaacccaac | 780 |
| agccaccccgt tcctcactc tcccaatagc agttacccaa actctcctgg gagcagcagc | 840 |
| agcacctacc ctcactctcc caccagctca gacccaggaa gccctttcca gatgccagct | 900 |
| gatacgcccc cacctgctta cctgcctcct gaagaccca tgacccagga tggctctcag | 960 |
| ccgatggaca caaacatgat ggcgcctccc ctgccctcag aaatcaacag aggagatgtt | 1020 |
| caggcggttg cttatgagga accaaaacac tggtgctcta ttgtctacta tgagctcaac | 1080 |

```
aatcgtgtgg gtgaagcgtt ccatgcctcc tccacaagtg tgttggtgga tggtttcact    1140
gatccttcca acaataagaa ccgtttctgc cttgggctgc tctccaatgt taaccggaat    1200
tccactattg aaaacaccag gcggcatatt ggaaaaggag ttcatcttta ttatgttgga    1260
ggggaggtgt atgccgaatg ccttagtgac agtagcatct tgtgcaaag tcggaactgc    1320
```
(note: line at 1320 reads: ggggaggtgt atgccgaatg ccttagtgac agtagcatct tgtgcaaag tcggaactgc)

```
aactaccatc atggatttca tcctactact gtttgcaaga tccctagtgg gtgtagtctg    1380 aaaatttta acaaccaaga atttgctcag ttattggcac agtctgtgaa ccatggattt    1440
gagacagtct atgagcttac aaaaatgtgt actatacgta tgagctttgt gaagggctgg    1500
ggagcagaat accaccgcca ggatgttact agcacccct gctggattga gatacatctg    1560
cacggccccc tccagtggct ggataaagtt cttactcaaa tgggttcacc tcataatcct    1620
atttcatctg tatcttaaat ggccccaggc atctgcctct ggaaaactat tgagccttgc    1680
atgtacttga aggatggatg agtcagacac gattgagaac tgacaaagga gccttgataa    1740
tacttgacct ctgtgaccaa ctgttggatt cagaaattta acaaaaaaa aaaaaaaca    1800 cacacacctt ggtaacatac tgttgatatc aagaacctgt ttagtttaca ttgtaacatt    1860
ctattgtaaa atcaactaaa attcagactt ttagcaggac tttgtgtaca gttaaaggag    1920
agatggccaa gccagggaca aattgtctat tagaaaacgg tcctaagaga ttctttggtg    1980
tttggcactt taaggtcatc gttgggcaga agtttagcat taatagttgt tctgaaacgt    2040
gttttatcag gtttagagcc catgttgagt cttcttttca tgggttttca taatatttta    2100
aaactatttg tttagcgatg gttttgttcg tttaagtaaa ggttaatctt gatgatatac    2160
ataataatct ttctaaaatt gtatgctgac catacttgct gtcagaataa tgctaggcat    2220 atgcttttg ctaaatatgt atgtacagag tatttgaag ttaagaattg attagactag    2280
tgaatttagg agtatttgag gtgggtgggg ggaagaggga aatgacaact gcaaatgtag    2340
actatactgt aaaaattcag tttgttgctt taaagaaaca aactgatacc tgaattttgc    2400
tgtgtttcca ttttttagag attttatca tttttttctc tctcggcatt cttttttctc    2460
atactcttca aaaagcagtt ctgcagctgg ttaattcatg taactgtgag agcaaatgaa    2520
taattcctgc tattctgaaa ttgcctacat gtttcaatac cagttatatg gagtgcttga    2580
atttaataag cagttttac ggagtttaca gtacagaaat aggctttaat ttcaagtga    2640 atttttgcc aaacttagta actctgttaa atatttggag gatttaaaga acatcccagt    2700
ttgaattcat ttcaaacttt ttaaattttt ttgtactatg tttggtttta ttttccttct    2760
gttaatcttt tgtattcact tatgctctcg tacattgagt acttttattc caaaactagt    2820
gggttttctc tactggaaat tttcaataaa cctgtcatta ttgcttactt tgattaaaaa    2880
```

<210> SEQ ID NO 96  
<211> LENGTH: 3056  
<212> TYPE: DNA  
<213> ORGANISM: Homo sapiens

<400> SEQUENCE: 96

```
ggcagctgag gagtggaggc tgggcagctc cgactccctg acgccagcgc gaccagatca      60
atccaggctc caggagaaag caggcgggcg ggcggagaaa ggagaggccg agcggctcaa     120
cccgggccga ggctcgggga gcggagagtg gcgcagcgcc cggccgtccg acccgggcc     180 gcgagacccc gctcgcccgg ccactcgtgc tcccacacgg acgggcgcgc cgccaacccg     240
gtgctgactg ggttactttt ttaaacacta ggaatggtaa tttctactct tctggacttc     300
```

```
aaactaagaa gttaaagaga cttctctgta aataaacaaa tctcttctgc tgtccttttg    360
catttggaga cagctttatt tcaccatatc caaggagtat aactagtgct gtcattatga    420
atgtgacaag tttatttttcc tttacaagtc cagctgtgaa gagacttctt gggtggaaac   480
agggcgatga agaagaaaaa tgggcagaga agctgttga tgctttggtg aaaaaactga     540
agaaaaagaa aggtgccatg gaggaactgg aaaaggcctt gagctgccca gggcaaccga    600
gtaactgtgt caccattccc cgctctctgg atggcaggct gcaagtctcc caccggaagg    660
gactgcctca tgtcatttac tgccgtgtgt ggcgctggcc cgatcttcag agccaccatg    720
aactaaaacc actggaatgc tgtgagtttc cttttggttc caagcagaag gaggtctgca    780
tcaatcccta ccactataag agagtagaaa gccctgtact tcctcctgtg ctggttccaa    840
gacacagcga atataatcct cagcacagcc tcttagctca gttccgtaac ttaggacaaa    900
atgagcctca catgccactc aacgccactt ttccagattc tttccagcaa cccaacagcc    960 acccgttttcc tcactctccc aatagcagtt acccaaactc tcctgggagc agcagcagca  1020
cctaccctca ctctcccacc agctcagacc caggaagccc tttccagatg ccagctgata   1080 cgccccacc tgcttacctg cctcctgaag accccatgac ccaggatggc tctcagccga    1140
tggacacaaa catgatggcg cctccccctgc cctcagaaat caacagagga gatgttcagg   1200
cggttgctta tgaggaacca aaacactggt gctctattgt ctactatgag ctcaacaatc    1260
gtgtgggtga agcgttccat gcctcctcca caagtgtgtt ggtggatggt ttcactgatc    1320
cttccaacaa taagaaccgt ttctgccttg ggctgctctc caatgttaac cggaattcca    1380
ctattgaaaa caccaggcgg catattggaa aaggagttca tctttattat gttggagggg   1440
aggtgtatgc cgaatgcctt agtgacagta gcatctttgt gcaaagtcgg aactgcaact    1500
accatcatgg atttcatcct actactgttt gcaagatccc tagtgggtgt agtctgaaaa    1560
tttttaacaa ccaagaattt gctcagttat ggcacagtc tgtgaaccat ggatttgaga    1620
cagtctatga gcttacaaaa atgtgtacta tacgtatgag cttttgtgaag ggctggggag   1680 cagaatacca ccgccaggat gttactagca cccccctgctg gattgagata catctgcacg   1740
gccccctcca gtggctggat aaagttctta ctcaaatggg ttcacctcat aatcctatt     1800 catctgtatc ttaaatggcc ccaggcatct gcctctggaa aactattgag ccttgcatgt    1860
acttgaagga tggatgagtc agacacgatt gagaactgac aaaggagcct tgataatact   1920
tgacctctgt gaccaactgt tggattcaga aatttaaaca aaaaaaaaaa aaaacacaca    1980
caccttggta acatactgtt gatatcaaga acctgtttag tttacattgt aacattctat    2040
tgtaaaatca actaaaattc agactttag caggactttg tgtacagtta aaggagagat    2100
ggccaagcca gggacaaatt gtctattaga aaacggtcct aagagattct ttggtgtttg    2160
gcactttaag gtcatcgttg gcagaagtt tagcattaat agttgttctg aaacgtgttt    2220
tatcaggttt agagcccatg ttgagtcttc ttttcatggg ttttcataat attttaaaac    2280
tatttgttta gcgatggttt tgttcgttta agtaaaggtt aatcttgatg atatacataa    2340
taatctttct aaaattgtat gctgaccata cttgctgtca gaataatgct aggcatatgc    2400
tttttgctaa atatgtatgt acagagtatt tggaagttaa gaattgatta gactagtgaa    2460
tttaggagta tttgaggtgg gtgggggga gagggaaatg acaactgcaa atgtagacta    2520
tactgtaaaa attcagtttg ttgcttaaaa gaaacaaact gataccctgaa ttttgctgtg   2580 tttccatttt ttagagattt ttatcatttt ttttctctctc ggcattcttt tttctcatac    2640
tcttcaaaaa gcagttctgc agctggttaa ttcatgtaac tgtgagagca aatgaataat    2700
```

```
tcctgctatt ctgaaattgc ctacatgttt caataccagt tatatggagt gcttgaattt    2760
aataagcagt ttttacggag tttacagtac agaaataggc tttaattttc aagtgaattt    2820
tttgccaaac ttagtaactc tgttaaatat ttggaggatt taaagaacat cccagtttga    2880
attcatttca aactttttaa attttttgt actatgtttg gttttatttt ccttctgtta     2940 atctttgta ttcacttatg ctctcgtaca ttgagtactt ttattccaaa actagtgggt     3000
tttctctact ggaaattttc aataaacctg tcattattgc ttactttgat taaaaa        3056
```

EARLY DEVELOPMENTAL GENOMIC ASSAY FOR CHARACTERIZING PLURIPOTENT STEM CELL UTILITY AND SAFETY

CROSS REFERENCE TO RELATED APPLICATIONS

This application is a continuation of U.S. application Ser. No. 14/897,410 filed Dec. 10, 2015, which is a 371 National Phase Entry of International Patent Application No. PCT/US2014/041513 filed on Jun. 9, 2014, which claims benefit under 35 U.S.C. § 119(e) of U.S. Provisional Application No. 61/833,092 filed on Jun. 10, 2013, the contents of each of which are incorporated herein by reference in their entirety.

GOVERNMENT SUPPORT

This invention was made, in part, with government support under NIH Roadmap Initiative on Epigenomics, Grant Number U01ES017155 awarded by National Institutes of Health. The Government has certain rights in the invention.

FIELD OF THE INVENTION

The present invention relates to arrays and methods for characterizing pluripotent stem cell populations to permit selection of pluripotent stem cell lines for further use.

SEQUENCE LISTING

The instant application contains a Sequence Listing which has been submitted electronically in ASCII format and is hereby incorporated by reference in its entirety. Said ASCII copy, created on Dec. 9, 2015, is named 002806-077891-PCT_SL.txt and is 436,312 bytes in size.

BACKGROUND OF THE INVENTION

One goal of regenerative medicine is to be able to convert pluripotent cells into other cell types for tissue repair and regeneration. Human pluripotent cell lines exhibit a level of developmental plasticity that is similar to the early embryo, enabling in vitro differentiation into all three embryonic germ layers (Rossant, 2008; Thomson et al., 1998). At the same time it is possible to maintain these pluripotent cell lines for many passages in the undifferentiated state (Adewumi et al., 2007). These unique characteristics render human embryonic stem (ES) and human induced pluripotent stem (iPS) cells a promising tool for biomedical research (Colman and Dreesen, 2009). ES cell lines have already been established as a model system for dissecting the cellular basis of monogenic human diseases.

However, several recent developments have greatly increased the need for an assay that can predict the behavior of pluripotent human cell lines. First, the continued derivation of human ES cell lines by many labs and the lifting of funding restrictions in the U.S. have substantially increased the number of ES cell lines from which investigators can choose. Additionally, it has become clear that not all human ES cell lines are equally suited for every purpose (Osafune et al., 2008). This suggests that any new research project should include a deliberate and informed selection of the cell lines that are most qualified for an application of interest.

The ability to reprogram somatic cells from patients into iPS cells has also led to a further increase in the number of pluripotent cell lines available to, and used by, the research community. As investigators gather together existing cell lines, or derive new ones for their application of interest, there is little information or guidance concerning how to select cell lines that are most appropriate for use.

Future applications of human pluripotent stem cell lines will likely include the study of common diseases that arise as the result of complex interactions between a person's genotype and their environment (Colman and Dreesen, 2009). In addition, pluripotent cells will eventually serve as a renewable source of both cells and tissue for transplantation medicine (Daley, 2010). Both of these proposed applications for pluripotent stem cells will require the selection of cell lines that reliably, reproducibly, efficiently and stably differentiate into disease-relevant cell types. However, a significant amount of variation has been reported in the efficiency by which different human ES cell lines or iPSC lines differentiate into different derivatives of the three embryonic germ layers (Di Giorgio et al., 2008; Osafune et al., 2008). Furthermore, it has been reported that iPS cells collectively deviate from ES cells in the expression of hundreds of genes (Chin et al., 2009), and their ability to differentiate down particular lineages (Hu et al., 2010). While some iPS cell lines can differentiate as efficiently as ES cells (Boland et al., 2009; Miura et al., 2009; Zhao et al., 2009), the published gene expression signatures of iPS cells are not reproducible (Stadtfeld et al., 2010). The long-term proliferation and differentiation potential of human pluripotent stem cells suggests that they can produce large quantities of various cell types for disease modeling and transplantation therapy. However, before embryonic stem (ES) cells or induced pluripotent stem (iPS) cells can be used with confidence in therapeutic application or disease modeling, or in drug screening or toxicity assays, the extent of variation between human pluripotent cell lines must be understood. In particular, it is necessary to establish a reference of normal variation among high-quality pluripotent cell lines, in order to provide a baseline against which variation from cell-line to cell-line can be identified and to permit systematic selection of a particular pluripotent stem cell best suited for a particular use.

Therefore, there is a need in the art for novel, effective and efficient methods for characterizing and validating cells, including pluripotent stem cell monitoring and validation, and for determining the quality of the, for example, pluripotent stem cell as well as its propensity to, for example, differentiate along a particular cell lineage, prior to its use, e.g., in therapeutic administration, disease modeling, drug development and screening and toxicity assays etc., to reduce administration of aberrant cells (e.g., non-pluripotent stem cells, or cells that are unlikely to differentiate along a desired lineage).

SUMMARY OF THE INVENTION

The present invention is directed to a set of early developmental gene biomarkers, or subsets thereof, which can be used to characterize cells. In one embodiment, these markers can be used to determine the differentiation potential of a pluripotent stem cell population. Aspects of the present invention relate to arrays, assays, systems, kits and methods to rapidly and inexpensively screen cells, including pluripotent cells, for their general quality (e.g., pluripotent capacity) and differentiation capacity. The present invention as disclosed herein therefore allows for a high throughput screening of the signature of gene expression of a set of early developmental genes, in a plurality of stem cell lines including, for example, pluripotent stem cell lines, to permit rapid identification and selection of cells, in some instances an automated selection of cells, which can be chosen for further use or for a particular utility. Accordingly, in one embodiment the present invention relates to a method of characterization of pluripotent stem cells, including induced pluripotent stem cells (iPSCs) by measuring the gene expression of a set of early developmental genes, or a subset thereof, which is highly predictive for how a specific cell line will perform in directed differentiation regimens and paradigms.

It is currently very difficult to predict how a pluripotent stem cell line will behave or which cell lineage the pluripotent stem cell line has a bias for differentiating into without either letting the pluripotent stem cell spontaneously differentiate, and/or differentiating the pluripotent stem cell along a variety of different cell lineages. Current systems to assess pluripotency, such as teratoma formation, are cumbersome, time consuming and very expensive, thus preventing these methods from becoming useful in a large scale characterization of stem cells. Additionally, teratoma formation is not able to predict which cell lineages the cell line will likely differentiate into, nor can these methods identify sub-optimal stem cell lines. Other gene expression analysis systems for characterizing stem cell lines require the pluripotent stem cell line to be cultured for a period of time (e.g., about 1 week) before analysis, or require the pluripotent stem cell to be differentiated (e.g., by directed differentiation) or to undergo spontaneous differentiation for a given period of time before analysis.

The inventors have surprisingly discovered as described herein that the expression of a subset of genes which are expressed in very early stages of development, herein referred to as "early developmental genes," can accurately predict whether the stem cell is still pluripotent, and/or whether the stem cell line has a propensity to differentiate along mesoderm, ectoderm and/or endoderm lineages. For example, the present invention is based on the discovery that the expression of an earlier set of developmental genes provides a meaningful insight into the cells' developmental and differentiation pathway.

For example, by measuring the gene expression of a set of early developmental genes in a stem cell line as disclosed herein, one is able to forecast the differentiation efficiency and pluripotency of a stem cell line being analyzed. For example, by measuring the expression level of a set of early developmental genes, the inventors have demonstrated the levels of these genes are highly predictive for determining the likely direction of the differentiation of the pluripotent stem cell line along particular lineages, e.g., mesoderm, ectoderm or endoderm lineages. Therefore, the invention as disclosed herein has broad utility and can be used to prospectively predict how well a given pluripotent stem cell will differentiate along any desired lineage, for example, hematopoietic lineage, endoderm lineage, pancreatic lineage, neuronal lineage such as a motor neuron lineage, and the like.

Accordingly, as the genes analyzed are expressed in very early stages of development, the invention as disclosed herein has a significant advantage over other gene expression systems used to characterize pluripotent stem cells in that it permits the characterization of the stem cell population at a much earlier time point than in previous assays, thus increasing the efficiency and reducing costs for such characterization. Accordingly, the invention as disclosed herein provides a rapid, inexpensive and quantitative approach for characterizing pluripotent stem cell lines. The methods described are highly efficient in predicting the differentiation ability of the cell as compared to traditional methods, and can identify stem cell lines which can be particularly suited for a particular purpose or use, or alternatively, unsuitable for a particular purpose or use. Additionally, the analysis of the expression of a set of early developmental genes is highly accurate at identifying the lineage propensity of the pluripotent stem cell on a single analysis, thus eliminating the need for replicates, further decreasing costs and effort required to characterize a stem cell population.

As demonstrated herein, the gene expression analysis of a set of early developmental genes in a pluripotent stem cell line can be performed on pluripotent stem cells at as early as embryonic day 2, which is reduced from analysis performed on cells at least 5-7 days of embryonic age. As little as 2 days in EB forming conditions is enough to obtain an accurate prediction of the likelihood that a given stem cell, e.g., ES cell or iPS cell line, will differentiate into a desired lineage or phenotype. Described herein is a set of markers that permit accurate prediction of the differentiation potential after as little as 2 days in EB forming conditions.

Accordingly, shortening the time prior to measuring gene expression is advantageous in that it decreases the time-to-results and also minimizes the logistical costs in terms of incubator space and need for media changes. Accordingly, in some embodiments, measurement of the gene expression of a set of early developmental genes permits one to determine the differentiation potential of a pluripotent stem cell population at a very early developmental stage, e.g., the gene expression analysis can be performed on a stem cell population that is at embryonic stage of at least about 2, or at least about 3, or at least about 4 or at least about 5 days. As discussed above, previously an investigator would have had to wait for the pluripotent stem cell line to reach embryonic stage 7 (Embryonic body 7 days; EB7) or greater, e.g., 16 days (EB16) and/or actually differentiate the cells before performing an analysis to determine the differentiation potential of the stem cell line.

Accordingly, in some embodiments, the ability of the pluripotent cell to differentiate into at least one of the mesoderm, endoderm and ectoderm lineages is determined by assessing the gene expression of a set of early developmental genes listed in Table 1 and/or Table 2 in a pluripotent stem cell line after less than one day in embryoid body (EB) forming conditions or supporting media. In some embodiments, the ability of the pluripotent cell to differentiate into at least one of the mesoderm, endoderm and ectoderm lineages is determined by measuring the gene expression of a set of at least 10, or at least 20 early developmental genes listed in Table 1 and/or Table 2 at anywhere between 0 days in EB forming conditions or supporting media, or between 0-14 days in EB forming conditions or supporting media, e.g., at least 1 day, or at least 2 days, or at least about 3 days, or at least about 4 days, or at least about 5 days, or at least about 6 days, or at least about 7 days, or more than about 7 days in EB forming conditions or supporting media, e.g., between 5-7 days in EB forming conditions or supporting media, or between about 7-10 days in EB forming conditions or supporting media, or between about 10-14 days in EB forming conditions or supporting media, or longer than 14 days in EB forming conditions or supporting media.

In some embodiments, the ability of the pluripotent cell to differentiate into at least one of the mesoderm, endoderm and ectoderm lineages is determined by measuring the gene expression of a set of at least 1, or at least 2 or at least 3 or at least 4 genes from the group of mesoderm early developmental genes, selected from the group consisting of: HAND1, ESM1, HAND2, HOPX, BMP10, FCN3 and GSC, and/or a set of endoderm early developmental genes selected from the group consisting of: LEFTY1, EOMES, NODAL and FOXA2, and/or a set of ectoderm early developmental genes selected from the group consisting of: TRPM8, POU4F1, OLFM3, WNT1, LMX1A and CDH9 and/or a set of early developmental selected from the group consisting of: IDO1, LCK, POU5F1 and HESX1 at anywhere between 0 days in EB forming conditions or supporting media, or between 0-14 days in EB forming conditions or supporting media, e.g., at least 1 day, or at least 2 days, or at least about 3 days, or at least about 4 days, or at least about 5 days, or at least about 6 days, or at least about 7 days, or more than about 7 days in EB forming conditions or supporting media, e.g., between 5-7 days in EB forming conditions or supporting media, or between about 7-10 days in EB forming conditions or supporting media, or between about 10-14 days in EB forming conditions or supporting media, or longer than 14 days in EB forming conditions or supporting media.

As disclosed herein, the measurement of the expression of a set of early developmental genes in a stem cell line can be preformed alone as a single indicator of the pluripotency and/or differentiation potential of the stem cell line. As demonstrated in the Examples, the inventors have optimized the set of early developmental genes to be measured so an array or assay is sufficiently sensitive to estimate the differentiation propensities and pluripotency of the stem cell line using RNA isolated directly from the undifferentiated pluripotent cell lines, e.g., the assays and arrays can detect low levels of cellular differentiation in an otherwise self-renewing culture media or conditions. Further, the expression analysis for a set of early developmental genes can be performed using a variety of different RNA preparation methods, culture media and the like. The inventors have also demonstrated that the gene expression of a set of early developmental genes in a stem cell line can be analyzed in a multiplex system, for example in a 96- or 384-well plate format, allowing multiple stem cell lines to be analyzed simultaneously, demonstrating the ability of this assay to be performed in a high-throughput system.

The expression of a set of early developmental genes can be measured to assess the differentiation potential of a variety of different stem cells selected from, but not limited to, a pluripotent, multipotent, unipotent, or somatic stem cell, including but not limited to precursor cells, embryonic stem (ES) cells, somatic stem cells, cancer stem cells, progenitor cells, induced pluripotent stem (iPS) cells, partially induced pluripotent (piPS) cells, reprogrammed cells, directly reprogrammed cells, etc., to determine the stem cell's propensity to differentiate into ectoderm, mesoderm and endoderm lineages and/or to predict if the stem cell line has the ability to differentiate along a desired and/or particular developmental pathway and into a specific cell lineage.

In some embodiments, while the present invention specifically contemplates using the arrays, assays and methods as disclosed herein to determine if a stem cell is pluripotent, any type of stem cell can be assessed. For simplicity, when referring to a pluripotent stem cell herein, this encompasses both pluripotent and non-pluripotent stem cells. In some embodiments, the stem cell is a pluripotent stem cell.

In some embodiments, the expression of a defined set of early developmental genes can be analyzed in a high throughput manner, e.g., to screen for particular stem cell characteristics in a plurality of pluripotent stem cell lines. The sets of early developmental genes can be any selected set of early developmental genes from Table 1, as disclosed herein. In some embodiments, a set of early developmental genes which are analyzed include at least 3 genes from the group disclosed in Table 2. In some embodiments, a set of early developmental genes which are analyzed include at least 3 genes from Table 2 and any combination of at least 10, or at least 20 genes as disclosed in Table 1 can be assessed in a differentiation propensity assay as disclosed herein. In some embodiments, a set of early developmental genes which are analyzed include at least 1, or at least 2, or at least 3, or at least 4 genes or more from the group of mesoderm early developmental genes, selected from the group consisting of: HAND1, ESM1, HAND2, HOPX, BMP10, FCN3 and GSC, and/or at least 1, or at least 2, or at least 3, or at least 4 genes or more from a set of endoderm early developmental genes selected from the group consisting of: LEFTY1, EOMES, NODAL and FOXA2, and/or at least 1, or at least 2, or at least 3, or at least 4 genes from a set of ectoderm early developmental genes selected from the group consisting of: TRPM8, POU4F1, OLFM3, WNT1, LMX1A and CDH9 and/or at least 1, or at least 2, or at least 3, or at least 4 genes from a set of early developmental selected from the group consisting of: IDO1, LCK, POU5F1 and HESX1.

In some embodiments, one can measure the expression of a set of early developmental genes and allow the automatic selection of a suitable pluripotent stem cell line or clones with desired characteristics (e.g., pluripotency and/or predisposition to differentiate along a desired lineage). Specifically, the present invention relates to the measurement of expression of a set of early developmental genes in a stem cell line, such that a stem cell deviating from a normal range of early differentiation gene expression pattern can be excluded, and the cells that fall within the normal ranges can be selected for further use. For example, one can screen for, or evaluate expression of a subset of early developmental genes as disclosed herein, and if a stem cell does not fit within the predetermined parameters for a pluripotent cell expressing the appropriate marker set, it can be discarded or not selected for further use. Statistical analysis methods can be used to automate the system. In some embodiments, the expression of a set of early developmental genes as disclosed in Table 1 is analyzed in a stem cell line at a pre-defined time point, e.g., at least 2 days in EB forming conditions but not longer than 5 days, or not longer than or 7 days, in EB forming conditions (e.g., self-renewing culture conditions).

Accordingly, by measuring the expression of a set of early developmental genes, the inventors have demonstrated an efficient and effective method to monitor and validate the differentiation propensity and pluripotency of a stem cell population in order to predict their therapeutic utility and safety profile, (e.g., determining if the pluripotent stem cell population is predisposed to continual self-renewal and/or has an increased efficiency to differentiate along a particular lineage which is important if the pluripotent stem cell is to be transplanted for therapeutic use), and also permits one to predict into which lineages and developmental pathways the pluripotent stem cell line will efficiently differentiate. As such, the invention as disclosed herein permits the user to select or choose a stem cell line with desirable characteristics, e.g., positively select for stem cells with similar characteristics to other pluripotent stem cells, or stem cells which have a predisposition to optimally differentiate into a desired cell type or along a specific cell lineage. Alternatively, the present invention permits one to negatively select, e.g., identify, and optionally discard, stem cells with undesirable characteristics, e.g., cells which are non-pluripotent and/or are likely to differentiate into a cell type which is not desired by the investigator. Accordingly, the present invention permits one to determine the likely direction of the differentiation of a stem cell line and thus permits one to identify and/or choose a particular stem cell population for its suitability for downstream applications, such as its suitability for therapeutic use, drug screening and toxicity assays, differentiation into a desired cell lineage, and the like. The ability to predict to which lineage a stem cell line will likely differentiate into prior to a therapeutic application and/or administration can avoid the introduction of aberrant cells (e.g., can avoid administering a non-pluripotent stem cell line and/or cells which are unlikely to differentiate along a specific desired lineage, or cells which have an increased propensity to differentiate along an undesired lineage).

Accordingly, one aspect of the present invention relates to an array composition for characterizing the differentiation potential of a pluripotent stem cell, comprising nucleic acids, e.g., oligonucleotides or primers (e.g., primer pairs), that amplify the mRNA of any combination of early developmental genes selected from those listed in Table 1. In some embodiments, the array comprises nucleic acids, e.g., oligonucleotides or primers, that amplify the mRNA of at least 3 early developmental genes selected from those listed in Table 1 or Table 2. In some embodiments, the amplified developmental genes are at least 90% identical to, or specifically hybridize with nucleic acids encoding genes selected from those listed in Table 1 and/or Table 2.

In some embodiments, the array comprises at least 10, or at least about 20, or at least about 30, or 30-60, or 60-90 or more than 90 different nucleic acids (e.g. oligonucleotides), or at least 10, or at least about 20, or at least about 30, or 30-60, or 60-90 or more than 90 pairs of nucleic acids (e.g., primers), that amplify the mRNA of a combination of early developmental genes selected from those listed in Table 1 or Table 2.

In some embodiments, the array comprises nucleic acids, e.g., oligonucleotides or primers, that amplify the mRNA of at least one pluripotent stem cell gene, at least one early mesoderm developmental gene, at least one ectoderm developmental gene, and at least one endoderm developmental gene selected from Table 1 and/or from Table 2. In some embodiments, the array comprises nucleic acids, e.g., oligonucleotides or primers, that amplify the mRNA of at least 4 pluripotent stem cell genes, at least 4 early mesoderm developmental genes, at least 4 ectoderm developmental genes, and at least 4 endoderm developmental genes selected from Table 1. In some embodiments, the array comprises nucleic acids, e.g., oligonucleotides or primers that amplify at least 1, or at least 2, or at least 3, or at least 4 genes or more from the group of mesoderm early developmental genes, selected from the group consisting of: HAND1, ESM1, HAND2, HOPX, BMP10, FCN3 and GSC, and/or at least 1, or at least 2, or at least 3, or at least 4 genes or more from a set of endoderm early developmental genes selected from the group consisting of: LEFTY1, EOMES, NODAL and FOXA2, and/or at least 1, or at least 2, or at least 3, or at least 4 genes from a set of ectoderm early developmental genes selected from the group consisting of: TRPM8, POU4F1, OLFM3, WNT1, LMX1A and CDH9 and/or at least 1, or at least 2, or at least 3, or at least 4 genes from a set of early developmental selected from the group consisting of: IDO1, LCK, POU5F1 and HESX1.

In some embodiments, the array comprises nucleic acids, e.g., oligonucleotides or primers, that amplify the mRNA corresponding to 1-10 control genes, such as, but not limited to control genes selected from the group consisting of: ACTB, JARID2, CTCF, SMAD1, GAPDH, β-actin, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLP0, PPIA, POLR2A, PGK1, IPO8, HMBS, GUSB, B2M, HPRT1 or 18S.

In some embodiments, the array comprises no more than 100, or no more than 90, or no more than 50 nucleic acids, e.g., oligonucleotides or primers. In some embodiments, the nucleic acids present on the array are sets of primers. In some embodiments, the nucleic acids, e.g., oligonucleotides or primers are immobilized on, or within a solid support. As a non-limiting example, the nucleic acids can be immobilized on the solid surface by the 5' end of said oligonucleotides. In some embodiments, the solid surface is selected from a group of materials comprising silicon, metal, and glass. In some embodiments, the solid support comprises oligonucleotides at assigned positions defined by x and y coordinates.

In some embodiments, the array comprises nucleic acids, e.g., primers that can amplify the mRNA of the early developmental genes by a method comprising: polymerase chain reaction (PCR); strand displacement amplification (SDA); loop-mediated isothermal amplification (LAMP); rolling circle amplification (RCA); transcription-mediated amplification (TMA); self-sustained sequence replication (3SR); nucleic acid sequence based amplification (NASBA); or reverse transcription polymerase chain reaction (RT-PCR). In some embodiments, the array allows for real-time PCR amplification of the early developmental genes, or a real-time PCR amplification of the early developmental genes with detection by SYBR green or a MNAzyme detection method.

In some embodiments, the array as disclosed herein is, e.g., an OpenArray®, which is commercially available from Life Technologies, wherein the oligonucleotides or primers are immobilized within the wells of the OpenArray®. In some embodiments, the array is configured as a 96 or 384 well plate comprising primers to a set of early developmental genes selected from Table 1 and/or Table 2 dried in the wells, where each of the wells of the solid support of the plate has a hydrophobic top and bottom surface and a hydrophilic interior wall of each well permitting the primers and reaction mixture to remain in each individual well. In some embodiments, an array encompassed for use in the present invention comprises primers to a set of early developmental genes selected from Table 1 and/or Table and is configured as an OpenArray® as disclosed in U.S. Pat. Nos. 6,387,331; 6,743,633; 6,893,877; 7,332,271 and 7,547,556 which are incorporated herein in their entirety by reference.

Another aspect of the present invention relates to a method to determine the differentiation potential of a pluripotent stem cell comprising performing array amplification using the nucleic acid derived from a stem cell line and an array as disclosed herein. In some embodiments, after the array amplification, the data is analyzed using a web-based analysis tool which can output an indicator of the potential of the pluripotent stem cell to differentiate along different lineages selected from: mesoderm lineage, ectoderm lineage and endoderm lineage and/or the pluripotency of the pluripotent stem cell.

Another aspect of the present invention relates to a method of determining the differentiation potential of a test stem cell line comprising detecting and comparing the expression in the stem cell line of a set of early developmental genes selected from any listed in Table 1 and/or Table 2 to the expression of the same genes by a control pluripotent stem cell sample, and, based on this comparison, determining the differentiation potential of the test stem cell line. In some embodiments, the gene expression is assayed by real time amplification, or wherein the detection comprises SYBR Green based real-time PCR.

In some embodiments, the expression values (e.g., expression levels) of the early developmental genes plus at least one control gene are measured in the stem cell line and a ΔCt is calculated for each gene, and the ΔCt value of each early developmental gene is compared to the ΔCt value of each early developmental gene in a data pool that contains reference ΔCt values from a plurality of reference pluripotent stem cells, to provide a ΔΔCt value. In some embodiments, the expression values (e.g., expression levels) of the early developmental genes plus at least one control gene are measured in the stem cell line and the average ΔCt for the genes in each of the mesoderm, ectoderm and endoderm early developmental gene subgroups is calculated. In some embodiments, a ΔΔCt value is calculated by comparing the average ΔCt value of the genes in each of the mesoderm, ectoderm and endoderm early developmental gene subgroups with the average ΔCt value of the same genes in each of the mesoderm, ectoderm and endoderm early developmental gene subgroups in a data pool that contains reference average ΔCt values for the same genes in the mesoderm, ectoderm and endoderm early developmental gene subgroups from a plurality of reference pluripotent stem cells. In some embodiments, a t-test is used to identify statistically significant ΔΔCt values from the comparison of the average ΔCt value of the genes in each of the mesoderm, ectoderm and endoderm early developmental gene subgroups as compared to reference ΔCt value for genes in each of the mesoderm, ectoderm and endoderm early developmental gene subgroups from a plurality of reference pluripotent stem cells in the data pool.

In some embodiments, a stem cell line, e.g., a pluripotent stem cell line which differs by a statistically significant amount in the expression level of a set of mesoderm, ectoderm and endoderm early developmental genes is selected (e.g., chosen) for further use and/or research, or optionally discarded, depending on the investigators interest, on the basis of such a statistically significant difference(s) in early developmental gene expression.

In some embodiments, the method comprises detecting and comparing the expression levels of at least 10, or at least about 20, or at least about 30, or 30-60, or 60-90 or more than 90 early developmental genes selected from those listed in Table 1.

In some embodiments, the method comprises detecting and comparing the expression levels of at least one pluripotent stem cell gene, at least one early mesoderm developmental gene, at least one ectoderm developmental gene, and at least one endoderm developmental gene selected from Table 1 and/or from Table 2. In some embodiments, the method comprises detecting and comparing the expression levels of at least 4 pluripotent stem cell genes, at least 4 early mesoderm developmental genes, at least 4 ectoderm developmental genes, and at least 4 endoderm developmental genes selected from Table 1.

In some embodiments, the methods as disclosed herein permit a prediction of the response of a pluripotent stem cell line to signals directing differentiation along different lineages selected from: mesoderm lineage, ectoderm lineage and endoderm lineage. In some embodiments, the method as disclosed herein permits the evaluation of the pluripotency of a pluripotent stem cell line.

Another aspect of the present invention relates to an assay for choosing a stem cell line, e.g., a pluripotent stem cell line for a desired use by characterizing the differentiation potential of the stem cell line, the assay comprising: (a) measuring the level of expression of a plurality of early developmental genes in the stem cell line selected from the genes listed in Table 1; and comparing the measured level of expression with a reference gene expression level for the same plurality of early developmental genes; and (b) choosing a stem cell line on the basis of there being no statistically significant difference in the level of gene expression of the measured early developmental genes as compared to the reference gene expression level for the early developmental genes; or choosing a stem cell line on the basis of there being a statistically significant difference in the expression level in at least one desired early developmental gene as compared to the reference expression level of the early developmental genes.

In some embodiments, the assay measures a plurality of early developmental genes selected from at least 10, or at least about 20, or at least about 30, or 30-60, or 60-90 or more than 90 early developmental genes selected from those listed in Table 1. In some embodiments, the assay measures a plurality of early developmental genes selected from at least one pluripotent stem cell gene, at least one early mesoderm developmental gene, at least one ectoderm developmental gene, and at least one endoderm developmental gene selected from Table 1 and/or from Table 2. In some embodiments, the assay measures a plurality of early developmental genes selected from at least 4 pluripotent stem cell genes, at least 4 early mesoderm developmental genes, at least 4 ectoderm developmental genes, and at least 4 endoderm developmental genes selected from Table 1.

In some embodiments, the assay measures a plurality of early developmental genes in a pluripotent stem cell line that has been cultured for at least about 2 days as embryoid bodies (EB), or at least about 3 days, or at least about 4 days, or at least about 5 days as embryoid bodies (EB). In some embodiments, the assay measures a plurality of early developmental genes in pluripotent stem cell that has been cultured for no longer than about 2 days as EBs, or for no longer than about 3 or about 4 days as EBs, or in self-renewing culture conditions.

In some embodiments, the assay measures a plurality of early developmental genes in stem cells using any method commonly known by persons of ordinary skill in the art, e.g., a method selected from the group consisting of: polymerase chain reaction (PCR); strand displacement amplification (SDA); loop-mediated isothermal amplification (LAMP); rolling circle amplification (RCA); transcription-mediated amplification (TMA); self-sustained sequence replication (3SR); nucleic acid sequence based amplification (NASBA); or reverse transcription polymerase chain reaction (RT-PCR).

In some embodiments, the assay uses real-time PCR amplification, or a real-time PCR amplification method with detection by SYBR green or an MNAzyme detection method to measure the expression level of a plurality of early developmental genes.

In some embodiments, the assay further comprises measuring the level of expression of at least one control gene in the pluripotent stem cell, for example, a control gene selected from the group consisting of: ACTB, JARID2, CTCF, SMAD1, GAPDH, β-actin, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLP0, PPIA, POLR2A, PGK1, IPO8, HMBS, GUSB, B2M, HPRT1 or 18S.

In some embodiments, the level of the expression of the control gene in a test stem cell line, e.g., a pluripotent stem cell line is compared with the level of the expression of an early developmental gene to provide the ΔCt of the level of gene expression of an early developmental gene measured in the test stem cell line. In some embodiments, the assay comprises comparing the level of gene expression of the same plurality of early developmental genes with a reference gene expression level of the same early developmental genes and comparing the ΔCt of the expression of an early developmental gene measured in the test stem cell with the average ΔCt of the gene expression of the same early developmental gene measured from a plurality of reference pluripotent stem cells.

In some embodiments, the assay can be used to choose a stem cell line, e.g., a pluripotent stem cell line which differs by a statistically significant amount in the expression level of at least one desired early developmental gene, by selecting a stem cell line which differs by a statistically significant amount (e.g., using a t-test or other appropriate statistical measurement) in the expression level of an early developmental gene which is a mesoderm developmental gene, an ectoderm developmental gene, or an endoderm developmental gene. In some embodiments, a statistical difference is a difference of at least 1, at least 2, or at least 3 standard deviations from the reference gene expression level for the early developmental gene.

In some embodiments, the reference gene expression level for an early developmental gene includes the range of normal variation for the expression of that early developmental gene in a plurality of pluripotent stem cells. In some embodiments, the reference gene expression level for an early developmental gene is an average of expression level for that early developmental gene, wherein the average is calculated from expression level of that early developmental gene in a plurality of pluripotent stem cell lines. In some embodiments, the plurality of pluripotent stem cell lines for a reference gene expression level is obtained from at least 5 or more pluripotent stem lines.

In some embodiments, the assay as disclosed herein can be used characterize the differentiation potential of a mammalian a stem cell line, e.g., a pluripotent stem cell, e.g., a human pluripotent stem cell. In some embodiments, the pluripotent stem cell is an ES cell, or an iPS cell, or a partial iPS cell (piPSC), an adult stem cell, or a stem cell produced by reprogramming a somatic stem cell to an earlier developmental state.

Another aspect of the present invention relates to a kit comprising an array as disclosed herein, and reagents to carry out amplification of the mRNA of the early developmental genes.

Another aspect of the present invention relates to use of an array as disclosed herein for characterizing the differentiation potential of a stem cell line, e.g., a pluripotent stem cell according to an assay as disclosed herein.

In some embodiments, the invention as disclosed herein is useful for screening a compound for an effect on the expression level of at least one early developmental gene selected from the group listed in Table 1 and/or Table 2. In some embodiments, such a screening comprises the steps of (i) contacting a pluripotent stem cell with a test compound for a pre-determined amount of time; (ii) performing the assay as disclosed herein; and (iii) determining an increase or decrease on the expression level of at least one early developmental gene in the presence of the compound as compared to the absence of the compound. In some embodiments, a test compound can be selected from the group consisting of a small organic molecule, a small inorganic molecule, a polysaccharide, a peptide, a protein, a nucleic acid, an extract made from biological materials such as bacteria, plants, fungi, animal cells, animal tissues, or any combination thereof. In some embodiments, a test compound is tested at concentrations in the range of about 0.01 nM to about 1000 mM. In some embodiments, the screening method is configured to be compatible with a high-throughput screening method.

The inventors have also demonstrated that the analyses of the gene expression of a set of early developmental genes can be used to provide a "lineage scorecard" that can be used to predict the differentiation propensities, pluripotency and utility of any stem cell line. In particular, the inventors have demonstrated that the gene expression of a set of early developmental genes from a plurality of pluripotent stem cell populations provide a reference level for the normal variation of early developmental gene expression levels among a variety of different pluripotent cell lines, which can be used to compare the gene expression levels of the same early developmental genes from a test stem cell line to permit one to predict the behavior (e.g., differentiation propensity and pluripotency) of the individual test stem cell population. Such a lineage scorecard therefore also provides a platform for systematic comparison between different classes of pluripotent stem cells, (e.g., ES cells versus iPS cells, or iPS cells versus partially induced iPS cells and other pluripotent or non-pluripotent stem cell lines and the like). Accordingly, the inventors demonstrate that use of datasets, or a standard or reference lineage scorecard and bioinformatics data tools permit high-throughput characterization of the differentiation propensity and pluripotency of human stem cell lines, e.g., pluripotent stem cell lines, such as iPS cells lines and embryonic cell lines.

Accordingly, another aspect of the present invention relates to a set of reference data or reference lineage scorecard, which refer to the average data or otherwise aggregated data of the expression of a set of early developmental genes from a number of different pluripotent stem cell lines. The reference data which constitute a "lineage scorecard" can be used by one of ordinary skill in the art to compare, for example using a computer algorithm or software, a stem cell line of interest to a normal, well-functioning stem cell or a known set of pluripotent stem cells. The comparison with the reference "lineage scorecard" can be used to effectively and accurately predict the utility of the stem cell line for a given application, as well as any specific characteristics (e.g., differentiation propensity and/or pluripotency) of the stem cell line of interest, e.g., an ES cell or iPS cell line etc.

In some embodiments, the lineage scorecard comprises a data set of gene expression for a range of early developmental genes (e.g., a subset or any combination of the genes listed in Table 1) from at least 5 stem cell populations to determine the differentiation propensity and pluripotency of the stem cell line to differentiate along ectoderm, mesoderm and endoderm lineages. In some embodiments, the data of the expression of the early developmental genes are connected to a data storage device, such as a data storage device which is a database located on a computer device.

Accordingly, another aspect of the present invention relates to a lineage scorecard of the differentiation potential and pluripotency of a stem cell line, e.g., a pluripotent stem cell line, the scorecard comprising a data set of the expression level of a plurality of early developmental genes from a plurality of stem cell lines.

In some embodiments, the lineage scorecard comprises a data set of the expression levels a plurality of early developmental genes selected from at least 10, or at least about 20, or at least about 30, or 30-60, or 60-90 or more than 90 early developmental genes selected from those listed in Table 1. In some embodiments, the lineage scorecard comprises a data set of the expression levels a plurality of early developmental genes selected from at least one pluripotent stem cell gene, at least one early mesoderm developmental gene, at least one ectoderm developmental gene, and at least one endoderm developmental gene selected from Table 1 and/or from Table 2. In some embodiments, the lineage scorecard comprises a data set of the expression levels a plurality of early developmental genes selected from at least 4 pluripotent stem cell genes, at least 4 early mesoderm developmental genes, at least 4 ectoderm developmental genes, and at least 4 endoderm developmental genes selected from Table 1.

In some embodiments, the data set of the expression levels of a plurality of early developmental genes are connected to a storage device, and the storage device is a database located on a computer.

In some embodiments, at least 5, or at least about 10, or at least about 15 reference pluripotent stem cell lines are used to generate an early developmental gene expression data set for the reference lineage scorecard. In some embodiments, an early developmental gene expression data set is obtained from at least 5 or more, or at least 6, or at least 7, or at least 8, or at least 9, or at least 10, or at least 11, or at least 12, or at least 13 or at least 14, or at least 15, or at least 16, or at least 17, or at least 18, or all 19 of the following reference pluripotent stem cells lines selected from the group; HUES64, HUES3, HUES8, HUES53, HUES28, HUES49, HUES9, HUES48, HUES45, HUES1, HUES44, HUES6, H1, HUES62, HUES65, H7, HUES13, HUES63, HUES66.

In some embodiments, the pluripotent stem cell populations used to generate an early developmental gene expression data set for a reference lineage scorecard are mammalian pluripotent stem cell populations, such as human pluripotent stem cell populations, or induced pluripotent stem (iPS) cell populations, or embryonic stem cell populations, or adult stem cell populations, or autologous stem cell populations, or embryonic stem (ES) stem cell populations.

In some embodiments, the lineage scorecard as disclosed herein can be used to validate and/or predict the behavior (e.g., differentiation propensity and/or pluripotency) of a stem cell line, e.g., a pluripotent stem cell population by predicting the optimal differentiation along a specific lineage and/or propensity to have undesirable characteristic, e.g., stem cell populations which have a predisposition to develop along lineages not desired by the investigator. Thus, in some embodiments, the lineage scorecard can be used in methods for, e.g., positive selection of a stem cell population with desirable characteristics (e.g., high differentiation potential along a specific lineage and/or pluripotent characteristics), and/or to negatively select cells (and optionally discard) stem cell lines with undesirable characteristics, e.g., stem cells with a predisposition to develop along lineages not desired by the investigator, or non-pluripotent stem cell lines.

In some embodiments, the lineage scorecard report provides an indication of suitable uses or applications for the pluripotent stem cell population, or in alternative embodiments, provide an indication of uses or applications that the pluripotent stem cell line is not suitable for.

Another aspect of the present invention relates to a method for generating a lineage score card comprising measuring the gene expression of a set of early differentiation genes in a plurality of pluripotent stem cell lines. In some embodiments, the method to generate a pluripotent stem cell score card can be used to generate a scorecard comprising the values of normal variations of the levels of gene expression of a set of early developmental genes from a plurality of pluripotent stem cell lines, for example, at least 5, or at least 6, or at least 7, or at least 8, or at least 9, or at least 10, or at least 15, or at least 20, or at least 30, or at least 40 or more than 40 different pluripotent stem cell populations.

Another aspect of the present invention relates to a method for selecting or choosing a stem cell line, e.g., a pluripotent stem cell population, comprising measuring the gene expression of a set of early developmental genes in a stem cell population and comparing the early developmental gene expression data with reference data for early developmental gene expression, and selecting a stem cell line which does not differ by a statistically significant amount in the expression of the early developmental genes expressed and thus in the stem cells' ability to differentiate along mesoderm, ectoderm and endoderm lineages as compared to a reference differentiation potential or reference pluripotent stem cell line. In some embodiments, a stem cell line is not selected if it differs by a statistically significant amount to the expression in the early developmental genes expressed and thus differs in its ability to differentiate along mesoderm, ectoderm and endoderm lineages as compared to a reference differentiation potential of a reference pluripotent stem cell line. In some embodiments, a stem cell line is also selected if it differs by a statistically significant amount to the expression in the early developmental genes expressed and thus identifies the stem cell line as one which is capable of differentiating along a desired cell lineage selected from: mesoderm, ectoderm and endoderm lineages, and can be selected based on it's propensity to differentiate along a particular lineage desired by the user.

Another aspect of the present invention relates to a computer system for generating a lineage scorecard of a pluripotent stem cell, comprising; (a) at least one memory containing at least one program comprising the steps of: (i) receiving gene expression data of a set of early developmental genes in the pluripotent stem cell line and comparing the expression data with a reference level of the same set of early developmental genes; (ii) generating a lineage scorecard based on the comparison of the expression of the early developmental genes as compared to reference levels of the same early developmental genes; and (b) a processor for running said program.

In some embodiments, the system further comprises an output or report-generating module for generating a stem cell lineage scorecard report based on the expression of the early developmental gene expression data set obtained from the test stem cell line. In some embodiments, the system comprises a memory, where the memory further comprises a database. In some embodiments, the database arranges the early developmental gene expression data set in a hierarchical manner, for example, where the database arranges the propensity of differentiation of the pluripotent stem cell of interest into different lineages in a hierarchical manner. In some embodiments, the memory of the system is connected to the first computer via a network, for example, a wide area network, or a world-wide network.

Another aspect of the present invention relates to a computer readable medium comprising instructions for generating a lineage scorecard of a test stem cell line, e.g., a pluripotent stem cell line, comprising: (i) receiving an early developmental gene expression data set from the test stem cell line and performing a comparison of the early developmental gene expression data set with a reference levels of the early developmental genes; (ii) generating a lineage scorecard based on the comparison of the early developmental gene expression data set as compared to reference levels of the early developmental genes.

Accordingly, another aspect of the present invention relates to a reference database comprising a lineage scorecard as disclosed herein. Another aspect of the present invention relates to a computer readable storage media comprising a reference database as disclosed herein. In some embodiments the computer readable storage medium is tangible, non-transitory storage media, for example, any available tangible or physical media that can be accessed by a computer. Computer readable medium do not encompass a signal, such as a carrier signal.

Another aspect of the present invention relates to a computer-readable, physical memory comprising computer-executable instructions for calculating the $\Delta$Ct for each early developmental gene measured, and wherein the $\Delta$Ct value of each early developmental gene is compared to the $\Delta$Ct value for each early developmental gene from a data pool that contains reference $\Delta$Ct values for each early developmental genes from a plurality of reference pluripotent stem cells, to provide a $\Delta\Delta$Ct value.

In some embodiments, the computer readable instructions enable calculation of the average $\Delta$Ct for the genes in each of the mesoderm, ectoderm and endoderm early developmental gene subgroups, and comparing the average $\Delta$Ct value of the genes in each of the mesoderm, ectoderm and endoderm early developmental gene subgroups with the average $\Delta$Ct value of the same genes in each of the mesoderm, ectoderm and endoderm early developmental gene subgroups from a data pool that contains reference average $\Delta$Ct values for the same genes in the mesoderm, ectoderm and endoderm early developmental gene subgroups from a plurality of reference pluripotent stem cells, to provide an average $\Delta\Delta$Ct value.

In some embodiments, the computer readable instructions further comprises instructions to perform a t-test to identify statistically significant $\Delta\Delta$Ct values from the comparison of the average $\Delta$Ct value of the genes in each of the mesoderm, ectoderm and endoderm early developmental gene subgroups as compared to average reference $\Delta$Ct value for genes in each of the mesoderm, ectoderm and endoderm early developmental gene subgroups from a plurality of reference pluripotent stem cells in the data pool.

In some embodiments, the gene expression of a set of early developmental genes is measured using RT-PCR, e.g., an RT-PCR assay comprising primers specific for a set of genes listed in Table 1 or at least 3 genes from Table 2. In some embodiments, the RT-PCR assay uses an array comprising primers for performing RT-PCR to amplify the mRNA of a set of early developmental genes from Table 1 and optionally can comprise primers for amplifying the mRNA of at least 3 early developmental genes from Table 2.

In some embodiments, the gene expression of a set of early developmental genes is measured using a microarray assay. In some embodiments, the RT-PCR array or microarray comprises a set of early developmental genes for analysis selected from at least about 20, or at least 30, or at least 40 selected from a subset of any combination of the genes listed in Table 1. In some embodiments, the RT-PCR array or microarray comprises a set of early developmental genes for analysis selected from at least about 3 or more genes from a subset of any combination of the genes listed in Table 2. In some embodiments, gene expression of a set of early developmental genes is determined using an RT-PCR array or microarray from a pluripotent stem cell line at about 2 days in culture (e.g., 2 days EB).

In some embodiments, the differentiation assay as disclosed herein is a high-throughput assay for assaying a plurality of different pluripotent stem cells, for example, permitting one to measure and assess the level of gene expression of a set of early developmental genes in a plurality of different induced pluripotent stem cells, wherein the stem cells are derived by reprogramming a somatic cell obtained from the same or a different subject, e.g., a mammalian subject or a human subject.

In some embodiments, measuring the gene expression of a set of early developmental genes in a stem cell line as disclosed herein can be used to identify and/or optimize and/or validate a differentiating media and/or differentiation factors which can increase the efficiency of a stem cell line to differentiate along a particular cell-type lineage. By way of an exemplary example only, in some embodiments, the arrays, assays and methods as disclosed herein can be used to confirm that mesoderm early developmental markers as disclosed herein are being expressed in a stem cell line cultured in a mesoderm induction medium. Alternatively, in some embodiments, the arrays, assays and methods as disclosed herein can be used to confirm that a pluripotent stem cell media maintains a stem cell line in a pluripotent state and does not induce the cell line to differentiate along a particular lineage.

Measurement of the gene expression of a set of early developmental genes can be performed using an array or assay which is configured for high-throughput analysis, for example using multiplex qRT-PCR and high-throughput sample processing for the rapid characterization of the differentiation propensity of hundreds or thousands of pluripotent stem cell lines (e.g., ES and/or iPS cell lines). For example, such a high-throughput array would be useful where it is desirable to characterize 100's and 1000's of stem cell lines in high-throughput centers. For example, this would be useful to identify and choose stem cell lines for utility in drug screening and/or for therapeutic use. Accordingly, the measurement of the expression of a set of early developmental genes as disclosed herein allow rapid and inexpensive characterization of large numbers of stem cell lines which would be highly expensive and impractical using traditional teratoma and/or other gene expression systems whereby the stem cells are required to undergo spontaneous or directed differentiation for a period of time prior to analysis. Alternatively, measurement of the expression of a set of early developmental genes as disclosed herein can be used on individual pluripotent stem cell lines to accelerate research and select those lines with desired lineage propensities to be used in research to address a research question of interest. For example, the expression of a set of early developmental genes as disclosed herein can be assessed in a stem cell line, e.g., a pluripotent stem cell line, as early as 2 days in EB in order to quickly identify the most suitable stem cell line (e.g., with the desired pluripotency and/or differentiation propensities) for further analysis or to address a research question of interest.

Another aspect of the present invention relates to a kit for measuring the gene expression of a set of early developmental genes, comprising reagents (e.g., oligonucleotide probes and/or primers and other reagents) necessary for measuring gene expression levels of a plurality of early developmental genes, e.g., a subset of any combination of the genes listed in Table 1 and/or Table 2. In some embodiments, the kit further comprises a lineage score card as disclosed herein. In some embodiments, the kit further comprises instructions for use. In some embodiments, the kit comprises a computer readable medium comprising instructions on a computer to compare the measured levels of the early developmental genes from the test stem cell line with reference levels of the same genes. In some embodiments, the kit comprises instructions to access to a software program available online (e.g., on a cloud) to compare the measured levels of the early developmental genes from the test stem cell line, e.g., pluripotent stem cell line, with reference levels of the same genes from reference pluripotent stem cell lines.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIGS. 1A-1D show prior art methods disclosed in WO2012/037456, which is incorporated herein in its entirety by reference, in which cell-line specific differentiation propensities can be measured by a quantitative EB assay. FIG. 1A shows a schematic outline of a prior art assay for quantifying cell-line specific differentiation propensities. The cell lines need to be differentiated for at least 7- to 14-days in culture before measuring lineage markers. Furthermore, the lineage markers were not early developmental genes. FIG. 1B shows a prior art lineage scorecard summarizing cell-line specific differentiation propensities of a set of low-passage human ES cell lines. The numbers indicate relative enrichment (positive values) or depletion (negative values) on a linear scale. They were calculated by performing moderated t-tests comparing all biological replicates for a given ES cell line to the ES-cell reference (consisting of biological replicates for all other ES cell lines), followed by a gene set enrichment analysis for sets of markers genes with relevance for the cellular lineage or germ layer of interest. All columns are centered on zero, such that an ES cell line will exhibit differentiation propensities of zero if it differentiates just like the average of all other ES cell lines that were used to calibrate the assay. Values should be interpreted relative to each other, with higher numbers indicating higher differentiation propensities and lower values indicating lower differentiation propensities, while the absolute values have no measurement unit and no direct biological interpretation. FIG. 1C shows prior art of a two-dimensional multidimensional scaling map of the transcriptional similarity of ES and iPS cell lines, ES-derived and iPS-derived EBs, and primary fibroblast cell lines. Gene expression of 500 lineage marker genes was measured using the nCounter system, and the normalized data were projected onto a plane such that the distance of the points to each other represents their distance in the 500-dimensional space of gene expression levels. Each point corresponds to a single biological replicate, and the projection was performed using multidimensional scaling. Two iPS cell lines were significantly impaired in their ability to form normal EBs (hiPS 15b, hiPS 29e, highlighted by an arrow and labeled as "impaired EBs"), and one iPS cell line completely failed to form normal EBs (hiPS 27e, highlighted by an arrow and labeled "failed EBs"), maintaining a gene expression profile that is reminiscent of pluripotent cells even after 16-day EB differentiation. All biological replicates of these three cell lines are highlighted by arrows, and all three cell lines also exhibit significantly reduced differentiation propensities according to the lineage scorecard (FIG. 1D). FIG. 1D shows a prior art lineage scorecard summarizing cell-line specific differentiation propensities of a set of human iPS cell lines. The scorecard was derived as described for FIG. 1B and normalized against the ES-cell reference. The scores were calculated across all biological replicates that were available fore each cell line. This scorecard required (i) pluripotent stem cells to be cultured for at least 7 or 14-days in culture, (ii) directed differentiation of the stem cell down a particular lineage, (iii) analysis of ~500 lineage markers and (iv) the gene expression analysis to be performed in replicates (e.g., duplicate or triplicate).

FIG. 2A shows that the PluriTest analysis of MicroArray data fails to distinguish Day 7 differentiated cells from undifferentiated cells and is limiting in just pluripotency assessment and not differentiation status. FIG. 2B shows that the lineage ScoreCard analysis of a focused set of 96 genes shows clear downregulation of pluripotent genes and upregulation of the differentiation genes classified into the three germ layers thus permitting assessment of both pluripotency as well as trilineage differentiation potential.

FIG. 3 is a comparison of the mean measured early developmental genes with the reference level expression levels. For each input sample (e.g., BJ fibroblasts, H9 ESCs and hNSC), and for each of six categories of early developmental genes (control, pluri, endo, mesendo, meso, ecto) the software reports mean (mu) and standard deviation of t-statistic (significance) and min and max p-value over the gene category.

FIG. 4 shows the expression levels of each category of early developmental gene relative to a reference standard for each category of early developmental genes. Using t-value as an indicator, a t-value of 0-1 indicates that the measured level of gene expression in that early developmental gene category is comparable with the reference gene expression level in the same category. A t-value of >1 indicates that the measured gene expression level in that early developmental gene category of the pluripotent cell line is higher than the reference gene expression level in the same category. A t-value of <0 indicates that the measured gene expression level in that early developmental gene category of the pluripotent cell line is lower than the reference gene expression level in the same category.

FIG. 5 shows pluripotent stem cells cultured at 2 and 4 days produce reliable results for levels of expression of each category of early developmental gene.

FIG. 6 shows that the expression of the early developmental genes of D4 and D7 is not affected if the pluripotent stem cells are cultured in an embryoid (EB) suspension or in a monolayer.

FIGS. 7A-7C show that the differentiation assay can identify outlier pluripotent stem cells, e.g., cell lines which are no-longer pluripotent, stem cell lines with an increased efficiency to differentiate along a particular cell lineage and/or pluripotent stem cells contaminated with mouse (e.g., MEF) cells. FIG. 7A shows an embodiment of a lineage scorecard to identify a bad clone or culture (e.g., BS4-iPS5 P8), when the pluripotent stem cell is compared to similar pluripotent stem cells lines at the same time point. FIG. 7B shows an embodiment of a lineage scorecard to identify a stem cell line which has a predisposition to differentiate along a particular lineage, showing that the hNSDup cell line has increased ectoderm levels indicating the cell line has a predisposition to differentiate along an ectoderm lineage. FIG. 7C shows an embodiment of a lineage scorecard to identify a stem cell line which is no longer pluripotent (e.g., see BJ fibroblasts and HJF fetal cells) which have a significant decrease in pluripotent genes, and that the contamination of a stem cell line with MEF has no effect on the expression levels of early developmental genes.

DETAILED DESCRIPTION OF THE INVENTION

Figure 1A:
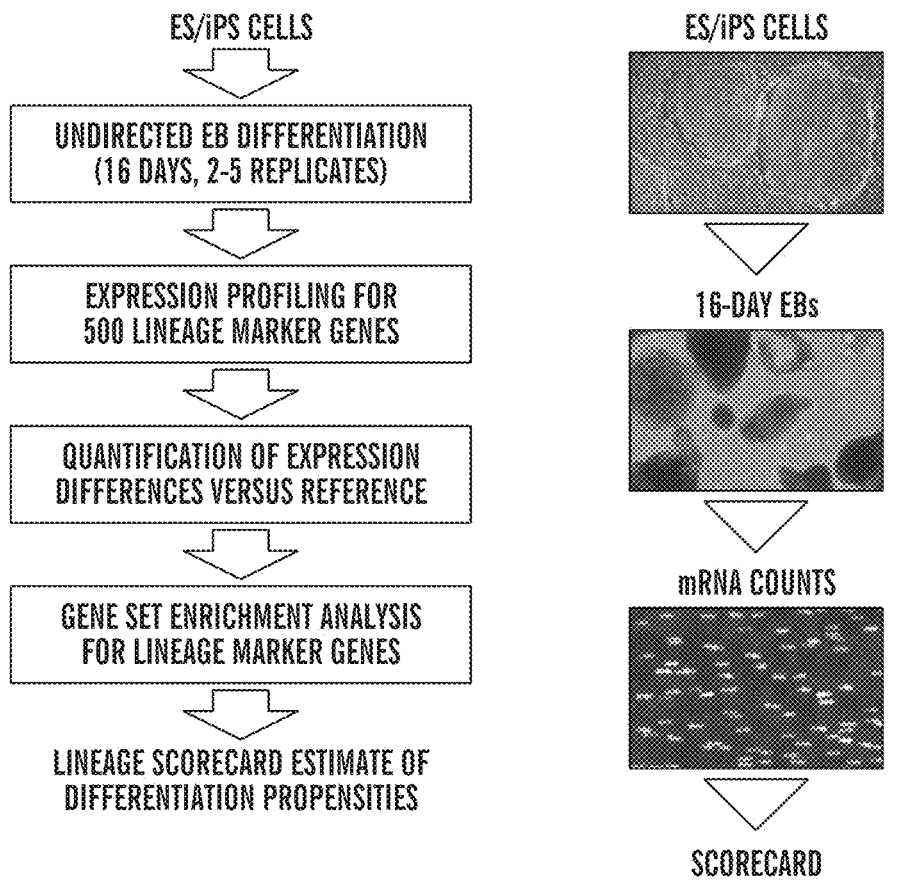
Figure 1C:
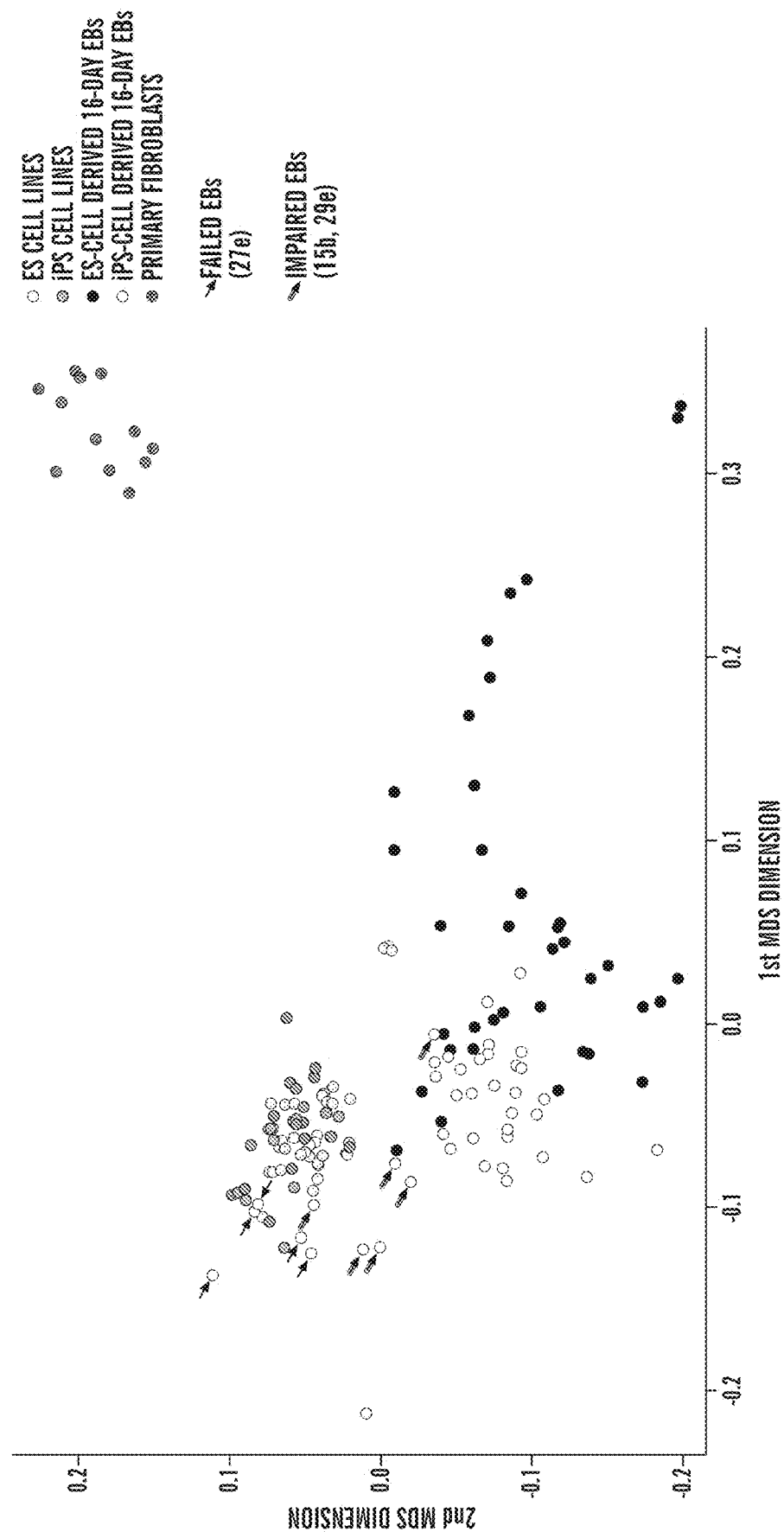

The present invention is directed a set of early developmental gene biomarkers, or subsets thereof, which can be used to characterize and determine the pluripotency and/or differentiation potential of a stem cell population. Aspects of the present invention relate to arrays, assays, systems, kits and methods to rapidly and inexpensively screen stem cell lines for their general quality (e.g., pluripotent capacity) and differentiation capacity.

As disclosed herein in the Examples, the inventors have surprisingly discovered that the expression of a subset of genes which are expressed in very early stages of development, herein referred to as "early developmental genes" can accurately predict if the stem cell line is pluripotent, and/or if the stem cell line has a propensity to differentiate along mesoderm, ectoderm and endoderm lineages, and/or if there is a favorable lineage that the stem cell line differentiates along. Thus, the set of early developmental genes disclosed herein provides meaningful insight into the cells' likely developmental and differentiation pathways at a very early stage of development, e.g., from about 2 days in EB culture conditions.

For example, by measuring the gene expression of a set of early developmental genes in a stem cell line, e.g., a pluripotent stem cell line as disclosed herein, one is able to forecast the differentiation efficiency of the stem cell line being analyzed. For example, the inventors have demonstrated that the levels of these genes are highly predictive for determining the likely direction of the differentiation of the stem cell line along particular lineages, e.g., mesoderm, ectoderm and endoderm lineages. Therefore, the present invention as disclosed herein has broad utility and can be used to prospectively predict how well a given stem cell will differentiate along any desired lineage, for example, hematopoietic lineage, endoderm lineage, pancreatic lineage, neuronal lineage such as a motor neuron lineage and the like.

Accordingly, the present invention generally relates to arrays, assays, methods, kits and systems for measuring a set of early developmental genes in a stem cell line, e.g., a pluripotent stem cell line, to predict the differentiation potential and/or pluripotency of the stem cell line. The present invention also relates to a reference database of the expression of a set of early developmental genes to produce a "lineage scorecard" for a stem cell line, where the gene expression of such a set of early developmental genes can predict the functionality and suitability of a stem cell line for a desired use, and can predict if the stem cell line will differentiate along a particular cell lineage, or differentiate with an increased efficiency along a particular cell lineage, such as neural stem cell, hematopoietic stem cell, pancreatic stem cell and other lineages. In some embodiments, a lineage scorecard further provides guidelines to determine if a stem cell line, e.g., a pluripotent stem cell of interest, falls within normal parameters of normal pluripotent stem cell variation and/or has a propensity to differentiate along a specific cell lineage. Such guidelines are preferably in a computer executable format.

In some embodiments, a lineage scorecard is a scorecard compiled from the expression data of a set of early developmental genes from a plurality of different pluripotent stem cells with desirable characteristics, for example, a pluripotent stem cell with propensity to differentiate into endoderm lineages, such as pancreatic lineages and the like, or other lineages, such as, for example, ectoderm or mesoderm lineages.

Another aspect of the present invention relates to a method for generating a lineage scorecard comprising performing a gene expression assay to predict the functionality and suitability of a stem cell line, e.g., a pluripotent stem cell line for a desired use. In some embodiments, a lineage scorecard reference data can be compared with the test stem cells' data to effectively and accurately predict the utility of the test stem cell line for a given application, as well as to identify specific characteristics of the stem cell line to determine their suitability for downstream applications, such as their suitability for therapeutic use, drug screening and toxicity assays, differentiation into a desired cell lineage, and the like.

In some embodiments, the gene expression of a set of early developmental genes measured in the methods, arrays, assays, kits and systems as disclosed herein includes at least 10, or at least 20 genes selected from any combination of the genes listed in Table 1. In some embodiments, the set of early developmental genes measured in the methods, arrays, assays, kits and systems as disclosed herein include at least 3 genes from any combination of the genes listed in Table 2.

In some embodiments, the differentiation assays, methods, systems and kits as disclosed herein can be used to characterize and determine the differentiation potential of a variety of stem cell lines, e.g., a pluripotent stem cell lines, such as, but not limited to embryonic stem cells, adult stem cells, autologous adult stem cells, iPS cells, and other pluripotent stem cell lines, such as reprogrammed cells, direct reprogrammed cells or partially reprogrammed cells. In some embodiments, a stem cell line is a human stem cell line. In some embodiments, a stem cell line, e.g., a pluripotent stem cell line is a genetically modified stem cell line. In some embodiments, where the stem cell line, e.g., a pluripotent stem cell line is for therapeutic use or for transplantation into a subject, a stem cell line is an autologous stem cell line, e.g., derived from a subject to which a population of stem cells will be transplanted back into, and in alternative embodiments, a stem cell line, e.g., a pluripotent stem cell line is an allogeneic pluripotent stem cell line.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "lineage scorecard" as disclosed herein refers to a listing of a summary of the gene expression differences of a plurality of early developmental genes in each category (e.g., pluripotent genes, early endoderm genes, early mesoderm genes, early ectoderm genes) in one or more pluripotent stem cell lines of interest as compared to a reference pluripotent stem cell line, and functions as record of the pluripontent stem cell's predicted performance, for example, differentiation ability and/or pluripotency capacity. A scorecard can exist in any form, for example, in a database, a written form, an electronic form and the like, and can be electronically or digitally recorded and stored in annotated databases. In some embodiments, a scorecard can be a graphical representation of a prediction of the pluripotent stem cell capabilities (e.g., differentiation capabilities, pluripotency etc.) as compared to a reference pluripotent cell line or plurality of lines. Accordingly, the scorecards as disclosed herein serve as an indicator or listing of the characteristics and potential of a pluripotent stem cell line and can be used to assist in fast and efficient selection of a particular pluripotent stem cell line for a particular use and/or to reach a specific objective.

The term "nucleic acid" or "nucleic acid sequence" as used herein is defined as a molecule comprised of two or more deoxyribonucleotides or ribonucleotides. The exact length of the sequence will depend on many factors, which in turn depends on the ultimate function or use of the sequence. The sequence can be generated in any manner, including chemical synthesis, DNA replication, reverse transcription, or a combination thereof. Due to the amplifying nature of the present invention, the number of deoxyribonucleotide or ribonucleotide bases within a nucleic acid sequence can be virtually unlimited. The term "oligonucleotide," as used herein, is interchangeably synonymous with the term "nucleic acid sequence".

As used herein, oligonucleotide sequences that are complementary to one or more of the genes described herein, refers to oligonucleotides that are capable of hybridizing under stringent conditions to at least part of the nucleotide sequence of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes.

The term "primer" as used herein refers to a sequence of nucleic acid which is complementary or substantially complementary to a portion of the target early developmental gene of interest. Typically 2 primers (e.g., a 3' primer and a 5' primer) are complementary to different portions of the target early developmental gene of interest and can be used to amplify a portion of the mRNA of the early developmental gene by RT-PCR.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to" refers to the binding, duplexing or hybridizing of a molecule substantially to or only to a particular nucleotide sequence or sequences under stringent conditions when that sequence is present in a complex mixture (e.g., total cellular) DNA or RNA.

The term "biomarker" means any gene, protein, or an EST derived from that gene, the expression or level of which changes between certain conditions. Where the expression of the gene correlates with a certain condition, the gene is a biomarker for that condition.

"Biomarker-derived polynucleotides" means the RNA transcribed from a biomarker gene, any cDNA or cRNA produced therefrom, and any nucleic acid derived therefrom, such as synthetic nucleic acid having a sequence derived from the gene corresponding to the biomarker gene.

As used herein, the term "gene" has its meaning as understood in the art. However, it will be appreciated by those of ordinary skill in the art that the term "gene" can include gene regulatory sequences (e.g., promoters, enhancers, etc.) and/or intron sequences. It will further be appreciated that definitions of gene include references to nucleic acids that do not encode proteins but rather encode functional RNA molecules such as tRNAs. For clarity, the term gene generally refers to a portion of a nucleic acid that encodes a protein; the term can optionally encompass regulatory sequences. This definition is not intended to exclude application of the term "gene" to non-protein coding expression units but rather to clarify that, in most cases, the term as used in this document refers to a protein coding nucleic acid. In some cases, the gene includes regulatory sequences involved in transcription, or message production or composition. In other embodiments, the gene comprises transcribed sequences that encode for a protein, polypeptide or peptide. In keeping with the terminology described herein, an "isolated gene" can comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof.

The term "signature" as used herein refers to the differential expression pattern. It could be expressed as the number of individual unique probes whose expression is detected when a cRNA product is used in microarray analysis. It could also be expressed as the number of individual genes whose expression is detected with real time RT-PCR. A signature can be exemplified by a particular set of biomarkers.

The term a "similarity value" is a number that represents the degree of similarity between two things being compared. For example, a similarity value can be a number that indicates the overall similarity between a cell sample expression profile using specific phenotype-related biomarkers and a control specific to that template. The similarity value can be expressed as a similarity metric, such as a correlation coefficient, or a classification probability or can simply be expressed as the expression level difference, or the aggregate of the expression level differences, between a cell sample expression profile and a baseline template.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

As used herein, the terms "measuring expression levels," "obtaining expression level," and "detecting an expression level" and the like, includes methods that quantify a gene expression level of, for example, a transcript of a gene, or a protein encoded by a gene, as well as methods that determine whether a gene of interest is expressed at all. In some embodiments, the assay provides an indicator if the pluripotent stem cell can differentiate along a particular lineage, e.g., mesoderm, ectoderm or endoderm lineage. In some embodiments, the indicator is a numerical value (e.g., the value from a t-test from the comparison of the average ΔCt for each of the measured mesoderm, or ectoderm or endoderm early developmental genes in the pluripotent stem cell as compared to reference ΔCt of the same genes in a reference set of pluripotent stem cells, as disclosed herein in the Examples). In some embodiments, the assay can provide a "yes" or "no" result without necessarily providing quantification, indicating that the pluripotent can or cannot, respectively, differentiate along each of the mesoderm, ectoderm or endoderm lineages, or "yes" or "no" to indicate that the stem cell line tested is or is not pluripotent, respectively. Alternatively, a measured or obtained expression level can be expressed as any quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. For example, in some embodiments, the assay can provide a heat map, with green indicator signals that pluripotent stem cell has a high propensity or likelihood of differentiating along a particular lineage (e.g., each of the mesoderm, ectoderm or endoderm lineages), a yellow indicator to signal that pluripotent stem cell has the ability to differentiate along a particular lineage and a red indicator to signal that pluripotent stem cell has a low propensity, or cannot differentiate along a particular lineage. In some embodiments, there is an indicator for each of: the pluripotency of the stem cell, the stem cell ability to differentiate along mesoderm lineage, the stem cells' ability to differentiate along a ectoderm lineage and a the stem cells' ability to differentiate along a endoderm lineage. The early developmental genes identified as being differentially expressed in the pluripotent stem cell line of interest can be used in a variety of nucleic acid or protein detection assays to detect or quantify the expression level of a gene or multiple genes in a given sample. Exemplary methods for detecting the level of expression of a gene include, but are not limited to, Northern blotting, dot or slot blots, reporter gene matrix (see for example, U.S. Pat. No. 5,569,588) nuclease protection, RT-PCR, microarray profiling, differential display, 2D gel electrophoresis, SELDI-TOF, ICAT, enzyme assay, antibody assay, MNAzyme-based detection methods (see U.S. Ser. No. 61/470,919, US 2011/0143338; US 2007/0231810; WO WO/2008/122084; WO/2007/041774; and Mokany et al., J Am Chem Soc. 2010 Jan. 27; 132(3): 1051-1059, each of which is incorporated by reference in its entirety), and the like. Optionally a gene whose level of expression is to be detected can be amplified, for example by methods that can include one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). In the preferred embodiment gene expression will be detected by RT-PCR, preferably using SYBR green.

The term "gene profile" as used herein is intended to refer to the expression level of a gene, or a set of genes, in a pluripotent stem cell sample. In one embodiment of the invention the term "gene profile" refers to the expression levels or status of a gene or a set of genes listed in Table 1 or to that of any selection of the genes of Table 1, which are described herein.

The term "differential expression" in the context of the present invention means the gene is upregulated or down-regulated in comparison to its normal variation of expression in a pluripotent stem cell. Statistical methods for calculating differential expression of genes are discussed elsewhere herein.

"Genes of Table 1" is used interchangeably herein with "gene listed in Table 1" and refers to the gene products of genes listed under "Early Developmental genes" in Table 1. By "gene product" is meant any product of transcription or translation of the genes, whether produced by natural or artificial means. In some embodiments of the invention, the genes referred to herein are those listed in Table 1. The same applies to "genes of Table 2", but rfers to the gene products of genes listed under early developmental genes in Table 2.

The term "hybridization" or "hybridizes" as used herein involves the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA, 46:453 (1960) and Doty et al., Proc. Natl. Acad. Sci. USA, 46:461 (1960) have been followed by the refinement of this process into an essential tool of modern biology.

The terms "complementary" or "substantially complementary" as used herein refer to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity. See M. Kanehisa, Nucleic Acids Res., 12:203 (1984), incorporated herein by reference. The term "at least a portion of" as used herein, refers to the complimentarity between a circular DNA template and an oligonucleotide primer of at least one base pair.

Partially complementary sequences will hybridize under low stringency conditions. This is not to say that conditions of low stringency are such that non-specific binding is permitted; low stringency conditions require that the binding of two sequences to one another be a specific (i.e., selective) interaction. The absence of non-specific binding can be tested by the use of a second target which lacks even a partial degree of complementarity (e.g., less than about 30% identity); in the absence of non-specific binding the probe will not hybridize to the second non-complementary target.

The term "stringency" refers to the degree of specificity imposed on a hybridization reaction by the specific conditions used for a reaction. When used in reference to nucleic acid hybridization, stringency typically occurs in a range from about $T_m$-5° C. (5° C. below the $T_m$ of the probe) to about 20° C., 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences. Suitably stringent hybridization conditions for nucleic acid hybridization of a primer or short probe include, e.g., 3×SSC, 0.1% SDS, at 50° C.

When used in reference to nucleic acid hybridization the art knows well that numerous equivalent conditions can be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution can be varied to generate conditions of either low or high stringency hybridization different from, but equivalent to, the above listed conditions.

The term "solid surface" as used herein refers to a material having a rigid or semi-rigid surface. Such materials will preferably take the form of chips, plates (e.g., microtiter plates), slides, small beads, pellets, disks or other convenient forms, although other forms can be used. In some embodiments, at least one surface of the solid surface will be substantially flat. In other embodiments, a roughly spherical shape is preferred.

The term "reprogramming" as used herein refers to a process that alters or reverses the differentiation state of a differentiated cell (e.g. a somatic cell). Stated another way, reprogramming refers to a process of driving the differentiation of a cell backwards to a more undifferentiated or more primitive type of cell. Complete reprogramming involves complete reversal of at least some of the heritable patterns of nucleic acid modification (e.g., methylation), chromatin condensation, epigenetic changes, genomic imprinting, etc., that occur during cellular differentiation as a zygote develops into an adult. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent.

The term "induced pluripotent stem cell" or "iPSC" or "iPS cell" refers to a cell derived from a complete reversion or reprogramming of the differentiation state of a differentiated cell (e.g. a somatic cell). As used herein, an iPSC is fully reprogrammed and is a cell which has undergone complete epigenetic reprogramming. As used herein, an iPSC is a cell which cannot be further reprogrammed to a more immature state (e.g., an iPSC cell is terminally reprogrammed).

The term "pluripotent" as used herein refers to a cell with the capacity, under different conditions, to differentiate to cell types characteristic of all three germ cell layers (endoderm, mesoderm and ectoderm). A pluripotent stem cell typically has the potential to divide in vitro for a long period of time, e.g., greater than one year or more than 30 passages.

The term "differentiated cell" refers to any primary cell that is not, in its native form, pluripotent as that term is defined herein. The term a "differentiated cell" also encompasses cells that are partially differentiated, such as multipotent cells, or cells that are stable non-pluripotent partially reprogrammed cells. It should be noted that placing many primary cells in culture can lead to some loss of fully differentiated characteristics. However, such cells are included in the term differentiated cells and the loss of fully differentiated characteristics does not render these cells non-differentiated cells (e.g. undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

As used herein, the term "adult cell" refers to a cell found throughout the body after embryonic development.

In the context of cell ontogeny, the term "differentiate", or "differentiating" is a relative term meaning a "differentiated cell" is a cell that has progressed further down the developmental pathway than its precursor cell. Thus in some embodiments, a reprogrammed cell as this term is defined herein, can differentiate to lineage-restricted precursor cells (such as a mesodermal stem cell), which in turn can differentiate into other types of precursor cells further down the pathway (such as an tissue specific precursor, for example, a cardiomyocyte precursor), and then to an end-stage differentiated cell, which plays a characteristic role in a certain tissue type, and can or cannot retain the capacity to proliferate further.

The term "embryonic stem cell" is used to refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "phenotype" refers to one or a number of total biological characteristics that define the cell or organism under a particular set of environmental conditions and factors, regardless of the actual genotype.

The term "cell culture medium" (also referred to herein as a "culture medium" or "medium") as referred to herein is a medium for culturing cells containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "self-renewing media" or "self-renewing culture conditions" refers to a medium for culturing stem cells which contains nutrients that allow a stem cell line to propagate in an undifferentiated state. Self-renewing culture media is well known to those of ordinary skill in the art and is ordinarily used for maintenance of stem cells as embroid bodies (EBs), where the stem cells divide and replicate in an undifferentiated state.

The term "cell line" refers to a population of largely or substantially identical cells that has typically been derived from a single ancestor cell or from a defined and/or substantially identical population of ancestor cells. The cell line can have been or can be capable of being maintained in culture for an extended period (e.g., months, years, for an unlimited period of time). Cell lines include all those cell lines recognized in the art as such. It will be appreciated that cells acquire mutations and possibly epigenetic changes over time such that at least some properties of individual cells of a cell line can differ with respect to each other.

The term "lineages" as used herein describes a cell with a common ancestry or cells with a common developmental fate. By way of an example only, stating that a cell that is of endoderm origin or is of "endodermal lineage" means the cell was derived from an endodermal cell and can differentiate along the endodermal lineage restricted pathways, such as one or more developmental lineage pathways which give rise to definitive endoderm cells, which in turn can differentiate into liver cells, thymus, pancreas, lung and intestine.

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2 SD) or greater difference in a value of the marker. The term refers to statistical evidence that there is a difference. It is defined as the probability of making a decision to reject the null hypothesis when the null hypothesis is actually true. Statistical significance can be determined by t-test or using a p-value.

As used herein, the term "DNA" is defined as deoxyribonucleic acid.

The term "differentiation" as used herein refers to the cellular development of a cell from a primitive stage towards a more mature (i.e. less primitive) cell.

The term "directed differentiation" as used herein refers to forcing differentiation of a cell from an undifferentiated (e.g. more primitive cell) to a more mature cell type (i.e. less primitive cell) via genetic and/or environmental manipulation. In some embodiments, a reprogrammed cell as disclosed herein is subject to directed differentiation into specific cell types, such as neuronal cell types, muscle cell types and the like.

The term "disease modeling" as used herein refers to the use of laboratory cell culture or animal research to obtain new information about human disease or illness. In some embodiments, a reprogrammed cell produced by the methods as disclosed herein can be used in disease modeling experiments.

The term "drug screening" as used herein refers to the use of cells and tissues in the laboratory to identify drugs with a specific function. In some embodiments, the present invention provides drug screening to identify compounds or drugs which alter (e.g., increase or decrease) the level of expression of a set of early developmental genes, as compared to in the absence of the compound or drug.

The term "marker" as used interchangeably with "biomarker" and describes the characteristics and/or phenotype of a cell. Markers can be used for selection of cells comprising characteristics of interest. Markers will vary with specific cells. Markers are characteristics, whether morphological, functional or biochemical (enzymatic) characteristics of the cell of a particular cell type, or molecules expressed by the cell type. Preferably, such markers are gene transcripts or their translation products (e.g., proteins). However, a marker can consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super minicomputer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" can refer to any storage device used for storing data accessible by a computer, as well as any other means for providing access to data by a computer. Examples of a storage-device-type computer-readable medium include, but is not limited to: a magnetic hard disk; a floppy disk; an optical disk, such as a CD-ROM and a DVD; DATs, a USB drive, a magnetic tape; a memory chip. A computer-readable medium is a tangible media not a signal, and does not include carrier waves or other wave forms for data transmission.

The term "software" is used interchangeably herein with "program" and refers to prescribed rules to operate a computer. Examples of software include: software; code segments; instructions; computer programs; and programmed logic.

The term a "computer system" can refer to a system having a computer, where the computer comprises a computer-readable medium embodying software to operate the computer.

The phrase "displaying or outputting" or providing an "indication" of the result of the expression analysis of a set of early developmental genes, or a prediction result, means that the results of a gene expression are communicated to a user using any medium, such as for example, orally, writing, visual display, etc., computer readable medium or computer system. It will be clear to one skilled in the art that outputting the result is not limited to outputting to a user or a linked external component(s), such as a computer system or computer memory, but can alternatively or additionally be outputting to internal components, such as any computer readable medium. It will be clear to one skilled in the art that the various sample classification methods disclosed and claimed herein, can, but need not be, computer-implemented, and that, for example, the displaying or outputting step can be done by, for example, by communicating to a person orally or in writing (e.g., in handwriting).

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean ±1%. The present invention is further explained in detail by the following, including the Examples, but the scope of the invention should not be limited thereto.

It is understood that the detailed description and the Examples that follow are illustrative only and are not to be taken as limitations upon the scope of the invention. Various changes and modifications to the disclosed embodiments, which will be apparent to those of skill in the art, can be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. All statements as to the date or representation as to the contents of these documents are based on the information available to the applicants and do not constitute any admission as to the correctness of the dates or contents of these documents.

Early Developmental Genes

One aspect of the present invention relates to measuring the gene expression of a set of early developmental genes to determine the differentiation potential and/or pluripotency of a stem cell line, e.g., a pluripotent stem cell line and/or for the production of a lineage scorecard for characterizing and/or comparing stem cell lines. A "lineage scorecard" is useful as a quantification of the differentiation potential and pluripotency of the stem cell line, e.g., a pluripotent stem cell of interest, and provides information of how efficiently the stem cell line of interest will differentiate into a particular lineage of interest as compared to previously established or reference pluripotent stem cell lines.

Accordingly, further aspects of the present invention provide a method for validating and/or monitoring a stem cell line, e.g., a pluripotent stem cell population, comprising generating a lineage score card of a stem cell line, by monitoring the gene expression of a set of early developmental genes and lineage marker genes, and to identify the characteristics of stem cell line, including predicting which stem cell lines are likely to differentiate along a desired cell lineage and/or which stem cell lines are pluripotent and which are non-pluripotent.

In some embodiments, for example, one can determine the differentiation propensity (or differentiation potential) for a given stem cell line by measuring the differentially expressed early developmental genes, followed by determining changes in gene expression levels of a set of early developmental target genes (e.g., some or a combination of genes listed in Tables 1) as compared to a reference or "standard" pluripotent stem cell line.

TABLE 1

List of early development target genes in each differentiation category (e.g., ectoderm early developmental genes, endoderm early developmental genes, mesoderm early developmental genes, pluripotent developmental genes) for determining the differentiation of a stem cell along a particular lineage as early as 2 days in culture, e.g., in self-renewing culture conditions or media.

| Assay ID/Name | Early Developmental Gene Target | Early Developmental Gene name | SEQ ID NO: | Accession number | Early Developmental gene category |
|---|---|---|---|---|---|
| Hs00940349_m1 | CDH9 | cadherin 9, type 2 (T1-cadherin) | 1 | NM_016279 | Ectoderm |
| Hs00264051_m1 | COL2A1 | collagen, type II, alpha 1 | 2 | NM_001844 | Ectoderm |
| Hs00542612_m1 | DMBX1 | diencephalon/mesencephalon homeobox 1 (OTX3) | 3 | NM_147192 | Ectoderm |
| Hs00609526_m1 | DRD4 | dopamine receptor D4 | 4 | NM_000797 | Ectoderm |
| Hs00154977_m1 | EN1 | engrailed homolog 1 | 5 | NM_001426 | Ectoderm |
| Hs00892663_m1 | LMX1A | LIM homeobox transcription factor 1, alpha | 6 | NM_177399 | Ectoderm |
| Hs00258900_m1 | MAP2 | microtubule-associated protein 2 | 7 | NM_031846 | Ectoderm |
| Hs00928272_m1 | MYO3B | myosin IIIB | 8 | NM_138995 | Ectoderm |
| Hs01075529_m1 | NOS2 | nitric oxide synthase 2A | 9 | NM_153292 | Ectoderm |
| Hs01354342_mH | NR2F1/NR2F2 | nuclear receptor subfamily 2, group F, member 1/member 2 | 10 | NM_005654 | Ectoderm |
| Hs00819630_m1 | NR2F2 | nuclear receptor subfamily 2, group F, member 2 | 11 | NM_021005 | Ectoderm |
| Hs00379238_m1 | OLFM3 | olfactomedin 3 | 12 | NM_058170 | Ectoderm |
| Hs00404545_m1 | PAPLN | papilin, proteoglycan-like sulfated glycoprotein | 13 | NM_173462 | Ectoderm |
| Hs00240950_m1 | PAX3 | paired box gene 3 | 14 | NM_181457 | Ectoderm |
| Hs00240871_m1 | PAX6 | paired box gene 6 | 15 | NM_000280 | Ectoderm |
| Hs00366711_m1 | POU4F1 | POU domain, class 4, transcription factor 1 | 16 | NM_006237 | Ectoderm |
| Hs00925195_ml | PRKCA | protein kinase C, alpha | 17 | NM_002737 | Ectoderm |
| Hs00299807_m1 | SDC2 | syndecan 2 | 18 | NM_002998 | Ectoderm |
| Hs01057642_s1 | SOX1 | SRY (sex determining region Y)-box 1 | 19 | NM_005986 | Ectoderm |
| Hs00375481_m1 | TRPM8 | transient receptor potential cation channel, subfamily M, member 8 | 20 | NM_024080 | Ectoderm |
| Hs01011247_m1 | WNT1 | wingless-type MMTV integration site family, member 1 | 21 | NM_005430 | Ectoderm |
| Hs00957433_m1 | ZBTB16 | zinc finger and BTB domain containing 16 | 22 | NM_006006 | Ectoderm |
| Hs00173490_m1 | AFP | alpha-fetoprotein | 23 | NM_001134 | Endoderm |
| Hs00418197_m1 | CABP7 | calcium binding protein 7 | 24 | NM_182527 | Endoderm |
| Hs00230412_m1 | CDH20 | cadherin 20, type 2 | 25 | NM_031891 | Endoderm |
| Hs00221623_m1 | CLDN1 | claudin 1 | 26 | NM_021101 | Endoderm |
| Hs00932617_m1 | CPLX2 | complexin 2 | 27 | NM_001008220 | Endoderm |
| Hs00154959_m1 | ELAVL3 | ELAV (embryonic lethal, abnormal vision, Drosophila)-like 3 (Hu antigen C) | 28 | NM_032281 | Endoderm |
| Hs00270129_m1 | FOXA1 | forkhead box A1 | 29 | NM_004496 | Endoderm |
| Hs00232764_m1 | FOXA2 | forkhead box A2 | 30 | NM_153675 | Endoderm |
| Hs00362818_m1 | FOXP2 | forkhead box P2 | 31 | NM_014491 | Endoderm |
| Hs00171403_m1 | GATA4 | GATA binding protein 4 | 32 | NM_002052 | Endoderm |
| Hs00232018_m1 | GATA6 | GATA binding protein 6 | 33 | NM_005257 | Endoderm |
| Hs00242160_m1 | HHEX | hematopoietically expressed homeobox | 34 | NM_002729 | Endoderm |
| Hs01004769_m1 | HMP19 | HMP19 protein | 35 | NM_015980 | Endoderm |

TABLE 1-continued

List of early development target genes in each differentiation category (e.g., ectoderm early developmental genes, endoderm early developmental genes, mesoderm early developmental genes, pluripotent developmental genes) for determining the differentiation of a stem cell along a particular lineage as early as 2 days in culture, e.g., in self-renewing culture conditions or media.

| Assay ID/Name | Early Developmental Gene Target | Early Developmental Gene name | SEQ ID NO: | Accession number | Early Developmental gene category |
|---|---|---|---|---|---|
| Hs01001602_m1 | HNF1B | transcription factor 2, hepatic (TF2); LF-B3; hepatocyte nuclear factor 1, beta | 36 | NM_000458 | Endoderm |
| Hs00230853_m1 | HNF4A | hepatocyte nuclear factor 4, alpha | 37 | NM_178849 | Endoderm |
| Hs00156145_m1 | KLF5 | Kruppel-like factor 5 (intestinal) | 38 | NM_001730 | Endoderm |
| Hs00745761_s1 | LEFTY2 | left-right determination factor 2/endometrial bleeding associated factor (EBAF) | 39 | NM_003240 | Endoderm |
| Hs00243679_m1 | PHOX2B | paired-like homeobox 2b, NBPhox, Phox2b | 40 | NM_003924 | Endoderm |
| Hs00275987_s1 | POU3F3 | POU domain, class 3, transcription factor 3 | 41 | NM_006236 | Endoderm |
| Hs00153357_m1 | PRDM1 | PR domain containing 1, with ZNF domain | 42 | NM_182907 | Endoderm |
| Hs00199455_m1 | RXRG | retinoid X receptor, gamma | 43 | NM_006917 | Endoderm |
| Hs00751752_s1 | SOX17 | SRY (sex determining region Y)-box 17 | 44 | NM_022454 | Endoderm |
| Hs00172872_m1 | EOMES | Eomesodermin, T-box brain 2, TBR2 | 45 | NM_005442 | Mesendoderm |
| Hs00999691_m1 | FGF4 | fibroblast growth factor 4 | 46 | NM_002007 | Mesendoderm |
| Hs00220998_m1 | GDF3 | growth differentiation factor 3 | 47 | NM_020634 | Mesendoderm |
| Hs00764128_s1 | LEFTY1 | left-right determination factor 1/left-right determination, factor B (LEFTYB) | 48 | NM_020997 | Mesendoderm |
| Hs00415443_m1 | NODAL | nodal homolog (mouse) | 49 | NM_018055 | Mesendoderm |
| Hs01057466_g1 | NPPB | natriuretic peptide precursor B | 50 | NM_002521 | Mesendoderm |
| Hs00187067_m1 | NR5A2 | nuclear receptor subfamily 5, group A, member 2 | 51 | NM_205860 | Mesendoderm |
| Hs00174969_m1 | PTHLH | parathyroid hormone-like hormone | 52 | NM_198964 | Mesendoderm |
| Hs00610080_m1 | T | T, brachyury homolog (mouse) | 53 | NM_003181 | Mesendoderm |
| Hs00979594_m1 | ABCA4 | ATP-binding cassette, sub-family A (ABC1), member 4 | 54 | NM_000350 | Mesoderm |
| Hs00993765_g1 | ALOX15 | arachidonate 15-lipoxygenase | 55 | NM_001140 | Mesoderm |
| Hs00205566_m1 | BMP10 | bone morphogenetic protein 10 | 56 | NM_014482 | Mesoderm |
| Hs00901463_m1 | CDH5 | cadherin 5, type 2, VE-cadherin (vascular epithelium) | 57 | NM_001795 | Mesoderm |
| Hs01078080_m1 | CDX2 | caudal type homeo box transcription factor 2 | 58 | NM_001265 | Mesoderm |
| Hs00197571_m1 | COLEC10 | collectin sub-family member 10 (C-type lectin) | 59 | NM_006438 | Mesoderm |
| Hs00199831_m1 | ESM1 | endothelial cell-specific molecule 1 | 60 | NM_007036 | Mesoderm |
| Hs00892390_m1 | FCN3 | ficolin (collagen/fibrinogen domain containing) 3 | 61 | NM_003665 | Mesoderm |
| Hs00230962_m1 | FOXF1 | forkhead box F1 | 62 | NM_001451 | Mesoderm |
| Hs02330376_s1 | HAND1 | heart and neural crest derivatives expressed 1 | 63 | NM_004821 | Mesoderm |
| Hs00232769_m1 | HAND2 | heart and neural crest derivatives expressed 2 | 64 | NM_021973 | Mesoderm |
| Hs01114113_m1 | HEY1 | hairy/enhancer-of-split related with YRPW motif 1 | 65 | NM_012258 | Mesoderm |

TABLE 1-continued

List of early development target genes in each differentiation category (e.g., ectoderm early developmental genes, endoderm early developmental genes, mesoderm early developmental genes, pluripotent developmental genes) for determining the differentiation of a stem cell along a particular lineage as early as 2 days in culture, e.g., in self-renewing culture conditions or media.

| Assay ID/Name | Early Developmental Gene Target | Early Developmental Gene name | SEQ ID NO: | Accession number | Early Developmental gene category |
|---|---|---|---|---|---|
| Hs04188695_m1 | HOPX | HOP homeobox, homeobox only domain, HOP, LAGY, NECC1, OB1, SMAP31 | 66 | NM_001145459 | Mesoderm |
| Hs00174360_m1 | IL6ST | interleukin 6 signal transducer (gp130, oncostatin M receptor) | 67 | NM_175767 | Mesoderm |
| Hs00231763_m1 | NKX2-5 | NK2 transcription factor related, locus 5 (Drosophila) | 68 | NM_004387 | Mesoderm |
| Hs00215292_m1 | ODAM | APIN hypothetical protein FLJ20513/APin protein | 69 | NM_017855 | Mesoderm |
| Hs00998018_m1 | PDGFRA | platelet-derived growth factor receptor, alpha polypeptide | 70 | NM_006206 | Mesoderm |
| Hs00229941_m1 | PLVAP | plasmalemma vesicle associated protein | 71 | NM_031310 | Mesoderm |
| Hs01111690_g1 | RGS4 | regulator of G-protein signalling 4 | 72 | NM_005613 | Mesoderm |
| Hs00950344_m1 | SNAI2 | snail homolog 2 (Drosophila) | 73 | NM_003068 | Mesoderm |
| Hs00356144_m1 | SST | somatostatin | 74 | NM_001048 | Mesoderm |
| Hs00195612_m1 | TBX3 | T-box 3 (ulnar mammary syndrome) | 75 | NM_016569 | Mesoderm |
| Hs00371997_m1 | TM4SF1 | transmembrane 4 superfamily member 1 | 76 | NM_014220 | Mesoderm |
| Mm01277163_m1 | CD44 | CD44R, chondroitin sulfate proteoglycan 8 (CSPG8), HCELL (hematopoietic cell E- and L-selectin ligand), IN, MC56, Pgp1 | 77 | NM_000610 | Other |
| Hs00171876_m1 | DNMT3B | DNA (cytosine-5-)-methyltransferase 3 beta | 78 | NM_175848 | Other |
| Hs00914223_m1 | EP300 | E1A binding protein p300 | 79 | NM_001429 | control |
| Hs00153408_m1 | MYC | v-myc myelocytomatosis viral oncogene homolog | 80 | NM_002467 | Other |
| Mr04269880_mr | SEV | sevenless | 81 | NM_078559.2 | Other |
| Hs01099660_g1 | CXCL5 | chemokine (C-X-C motif) ligand 5 | 82 | NM_002994 | Pluri |
| Hs00172696_m1 | HESX1 | homeobox, ES cell expressed 1, ANF, RPX | 83 | NM_003865 | Pluri |
| Hs00984148_m1 | IDO1 | indoleamine-pyrrole 2,3 dioxygenase | 84 | NM_002164 | Pluri |
| Hs00178427_m1 | LCK | lymphocyte-specific protein tyrosine kinase | 85 | NM_005356 | Pluri |
| Hs02387400_g1 | NANOG | Nanog homeobox | 86 | NM_024865.2 | Pluri |
| Hs00742896_s1 | POU5F1 | POU domain, class 5, transcription factor 1 | 87 | NM_203289 | Pluri |
| Hs01053049_s1 | SOX2 | SRY (sex determining region Y)-box 2 | 88 | NM_003106 | Pluri |
| Hs01001179_m1 | TRIM22 | tripartite motif-containing 22 | 89 | NM_006074 | Pluri |

In some embodiments, the present invention encompasses measuring the gene expression of a set of early developmental genes selected from at least 3 genes from Table 2.

TABLE 2

List of early development target genes for determining the differentiation of a stem cell along a particular lineage as early as 2 days in culture.

| Assay ID/Name | Early Developmental Gene Target | SEQ ID NO: | Early Developmental gene category |
|---|---|---|---|
| Hs00940349_m1 | CDH9 | 1 | Ectoderm |
| Hs00542612_m1 | DMBX1 | 3 | Ectoderm |
| Hs00609526_m1 | DRD4 | 4 | Ectoderm |
| Hs00928272_m1 | MYO3B | 8 | Ectoderm |
| Hs01075529_m1 | NOS2 | 9 | Ectoderm |
| Hs00379238_m1 | OLFM3 | 12 | Ectoderm |
| Hs00404545_m1 | PAPLN | 13 | Ectoderm |
| Hs00375481_m1 | TRPM8 | 20 | Ectoderm |
| Hs01011247_m1 | WNT1 | 21 | Ectoderm |
| Hs00418197_m1 | CABP7 | 24 | Endoderm |
| Hs00230412_m1 | CDH20 | 25 | Endoderm |
| Hs00932617_m1 | CPLX2 | 27 | Endoderm |
| Hs00154959_m1 | ELAVL3 | 28 | Endoderm |
| Hs00362818_m1 | FOXP2 | 31 | Endoderm |
| Hs01004769_m1 | HMP19 | 35 | Endoderm |
| Hs00243679_m1 | PHOX2B | 40 | Endoderm |
| Hs00197571_m1 | COLEC10 | 59 | Mesoderm |
| Hs00199831_m1 | ESM1 | 60 | Mesoderm |
| Hs00892390_m1 | FCN3 | 61 | Mesoderm |
| Hs00230962_m1 | FOXF1 | 62 | Mesoderm |
| Hs04188695_m1 | HOPX | 66 | Mesoderm |
| Hs00215292_m1 | ODAM | 69 | Mesoderm |
| Hs00229941_m1 | PLVAP | 71 | Mesoderm |
| Hs00371997_m1 | TM4SF1 | 76 | Mesoderm |
| Mr04269880_mr | SEV | 81 | Other |
| Hs00984148_m1 | IDO1 | 84 | Pluri |

In some embodiments, the present invention encompasses measuring the gene expression of at least one gene from the group of mesoderm early developmental genes, selected from the group consisting of: HAND1, ESM1, HAND2, HOPX, BMP10, FCN3 and GSC. In some embodiments, the present invention encompasses measuring the gene expression of at least one gene from the group of endoderm early developmental genes, selected from the group consisting of: LEFTY1, EOMES, NODAL and FOXA2. In some embodiments, the present invention encompasses measuring the gene expression of at least one gene from the group of ectoderm early developmental genes, selected from the group consisting of: TRPM8, POU4F1, OLFM3, WNT1, LMX1A and CDH9. In some embodiments, the present invention encompasses measuring the gene expression of at least one gene from the group of pluripotent genes, selected from the group consisting of: IDO1, LCK, POU5F1 and HESX1.

In some embodiments, the present invention encompasses measuring the gene expression of at least 2 or at least 3 or at least 4 genes from the group of mesoderm early developmental genes, selected from the group consisting of: HAND1, ESM1, HAND2, HOPX, BMP10, FCN3 and GSC. In some embodiments, the present invention encompasses measuring the gene expression of at least 2 or at least 3 or at least 4 genes from the group of endoderm early developmental genes, selected from the group consisting of: LEFTY1, EOMES, NODAL and FOXA2. In some embodiments, the present invention encompasses measuring the gene expression of at least 2 or at least 3 or at least 4 genes from the group of ectoderm early developmental genes, selected from the group consisting of: TRPM8, POU4F1, OLFM3, WNT1, LMX1A and CDH9. In some embodiments, the present invention encompasses measuring the gene expression of at least 2 or at least 3 or at least 4 genes from the group of pluripotent genes, selected from the group consisting of: IDO1, LCK, POU5F1 and HESX1.

In some embodiments, the present invention also encompasses measuring the gene expression of genes which identify if a stem cell line, e.g., a pluripotent stem cell line has the ability to differentiate along a neuronal lineages, pancreas lineages, cardiovascular lineages, hematopoietic and other lineages, e.g., bone, skin, liver, kidney, blood, lineages etc.

In some embodiments, the present invention also encompasses measuring the gene expression of at least one gene, or at least 2, or at least 3, or at least 4 or more genes from a set of early developmental neuronal genes selected from the group consisting of: PAX3, PAX6, MAP2, LMX1A, SOX1, SOX2, SNAI2, EOMES, EN1 and NKX2-5. In some embodiments, the present invention also encompasses measuring the gene expression of at least one gene, or at least 2, or at least 3, genes from a set of early developmental hematopoietic genes selected from the group consisting of: ZBTB16, T and CDH5. In some embodiments, the present invention also encompasses measuring the gene expression of at least one gene, or at least 2, or at least 3, or at least 4 or more genes from a set of early developmental liver genes selected from the group consisting of: GATA4, HNF4A, HHEX, TBX3, AFP, HNF1B and FOXA2. In some embodiments, the present invention also encompasses measuring the gene expression of at least one gene, or at least 2, or at least 3, or at least 4 or more genes from a set of early developmental cardiac or cardiovascular genes selected from the group consisting of: ZBTB16, T, CDH5, GATA4 and HAND1. In some embodiments, the present invention also encompasses measuring the gene expression of at least one gene, or at least 2, or at least 3, or at least 4 or more genes from a set of early developmental pancreatic genes selected from the group consisting of: SST, PAX6, HHEX and FOXA2.

The gene SRY can also be used in the assay, methods and systems as disclosed herein as a sex determining gene and to aid identifying cell ID. In some embodiments, the assay, methods and systems can comprise software to analyze this gene. In some embodiments, the assay, methods and systems as disclosed herein can comprise SEV to detect Sendai dilution into CytoTune-derived iPSCs. In some embodiments, the assay, methods and systems as disclosed herein can comprise genes for exogenous versus endogenous reprogramming factors, e.g., Sox2, Oct4, c-myc, Klf4, as well as other known reprogramming genes or factors known by persons of ordinary skill in the art.

In some embodiments, a control gene is assayed, for example, one or more of the control genes listed in Table 3. In some embodiments, a control gene is selected from at least one from ACTB, CTCF, SMAD1 or EP300. In some embodiments, a control gene in Table 3 can be substituted with another control gene, e.g., a housekeeping gene, such as EP300, β-actin, HSP90, GAPDH and the like. A housekeeping gene is a constitutive gene that is required for the maintenance of basic cellular function, and is expressed in all cells of an organism under normal and patho-physiological conditions. Examples of other control genes which can be substituted for a control gene in Table 3 include, but are not limited to, EP300, APDH, β-actin, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLP0, PPIA, POLR2A, PGK1, IPO8, HMBS, GUSB, B2M, HPRT1 or 18S.

In some embodiments, the control ACTB gene can be replaced with a species specific version for the particular pluripotent stem cell line being assessed (e.g., use a mouse ACTB gene for a mouse pluripotent stem cell line being assessed). In some embodiments, a control gene used in the assay and methods as disclosed herein is CD44 (Mm01277167_m1 or Mm01277164_m1), which is a mouse specific housekeeping gene and does not amplify genomic DNA and is ideal to detect residual MEF contamination).

TABLE 3

List of control genes for use in the assay, methods, kits and systems disclosed herein.

| Assay ID/Name | Control gene | SEQ ID NO: | Assay gene category |
|---|---|---|---|
| Hs01060665_g1 | ACTB | 90 | Controls |
| Hs99999903_m1 | ACTB | 90 | Controls |
| Hs00902008_m1 | CTCF | 91 & 92 | Controls |
| Hs01004460_m1 | JARID2 | 93 & 94 | Controls |
| Hs00195432_m1 | SMAD1 | 95 & 96 | Controls |

The differentiation assays, methods, systems and kits as disclosed herein have substantial utility for determining the quality and utility for various types of pluripotent stem cells and precursor cells (e.g., ES cell, somatic stem cells, hematopoietic stem cells, leukemic stem cells, skin stem cells, intestinal stem cells, gonadal stem cells, brain stem cells, muscle stem cells (muscle myoblasts, etc.), mammary stem cells, neural stem cells (e.g., cerebellar granule neuron progenitors, etc.), etc), and for example the stem cell/precursor cells described in Table 1 of Sparmann & Lohuizen, Nature 6, 2006 (Nature Reviews Cancer, November 2006), incorporated herein by reference), as well as in vitro and in vivo derived stem cells, such as induced pluripotent stem cells (iPSC).

Arrays

One aspect of the present invention relates to an array composition for characterizing the differentiation potential and/or pluripotency of a stem cell line, e.g., a pluripotent stem cell, comprising nucleic acid sequences that amplify the mRNA of any combination of early developmental genes selected from those listed in Table 1. In some embodiments, the array comprises nucleic acid sequences, e.g., oligonucleotides or primers, that amplify the mRNA of at least 3 early developmental genes selected from those listed in Table 2. In some embodiments, the amplified developmental genes are at least 90% identical to or specifically hybridize to nucleic acids encoding genes selected from those listed in Table 1 and/or Table 2.

In some embodiments, the array comprises oligonucleotides (e.g., probes or primers) which specifically hybridize to the mRNA expressed by a set of early developmental genes selected from any combination of genes listed in Table 1 and/or Table 2. In some embodiments, the arrays can be present as part of a kit as disclosed herein, wherein the kits comprises reagents, in addition to the arrays which can be used for measuring the expression levels of a plurality of early developmental genes by PCR-based methods, e.g., RT-PCR In some embodiments, the kit can be used for carrying out a method as disclosed herein, comprises: an array and reagents for measuring the expression of a set of early developmental genes selected from a combination of the genes listed in Table 1 and/or table 2.

In some embodiments, the array and reagents for measuring the expression of a set of early developmental genes can be selected from at least 1, or at least 2 or at least 3 or at least 4 genes from the group of mesoderm early developmental genes, selected from the group consisting of: HAND1, ESM1, HAND2, HOPX, BMP10, FCN3 and GSC. In some embodiments, the array and reagents for measuring the expression of a set of early developmental genes can be selected from at least 1, or at least 2 or at least 3 or at least 4 genes from the group of endoderm early developmental genes, selected from the group consisting of: LEFTY1, EOMES, NODAL and FOXA2. In some embodiments, the array and reagents for measuring the expression of a set of early developmental genes can be selected from at least 1, or at least 2 or at least 3 or at least 4 genes from the group of ectoderm early developmental genes, selected from the group consisting of: TRPM8, POU4F1, OLFM3, WNT1, LMX1A and CDH9. In some embodiments, the array and reagents for measuring the expression of a set of early developmental genes can be selected from at least 1, or at least 2 or at least 3 or at least 4 genes from the group of pluripotent genes, selected from the group consisting of: IDO1, LCK, POU5F1 and HESX1.

In some embodiments, the array comprises at least 10, or at least about 20, or at least about 30, or 30-60, or 60-90 or more than 90 nucleic acid sequences (e.g. oligonucleotides), or at least 10, or at least about 20, or at least about 30, or 30-60, or 60-90 or more than 90 pairs of nucleic acid sequences (e.g., primers), that amplify the mRNA of a combination of 10 early developmental genes selected from those listed in Table 1.

In some embodiments, the array comprises nucleic acid sequences that amplify the mRNA of at least one pluripotent stem cell gene, at least one early mesoderm developmental gene, at least one ectoderm developmental gene, and at least one endoderm developmental gene selected from Table 1 and/or from Table 2. In some embodiments, the array comprises nucleic acid sequences, e.g., oligonucleotides or primers, that amplify the mRNA of at least 4 pluripotent stem cell genes, at least 4 early mesoderm developmental genes, at least 4 ectoderm developmental genes, and at least 4 endoderm developmental genes selected from Table 1.

In some embodiments, the array comprises nucleic acid sequences (e.g., oligonucleotides and/or primers) which specifically hybridize to the mRNA of at least one, or at least about 2, or at least about 3, or at least about 4, or at least about 5 or at least about 10, or at least about 20, or at least about 30, or more than 30 pluripotency genes, and/or probes for at least one, or at least about 2, or at least about 3, or at least about 4, or at least about 5 or at least about 10, or at least about 20, or at least about 30, or more than 30 early mesoderm genes, and/or probes for at least one, or at least about 2, or at least about 3, or at least about 4, or at least about 5 or at least about 10, or at least about 20, or at least about 30, or more than 30 early ectoderm genes, and/or probe for at least one, or at least about 2, or at least about 3, or at least about 4, or at least about 5, or at least about 10, or at least about 20, or at least about 30, or more than 30 early endoderm genes. Such early ectoderm genes, and/or early endoderm genes, and/or early mesoderm and/or pluripotent genes can be selected from any combination listed in Table 1 or in table 2. Alternatively, the early developmental genes can be from other genes not listed in Table 1, but are expressed in a cell which is at least 2 days EB, and where the cell has the ability to differentiate into that particular cell lineage at a later time point.

In some embodiments, the array comprises nucleic acid sequences (e.g., oligonucleotides and/or primers) which specifically hybridize to the mRNA of at least one, or at least about 2, or at least about 3, or at least about 4, or at least about 5 genes from Table 2. In some embodiments, the array comprises probes (e.g., oligonucleotides and/or primers) which specifically hybridize to the mRNA of at least one, or at least 2, or at least 3 genes from each lineage subtype (e.g., ectoderm, mesoderm and endoderm subtypes) as disclosed in Table 2.

In some embodiments, any of the genes listed in Table 1 and/or Table 2 can be substituted for alternative early developmental genes. For example, in some embodiments, in addition to comprising probes (e.g., oligonucleotides and/or primers) which specifically hybridize to the mRNA of at least 10, or at least 20 early developmental genes selected from Table 1, the array can comprise additional reagents (e.g., probes, e.g., oligonucleotides and/or primers) which specifically hybridize to the mRNA of other early development genes for measuring the expression of different early developmental genes not listed in Table 1. Such genes are known by persons of ordinary skill in the art and are envisioned for use in the assays, kits, methods, systems as disclosed herein. In some embodiments, for example, a mesoderm gene can be substituted for GSC (goosecoid homeobox) (the human mRNA corresponding to accession number NM_173849.2).

For example, in some embodiments alternative genes can include, but are not limited to markers for ectoderm germ cells include, but are not limited to, NCAM1, EN1, FGFR2, GATA2, GATA3, HAND1, MNX1, NEFL, NES, NOG, OTX2, PAX3, PAX6, PAX7, SNAI2, SOX10, SOX9, TDGF1, APOE, PDGFRA, MCAM, FUT4, NGFR, ITGB1, CD44, ITGA4, ITGA6, ICAM1, THY1, FAS, ABCG2, CRABP2, MAP2, CDH2, NES, NEUROG3, NOG, NOTCH1, SOX2, SYP, MAPT, TH. In some embodiments, alternative genes can include, but are not limited to markers for human endoderm germ cells include, but are not limited to APOE, CDX2, FOXA2, GATA4, GATA6, GCG, ISL1, NKX2-5, PAX6, PDX1, SLC2A2, SST, ITGB1, CD44, ITGA6, THY1, CDX2, GATA4, HNF1A, HNF1B, CDH2, NEUROG3, CTNNB1, SYP, and markers for mesoderm germ cells include, but are not limited to, CD34, DLL1, HHEX, INHBA, LEF1, SRF, T, TWIST1, ADIPOQ, MME, KIT, ITGAL, ITGAM, ITGAX, TNFRSF1A, ANPEP, SDC1, CDH5, MCAM, FUT4, NGFR, ITGB1, PECAM1, CDH1, CDH2, CD36, CD4, CD44, ITGA4, ITGA6, ITGAV, ICAM1, NCAM1, ITGB3, CEACAM1, THY1, ABCG2, KDR, GATA3, GATA4, MYOD1, MYOG, NES, NOTCH1, SPI1, STAT3. In mouse, markers of endoderm germ cells include, Gata4, FoxA2, PDX1, Nodal, Sox7 and Sox17. In mouse, markers of mesoderm germ cells include, Brachycury, GSC, LEF1, Mox1 and Tie1. In mouse, markers of ectoderm germ cells include criptol, EN1, GFAP, Islet 1, LIM1 and Nestin. Accordingly, one can select specific sets of early developmental target genes (e.g., early mesoderm genes or early endoderm genes or early ectoderm genes) to develop a "customized array" for accurate characterization of a pluripotent stem cell line to identify particular desired or undesirable characteristics.

In some embodiments, the nucleic acid sequences in the array are primers, e.g., RT-PCR primers or hybridization probes that specifically hybridize to the mRNA of a subset of early developmental genes as disclosed in Table 1. In some embodiments, the nucleic acid sequences, e.g., primers (e.g., RT-PCR primers) can be immobilized on a solid support. In some embodiments, the array comprises nucleic acid sequences (e.g., oligonucleotides and/or primers) which specifically hybridize to the mRNA of at least 1, or at least 2, or at least 3, or at least 4 or least 5 control genes. Control genes include those listed in Table 3, but are not limited to ACTB, JARID2, CTCF, SMAD1, β-actin, GAPDH and the like. In some embodiments, nucleic acid sequences that amplify a control gene can be present at multiple locations in the same array.

In some embodiments, the array comprises nucleic acid sequences, e.g., oligonucleotides or primers, that amplify the mRNA of at least sequences corresponding to 1-10 control genes, such as, but not limited to the control genes selected from the group consisting of: ACTB, JARID2, CTCF, SMAD1, GAPDH, β-actin, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLP0, PPIA, POLR2A, PGK1, IPO8, HMBS, GUSB, B2M, HPRT1 or 18S.

In some embodiments, the array comprises no more than 100, or no more than 90, or no more than 50 nucleic acid sequences, e.g., oligonucleotides or primers. In some embodiments, the nucleic acid sequences present on the array are sets of primers. In some embodiments, the nucleic acid sequences, e.g., oligonucleotides or primers are immobilized on, or within a solid support. Nucleic acid sequences can be immobilized on the solid support by the 5' end of said oligonucleotides. In some embodiments, the solid support is selected from a group of materials comprising silicon, metal, and glass. In some embodiments, the solid support comprises oligonucleotides at assigned positions defined by x and y coordinates.

In some embodiments, the array comprises nucleic acid sequences, e.g., primers that can amplify the mRNA of the early developmental genes by a method comprising: polymerase chain reaction (PCR); strand displacement amplification (SDA); loop-mediated isothermal amplification (LAMP); rolling circle amplification (RCA); transcription-mediated amplification (TMA); self-sustained sequence replication (3SR); nucleic acid sequence based amplification (NASBA) or reverse transcription polymerase chain reaction (RT-PCR). In some embodiments, the array allows for real-time PCR amplification of the early developmental genes, or a real-time PCR amplification of the early developmental genes with detection by SYBR green method or an MNAzyme detection method.

In some embodiments, the array as disclosed herein is an OpenArray®, e.g., which is commercially available from Life Technologies, wherein the nucleic acid sequences, e.g., oligonucleotides or primers are immobilized within the wells of the OpenArray®. In some embodiments, an array encompassed for use in the present invention comprises primers to a set of early developmental genes selected from Table 1 and/or Table and is configured as an OpenArray® as disclosed in U.S. Pat. Nos. 6,387,331; 6,743,633; 6,893,877; 7,332,271 and 7,547,556 which are incorporated herein in their entirety by reference. In some embodiments, the array is any array using primers for RT-PCR. In some embodiments, the array is a hybridization array such as a microarray.

Accordingly, the present invention contemplates a method of generating an array, comprising providing a solid support comprising a plurality of positions for oligonucleotides, the positions defined by x and y coordinates; a plurality of different oligonucleotides (or primer pairs), each comprising a sequence which is complementary to at least a portion of the sequence of an early developmental gene being measured, where each oligonucleotide (or primer pair) is placed in a known position on the solid support to create an ordered array.

In one embodiment of the present invention, oligonucleotides that are immobilized by the 5' end on a solid surface by a chemical linkage are contemplated. In some embodiments, the oligonucleotides are primers, and can be approximately 17 bases in length, although other lengths are also contemplated.

In another embodiment of the present invention, a method of hybridizing target nucleic acid fragments is contemplated which comprises providing an ordered array of immobilized oligonucleotides representing sequences in Table 1 and/or Table 2 and/or Table 3 and providing a plurality of fragments of a target nucleic acid; and bringing the fragments of the target nucleic acid into contact with the array under conditions such that at least one of the fragments hybridizes to one of the immobilized oligonucleotides on the array.

In another embodiment of the present invention, a method of generating an array capable of hybridizing to fragments of a target early developmental gene nucleic acid is contemplated, comprising providing a solid support comprising positions for oligonucleotides, the positions defined by x and y coordinates; a plurality of oligonucleotides, each oligonucleotide comprising a sequence complementary to a different portion of the early developmental gene target nucleic acid.

The arrays as disclosed herein allow for amplification of the mRNA of a set of early developmental genes as disclosed herein from a stem cell line, e.g., a pluripotent cell line of interest. Methods for preparing total and poly(A)+ RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., CURRENT PROTOCOLS IN MOLECULAR BIOLOGY, vol. 2, Current Protocols Publishing, New York (1994)).

RNA can be isolated from eukaryotic cells by procedures that involve lysis of the cells and denaturation of the proteins contained therein. Stem cells of interest include pluripotent stem cells, including but not limited to ES cells, adult stem cells and iPSC cells, from mammals including human species. Additional steps can be employed to remove DNA. Cell lysis can be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979)). Poly(A)+ RNA is isolated by selection with oligo-dT cellulose (see Sambrook et al, MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors can be added to the lysis buffer. Likewise, for certain cell types, it can be desirable to add a protein denaturation/digestion step to the protocol.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex. (see Ausubel et al., CURRENT PROTOCOLS IN MOLECULAR BIOLOGY, vol. 2, Current Protocols Publishing, New York (1994). Once bound, poly(A)+ mRNA is eluted from the affinity column using 2 mM EDTA/0.1% SDS.

The sample of RNA can comprise a plurality of different mRNA molecules, each different mRNA molecule having a different nucleotide sequence. In a specific embodiment, the mRNA molecules in the RNA sample comprise at least 100 different nucleotide sequences. More preferably, the mRNA molecules of the RNA sample comprise mRNA molecules corresponding to each of the early developmental biomarker genes. In another specific embodiment, the RNA sample is a mammalian RNA sample.

In a specific embodiment, total RNA or mRNA from the pluripotent stem cell population is used in the assays and methods as disclosed herein. The source of the RNA can be pluripotent cells or stem cells of an animal, human, mammal, primate, non-human animal, dog, cat, mouse, rat, bird, etc. In specific embodiments, the methods of the invention are used with a sample containing mRNA or total RNA from $1 \times 10^6$ cells or less. In another embodiment, proteins can be isolated from the foregoing sources, by methods known in the art, for use in expression analysis at the protein level.

Probes to the homologs of the early developmental gene biomarker sequences disclosed herein can be employed preferably wherein non-human nucleic acid is being assayed.

Methods to Determine the Differentiation Potential of Pluripotent Stem Cells

Another aspect of the present invention relates to a method of to determine the differentiation potential of a pluripotent stem cell comprising performing array amplification using the nucleic acid derived from a pluripotent stem cell and an array as disclosed herein. In some embodiments, after the array amplification, the data are analyzed using a web based analysis tool which can output an indicator that is used to determine the differentiation potential of the pluripotent stem cell to differentiate along different lineages selected from: mesoderm lineage, ectoderm lineage and endoderm lineage and/or the pluripotency of the pluripotent stem cell.

Another aspect of the present invention relates to a method of determining the differentiation potential of a pluripotent stem cell line comprising detecting and comparing the expression in the pluripotent stem cell line of a set of early developmental genes selected from those listed in Table 1 and/or Table 2 to the expression of the same genes by a control pluripotent stem cell sample, and based on this comparison, determining the differentiation potential of the pluripotent stem cell line. In some embodiments, the gene expression is assayed by real time amplification, or the detection comprises SYBR Green based real-time PCR.

In some embodiments, the expression values (e.g., expression levels) of the early developmental genes plus at least one control gene are measured in the pluripotent stem cell line and a $\Delta Ct$ is calculated for each gene, and the $\Delta Ct$ value of each early developmental gene is compared to the ΔCt value of that early developmental gene in a data pool that contains reference ΔCt values from a plurality of reference pluripotent stem cells, to provide a ΔΔCt value. In some embodiments, the expression values (e.g., expression levels) of the early developmental genes plus at least one control gene are measured in the pluripotent stem cell line and the average ΔCt for the genes in each of the mesoderm, ectoderm and endoderm early developmental gene subgroups is calculated. A ΔΔCt value is calculated by subtracting the average ΔCt value of the genes in each of the subgroups with the average ΔCt value of the same genes in each of the subgroups in a data pool that contains reference average ΔCt values for the same genes in each subgroups from a plurality of reference pluripotent stem cells. In some embodiments, a t-test is used to identify statistically significant ΔΔCt values from the comparison of the average ΔCt value of the genes in each of the mesoderm, ectoderm and endoderm early developmental gene subgroups as compared to reference ΔCt value for genes in each of the mesoderm, ectoderm and endoderm early developmental gene subgroups from a plurality of reference pluripotent stem cells in the data pool.

In some embodiments, a pluripotent stem cell line which differs by a statistically significant amount in the expression level of a set of mesoderm, ectoderm and endoderm early developmental genes is selected (e.g., chosen) or discarded for further use on the basis of such statistically significant differences in early developmental gene expression.

Assays to Determine the Differentiation Potential of Pluripotent Stem Cells

In some embodiments, the present invention provides a method for selecting a stem cell line, e.g., a pluripotent stem cell line, comprising measuring the differentiation potential of the stem cell line by detecting the level of gene expression of a set of early developmental and lineage marker genes selected from a combination of the genes listed in Table 1 and/or Table 2; and comparing the levels of the gene expression of the early developmental genes with a reference level of the early developmental genes. A stem cell line which does not differ by a statistically significant amount (e.g., about 2SD) in the level of the gene expression of the early developmental genes can be selected or chosen as one for which the differentiation potential and propensity to differentiate along mesoderm, ectoderm and endoderm lineages will be similar to that of a reference pluripotent stem cell line having that pattern of early developmental gene expression. Under this method, a stem cell line which differs by a statistically significant amount in the level of the expression of the early developmental genes as compared to the reference set can be discarded as likely having a different potential for differentiation relative to a reference pluripotent stem cell line. In alternative embodiments, a stem cell line which differs by a statistically significant amount in the level of the expression of the early developmental genes as compared to the reference set can be selected as having an increased propensity to differentiate along a particular lineage that is desired by the user.

In some embodiments, the reference gene expression level for an early developmental gene is a range of normal variation for that early developmental target gene, and in some embodiments the reference level is an average of expression level for that early developmental target gene, wherein the average is calculated from expression level of that early developmental target gene in a plurality of pluripotent stem cell lines, for example, at least 5 or more different pluripotent stem cell lines.

In some embodiments, the gene expression level of a set of early developmental genes, e.g., those or a subset of those listed in Table 1, provides information on the stem cells' ability to differentiate into a lineage selected from the group consisting of mesoderm, endoderm, ectoderm, neuronal, hematopoietic lineages, and any combinations thereof, where the reference gene expression level of a set of early developmental genes is generated from a plurality of pluripotent stem cell lines, for example, at least 5 different pluripotent stem cell lines. In some embodiments, the gene expression level of a set of early developmental genes from a test pluripotent stem cell and/or a reference pluripotent stem cell is determined by measuring the gene expression of a set of early developmental genes, e.g., those or a subset of those listed in Table 1, as disclosed herein.

In some embodiments, a set of early developmental genes are selected from any of about 20, or at least about 30, or at least about 40 or at least about 50, or at least about 60, or at least about 70, or at least about 80 or at least about 90 or more than 90 genes from any combination from the list in Table 1, are measured in the pluripotent cell line, and compared to the reference early developmental gene level of the same set. In some embodiments, a set of early developmental genes are selected from any of about 2, or 3, or 4 or 5 or more than 5 genes from any combination from the list in Table 2, are measured in the pluripotent cell line, and compared to the reference early developmental gene level of the same set.

Accordingly, another aspect of the present invention relates to an assay for choosing a stem cell line, e.g., a pluripotent stem cell line for a desired use by characterizing the differentiation potential of the stem cell, the assay comprising: (a) measuring the level of expression of a plurality of early developmental genes in the pluripotent stem cell line selected from the genes listed in Table 1; and comparing the level of gene expression of the plurality of early developmental genes in the pluripotent stem cell with a reference gene expression level for the same plurality of early developmental genes; and (b) choosing a stem cell line on the basis of there being no statistically significant difference in the level of gene expression of the measured early developmental genes as compared to the reference gene expression level for the early developmental genes; or choosing a stem cell line on the basis of there being a statistically significant difference in the expression level in at least one desired early developmental gene as compared to the reference expression level of the early developmental genes.

In some embodiments, the assay measures a plurality of early developmental genes in a stem cell line, e.g., a pluripotent stem cell line, that has been cultured for at least about 2 days in self-renewing culture conditions, e.g., as embryoid bodies (EB) under EB forming conditions, or at least about 3 days, or at least about 4 days, or at least about 5 days as embryoid bodies (EB) and/or under EB forming conditions (e.g., in self-renewing culture media). In some embodiments, the assay measures a plurality of early developmental genes in a stem cell line that has been cultured for no longer than about 2 days in EB forming conditions, or for no longer than about 3 or about 4 days in EB forming conditions. In some embodiments, the assay is performed on a stem cell which is at least about 0 days or at least about 1 day or at least about 2 days or at least about 3 days or more than 3 days of culturing the EB. As disclosed herein in the Examples, the differentiation assay can be performed as early as 2 days of culturing the EBs with meaningful results in predicting the differentiation potential and/or pluripotency of the stem cell line and/or determining if the stem cell is no longer pluripotent.

In some embodiments, the level of the expression of the control gene in a stem cell line, e.g., a pluripotent stem cell is compared with the level of the expression of an early developmental gene to provide the ΔCt of the level of gene expression of an early developmental gene measured in the stem cell line. In some embodiments, the assay comprises comparing the level of gene expression of the same plurality of early developmental genes with a reference gene expression level of the same early developmental genes comprises comparing the ΔCt of the level of gene expression of an early developmental gene measured in the pluripotent stem cell with the average ΔCt of the level of gene expression of the same early developmental gene measured from a plurality of reference pluripotent stem cells.

In some embodiments, the assay can be used to choose a stem cell line, e.g., a pluripotent stem cell line which differs by a statistically significant amount in the expression level of at least one desired early developmental gene, by selecting a stem cell line which differs by a statistically significant amount (e.g., using a t-test or other appropriate statistical measurement) in the expression level of an early developmental gene which is a mesoderm developmental gene, an ectoderm developmental gene, or an endoderm developmental gene. In some embodiments, a statistical difference is a difference of at least 1, at least 2, or at least 3 standard deviations from the reference gene expression level for the early developmental gene.

In some embodiments, the reference gene expression level for an early developmental gene is the range of normal variation for the expression of that early developmental gene in a plurality of pluripotent stem cells. In some embodiments, the reference gene expression level for an early developmental gene is an average of expression level for that early developmental gene, wherein the average is calculated from expression level of that early developmental gene in a plurality of pluripotent stem cell lines. In some embodiments, the plurality of pluripotent stem cell lines for a reference gene expression level is obtained from at least 5 or more pluripotent stem lines.

In some embodiments, the assay as disclosed herein can be used to characterize the differentiation potential of a mammalian pluripotent stem cell, e.g., a human pluripotent stem cell. In some embodiments, the pluripotent stem cell is an ES cell, or an iPS cell, or a partial iPS cell (piPSC), or an adult stem cell.

In some embodiments, if the level of expression of at least one or at least 2 or at least 3 or more than 3 early developmental genes selected from Table 1 and/or Table 2 which are measured in the stem cell line is expressed at a statistically significant different increased level as compared to a reference level of gene expression of the same early developmental gene, it indicates that the stem cell line will differentiate down a particular cell lineage, and/or not be pluripotent.

In some embodiments, a stem cell line, e.g., a pluripotent stem cell line is a mammalian pluripotent stem cell line, such as a human pluripotent stem cell line.

In some embodiments, the assay is a high-throughput assay for assaying a plurality of different stem cell lines, for example, but not limited to permitting one to assess a plurality of different induced pluripotent stem cells derived from reprogramming a somatic cell obtained from the same or a different subject, e.g., a mammalian subject or a human subject. In some embodiments, the assay is a 96-well format, and in some embodiments, the assay is in a 384-well format, permitting multiple pluripotent stem cell lines to be assayed at the same time. In some embodiments, the assay is an automated format, enabling high-throughput analysis of 96- and/or 384-well plates.

In some embodiments, the assay as disclosed herein can be used to generate a lineage scorecard as disclosed herein from at least one, or a plurality of stem cell lines.

In some embodiments, in the differentiation assay and methods as disclosed herein, the expression level in a set of early developmental genes is measured before the stem cell has been cultured in a differentiation medium, where the results of the expression levels of a set of early developmental genes permits one to predict the linage differentiation bias of the stem cell line. Importantly, the differentiation assay can be performed on a stem cell line as early as at least about 2 days, or at least 3 days or at least about 4 days or more than 4 days in self-renewing culture conditions. In some embodiments, the levels of early developmental genes can be measured in a differentiation assay which is performed on a stem cell line which has been cultured less than 1 day, or for about 1 day, or about 2 days, or about 3 days, or about 4 days, or about 5 days, or about 6 days, or about 7 days.

In alternative embodiments, the expression level of a set of early developmental genes as disclosed herein is measured after a stem cell line, e.g., a pluripotent stem cell line, has been cultured for at least 2 days, where the results of the expression levels of a set of early developmental genes permits one to predict the pluripotency and/or lineage differentiation bias of the stem cell line. In some embodiments, the stem cell line, e.g., a pluripotent stem cell line has not been allowed to spontaneously differentiate. After a pre-defined period of time of the stem cell line in culture (e.g., at least 2 days, but no longer than 7 days), the nucleic acid material from the cells is collected and the mRNA is used as starting material for gene expression analysis of the early developmental genes as disclosed herein.

In alternative embodiments, the stem cell line, e.g., pluripotent stem cell line has been allowed to spontaneously differentiate for a pre-defined period of time. In some embodiments, the expression level of a set of early developmental genes is measured in the stem cell line after directed differentiation along a particular lineage. For example, the differentiation assay can be performed on stem cells that have undergone direct differentiation along a specific lineage (e.g., neuronal lineage, pancreatic lineage, cardiac lineage etc.) for a pre-defined period of time, after which the nucleic acid material from the differentiated cells is collected and used as starting material for gene expression of the early developmental genes. In some embodiments, the differentiation assay is performed on a stem cell line after spontaneous or direct differentiation for at least 0 days, or for about 1 day, or about 2 days, or about 3 days, or about 4 days, or about 5 days, or about 6 days, or about 7 days. In some embodiments, a stem cell line is directed to be differentiated along one or more different lineages. In some embodiments, the differentiation of the stem cell line can be assessed by the differentiation assay as disclosed herein.

In additional aspects, the stem cell line, e.g., pluripotent stem cells are cultured under different conditions and in different culture media and analyzed for their expression of early developmental genes. As disclosed herein in the Examples, different culture media, culture techniques and RNA extraction methods do not affect the results of the gene expression of early developmental genes. For example, maintenance in suboptimal culture conditions, such as the cultivation to high density, does not affect the results.

While the measurement of gene expression as described above focuses mostly on the effect of single genes, in some embodiments, the lineage scorecard measures the gene expression of a combination of early developmental target genes (e.g., any combination of genes listed in Tables 1 and in some embodiments, alternative early developmental genes not listed in Table 1), to predict a cell line's quality (e.g., is no longer pluripotent) and utility (e.g., likely to differentiate, or not, along specific lineages of interest). In some embodiments, alternative genes can include, but are not limited to markers for ectoderm germ cells include, but are not limited to, NCAM1, EN1, FGFR2, GATA2, GATA3, HAND1, MNX1, NEFL, NES, NOG, OTX2, PAX3, PAX6, PAX7, SNAI2, SOX10, SOX9, TDGF1, APOE, PDGFRA, MCAM, FUT4, NGFR, ITGB1, CD44, ITGA4, ITGA6, ICAM1, THY1, FAS, ABCG2, CRABP2, MAP2, CDH2, NES, NEUROG3, NOG, NOTCH1, SOX2, SYP, MAPT, TH. In some embodiments, alternative genes can include, but are not limited to markers for human endoderm germ cells include, but are not limited to, APOE, CDX2, FOXA2, GATA4, GATA6, GCG, ISL1, NKX2-5, PAX6, PDX1, SLC2A2, SST, ITGB1, CD44, ITGA6, THY1, CDX2, GATA4, HNF1A, HNF1B, CDH2, NEUROG3, CTNNB1, SYP, and markers for mesoderm germ cells include, but are not limited to, CD34, DLL1, HHEX, INHBA, LEF1, SRF, T, TWIST1, ADIPOQ, MME, KIT, ITGAL, ITGAM, ITGAX, TNFRSF1A, ANPEP, SDC1, CDH5, MCAM, FUT4, NGFR, ITGB1, PECAM1, CDH1, CDH2, CD36, CD4, CD44, ITGA4, ITGA6, ITGAV, ICAM1, NCAM1, ITGB3, CEACAM1, THY1, ABCG2, KDR, GATA3, GATA4, MYOD1, MYOG, NES, NOTCH1, SPI1, STAT3. In mouse, markers of endoderm germ cells include, Gata4, FoxA2, PDX1, Nodal, Sox7 and Sox17. In mouse, markers of mesoderm germ cells include, Brachycury, GSC, LEF1, Mox1 and Tie1. In mouse, markers of ectoderm germ cells include criptol, EN1, GFAP, Islet 1, LIM1 and Nestin. In some embodiments, a partially reprogrammed cell is an undifferentiated cell. Accordingly, one can select specific sets of early developmental target genes (e.g., early mesoderm genes or early endoderm genes or early ectoderm genes) to develop a "customized scorecard" for sensitive and accurate characterization of a pluripotent stem cell line to identify particular desired or undesirable characteristics. This is one of the key advantages of use of the scorecard as disclosed herein to determine the quality and utility of a particular pluripotent stem cell line.

In some embodiments, the differentiation assay can be configured to be automated e.g., to be run by a robot. In some embodiments, a robot can also perform RNA extraction of an entire multiwell plate, and pipettes the RNA from each well into separate qPCR plates (e.g., when using 96-well qPCR plates) or into ¼ of a plate (e.g., when using 384-well qPCR plates). For example, where one stem cell line is to be analyzed, the RNA from the stem cell line can be pipetted into each well of a 96-well plate, and each well of the 96-well plate used to measure a different early development gene and/or control. In some embodiments, were multiple stem cell lines are to be analyzed, the RNA from each stem cell line can be plated into ¼ of the individual wells of a 384-well plate, where a 384-well plate can be used for the analysis of 4 stem cell lines at the same time. Reverse transcription is performed in the same plate, and barcoded Ct tables are transferred to the computer.

Another aspect of the present invention relates to the use of a stem cell line, e.g., a pluripotent stem cell line, which has been validated and characterized using the methods and lineage scorecards as disclosed herein, for treatment of a subject by administering to a subject a stem cell population, for example a treatment of a mammalian subject, e.g., a mouse or rodent animal model or a human subject, such as for regenerative medicine and cell replacement/enhancement therapy. In some embodiments, a subject suffers from or is diagnosed with a disease or condition selected from the group consisting of cancer, diabetes, cardiac failure, muscle damage, Celiac Disease, neurological disorder, neurodegenerative disorder, lysosomal storage disease, and any combinations thereof. In some embodiments, the pluripotent stem cell is administered locally, or alternatively, administration is transplantation of the pluripotent stem cell into the subject.

In some embodiments, a stem cell line, e.g., a pluripotent stem cell is differentiated before administering the stem cell population, or differentiated progeny thereof to the subject, for example, a stem cell population can be differentiated along a lineage selected from the group consisting of mesoderm, endoderm, ectoderm, neuronal, hematopoietic lineages, and any combinations thereof, or differentiated into an insulin producing cell (pancreatic cell, beta-cell, etc.), neuronal cell, muscle cell, skin cell, cardiac muscle cell, hepatocyte, blood cell, adaptive immunity cell, innate immunity cell and the like.

In some embodiments, the differentiation assay is a high-throughput assay for assaying a plurality of different stem cell lines, e.g., a pluripotent stem cell lines, including a plurality of different induced pluripotent stem cells from a subject, such as a human or other mammalian subject.

Another aspect of the present invention relates to the use of the assay as disclosed herein to generate a lineage scorecard from at least one or a plurality of stem cell lines, e.g., pluripotent stem cell lines.

In some embodiments, the methods, assays, arrays and systems as disclosed herein can be performed by a service provider, for example, where an investigator can have one or more samples (e.g., an array of samples) each sample comprising a stem cell line, or a different population of stem cells, for assessment using the methods, differentiation assays, kits and systems as disclosed herein in a diagnostic laboratory operated by the service provider. In such an embodiment, after performing the assays of the invention as disclosed, the service provider performs the analysis and provide the investigator a report, e.g., a lineage scorecard of the characteristics of each stem cell line analyzed. In alternative embodiments, the service provider can provide the investigator with the raw data of the assays and leave the analysis to be performed by the investigator. In some embodiments, the report is communicated or sent to the investigator via electronic means, e.g., uploaded on a secure web-site, or sent via e-mail or other electronic communication means. In some embodiments, the investigator can send the samples to the service provider via any means, e.g., via mail, express mail, etc., or alternatively, the service provider can provide a service to collect the samples from the investigator and transport them to the diagnostic laboratories of the service provider. In some embodiments, the investigator can deposit the samples to be analyzed at the location of the service provider diagnostic laboratories. In alternative embodiments, the service provider provides a stop-by service, where the service provider send personnel to the laboratories of the investigator and also provides the kits, apparatus, and reagents for performing the assays on the investigators stem cell lines in the investigators laboratories, and analyze the results and provides a report to the investigator of the characteristics of each stem cell line analyzed, or plurality of stem cell lines analyzed.

Lineage Scorecard

In some aspects of the invention, the invention relates to generating a lineage scorecard of a stem cell line, e.g., a pluripotent stem cell line, for validating and monitoring and to serve as a general quality control of the stem cell line, by monitoring the of expression of a set of early developmental genes and lineage marker genes to allow identification of characteristics of the stem cell line and to accurately and quickly predict which pluripotent stem cell lines are likely to be pluripotent (or likely not be pluripotent) and/or differentiate along a range of cell lineages.

One aspect of the present invention relates to a lineage scorecard of the differentiation propensity of a stem cell line, e.g., a pluripotent stem cell, the scorecard comprising a data set comprising the gene expression levels for a plurality of early developmental target genes from at least 5 stem cell populations In some embodiments, the plurality of early developmental target genes is at least about 20, or at least about 30, or at least about 40, or at least about 50, or at least about 60, or at least about 70, or at least about 80, or at least about 90 or more than 90 early developmental genes selected from any combination listed in Table 1. In some embodiments, some of the genes listed in Table 1 can be substituted for alternative early developmental genes. For example, in some embodiments, the plurality of early developmental genes include at least about 20, or at least about 30, or more than 30 genes selected from Table 1 and can include at least 1 or at least about 5, or at least about 10, or at least about 20 or more than 20 different early developmental genes which are not listed in Table. In some embodiments, the plurality of early developmental target genes is at least about 10, or at least about 20, or at least about 30, or more than 30 pluripotent genes, and/or probes for at least about 10, or at least about 20, or at least about 30, or more than 30 early mesoderm genes, and/or probes for at least about 10, or at least about 20, or at least about 30, or more than 30 early ectoderm genes, and/or probes for at least about 10, or at least about 20, or at least about 30, or more than 30 early endoderm genes.

In some embodiments, a data set of the level of expression of a set of early developmental genes can be connected to, or sent to, a data storage device, such as a data storage device comprising a database located on a computer device.

In some embodiments, at least 15 pluripotent stem cells lines are used to generate a data set of the expression of early developmental genes for a reference lineage scorecard. In some embodiments, a data set of the expression of early developmental genes are obtained from at least 5 or more, or at least 6, or at least 7, or at least 8, or at least 9, or at least 10, or at least 11, or at least 12, or at least 13 or at least 14, or at least 15, or at least 16, or at least 17, or at least 18, or all 19 of the following pluripotent stem cells lines selected from the group; HUES64, HUES3, HUES8, HUES53, HUES28, HUES49, HUES9, HUES48, HUES45, HUES1, HUES44, HUES6, H1, HUES62, HUES65, H7, HUES13, HUES63, HUES66.

In some embodiments, the pluripotent stem cell populations used to generate the data sets for the reference lineage scorecard can be mammalian pluripotent stem cell populations, such as human pluripotent stem cell populations, or induced pluripotent stem (iPS) cell populations, or embryonic stem cell populations, or adult stem cell populations, or autologous stem cell populations, or embryonic stem (ES) stem cell populations.

In some embodiments, the lineage scorecard as used herein can be used in methods to select for, e.g., positive selection of a stem cell population with desirable characteristics (e.g., high differentiation potential along a specific lineage and/or pluripotency), and/or to negatively select, e.g., identify and optionally discard, stem cell lines with undesirable characteristics, e.g., cells which are no longer pluripotent, and/or do not differentiate along a desired cell lineage.

Another aspect of the present invention relates to a method for generating a stem cell lineage scorecard comprising measuring the gene expression of a set of early developmental target genes in a plurality of stem cell lines. In some embodiment, if the method is done in replicates (e.g., duplicate, triplicate etc.), the method further comprises calculating an average gene expression level for each early developmental target gene measured. In some embodiments, the methods are sufficiently reliable such that only one (e.g., a single) measurement of the gene expression of early developmental genes is required to create a lineage scorecard, thus eliminating the time and expense of duplicates and triplicate experiments, as well as calculating the average gene expression for each early developmental gene measured.

In some embodiments, a data set of the measured expression levels of the early developmental genes are connected to a data storage device, for example, a data storage device which is a database located on a computer device. In some embodiments, the database is located on a network, for example, a remote network accessible for example, via the network (e.g., a cloud) or similar web accessible network.

In some embodiments, stem cell lines for generating a lineage score card as disclosed herein are mammalian pluripotent stem cell lines, e.g., human pluripotent stem cell line, including embryonic stem cells and/or induced pluripotent stem (iPS) cell lines, and/or adult stem cells, or somatic stem cells, or autologous stem cells.

Another aspect of the present invention relates to the use of the lineage scorecard as disclosed herein to distinguish an induced pluripotent stem cell from an embryonic stem cell line. In some embodiments, a lineage scorecard as disclosed herein can distinguish a pluripotent stem cell line from a non-pluripotent stem cell, or a stem cell line which has lost its pluripotency. In some embodiments, a lineage scorecard as disclosed herein can be used to distinguish a stem cell line, e.g., a pluripotent stem cell line, which has an increased efficiency to differentiate along neuronal lineages or a stem cell line, e.g., a pluripotent stem cell line, which has an increased efficiency to differentiate along mesoderm lineages, and/or ectoderm lineages and/or endoderm lineages.

In some embodiments, a stem cell line where the average $\Delta Ct$ for the gene expression level of a subgroup of early developmental genes (e.g., subgroups of mesoderm, ectoderm, endoderm and pluripotent early developmental gene subgroups) is statistically significantly different to the reference average $\Delta Ct$ for that category, as determined by a t-test, will be considered an outliner stem cell line, which is unlikely to differentiate along the same lineages as a reference pluripotent stem cell line.

As discussed above, in each defined group or category (e.g., control, pluripotent gene, early endoderm developmental genes, early mesendoderm developmental gene, early mesoderm developmental genes, early ectoderm developmental gene), the $\Delta Ct$ is averaged and the averaged $\Delta Ct$ is compared using a t-test to the reference $\Delta Ct$ for that category to provide a t-value. A t-value of 0-1 indicates that the measured level of gene expression in that early developmental gene category is comparable with the reference gene expression level in the same category. A t-value of >1 indicates that the measured gene expression level in that early developmental gene category of the pluripotent cell line is higher than the reference gene expression level in the same category. A t-value of <0 indicates that the measured gene expression level in that early developmental gene category of the pluripotent cell line is lower than the reference gene expression level in the same category. Accordingly, the t-values can be used to negatively select a stem cell line, (e.g., isolate and optionally discard the cells with undesirable characteristics, e.g., cells which have been identified as unlikely to differentiate along particular lineages), and/or positively select for stem cell lines as those identified to have an increased efficiency or potential to differentiate along a particular cell lineage, or positively select a stem cell line which has a t-value indicating that it does not statistically differ from a reference pluripotent stem cell line.

In some embodiments, a stem cell line in which a gene expression level of an early developmental target gene which is statistically significantly different (FDR<10%), and/or which as an absolute difference of >1 fold change of level of gene expression as compared to the normal variation of gene expression for that gene (e.g., the normal reference value) in a reference pluripotent stem cell line would be considered a gene expression outlier. A stem cell line which has numerous, e.g., at least about 5, or at least about 6, or at least about 7, or at least about 8, or at least about 5-10, or at least about 10-15, or at least about 10-50, or at least about 50-100 or more total outlier gene expression genes (as determined by t-test) as compared to a reference pluripotent stem cell will be considered an outlier stem cell line. In some embodiments, such a stem cell line would be identified as a stem cell line that has an increased propensity to differentiate along a specific lineage. For example, if the expression of at least about 2, or at least about 3 or more early mesoderm genes expressed in the stem cell line are statistically different and/or absolutely different by >1 as compared to a reference level for the same early developmental gene, the stem cell line is identified as having an increased or decreased propensity to differentiate along a mesoderm cell lineage as compared to other stem cell lines. Accordingly, such a stem cell line can be either positively selected, or alternatively negatively selected, (e.g., isolated and optionally discarded as a stem cell line with undesirable characteristics) depending on the desired use or utility of the stem cell line.

In some embodiments, a stem cell line which has a gene expression level of an early developmental gene which is statistically significantly different (FDR<5%) and/or has an absolute difference of >1 log-2 fold change of level of the early developmental gene expression as compared to the normal variation of gene expression for that early developmental gene (e.g., the normal reference value) in a reference pluripotent stem cell line would be considered a differentiation outlier gene. A stem cell which has numerous, e.g., at least about 5, or at least about 6, or at least about 7, or at least about 8, or at least about 5-10, or at least about 10-15, or at least about 10-50, or at least about 50-100 or more total outlier lineage gene expression genes as compared to a reference pluripotent stem cell line would be considered an outlier stem cell line, which would be identified as not able, or unlikely to differentiate along the same lineages as a reference pluripotent stem cell line. Accordingly, such a stem cell line can be negatively selected, e.g., isolate and optionally discard the cells with undesirable characteristics, e.g., stem cells which are unlikely to differentiate along particular lineages, and/or alternatively positively selected as a stem cell line which is indicated to have an increased efficiency or potential to differentiate along a particular cell lineage.

Kits

Another aspect of the present invention relates to kits for characterizing the differentiation potential of a stem cell line, e.g., a pluripotent cell line, comprising an array as disclosed herein. In some embodiments, a kit comprises an array as disclosed herein and reagents for measuring the expression levels of a plurality of early developmental genes by RT-PCR. The kit can further comprise instructions for use.

In some embodiments, the kit for carrying out the methods as disclosed herein comprises probes (e.g., oligonucleotides and/or primers) which specifically hybridize to the mRNA of at least about 20, or at least about 30, or at least about 40, or at least about 50, or at least about 60, or at least about 70, or at least about 80, or at least about 90 or more than 90 early developmental genes selected from those listed in Table 1. In some embodiments, the kit comprises probes (e.g., oligonucleotides and/or primers) which specifically hybridize to the mRNA of at least about 3 or more genes selected from Table 2.

Another aspect of the present invention relates to a kit for carrying out a methods and assays as disclosed herein, where the kit comprises: reagents for measuring the expression of a set of early developmental genes selected from at least 20 or at least 30 from the genes listed in Table 1. In some embodiments, the reagents are probes, e.g., RT-PCR primers or hybridization probes that specifically hybridize to a set of early developmental genes selected from a subset of at least 20 from the genes listed in Table 1. In some embodiments, the probes, e.g., RT-PCR probes can be immobilized on a solid support. In some embodiments, in addition to comprising probes for at least 20 early developmental genes selected from Table 1, the kit can comprise additional reagents for measuring the expression of different early developmental genes not listed in Table 1. In some embodiments, the kit also comprises probes for at least 1, or at least 2, or at least 3, or at least 4 or least 5 control genes. Control genes include, but are not limited those listed in Table 3 and/or any from the combination of: ACTB, JARID2, CTCF, SMAD1, β-actin, GAPDH, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLP0, PPIA, POLR2A, PGK1, IPO8, HMBS, GUSB, B2M, HPRT1 or 18S and the like. In some embodiments, a probe for a control gene can be present multiple times in the same assay or kit. In some embodiments, the kit and/or assay as disclosed herein comprises probes for at least about 10, or at least about 20, or at least about 30, or more than 30 pluripotent genes, and/or probes for at least about 10, or at least about 20, or at least about 30, or more than 30 early mesoderm genes, and/or probes for at least about 10, or at least about 20, or at least about 30, or more than 30 early ectoderm genes, and/or probes for at least about 10, or at least about 20, or at least about 30, or more than 30 early endoderm genes.

Accordingly, the present invention relates to a kit for determining the differentiation potential of a stem cell line, comprising reagents (e.g., probes and other reagents) necessary for measuring gene expression levels of a plurality of early developmental genes, e.g., such as any combination of genes listed in Table 1. In some embodiments, the kit further comprises a lineage score card as disclosed herein. In some embodiments, the kit further comprises instructions for use.

In some embodiments, the kit comprises a computer readable medium comprising instructions encoded thereupon for running a software program on a computer to compare the levels of the early developmental genes measured in the test stem cell line with reference levels of the same early developmental genes. In some embodiments, the kit comprises instructions to access a software program available online (e.g., on a cloud) to compare the measured levels of the early developmental genes from the test pluripotent stem cell with reference levels of the early developmental genes for pluripotent stem cells.

In some embodiments, the kit reagents include probes e.g., RT-PCR primers or hybridization probes that specifically hybridize to a set of early developmental genes selected from a subset of at least 20 from the genes listed in Table 1. In some embodiments, the probes, e.g., RT-PCR probes can be immobilized on a solid support. In some embodiments, the kit and/or assay as disclosed herein comprises probes for at least about 10, or at least about 20, or at least about 30, or more than 30 pluripotency genes, and/or probes for at least about 10, or at least about 20, or at least about 30, or more than 30 early mesoderm genes, and/or probes for at least about 10, or at least about 20, or at least about 30, or more than 30 early ectoderm genes, and/or probes for at least about 10, or at least about 20, or at least about 30, or more than 30 early endoderm genes.

In some embodiments, the kit is in a 96-well or 384-well format and comprises probes to hybridize with a set of early developmental genes, e.g., a subset or all of those listed in Table 1. In some embodiments, the kit can be configured to be automated e.g., to be run by a robot. For example, samples can be added to the array of the kit using a robot etc., and the robot can perform the RT-PCR protocol and readout of the levels of the expression of the measured early developmental genes.

In some embodiments, a kit further comprises the reagents for reprogramming a somatic cell or differentiated cell into an induced pluripotent stem cell (iPSC) and also comprises the reagents for quality-assessing the generated iPS cell lines. Examples of reagents used to reprogram a somatic cell into an induced pluripotent stem (iPS) cell are well known to persons of ordinary skill in the art, and include those as discussed herein, for example, but not limited to the methods and reagents for reprogramming a somatic cell to an iPS cell or an piPS cell, as disclosed in International patent applications; WO2007/069666; WO2008/118820; WO2008/124133; WO2008/151058; WO2009/006997; and U.S. Patent Applications US2010/0062533; US2009/0227032; US2009/0068742; US2009/0047263; US2010/0015705; US2009/0081784; US2008/0233610; U.S. Pat. No. 7,615,374; U.S. patent application Ser. No. 12/595,041, EP2145000, CA2683056, AU8236629, 12/602,184, EP2164951, CA2688539, US2010/0105100; US2009/0324559, US2009/0304646, US2009/0299763, US2009/0191159, the contents of which are incorporated herein in their entirety by reference. In some embodiments, the kit comprises the reagents for virally-induced or chemically induced generation of reprogrammed cells e.g., iPS cells, as disclosed in EP1970446, US2009/0047263, US2009/0068742, and 2009/0227032, which are incorporated herein in their entirety by reference. In some embodiments, iPS cells can be reprogrammed using modified RNA (mod-RNA) as disclosed in US2012/0046346, which is incorporated herein in its entirety by reference.

In some embodiments, a kit as disclosed herein also comprises at least one reagent for selecting a desired stem cell line, e.g., a pluripotent stem cell line among many cell lines, e.g., reagents to select one or more appropriate stem cell lines for the intended use of the stem cell line. Such agents are well known in the art, and include without limitation, labeled antibodies to select for cell-specific lineage markers and the like. In some embodiments, the labeled antibodies are fluorescently labeled, or labeled with magnetic beads and the like. In some embodiments, a kit as disclosed herein can further comprise at least one or more reagents for profiling and annotating an existing ES cell and/or iPS cell bank in high throughput, according to the methods as disclosed herein.

In one aspect the invention provides a kit comprising a pluripotent stem cell selected by a differentiation assay, method, or system of the invention. In addition to the above mentioned component(s), the kit can also include informational material. The informational material can be descriptive, instructional, marketing or other material that relates to the methods described herein and/or the use of the components for the assays, methods and systems described herein. For example, the informational material can describe methods for selecting a pluripotent stem cell, for characterizing a plurality of properties of a pluripotent cell, or generating a scorecard according to the invention. Without limitations, if a kit includes material suitable for administering to a subject, the kit can optionally include a delivery device.

Alternative Assays for Measuring Gene Expression Levels of Early Developmental Genes In some embodiments, the assays, systems and methods comprise a quantitative gene profiling assay of a set of early developmental genes, such as via RT-PCT and/or a microarray or the like. Any method for determining gene expression levels commonly known to persons of ordinary skill in the art are encompassed for use in the methods, systems and assays as disclosed herein, and include Affymetrix gene expression systems, microarray methods, and other methods to measure DNA or transcript expression. In some embodiments, gene expression is measured using cDNA and RNA sequencing, imaging-based methods such as Nano String and a wide range of methods that use PCR as well as qPCR. Normalization for these methods has been widely described. In some embodiments, a gcRMA algorithm for normalizing Affymetrix microarray data can be used. In some embodiments, commercially available assays available from Life Technologies Inc., can be used to measure the gene expression of a set of early developmental genes.

In some embodiments, gene expression is determined on any gene level, for example, the expression of non-coding genes, as well as non-coding transcripts e.g., natural antisense transcripts (NATs), microRNA (miRNAs) genes and all other types of nucleic acid and/or RNA transcripts that are normally or abnormally present in pluripotent and differentiated cells.

In some embodiments, the level of gene expression measured is the level of gene transcript, e.g., at the level of messenger RNA (mRNA). In some embodiments, detection uses nucleic acid or nucleic acid analogues, for example, but not limited to, nucleic acid analogues including DNA, RNA, PNA, pseudo-complementary DNA (pcDNA), locked nucleic acid and variants and homologues thereof. In some embodiments, gene transcript expression can be assessed by reverse-transcription polymerase-chain reaction (RT-PCR) or quantitative RT-PCR by methods known to persons of ordinary skill in the art.

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

In an alternative embodiment, expression of a target gene can be measured by reverse-transcription (RT) PCR and by quantitative RT-PCR (QRT-PCR) or real-time PCR methods. Methods of RT-PCR and QRT-PCR are well known in the art, and are described in more detail below.

Real time PCR is an amplification technique that can be used to determine levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA is extracted from a biological sample, e.g. a tumor and normal tissue, and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes can be obtained commercially from, for example, Perkin Elmer/Applied Biosystems (Foster City, Calif.). To quantitate the amount of the specific nucleic acid of interest in a sample, a standard curve is generated using a control. Standard curves can be generated using the Ct values determined in the real-time PCR, which are related to the initial concentration of the nucleic acid of interest used in the assay. Standard dilutions ranging from $10-10^6$ copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan® probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

The TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq®, results in the cleavage of the TaqMan probe. This cleavage separates the 5' fluorescent dye and the 3' quenching agent, thereby resulting in an increase in fluorescence as a function of amplification (see, for example, at the world-wide web site: "perkin-elmer-dot-com").

In another embodiment, detection of RNA transcripts can be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

Detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). One suitable method for detecting enzyme mRNA transcripts is described in reference Pabic et. al. Hepatology, 37(5): 1056-1066, 2003, which is herein incorporated by reference in its entirety.

Other known amplification methods which can be utilized in the methods described herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

In situ hybridization visualization can also be employed, wherein a radioactively labeled antisense RNA probe is hybridized with a thin section of a biopsy sample, washed, cleaved with RNase and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used.

Alternatively, mRNA expression can be detected on a DNA array, chip or a microarray. In such an embodiment, probes can be affixed to surfaces for use as "gene chips." Such gene chips can be used to detect genetic variations by a number of techniques known to one of skill in the art. In one technique, oligonucleotides are arrayed on a gene chip for determining the DNA sequence by the sequencing by hybridization approach, such as that outlined in U.S. Pat. Nos. 6,025,136 and 6,018,041. The probes also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

Oligonucleotides corresponding to a target gene are immobilized on a chip which is then hybridized with labeled nucleic acids of a test sample obtained from a pluripotent stem cell or putative pluripotent stem cell. A positive hybridization signal is obtained with a sample containing a target gene mRNA transcript. Methods of preparing DNA arrays and their use are well known in the art. (See, for example U.S. Pat. Nos. 6,618,6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858).

Microarrays

In some embodiments, the assays and kits as described herein for measuring a set of early developmental genes include use of a microarray. A microarray is an array in which probes, typically nucleic acids such as oligonucleic acid hybridization probes, which are arranged at discrete locations, which are separate from one another and are typically arrayed at a density of between, about 100/cm$^2$ to 1000/cm$^2$, but can be arrayed at greater densities such as 10000/cm$^2$. The principle of a microarray experiment is that mRNA from a given cell line or tissue is used to generate a labeled sample typically labeled cDNA, termed the 'target', which is hybridized in parallel to a large number of nucleic acid sequences, typically DNA sequences, immobilized on a solid surface in an ordered array.

Tens of thousands of transcript species can be detected and quantified simultaneously. Although many different microarray systems have been developed, the most commonly used systems today can be divided into two groups, according to the arrayed material: complementary DNA (cDNA) and oligonucleotide microarrays. The arrayed material has generally been termed the probe since it is equivalent to the probe used in a northern blot analysis. Probes for cDNA arrays are usually products of the polymerase chain reaction (PCR) generated from cDNA libraries or clone collections, using either vector-specific or gene-specific primers, and are printed onto glass slides or nylon membranes as spots at defined locations. Spots are typically 10-300 µm in size and are spaced about the same distance apart. Using this technique, arrays consisting of more than 30,000 cDNAs can be fitted onto the surface of a conventional microscope slide. For oligonucleotide arrays, short 20-25 mers are synthesized in situ, either by photolithography onto silicon wafers (high-density-oligonucleotide arrays from Affymetrix or by ink-jet technology (developed by Rosetta Inpharmatics, and licensed to Agilent Technologies).

Alternatively, presynthesized oligonucleotides can be printed onto glass slides. Methods based on synthetic oligonucleotides offer the advantage that because sequence information alone is sufficient to generate the DNA to be arrayed, no time-consuming handling of cDNA resources is required. Also, probes can be designed to represent the most unique part of a given transcript, making the detection of closely related genes or splice variants possible. Although short oligonucleotides can result in less specific hybridization and reduced sensitivity, the arraying of presynthesized longer oligonucleotides (50-100 mers) has recently been developed to counteract these disadvantages.

Thus in performing a microarray to ascertain the level of gene expression of target genes in pluripotent stem cells, the following steps can be performed: obtain mRNA from the sample comprising pluripotent stem cells and prepare nucleic acids targets, contact the array under conditions, typically as suggested by the manufactures of the microarray (suitably stringent hybridization conditions such as 3×SSC, 0.1% SDS, at 50° C.) to bind corresponding probes on the array, wash if necessary to remove unbound nucleic acid targets and analyze the results.

It will be appreciated that the mRNA can be enriched for sequences of interest such as those present in a gene profile as described herein by methods known in the art, such as primer specific cDNA synthesis. The population can be further amplified, for example, by using PCR technology. The targets or probes are labeled to permit detection of the hybridization of the target molecule to the microarray. Suitable labels include isotopic or fluorescent labels which can be incorporated into the probe.

The Affymetrix HG-U133. Plus 2.0 gene chips can be used and hybridized, washed and scanned according to the standard Affymetrix protocols. Some RNAs can be replicated on arrays, making 96 the total number of available hybridizations for subsequent analysis.

To monitor mRNA levels, for example, mRNA is extracted from the sample comprising pluripotent stem cells to be tested, reverse transcribed, and fluorescent-labeled cDNA probes are generated. The microarrays capable of hybridizing to gene expression target cDNA's are then probed with the labeled cDNA probes, the slides scanned and fluorescence intensity measured. This intensity correlates with the hybridization intensity and expression levels.

Methods of "quantitative" amplification are well known to those of skill in the art. For example, one approach to quantitative PCR involves simultaneously co-amplifying a known quantity of a control sequence using the same primers. This provides an internal standard that can be used to calibrate the PCR reaction. Detailed protocols for quantitative PCR are provided, for example, in Innis et al. (1990) PCR Protocols, A Guide to Methods and Applications, Academic Press, Inc. N.Y.

Although the same procedures and hardware described by Affymetrix could be employed in connection with the present invention, other alternatives are also available. Many reviews have been written detailing methods for making microarrays and for carrying out assays (see, e.g., Bowtell, Nature Genetics Suppl. 27:25-32 (1999); Constantine, et al, Life ScL News 7:11-13 (1998); Ramsay, Nature Biotechnol. 16:40-44 (1998)). In addition, patents have issued describing techniques for producing microarray plates, slides and related instruments (U.S. Pat. Nos. 6,902,702; 6,594,432; 5,622,826, which are incorporated herein in their entirety by reference) and for carrying out assays (U.S. Pat. Nos. 6,902,900; 6,759,197 which are incorporated herein in their entirety by reference). The two main techniques for making plates or slides involve either polylithographic methods (see U.S. Pat. Nos. 5,445,934; 5,744,305 which are incorporated herein in their entirety by reference) or robotic spotting methods (U.S. Pat. No. 5,807,522 which is incorporated herein in its entirety by reference). Other procedures can involve inkjet printing or capillary spotting (see, e.g., WO 98/29736 or WO 00/01859 which are incorporated herein in their entirety by reference).

The substrate used for microarray plates or slides can be any material capable of binding to and immobilizing oligonucleotides including plastic, metals such a platinum and glass. A preferred substrate is glass coated with a material that promotes oligonucleotide binding such as polylysine (see Chena, et al, Science 270:467-470 (1995)). Many schemes for covalently attaching oligonucleotides have been described and are suitable for use in connection with the present invention (see, e.g., U.S. Pat. No. 6,594,432 which is incorporated herein in its entirety by reference). The immobilized oligonucleotides should be, at a minimum, 20 bases in length and should have a sequence exactly corresponding to a segment in the gene targeted for hybridization.

Computer Systems

Another aspect of the present invention relates to a computer system for generating a lineage scorecard of a pluripotent stem cell, comprising: (i) at least one memory containing at least one program comprising the steps of: (a) receiving gene expression data of a set of early developmental genes selected from a combination of at least 20 from the list in Table 1 and performing a comparison of the gene expression levels of the early developmental genes with a reference gene expression level of the same target genes; (b) generating a lineage scorecard based on the comparison of the expression of the early developmental gene as compared to the reference gene expression levels for the same set of early developmental genes; and (ii) a processor for running said program. In some embodiments, the system further comprises a report generating module which generates a lineage scorecard report based on differentiation propensity of the pluripotent stem cell line tested. In some embodiments, the system comprises a memory, wherein the memory comprises a database. In some embodiments, the database arranges the gene expression of the set of early developmental genes in a hierarchical manner, e.g., the levels of expression the early developmental genes clustered according to group, e.g., expression levels of pluripotent genes, early mesoderm genes, early ectoderm genes or early endoderm genes. In some embodiments, the memory is connected to the first computer via a network, e.g., a local network (LAN) or a wide area network, such as the internet, where access to the network is via a secure site or via password access.

In some embodiments, the system as disclosed herein provides a lineage scorecard which provides an indication of suitable uses, utility or applications of the pluripotent stem cell line tested.

Another aspect of the present invention relates to a computer readable medium comprising instructions for generating a lineage scorecard of a pluripotent stem cell line, comprising: (i) receiving gene expression data of a set of early developmental genes selected from a combination of at least 20 from the list in Table 1 and performing a comparison of the gene expression levels of the early developmental genes with a reference gene expression level of the same target genes, and (ii) generating a lineage scorecard based on the comparison of the expression of the early developmental gene as compared to the reference gene expression levels for the same set of early developmental genes.

One aspect of the present invention relates to a computerized system for processing the differentiation assay data and generating a measure or rating of the pluripotent stem cell as propensity to differentiate along one or more cell lineages, and/or generating a lineage scorecard as disclosed herein.

In some embodiments, a computer system for generating a lineage scorecard of a pluripotent stem cell, comprising: (i) at least one memory containing at least one program comprising the steps of: (a) receiving gene expression data of a set of early developmental genes selected from a combination of at least 20 from any combination of genes listed in Table 1, and performing a comparison of the gene expression levels of the early developmental genes with a reference gene expression level of the same target genes; (b) generating a lineage scorecard based on the comparison of the expression of the early developmental gene as compared to the reference gene expression levels for the same set of early developmental genes; and (ii) a processor for running said program. In some embodiments, the system further comprises a report generating module which generates a lineage scorecard report based on differentiation propensity of the pluripotent stem cell line tested. In some embodiments, the system comprises a memory, wherein the memory comprises a database. In some embodiments, the database arranges the gene expression of the set of early developmental genes in a hierarchical manner, e.g., the levels of expression the early developmental genes clustered according to group, e.g., expression levels of pluripotent genes, early mesoderm genes, early ectoderm genes or early endoderm genes. In some embodiments, the memory is connected to the first computer via a network, e.g., a local network (LAN) or a wide area network, such as the internet, where access to the network is via a secure site or via password access.

In some embodiments, the system as disclosed herein provides a lineage scorecard which provides an indication of suitable uses, utility or applications of the pluripotent stem cell line tested.

In some embodiments, the computer program is adapted to control the operation of the computer system to implement a method that further includes: (i) receiving gene expression data (e.g., gene expression levels) of the early developmental genes expressed in the pluripotent stem cell line of interest and comparing the gene expression data (e.g., gene expression levels) with a reference early developmental gene expression data (e.g., gene expression levels of the same second set of early developmental target genes in a control pluripotent stem cell line or a plurality of pluripotent stem cell lines); (ii) generating a lineage scorecard based on the comparison of the gene expression data (e.g., gene expression levels of the early developmental genes) as compared to reference gene expression data (e.g., reference early developmental gene expression levels in reference pluripotent stem cell line(s)).

Another aspect of the present invention relates to a computer readable medium comprising instructions for generating a lineage scorecard of a pluripotent stem cell line, comprising: (i) receiving gene expression data of a set of early developmental genes selected from a combination of at least 20 from any combination of genes listed in Table 1 and performing a comparison of the gene expression levels of the early developmental genes with a reference gene expression level of the same target genes, and (ii) generating a lineage scorecard based on the comparison of the expression of the early developmental gene as compared to the reference gene expression levels for the same set of early developmental genes.

The computer system can include one or more general or special purpose processors and associated memory, including volatile and non-volatile memory devices. The computer system memory can store software or computer programs for controlling the operation of the computer system to make a special purpose system according to the invention or to implement a system to perform the methods according to the invention. The computer system can include an Intel or AMD x86 based single or multi-core central processing unit (CPU), an ARM processor or similar computer processor for processing the data. The CPU or microprocessor can be any conventional general purpose single- or multi-chip microprocessor such as an Intel Pentium processor, an Intel 8051 processor, a RISC or MISS processor, a Power PC processor, or an ALPHA processor. In addition, the microprocessor can be any conventional or special purpose microprocessor such as a digital signal processor or a graphics processor. The microprocessor typically has conventional address lines, conventional data lines, and one or more conventional control lines. As described below, the software according to the invention can be executed on dedicated system or on a general purpose computer having a DOS, CPM, Windows, Unix, Linix or other operating system. The system can include non-volatile memory, such as disk memory and solid state memory for storing computer programs, software and data and volatile memory, such as high speed ram for executing programs and software.

Computer-readable physical storage medium useful in various embodiments of the invention can include any physical computer-readable storage medium, e.g., solid state memory (such as flash memory), magnetic and optical computer-readable storage media and devices, and memory that uses other persistent storage technologies. In some embodiments, a computer readable medium can be any tangible media that allows computer programs and data to be accessed by a computer. Computer readable medium can include volatile and nonvolatile, removable and non-removable tangible media implemented in any method or technology capable of storing information such as computer readable instructions, program modules, programs, data, data structures, and database information. In some embodiments of the invention, computer readable medium includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store information and which can read by a computer including and any suitable combination of the foregoing.

Computer-readable physical storage medium is also commonly referred to as storage devices, Carrier waves and other signal-based storage or transmission media are not included within the scope of storage devices or physical computer-readable storage medium encompassed by the term and useful according to the invention. The storage device can be adapted or configured for having recorded thereon the reference data of levels of expression of early developmental genes from a plurality of pluripotent stem cells (e.g., including ΔCt levels for individual early developmental genes of Table 1 and/or Table 2, as well as average ΔCt levels for subgroups of early developmental genes). Such information can be provided in digital form that can be transmitted and read electronically, e.g., via the Internet, on diskette, via USB (universal serial bus) or via any other suitable mode of communication.

The present invention can be implemented on a stand-alone computer or as part of a networked computer system. In a stand-alone computer, all the software and data can reside on local memory devices, for example an optical disk or flash memory device can be used to store the computer software for implementing the invention as well as the data. In alternative embodiments, the software or the data or both can be accessed through a network connection to remote devices. In one networked computer system embodiment, the invention use a client-server environment over a public network, such as the internet or a private network to connect to data and resources stored in remote and/or centrally located locations. In this embodiment, a server including a web server can provide access, either open access, pay as you go or subscription based access to the information provided according to the invention. In a client server environment, a client computer executing a client software or program, such as a web browser, connects to the server over a network. The client software or web browser provides a user interface for a user of the invention to input data and information and receive access to data and information. The client software can be viewed on a local computer display or other output device and can allow the user to input information, such as by using a computer keyboard, mouse or other input device. The server executes one or more computer programs that enable the client software to input data, process data according to the invention and output data to the user, as well as provide access to local and remote computer resources. For example, the user interface can include a graphical user interface comprising an access element, such as a text box, that permits entry of data from the assay, e.g., the DNA methylation data levels or DNA gene expression levels of target genes of a reference pluripotent stem cell population and/or pluripotent stem cell population of interest, as well as a display element that can provide a graphical read out of the results of a comparison with a score card, or data sets transmitted to or made available by a processor following execution of the instructions encoded on a computer-readable medium.

Embodiments of the invention also provide for systems (and computer readable medium for causing computer systems) to perform a method for determining quality assurance of a pluripotent stem cell population according to the methods as disclosed herein.

In some embodiments of the invention, the computer system software can include one or more functional modules, which can be defined by computer executable instructions recorded on computer readable medium and which cause a computer to perform a method according to the invention, when executed. The modules can be segregated by function for the sake of clarity, however, it should be understood that the modules need not correspond to discreet blocks of code and the described functions can be carried out by the execution of various software code portions stored on various media and executed at various times. Furthermore, it should be appreciated that the modules can perform other functions, thus the modules are not limited to having any particular function or set of functions. In some embodiments, functional modules for producing a deviation score card are, for example, but are not limited to, a storage module, a gene mapping module, a reference comparison module, a normalization module, a relevance filter module, a gene set module, and a scorecard display module to display the deviation scorecard. Functional modules for producing a lineage scorecard are, for example, but are not limited to, a storage device, an assay normalization module, a sample normalization module, a reference comparison module, a gene set module, an enrichment analysis module, and a scorecard display module to display the lineage scorecard. The functional modules can be executed using one or multiple computers, and by using one or multiple computer networks.

The information embodied on one or more computer-readable medium can include data, computer software or programs, and program instructions, that, as a result of being executed by a computer, transform the computer to a special purpose machine and can cause the computer to perform one or more of the functions described herein. Such instructions can be originally written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable medium on which such instructions are embodied can reside on one or more of the components of a computer system or a network of computer systems according to the invention.

In some embodiments, a computer-readable medium can be transportable such that the instructions stored thereon can be loaded onto any computer resource to implement the aspects of the present invention discussed herein. In addition, it should be appreciated that the instructions stored on computer readable medium are not limited to instructions embodied as part of an application program running on a host computer. Rather, the instructions can be embodied as any type of computer code (e.g., object code, software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

In some embodiments, a system as disclosed herein, can receive gene expression level data of the set of developmental genes measured from an automated gene expression analysis system, e.g., an automated protein expression analysis including but not limited to mass spectrometry systems including MALDI-TOF, or Matrix Assisted Laser Desorption Ionization—Time of Flight systems; SELDI-TOF-MS ProteinChip array profiling systems, e.g. Machines with Ciphergen Protein Biology System II™ software; systems for analyzing gene expression data (see for example U.S. 2003/0194711); systems for array based expression analysis, for example HT array systems and cartridge array systems available from Affymetrix (Santa Clara, Calif. 95051) AutoLoader, Complete GeneChip® Instrument System, Fluidics Station 450, Hybridization Oven 645, QC Toolbox Software Kit, Scanner 3000 7G, Scanner 3000 7G plus Targeted Genotyping System, Scanner 3000 7G Whole-Genome Association System, GeneTitan™ Instrument, GeneChip® Array Station, HT Array; an automated ELISA system (e.g. DSX® or D52® form Dynax, Chantilly, Va. or the ENEASYSTEM III®, Triturus®, The Mago® Plus); Densitometers (e.g. X-Rite-508-Spectro Densitometer®, The HYRYS™ 2 densitometer); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, Becton Dickinson); radio isotope analyzers (e.g. scintillation counters).

In some embodiments of the present invention, the reference data can be electronically or digitally recorded, annotated and retrieved from databases including, but not limited to GenBank (NCBI) protein and DNA databases such as genome, ESTs, SNPS, Traces, Celara, Ventor Reads, Watson reads, HGTS, etc.; Swiss Institute of Bioinformatics databases, such as ENZYME, PROSITE, SWISS-2DPAGE, Swiss-Prot and TrEMBL databases; the Melanie software package or the ExPASy WWW server, etc., the SWISS-MODEL, Swiss-Shop and other network-based computational tools; the Comprehensive Microbial Resource database (The institute of Genomic Research). The resulting information can be stored in a relational data base that can be employed to determine homologies between the reference data or genes or proteins within and among genomes.

In some embodiments, the gene expression levels of early developmental target genes in a pluripotent stem cell can be received from a memory, a storage device, or a database. The memory, storage device or database can be directly connected to the computer system retrieving the data, or connected to the computer through a wired or wireless connection technology and retrieved from a remote device or system over the wired or wireless connection. Further, the memory, storage device or database, can be located remotely from the computer system from which it is retrieved.

Examples of suitable connection technologies for use with the present invention include, for example parallel interfaces (e.g., PATA), serial interfaces (e.g., SATA, USB, Firewire,), local area networks (LAN), wide area networks (WAN), Internet, Intranet, and Extranet, and wireless (e.g., Blue Tooth, Zigbee, WiFi, WiMAX, 3G, 4G) communication technologies As used herein, "stored" refers to a process for recording information, e.g., data, programs and instructions, on the storage device, that can be read back at a later time. Those skilled in the art can readily adopt any of the presently known methods for recording information on known media to contribute to a reference scorecard data, e.g., the level of DNA methylation, and/or gene expression level, and/or differentiation propensity data of a pluripotent stem cell as disclosed in the methods herein.

A variety of software programs and formats can be used to store the lineage scorecard data and/or level of expression of early developmental genes and information on the storage device. Any number of data processor structuring formats (e.g., text file or database) can be employed to obtain or create a medium having recorded scorecard data thereon.

In one embodiment, the reference scorecard data can be electronically or digitally recorded and annotated from databases including, but not limited to protein expression databases commonly known in the art, such as Yale Protein Expression Database (YPED), as well as GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting information of the level of DNA methylation, and/or Gene expression level, and/or differentiation propensity data of a pluripotent stem cell line can be stored in a relational database that can be employed to determine differences as compared to different pluripotent stem cell populations, or compared to reference DNA methylation levels, reference Gene expression levels and reference propensity differentiation data between different pluripotent stem cell populations, e.g., ES cells, and iPS cells and piPS cells, and somatic stem cells, or among pluripotent stem cells of the same type (e.g., iPS cells) from different genomes, species and different populations of individuals.

In some embodiments, the system has a processor for running one or more programs, e.g., where the programs can include an operating system (e.g., UNIX, Windows), a relational database management system, an application program, and a World Wide Web server program. The application program can be a World Wide Web application that includes the executable code necessary for generation of database language statements (e.g., Structured Query Language (SQL) statements). The executables can include embedded SQL statements. In addition, the World Wide Web application can include a configuration file which contains pointers and addresses to the various software entities that provide the World Wide Web server functions as well as the various external and internal databases which can be accessed to service user requests. The Configuration file can also direct requests for server resources to the appropriate hardware devices, as can be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers. In other embodiments of the invention, other interfaces, such as HTTP, FTP, SSH and VPN based interfaces can be used to connect to the Internet databases.

In one embodiment, the system as disclosed herein can be used to compare gene expression profiles (e.g., gene expression profiles or levels of gene expression of a plurality of early developmental target genes). For example, the system can receive onto its memory gene expression profiles or data of the test pluripotent stem cell line and compare it with one or more stored gene expression profiles (e.g. the normal variation of early developmental gene expression in one or more reference pluripotent stem cell lines), or compare with one or more early developmental gene expression profiles from the pluripotent stem cell line previously analyzed at an earlier time point. In some embodiments, gene expression profiles can be obtained using Affymetrix Microarray Suite software version 5.0 (MAS 5.0) (available from Affymetrix, Santa Clara, Calif.) to analyze the relative abundance of a gene or genes on the basis of the intensity of the signal from probe sets, and the MAS 5.0 data files can be transferred into a database and analyzed with Microsoft Excel and GeneSpring 6.0 software (available from Agilent Technologies, Santa Clara, Calif.). In some embodiments, a comparison algorithm of MAS 5.0 software can be used to obtain a comprehensive overview of how many transcripts are detected in given samples and allows a comparative analysis of 2 or more microarray data sets. In some embodiments however, only one data set is required (e.g., a set of early developmental genes is measured only once in a given pluripotent stem cell line, eliminating the cost, time and resources required for duplicate and triplicate data sets).

In some embodiments of this aspect and all other aspects of the present invention, the system can compare the data in a "comparison module" which can use a variety of available software programs and formats for the comparison operative to compare sequence information determined in the determination module to reference data. In one embodiment, the comparison module is configured to use pattern recognition techniques to compare sequence information from one or more entries to one or more reference data patterns. The comparison module can be configured using existing commercially-available or freely-available software for comparing patterns, and can be optimized for particular data comparisons that are conducted. The comparison module can also provide computer readable information related to the sequence information that can include, for example, determination of the concentration of a sequence in the sample (e.g. amino acid sequence/protein expression levels, or nucleotide (RNA or DNA) expression levels), or determination of a Gene expression profile.

In some embodiments, the system comprises comparison software which is used to determine whether the gene expression level data of early developmental genes for a pluripotent stem cell of interests falls outside a reference gene expression levels for that early developmental gene as disclosed herein, e.g., outside the normal variation of gene expression levels for the early developmental target genes) for a plurality of pluripotent stem cells. For example, where the gene expression level of an early developmental gene for a pluripotent stem cell of interest expression is higher by a statically significantly amount above a reference gene expression level for that early developmental gene, it indicates likelihood of expression of the early developmental target gene, and the software can be configured to signal (or otherwise indicate) the likelihood of optimal differentiation along that cell lineage.

By providing gene expression level data of early developmental genes in computer-readable form, one can use the gene expression level data for a pluripotent stem cell to compare with gene expression levels of early developmental genes of other pluripotent stem cells within the storage device. For example, search programs can be used to identify relevant reference data (i.e. reference expression levels of early developmental genes) that match the expression level of a same early developmental target gene for the pluripotent stem cell of interest. The comparison made in computer-readable form provides computer readable content which can be processed by a variety of means. The content can be retrieved from the comparison module, the retrieved content.

In some embodiments, the comparison module provides computer readable comparison result that can be processed in computer readable form by predefined criteria, or criteria defined by a user, to provide a report which comprises content based in part on the comparison result that can be stored and output as requested by a user using a display module. In some embodiments, a display module enables display of a content based in part on the comparison result for the user, wherein the content is a report indicative of the results of the comparison of the pluripotent stem cell of interest with a scorecard, or the utility of the pluripotent stem cell, e.g., expression levels of specific early developmental genes, e.g., early mesoderm genes and/or early ectoderm genes, and/or early endoderm genes, as well as expression of pluripotent stem cells.

In some embodiments, the display module enables display of a report or content based in part on the comparison result for the end user, wherein the content is a report indicative of the results of the comparison of the pluripotent stem cell of interest with a lineage scorecard, or the utility of the pluripotent stem cell, e.g., expression levels of specific early developmental genes, e.g., early mesoderm genes and/or early ectoderm genes, and/or early endoderm genes, as well as expression of pluripotent stem cells.

The computer instructions can be implemented in software, firmware or hardware and include any type of programmed step undertaken by modules of the information processing system. The computer system can be connected to a local area network (LAN) or a wide area network (WAN). One example of the local area network can be a corporate computing network, including access to the Internet, to which computers and computing devices comprising the data processing system are connected. In one embodiment, the LAN uses the industry standard Transmission Control Protocol/Internet Protocol (TCP/IP) network protocols for communication. Transmission Control Protocol Transmission Control Protocol (TCP) can be used as a transport layer protocol to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection. Finally, TCP is responsible for encapsulating information into a datagram structure. In alternative embodiments, the LAN can conform to other network standards, including, but not limited to, the International Standards Organization's Open Systems Interconnection, IBM's SNA, Novell's Netware, and Banyan VINES.

In some embodiments, the computer system as described herein can include any type of electronically connected group of computers including, for instance, the following networks: Internet, Intranet, Local Area Networks (LAN) or Wide Area Networks (WAN). In addition, the connectivity to the network can be, for example, remote modem, Ethernet (IEEE 802.3), Token Ring (IEEE 802.5), Fiber Distributed Datalink Interface (FDDI) or Asynchronous Transfer Mode (ATM). The computing devices can be desktop devices, servers, portable computers, hand-held computing devices, smart phones, set-top devices, or any other desired type or configuration. As used herein, a network includes one or more of the following, including a public internet, a private internet, a secure internet, a private network, a public network, a value-added network, an intranet, an extranet and combinations of the foregoing.

In one embodiment of the invention, the computer system can comprise a pattern comparison software can be used to determine whether the patterns of gene expression levels in a pluripotent stem cell line of interest are indicative of that cell line being an outlier and predictive of a stem cell line functioning outside the normal characteristics of reference pluripotent stem cell lines, or the likelihood of the pluripotent stem cell line having a low efficiency or increased efficiency of differentiating along a particular cell line of interest or having lost is pluripotent state. In this embodiment, the pattern comparison software can compare at least some of the data (e.g., gene expression levels of early developmental genes) of the pluripotent stem cell of interest with predefined patterns of gene expression levels (gene expression levels of early developmental target genes) of reference pluripotent stem cell lines to determine how closely they match. The matching can be evaluated and reported in portions or degrees indicating the extent to which all or some of the pattern matches.

In some embodiments of this aspect and all other aspects of the present invention, a comparison module provides computer readable data that can be processed in computer readable form by predefined criteria, or criteria defined by a user, to provide a retrieved content that can be stored and output as requested by a user using a display module.

Display Module

In accordance with some embodiments of the invention, the computerized system can include or be operatively connected to a display module, such as computer monitor, touch screen or video display system. The display module allows user instructions to be presented to the user of the system, to view inputs to the system and for the system to display the results to the user as part of a user interface. Optionally, the computerized system can include or be operative connected to a printing device for producing printed copies of information output by the system. In some embodiments, the display module is a computer screen present at the location of the end user, which is connected to a system or computer which is processed on a comparison module or computer located at a different location, e.g., on a server at a remote location, which is accesable to the user using a secure access via the internet or world wide web etc.

In some embodiments, the results can be displayed on a display module or printed in a report, e.g., a lineage scorecard report to indicate the utility of the pluripotent stem cell of interest, e.g., utility for a particular therapeutic use based on the likelihood of differentiating along a certain cell line lineage based on the data from the level of gene expression of early developmental genes in the pluripotent stem cell.

In some embodiments, the scorecard report is a hard copy printed from a printer. In alternative embodiments, the computerized system can use light or sound to report the scorecard, e.g., to indicate the quality and utility of a pluripotent stem cell line of interest. For example, in all aspects of the invention, the scorecard produced by the methods, differentiation assays, systems and present in the kits as disclosed herein can comprise a report which is color coded to signal or indicate the quality of the pluripotent stem cell of interest as compared to one or more reference pluripotent stem cell lines (e.g., the standard human ES cell lines and iPS cells as tested herein), or compared to another "gold" standard pluripotent stem cell line of the investigators' choice.

For example, a red color or other predefined signal can indicate that the pluripotent stem cell line is an outlier pluripotent stem cell line, and has one or more early developmental genes vary by a statistically significant amount as compared to levels in one or more reference pluripotent stem cell lines, thus signaling that the pluripotent stem cell line has different characteristics to the reference pluripotent stem cell lines, e.g., can have an increased or decreased predisposition to differentiate into a particular cell lineage. In another embodiment, a yellow or orange color or other predefined signal can indicate that the pluripotent stem cell line can have one early developmental genes which varies by a statistically significant amount as compared to levels in one or more reference pluripotent stem cell lines, thus signaling that the pluripotent stem cell line has slightly different characteristic to the reference pluripotent stem cell line(s), but that difference can not be important to the function, e.g., the pluripotent stem cell line of interest is still of the characteristic quality to be used, and does not have an altered predisposition to differentiate along a particular cell lineage etc. In another embodiment, a green color or other predefined signal can indicate that the pluripotent stem cell line is of high quality and the level of expression of the majority of a set of early developmental genes does not vary by a statistically significant amount as compared to levels in one or more reference pluripotent stem cell lines, thus signaling that the pluripotent stem cell line is of high quality and likely to have similar characteristic to the reference pluripotent stem cell line(s). In alternative embodiments, other signals or colors can be used to signal that a pluripotent stem cell has an increased propensity to differentiate along a particular cell lineage, e.g., a mesoderm lineage, or an ectoderm lineage or an endoderm lineage. Different signals or colors can be used to signal likely differentiation along each lineage.

In some embodiments, a "heat map" or gradient color scheme can be used in the report, e.g., scorecard report to signal the quality of the pluripotent stem cell line, for example, where the gradient is a red to yellow to green gradient, where a red signal will signal an inferior and/or poor quality, and a yellow signal will indicate a good quality and a green signal will indicate a high quality pluripotent stem cell of interest as compared to one or more reference pluripotent stem cell line(s). Colors between red and yellow and yellow and green will signal the characteristics of the pluripotent stem cell line with respect to a red-yellow-green scale. Other color schemes and gradient schemes in the report are also encompassed.

In some embodiments, the report indicates a plurality oft values for the expression level of a plurality of early developmental gene relative to a reference gene expression level for that early developmental gene. A t-value of 0-1 between the measured early developmental gene and the reference expression level for that early developmental gene indicates that the expression levels are comparable and not statistically significant. A t-value of >1 between the measured early developmental gene in the pluripotent stem cell and the reference expression level for that early developmental gene indicates that the expression level of the early developmental gene is higher in the pluripotent stem cell as compared to the reference expression level for that gene. A t-value of <0 between the measured early developmental gene in the pluripotent stem cell and the reference expression level for that early developmental gene indicates that the expression level of the early developmental gene is lower in the pluripotent stem cell as compared to the reference expression level for that gene.

In some embodiments, a report indicates a green signal or similar signal (e.g., upward arrow) where the t-value for the early developmental gene is >1, indicating that the level of the early developmental gene in the pluripotent stem cell is higher as compared to the reference level for that early developmental gene. In some embodiments, the report indicates a yellow signal or similar signal (e.g., horizontal arrow, an 45° upward or downward angled arrow) where the t-value for the early developmental gene is between 0-1, indicating that the level of the early developmental gene in the pluripotent stem cell is comparable with the reference level for that early developmental gene. In some embodiments, a report indicates a red signal or similar signal (e.g., downward arrow) where the t-value for the early developmental gene is <0, indicating that the level of the early developmental gene in the pluripotent stem cell is lower as compared to the reference level for that early developmental gene. In some embodiments, the report indicates the t-values, and/or a symbol (e.g., directional arrows) for each early developmental gene measured in the differentiation assay. In alternative embodiments, the report indicates a summary of the t-values for the pluripotent stem cell measured, for example, the median or average t-values for the early developmental genes in each category, e.g., pluripotent stem cell genes, early mesoderm genes, early ectoderm genes, early endoderm genes and the like.

Any method or t-test to calculate t values is encompassed for use in the methods and assays and systems as disclosed herein. In some embodiments, the ΔCt of the early developmental gene is compared with the reference ΔCt for the same early developmental gene in a t-test. The ΔCt for each early developmental gene expressed in the pluripotent stem cell line is determined by comparing the Ct level of the early developmental gene measured in the pluripotent stem cell line with the median Ct value for a control gene (e.g., ACTB) measured in the same pluripotent stem cell line.

In some embodiments, the report, e.g., lineage scorecard can display the total %, and/or absolute total number of early developmental genes which have a different level of gene expression as compared to the normal variation of early developmental gene expression. As an illustrative example only, the score card can indicate that the test pluripotent stem cell has 21% genes of the genes assessed expressed at a different level as compared to the normal variation, and also indicate that the normal variation (e.g., in a plurality of reference pluripotent stem cell lines).

In some embodiments, the report, e.g., scorecard, can display the normalized values of the test pluripotent stem cell line, which are normalized to a reference pluripotent stem cell line (e.g., a selected "gold" standard line of the investigators choice) or the normal variation in reference pluripotent stem cell lines. Accordingly, a scorecard can display the % difference, and/or the change in absolute number of early developmental genes which are differentially expressed as compared to the normal variation of early developmental gene expression levels. As an illustrative example only, the lineage scorecard can indicate that the test pluripotent stem cell has 20 total (or 22%) of the 90 early developmental genes assessed that have increased gene expression (e.g., a t-value of >1) as compared to the normal variation of the early developmental genes. In some embodiments, this can be broken up, such as in an exemplary example, to indicate that 12 of the 20 genes which are increased are characterized as mesoderm early developmental genes, 4 are characterized as endoderm early developmental genes, and 4 are characterized as ectoderm early developmental genes.

In an alternative embodiment, the report, e.g., lineage scorecard can display the % or relative differentiation propensities to differentiate along specific lineages, e.g., neuronal, endoderm, ectoderm, mesoderm, pancreatic, cardiac lineages etc.

In some embodiments, the report, e.g., scorecard can also present text, either verbally or written, giving a recommendation of which applications and/or utility the pluripotent cell line is appropriate for, and/or which applications and/or utility the pluripotent cell line is not appropriate for.

In some embodiments of this aspect and all other aspects of the present invention, the report data, e.g., a lineage scorecard from the comparison module can be displayed on a computer monitor as one or more pages of the printed report, e.g., scorecard. In one embodiment of the invention, a page of the retrieved content can be displayed through printable media. The display module can be any device or system adapted for display of computer readable information to a user. The display module can include speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc.

In some embodiments of the present invention, a World Wide Web browser can be used to provide a user interface to allow the user to interact with the system to input information, construct requests and to display retrieved content. In addition, the various functional modules of the system can be adapted to use a web browser to provide a user interface. Using a Web browser, a user can construct requests for retrieving data from data sources, such as data bases and interact with the comparison module to perform comparisons and pattern matching. The user can point to and click on user interface elements such as buttons, pull down menus, scroll bars, etc. conventionally employed in graphical user interfaces to interact with the system and cause the system to perform the methods of the invention. The requests formulated with the user's Web browser can be transmitted over a network to a Web application that can process or format the request to produce a query of one or more database that can be employed to provide the pertinent information related to the DNA methylation levels and gene expression levels, the retrieved content, process this information and output the results, e.g. at least one of any of the following: (i) display of the average or median t-value (and optionally a directional arrow) for early developmental genes in each category (e.g., pluripotent stem cell genes, early mesoderm genes, early ectoderm genes, early endoderm genes and the like); (ii) display of the t-value for each early developmental gene assessed (and optionally a directional arrow); (iii) display of number of early developmental genes (% and/or absolute numbers) with an t-value of >1 (e.g., higher expression as compared to the reference early gene expression level); (iv) display of number of early developmental genes (% and/or absolute numbers) with an t-value of <0 (e.g., lower expression as compared to the reference early gene expression level); (v) display of number of early developmental genes (% and/or absolute numbers) with an t-value of between 0-1 (e.g., comparable expression as compared to the reference early gene expression level)). In one embodiment, the gene expression level of early developmental genes of one or more reference pluripotent stem cell lines can also displayed.

Example Workflow of a High-Throughput Sample Processing to Produce a Deviation or Lineage Scorecard As an exemplary example, but by no way a limitation, a lineage scorecard workflow is illustrated by the following case study: An individual researcher or a large company (or foundation) plans to establish a stem cell bank providing HLA-matched iPS cell lines for X % of the US population, which requires 10,000 iPS cell lines. All cell lines will be commercially available, and to make the resource most valuable to researchers and companies, it is planned to publish scorecard characterizations for each cell line. To facilitate automatization, all iPS cell lines are grown in 96-well plates or 384-well plates. Most sample processing is robotized, and all cell lines are barcoded and tracked by a central LIMS. The scorecard characterization is performed as follows:

(1) Deviation scorecard/confirmation of pluripotency: A researcher loads a liquid-handling robot as follows: (i) one 96-well or 384-well plate with one iPS cell line per well; (ii) 96-well or 384-well mRNA extraction kit, (iii) custom qPCR plates (96-well or 384-well) with pre-spotted probes (e.g., oligonucleotides and/or primers) that are specific to at least 20-genes listed in Table 1 and at least 1 oligonucleotide (or primer pair) that is specific for at least one control gene.

(2) A robot performs RNA extraction of the entire plate and pipettes the RNA from each well into separate qPCR plates (when using 96-well qPCR plates) or into ¼ of a plate (when using 384-well qPCR plates). Reverse transcription is performed in the same plate, and barcoded Ct tables are transferred to computer readable media on the computer.

(3) Lineage scorecard/quantification of differentiation potential: For example, starting from a 96-well plate with one iPS cell line per well, a researcher will harvest the cells from each well and plate them into a new 96-well plate.

(4) After a defined period of time (e.g. n days) of culture of the pluripotent stem cells, the plates are loaded into a liquid-handling robot and qPCR analysis is performed as described in steps 1 and 2, with the only exception that custom qPCR plates with early differentiation-specific marker genes are used.

(5) Upon completion of the experiments, the researcher loads the unprocessed Ct values into a custom lineage scorecard software. This software imports the output data format from any of the common qPCR machines, performs relative normalization using a number of house-keeping genes and calculates the scorecard prediction.

(6) Gene set selection. As disclosed herein, the lineage scorecard requires the measurement of the expression level of a set of early developmental markers. In some embodiments, the assay for generation of data for the deviation scorecard can consist of a single 96-well qPCR plate (or in some embodiments, four samples on a 384-well qPCR plate) with the most relevant genes for determining whether or not a given cell line classifies as pluripotent. In some embodiments, the assay for generation of data for the lineage scorecard can consist of two 96-well plates (or in some embodiments, two samples on a 384-well qPCR plate) with the most relevant genes for quantifying the differentiation propensities of a given cell line.

In some embodiments, the optimal gene selection of the early developmental genes for the lineage scorecards using a multiplex qPCR assay can be further validated and optimized. While replicates are not necessary in the present invention, in some embodiments, multiple plates are used for the differentiation assay of each cell line, which includes plates for each biological stem cell line of interest in replicate, plates for a stem cell line in its pluripotent state and one for the stem cell line in its EB state. In some embodiments, genes to be included in such a 384-well qPCR plate ("tech-dev plate") can be selected using the following gene set selection:

1. Normalization: Each plate contains at least 1 normalization gene. These can be in duplicate, can be a positive control or negative control. Control normalization genes which can be used can be selected from, for example, ACTB, JARID2, CTCF, SMAD1, GAPDH and β-actin. In some embodiments, the plate comprises at least 2 control genes.

2. Supported cell types/lineages: Early developmental genes can be selected which are expressed after at least 2 days of the pluripotent stem cell in culture (e.g., 2D EB) and identify subsequent differentiation of the pluripotent stem cell into ectoderm, mesoderm and endoderm germ layers as well as the neural and hematopoietic lineages. In some embodiments, these genes are selected from those listed in Table 1, and can optionally include additional early developmental genes not in Table 1. In some embodiments, a subset of the early developmental genes assessed is the same as those on the NanoString nCounter Gene Expression Code Assay (available from NanoString Technologies) for the qPCR-based scorecard (ectoderm, mesoderm and endoderm germ layers as well as the neural and hematopoietic lineages). In addition, in some embodiments, the list of early developmental genes can comprise additional categories of early developmental gene sets, including but not limited to early developmental genes for a: pluripotent cell signature, epidermis, mesenchymal stem cells, bone, cartilage, fat, muscle, blood vessel, heart, lymphoid cells, myeloid cells, liver, pancreas, epithelium, motor neurons, monocytes-macrophages.

Validation: In some embodiments, one can validate a qPCR plate for assays for producing data for a lineage scorecard. Validation can be performed in three phases. During an initial validation phase, one will assess the qPCR plate to determine if it provides similar accuracy and predictive power as the NanoString nCounter Gene Expression Code Assay (available from NanoString Technologies). A second biological validation phase can be performed which will assess and confirm the predictiveness of the qPCR-based lineage scorecard for many more pluripotent stem cell lines and the propensity of the stem cell assessed to differentiate into a variety of different lineages of interest. A final assay validation can be performed which will optimize the qPCR plate for technical consistency with all earlier data. More specifically, in some embodiments, a validation phases will be conducted as follows:

1. Technical qPCR assay validation. One can directly compare the results from a NanoString-based scorecard with a qPCR-based lineage scorecard as disclosed herein, comparing the accuracy, sensitivity and robustness of each gene between the NanoString and the qPCR platform. Furthermore, one can also confirm that the qPCR-based lineage scorecard is able to predict cell-line specific differences in the efficiency of, for example, directed differentiation on a particular lineage (e.g., ectoderm, endoderm or mesoderm lineage).

2. Biological qPCR assay validation and extension of scope. The inventors have extensively validated the lineage scorecard for predicting the differentiation of pluripotent stem cells into all three germ lines by at least 2 days in culture (e.g., 2D EB). Accordingly, one can validate the lineage scorecard predictability using several different culture media, as well as RNA preparations, culture conditions etc., to quantitatively determine the efficiencies and consistency predicting the differentiation potential of pluripotent stem cells into various different lineages. Furthermore, one can validate the qPCR differentiation assays using at least about 100 or more pluripotent stem cell lines, for example, selected from but not limited to, human pluripotent cell lines, partially reprogrammed cell lines, embryonic cancer cell lines etc., in order to calibrate the lineage scorecard. Such validation can be used to optimize and redesign the qPCR-based lineage scorecard assay for large-scale production, and for example, tailor it to a particular stem cell line or lineage preference.

3. Technical validation. In some embodiments, further validation can be desired to validate software and assay handling for a qPCR differentiation assay. For example, stability of the plates, ease of reading the output from the qPCR plates and the like can be optimized. Approaches for such validation and optimization are known by persons of ordinary skill in the art.

Algorithm and Methods of Bioinformatic Analysis for Producing a Score Card for a Pluripotent Stem Cell Line.

As discussed herein, the lineage scorecard as disclosed herein relates to the expression of a plurality of early developmental genes in an differentiation expression assay (e.g., identifying the differentially regulated (e.g., unregulated and/or downregulated) early developmental genes in a stem cell line, e.g., a pluripotent stem cell line, as compared to the normal variation of expression level for the set of early developmental genes in reference pluripotent cell lines.

Many different ways to determine the extent of the different gene expression of early developmental genes as compared to the reference level of the early developmental gene expression are encompassed for use in the methods and systems as disclosed herein. Accordingly, different bioinformatic methods in order to obtain a practically useful indication of a pluripotent cell line's quality and utility are encompassed.

For example, in some embodiments, the differentiation assay need not be done in replicate. For instance, a t-test can be used to calculate t values of the differential expression of an early expression gene in the pluripotent stem cell as compared to the reference level of expression of the early developmental gene. Accordingly, in some embodiments, the $\Delta Ct$ of the early developmental gene is compared with the reference $\Delta Ct$ for the same early developmental gene in a t-test. Any method to calculate the t-value is encompassed for use in the methods and assays and systems as disclosed herein. Other statistical tests can also be used (e.g. Fisher's exact test, ANOVA). The $\Delta Ct$ for each early developmental gene expressed in the pluripotent stem cell line is determined by comparing the Ct of the early developmental gene measured in the pluripotent stem cell line with the median Ct value for a control gene (e.g., ACTB) measured in the same pluripotent stem cell line.

As disclosed in the Examples, a scorecard as disclosed herein summarizes if one or more stem cell lines of interest, e.g., a pluripotent stem cell lines, deviates from one or more reference pluripotent cell lines with respect to expression of early developmental genes. As used herein, a reference pluripotent cell line can be any number of ES cells of interest. In alternative embodiments, a reference pluripotent cell line is used as a basis of the gene expression levels of early developmental genes for normal ranges for a number of iPSC and/or ES cells, for example, at least about 10- or at least about 20 low passage ES cell lines as used herein in the Examples.

Lineage Scorecard Calculation

A lineage scorecard as disclosed herein quantifies the differentiation propensity and/or pluripotency of a stem cell line of interest relative to one or more reference pluripotent stem cell lines, e.g., high quality and/or low-passage pluripotent stem cell lines, such as the reference values for the 19 low-passage ES cell lines as used herein in the Examples. One algorithm for calculating the lineage scorecard uses a combination of moderated t-tests (Smyth, 2004) and gene set enrichment analysis performed on t-scores (Nam and Kim, 2008; Subramanian et al., 2005).

To provide a biological basis for quantifying lineage-specific differentiation propensities, the inventors created several sets of early developmental genes for each of the three germ layers (ectoderm, mesoderm, endoderm) as well as for the neural and hematopoietic lineages. In some instances, Bioconductor's Limma™ package can be used to perform moderated t-tests comparing the gene expression in the EBs obtained for the cell line of interest to the EBs obtained for the ES cell reference, and the mean t-scores were calculated across all genes that contribute to a relevant gene set. High mean t-scores (e.g., >1) indicate increased expression of the gene set's genes in the tested EBs and are considered indicative of a high differentiation propensity for the corresponding lineage. In contrast, low mean t-scores (e.g., <0) indicate decreased expression of relevant genes and are considered indicative of a low differentiation propensity for the corresponding lineage. To increase the robustness of the analysis, the mean t-scores can be averaged over all gene sets assigned to a given lineage. The lineage scorecard diagrams (FIG. 4-7) list these "means of gene-set mean t-scores" as quantitative indicators of cell-line specific differentiation propensities. The lineage scorecard analyses and validations can be performed using custom R scripts (see the world wide web at "r-project.org\").

As demonstrated herein in the Examples section, expression of early developmental genes can be used as a reliable and robust test for predicting the differentiation potential of a pluripotent stem line into a particular cell lineage.

An algorithm for calculating the lineage scorecard includes the following steps:

(i) Data Import: Import gene expression data of at least 20 early developmental genes selected from any combination of genes listed in Table 1 from (i) at least 2 day embryoid bodies (2D EBs) of the pluripotent stem cell of interest, and (ii) at least one, or at least about 5, or at least about 10 or more embryoid bodies at the same time point (e.g., 2 day embryoid bodies (2D EBs)) from reference pluripotent stem cell lines (e.g., pluripotent stem cell lines which are used as high quality reference pluripotent stem cell control cell lines). In some embodiments, the gene expression data is microarray data.

(ii) Optional step of Assay Normalization: Use positive spike-in controls to calculate an assay normalization factor and rescale the data accordingly. In some embodiments the spike-in normalization is needed for each experiment or replicate experiment.

(iii) Sample normalization: Perform variance stabilization and normalization across all experiments. In some embodiments, variance stabilization and normalization can be performed by readily available software by one of ordinary skill in the art, such as Bioconductor's VSN package).

(iv) Reference Comparison: Compare the normalized gene expression values for each early developmental gene (e.g., from any combination of genes listed in Table 1) of EBs from each pluripotent stem cell line of interest with the and normalized gene expression values for the same early developmental genes in the EBs of the reference pluripotent stem cell lines at the same time point (e.g., at least 2 days in EB; 2D EBs). In some embodiments, statistical analysis is used for the comparison, for example use of a moderated t-test for each marker gene to compare the level of the expression of the early developmental gene in pluripotent stem cell lines of interest with the reference expression levels of the same set of early developmental genes values obtained from a plurality of reference high-quality EBs. In some embodiments, a statistical package such as, for example, using Bioconductor's limma package can be used.

(v) Gene Sets: Load early developmental gene sets containing relevant genes that are characteristic and predictive of the pluripotent stem cell differentiating along a specific cellular lineage or germ layer of interest.

(vi) Enrichment analysis: For each early developmental gene set, calculate the mean t-scores of all marker genes that belong to each set.

(vii) Lineage Scorecard Report: For each pluripotent stem cell line of interest, list the mean of the t-scores for all the relevant early development gene sets (e.g., early mesoderm genes, early endoderm genes, early ectoderm genes), to provide a lineage scorecard estimate for the lineage that the pluripotent stem cell will differentiate into (See FIGS. 4, 5, 6 and 7A-7C for example).

Bioinformatics Analysis and Data Access

In addition to method-specific data normalization and the calculation of the scorecard (described above), bioinformatics analyses of the data set can be conducted as follows:

(i) Hierarchical clustering. Hierarchical clustering can be performed as disclosed herein using the gene expression levels (e.g., for each Ensembl gene by averaging over all associated probes on the microarray). Prior to hierarchical clustering, one can separately normalize each of the two datasets separately to zero mean and unit variance in order to give equal weight to both datasets.

(ii) Annotation clustering and promoter characteristics. One can identify common characteristics among the most variable genes using commonly available software packages, such as, for example, DAVID (Huang et al., 2007) and EpiGRAPH (Bock et al., 2009) with default parameters and based on Ensembl gene annotations (promoters were defined as the −5 kb to +1 kb sequence window surrounding the transcription start site).

(iii) Classification of ES vs. iPS cell lines. One can easily validate ES and iPS gene signatures using the mean expression levels of the early developmental genes in a given signature. Logistic regression can be used to select a discriminatory threshold, and the predictiveness of each signature can be evaluated by leave-one-out cross-validation. To derive new classifiers, support vector machines can be trained on, e.g., gene expression data.

(iv) Linear models of epigenetic memory. One can also generate linear models of early developmental gene expression levels. For example, as disclosed herein, two alternative linear models can be constructed for gene expression. One model can be used to regress the iPS-cell specific mean gene expression levels of each gene on the ES-cell specific mean gene expression levels. A second model regresses the iPS-cell specific mean gene expression levels of each gene on the ES-cell specific and the fibroblast-specific mean gene expression levels.

Gene expression analysis can also be performed by a number of methods. Typical example include, but are not limited to, gene expression microarrays, cDNA and RNA sequencing, imaging-based methods such as NanoString and a wide range of methods that use PCR as well as qPCR. Normalization for these methods has been widely described. In some embodiments, a gcRMA algorithm can be used for normalizing Affymetrix microarray data. In some embodiments one can use a VSN algorithm for normalizing NanoString data or the data from an array as disclosed herein.

In some embodiments, gene expression is determined on any gene level, for example, the expression of non-coding genes, microRNA genes and all other types of RNA transcripts that are normally or abnormally present in pluripotent and differentiated cells.

Once the gene expression data are normalized, genes of relevance for cell line quality and utility are identified using standard methods for detecting differential gene expression between samples and/or groups of samples. Examples include t-test and its variants, non-parametric alternatives of the t-test, and ANOVA. In some embodiments, the limma package is encompassed for use in the methods and systems as disclosed herein, which implements a moderated t statistic.

While the differentiation gene expression assay as described above focuses mostly on the effect of single genes, in some embodiments, the lineage scorecard uses the combination of data for multiple genes to predict a cell line's quality and utility. This is the most critical and bioinformatically complex step for the creation of a lineage scorecard.

In some embodiments, the information from multiple genes is currently aggregated by mean and standard deviation calculations; however, by using statistical learning methods such as support vector machines, linear and logistic regression, hierarchical models, Bayesian algorithms and the like the effect of aggregation can be reduced. Any mathematical function that takes multiple measurements of candidate gene expression into account to produce a numeric or categorical value that describes an aspect of pluripotent cell quality and utility could be considered a predictor and an element of the scorecard as disclosed herein.

Importantly, these mathematical functions will in many cases take prior biological knowledge into account. In particular, the inventors have curated a substantial number of early developmental gene sets from the literature, from public databases and from functional genomics data to inform these predictors. In one embodiment of the lineage scorecard, one can use gene expression data from either the pluripotent cell or its differentiating progeny to assign differential expression scores to each gene, and then use the resulting t-scores to perform a (parametric or non-parametric) gene set enrichment analysis for sets of early developmental genes that represent the three germ layers as well as other interesting cell types, cellular pathways and networks, as well as other functionally or otherwise defined sets of genes.

While the bioinformatic methods described above were applied in the Examples herein, they can also be applied directly to the gene expression analysis of early developmental genes of pluripotent cells, and it is also possible to induce the pluripotent cell lines to differentiate such that certain aspects of their quality and utility become more evident. This can be performed using a wide range of perturbations, from simple growth factor withdrawal and physical manipulation (as used herein for undirected embryoid body differentiation) over a wide range of chemical, peptide and protein treatments (often in combination) to the plating on dedicated surfaces and the induced expression of specific genes.

One can analyze the gene expression data of a plurality of early developmental genes using a variety of methods, for example, as disclosed in Harr et al., Nucleic acid research, 2006; 34(2): e8, "Comparison of algorithms for the analysis of Affymetrix microarray data as evaluated by co-expression of genes in known operons", and in the book entitled "Methods in microarray normalization" Edited By Phillip Stafford, Drug Discovery Series/10, published by CRC Press (which are incorporated herein in its entirety by reference). The gcRMA algorithm (GC [GC content} robust multichip analysis (RMA)) uses both the quantile normalization and medium polish summarization methods of the RMA algorithm. A stochastic model can be used to describe the observed PM and MM probe signals for each probe pair on an array. One particular models is:

$$PM_{\mu i}=0_{ni}+N_{1ni}+S_{ni}$$

$$NM_{ni}=0_{ni}+N_{2ni}$$

Where $0_{ni}$ represents the optical noise, $N_1$ and $N_2$ represents nonspecific binding, and $S_{nj}$ is a quantity proportion to the RNA expression in the sample. In addition, the model assumes O follows a normal distribution $N(\mu 0, \sigma^2_0)$ and that $\log_2 (N_{1ni})$ and $\log_2 (N_{2ni})$ follow a bivariate-normal distribution with equal variances $\sigma^2_N$ and correlation 0.7, constant across probe pairs. The means of the distribution for the nonspecific binding terms are dependent on the probe sequence. The optical noise and nonspecific binding terms are assumed to be independent.

The method by which gcRMA includes information about the probe sequence is to compare an affinity based on the sum of position-dependent base affinities. In particular, the affinity of a probe is given by:

$$A = \sum_{k=1}^{25} \sum_{b \in (A,C,G,T)} \mu b(k) 1 \beta_k = j$$

where the $\mu_b(k)$ are modeled as spline functions with 5 degrees of freedom. In practice, $\mu b(k)$ for a single microarray (e.g., U113A microarray chips) are either estimated using the observed data for all chips in an experiment or based on some hard-coded estimates from a specific NSB experiment carried out by the creators of gcRMA. This means for the $N_1$ and $N_2$ random variables in the gcRMA model are modeled using a smooth function h of the probe affinities.

The optical noise parameters $\mu_o$, $\sigma^2_o$ are estimated as follows: The variability due to optical noise is so much smaller than the variability due to the nonspecific binding and thus effectively constant. For simplicity this is set to 0. The mean values are estimated using the lowest PM or MM probe intensities on the array, with a correlation factor to avoid negatives. Next, all probe intensities are correlated by subtracting this constant $\mu_o$. To estimate $h(A_{ni})$ a Loess curve fit to a scatterplot is used relating the corrected log(MM) intensities to all the MM probe affinities. The negative residuals from this Loess plot are used to estimate $\sigma^2_N$. Finally, the background adjustment procedure for gcRMA is to compute the expected value of S given the observed PM, MM and model parameters. Note, that although gcRMA uses the medium polish summarization of RMA, the PLM summarization approach should not be used in its place if one wants to carry out quality assessment, although the expression estimates generated in this way are otherwise satisfactory.

In some embodiments, one can also use other methods for gene expression normalization, for example, the MAS5.0 algorithm (Microarray suite 5.0) or the RMA algorithm (robust multichip analysis), which are explained in detail in the "Method for microarray normalization" edited by Phillip Stafford.

Statistical Methods

Methods for statistical clustering and software for the same are discussed below. For example, one parameter used in quantifying the differential expression of early developmental genes is the fold change, which is a metric for comparing a gene's mRNA-expression level between two distinct experimental conditions. Its arithmetic definition differs between investigators. However, the greater the fold change the more likely that the differential expression of the relevant genes will be adequately separated, rendering it easier to decide which category the pluripotent stem cell falls into.

The fold change for an upregulated gene can be, for example, at least 1.4, at least 1.5, at least 1.6, at least 1.7, at least 1.8, at least 1.9 or at least 2.0 or more log-2 change. In one embodiment, in which the expression level is measured using PCR, the fold change is at least 2.0.

The fold change for a down-regulated gene can be 0.6 or less than 0.6, for example it can be 0.5 or less than 0.5, 0.4 or less than 0.4, 0.3 or less than 0.3, 0.2 or less than 0.2 or can be 0.1 or less than 0.1 log-2 change. Accordingly, a fold change of 0.1 indicates that the expression of a gene is down-regulated 10 times. A fold change of 2.0 indicates that the expression of a gene is upregulated 2 times.

For example: If the fold change of the expression of an early developmental target gene in a pluripotent stem cell is =2.0 (as compared to the normal variation of gene expression of that gene), it indicates that the gene is an "outlier" gene. Similarly, if the fold change of the expression of an early developmental target gene in a pluripotent stem cell is =0.5 (as compared to the normal variation of gene expression of that gene) of a gene=0.5, it indicates that the gene is an outlier gene. The higher number of early developmental genes in the test pluripotent stem cell line which are "outlier" genes indicates that the pluripotent stem cell line can have particular propensity to differentiate along specific lineages. For example, if the test pluripotent stem cell has at least about 10 outlier early developmental genes, the pluripotent stem cell line is identified as being an outlier pluripotent stem cell line and can have an increased efficiency or low efficiency to differentiate along a particular lineage.

Alternatively, if the fold change of the expression of an early developmental target gene in a pluripotent stem cell indicates a t-value of 0-1, the pluripotent stem cell is comparable with the pluripotent stem cell. A t-value of >1 indicates that expression of the measured early developmental gene is higher than the reference gene expression level of the same gene or group of genes in the same category, and that the pluripotent stem cell differs from a reference pluripotent stem cell line (e.g., is an outlier pluripotent stem cell). Such a pluripotent stem cell line will likely differentiate along the lineage of the category to which the early developmental gene belongs (e.g., endoderm, ectoderm or mesoderm lineages). A t-value of <0 indicates that expression of the measured early developmental gene is lower than the reference gene expression level of the same gene or group of genes in the same category, and that the pluripotent stem cell is an outlier in that it differs from a reference pluripotent stem cell line. Such a pluripotent stem cell line will likely not differentiate along the lineage of the category to which the early developmental gene belongs (e.g., endoderm, ectoderm or mesoderm lineages). The particular propensity of a pluripotent stem cell can be determined on the basis of exactly which genes or subgroups of genes are outliers.

Another parameter also used to quantify differential expression is the "p" value. It is thought that the lower the p value the more differentially expressed the gene is likely to be, indicating that the gene is an outlier gene as compared to the normal variation of gene expression in a pluripotent stem cell. p values can for example include 0.1 or less, such as 0.05 or less, in particular 0.01 or less. p values as used herein include corrected p values and/or also uncorrected p values.

Uses of the Scorecards.

In some embodiments, the methods, differentiation assays, systems, kits and lineage scorecards as disclosed herein can be used in a variety of ways clinically and in research applications. For instance, methods, differentiation assays, systems, kits and lineage scorecards as disclosed herein are useful for identifying the propensity of a pluripotent stem cell line to differentiate along a particular lineage in response to a drug, or for selecting a plurality of stem cell lines, e.g., a pluripotent stem cell lines that have the same properties to be used in a drug screen, which is useful to ensure the quality of the drug screen and ensure that any potential hits are the effect of the drug rather than due to variations in the different stem cell lines. In some embodiments, the aspects as disclosed herein are useful for identifying and selecting a stem cell line, e.g., a pluripotent stem cell line which would be suitable for therapeutic use, e.g., stem cell therapy or other regenerative medicine, to ensure that the stem cell line has the propensity to differentiate along a desired cell lineage and not differentiate along an undesired cell lineage. Similarly, aspects as disclosed herein are useful for characterizing and validating an iPSC generated from a mammal, e.g., a human, to ensure that the iPSC possesses desired qualities, and can be compared to other pluripotent stem cells.

In some embodiments, the methods, differentiation assays, systems, kits and lineage scorecards as disclosed herein can be used in clinics to determine clinical safety and utility of a particular pluripotent stem cell line.

In some embodiments, the methods, differentiation assays, systems, kits and lineage scorecards as disclosed herein can be used as a quality control to monitor the characteristics of a stem cell line, e.g., a pluripotent stem cell line, over multiple passages and/or before and after cryopreservation procedures, for example, to ensure that no significant epigenetic or functional genomic changes have occurred over time (e.g., over passages and after cryopreservation). For example, the methods, systems, kits and scorecards as disclosed herein can be used to characterize all stem cells in a stem cell bank, to catalogue each stem cell line which is placed in the bank, and to ensure that the stem cells have the same properties after thawing as they did prior to cryopreservation.

In some embodiments, the raw data (e.g., early developmental gene expression data) and/or lineage scorecard data for each stem cell line can be stored in a centralized database, where the data and/or scorecard can be used to select a pluripotent stem cell line for a particular use or utility. Accordingly, one aspect of the present invention relates to a database comprising at least one of: early developmental gene expression data, and lineage scorecard for a plurality of stem cell lines, e.g., pluripotent stem cell lines, and in some embodiments, the database comprises the early developmental gene expression data, and/or lineage scorecard for a plurality of stem cell lines, e.g., pluripotent stem cell lines in a stem cell bank.

In some embodiments, the methods, differentiation assays, systems, kits and lineage scorecards as disclosed herein can be used in research to monitor functional genomic changes as a stem cell line, e.g., a pluripotent stem cell line, differentiates along different lineages. In some embodiments, aspects as disclosed herein can be used to monitor and determine the characteristics of stem cell lines from subjects with particular diseases, e.g., one can monitor stem cell lines, e.g., pluripotent stem cell lines from subjects with genetic defects or particular genetic polymorphisms, and/or having a particular disease. For example, one can monitor and determine the functional genomic differences between an iPSC cell derived from a subject with a neurodegenerative disease, such as ALS, as compared to a normal iPSC cell from a healthy subject (or a non-ALS subject), such as a healthy sibling. Similarly, one can determine if iPS cells are comparable in functional genomics and/or differentiation propensity as compared to ES cells or other pluripotent stem cells. Additionally, the aspects as disclosed herein can fully characterize the pluripotency of a stem cell line without the need for teratoma assays and/or generation of chimera mice, therefore significantly increasing the high-throughput ability of characterizing pluripotent stem cell lines.

In some embodiments, the lineage scorecard can be included in an "all-included" kit for making and validating patient-specific iPS-cell lines. For example, in such an embodiment, the kit can comprise (i) a sample collection device, e.g., needle or tube as required for collecting patient somatic or differentiated cells, and in some embodiments, a patient consent form, (ii) reagents for reprogramming the patients' collected somatic or differentiated cell into an iPS cell, e.g., where the kit comprises any number or combination of reprogramming factors, such as virus/DNA/RNA/protein as described herein, and ES-cell media), and (iii), the differentiation assays for generating a lineage scorecard as disclosed herein, e.g., reagents for measuring the gene expression of a plurality of early developmental genes. In some embodiments, the kit can comprise one or more reference pluripotent stem cell lines, which can be used as a positive control (or a negative control, e.g., where the pluripotent stem cell line has been identified with an undesirable characteristic) as a quality control for the kit. In some embodiments, the kit can also comprise a reference lineage scorecard of one or more reference pluripotent stem cell lines to be used, for example, for comparison purposes for with the stem cell line being tested, e.g., a patient iPS cell line being assessed. In some embodiments, the "all-included" kit can be used for utility prediction of the patient iPS cell line based on the results from the quality control (e.g., as determined by the bioinformatic determination as disclosed herein). In some embodiments, an "all-included" kit can also additionally comprise the materials, reagents and protocols for directed differentiation of the newly generated patient iPS cell line into a particular cell type of interest (e.g., cardiomyocytes, beta cells, hepatocytes, hair follicle stem cells, cartilage, pancreatic cells (including beta-cells), hematopoietic cells, and the like).

In some embodiments, the methods, differentiation assays, systems, kits and lineage scorecards as disclosed herein can be used to provide a service, such as a "cell-to-quality assured pluripotent stem cell line" service, which can be carried out, for example, directly in a clinic, or in a clinical diagnostics lab, or as a mail-in service carried out by a dedicated facility. For example, such a service would operate in which an investigator, or a patient sends a pluripotent stem cell or, in some embodiments, somatic cells (e.g., differentiated cells) into the service provider, whereby if somatic cells are sent, the service provider generates iPS cell lines from the somatic cells using commonly known methods as disclosed herein. The service provider performs methods, differentiation assays, systems, kits and lineage scorecards as disclosed herein on the investigator-provided, or generated pluripotent iPS cell lines, for example, the service provider will perform (i) the differentiation assay (e.g., measure the gene expression of a plurality of early developmental genes), and subsequently perform the analysis to generate a lineage scorecard for each individual iPS cell analyzed. The service provider can also optionally suggest the suitability of one or more selected iPS cell lines for a particular use, e.g., the service provider can suggest "iPS cell line 1" which was identified to have a high efficiency of differentiating along endoderm differentiation pathways would be suitable for differentiation into pancreatic cells, or similarly the service provider can suggest "iPS cell line 2" which was identified to have a high efficiency of differentiating along hepatic lineages would be suitable for differentiation into liver cells for use in liver cell regenerative medicine. Similarly, the service provider can suggest "iPS cell line 6" which was identified to have decreased pluripotent stem cell genes, can not be suitable for therapeutic uses in regenerative medicine due to a risk of potential cancer formation. In some embodiments, the service provider does not make a recommendation, but rather provide a report of the scorecard for each iPS cell line generated and analyzed by the service provider. In some embodiments, the service provider returns the iPS cell lines to the investigator, or patient with a copy of the report scorecard.

In some embodiments, the methods, differentiation assays, systems, kits and lineage scorecards as disclosed herein can be used in creating a database, where such a database would be useful in organizing and cataloguing a pluripotent stem cell repository, e.g., a central repository (e.g., a tissue and/or cell bank) containing a large number of quality-controlled and utility-predicted pluripotent cell lines, such that one can use a database comprising the data of each scorecard for each pluripotent stem cell line in the bank to specifically select a particular pluripotent stem cell line for the investigators' intended use. For example, a user of the database can click a "suggest best cell line for my application" button on the website linked to the database, and obtain information and the identity of a number useful cell lines for the investigator's particular use. In some embodiments, the use of such a database can be easily extended such that a user can upload the data from the array or assays as disclosed herein (e.g., gene expression data) for a particular pluripotent stem cell type of interest. This data can be run through the scorecard algorithm as disclosed herein and the results compared with the database scorecard results for the pluripotent stem cell bank. In a simple analogy, the database could function similar to Google's "search for similar sites", whereby the database could be used as an efficient way to select useful cell lines for novel and/or mixed tissue types, or to identify pluripotent stem cell lines in a cell bank that can have potential to differentiate into a desired differentiated stem cell line.

In some embodiments, the methods, differentiation assays, systems, kits and lineage scorecards as disclosed herein can be used for identification and selection of a desired stem cell line, e.g., a pluripotent stem cell line for mass production, for example use of the methods, assays and scorecards as disclosed herein to identify and characterize and validate the quality of stem cell lines that grow well and/or efficiently in large quantities, e.g., large batch cultures or in bioreactors, and selection of stem cell lines that can be differentiated efficiently in bulk cultures into a specific cell type.

In another embodiment, methods, differentiation assays, systems, kits and lineage scorecards as disclosed herein can be used for selection of a stem cell line based on properties of pluripotent robustness. For example, the methods, differentiation assays, systems, kits and lineage scorecards as disclosed herein can be used to identify a stem cell line, e.g., a pluripotent stem cell line which is easy to culture in vitro (e.g., require little attention, and/or do not readily spontaneously differentiate, and/or maintain the pluripotency properties). For example, in some embodiments, a stem cell line can be assessed using the methods, assays and lineage scorecards prior to culturing, and then at different time points during and/or after culturing, and under different culture conditions and/or media conditions to identify one or more stem cell lines which maintain their initial qualities in short- and/or long-term culture conditions.

In another embodiment, the methods, differentiation assays, systems, kits and lineage scorecards as disclosed herein can be used for selection of a stem cell line, e.g., a pluripotent stem cell line for drug responsiveness, for example, a stem cell line can be assessed using the methods, assays and scorecards as disclosed herein prior to, during, and after contacting with a drug or other agent or stimulus (e.g., electric stimuli for cardiac pluripotent progenitors) to generate a drug metabolism and/or pharmacogenomics signature of the stem cell line. This can be used to identify stem cell lines which can be particularly useful for drug screening and drug discovery, including, for example drug toxicity assays.

In another embodiment, the methods, differentiation assays, systems, kits and lineage scorecards as disclosed herein can be used for selection of a stem cell line, e.g., a pluripotent stem cell line, based on its safety profile. For example, a stem cell line can be assessed using the methods, differentiation assays, systems, kits and lineage scorecards as disclosed herein to identify its likelihood the stem cell will differentiate into a particular cell type, or likelihood to dedifferentiate, which is very useful in validating the safety of a stem cell line or its differentiated progeny in clinical applications, such as cell replacement therapy and regenerative medicine.

In another embodiment, the methods, differentiation assays, systems, kits and lineage scorecards as disclosed herein can be used for selection of a stem cell line, e.g., a pluripotent stem cell line for efficacy. For example, one can use a lineage scorecard prediction of a particular pluripotent stem cell line to predict whether, and/or how well (e.g., how efficiently) differentiated cells derived from the stem cell line will continue to differentiate along a particular desired cell lineage, and/or if they will proliferate once implanted into a subject, e.g., a human patient or in an animal model (e.g., a rat or mouse disease model etc.). More generally, in some embodiments, a lineage scorecard can be used to predict not only the behavior of a stem cell line, but also that of differentiated cells that are directly or indirectly derived from the stem cell line.

In another embodiment, the methods, differentiation assays, systems, kits and lineage scorecards as disclosed herein can be used for selection of a stem cell line, e.g., a pluripotent stem cell line which has the same or very similar characteristics of a pluripotent stem cell in vivo (e.g., to select pluripotent stem cell which are a truthful representation of the cell in an in vivo environment). For example, a stem cell line can be assessed using the methods, differentiation assays, systems, kits and lineage scorecards as disclosed herein to identify a stem cell line suitable for disease modeling, as it is important to use stem cell lines that closely resemble their corresponding cells in vivo. Accordingly, one of ordinary skill in the art can use the lineage scorecard as disclosed herein to predict which stem cell line, e.g., which pluripotent cell line best resembles their corresponding cells in vivo, e.g. by comparing the properties (listed on the scorecard) of the stem cell line with corresponding cells harvested from a subject (e.g. an animal model, or disease model such as a rodent disease model), to minimize deviations from the stem cell line as compared to how the cell behaves in vivo.

In another embodiment, the methods, differentiation assays, systems, kits and lineage scorecards as disclosed herein can be used for selection and/or quality control, and/or validation of a stem cell line in different or new states of pluripotency or multipotency, for example to provide information regarding which stem cell lines are useful for differentiating and making cell types in vitro but do not fall under the usual definition of human ES cell lines (e.g., human ground-state ES cell and partially reprogrammed cell lines, e.g., partially induced pluripotent stem (piPS) cells, which are capable of being reprogrammed further to a pluripotent stem cell).

It has been shown that continued in vitro culture and passaging improves the quality of iPS cell lines (see Polo et al., Nat Biotechnol. 2010 August; 28(8):848-55, and Nat Rev Mol Cell Biol. 2010 September; 11(9):601, and Nat Rev Genet. 2010 September; 11(9):593). On the other hand, continued passaging is expensive. Accordingly, in some embodiments, the methods, differentiation assays, systems, kits and lineage scorecards as disclosed herein can be used for measuring how much passaging is sufficient for improving the quality of the stem cell line, e.g., the pluripotent stem cell line.

In further embodiments, the methods, differentiation assays, systems, kits and lineage scorecards as disclosed herein can be used in a variety of different research and clinical uses to characterize, monitor and validate stem cell lines, e.g., pluripotent stem cell lines. For example, typical application includes in areas such as, but not limited to, (i) labs and/or companies interested in disease mechanisms (e.g., using the kits or services as disclosed herein to reduce the complexity of generating iPS cell lines, as well as differentiated cells for disease modeling and small-scale drug screening, (ii) labs and/or companies trying to identify small molecules and/or biologicals for a given disease target (e.g., using the kits and/or services as disclose herein to enable the production of large numbers of highly standardized cells for drug screening), (iii) clinical and pre-clinical research groups for quality control and validating stem cell lines where they are interested in producing cells for implantation into humans or animals (e.g., using a kit and/or service as disclosed herein to permits quality control at a level of accuracy that will be sufficient for regulatory approval, e.g., FDA approval), (iv) tissue banks that desire to give their customers information, including advice and data about the performance, quality and utility of the stem cell lines, e.g., pluripotent stem cell lines on offer (e.g., using a kit and/or service as disclosed herein to provide unbiased assessment of the quality and/or utility of a large number of pluripotent cell lines, in an inexpensive high throughput manner,—it is contemplated that the assays can ultimately be performed on 1,000-100,000s of pluripotent stem cell lines to cover the whole population of cell lines stored in the cell bank), (v) private consumers who desire to generate, and optionally, bank at least one or more stem cell lines, e.g., pluripotent stem cell lines, e.g., iPS cell lines (or piPS cell lines) generated from their somatic differentiated cells, either for themselves and/or their children or other offspring, for example, as a type of health insurance policy for future regenerative medicine purposes.

Stem Cells for Analysis of Early Developmental Gene Expression and for Generating a Reference Lineage Scorecard.

As disclosed herein, the gene expression of a set of early developmental genes can be used to validate and monitor any stem cell line, from any species, e.g. a mammalian species, such as a human. In some embodiments, the present invention specifically contemplates using the arrays, assays and methods as disclosed herein to determine if a stem cell is pluripotent. Any type of stem cell can be assessed. For simplicity, when referring to analysis of a pluripotent stem cell herein, this encompasses analysis of both pluripotent and non-pluripotent stem cells.

In some embodiments, the stem cell is a pluripotent stem cell. Generally, a pluripotent stem cell to be analyzed according to the methods described herein can be obtained or derived from any available source. Accordingly, a pluripotent cell can be obtained or derived from a vertebrate or invertebrate. In some embodiments, the pluripotent stem cell is mammalian pluripotent stem cell. In all aspects as disclosed herein, pluripotent stem cells for use in the methods, assays and to generate scorecards or to compare with an existing scorecard as disclosed herein can be any pluripotent stem cell.

In some embodiments, the pluripotent stem cell is a primate or rodent pluripotent stem cell. In some embodiments, the pluripotent stem cell is selected from the group consisting of chimpanzee, cynomologous monkey, spider monkey, macaques (e.g. Rhesus monkey), mouse, rat, woodchuck, ferret, rabbit, hamster, cow, horse, pig, deer, bison, buffalo, feline (e.g., domestic cat), canine (e.g. dog, fox and wolf), avian (e.g. chicken, emu, and ostrich), and fish (e.g., trout, catfish and salmon) pluripotent stem cell.

In some embodiments, the pluripotent stem cell is a human pluripotent stem cell. In some embodiments, the pluripotent stem cell is a human stem cell line known in the art. In some embodiments, the pluripotent stem cell is an induced pluripotent stem (iPS) cell, or a stably reprogrammed cell which is an intermediate pluripotent stem cell and can be further reprogrammed into an iPS cell, e.g., partial induced pluripotent stem cells (also referred to as "piPS cells"). In some embodiments, the pluripotent stem cell, iPSC or piPSC is a genetically modified pluripotent stem cell.

In some embodiments, the pluripotent state of a pluripotent stem cell used in the present invention can be confirmed by various methods. For example, the pluripotent stem cells can be tested for the presence or absence of characteristic ES cell markers. In the case of human ES cells, examples of such markers include SSEA-4, SSEA-3, TRA-1-60, TRA-1-81 and OCT 4, and are known in the art.

While the methods of the present invention allow the pluripotency (or lack thereof) to be assessed by measuring the level of expression of a subset of early pluripotent genes listed in Table 1 of a stem cell which is at least 2 days in culture, if necessary, the pluripotency of a stem cell line can also be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types. Methods for producing chimeric animals are well known in the art and are described in U.S. Pat. No. 6,642,433, which is incorporated by reference herein.

Yet another method of confirming pluripotency is to observe ES cell differentiation into embryoid bodies and other differentiated cell types when cultured under conditions that favor differentiation (e.g., removal of fibroblast feeder layers). This method has been utilized and it has been confirmed that the subject pluripotent cells give rise to embryoid bodies and different differentiated cell types in tissue culture.

In this regard, it is known that some mouse embryonic stem (ES) cells have a propensity of differentiating into some cell types at a greater efficiency as compared to other cell types. Similarly, human pluripotent (ES) cells can possess selective differentiation capacity. Accordingly, the present invention can be used to identify and select a pluripotent stem cell with desired characteristics and differentiation propensity for the desired use of the pluripotent stem cell. For example, where the pluripotent cell line has been screened according to the methods of the invention, a pluripotent stem cell can be selected due to its increased efficiency of differentiating along a particular cell line, and can be induced to differentiate to obtain the desired cell types according to known methods. For example, a human pluripotent stem cell, e.g., a ES cell or iPS cell can be induced to differentiate into hematopoietic stem cells, muscle cells, cardiac muscle cells, liver cells, islet cells, retinal cells, cartilage cells, epithelial cells, urinary tract cells, etc., by culturing such cells in differentiation medium and under conditions which provide for cell differentiation, according to methods known to persons of ordinary skill in the art. Medium and methods which result in the differentiation of ES cells are known in the art as are suitable culturing conditions.

One can use any method for reprogramming a somatic cell to an iPS cell or an piPS cell, for example, as disclosed in International patent applications; WO2007/069666; WO2008/118820; WO2008/124133; WO2008/151058; WO2009/006997; and U.S. Patent Applications US2010/0062533; US2009/0227032; US2009/0068742; US2009/0047263; US2010/0015705; US2009/0081784; US2008/0233610; U.S. Pat. No. 7,615,374; U.S. patent application Ser. No. 12/595,041, EP2145000, CA2683056, AU8236629, 12/602,184, EP2164951, CA2688539, US2010/0105100; US2009/0324559, US2009/0304646, US2009/0299763, US2009/0191159, the contents of which are incorporated herein in their entirety by reference. In some embodiments, an iPS cell for use in the methods as described herein can be produced by any method known in the art for reprogramming a cell, for example virally-induced or chemically induced generation of reprogrammed cells, as disclosed in EP1970446, US2009/0047263, US2009/0068742, and 2009/0227032, which are incorporated herein in their entirety by reference. In some embodiments, iPS cells can be reprogrammed using modified RNA (mod-RNA) as disclosed in US2012/0046346, which is incorporated herein in its entirety by reference.

In some embodiments, an iPS cell for use in the methods, differentiation assays and to generate lineage scorecards or to compare with an existing lineage scorecard as disclosed herein can be produced from the incomplete reprogramming of a somatic cell by chemical reprogramming, such as by the methods as disclosed in WO2010/033906, the content of which is incorporated herein in its entirety by reference. In alternative embodiments, the stable reprogrammed cells disclosed herein can be produced from the incomplete reprogramming of a somatic cell by non-viral means, such as by the methods as disclosed in WO2010/048567 the contents of which is incorporated herein in its entirety by reference.

Other stem cells for use in the methods as disclosed herein can be any stem cell known to persons of ordinary skill in the art. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including methods for isolating and culturing them, can be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96(25): 14482 86, 1999; Zuk et al., Tissue Engineering, 7:211 228, 2001 ("Zuk et al."); particularly Chapters 33 41; and U.S. Pat. Nos. 5,559,022, 5,672,346 and 5,827,735. Descriptions of stromal cells, including methods for isolating them, can be found in, among other places, Prockop, Science, 276:71 74, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963,489.

Additional pluripotent stem cells for use in the the methods, differentiation assays and to generate lineage scorecards or to compare with an existing lineage scorecard as disclosed herein can be any cells derived from any kind of tissue (for example embryonic tissue such as fetal or pre-fetal tissue, or adult tissue), which stem cells have the characteristic of being capable under appropriate conditions of producing progeny of different cell types that are derivatives of all of the 3 germinal layers (endoderm, mesoderm, and ectoderm). These cell types can be provided in the form of an established cell line, or they can be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). In some embodiments, an embryo has not been destroyed in obtaining a pluripotent stem cell for use in the methods, assays, systems and to generate scorecards or to compare with an existing scorecard as disclosed herein.

In another embodiment, the stem cells, e.g., adult or embryonic stem cells can be isolated from tissue including solid tissues (the exception to solid tissue is whole blood, including blood, plasma and bone marrow) which were previously unidentified in the literature as sources of stem cells. In some embodiments, the tissue is heart or cardiac tissue. In other embodiments, the tissue is for example but not limited to, umbilical cord blood, placenta, bone marrow, or chondral villi.

Stem cells of interest for use in the methods, assays, systems and to generate scorecards or to compare with an existing scorecard as disclosed herein also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2): 205-16; etc.).

Therapeutic Uses

Various disease and disorders have been suggested as potential targets for stem cell therapy, such as cancer, diabetes, cardiac failure, muscle damage, Celiac Disease, neurological disorder, neurodegenerative disorder, and lysosomal storage diseases, as well as, any of the following diseases, ALS, Parkinson, monogenetic diseases and Mendelian diseases, ageing, general wear and tear of the human body, rheumatic arthritis and other inflammatory diseases, birth defects, etc. Accordingly, the assays, methods, systems and kits of the invention can be used to select a stem cell line, e.g., a pluripotent stem cell line, for administering to a subject for treatment or for development of fully or partially differentiated cells for transplantation.

Therefore, in one aspect the invention provides for a method of treatment, prevention, or amelioration of disease or disorder in a subject, the method comprising administering to the subject a pluripotent stem cell, or fully or partially differentiated cells derived from pluripotent cells, and differentiated cells obtained by other methods that involve reprogramming (e.g. transdifferentiation), wherein the stem cell is selected by methods and assays that measure the gene expression of a set of early developmental genes as disclosed herein. Without limitation, a pluripotent stem cell can be treated for differentiation along a specific lineage before administration to a subject.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but can not be a complete cure for the disease. As used herein, the term "treatment" includes prophylaxis. Alternatively, treatment is "effective" if the progression of a disease is reduced or halted. In some embodiments, the term "treatment" can also mean prolonging survival as compared to expected survival if not receiving treatment. Those in need of treatment include those already diagnosed with a disease or condition, as well as those likely to develop a disease or condition due to genetic susceptibility or other factors which contribute to the disease or condition, such as a non-limiting example, weight, diet and health of a subject are factors which can contribute to a subject likely to develop diabetes mellitus. Those in need of treatment also include subjects in need of medical or surgical attention, care, or management. The subject is usually ill or injured, or at an increased risk of becoming ill relative to an average member of the population and in need of such attention, care, or management.

Routes of administration suitable for the methods of the invention include both local and systemic administration or transplantation. Generally, local administration results in of the cells being delivered to a specific location as compared to the entire body of the subject, whereas, systemic administration results in delivery of the cells to essentially the entire body of the subject. Exemplary modes of administration include, but are not limited to, injection, infusion, instillation and inhalation. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

One preferred method of administration is transplantation of such a pluripotent cell, or differentiated progeny derived from the pluripotent stem cell, in a subject. The term "transplantation" includes, e.g., autotransplantation (removal and transfer of cell(s) from one location on a patient to the same or another location on the same patient), allotransplantation (transplantation between members of the same species), and xenotransplantation (transplantations between members of different species). The ordinary skilled artisan is well aware of methods for implanting or transplantation of cells for treatment of various disease, which are amenable to the present invention.

As used herein, the terms "administering," "introducing" and "transplanting" are used interchangeably in the context of the placement of reprogrammed cells as disclosed herein, or their differentiated progeny into a subject, by a method or route which results in at least partial localization of the reprogrammed cells, or their differentiated progeny at a desired site. The reprogrammed cells, or their differentiated progeny can be administered directly to a tissue of interest, or alternatively be administered by any appropriate route which results in delivery to a desired location in the subject where at least a portion of the reprogrammed cells or their progeny or components of the cells remain viable. The period of viability of the reprogrammed cells after administration to a subject can be as short as a few hours, e. g. twenty-four hours, to a few days, to as long as several years.

In the context of administering a pluripotent stem cell, the term "administering" also include transplantation of such a cell in a subject. As used herein, the term "transplantation" refers to the process of implanting or transferring at least one cell to a subject. The term "transplantation" includes, e.g., autotransplantation (removal and transfer of cell(s) from one location on a patient to the same or another location on the same patient), allotransplantation (transplantation between members of the same species), and xenotransplantation (transplantations between members of different species).

For administration to a subject, the pluripotent stem cells can be provided in pharmaceutically acceptable compositions. These pharmaceutically acceptable compositions comprise one or more of the pluripotent cells, formulated together with one or more pharmaceutically acceptable carriers (additives) and/or diluents.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), involved in carrying or transporting the stem cell from one organ, or portion of the body, to another organ, or portion of the body. Each carrier must be "acceptable" in the sense of being compatible with the other ingredients of the formulation and not injurious to the patient. The terms such as "excipient", "carrier", "pharmaceutically acceptable carrier" or the like are used interchangeably herein.

The pluripotent stem cell, or its differentiated progeny, can be administrated to a subject in combination with a pharmaceutically active agent. As used herein, the term "pharmaceutically active agent" refers to an agent which, when released in vivo, possesses the desired biological activity, for example, therapeutic, diagnostic and/or prophylactic properties in vivo. It is understood that the term includes stabilized and/or extended release-formulated pharmaceutically active agents. Exemplary pharmaceutically active agents include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

As used herein, a "subject" means a human or animal. A subject can be one who has been previously diagnosed with or identified as suffering from or having a disorder characterized with a disease for which a stem cell based therapy would be useful. A subject can be one who is not currently being treated with a stem cell based therapy.

In some embodiments of the aspects described herein, the method further comprising selecting a subject with a disease that would benefit from a stem cell based therapy.

As used herein, the term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuro-inflammatory and demyelinating states or diseases such as leukoencephalopathies, and leukodystrophies. Exemplary, neurodegenerative disorders include, but are not limited to, AIDS dementia complex, Adrenoleukodystrophy, Alexander disease, Alpers' disease, Alzheimer's disease, Amyotrophic lateral sclerosis, Ataxia telangiectasia, Batten disease, Bovine spongiform encephalopathy, Canavan disease, Corticobasal degeneration, Creutzfeldt-Jakob disease, Dementia with Lewy bodies, Fatal familial insomnia, Frontotemporal lobar degeneration, Huntington's disease, Infantile Refsum disease, Kennedy's disease, Krabbe disease, Lyme disease, Machado-Joseph disease, Multiple sclerosis, Multiple system atrophy, Neuroacanthocytosis, Niemann-Pick disease, Parkinson's disease, Pick's disease, Primary lateral sclerosis, Progressive supranuclear palsy, Refsum disease, Sandhoff disease, Diffuse myeloclastic sclerosis, Spinocerebellar ataxia, Subacute combined degeneration of spinal cord, Tabes dorsalis, Tay-Sachs disease, Toxic encephalopathy, and Transmissible spongiform encephalopathy.

Drug Screening and Other Uses

The characterization of the differentiation potential of a plurality of stem cell lines, e.g., pluripotent stem cell lines, by measuring the gene expression of a set of early developmental genes as disclosed herein can be used to develop in vitro assays based on such characterized pluripotent stem cell lines. Existing assays for drug screening/testing and toxicology studies have several shortcomings because they can include pluripotent stem cells which are poorly characterized and/or pluripotent stem cell lines which are abnormal or deviate from a typical pluripotent stem cell line in terms of its differentiation capacity and potential. Accordingly, by measuring the gene expression of a set of early developmental genes as disclosed herein, one can identify and choose and/or validate a stem cell line suitable for use in the assay that can differentiate along a lineage which is phenotypic of a disease. In addition to, or alternatively, measuring the gene expression of a set of early developmental genes in a pluripotent stem cell line as disclosed herein can be used to identify and/or validate the stem cell line as one that can differentiate into an organ, and/or tissue lineage, or a part thereof. Such identified stem cells then can be chosen for use in screening assays to screen a test compound and or in disease modeling assays.

Furthermore, the flurry of new information now available on the molecular and cellular level related to human diseases makes it crucial to develop and test hypotheses about pathogenetic interrelations. The experimental access to specific cell types from all developmental stages and even from blastocysts deemed to harbor pathology based on pre-implantation genetic diagnosis can be useful in modeling and understanding aspects of human disease. Thus, such cell lines would also be valuable for the testing of drugs.

Accordingly, the present invention provides methods and assays for screening a test compound for biological activity, the method comprising: (a) obtaining a stem cell, e.g., a pluripotent stem cell, wherein the stem cell is identified and validated for differentiation along a specific lineage; (b) optionally causing or permitting the stem cell to differentiate to the desired specific lineage; (c) contacting the stem cell with a test compound; and (d) determining any effect of the compound on the level of gene expression of a set of early developmental genes in the stem cell as compared to in the absence of the compound. The effect on the stem cell can be one that is observable directly or indirectly by use of reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell morphology, or a combination thereof. In some instances, a biological activity can refer to the ability of a test compound to produce a toxic effect in a biological sample.

As discussed above, the specific lineage can be a lineage which is phenotypic and/or genotypic of a disease. Alternatively, the specific lineage can be lineage which is phenotypic and/or genotypic of an organ and/or tissue or a part thereof.

As used herein, the term "test compound" refers to the collection of compounds that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and commercially available. A comprehensive list of compound libraries can be found at http://www.broad.harvard.edu/chembio/platform/screening/compound_libraries/index.htm. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Without limitation, the compounds can be tested at any concentration that can exert an effect on the cells relative to a control over an appropriate time period. In some embodiments, compounds are tested at concentration in the range of about 0.01 nM to about 1000 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a pharmaceutical company can perform as many as 100,000 assays per day in parallel.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Uses to Optimize Differentiating Media and Differentiation Factors.

In some embodiments, the characterization of the differentiation potential of a plurality of stem cell lines, e.g., pluripotent stem cell lines, by measuring the gene expression of a set of early developmental genes as disclosed herein can be used to develop in vitro assays based on such characterized stem cell lines. Accordingly, by measuring the gene expression of a set of early developmental genes as disclosed herein, one can identify and choose and/or validate and/or optimize a differentiation media and/or or differentiation factors which increase the efficiency of a stem cell line to differentiate along a particular cell-type lineage. By way of an exemplary example only, in some embodiments, the arrays, assays and methods as disclosed herein can be used to confirm that mesoderm early developmental markers as disclosed herein are being expressed in a stem cell line cultured in a mesoderm induction medium. Such identified media and/or differentiation factors then can be chosen for use in differentiation protocols to differentiate stem cell line along a particular lineage. Alternatively, in some embodiments, the arrays, assays and methods as disclosed herein can be used to confirm that a stem cell media, e.g., a pluripotent stem cell media maintains a stem cell in a pluripotent state and does not induce the cell line to differentiate along a particular lineage, for example, by measuring a set of early gene expression markers in the stem cell line cultured in the test pluripotent media as disclosed herein and checking that the levels of the measured early developmental markers do not differ by a statistically significant amount as compared to a reference level for the measured early developmental markers, or the mean level of measured early developmental markers in a plurality of reference pluripotent stem cell lines.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments.

Any variations in the exemplified methods which occur to the skilled artisan are intended to fall within the scope of the present invention.

The developmental potential of human pluripotent stem cells suggests that they can produce disease-relevant cell types for biomedical research as well as cells for transplantation to address a disease. However, substantial variation has been reported among pluripotent cell lines, which could affect their utility and clinical safety. Such cell-line specific differences must be better understood before one can confidently use embryonic stem (ES) or induced pluripotent stem (iPS) cells in translational research. Towards this goal, the inventors have established genome-wide reference maps of developmental gene expression for 20 previously derived human ES lines and 12 human iPS cell lines, and have measured the in vitro differentiation propensity of these cell lines. This resource enabled the inventors to assess the epigenetic and transcriptional similarity of ES and iPS cells and to predict the differentiation efficiency of individual cell lines. The combination of assays yields a scorecard for quick and comprehensive characterization of pluripotent cell lines.

Pluripotent cell lines are valuable tools for disease modeling, drug screening and regenerative medicine. However, current validation assays of the differentiation potential of human pluripotent cell lines are cumbersome and not always accurate, take a long time and cannot be performed before about 7 days of embroyonic age, which tends to slow down research and has led to some confusion about the potency of human iPS cells. To systematically address these issues, the inventors have established a set of early differentiaon marker genes to identify the differentiation potential of a stem cell population at a very early stage of development. Such a quantitative differentiation assay assesses the differentiation propensities of these cell lines as early as 2-days in EB forming conditions (e.g., EB day 2). Using this dataset, the inventors quantified the deviation of each ES or iPS cell line from the ES-cell reference, giving rise to a scorecard of cell line quality and utility, particularly with respect to the stem cell line's differentiation capacity and the lineage the cell line is most applicable for. The inventors validated this scorecard by showing that it accurately predicts cell-line specific differences in the expression of early developmental markers for endoderm, ectoderm and mesoderm cell lineages, as well as decrease in pluripotent stem cell markers at a developmental stage as early as 2 days. In summary, the inventors have developed methods, systems and kits for a rapid, cost effective, high-throughput characterization of the differentiation potential of human pluripotent cell lines using gene expression of early developmental markers on a stem cell line as early as developmental stage of 2 days.

Methods

ES and iPSC Cell Lines and Culture Conditions

A total of 20 human ES cell lines, 13 human iPS cell lines and 6 primary fibroblast cell lines were included in the current study. The ES cell lines were obtained from the Human Embryonic Stem Cell Facility of the Harvard Stem Cell Institute (17 ES cell lines) and from WiCell (3 ES cell lines). The iPS cell lines were derived by retroviral transduction of OCT4, SOX2 and KLF4 in dermal fibroblasts. The fibroblasts were derived by skin puncture from the forearm of each respective donor and grown as previously described (Dimos et al., 2009). All pluripotent cell lines have been characterized by conventional methods (Chen et al., 2009; Cowan et al., 2004, Boulting et al., submitted), confirming that they qualify as pluripotent according to established standards (Maherali and Hochedlinger, 2008). The pluripotent stem cells were grown in human ES media consisting of KO-DMEM (Invitrogen), 10% KOSR (Invitrogen), 10% plasmanate (Talecris), 1% glutamax or L-glutamin, non-essential amino acids, penicillin/streptomycin, 0.1% 2-mercaptoethanol and 10-20 ng/ml bFGF. Cultures were grown on a monolayer of irradiated CF1-MEFs (GlobalStem) and passaged using trypsin (0.05%) or dispase (Invitrogen). Before collection of DNA and RNA for analysis, ES and iPS cells were either isolated by trypsin (0.05%) or dispase treatment, or plated on matrigel (BD Biosciences) for one passage and fed with human ES media conditioned in CF1-MEFs for 24 h.

Differentiation Protocols

A total of five ES/iPS cell differentiation protocols were used in the current study:

(i) Non-directed EB differentiation. Undifferentiated cells were harvested using dispase or trypsin and plated in suspension in low-adherence plates in the presence of human ES cell culture media without bFGF and plasmanate. Cell aggregates (EBs) were allowed to grow for a total of 16 days, refreshing media every 48 h.

(ii) Monocyte/macrophage differentiation. Undifferentiated cells were treated with multiple recombinant proteins following a published protocol for hematopoietic differentiation (Grigoriadis et al., 2010). Briefly, feeder depleted pluripotent cells were grown as small aggregates in suspension in 6-well low attachment plates (Corning) in StemPro-34 medium (Invitrogen) containing penicillin/streptomycin, glutamine (2 mM), monothioglycerol (0.0004M), ascorbic acid (50 µg/ml) (Sigma-Aldrich) and BMP4 (10 ng/ml) (R&D Systems) for 24 h. To induce primitive streak/mesoderm formation, EBs were washed and cultured further in the StemPro-34 differentiation medium, supplemented with human recombinant bFGF (5 ng/ml) (Millipore) for another 3 days. At day 4, EBs were harvested again and cultured in the differentiation medium described above, additionally containing hVEGF (10 ng/ml) (PeproTech), hbFGF (1 ng/ml), hIL-6 (10 ng/ml) (PeproTech), hIL-3 (40 ng/mL) (PeproTech), hIL-11 (5 ng/mL) (PeproTech), and human recombinant SCF (100 ng/mL) (PeproTech) for another 4 days to induce hematopoietic specification. From day 8 onwards, cells were further cultured in StemPro-34 medium, containing hVEGF (10 ng/ml), human erythropoietin (4 U/ml) (Cell Sciences), human thrombopoietin (50 ng/ml) (Cell Sciences), and human stem cell factor, hIL-6, hIL-11, and hIL-3 to promote hematopoietic cell maturation and expansion.

(iii) Mesoderm differentiation. Undifferentiated cells were treated with Activin A and BMP4 according to a published protocol that fosters mesoderm differentiation (Laflamme et al., 2007). Briefly, cells were harvested by incubation with collagenase IV (Invitrogen) and plated onto a Matrigel-coated cell culture dish. To induce mesoderm differentiation, cells were cultured in RPMI-B27 medium (Invitrogen) supplemented with human recombinant Activin A (100 ng/ml) (R&D Systems) for 24 h. Human recombinant BMP4 (10 ng/ml) was added to the medium for four days, after which cells were fed further with supplement-free RBMI-B27 medium.

(iv) Ectoderm differentiation. Undifferentiated cells were harvested by incubation with collagenase IV (Invitrogen) and plated onto a Matrigel-coated cell culture dish. Cells were grown in KO-DMEM (Invitrogen) medium, containing knockout serum replacement (Invitrogen), supplemented with Noggin (500 ng/ml) (R&D Systems) and SB431542 (10 µM) (Tocris).

(v) Motor neuron differentiation. Undifferentiated cells were differentiated following a published protocol (DiGiorgio et al., 2008), as described in more detail by Boulting et al. (submitted).

Gene Expression Profiling

Gene Expression of the set of genes in Table 1 was performed by RT-PCR analysis. To identify gene in which a given cell line deviates from the reference of all human ES cell lines sample, the inventors performed a moderated t-test as implemented in the limma package (Smyth, 2005), comparing the cell line of interest to the reference of all human ES cell lines included in this study (but excluding the cell line that is being tested). All statistical analyses were performed using the R statistics package (world-wide web at: r-project.org/) and the source code is available on request from the authors.

Quantitative RT-PCR Analysis

Total RNA was isolated using RNeasy kit (Qiagen) according to manufacturer's recommendation followed by cDNA synthesis using standard protocols. Briefly, cDNA was synthesized using Superscript II Reverse Transcriptase (Invitrogen) and Random Hexamers (Invitrogen) with 500 ng of total RNA input. SYBR Green PCR master mix (Applied Biosystems) was used for qPCR analysis, which was done on a StepOnePlus real time PCR system (Applied Biosystems). PCR conditions were as follow: 94° C. initial denaturation for 5 min, 94° C. 15 s, 60° C. 15 s, 72° C. 30 s for 40 cycles, and 72° C. for 10 min. Relative quantification was calculated using the comparative threshold cycle (ΔΔCt) method.

Quantitative Embryoid Body Assay and Lineage Scorecard

For embryoid body differentiation, ES/iPS cells were treated with dispase or trypsin and plated in suspension in low-adherence plates in the presence of human ES culture media without bFGF and plasmanate. Cell aggregates or embryoid bodies were allowed to grow for at least 2 days, refreshing media every 48 h. After 2 days, cells were lysed and total RNA was extracted using Trizol (Invitrogen), followed by column clean-up using RNeasy kit (Qiagen). Subsequently, 300 to 500 ng of RNA was used for analysis on the NanoString nCounter system according to manufacturer's instructions. 100 genes that were selected for their ability to monitor cell state, pluripotency and differentiation into mesoderm, ectoderm and endoderm lineages at an early developmental stage were selected. Data analysis was performed in much the same way as normal quantitative PCR using TaqMan assay is performed. Specifically, the inventors used a moderated t-test to compare the gene expression in the embryoid bodies for the cell line of interest to the reference of all ES-cell derived embryoid bodies included in this study (but excluding the cell line that is being tested). To prepare for gene set testing, the inventors calculated the mean and standard deviation of the t-scores over the early developmental genes in each subgroup (e.g., ectoderm, endoderm and mesoderm lineage subgroups). Next, the inventors calculated the mean t-score separately for all gene sets that were defined a priori, and the inventors performed a parametric test against the mean over all genes as described previously (Kim 2005). For the lineage scorecard diagram, the inventors plotted the signed difference between the gene test mean and the global mean of the t-scores independent of significance, averaged over all contributing gene sets.

Lineage Scorecard Calculation

The lineage scorecard quantifies the differentiation propensity of a cell line of interest relative to a reference constituted by 19 low-passage ES cell lines (Table 4). The algorithm for calculating the lineage scorecard uses a combination of moderated t-tests (Smyth, 2004) and gene set enrichment analysis performed on t-scores (Nam and Kim, 2008; Subramanian et al., 2005). To provide a biological basis for quantifying lineage-specific differentiation propensities, several sets of early developmental marker genes for each of the three germ layers (ectoderm, mesoderm, endoderm). Bioconductor's limma package can also be used to perform moderated t-tests comparing the gene expression in the EBs obtained for the cell line of interest to the EBs obtained for the ES cell reference, and the mean t-scores were calculated across all genes that contribute to a relevant gene set. High mean t-scores (e.g., >1) indicate increased expression of the gene set's genes in the tested EBs and are considered indicative of a high differentiation propensity for the corresponding lineage. In contrast, low mean t-scores (e.g., <0) indicate decreased expression of relevant genes and are considered indicative of a low differentiation propensity for the corresponding lineage. To increase the robustness of the analysis, the mean t-scores were averaged over all gene sets assigned to a given lineage. The lineage scorecard diagrams (FIG. 3-7) list these "means of gene-set mean t-scores" as quantitative indicators of cell-line specific differentiation propensities. The lineage scorecard analyses and validations were performed using custom R scripts (available from world-wide web: r-project.org/).

Example 1

Variation in Gene Expression Between hES Cell Lines

There are many properties of a given ES cell line that could influence its early developmental gene expression profile and its potential differentiation. These could include the genetic background of a cell line, the way in which a line is cultured, selective pressure applied by extended in vitro growth, or unexplained stochastic noise. Before one can attempt to study the potential underlying causes of the variance in pluripotent stem cell line behavior, it is crucial to first determine both the nature and extent of variation that exists within a substantial cohort of lines.

Table 4: Summary of cell lines used in the high-throughput experiments. *verified by presence/absence of chrY and evidence of X-chromosome inactivation in the RRBS, microarray and/or Nano String data.

TABLE 4

| Cell Line | Reference | Donor Age | Donor Sex* | Sibling Pairs (ES)/ Donor (iPS) | Passage No. for RRBS | Passage No. for Microarray | Passage No. for Lineage Scorecard |
|---|---|---|---|---|---|---|---|
| HUES1 | Cowan et al. 2004 | NA | female | | 22 | 26 | 26, 26 |
| HUES3 | Cowan et al. 2004 | NA | male | | 27 | 27 | 27, 28 |
| HUES6 | Cowan et al. 2004 | NA | female | | 23 | 23 | 19, 21 |

TABLE 4-continued

| Cell Line | Reference | Donor Age | Donor Sex* | Sibling Pairs (ES)/ Donor (iPS) | Passage No. for RRBS | Passage No. for Microarray | Passage No. for Lineage Scorecard |
|---|---|---|---|---|---|---|---|
| HUES8 | Cowan et al. 2004 | NA | male | | 27 | 27 | 25, 26 |
| HUES9 | Cowan et al. 2004 | NA | female | | 21 | 21 | 19, 18 |
| HUES13 | Cowan et al. 2004 | NA | male | | 47 | 47 | NA |
| HUES28 | Chen et al. 2009 | NA | female | | 17 | 17 | 13, 15 |
| HUES44 | Chen et al. 2009 | NA | female | | 18 | 18 | 15, 16 |
| HUES45 | Chen et al. 2009 | NA | female | | 20 | 20 | 17, 19 |
| HUES48 | Chen et al. 2009 | NA | female | | 19 | 19 | 16, 17 |
| HUES49 | Chen et al. 2009 | NA | female | | 17 | 17 | 14, 14 |
| HUES53 | Chen et al. 2009 | NA | male | A | 17 | 18 | 17, 18 |
| HUES62 | Chen et al. 2009 | NA | female | B | 14 | 17 | 15, 16, 16, 16, 18 |
| HUES63 | Chen et al. 2009 | NA | male | B | 19 | 14 | 19, 17 |
| HUES64 | Chen et al. 2009 | NA | male | B | 19 | 19 | 18, 20 |
| HUES65 | Chen et al. 2009 | NA | male | | 19 | 19 | 16, 17 |
| HUES66 | Chen et al. 2009 | NA | female | A | 20 | 20 | 15, 15 |
| H1 | Thomson et al. 1998 | NA | male | | 34 | 34 | 33, 34 |
| H7 | Thomson et al. 1998 | NA | female | | 48 | 48 | NA |
| H9 | Thomson et al. 1998 | NA | female | | NA | 58 | 57, 58 |
| hiPS 11a | Boulting et al. | 36 | male | 11 | 22 | 22 | 14, 18, 27, 29 |
| hiPS 11b | Boulting et al. | 36 | male | 11 | 13 | 13 | 15, 18, 25, 31 |
| hiPS 15b | Boulting et al. | 48 | female | 15 | 27 | 16 | 29, 30, 41, 44 |
| hiPS 17a | Boulting et al. | 71 | female | 17 | 14 | 12 | 10, 16, 17, 19 |
| hiPS 17b | Boulting et al. | 71 | female | 17 | 32 | 32 | 18, 20, 38 |
| hiPS 18a | Boulting et al. | 48 | female | 18 | 30 | 30 | 31, 32, 46 |
| hiPS 18b | Boulting et al. | 48 | female | 18 | 27 | 27 | 20, 37 |
| hiPS 18c | Boulting et al. | 48 | female | 18 | 36 | 27 | 30, 32 |
| hiPS 20b | Boulting et al. | 55 | male | 20 | 43 | 43 | 26, 31, 46, 50 |
| hiPS 27b | Boulting et al. | 29 | female | 27 | 31 | 31 | 27, 28 |
| hiPS 27e | Boulting et al. | 29 | female | 27 | 32 | 30 | 30, 31, 32, 32, 35 |
| hiPS 29d | Boulting et al. | 82 | female | 29 | NA | NA | 14, 15 |
| hiPS 29e | Boulting et al. | 82 | female | 29 | NA | NA | 25, 27 |
| hFib__11 | Boulting et al. | 36 | male | 11 | 8 | 8 | 7, 8 |
| hFib__15 | Boulting et al. | 48 | female | 15 | 7 | 7 | 6, 7 |
| hFib__17 | Boulting et al. | 71 | female | 17 | 7 | 7 | 6, 7 |
| hFib__18 | Boulting et al. | 48 | female | 18 | 7 | 7 | 6, 7 |
| hFib__20 | Boulting et al. | 55 | male | 20 | 7 | 7 | 6, 7 |
| hFib__27 | Boulting et al. | 29 | female | 27 | 7 | 7 | 6, 7 |

*verified by presence/absence of chrY and evidence of X-chromosome inactivation in the RRBS, microarray and/or Nano String data Any appropriate method for positive selection of cell lines should be simple to perform in a short period of time, be inexpensive and be predictive for applications in differentiation down as many distinct lineages as possible. The inventors assessed if the differentiation of a given cell-line was initiated in a relatively unbiased manner, then its natural differentiation propensities might be predictive of its performance in directed differentiation protocols. In other words, the inventors assessed if a cell line that had a natural propensity to form ectoderm or cells of the neural lineage would also perform optimally in for example motor neuron directed differentiation. To assess this, the inventors designed a simple, rapid, and inexpensive assay for pluripotent cell line differentiation propensities (FIGS. 3-7C).

The inventors initial results demonstrated that a simple transcriptional assay using early developmental genes can predict the reproducible behavior of a given ES cell line. The inventors assessed whether this "lineage scorecard" could be used to predict the behavior of iPS cells. To this end, the inventors selected several well characterized iPS cell lines (Boulting et al), performed standard EB differentiation, collected RNAs, analyzed them using the an array of early developmental genes as disclosed in Table 1 and normalized the resulting data to the "reference" ES cell-derived EBs. The result was a lineage "scorecard" for the behavior of the selected iPS cell lines (FIG. 4).

Example 2

Toward High-Throughput Evaluation of Pluripotent Cell Quality and Utility

The inventors have demonstrated use of the differentiation assays as disclosed herein to design a "lineage scorecard" that can predict the differentiation propensities of any pluripotent cell line. The scorecard output provides a systematic estimate of a cell line's differentiation propensities.

Here, the inventors demonstrate that only one differentiation gene expression assay of early developmental genes is required to quantitative and characterize a stem cell without compromising the accuracy of the score-card relative to methods involving more than one type of assay, e.g., methylation assay, gene expression assay and a differentiation assay, or gene expression on differentiated or spontaneously differentiated stem cells.

As disclosed herein, the quantitative differentiation assay could be performed alone as a single indicator of the differentiation potential of the stem cells line. Additionally, the inventors demonstrate by assessing the expression of a distinct range of early developmental genes, a significant reduction the total length of time required to perform the quantitative differentiation assay. Effectively, the inventors have demonstrated that the early gene expression analysis can be performed on embryonic stem cells at embryonic day 2, reduced from analysis performed at least at 5-days or 7-days of embryonic age. By "embryonic day n" is meant n days in culture in EB forming conditions. Accordingly, shortening the duration of the assay is advantageous as it decreases the time-to-results and also minimizes the logistical costs in terms of incubator space and need for media changes. The inventors optimized the quantitative differentiation assay so it is sensitive enough to estimate differentiation propensities using RNA isolated directly from the undifferentiated pluripotent cell lines, most likely by detecting low levels of cellular differentiation in otherwise self-renewing cultures. Additionally, the inventors have demonstrated that the differentiation assay performed only once is sufficient to determine the differentiation propensity of the stem cell line, thus eliminating the expense and time required for duplicate and triplicate assays. Further, the differentiation assay can be performed using a variety of different RNA preparation methods, culture media and the like. The inventors have also demonstrated that the differentiation assay can be performed in multiplex for high-throughput analysis, for example in a 96- and 384-well plates, allowing multiple stem cell lines to be analyzed simultaneously.

Example 3

The inventors also investigated how robust and reproducible the results from the "scorecard" remained when the inventors compared the same pluripotent stem lines across several passages and between independent labs. Because the inventors' methods for analyzing DNA methylation and transcription have been shown to be reproducible (Gu et al., 2010; Irizarry et al., 2005) and because the inventors have already investigated how these measures change with passage (data not shown), the inventors focused on the reproducibility of the quantitative differentiation assay. Because differentiation of ES cells in EBs is likely to be sensitive to differences in such parameters as physical handling, media renewal and plasticware, the inventors assessed how predictive the results from the differentiation assay would be of cell line behavior in another lab and with a distinct investigator.

To further confirm the robustness and reproducibility of the scorecard for predicting the behavior of iPS cell lines, the inventors performed a variety of quality control experiments using different culture and sample preparation and gene expression methodology. The inventors therefore performed a systematic comparison in which two different cell lines (H9 ESC and BS3-C iPSC) were evaluated by two different investigators in two different labs, performing the EB assay separately and independently.

The focused set of early developmental genes listed in Table 1 is a good indicator of cell state. Thus, the assay as disclosed herein can cluster the cell lines by cell state, which is not achievable by other methods, such as the TaqMan Open Array (data not shown).

Figure 2A:
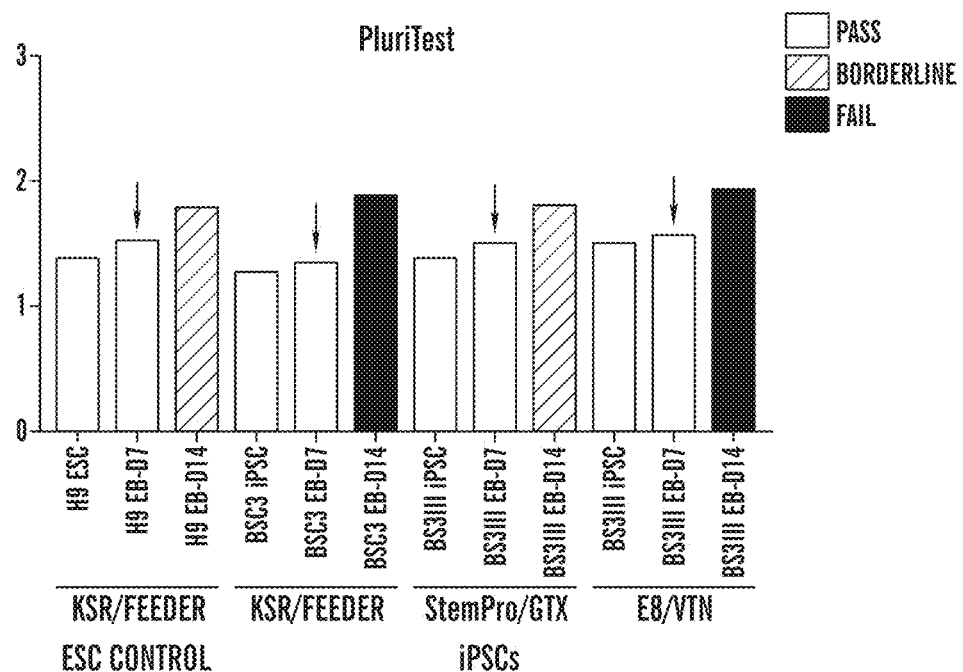
FIG. 2A-2B.
Figure 2B:
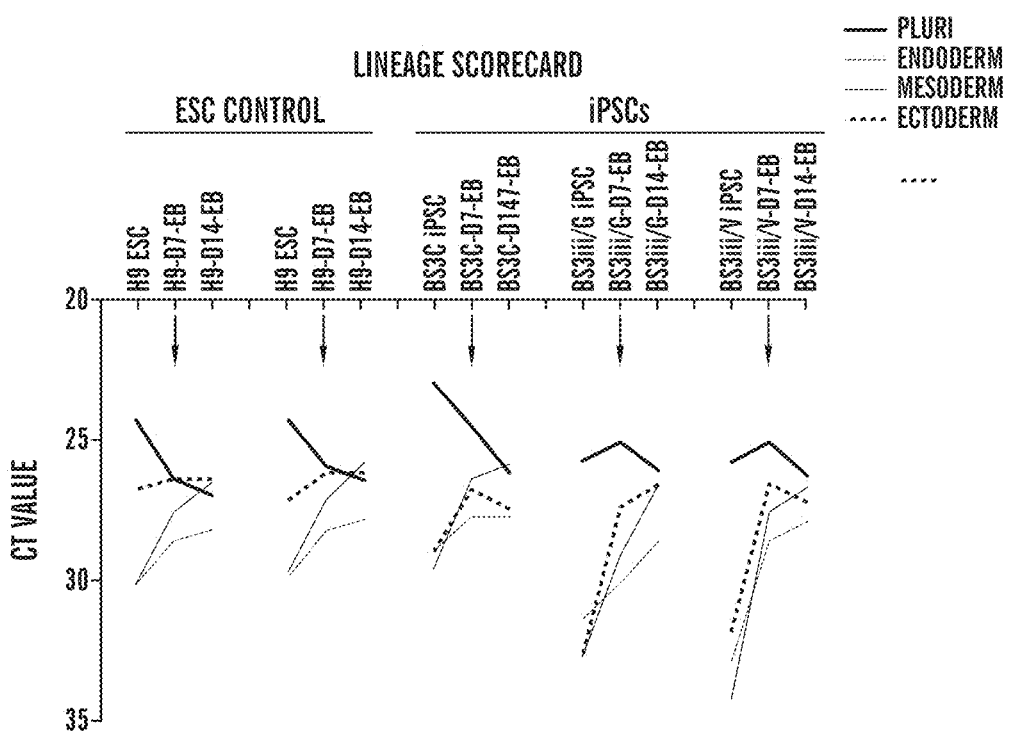
Figure 8:
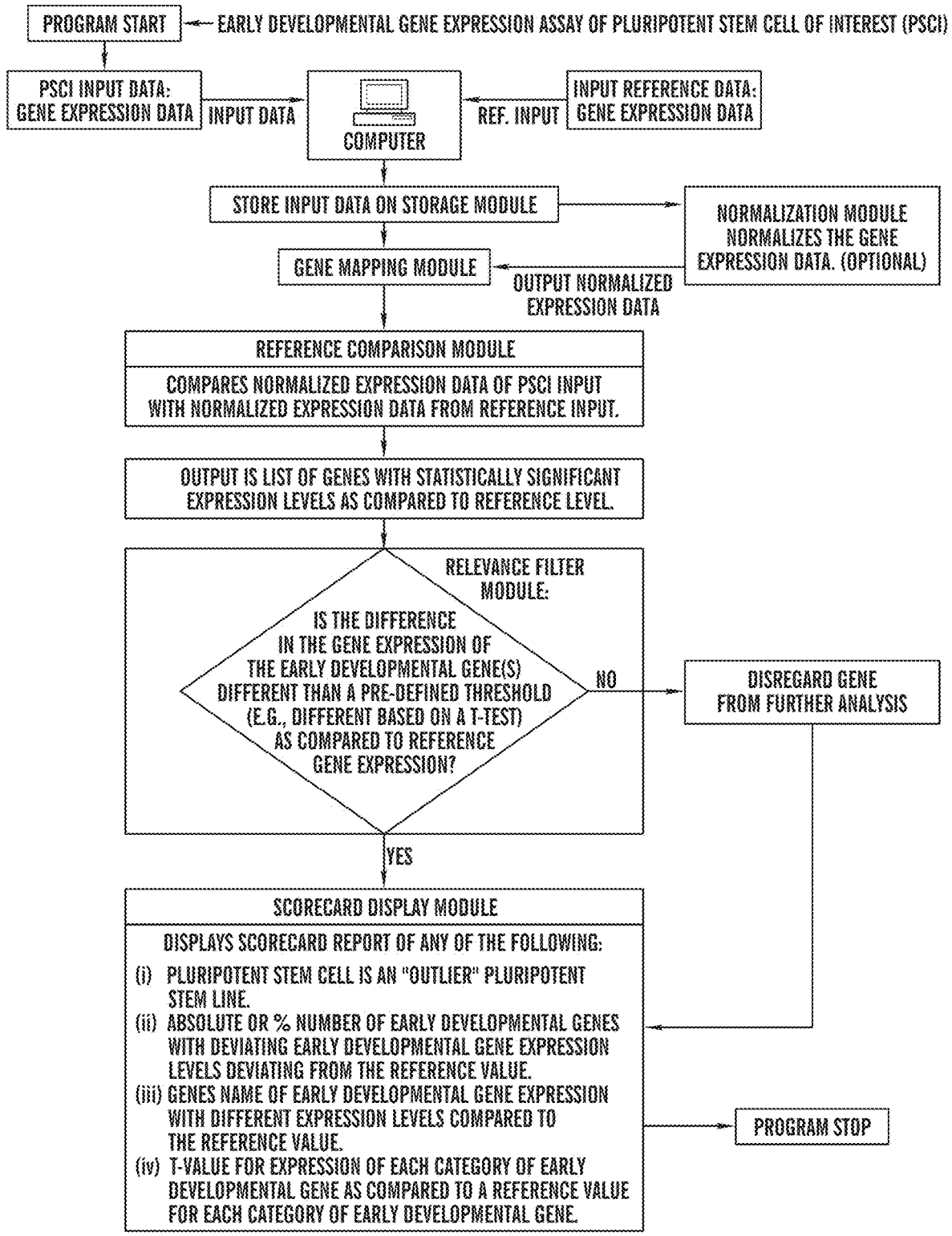
FIG. 8 shows a flow chart of an embodiment of instructions for a computer program for producing a lineage scorecard as disclosed herein for a pluripotent stem cell line of interest. The data are inputed into a computer comprising a processor and associated memory or storage device, and a gene mapping module, a reference comparison module, a normalization module a relevance filter module a gene set module and a scorecard display module to display the deviation scorecard.
Figure 9:
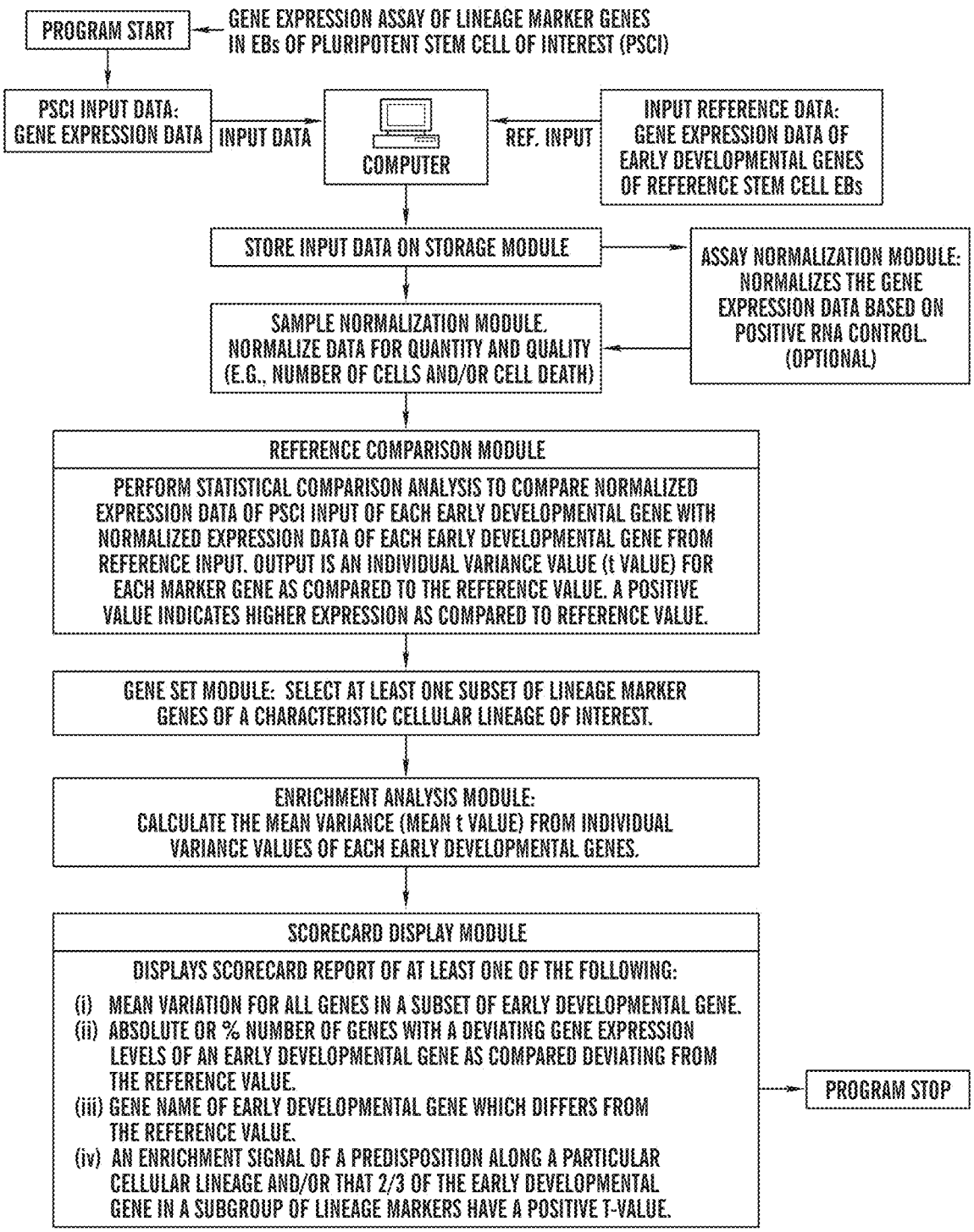
FIG. 9 shows a flow chart of one embodiment of instructions for a computer program for producing a lineage scorecard for a pluripotent stem cell line of interest. The data obtained for the generation of the deviation scorecard are gene expression data of early developmental genes for the pluripotent stem cell line of interest. The data are inputed into a computer comprising a processor and associated memory and/or storage device, and an assay normalization module. A sample normalization module, a reference comparison module, a gene set module, an enrichment analysis module and a scorecard display module to display the lineage scorecard.
Figure 10:
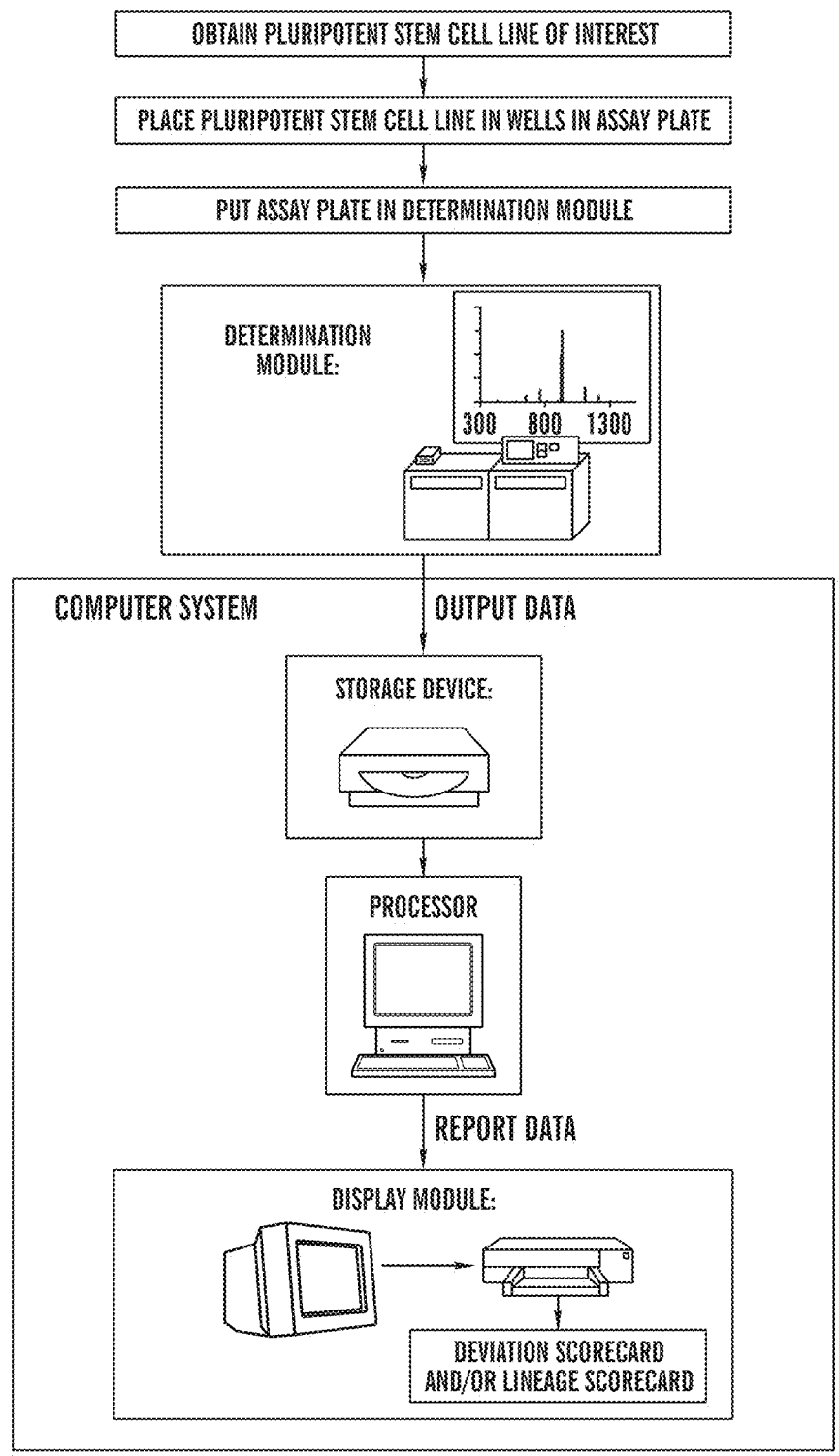
FIG. 10 shows a simplified block diagram of an embodiment of the present invention which relates to a high-throughput system for characterizing the differentiation propensity of a pluripotent stem cell of interest and producing a lineage scorecard. The determination module can be any apparatus or machine for measuring gene expression.
Figure 11:
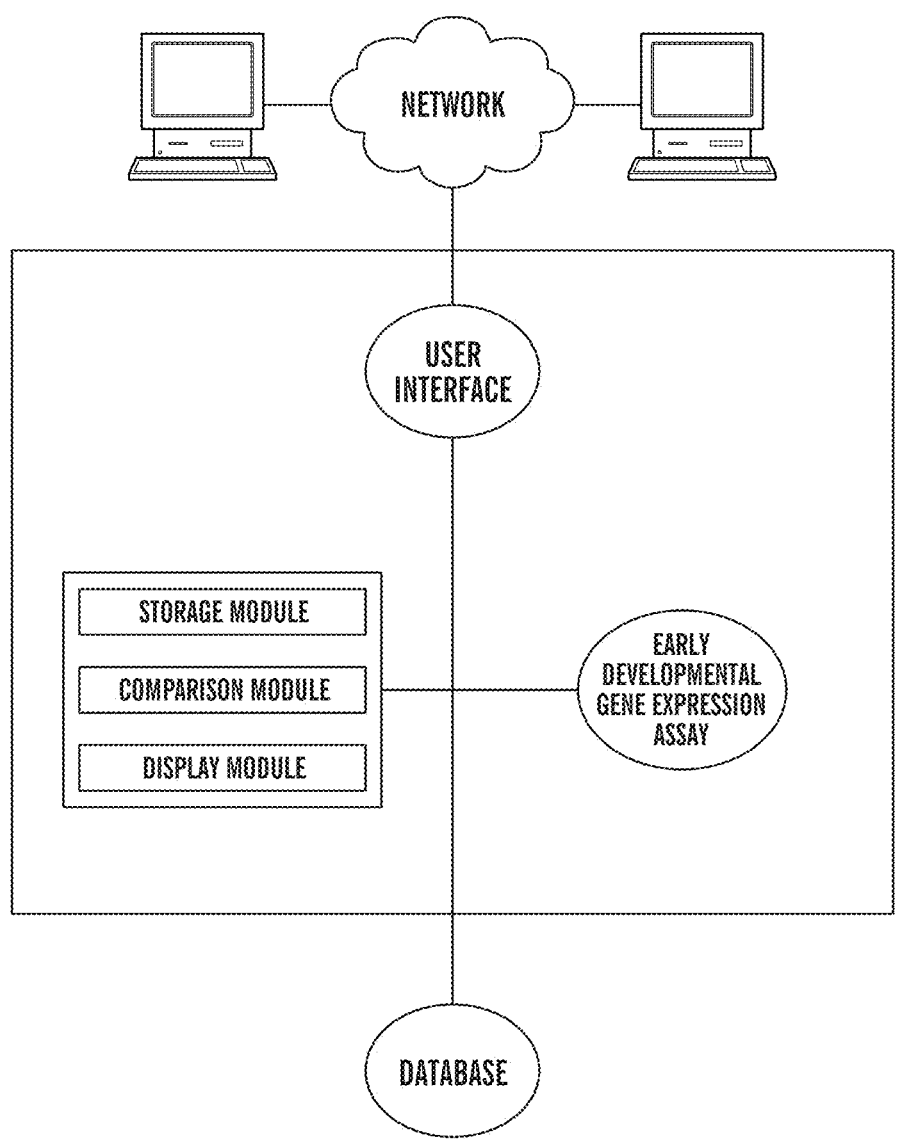
FIG. 11 shows a simplified block diagram of an embodiment of the present invention which permits the data gene expression differentiation assays to be configured to be processed by a computer system at any location and accessible through a user interface, where the data for each pluripotent stem cell are stored in a database.

In a direct comparison with other assays, the lineage scorecard as disclosed herein was demonstrated to be superior and more accurate than other assays, such as the PluriTest™ (Franz-Josef Müller et al., A bioinformatic assay for pluripotency in human cells, Nature Methods, 2011, 8; 315-317), in identifying pluripotent stem cells. As shown in FIG. 2A, while the Pluritest™ indicated that the stem cell line was not pluripotent at 14 days, but indicated that the stem cell line was pluripotent at 7 days. In contrast, FIG. 2B shows that the assay used herein was more sensitive, indicating that at 7 days, the expression of pluripotent genes was down and the expression of differentiation genes was increased. Accordingly, the assays as disclosed herein are more sensitive to determine the pluripotency of a stem cell line (or lack of pluripotency) at 7 days or earlier, e.g., by 5 days in culture.

Quality Control Experiments Demonstrate Consistency in the Measured Levels of Expression of the Early Developmental Genes Regardless User Differences, Culture Method, RNA Isolation Methods and PCR Mixes.

Different users in different labs demonstrate a high accuracy of predictability of pluripotency and differentiation potential using the assay as demonstrated herein. For example, different users, using different culturing methods and different stem cell culture media (e.g., conditioned media, StemPro/Geltrex and essential8/vitronectin), as well as different cell and RNA preparation showed little variability in the levels of expression of the early developmental genes of the assay in the same cell lines at the same timepoint (data not shown), demonstrating consistency and accuracy of the assay. Additionally, no significant difference in RNA quality was observed with different RNA isolation methods (e.g., Trizol PureLink™ or Trizol™), and resulted in high RNA purity and little variability in RNA yields (data not shown). Furthermore, the levels of expression of the early developmental genes was not affected by the different PCR master mixes (e.g. TaqMan® Universal master mix, TaqMan® Gene Expression Mix, TaqMan® Fast Advanced Master Mix, TaqMan® Genotyping Master Mix) used for amplification of the early developmental genes in the differentiation assay (data not shown).

Different lots of plates performed comparably for pluripotent samples (e.g., pluripotent cells cultured to the same time point, e.g., 3-days or 4-days or 5-days in EB), but with less consistency and higher variability with differentiated stem cell lines (data not shown). Accordingly, the assay plates are consistent from lot to lot and thus a pluripotent stem cell line can be assayed a single time, and does not need to be assayed in replicates. Different instruments (e.g., Viia7, QuantStudio and StepOne Plus) for the RT-PCR resulted in high correlation in the level of expression of the early developmental genes measured in the assay.

Accordingly, Trizol and PureLink isolated RNA have quality with in the acceptable range. TaqMan Gene expression Master mix and Universal Master Mix II both can be used as PCR master mixes under Standard PCR conditions (not Fast). Undifferentiated pluripotent samples harvested by different methods all show high level of correlation in gene expression when normalized to housekeeping gene. A clear change in gene expression pattern was observed between undifferentiated and differentiated EB samples and clustered away form the pluripotent cells. The majority of the gene assays show predicted expression in pluripotent and differentiated cells.

Example 4

Algorithm and Data Analysis

For each input sample and each of six categories of genes (control, pluri, endo, mesendo, meso, ecto) the software reports mean (mu) and standard deviation of t-statistic (significance) and min and max p-value over the gene category. The Reference Gene is calculated as follows: The median Ct value across ACTB will be used as a base to compute $\Delta$Ct values. The Reference Sample value provides a base $\Delta$Ct and is calculated as follows: T- and P-values are computed between the distribution defined by this group of samples (6 replicates of PSC-data comprised of 1 ESC and 1iPSC line prepared using two different methods by two users) and each unknown sample. There is a reference based on gene expression levels at in at least about 20 cell lines which are both differentiated and undifferentiated.

Accordingly, the ΔCt is determined for all early developmental genes measured in the pluripotent stem cell. In each defined group or category (e.g., control, pluripotent gene, early endoderm developmental genes, early mesendoderm developmental gene, early mesoderm developmental genes, early ectoderm developmental gene), the ΔCt is averaged and the averaged ΔCt is compared using a t-test to the reference ΔCt for that category (FIG. 3). Using t-value as an indicator (see FIG. 3), a t-value of 0-1 indicates that the measured level of gene expression in that early developmental gene category is comparable with the reference gene expression level in the same category. A t-value of >1 indicates that the measured gene expression level in that early developmental gene category of the pluripotent cell line is higher than the reference gene expression level in the same category. A t-value of <0 indicates that the measured gene expression level in that early developmental gene category of the pluripotent cell line is lower than the reference gene expression level in the same category.

Example 5

Analysis of Undifferentiated and Differentiated Pairs

The results of the differentiation assay which measured the levels of the early developmental genes can be displayed in a number of different ways. As demonstrated in FIG. 4, the t-value of each category of developmental gene can be displayed (e.g., the t-value comparison of the average ΔCt for all the genes in each category is compared with the average ΔCt for the same set of genes in the reference pluripotent stem cell lines). If the t-value is between 0-1, a signal, e.g., yellow signal or an arrow (e.g., horizontal or directional 45° upward or downward arrow) indicates that the measured level of gene expression in that early developmental gene category is comparable with the reference gene expression level in the same category. If the t-value is >1, a signal, e.g., green color or an upwards arrow indicates that the measured gene expression level in that early developmental gene category of the pluripotent cell line is higher than the reference gene expression level in the same category. If the t-value is <0, a signal, e.g., a red color or downwards arrow indicates that the measured gene expression level in that early developmental gene category of the pluripotent cell line is lower than the reference gene expression level in the same category. As shown in FIG. 3, the differentiation potential of a pluripotent stem cell can be determined by looking at the pluripotent genes and the three germ line early developmental genes (e.g., meso, endo, and ecto). For example, the analysis of the BS3C cells, shows the BS3C iPSC have comparable levels of pluripotent genes, mesoderm genes, endoderm genes and ectoderm genes as compared to the reference standard, whereas 7D and 14D BS3C cells have decreased pluripotent stem cells and increased expression levels for the mesoderm genes, endoderm genes and ectoderm genes, indicating that the genes are no longer pluripotent and have begun to differentiate.

Example 6

Differentiated Times and Methods

The inventors assessed whether the duration of the differentiation assay could be reduced from being performed on pluripotent stem cells at 7 days to cells which were at least 2 days. In this case, the inventors demonstrated an excellent agreement between the expression of early developmental genes in each category (e.g., pluripotent, mesoderm, ectoderm and endoderm) on a representative iPS cell lines (FIG. 5), demonstrating that it is possible to reduce the duration at which the time of the differentiation assay is performed without jeopardizing its accuracy. This was a surprising finding allowing reduced cost associated with a quicker determination of the characterization of the differentiation potential of a pluripotent stem cell line.

Accordingly, herein the inventors demonstrate that the assays, methods and systems can be performed on pluripotent stem cells as early as 2 days in culture (e.g., EB Day 2). As demonstrated in FIG. 5, pluripotent stem cells cultured at 2 and 4 days produce reliable results for levels of expression of early developmental genes. Furthermore, the assay, methods and systems can be performed on pluripotent stem cells in EB suspension or in a monolayer, as demonstrated in FIG. 6. As shown in FIG. 7A, the differentiation assays, methods and systems as disclosed herein can be used to identify a bad clone or culture (e.g., BS4-iPS5 P8), when the pluripotent stem cell is compared to similar pluripotent stem cells lines at the same time point. FIG. 7B shows that the differentiation assays, methods and systems as disclosed herein can also identify cell lines which have a predisposition to differentiate along a particular lineage, e.g., in FIG. 7B, the hNSDup cell line has increased ectoderm levels indicating the cell line has a predisposition to differentiate along an ectoderm lineage. Furthermore, the differentiation assays, methods and systems as disclosed herein are useful for identifying stem cell lines which are no longer pluripotent, as demonstrated in FIG. 7C shows BJ fibroblasts and HJF fetal cells have a significant decrease in pluripotent genes. Additionally, the assay can also detect the effect of contamination of MEF (see FIG. 7C).

Example 7

Until recently, only a few human pluripotent cell lines were widely available for biomedical research. For this reason, researchers have mostly relied on these readily accessible and well characterized cell lines (Cowan et al., 2004; Mitalipova et al., 2003; Thomson et al., 1998). Funding restrictions placed on human ES cell research in the United States further limited the selection of cell lines available. As a result, investigators simply used any lines they could for their application of interest with little need for a diagnostic that could predict how well a given cell line would behave in a given assay.

However, the continued derivation of human ES cell lines by many labs (Chen et al., 2009) and the lifting of funding restrictions in the US, has substantially increased the number of ES cell lines that investigators can choose from. Additionally, it has become clear that not all human ES cell lines are equally suited for every purpose (Osafune et al., 2008). This suggests that any new research project should perform a deliberate and informed selection of the cell lines that are most qualified for an application of interest.

The discovery of factors that reprogram somatic cells from patients into iPS cells has lead to a further inflection in the number of pluripotent cell lines available to, and needed by, the research community. As investigators gather together existing cell lines, or derive new ones for their application of interest, there is little information or guidance concerning how to select cell lines that are most appropriate. The inventors herein provide a clear path to guide investigators to proceed from patient samples, to fully reprogrammed iPS cells, to a selected and manageable set of lines that can be used at a reasonable scale for disease modeling.

Here, the inventors demonstrate methods to accurately predict the differentiation propensities of human pluripotent cell lines, thereby allowing investigators to select lines that would perform optimally in their given application. Importantly, the use of the "scorecard" as disclosed herein for pluripotent cell line quality and utility, can be readily scaled for the characterization of any number of pluripotent cell lines, e.g., as few as about 5 pluripotent stem cell lines to 10's and 100's and 1000's of pluripotent stem cell lines.

In aggregate, the scorecard as disclosed herein reports the differentiation characteristics and likely behavior of a given pluripotent cell line that an investigator would wish to understand before investing significant time and resources into its use in any particular application. For instance, the scorecard as disclosed herein incorporates developmental gene expression profiles for the pluripotent cell lines, allowing investigators to be confident that cell lines they select have the ability, or even increased efficiency to differentiate into their desirable cell lineage, and are not non-pluripotent stem cell lines.

For those interested in developing cell therapies, it can be critical to demonstrate that a pluripotent cell line being put forward for clinical development fits to "standard" criteria from preparation to preparation and can either differentiate into all three germ line lineages, and/or in certain criteria, the stem cell line selected has an increased efficiency of differentiating along a particular cell lineage. Accordingly, the inventors production and use of the "scorecard" as disclosed herein is useful for these important safety measures before administering a pluripotent stem cell or their progeny to a subject in therapeutic use.

The quantitative differentiation assay as disclosed herein provides information on a pluripotent cell line propensity to differentiate along a number and/or a particular cell lineage, as well as if the stem cell line is no longer pluripotent. As disclosed herein, this quantitative differentiation assay uses DNA expression profiles of early developmental genes expressed in specific lineages as a measure to quantitatively demonstrate the differentiation potential of the stem cell to differentiate along each lineage (e.g., mesoderm, ectoderm and endoderm) as well as specific lineages, e.g., neuronal lineages, pancreatic lineages etc.

Epigenetic and transcriptional differences can distinguish the average ES cell line from the average iPS cell line, but these differences are insufficient to draw conclusions about the characteristics of any single ES or iPS cell line under consideration. Herein, by using the differentiation assay, the inventors determined that some stem cell lines are more suited for a given application than others, and the same is true of iPS cells.

The inventors also determined that rather than trying to find the optimal ES cell line or the perfect reprogramming protocol for all needs and applications, what seems to be required is a rapid assay that can match suitable cell lines to a given application. Accordingly, the methods, systems and kits of the differentiation assay as disclosed herein are useful to determine and predict the propensities of human pluripotent cell lines, such that an appropriate pluripotent stem cell with desired propensities could be matched and selected for use in specific downstream applications.

In some embodiments, the differentiation assay can be adapted in different ways to assess the selective pressures of in vitro culture on the differentiation of the stem cell clone. Accordingly, based on this data, ES cell lines are also useful to provide a model system for investigating the ramifications of cellular competition and adaption to growth conditions.

Presently, without the current invention, after obtaining an existing pluripotent stem cell line, or generating a new one, an investigator would perform a number of time-consuming, laborious and expensive assays including immunostaining for specific antigens and teratoma generation. While these assays can provide some confidence that a given cell line is pluripotent, they are unable to predict whether a pluripotent cell line is well suited to a given application. In contrast, the present methods, kits, systems, differentiation assays and differentiation scorecards as disclosed herein are useful to predict the behavior of the pluripotent stem cell in a quick, efficient and effective manner, which is not time or labor intensive and relatively inexpensive.

Accordingly, using the methods, kits, systems, assays and scorecards as disclosed herein, a researcher interested in disease modeling of, for example, cells which differentiate along an ectoderm lineage, and then into neurons, which can be used in the treatment of neurodegenerative diseases, e.g., amyotrophic lateral sclerosis (ALS). In some embodiments, an investigator could analyze their pluripotent stem cells of interest and perform the quantitative differentiation assay and array as disclosed herein. The researcher can then select those pluripotent stem cell lines exhibiting normal to high differentiation propensity to differentiate into an ectoderm lineage (see FIG. 7B) and then into neural lineages for further studies. Accordingly, using the methods, assays, kits and systems and scorecards as disclosed herein, an investigator can inspect cell lines for variation in the parameters that would best predict the utility of the pluripotent stem cell line in their particular desired application (FIG. 7E).

The inventors methods, assays, scorecards and kits as disclosed herein enable an investigator to delay the most time-consuming and expensive assay, teratoma formation, to be started on a particular pluripotent stem cell line only at a time when the "scorecard" has predicted that the selected pluripotent cell line is likely to differentiate into motor neurons, or other cells of interest at a high efficiency. Over time, the use of the methods, assays, scorecards and kits as disclosed herein can enable one to eliminate the teratoma generation assay completely if the methods, assays, scorecards as disclosed herein are used to accurately predict pluripotent stem cell lines with the potential to form a teratoma.

In conclusion, the discovery of human pluripotent cells and the reprogramming methods to produce human iPS cells from selected patient populations has revolutionized how researchers think about studying and treating human disease. However, if use of human pluripotent stem cells and iPS cells are to efficiently and effectively used in research as well as cell therapy and therapeutic use to improve the lives of patients, it is imperative to establish a quality assessment and validation method such as the methods, assays, systems and "scorecard" as disclosed herein to streamline, standardize and optimize the selection of pluripotent cell lines for studying, for drug development and toxicity assays as well as for a particular therapeutic implication, or for treating a given indication or disease.

REFERENCES

The references are incorporated herein in their entirety by reference.

The invention claimed is:

1. An array composition for characterizing the differentiation potential of a pluripotent stem cell, wherein the array comprises a solid support and located on the solid support at assigned positions defined by x and y coordinates are at least 30 pairs of amplification primers and at least 30 oligonucleotides probes, and wherein the array comprises no more than 100 pairs of amplification primers and no more than 100 oligonucleotide probes,
wherein the oligonucleotide probes comprise an attached fluorescent dye and specifically hybridize to mRNA or cDNA of at least 30 early developmental genes selected from the group consisting of SEQ ID NO: 11, 14, 15, 19, 20, 21, 22, 23, 30, 32, 33, 34, 36, 37, 44, 45, 46, 48, 49, 53, 62, 63, 65, 66, 68, 70, 78, 84, 86, 87 and 88, and
wherein the at least 30 pairs of amplification primers that specifically amplify mRNA of a set of at least 30 early developmental genes selected from the group consisting of SEQ ID NO: 11, 14, 15, 19, 20, 21, 22, 23, 30, 32, 33, 34, 36, 37, 44, 45, 46, 48, 49, 53, 62, 63, 65, 66, 68, 70, 78, 84, 86, 87 and 88.

2. A method of determining the differentiation potential of a pluripotent stem cell line comprising;
providing the array of claim 1;
amplifying mRNA to produce cDNA, of said set of at least 30 early developmental genes selected from the group consisting of SEQ ID NO: 11, 14, 15, 19, 20, 21, 22, 23, 30, 32, 33, 34, 36, 37, 44, 45, 46, 48, 49, 53, 62, 63, 65, 66, 68, 70, 78, 84, 86, 87 and 88 in said pluripotent stem cell line, wherein the amount of cDNA produced corresponds to the amount of mRNA for each early developmental gene amplified;
measuring the level of cDNA for each of the at least 30 early developmental genes amplified in the pluripotent stem cell; and
comparing the level of cDNA expression of the measured set of at least 30 early developmental genes to the level of expression of the same early developmental genes in a control pluripotent stem cell sample, and based on this comparison, determining the differentiation potential of the pluripotent stem cell line.

3. A kit comprising:
a. the array of claim 1; and
b. reagents to carry out amplification of the mRNA of the at least 30 early developmental genes.

4. The array of claim 1, wherein at least 4 of the 30 oligonucleotides probes or at least 30 pairs of amplification primers are ectoderm genes, at least 4 of the 30 oligonucleotides probes or at least 30 pairs of amplification primers are endoderm genes and at least 4 of the 30 oligonucleotides probes or at least 30 pairs of amplification primers are mesoderm genes.

5. A method of determining the differentiation potential of a pluripotent stem cell line comprising;
providing the array of claim 1; and
amplifying the mRNA, to produce cDNA, of a set of at least 12 early developmental genes selected from the group consisting of:
at least 4 ectoderm genes selected from the group consisting of SEQ ID NO: 11, 14, 15, 19, 20, 21 and 22;
at least 4 endoderm genes selected from the group consisting of SEQ ID NO: 23, 30, 32, 33, 34, 36, 37, 44, 45, 46, 48 and 49; and
at least 4 mesoderm genes selected from the group consisting of SEQ ID NO: 53, 62, 63, 65, 66, 68 and 70;
in said pluripotent stem cell line, wherein the amount of cDNA produced corresponds to the amount of mRNA for each early developmental gene amplified;
measuring the level of cDNA for each of the at least 12 early developmental genes amplified in the pluripotent stem cell;
comparing the level of cDNA expression of the measured set of at least 12 early developmental genes to the level of expression of the same early developmental genes in a control pluripotent stem cell sample, and based on this comparison, determining the differentiation potential of the pluripotent stem cell line.

6. An array composition for characterizing the differentiation potential of a pluripotent stem cell, wherein the array comprises a solid support and located on the solid support at assigned positions defined by x and y coordinates are at least 12 pairs of amplification primers and at least 12 oligonucleotides, and wherein the array comprises no more than 100 pairs of amplification primers and no more than 100 oligonucleotide probes,
wherein the oligonucleotide probes have an attached fluorescent dye and hybridize to mRNA or cDNA of at least 12 early developmental genes, and wherein the at least 12 pairs of amplification primers amplify the mRNA of a set of at least 12 early developmental genes selected from the group of
at least 4 ectoderm genes selected from the group consisting of SEQ ID NO: 11, 14, 15, 19, 20, 21 and 22;
at least 4 endoderm genes selected from the group consisting of SEC ID NO: 23, 30, 32, 33, 34, 36, 37, 44, 45, 46, 48 and 49; and
at least 4 mesoderm genes selected from the group consisting of SEQ ID NO: SEQ ID NO: 53, 62, 63, 65, 66, 68 and 70.

7. A kit comprising:
a. the array of claim 6; and
b. reagents to carry out amplification of the mRNA of the at least 12 early developmental genes.

* * * * *

UNITED STATES PATENT AND TRADEMARK OFFICE
CERTIFICATE OF CORRECTION

PATENT NO. : 10,626,445 B2
APPLICATION NO. : 15/983209
DATED : April 21, 2020
INVENTOR(S) : Meissner et al.

Page 1 of 1

It is certified that error appears in the above-identified patent and that said Letters Patent is hereby corrected as shown below:

In the Specification

Column 1, Lines 20-24:
"This invention was made, in part, with government support under NIH Roadmap Initiative on Epigenomics, Grant Number U01ES017155 awarded by National Institutes of Health. The Government has certain rights in the invention."

Should be replaced with:
— This invention was made with government support under ES017155 awarded by the National Institutes of Health. The government has certain rights in the invention. —

Signed and Sealed this
Thirtieth Day of June, 2020

Andrei Iancu
*Director of the United States Patent and Trademark Office*